US012799128B2

(12) United States Patent
Kercher et al.

(10) Patent No.: US 12,799,128 B2
(45) Date of Patent: Nov. 17, 2026

(54) KRAS INHIBITORS

(71) Applicant: ELI LILLY AND COMPANY, Indianapolis, IN (US)

(72) Inventors: Timothy Scott Kercher, Longmont, CO (US); Desta Bume, Commerce City, CO (US); Andrew Dilger, Golden, CO (US); Adedoyin David Abraham, Thornton, CO (US); Alberto Valero De La Cruz, Madrid (ES); Julián Priego Soler, Madrid (ES); Maria Lourdes Prieto Vallejo, Madrid (ES); Mario Barberis, Madrid (ES); Miguel Garzón Sanz, Madrid (ES); Ramkumar Rajamani, Acton, MA (US); Sean Aronow, Boulder, CO (US); Shane Michael Walls, Broomfield, CO (US); Sonia Maria Gutierrez Sanfeliciano, Carmel, IN (US); Victoriano Molero Flórez, Madrid (ES); Xiaohong Chen, Broomfield, CO (US)

(73) Assignee: Eli Lilly and Company, Indianapolis, IN (US)

( * ) Notice: Subject to any disclaimer, the term of this patent is extended or adjusted under 35 U.S.C. 154(b) by 314 days.

(21) Appl. No.: 18/621,291

(22) Filed: Mar. 29, 2024

(65) Prior Publication Data

US 2024/0343736 A1 Oct. 17, 2024

Related U.S. Application Data

(60) Provisional application No. 63/493,051, filed on Mar. 30, 2023.

(51) Int. Cl.

| | |
|---|---|
| ***C07D 491/048*** | (2006.01) |
| ***A61K 31/519*** | (2006.01) |
| ***A61K 31/537*** | (2006.01) |
| ***A61K 31/5377*** | (2006.01) |
| ***A61P 35/00*** | (2006.01) |
| ***C07D 519/00*** | (2006.01) |

(52) U.S. Cl.

CPC ........ *C07D 491/048* (2013.01); *A61K 31/519* (2013.01); *A61K 31/537* (2013.01); *A61K 31/5377* (2013.01); *A61P 35/00* (2018.01); *C07D 519/00* (2013.01)

(58) Field of Classification Search

CPC ... C07D 519/00; C07D 491/048; A61P 35/00; A61K 31/519; A61K 31/537; A61K 31/5377

See application file for complete search history.

(56) References Cited

FOREIGN PATENT DOCUMENTS

| | | | |
|---|---|---|---|
| WO | 2021/118877 | A1 | 6/2021 |
| WO | 2022/148422 | A1 | 7/2022 |
| WO | 2022/177917 | A2 | 8/2022 |
| WO | 2022/221739 | A1 | 10/2022 |
| WO | 2022/261154 | A1 | 12/2022 |
| WO | 2023/061294 | A1 | 4/2023 |
| WO | 2023/183585 | A1 | 9/2023 |

OTHER PUBLICATIONS

International Search Report and Written Opinion mailed Jun. 25, 2024, for PCT application No. PCT/US2024/022131 filed Mar. 29, 2024.

*Primary Examiner* — Rebecca L Anderson
(74) *Attorney, Agent, or Firm* — Stefan Ochiana

(57) ABSTRACT

The present invention provides compounds of the formula:

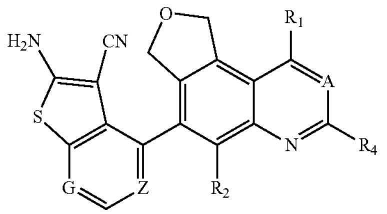

wherein A, Z, G, $R_1$, $R_2$, and $R_4$ are as described herein, pharmaceutically acceptable salts thereof, and methods of using these compounds and pharmaceutically acceptable salts thereof for treating patients for cancer.

37 Claims, No Drawings

KRAS INHIBITORS

CROSS-REFERENCE TO RELATED PATENT APPLICATIONS

The present application claims the benefit of priority to U.S. Provisional Application No. 63/493,051, filed on Mar. 30, 2023, and to European Patent Application Nos. EP 23382530.6, filed on Jun. 2, 2023, and EP 23382855.7, filed on Aug. 18, 2023, the contents of which are incorporated herein by reference in their entireties.

BACKGROUND

The MAPK/ERK signaling pathway relays extracellular stimuli to the nucleus, thereby regulating diverse cellular responses including cell proliferation, differentiation, and apoptosis. KRas protein is an initiator of the MAPK/ERK signaling pathway and functions as a switch responsible for inducing cell division. In its inactive state, KRas binds guanosine diphosphate (GDP), effectively sending a negative signal to suppress cell division. In response to an extracellular signal, KRas is allosterically activated allowing for nucleotide exchange of GDP for guanosine triphosphate (GTP). In its GTP-bound active state, KRas recruits and activates proteins necessary for the propagation of growth factor induced signaling, as well as other cell signaling receptors. Examples of the proteins recruited by KRas-GTP are c-Raf and PI3-kinase. KRas, as a GTP-ase, converts the bound GTP back to GDP, thereby returning itself to an inactive state, and again propagating signals to suppress cell division. KRas gain of function mutations exhibit an increased degree of GTP binding and a decreased ability to convert GTP into GDP. The result is an increased MAPK/ERK signal which promotes cancerous cell growth. Missense mutations of KRas at codon 12 are the most common mutations and markedly diminish GTPase activity.

Oncogenic KRas mutations have been identified in approximately 30% of human cancers and have been demonstrated to activate multiple downstream signaling pathways. Despite the prevalence of KRas mutations, it has been a difficult therapeutic target. (Cox, A. D. *Drugging the Undruggable RAS: Mission Possible*? Nat. Rev. Drug Disc. 2014, 13, 828-851; Pylayeva-Gupta, y et al. *RAS Oncogenes: Weaving a Tumorigenic Web*. Nat. Rev. Cancer 2011, 11, 761-774).

Thus far, work has focused on KRas G12C mutant inhibitors (e.g., WO2019/099524, WO2020/081282, WO2020/101736, WO2020/146613, and WO2021/118877 disclose KRas G12C inhibitors), whereas WO2021/041671 discloses small molecules inhibitors of KRas G12D and WO2017/011920 discloses small molecule inhibitors of KRas G12C, G12D, and G12V.

There remains a need to provide alternative, small molecule KRas inhibitors. In particular, there is a need to provide more potent, orally deliverable KRas inhibitors that are useful for treating cancer. More particularly, there is a need to provide small molecule inhibitors that specifically inhibit KRas GTP activity. There is also a need to provide small molecule KRas inhibitors that exhibit greater efficacy at the same or reduced KRas inhibitory activity. Further, there is a desire to provide KRas inhibitors that exhibit better pharmacokinetic/pharmacodynamic properties. Also, there is a need to provide more potent KRas inhibitors that exhibit increased efficacy with reduced or minimized untoward or undesired effects. Further, there is a need to provide more potent KRas inhibitors that exhibit selective inhibition preference for KRas G12C, G12D, and/or G12V mutants over HRAS or NRAS. The present invention addresses one or more of these needs by providing novel KRas inhibitors.

SUMMARY

Compounds of Formula I are provided herein:

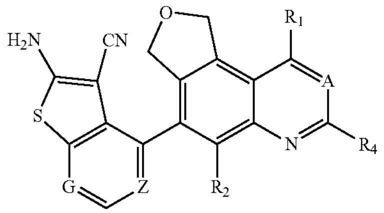

wherein:

A is —C(H)—, or —N—;

Z is —C($R_{3c}$)— or —N—;

G is —C($R_{3b}$)— or —N—;

$R_1$ is a group of the formula

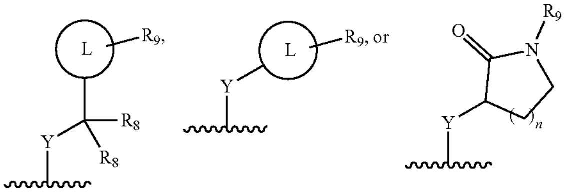

wherein n is 0, 1, or 2;

Y is either —N($R_8$)—, or —O—;

L is a 5-6 membered heteroaryl containing 1 to 3 heteroatoms selected from O, N, or S, wherein the 5-6 membered heteroaryl may be optionally fused with a $C_{3-6}$ cycloalkyl ring to form a bicyclic ring structure;

$R_2$ is H, halogen, or methyl;

$R_{3b}$, and $R_{3c}$ are each independently H, halogen, or methyl;

$R_4$ is H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —CH($CH_3$)—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; or $R_4$ is a N-linked cyclic amine or a group of the formula

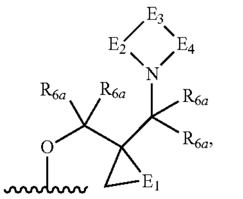

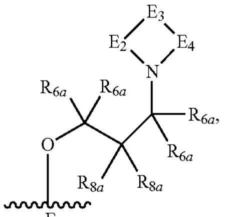

or

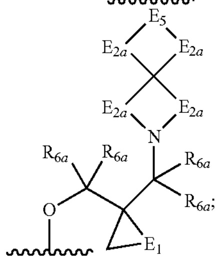

wherein the N-linked cyclic amine is a N-linked:

i. azetidine substituted with $R_{4a}$ and $R_{4b}$;

ii. pyrrolidine, piperidine, piperazine, morpholine, diazepane, imidazole or pyrazole; each of which is optionally bridged by a $C_{1-3}$ alkylene, and each of which is optionally substituted with one or more halogen; hydroxyl; —$NR_{6a}R_{6a}$; (1-methylpiperidin-4-yl)oxy; $C_{1-3}$ alkoxy optionally substituted with —$NR_{6a}R_{6a}$; $C_{1-3}$ alkyl optionally substituted with one or more halogen, —$NR_{6a}R_{6a}$ or hydroxyl; an imidazole optionally substituted with a methyl; a monocyclic ring selected from azetidine, piperidine, piperazine, morpholine, oxazepane, or diazepane; a bicycle selected from hexahydro-1H-furo[3,4-c]pyrrole, octahydropyrrolo[3,4-c]pyrrole, or octahydropyrrolo[1,2-a]pyrazine; or a spirocycle selected from 4,7-diazaspiro[2.5]octane, 2-oxa-7-azaspiro[3.5]nonane, 2,6-diazaspiro[3.4]octane, or 2-azaspiro[3.3]heptane; wherein the monocyclic ring is optionally bridged by a $C_{1-3}$ alkylene, and can optionally be substituted with one or more halogen, hydroxyl, —CN, $C_{1-3}$ alkoxy, —$NR_{10}R_{10}$, cyclopropyl, oxetane, —CO—$C_{1-3}$ alkyl, or a $C_{1-3}$ alkyl optionally substituted with hydroxyl, $C_{1-3}$ alkoxy, —$NR_{10}R_{10}$, halogen, or —$CF_3$; and wherein the bicyclo or spirocyclo is each optionally substituted with a methyl or a halogen; or iii. 2,6-diazabicyclo[3.2.0]heptane, 3,6-diazabicyclo[3.2.0]heptane, 3,6-diazabicyclo[3.2.1]octane, 2,6-diazabicyclo[3.2.1]octane, 3-azabicyclo[3.1.0]hexane, 3-azabicyclo[3.2.0]heptane, 2-azabicyclo[3.2.0]heptane, octahydro-1H-pyrrolo[3,4-b]pyridine, octahydro-1H-pyrrolo[3,2-b]pyridine, octahydro-6H-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, hexahydro-1H-furo[3,4-b]pyrrole, octahydro-1H-pyrrolo[3,2-b]pyridine, (3as,6as)-tetrahydro-1H,4H-3a,6a-(methanooxymethano)pyrrolo[3,4-c]pyrrole, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, 5-azaspiro[2.4]heptane, 2-oxa-6-azaspiro[3.4]octane, 2,7-diazaspiro[4.4]nonane, 2-oxa-6-azaspiro[3.4]octane or 1-oxa-7-azaspiro[4.4]nonane; each of which is optionally substituted with one or more halogen, —$NR_{6a}R_{6a}$ or a $C_{1-3}$ alkyl optionally substituted with —$NR_{6a}R_{6a}$ or hydroxyl;

$R_{4a}$ is $NR_{4c}R_{4d}$, cyclopropyl, azetidine, pyrrolidine, piperidine, piperazine, morpholine or imidazole, wherein the cyclopropyl, azetidine, pyrrolidine, piperidine, piperazine, or morpholine is optionally substituted with halogen, hydroxyl, $C_{1-3}$ alkoxy or —$NR_{6a}R_{6a}$;

$R_{4b}$ is H, hydroxyl, or $C_{1-3}$ alkyl;

$R_{4c}$ is independently cyclopropyl, or oxetane;

$R_{4d}$ is independently $C_{1-3}$ alkyl;

each $R_{6a}$ is independently H or deuterium;

each $R_{6b}$ is independently H, trideuteromethyl, a $C_{3-5}$ cycloalkyl, a N-methyl pyrrolidine, tetrahydrofuran, tetrahydropyran, bicyclo[1.1.1]pentan-1-yl, bicyclo[1.1.1]pentan-1-ol, or a $C_{1-3}$ alkyl optionally substituted with one or more deuterium, hydroxyl, methyl, methoxy, halogen, cyclopropyl, oxetane, tetrahydrofuran, tetrahydropyran, —CO—NHMe, or —CO—$NH_2$, wherein the $C_{3-5}$ cycloalkyl is optionally substituted with one or more hydroxyl or methyl;

$E_1$ is —O—$C_{1-3}$ alkylene, or $C_{1-3}$ alkylene optionally substituted with one or more halogens;

$E_2$, and $E_4$ are each independently $C_{1-3}$ alkylene optionally substituted with one or more hydroxyl, $C_{1-3}$ alkoxy, or halogen, and wherein $E_2$ and $E_4$ can optionally be bridged by a bond or a $C_{1-3}$ alkylene; and $E_3$ is —O—, —$CR_{7a}R_{7a}$—, —$NR_{9a}$—, or —CO—$NR_{6b}$—; or the ring

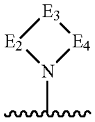

is hexahydro-1H-furo[3,4-c]pyrrole;

Each $E_{2a}$ is independently a $C_{1-3}$ alkylene optionally substituted with one or more hydroxyls;

$E_5$ is —O—, —$CR_{7a}R_{7a}$—, or —$NR_{9a}$—;

each $R_7$ is independently H, or $C_{1-3}$ alkyl;

each $R_{7a}$ is independently H, halogen, CN, hydroxyl, $C_{1-3}$ alkoxy, or $C_{1-3}$ alkyl optionally substituted with one or more halogens or hydroxyls;

each $R_8$ is each independently H or $C_{1-3}$ alkyl; and each $R_{8a}$ is independently a $C_{1-3}$ alkyl;

$R_9$ is a H, —CO—$C_{1-3}$ alkyl, —CO—$NR_8R_8$, —$NR_{9a}R_{9a}$, $C_{1-4}$ alkyl, or $C_{3-6}$ cycloalkyl, wherein the $C_{1-4}$ alkyl or $C_{3-6}$ cycloalkyl is optionally substituted with one or more halogen;

$R_{9a}$ is each independently H, optionally substituted $C_{1-3}$ alkyl or —CO—$C_{1-3}$ alkyl; wherein the optionally substituted $C_{1-3}$ alkyl is optionally substituted with one or more halogens; and $R_{10}$ is H or $C_{1-3}$ alkyl optionally substituted with one or more deuterium; or a pharmaceutically acceptable salt thereof.

Also provided herein are methods of using the compounds of Formula I, pharmaceutically acceptable salts thereof, and pharmaceutical compositions thereof, to treat cancer, in particular for the treatment of lung cancer, pancreatic cancer, cervical cancer, esophageal cancer, endometrial cancer, ovarian cancer, cholangiocarcinoma, and colorectal cancer. The methods include administering a therapeutically effective amount of a compound of Formula I, or a pharmaceutically acceptable salt thereof, to a patient in need thereof.

Further provided herein, are compounds of Formula I, and pharmaceutically acceptable salts thereof, for use in therapy. Additionally provided herein, are the compounds of Formula I, and pharmaceutically acceptable salts thereof, for use in the treatment of cancer, in particular for the treatment of lung cancer, pancreatic cancer, cervical cancer, esophageal cancer, endometrial cancer, ovarian cancer, cholangiocarcinoma, and colorectal cancer. Also additionally provided herein is the use of compounds of Formula I, or pharmaceutically acceptable salts thereof, in the manufacture of a medicament for treating cancer, in particular for the treatment of lung cancer, pancreatic cancer, cervical cancer, esophageal cancer, endometrial cancer, ovarian cancer, cholangiocarcinoma, and colorectal cancer.

DETAILED DESCRIPTION

Novel inhibitors of the KRas gain of function mutation G12C, G12D, and/or G12V are described herein. These new compounds could address the needs noted above for inhibitors of KRas GTP activity in gain of function mutants in the treatment of cancers such as lung cancer, colorectal cancer, pancreatic cancer, bladder cancer, cervical cancer, endometrial cancer, ovarian cancer, cholangiocarcinoma or esophageal cancer. The present invention provides a compound of Formula I:

Formula I

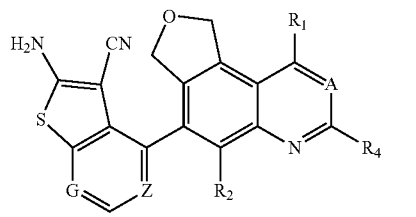

wherein A, Z, G, R1, R2, and R4 are as defined above, or a pharmaceutically acceptable salt thereof.

As used herein, the term halogen means fluoro (F), chloro (Cl), bromo (Br), or iodo (I). As used herein, the term alkyl means saturated linear or branched-chain monovalent hydrocarbon radicals of one to a specified number of carbon atoms, e.g., "$C_{1-4}$ alkyl" or "$C_{1-3}$ alkyl." Examples of alkyls include, but are not limited to, methyl, ethyl, propyl, 1-propyl, isopropyl, butyl, and iso-butyl. As used herein, the term cycloalkyl means saturated cyclic monovalent hydrocarbon radicals containing a specified number of carbon atoms, e.g., "$C_{4-6}$ cycloalkyl." Examples of cycloalkyls include, but are not limited to cyclopropyl, cyclobutyl, cyclopentyl, cyclohexyl, and cylcoheptyl. As used herein, the term heteroalkyl means saturated linear or branched-chain monovalent hydrocarbon radicals containing a specified number of atoms including both carbon atoms and one or more heteroatoms, e.g., "$C_{2-3}$ heteroalkyl" and "$C_{2-4}$ heteroalkyl." For example, $C_4$ heteroalkyl means a saturated linear or branched-chain monovalent hydrocarbon radical containing at least one carbon atoms and at least one heteroatom, wherein the total number of carbon and heteroatoms adds up to 4 atoms. As used herein, the term heterocycloalkyl means saturated cyclic heteroalkyl groups containing a specified number of atoms including both carbon atoms and one or more heteroatoms, e.g., "$C_{4-6}$ heterocycloalkyl." Examples of heterocycloalkyls include but are not limited to, dioxane, tetrahydrofuran, piperidine, piperazine, azetadine, and pyrrolidine. As used herein, the terms heteroaryl, used alone or as part of a larger moiety, e.g., heteroaralkyl, or heteroaralkoxy, refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom' refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl pyrazolyl, triazolyl, tetrazolyl, oxazolyl, isoxazolyl, oxadiazolyl, thiazolyl, isothiazolyl, thiadiazolyl pyridyl, pyridazinyl, pyrimidinyl, pyrazinyl, indolizinyl, purinyl, naphthyridinyl, and pteridinyl. The term heteroaryl as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenox azinyl, tetrahydroquinolinyl, tetrahydroisoquinolinyl, and pyrido 2,3-b-1,4-oxazin-3 (4H)-one. A heteroaryl group may be mono- or bicyclic. The term heteroaryl may be used interchangeably with the terms heteroaryl ring, heteroaryl group, or heteroaromatic, any of which terms include rings that are optionally substituted. The term heteroaralkyl refers to an alkyl group substituted by a heteroaryl, wherein the alkyl and heteroaryl portions independently are optionally substituted.

As used herein, the term "partially unsaturated refers to a ring moiety that includes at least one double or triple bond. The term "partially unsaturated is intended to encompass rings having multiple sites of unsaturation but is not intended to include aryl or heteroaryl moieties, as herein defined.

In an embodiment of a compound of Formula I or a pharmaceutically acceptable salt thereof, $R_4$ is H, methyl, $—CH_2—OH$, $—O—R_5—R_6$, $—O—R_6$, N-linked cyclic amine, or azetidine optionally substituted with $NR_7R_7$, wherein $R_5$ is $—CH_2—$, $—CH(CH_3)—$, or $—CH_2—CH_2—$, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; or $R_4$ is a N-linked cyclic amine or a group of the formula

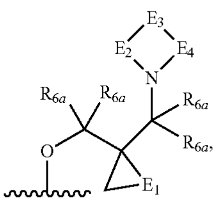

,

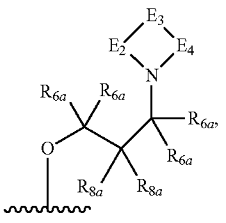

, or

-continued

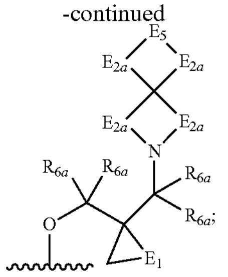

wherein the N-linked cyclic amine is a N-linked:

i. azetidine substituted with $R_{4a}$ and $R_{4b}$ ii. pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, a $C_{1-3}$ alkyl, or an imidazole optionally substituted with a methyl; wherein the azetidine is optionally substituted with hydroxyl or $C_{1-3}$ alkoxy; and the $C_{1-3}$ alkyl is optionally substituted with halogen-$NR_{6a}R_{6a}$ or hydroxyl; or iii. 2,6-diazabicyclo[3.2.0]heptane, 3,6-diazabicyclo[3.2.0]heptane, 3-azabicyclo[3.1.0]hexane, 3-azabicyclo[3.2.0]heptane, octahydro-1H-pyrrolo[3,4-b]pyridine, octahydro-6-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, or 5-azaspiro[2.4]heptane; each of which is optionally substituted with one or more halogen, —$NR_{6a}R_{6a}$ or a $C_{1-3}$ alkyl optionally substituted with —$NR_{6a}R_{6a}$;

$R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$ each $R_{6b}$ is independently H, trideuteromethyl, a $C_{3-5}$ cycloalkyl, or a $C_{1-3}$ alkyl optionally substituted with hydroxyl; and $R_9$ is a H, —CO—$C_{1-3}$ alkyl, —$NR_{9a}R_{9a}$, $C_{1-4}$ alkyl, or $C_{3-6}$ cycloalkyl, wherein the $C_{1-4}$ alkyl or $C_{3-6}$ cycloalkyl is optionally substituted with one or more halogen.

In an embodiment of a compound of Formula I or a pharmaceutically acceptable salt thereof, $R_1$ is a group of the formula

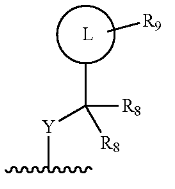 or 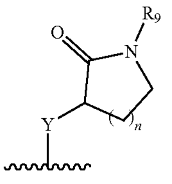

wherein n is 0, 1, or 2;

Y is either —$N(R_8)$—, or —O—;

L is a 5-6 membered heteroaryl containing 1 to 3 heteroatoms selected from O, N, or S, wherein the 5-6 membered heteroaryl may be optionally fused with a $C_{3-6}$ cycloalkyl ring to form a bicyclic ring structure;

$R_2$ is H, halogen, or methyl;

$R_4$ is H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; and $R_9$ is a H, $C_{1-4}$ alkyl, or $C_{3-6}$ cycloalkyl, or a pharmaceutically acceptable salt thereof wherein the $C_{1-4}$ alkyl or $C_{3-6}$ cycloalkyl is optionally substituted with one or more halogen.

In an embodiment of a compound of Formula I or a pharmaceutically acceptable salt thereof, $R_1$ is a group of the formula

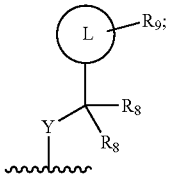

L is a 5-membered heteroaryl containing 1 to three heteroatoms selected from O, N, or S, wherein the 5-membered heteroaryl may be optionally fused with a $C_{3-6}$ cycloalkyl ring to form a bicyclic ring structure;

$R_4$ is H, methyl, —$CH_2$—OH, —O—$R_5$—$R_6$, —O—$R_6$, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; and $R_9$ is a H, $C_{1-4}$ alkyl, or $C_{3-6}$ cycloalkyl, or a pharmaceutically acceptable salt thereof;

In an embodiment of a compound of Formula I or a pharmaceutically acceptable salt thereof, G is —N—.

In an embodiment of a compound of Formula I or a pharmaceutically acceptable salt thereof, G is —$C(R_{3b})$—.

In an embodiment of a compound of Formula I or a pharmaceutically acceptable salt thereof, G is —$C(R_{3b})$—, wherein $R_{3b}$ is H or halogen.

In an embodiment of a compound of Formula I or a pharmaceutically acceptable salt thereof, G is —C(F)—.

In an embodiment of a compound of Formula I or a pharmaceutically acceptable salt thereof, G is —C(H)—.

In an embodiment of a compound of Formula I or a pharmaceutically acceptable salt thereof, G is —C($CH_3$)—.

In an embodiment of a compound of Formula I or a pharmaceutically acceptable salt thereof, Z is —N—.

In an embodiment of a compound of Formula I or a pharmaceutically acceptable salt thereof, Z is —C($R_{3c}$)—.

In an embodiment of a compound of Formula I or a pharmaceutically acceptable salt thereof, Z is —C($R_{3c}$)—, wherein $R_{3c}$ is H or halogen.

In an embodiment of a compound of Formula I or a pharmaceutically acceptable salt thereof, Z is —C(H)—.

In an embodiment of a compound of Formula I or a pharmaceutically acceptable salt thereof, Z is —C(F)—.

In an embodiment of a compound of Formula I or a pharmaceutically acceptable salt thereof, G is —N—, and Z is —C($R_{3c}$)—.

In an embodiment of a compound of Formula I or a pharmaceutically acceptable salt thereof, G is —N—, and Z is —C(H)—.

In an embodiment of a compound of Formula I or a pharmaceutically acceptable salt thereof, G is —N—, and Z is —C(F)—.

In an embodiment of a compound of Formula I or a pharmaceutically acceptable salt thereof, G is —C($R_{3b}$)—, and Z is —N—.

In an embodiment of a compound of Formula I or a pharmaceutically acceptable salt thereof, G is —C($R_{3b}$)—, wherein $R_{3b}$ is H or halogen, and Z is —N—.

In an embodiment of a compound of Formula I or a pharmaceutically acceptable salt thereof, G is —C(F)—, and Z is —N—.

In an embodiment of a compound of Formula I or a pharmaceutically acceptable salt thereof, G is —C(H)—, and Z is —N—.

In an embodiment of a compound of Formula I or a pharmaceutically acceptable salt thereof, G is —C($CH_3$)—, and Z is —N—.

In an embodiment of a compound of Formula I or a pharmaceutically acceptable salt thereof, $R_{3b}$, and $R_{3c}$ are each independently H or halogen.

In an embodiment of a compound of Formula I or a pharmaceutically acceptable salt thereof, A is —N—.

In an embodiment of a compound of Formula I or a pharmaceutically acceptable salt thereof, A is —C(H)—.

In an embodiment of a compound of Formula I or a pharmaceutically acceptable salt thereof, $R_2$ is F or Cl.

In an embodiment of a compound of Formula I, or a pharmaceutically acceptable salt thereof, A is —C(H)—, Z is —C(F)—, G is —N—, and $R_2$ is F.

In an embodiment of a compound of Formula I, or a pharmaceutically acceptable salt thereof, A is —N—, Z is —C(F)—, G is —N—, and $R_2$ is F.

In an embodiment of a compound of Formula I, or a pharmaceutically acceptable salt thereof, A is —C(H)—, Z is —C(H)—, G is —N—, and $R_2$ is F.

In an embodiment of a compound of Formula I, or a pharmaceutically acceptable salt thereof, A is —N—, Z is —C(H)—, G is —N—, and $R_2$ is F.

In an embodiment of a compound of Formula I, or a pharmaceutically acceptable salt thereof, A is —C(H)—, Z is —N—, G is —N—, and $R_2$ is F.

In an embodiment of a compound of Formula I, or a pharmaceutically acceptable salt thereof, A is —N—, Z is —N—, G is —N—, and $R_2$ is F.

In an embodiment of a compound of Formula I, or a pharmaceutically acceptable salt thereof, A is —C(H)—, Z is —C(F)—, G is —C(H)—, and $R_2$ is F.

In an embodiment of a compound of Formula I, or a pharmaceutically acceptable salt thereof, A is —N—, Z is —C(F)—, G is —C(H)—, and $R_2$ is F.

In an embodiment of a compound of Formula I, or a pharmaceutically acceptable salt thereof, A is —C(H)—, Z is —C(H)—, G is —C(H)—, and $R_2$ is F.

In an embodiment of a compound of Formula I, or a pharmaceutically acceptable salt thereof, A is —N—, Z is —C(H)—, G is —C(H)—, and $R_2$ is F.

In an embodiment of a compound of Formula I, or a pharmaceutically acceptable salt thereof, A is —C(H)—, Z is —N—, G is —C(H)—, and $R_2$ is F.

In an embodiment of a compound of Formula I, or a pharmaceutically acceptable salt thereof, A is —N—, Z is —N—, G is —C(H)—, and $R_2$ is F.

In an embodiment of a compound of Formula I, or a pharmaceutically acceptable salt thereof, A is —C(H)—, Z is —C(F)—, G is —C(F)—, and $R_2$ is F.

In an embodiment of a compound of Formula I, or a pharmaceutically acceptable salt thereof, A is —N—, Z is —C(F)—, G is —C(F)—, and $R_2$ is F.

In an embodiment of a compound of Formula I, or a pharmaceutically acceptable salt thereof, A is —C(H)—, Z is —C(H)—, G is —C(F)—, and $R_2$ is F.

In an embodiment of a compound of Formula I, or a pharmaceutically acceptable salt thereof, A is —N—, Z is —C(H)—, G is —C(F)—, and $R_2$ is F.

In an embodiment of a compound of Formula I, or a pharmaceutically acceptable salt thereof, A is —C(H)—, Z is —N—, G is —C(F)—, and $R_2$ is F.

In an embodiment of a compound of Formula I, or a pharmaceutically acceptable salt thereof, A is —N—, Z is —N—, G is —C(F)—, and $R_2$ is F.

In an embodiment of a compound of Formula I, or a pharmaceutically acceptable salt thereof, A is —C(H)—, Z is —C(F)—, G is —N—, and $R_2$ is Cl.

In an embodiment of a compound of Formula I, or a pharmaceutically acceptable salt thereof, A is —N—, Z is —C(F)—, G is —N—, and $R_2$ is Cl.

In an embodiment of a compound of Formula I, or a pharmaceutically acceptable salt thereof, A is —C(H)—, Z is —C(H)—, G is —N—, and $R_2$ is Cl.

In an embodiment of a compound of Formula I, or a pharmaceutically acceptable salt thereof, A is —N—, Z is —C(H)—, G is —N—, and $R_2$ is Cl.

In an embodiment of a compound of Formula I, or a pharmaceutically acceptable salt thereof, A is —C(H)—, Z is —N—, G is —N—, and $R_2$ is Cl.

In an embodiment of a compound of Formula I, or a pharmaceutically acceptable salt thereof, A is —N—, Z is —N—, G is —N—, and $R_2$ is Cl.

In an embodiment of a compound of Formula I, or a pharmaceutically acceptable salt thereof, A is —C(H)—, Z is —C(F)—, G is —C(H)—, and $R_2$ is Cl.

In an embodiment of a compound of Formula I, or a pharmaceutically acceptable salt thereof, A is —N—, Z is —C(F)—, G is —C(H)—, and $R_2$ is Cl.

In an embodiment of a compound of Formula I, or a pharmaceutically acceptable salt thereof, A is —C(H)—, Z is —C(H)—, G is —C(H)—, and $R_2$ is Cl.

In an embodiment of a compound of Formula I, or a pharmaceutically acceptable salt thereof, A is —N—, Z is —C(H)—, G is —C(H)—, and $R_2$ is Cl.

In an embodiment of a compound of Formula I, or a pharmaceutically acceptable salt thereof, A is —C(H)—, Z is —N—, G is —C(H)—, and $R_2$ is Cl.

In an embodiment of a compound of Formula I, or a pharmaceutically acceptable salt thereof, A is —N—, Z is —N—, G is —C(H)—, and $R_2$ is Cl.

In an embodiment of a compound of Formula I, or a pharmaceutically acceptable salt thereof, A is —C(H)—, Z is —C(F)—, G is —C(F)—, and $R_2$ is Cl.

In an embodiment of a compound of Formula I, or a pharmaceutically acceptable salt thereof, A is —N—, Z is —C(F)—, G is —C(F)—, and $R_2$ is Cl.

In an embodiment of a compound of Formula I, or a pharmaceutically acceptable salt thereof, A is —C(H)—, Z is —C(H)—, G is —C(F)—, and $R_2$ is Cl.

In an embodiment of a compound of Formula I, or a pharmaceutically acceptable salt thereof, A is —N—, Z is —C(H)—, G is —C(F)—, and $R_2$ is Cl.

In an embodiment of a compound of Formula I, or a pharmaceutically acceptable salt thereof, A is —C(H)—, Z is —N—, G is —C(F)—, and $R_2$ is Cl.

In an embodiment of a compound of Formula I, or a pharmaceutically acceptable salt thereof, A is —N—, Z is —N—, G is —C(F)—, and $R_2$ is Cl.

In an embodiment of a compound of Formula I or a pharmaceutically acceptable salt thereof, $R_9$ is a H, —CO—$C_{1-3}$ alkyl, —$NR_{9a}R_{9a}$, $C_{1-4}$ alkyl, or $C_{3-6}$ cycloalkyl.

In an embodiment of a compound of Formula I or a pharmaceutically acceptable salt thereof, $R_9$ is a H, $C_{1-4}$ alkyl, or $C_{3-6}$ cycloalkyl.

In an embodiment of a compound of any of Formula I or a pharmaceutically acceptable salt thereof, Y is —$N(R_8)$—.

In an embodiment of a compound of any of Formula I or a pharmaceutically acceptable salt thereof, Y is —O—.

In an embodiment of a compound of Formula I or a pharmaceutically acceptable salt thereof, L is a 5-membered heteroaryl optionally fused with a cyclohexyl ring to form a bicyclic ring.

In an embodiment of a compound of Formula I or a pharmaceutically acceptable salt thereof, L is a 5-membered heteroaryl optionally fused with a cyclohexyl ring to form a bicyclic ring, wherein the 5-membered heteroaryl is selected from oxazole, isothiazole, thiazole, thiadiazole, imidazole, oxadiazole, triazole, isoxazole, or pyrazole.

In an embodiment of a compound of Formula I or a pharmaceutically acceptable salt thereof, L is selected from oxazole, isothiazole, thiazole, thiadiazole, imidazole, oxadiazole, triazole, isoxazole, pyrazole, 4,5,6,7-tetrahydro-1,2-benzoxazole or 4,5,6,7-tetrahydro-1H-indazole.

In an embodiment of a compound of Formula I or a pharmaceutically acceptable salt thereof, L is selected from oxazole, isothiazole, thiazole, thiadiazole, imidazole, oxadiazole, triazole, isoxazole, or pyrazole.

In an embodiment of a compound of Formula I or a pharmaceutically acceptable salt thereof, L is a 5-6 membered heteroaryl containing 1 to 3 heteroatoms selected from O, N, or S, wherein the 5-6 membered heteroaryl may be optionally fused with a $C_{3-6}$ cycloalkyl ring to form a bicyclic ring structure.

In an embodiment of a compound of Formula I or a pharmaceutically acceptable salt thereof, L is a 5-6 membered heteroaryl containing 1 to 3 heteroatoms selected from O, N, or S, wherein the 5-6 membered heteroaryl is selected from oxazole, isothiazole, thiazole, thiadiazole, imidazole, oxadiazole, triazole, isoxazole, pyrazole, pyridine, pyridazine, pyrimidine, pyrazine, or triazine.

In an embodiment of a compound of Formula I or a pharmaceutically acceptable salt thereof, L is selected from oxazole, isothiazole, thiazole, thiadiazole, imidazole, oxadiazole, triazole, isoxazole, pyrazole, 4,5,6,7-tetrahydro-1,2-benzoxazole, 4,5,6,7-tetrahydro-1H-indazole, pyridine, pyridazine, pyrimidine, or pyrazine.

In an embodiment of a compound of Formula I or a pharmaceutically acceptable salt thereof, L is selected from oxazole, isothiazole, thiazole, thiadiazole, imidazole, oxadiazole, triazole, isoxazole, or pyrazole.

In an embodiment of a compound of Formula I or a pharmaceutically acceptable salt thereof, L is selected from pyridine, pyridazine, pyrimidine, or pyrazine.

In an embodiment of a compound of Formula I or a pharmaceutically acceptable salt thereof, $R_1$ is selected from

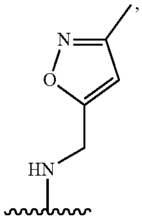 , 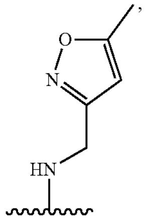 , 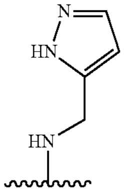 ,

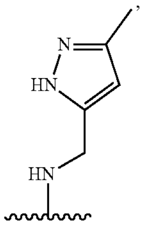 , 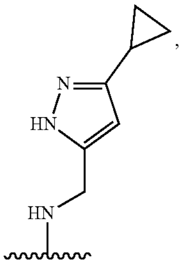 , 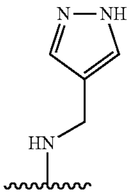 ,

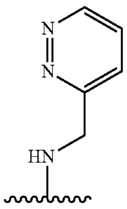 , 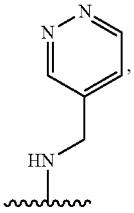 , 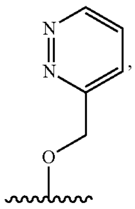 ,

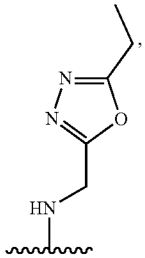 , 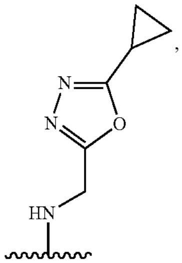 , 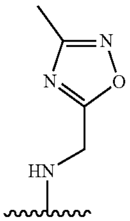 ,

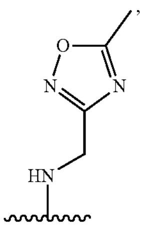 , 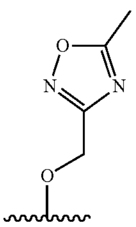 , 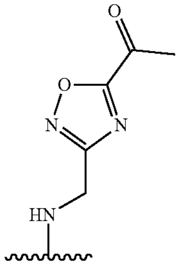 ,

-continued
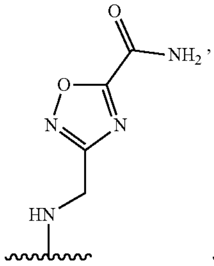, 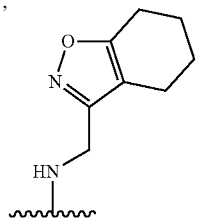,
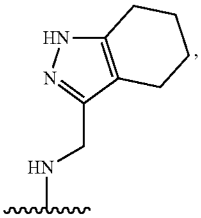, 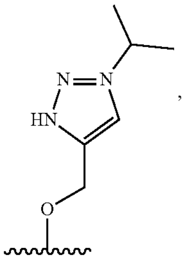,
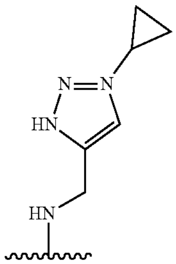, 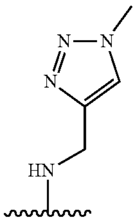,
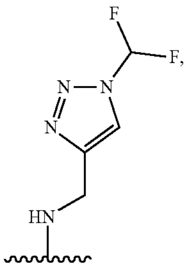 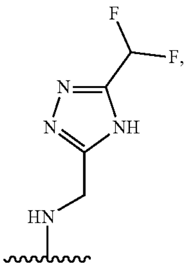
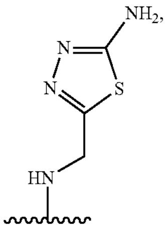 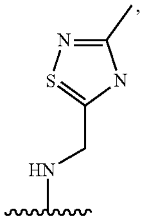,
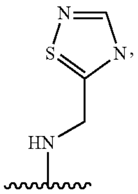 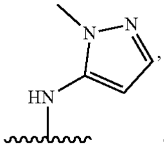, 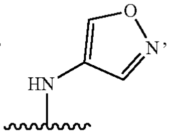
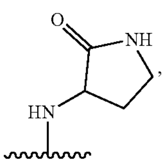, 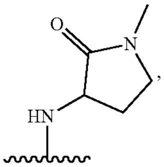,
-continued
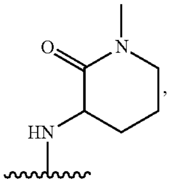, or 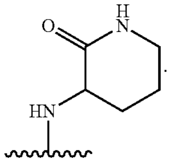.
In an embodiment of a compound of Formula I or a pharmaceutically acceptable salt thereof, $R_1$ is selected from
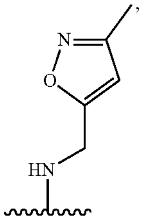, 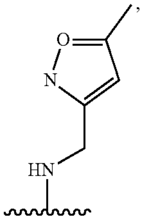, 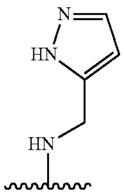,
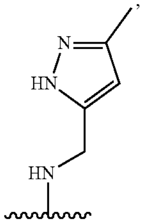, 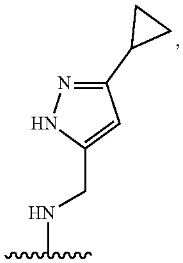, 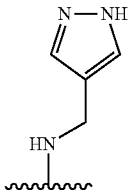,
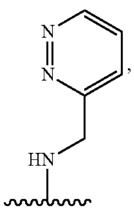, 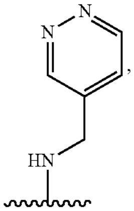, 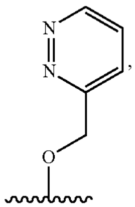,
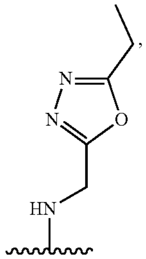, 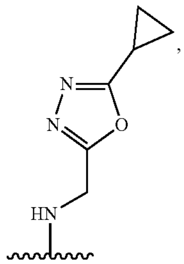, 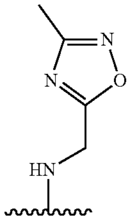,
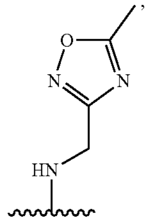, 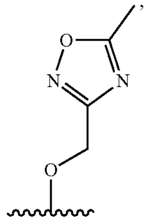, -continued
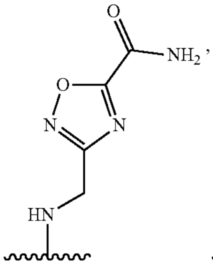
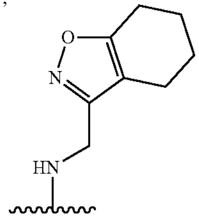
,
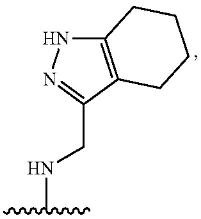
,
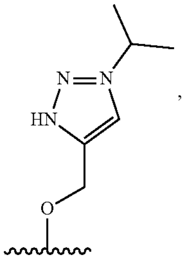
,
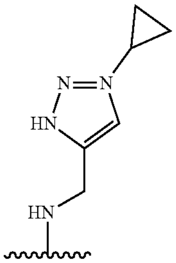
,
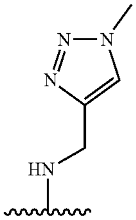
,
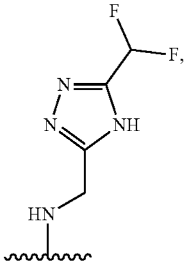
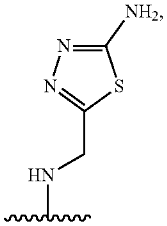
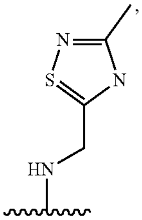
,
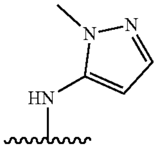
,
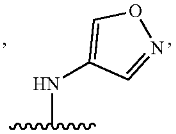
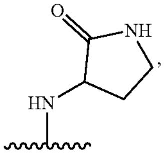
,
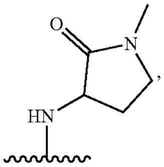
, or
-continued
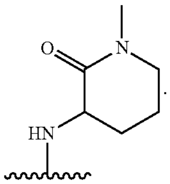
.
In an embodiment of a compound of Formula I or a pharmaceutically acceptable salt thereof, $R_1$ is selected from
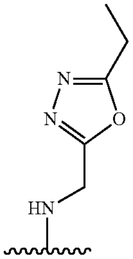
,
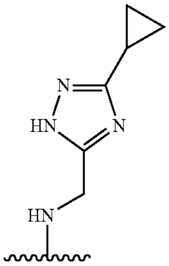
,
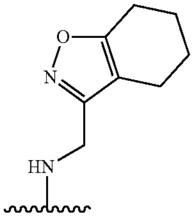
,
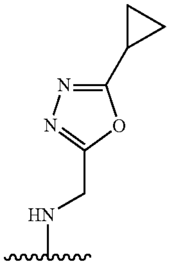
,
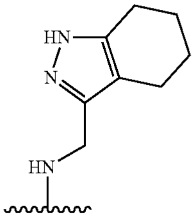
,
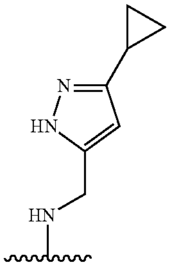
,
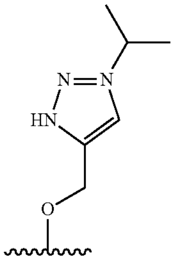
,
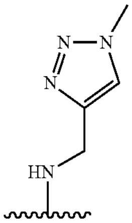
,
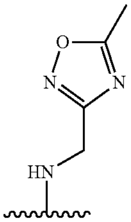
,
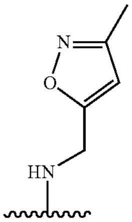
,
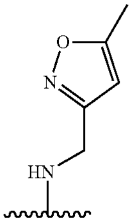
,
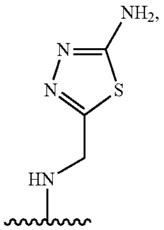
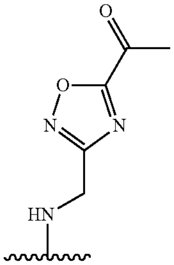
,
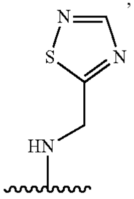
, -continued
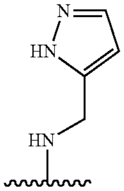,
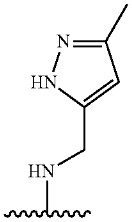,
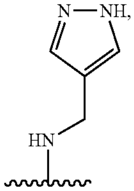
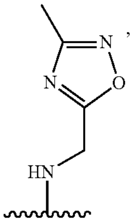,
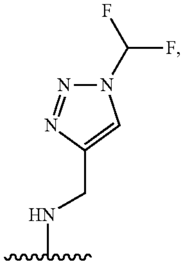
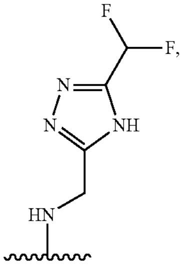
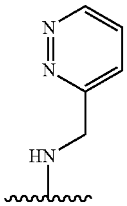,
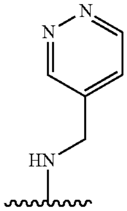,
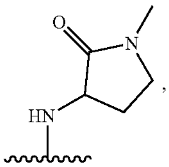,
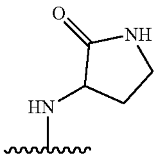,
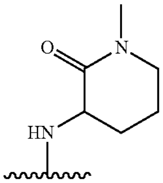,
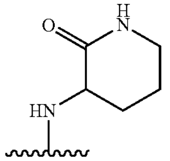, or
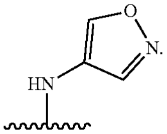 [SMILES: *Nc1cnoc1]
In an embodiment of a compound of Formula I or a pharmaceutically acceptable salt thereof, $R_1$ is selected from
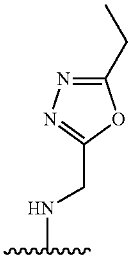,
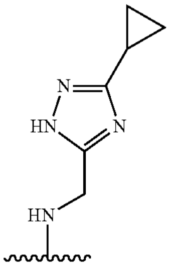,
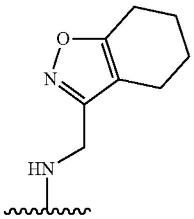,
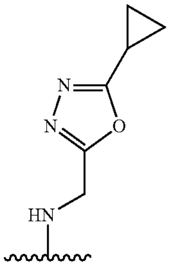,
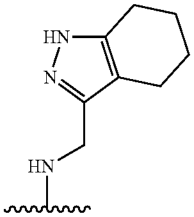,
-continued
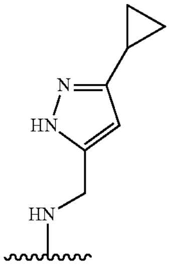,
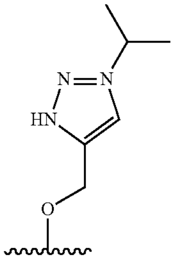,
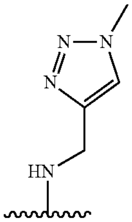,
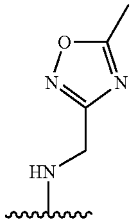,
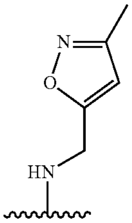,
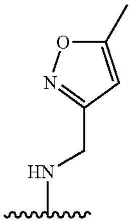,
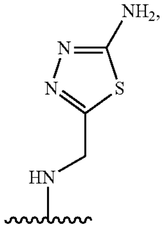
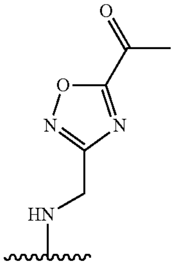,
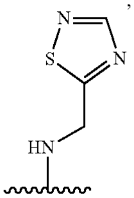,
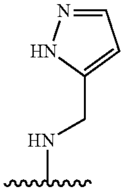,
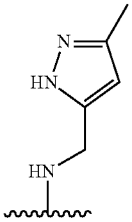,
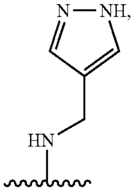
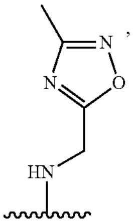,
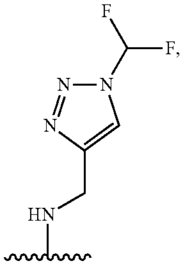
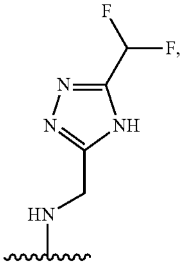
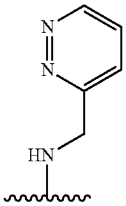, or
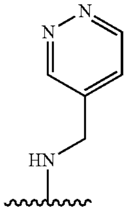.
In an embodiment of a compound of Formula I or a pharmaceutically acceptable salt thereof, $R_1$ is selected from

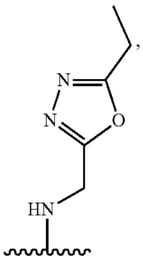,
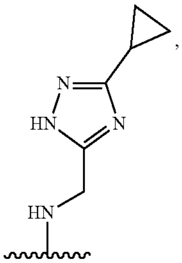,
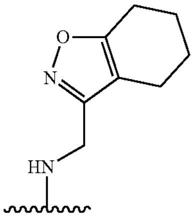,
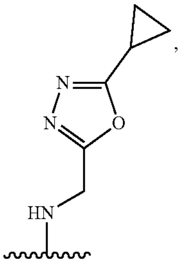,
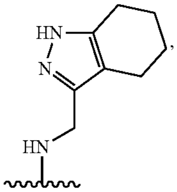,
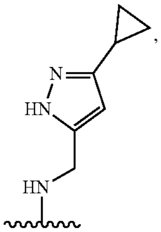,
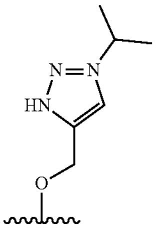,
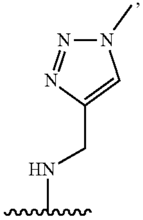,
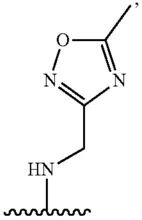,
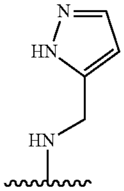,
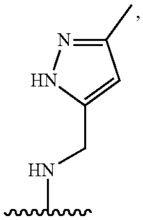,
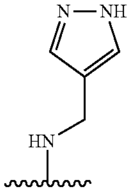,
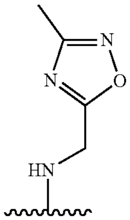,
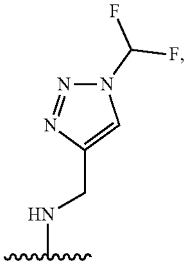, or
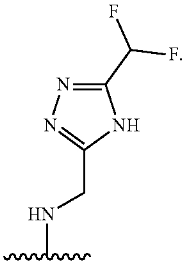.

In an embodiment of a compound of Formula I or a pharmaceutically acceptable salt thereof, $R_1$ is selected from

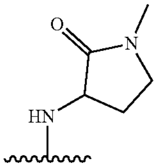,
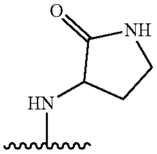,
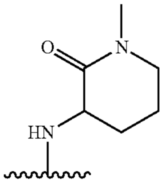, or
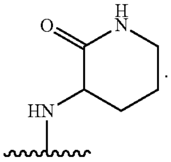.

In an embodiment of a compound of Formula I or a pharmaceutically acceptable salt thereof, $R_1$ is selected from

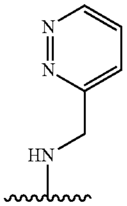 or 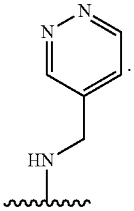.

In an embodiment of a compound of Formula I or a pharmaceutically acceptable salt thereof, $R_1$ is selected from

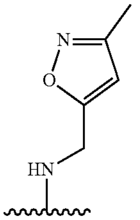,
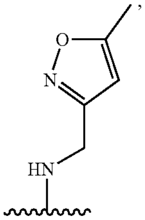,
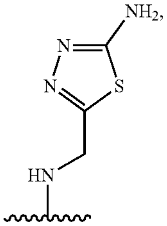,
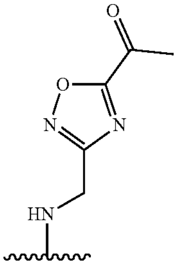, or
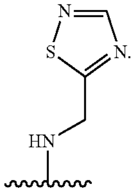.

In an embodiment of a compound of Formula I or a pharmaceutically acceptable salt thereof, $R_1$ is selected from

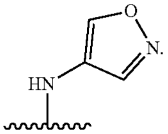.

In an embodiment of a compound of Formula I or a pharmaceutically acceptable salt thereof, $R_4$ is selected from H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl, or a pharmaceutically acceptable salt thereof.

In an embodiment of a compound of Formula I or a pharmaceutically acceptable salt thereof, $R_4$ is a N-linked:

i. azetidine substituted with $R_{4a}$ and $R_{4b}$ ii. pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, a $C_{1-3}$ alkyl, or an imidazole optionally substituted with a methyl; wherein the azetidine is optionally substituted with hydroxyl or $C_{1-3}$ alkoxy; and the $C_{1-3}$ alkyl is optionally substituted with halogen-$NR_{6a}R_{6a}$ or hydroxyl; or iii. 2,6-diazabicyclo[3.2.0]heptane, 3,6-diazabicyclo[3.2.0]heptane, 3-azabicyclo[3.1.0]hexane, 3-azabicyclo[3.2.0]heptane, octahydro-1H-pyrrolo[3,4-b]pyridine, octahydro-6-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, or 5-azaspiro[2.4]heptane; each of which is optionally substituted with one or more halogen, —$NR_{6a}R_{6a}$ or a $C_{1-3}$ alkyl optionally substituted with —$NR_{6a}R_{6a}$.

In an embodiment of a compound of Formula I or a pharmaceutically acceptable salt thereof, $R_4$ is a N-linked cyclic amine selected from a N-linked:

i. azetidine substituted with $R_{4a}$ and $R_{4b}$;

ii. pyrrolidine, piperidine, piperazine, or morpholine; each of which is optionally bridged by a $C_{1-3}$ alkylene, and each of which is optionally substituted with one or more halogen, hydroxyl, —$NR_{6a}R_{6a}$, imidazole or a $C_{1-3}$ alkyl; wherein the imidazole is optionally substituted with a methyl; and the $C_{1-3}$ alkyl is optionally substituted with —$NR_{6a}R_{6a}$ or hydroxyl; or iii. octahydropyrrolo[1,2-a]pyrazine, octahydropyrrolo[3,4-c]pyrrole, 1,6-diazaspiro[3.3]heptane, or 1,6-diazaspiro[3.4]octane; each of which is optionally substituted with one or more halogen, or a $C_{1-3}$ alkyl.

In an embodiment of a compound of Formula I or a pharmaceutically acceptable salt thereof, $R_4$ is a group of the formula

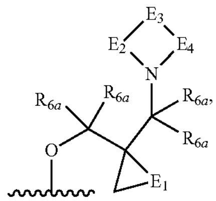

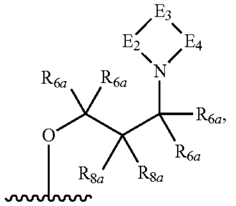

or

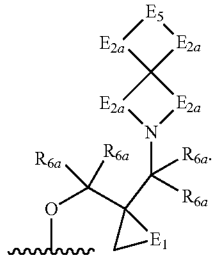

In an embodiment of a compound of Formula I or a pharmaceutically acceptable salt thereof, $R_4$ is a group of the formula

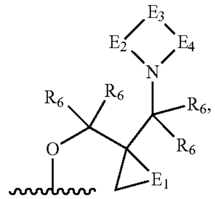

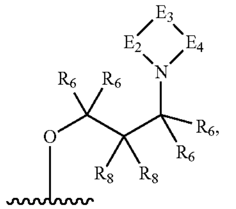

or

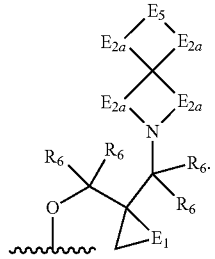

wherein $E_2$, and $E_4$ are each independently $C_{1-3}$ alkylene optionally substituted with one or more hydroxyl or halogen, and wherein $E_2$ and $E_4$ can optionally be bridged by a bond or a $C_{1-3}$ alkylene; and $E_3$ is —O—, —$CR_7R_7$—, —$NR_9$—, or —CO—$NR_{6a}$—; or a pharmaceutically acceptable salt thereof.

In an embodiment of a compound of Formula I or a pharmaceutically acceptable salt thereof, $R_4$ is

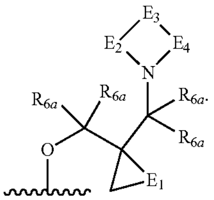
In an embodiment of a compound of Formula I or a pharmaceutically acceptable salt thereof, $R_4$ is selected from methyl, methoxy, $—CH_2—OH$,
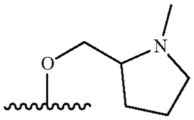,
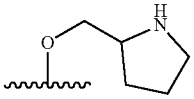,
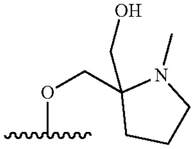,
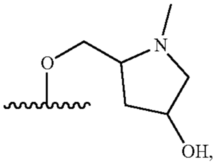,
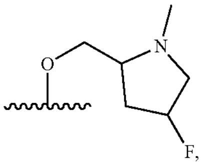,
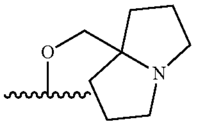,
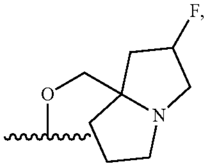,
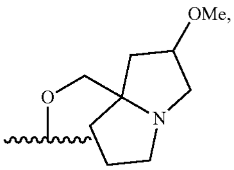,
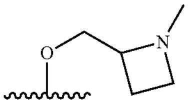,
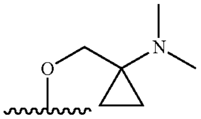,
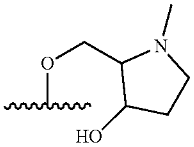,
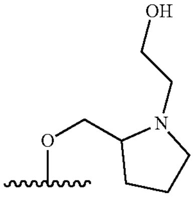,
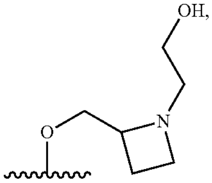,
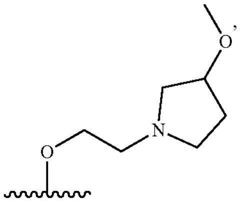,
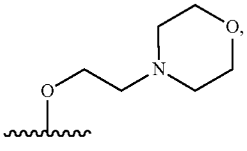,
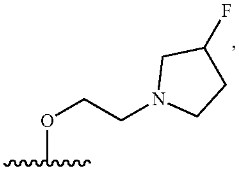,
-continued
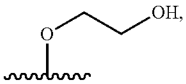,
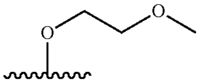,
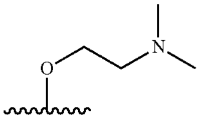,
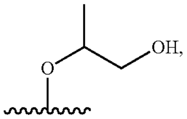,
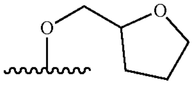,
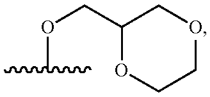,
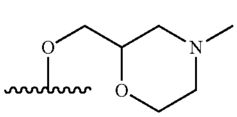,
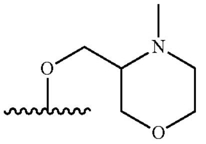,
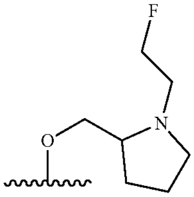,
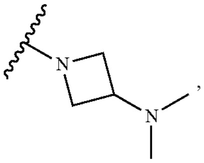,
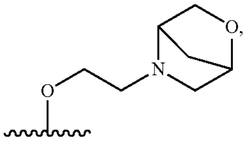,
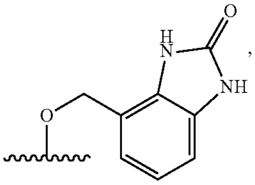,
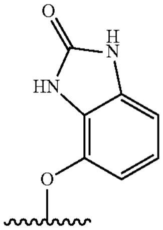,
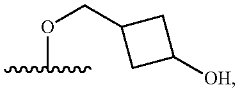,
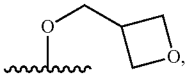,
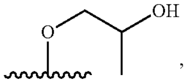,
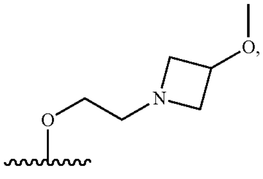,
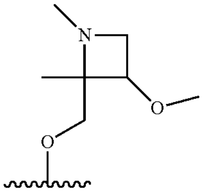,
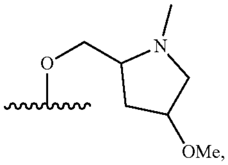,
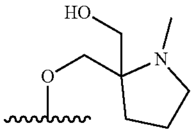,
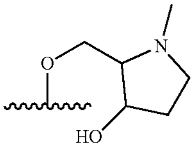,
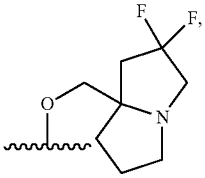

-continued
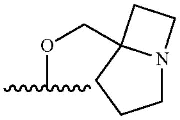
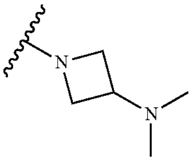
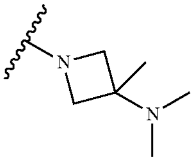
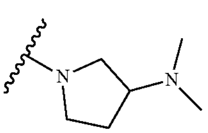
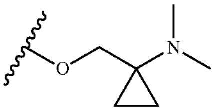
or
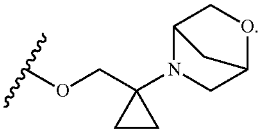
In an embodiment of a compound of Formula I or a pharmaceutically acceptable salt thereof, $R_4$ is selected from methyl, methoxy, —$CH_2$—OH,
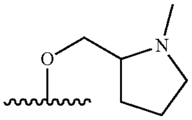
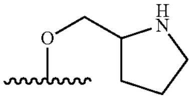
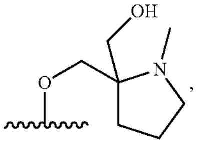
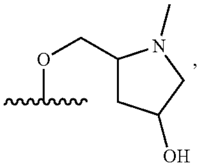
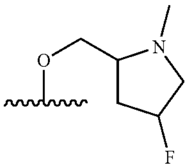
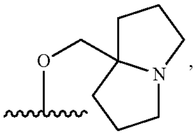
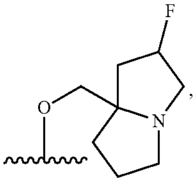
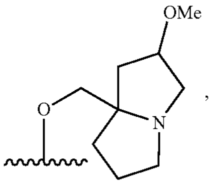
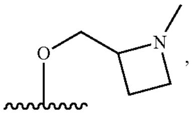
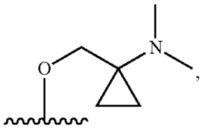
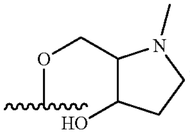
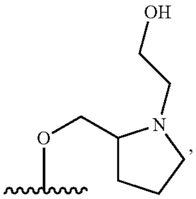
-continued
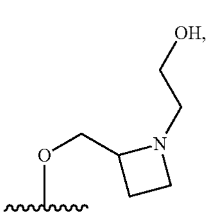
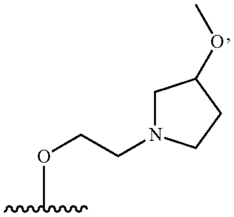
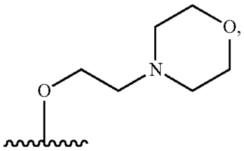
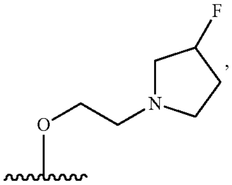
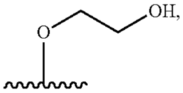
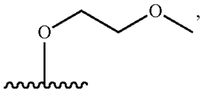
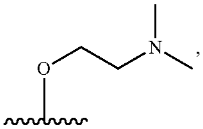
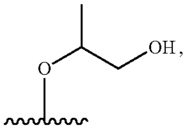
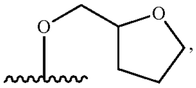
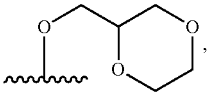
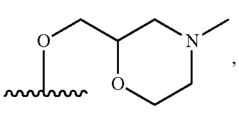
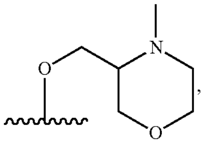
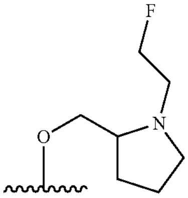
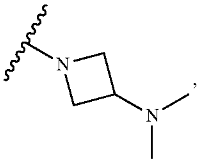
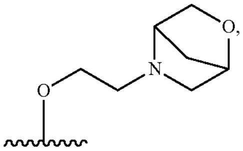
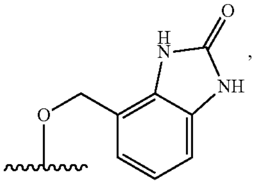
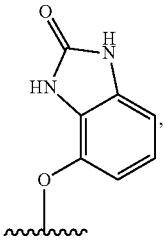
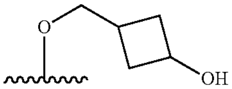
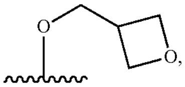
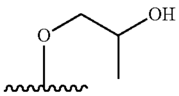
, -continued
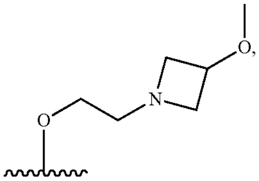 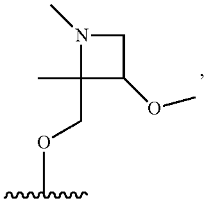,
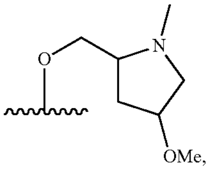 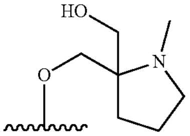,
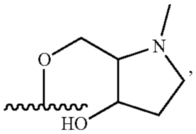, 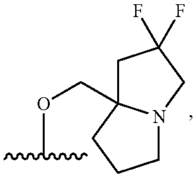,
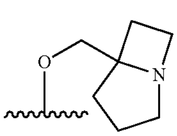, 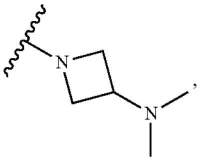,
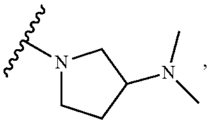, or 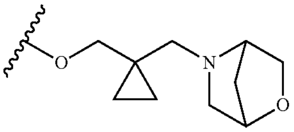,
In an embodiment of a compound of Formula I or a pharmaceutically acceptable salt thereof, $R_4$ is selected from
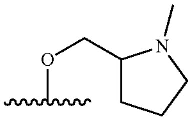, 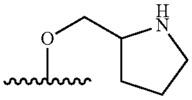,
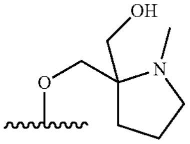, 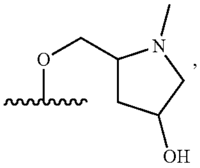,
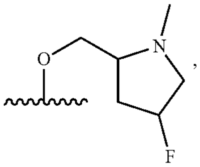, 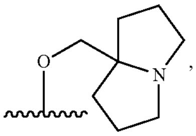,
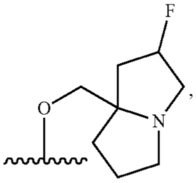, 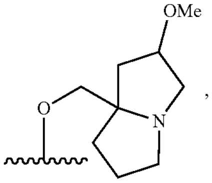,
-continued
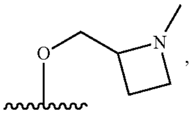, 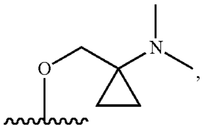,
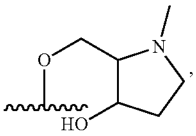, 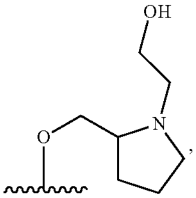,
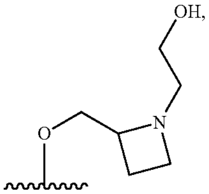 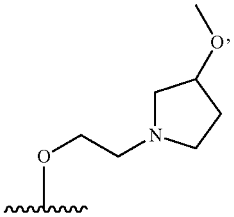
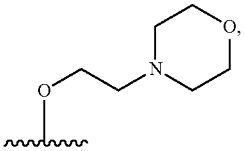 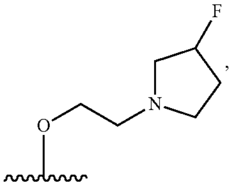,
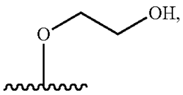 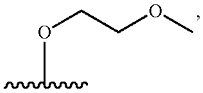,
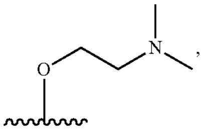, 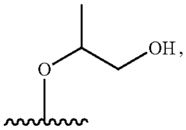
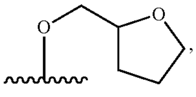, 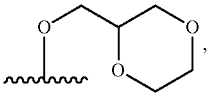,
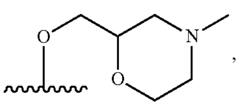, 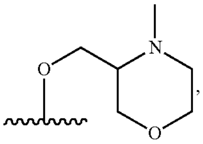,
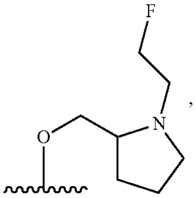, 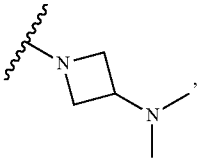,
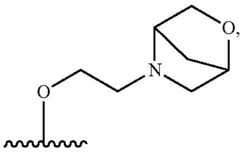 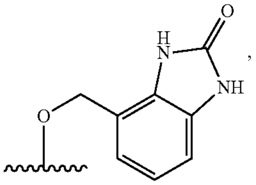, -continued
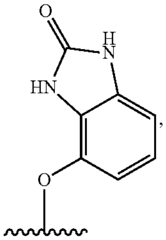,
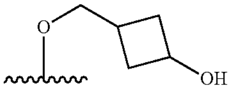,
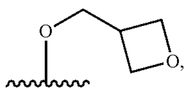,
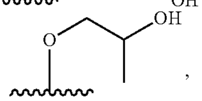,
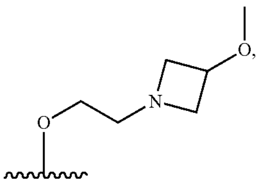,
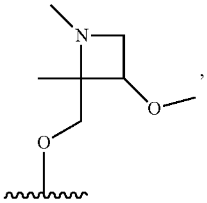,
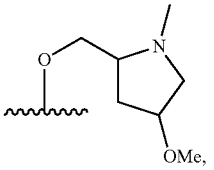,
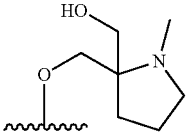,
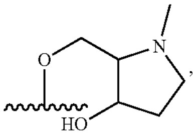,
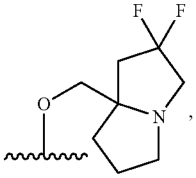, or
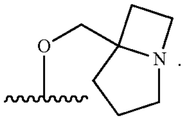.
In an embodiment of a compound of Formula I or a pharmaceutically acceptable salt thereof, $R_4$ is selected from
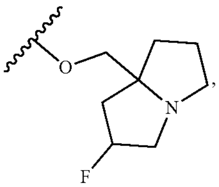,
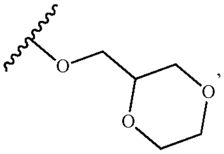,
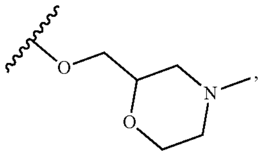,
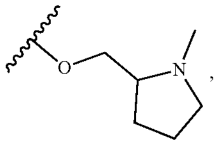,
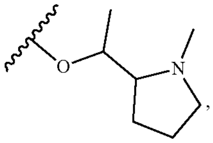,
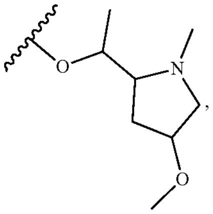,
-continued
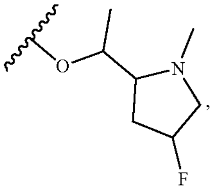,
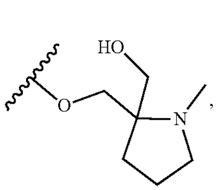,
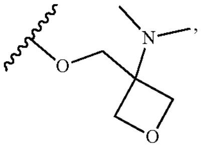,
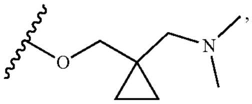,
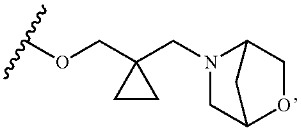,
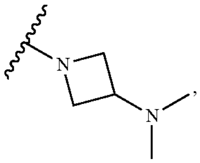,
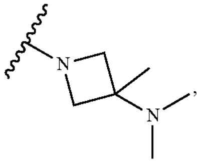,
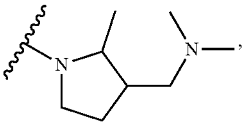,
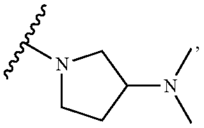,
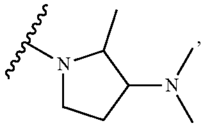,
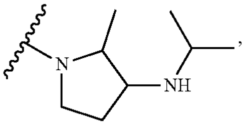,
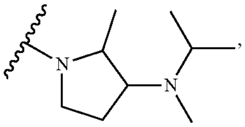,
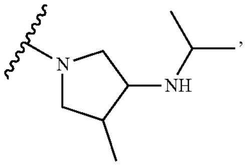,
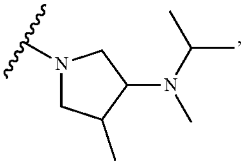,
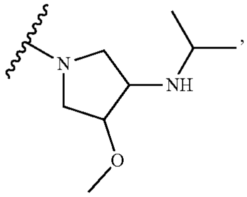,
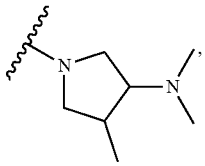,
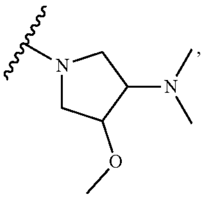,
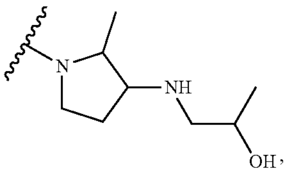, -continued

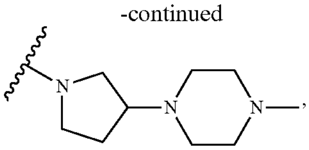

, or

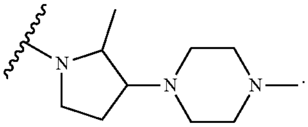

In an embodiment of a compound of Formula I or a pharmaceutically acceptable salt thereof, $R_4$ is selected from

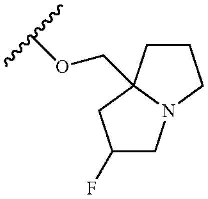

,

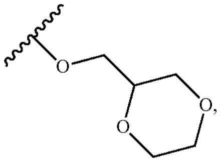

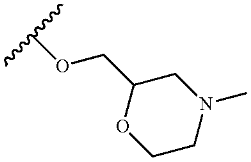

, or

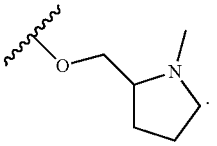

In an embodiment of a compound of Formula I or a pharmaceutically acceptable salt thereof, $R_4$ is the N-lined cyclic amine

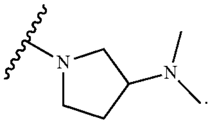 [SMILES: *N1CCC(N(C)C)C1 ; "."]

In an embodiment of a compound of Formula I or a pharmaceutically acceptable salt thereof, $R_4$ is

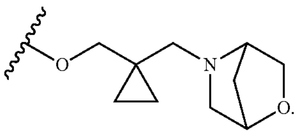 [SMILES: *OCC1(CN2CC3CC2CO3)CC1]

In an embodiment of a compound of Formula I or a pharmaceutically acceptable salt thereof, $R_4$ is the N-lined cyclic amine

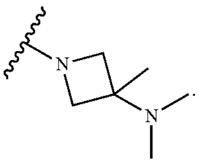 [SMILES: *N1CC(C)(N(C)C)C1]

In the above embodiments of the compounds of Formula I, or a pharmaceutically acceptable salt thereof, $R_4$ is a group of the formula

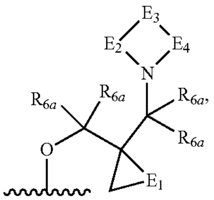

or

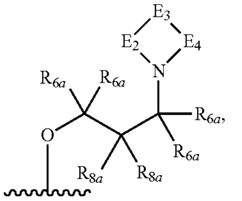

wherein $E_2$ and $E_4$ can optionally be bridged by a bond or a $C_{1-3}$ alkylene. Examples of these compounds of Formula I are shown below:

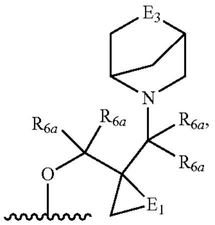

or

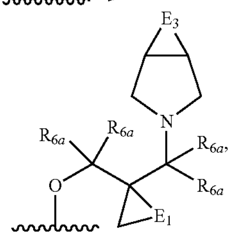

or a pharmaceutically acceptable salt thereof.

In the above embodiments of the compounds of Formula I, or a pharmaceutically acceptable salt thereof, $R_4$ is a group of the formula

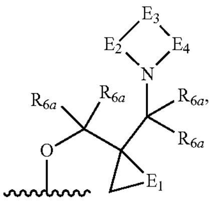

or

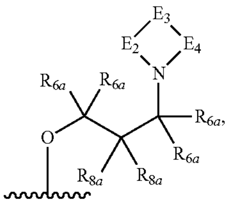

wherein $E_3$ can be —CO—$NR_{6b}$—. Examples of these compounds of Formula I are shown below:
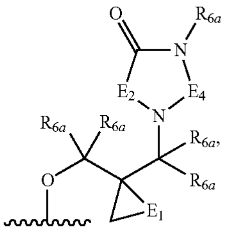
or a pharmaceutically acceptable salt thereof.
In an embodiment of a compound of Formula I or a pharmaceutically acceptable salt thereof, $R_4$ is selected from
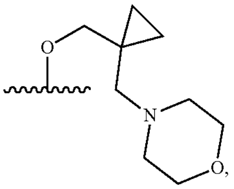
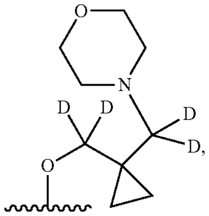
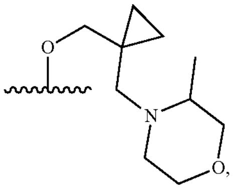
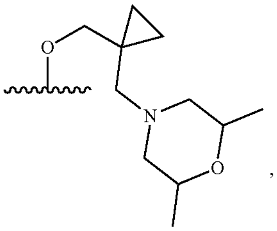
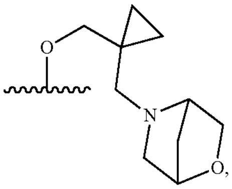
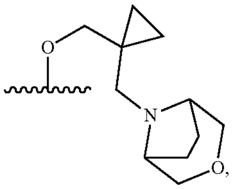
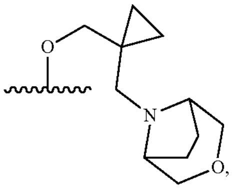
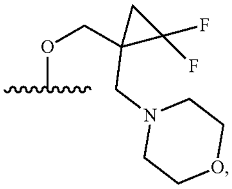
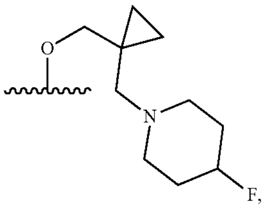
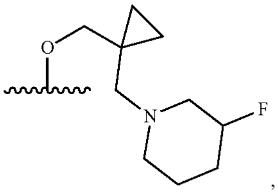
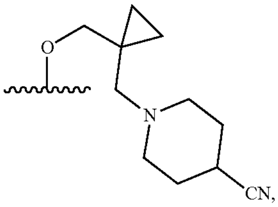
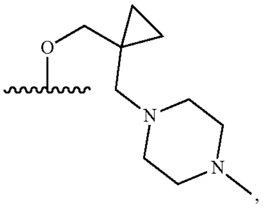
-continued
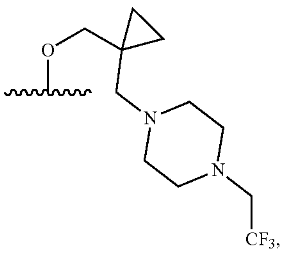
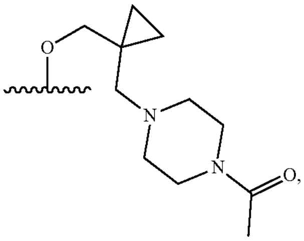
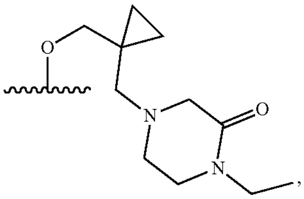
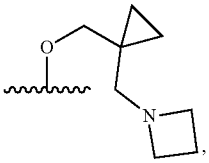
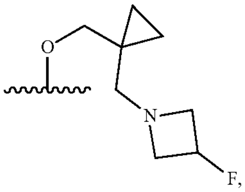
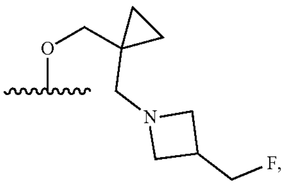
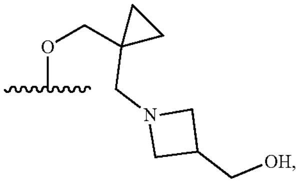
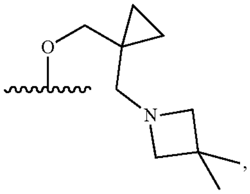
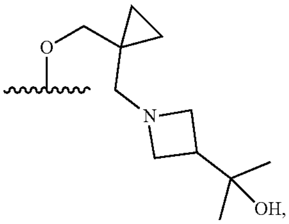
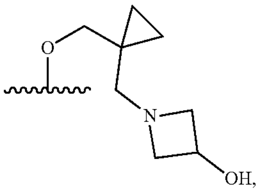
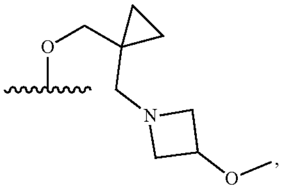
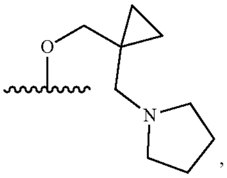
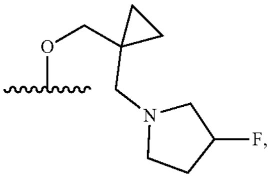
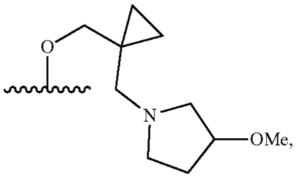

-continued
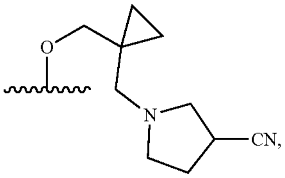
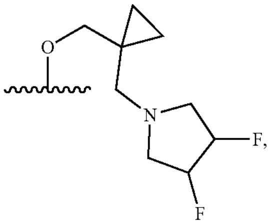
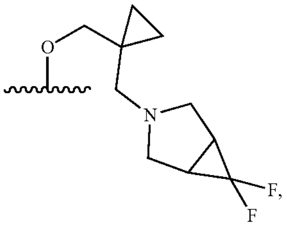
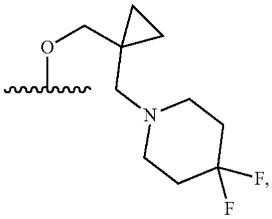
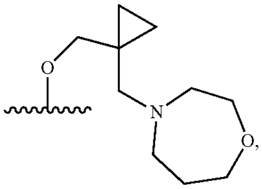
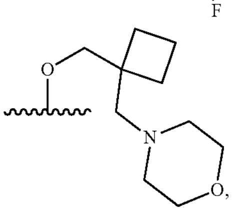
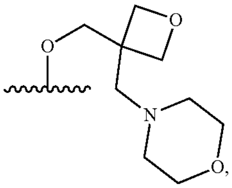
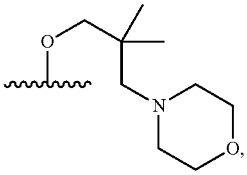
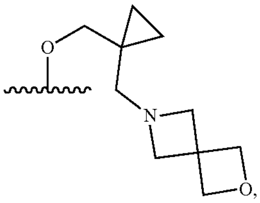
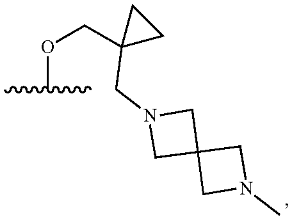
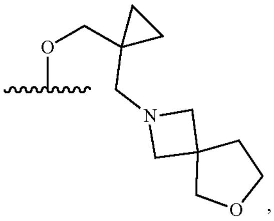
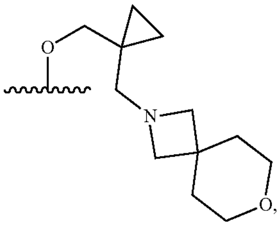
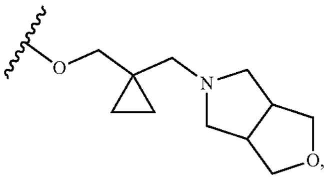
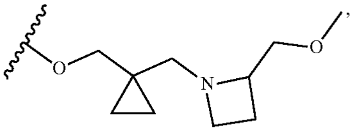
-continued
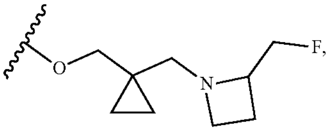
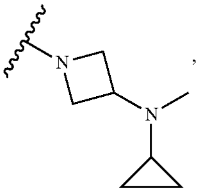
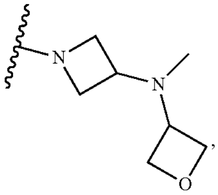
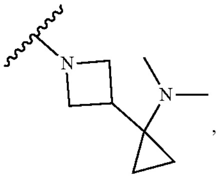
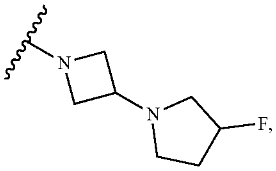
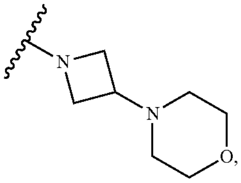
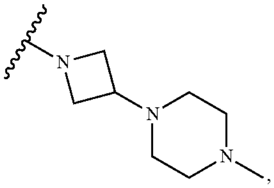
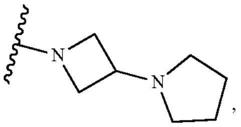
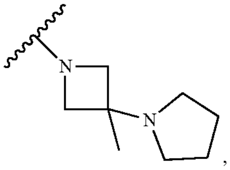
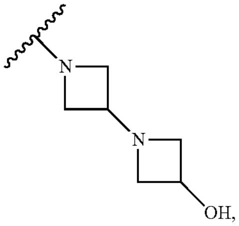
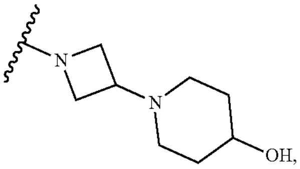
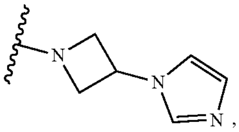
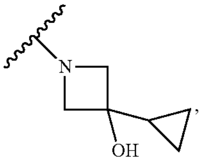
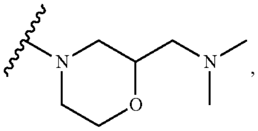
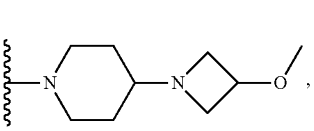
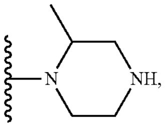
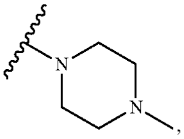
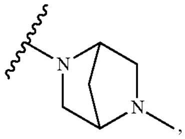

-continued
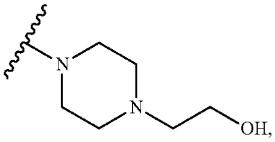
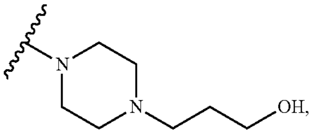
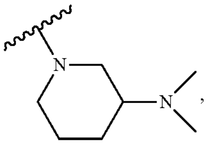,
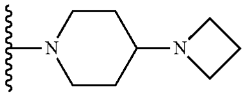,
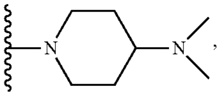,
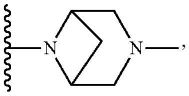,
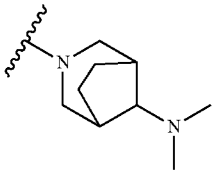
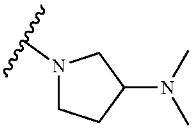
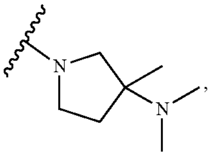,
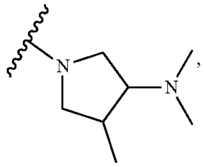,
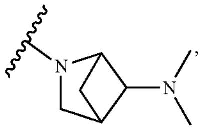,
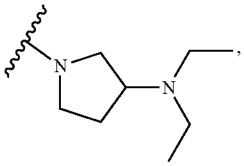,
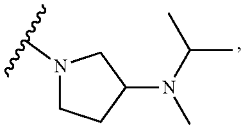,
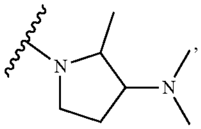,
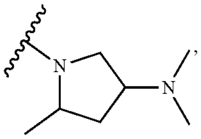,
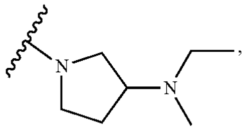,
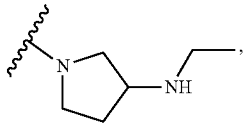,
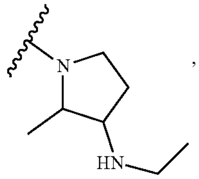,
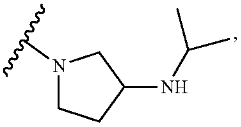,
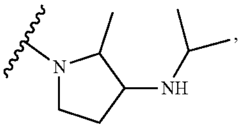,
-continued
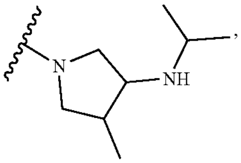,
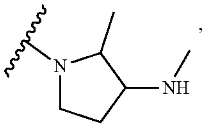,
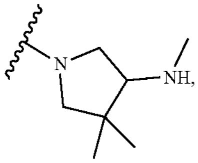
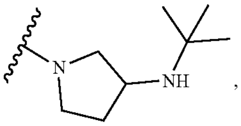,
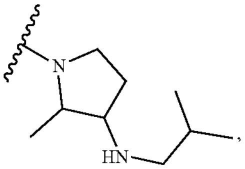,
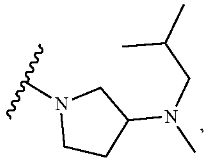,
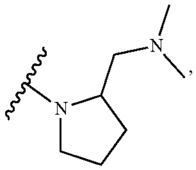
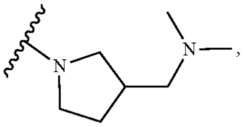,
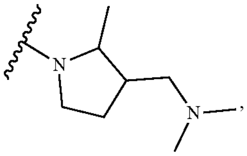,
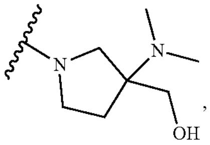,
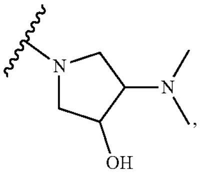
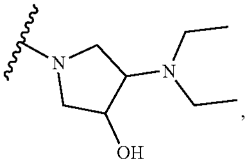,
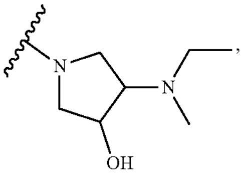,
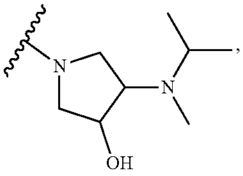,
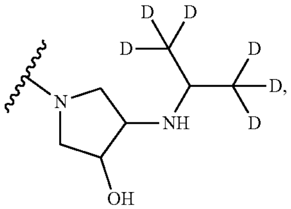
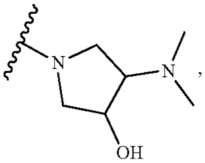,
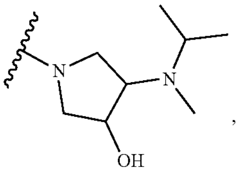,
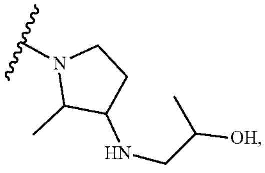

-continued
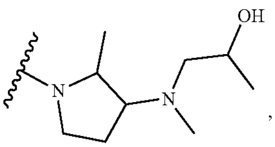,
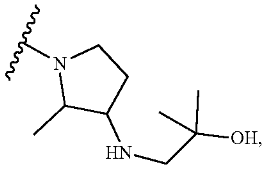
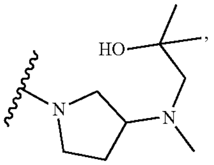
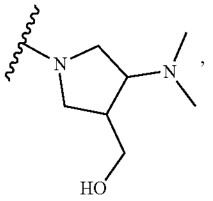
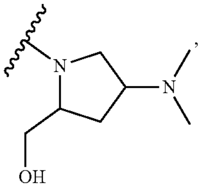
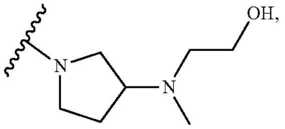
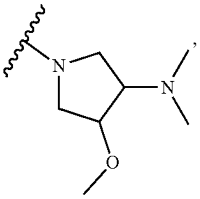
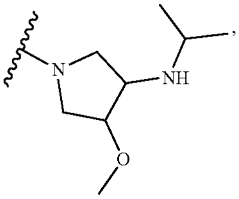
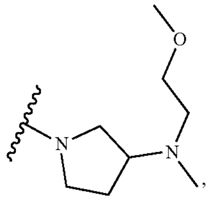
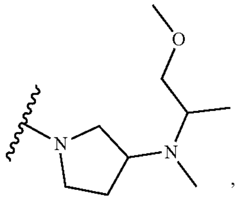
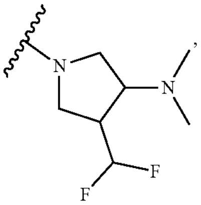
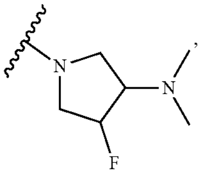
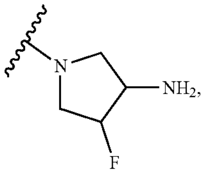
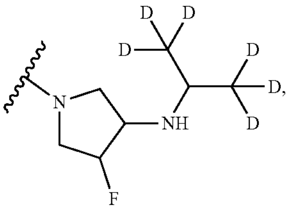
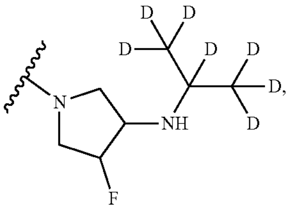
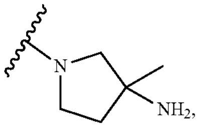
-continued
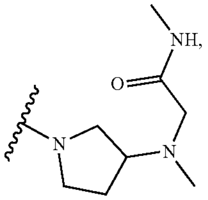
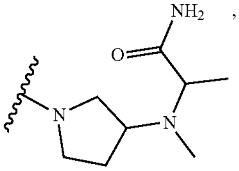
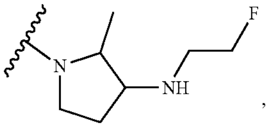,
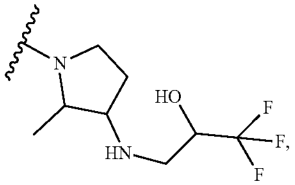
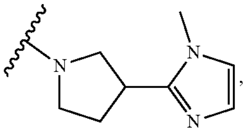
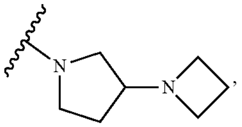
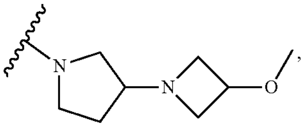
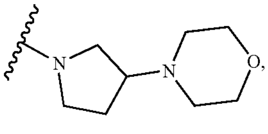
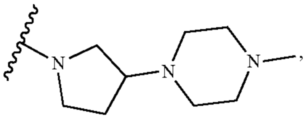
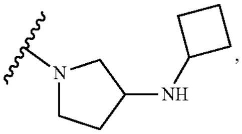
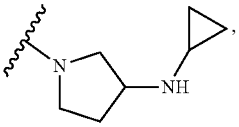
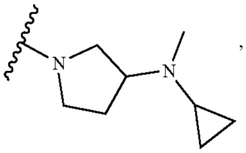
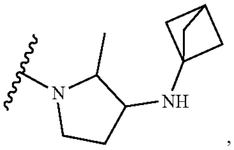,
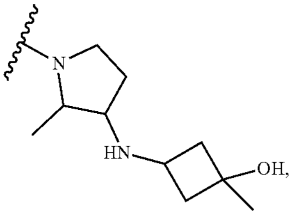
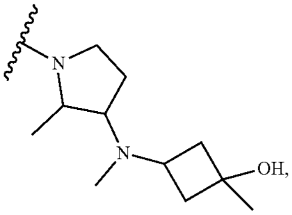
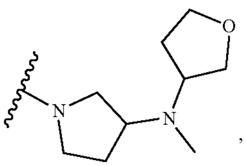
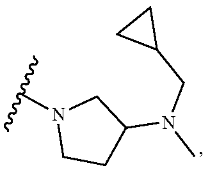
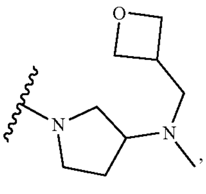

-continued
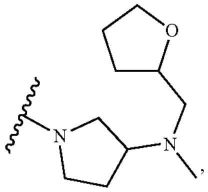,
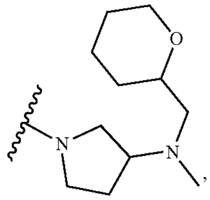,
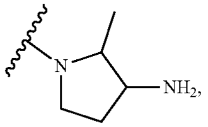,
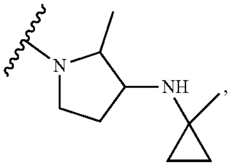,
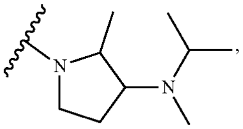,
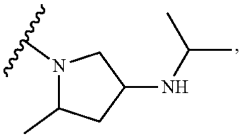,
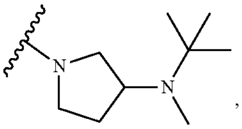,
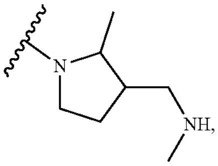,
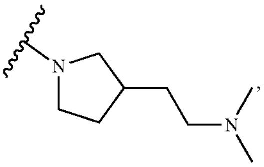,
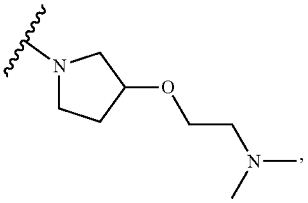,
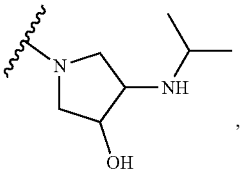,
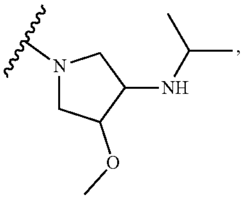,
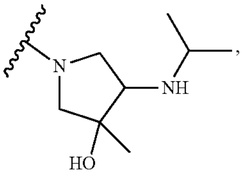,
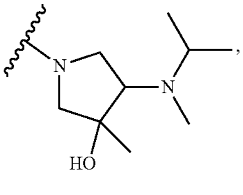,
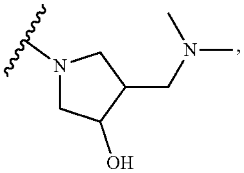,
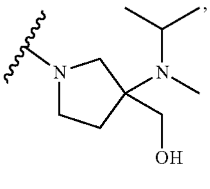,
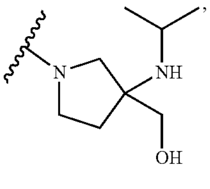,
-continued
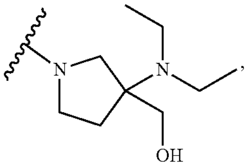,
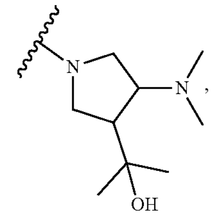,
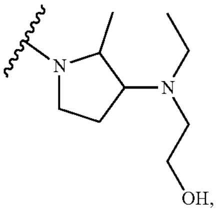,
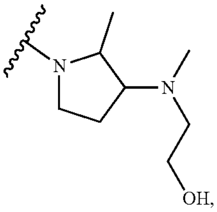,
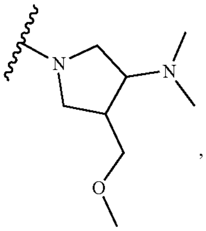,
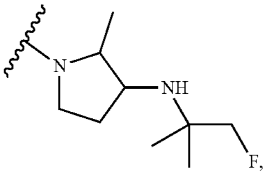,
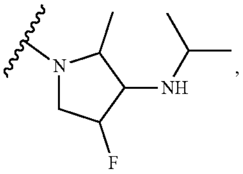,
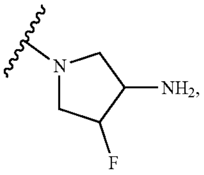,
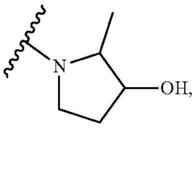,
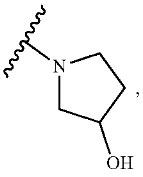,
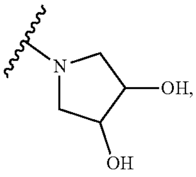,
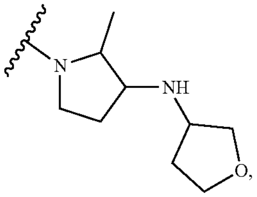,
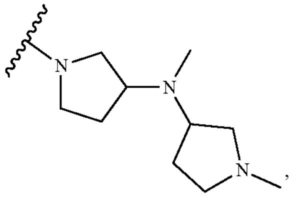,
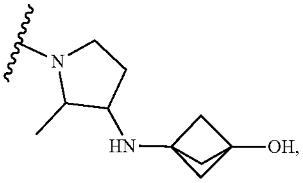,
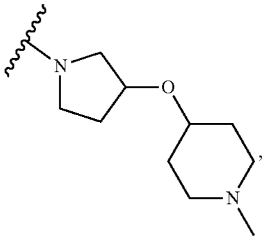,
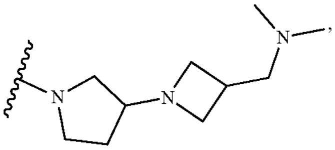, -continued
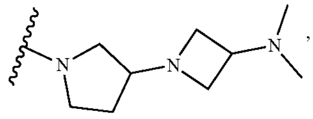, 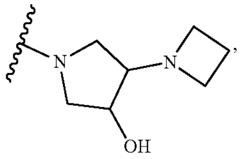,
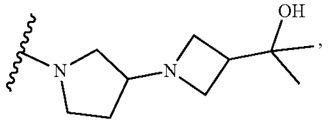,
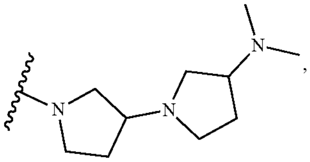, 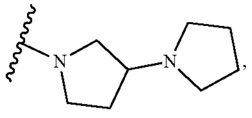,
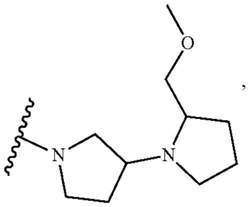, 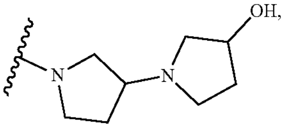
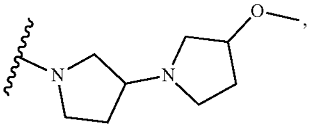, 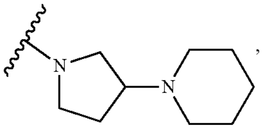,
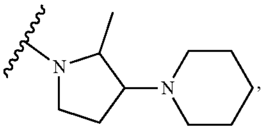,
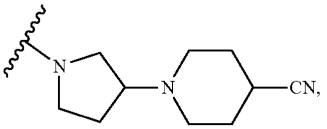
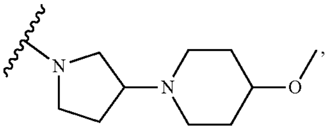,
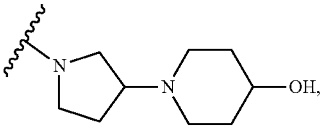
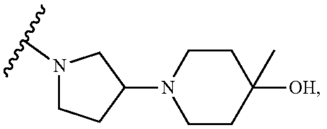
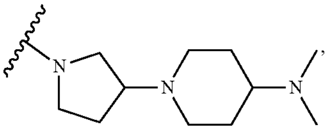,
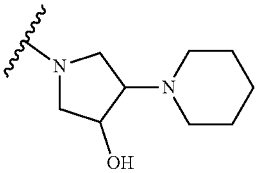, 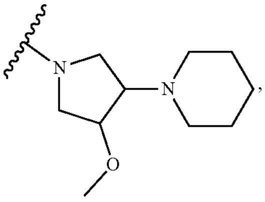,
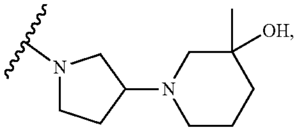
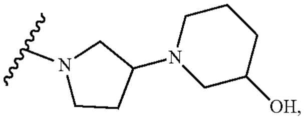
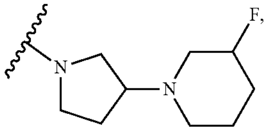
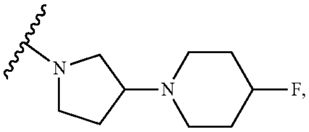
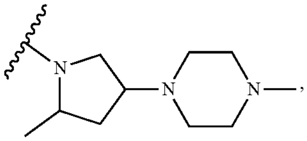,
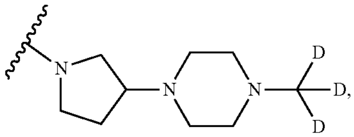
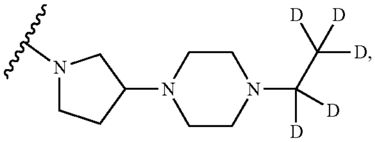
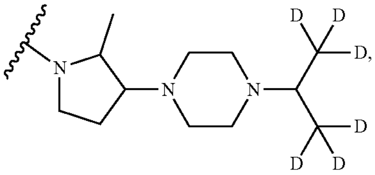
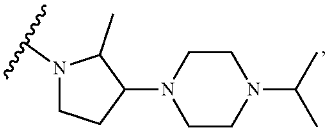,
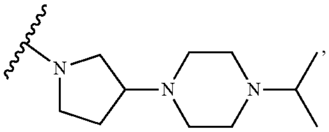,
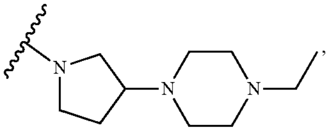,

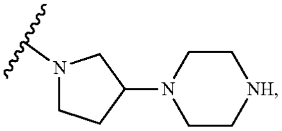
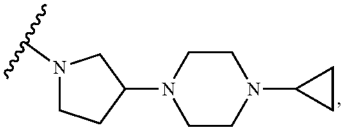
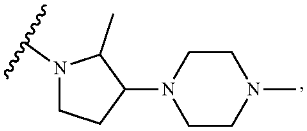
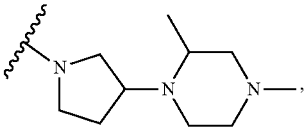
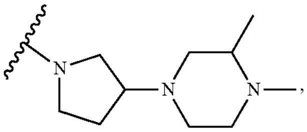
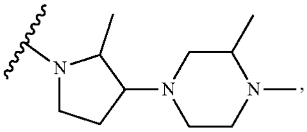
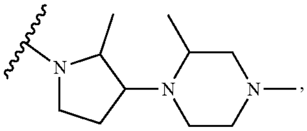
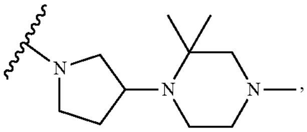
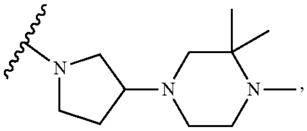
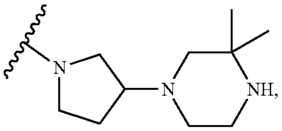
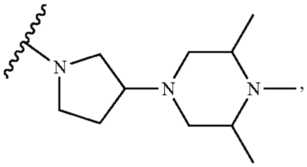
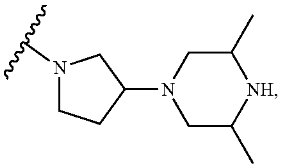
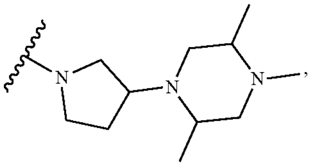
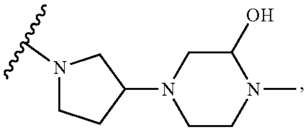
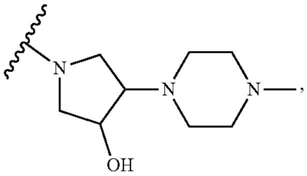
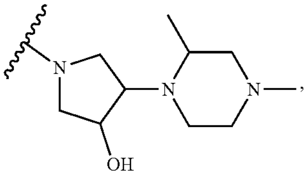
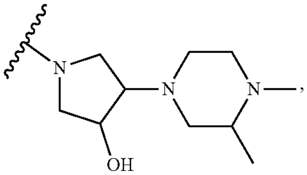
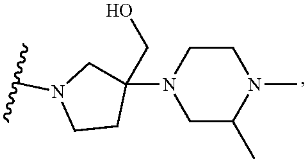
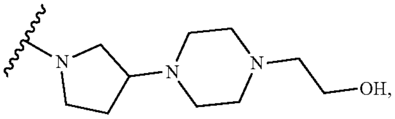
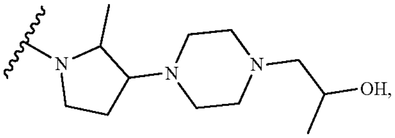
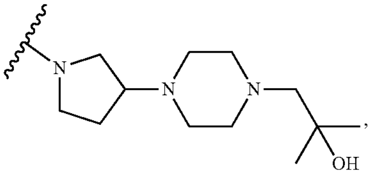
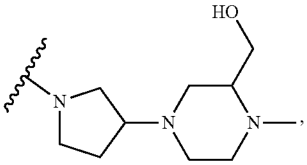
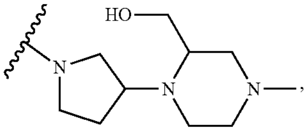

-continued
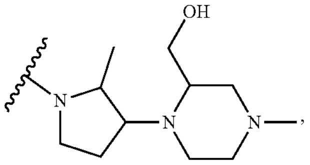
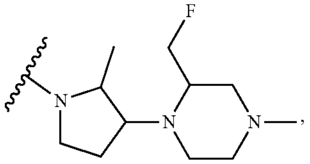
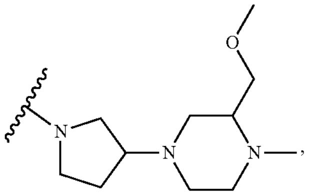
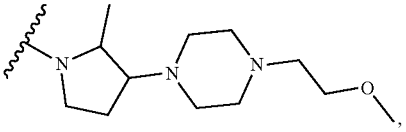
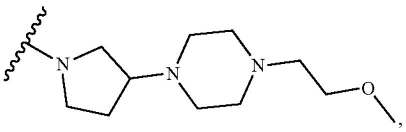
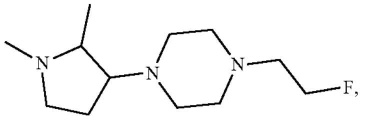
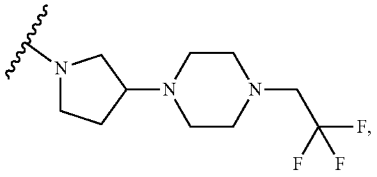
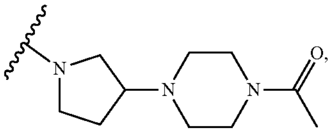
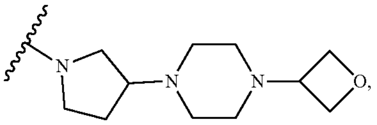
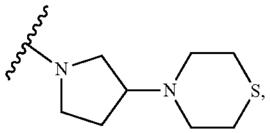
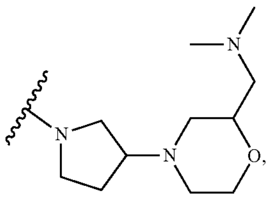
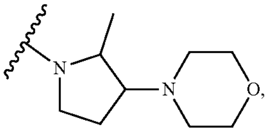
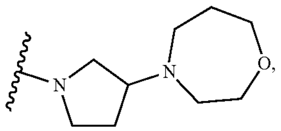
-continued
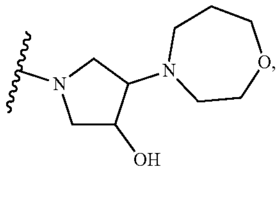
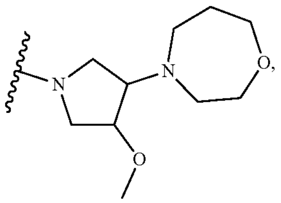
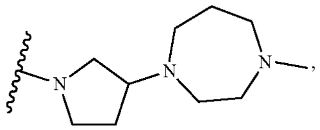
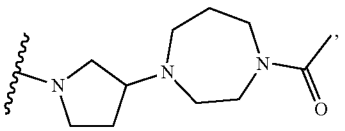
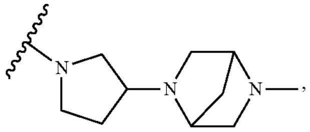
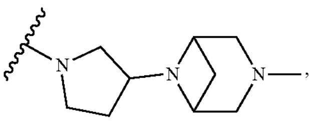
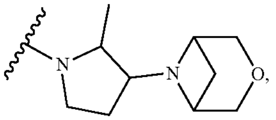
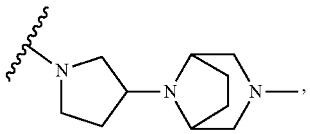
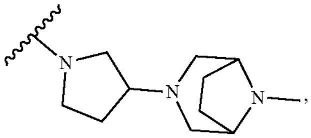
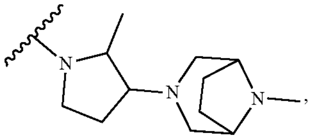
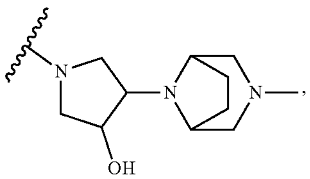
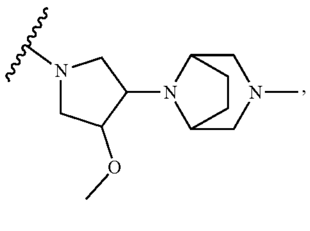

-continued
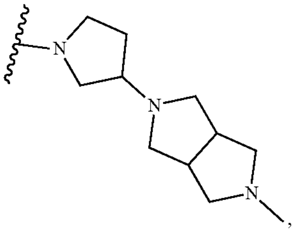,
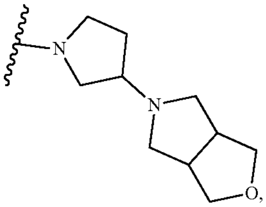,
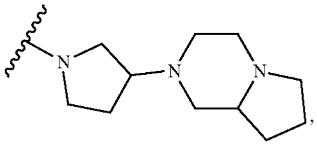,
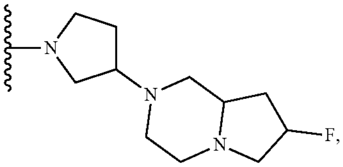,
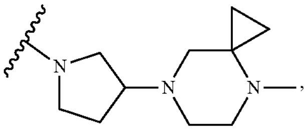,
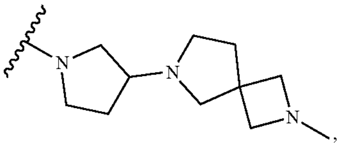,
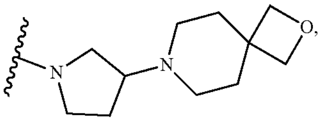,
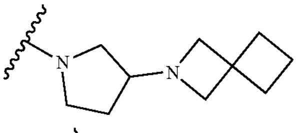, 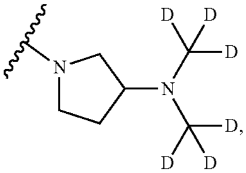,
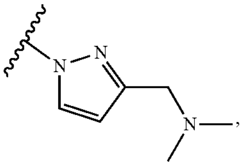, 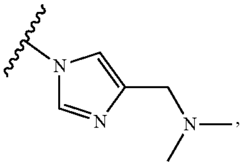,
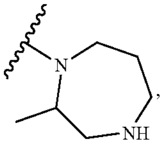, 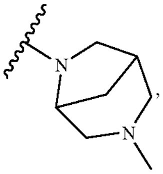, 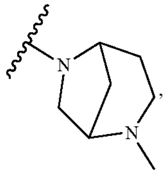,
-continued
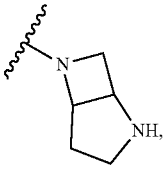, 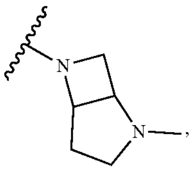,
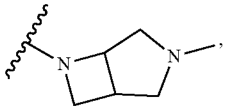, 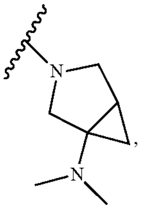,
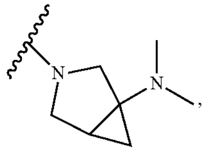, 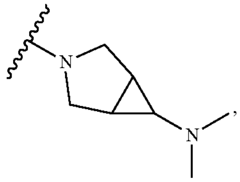,
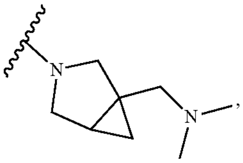, 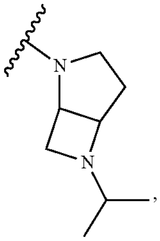, 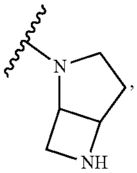,
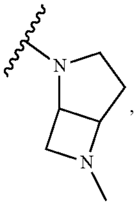, 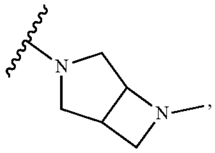, 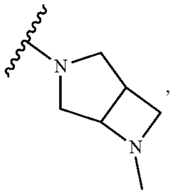,
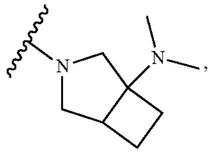, 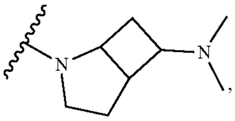,
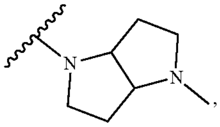, 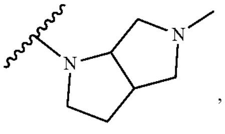,
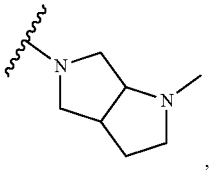, 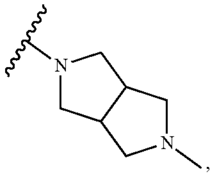, -continued
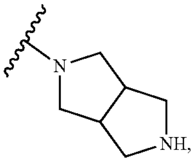
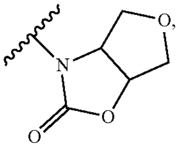
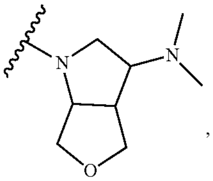
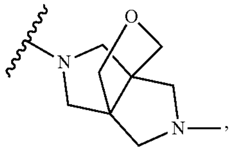
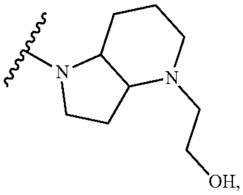
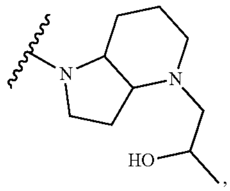
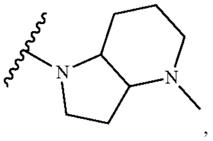
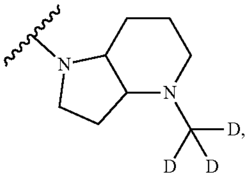
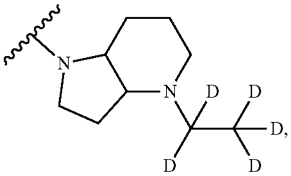
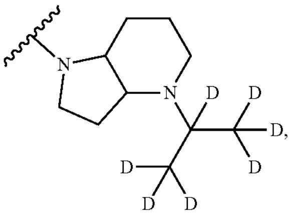
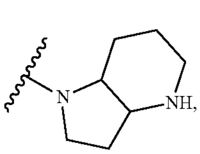
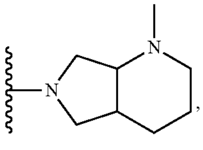
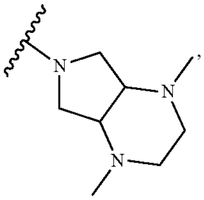
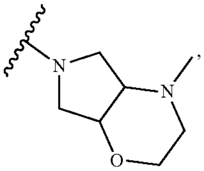
-continued
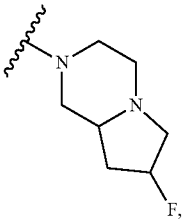
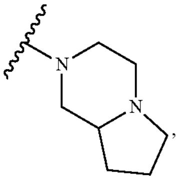
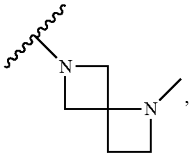
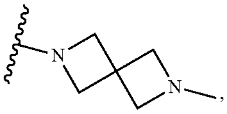
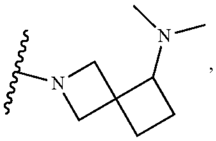
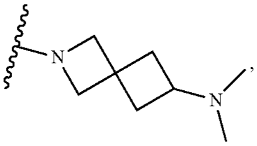
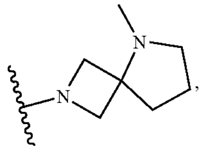
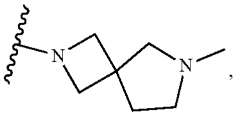
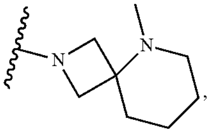
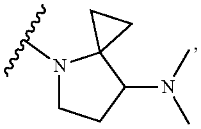
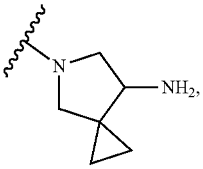
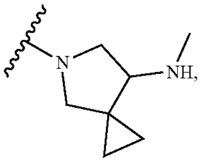
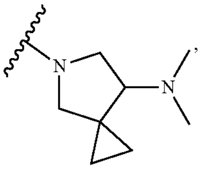
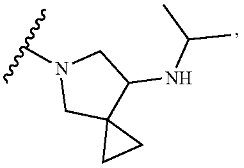
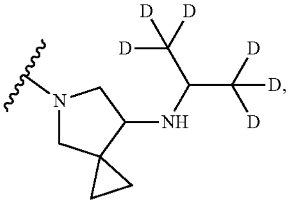
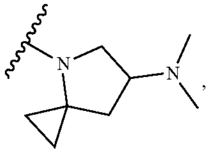
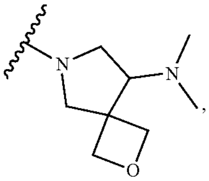
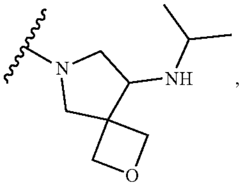

-continued
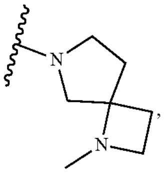,
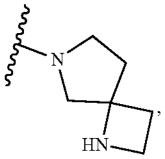,
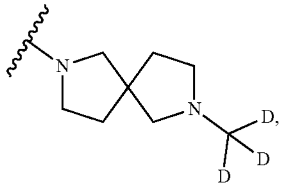,
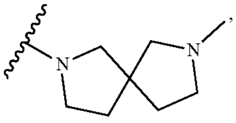
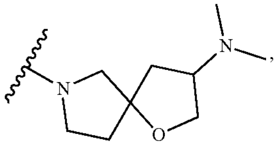,
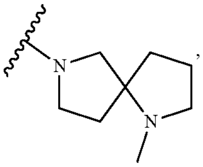,
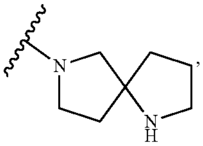,
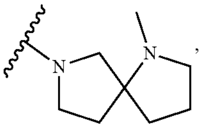, or
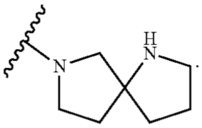.
In an embodiment of a compound of Formula I or a pharmaceutically acceptable salt thereof, $R_4$ is a N-linked cyclic amine selected from
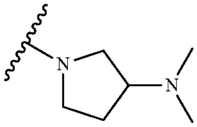
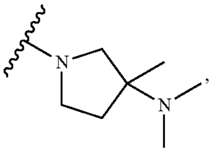,
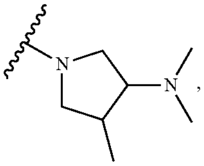,
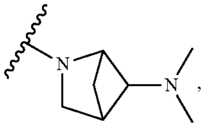,
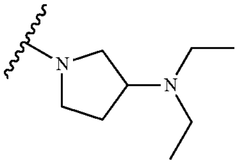,
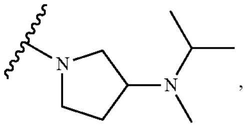,
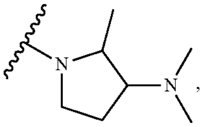,
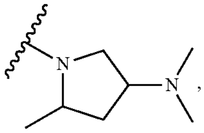,
-continued
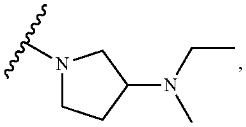,
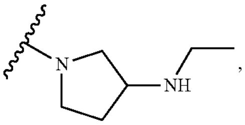,
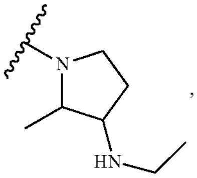,
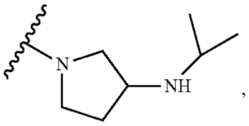,
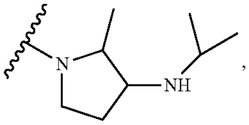,
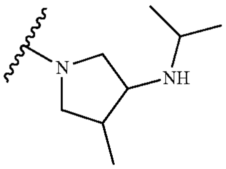,
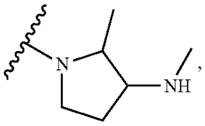,
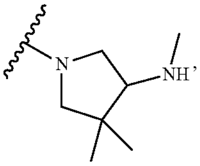
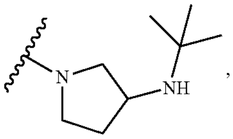,
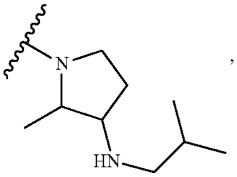,
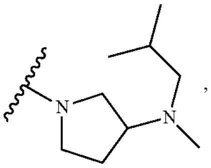,
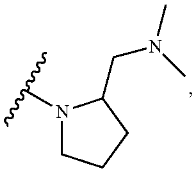,
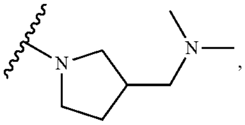,
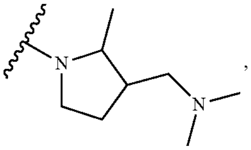,
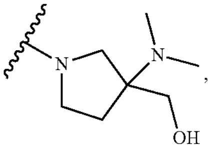,
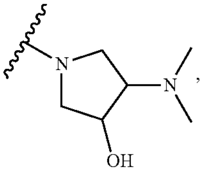
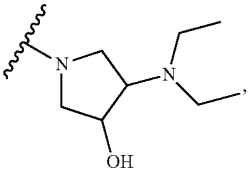
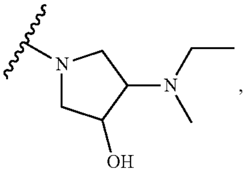,
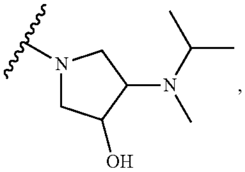,
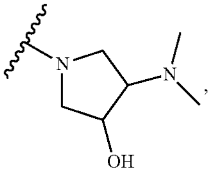

-continued
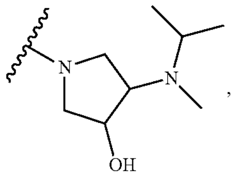, 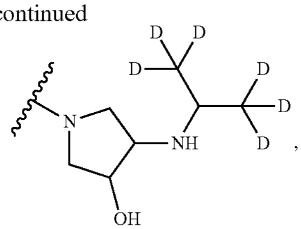,
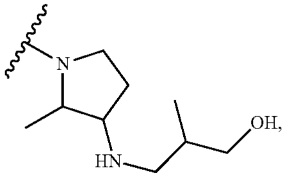 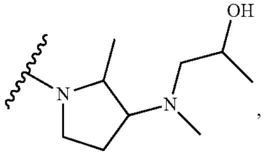,
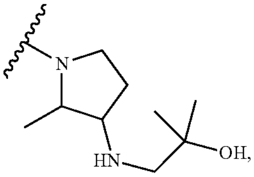 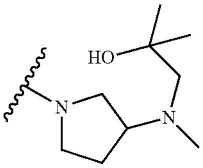,
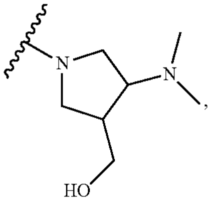 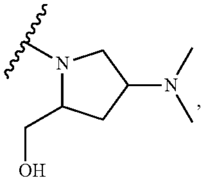
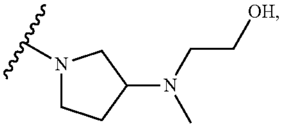 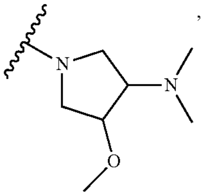,
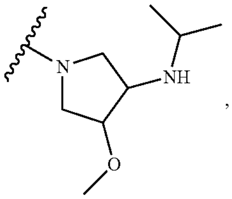, 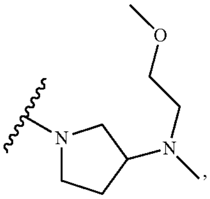
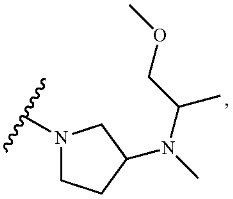 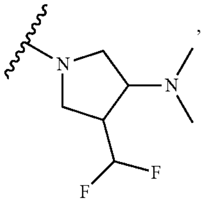,
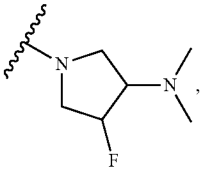 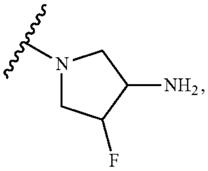
-continued
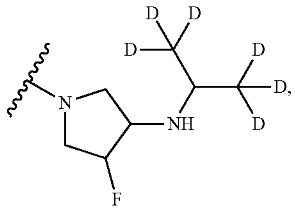
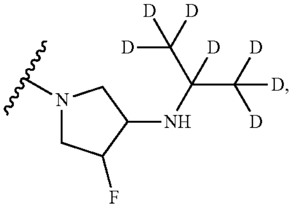 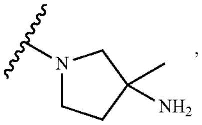,
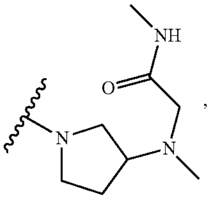 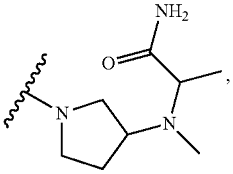
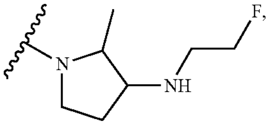 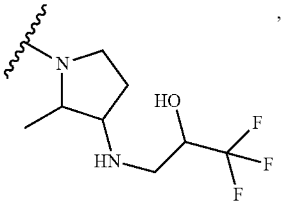,
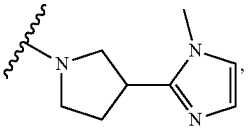 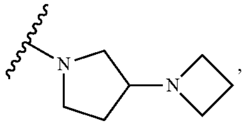
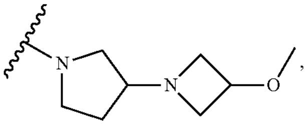
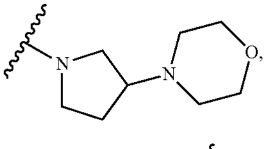
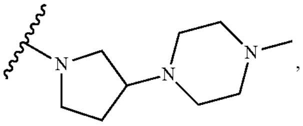 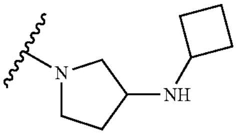,
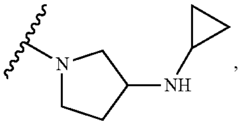, 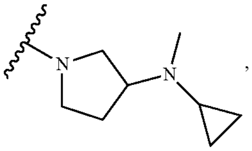, -continued
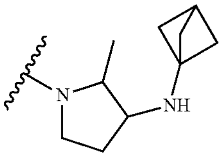, 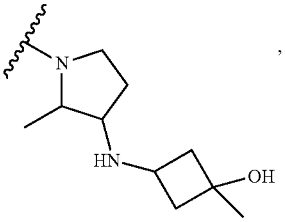,
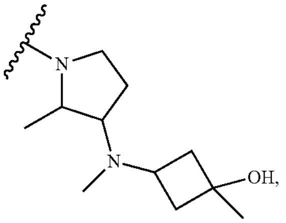 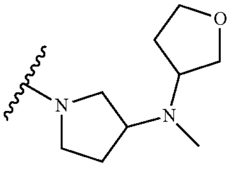,
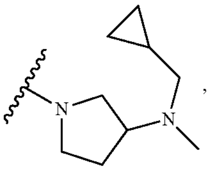, 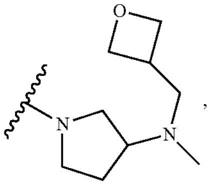,
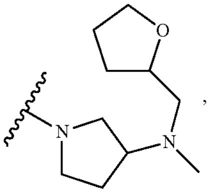, 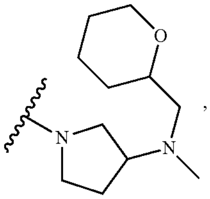,
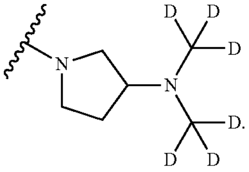 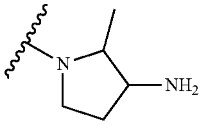,
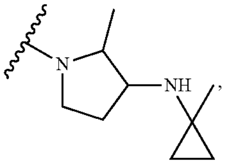, 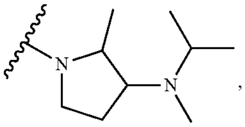,
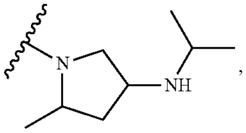, 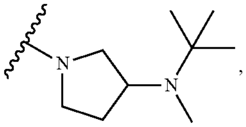,
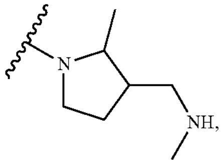 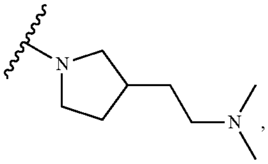,
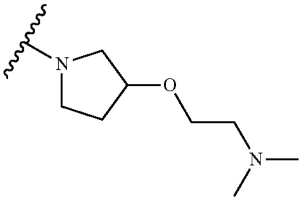, 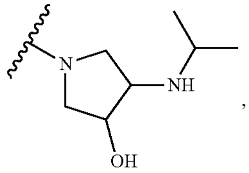,
-continued
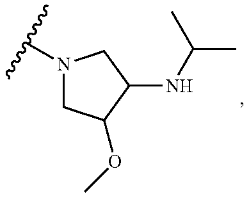, 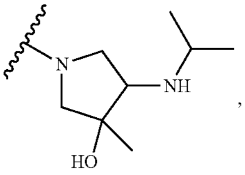,
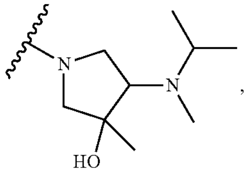, 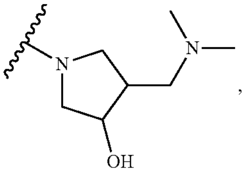,
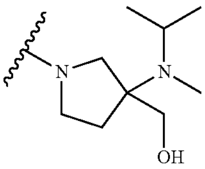 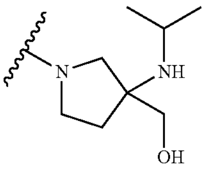,
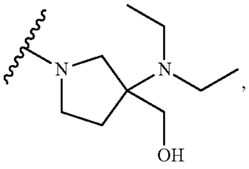, 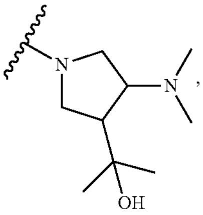
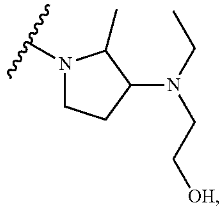 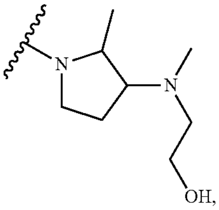
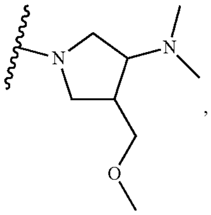, 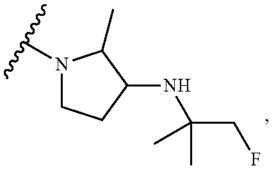,
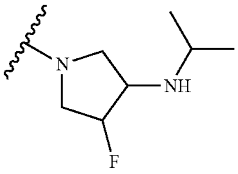,
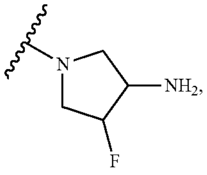 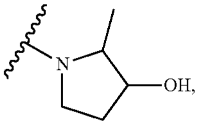 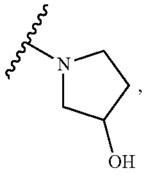, -continued
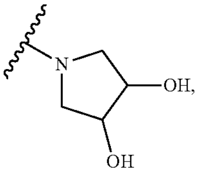
,
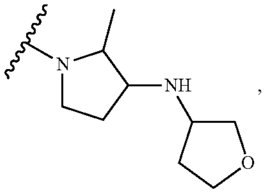
,
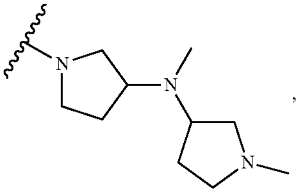
,
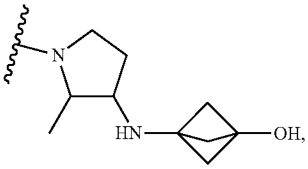
,
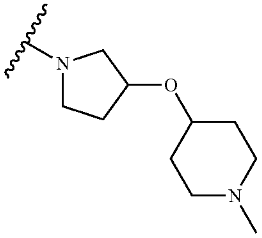
,
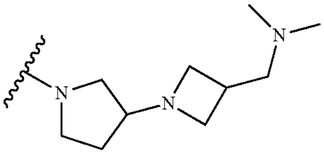
,
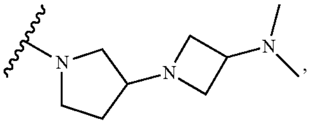
,
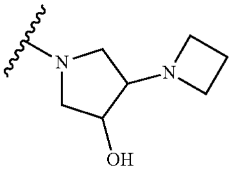
,
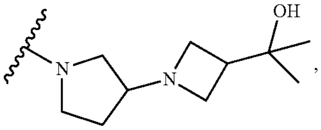
,
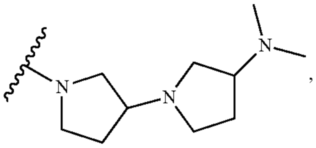
,
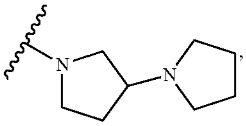
,
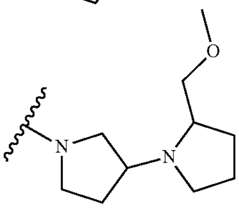
,
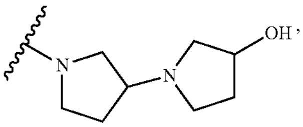
,
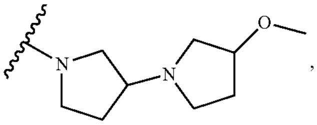
,
-continued
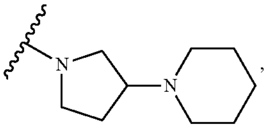
,
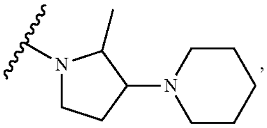
,
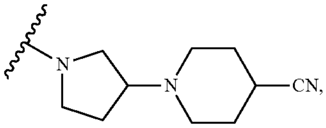
,
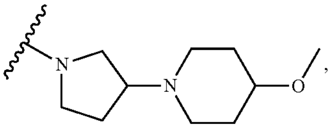
,
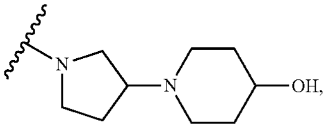
,
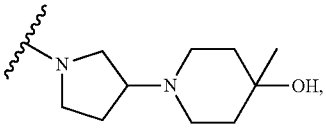
,
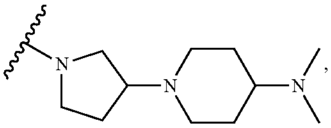
,
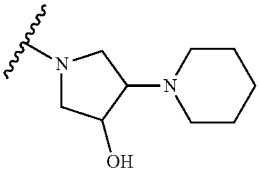
,
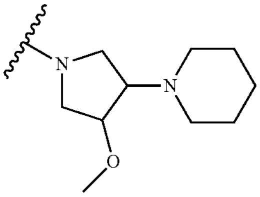
,
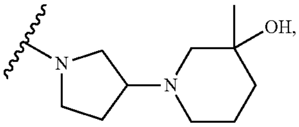
,
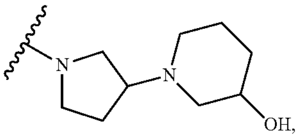
,
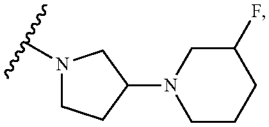
,
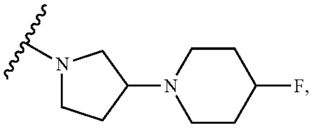
,
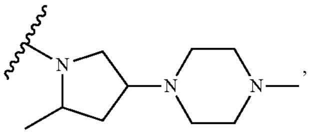
, -continued
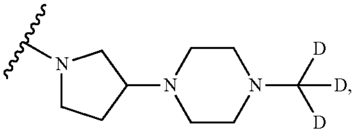
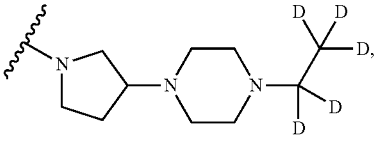
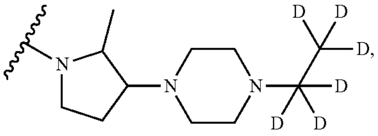
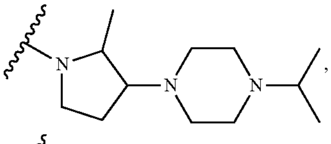
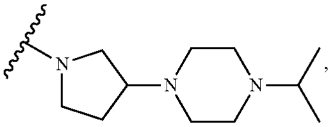
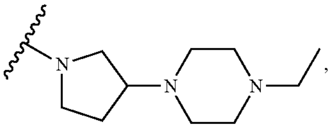
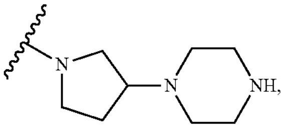
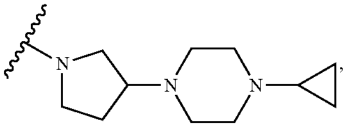
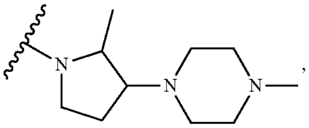
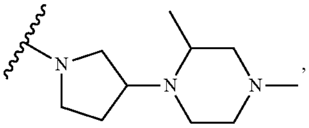
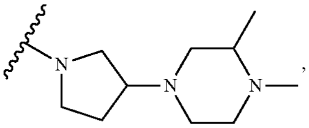
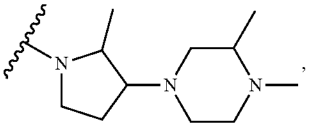
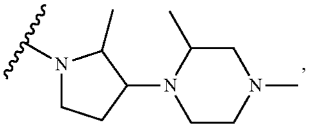
-continued
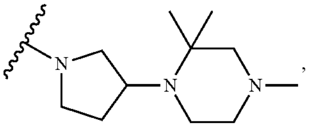
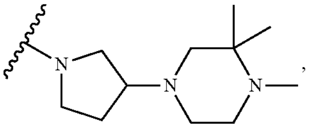
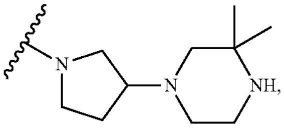
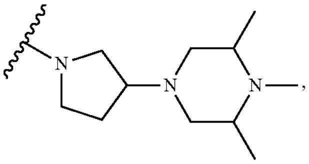
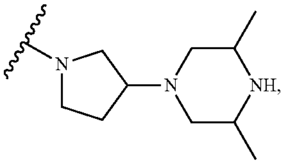
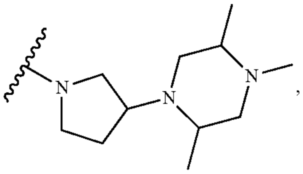
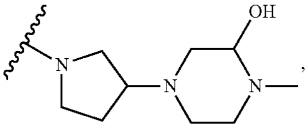
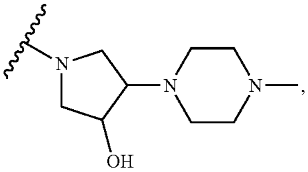
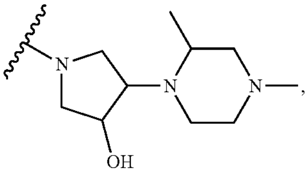
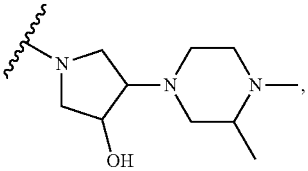
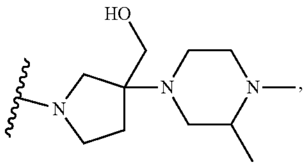

-continued
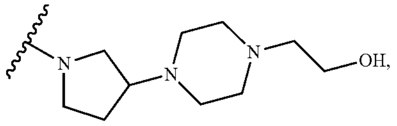
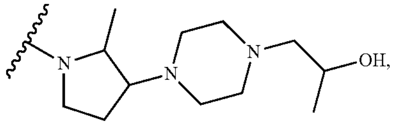
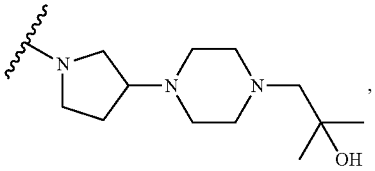
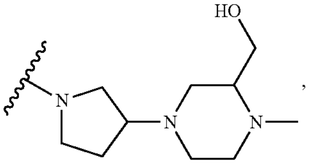
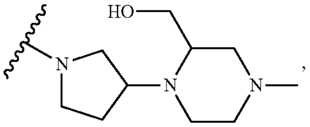
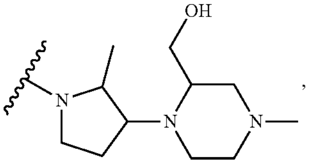
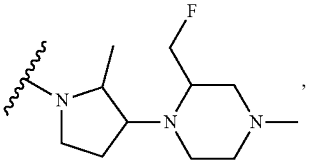
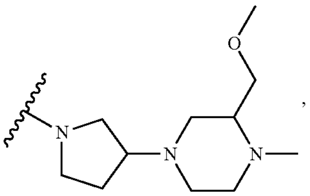
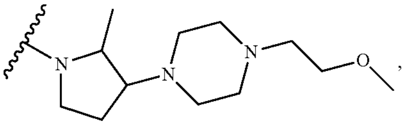
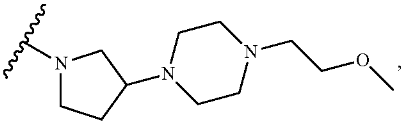
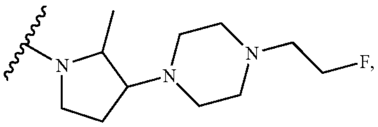
-continued
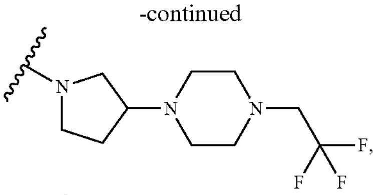
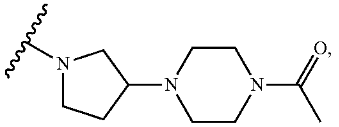
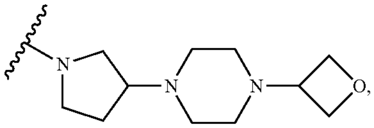
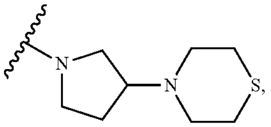
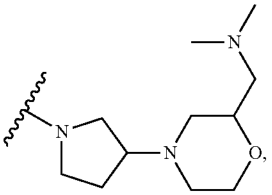
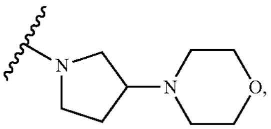
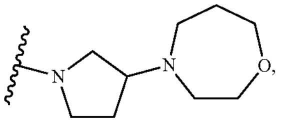
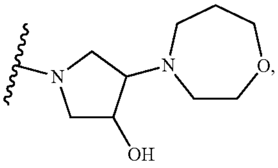
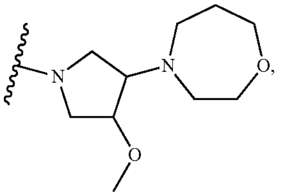
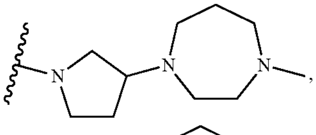
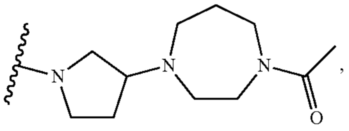
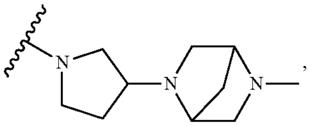
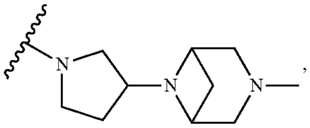
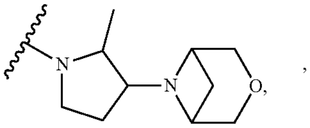

-continued
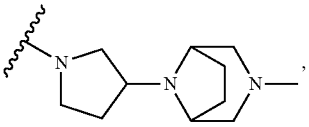,
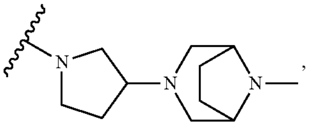,
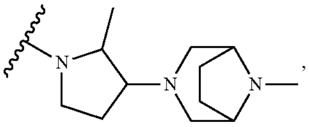,
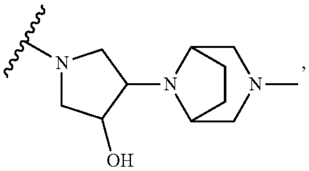,
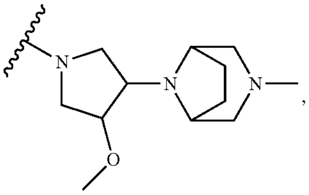,
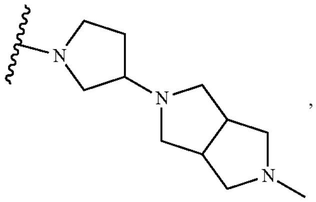,
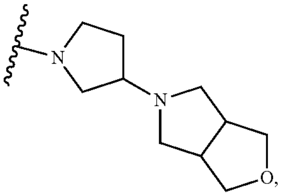
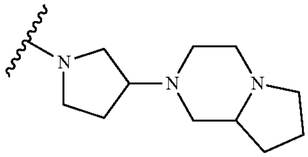,
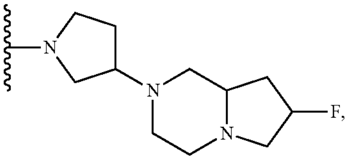
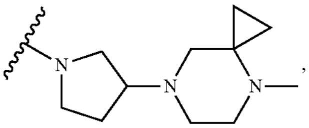,
-continued
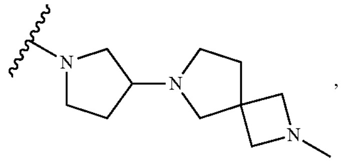,
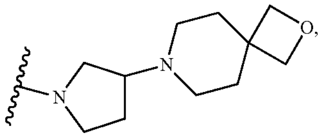 or
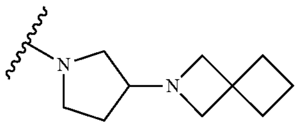.
In an embodiment of a compound of Formula I or a pharmaceutically acceptable salt thereof, $R_4$ is a N-linked cyclic amine selected from
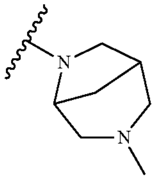, 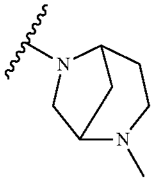, 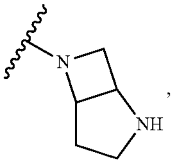,
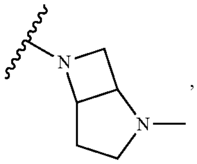, 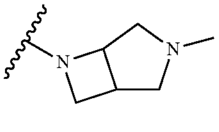,
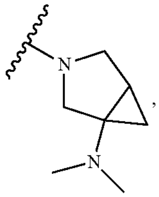, 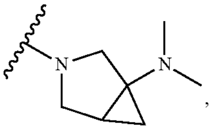,
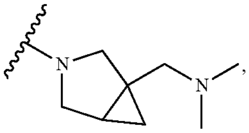, 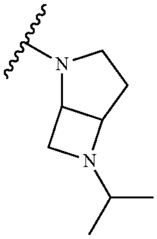,
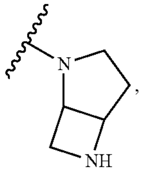, 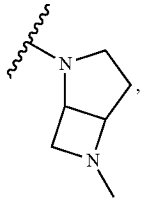, 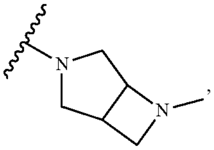, -continued
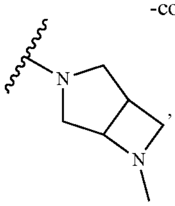,
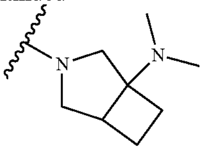,
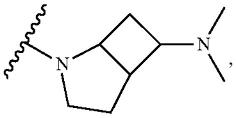,
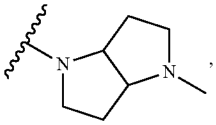,
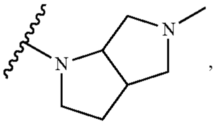,
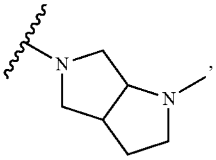,
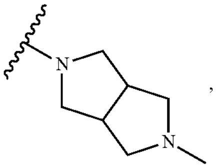,
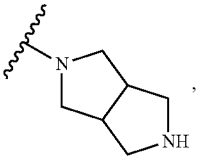,
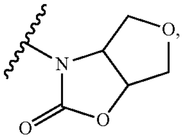
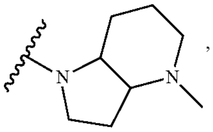,
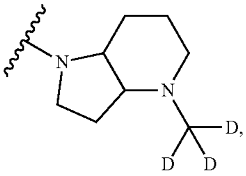
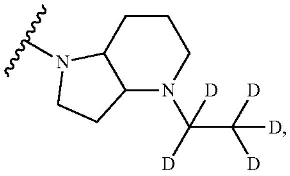
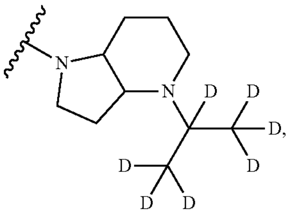
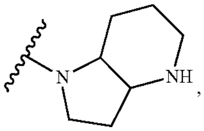,
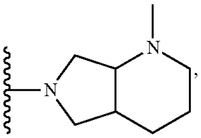,
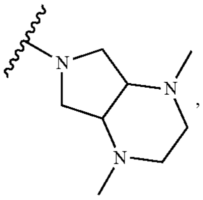,
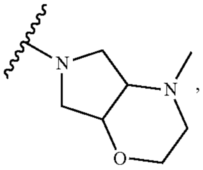,
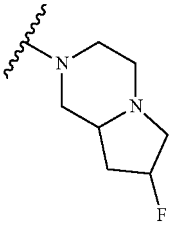,
-continued
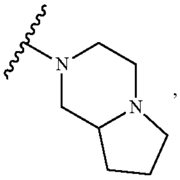,
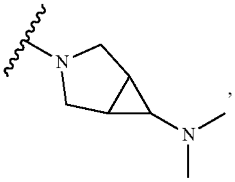,
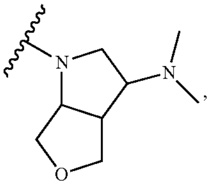,
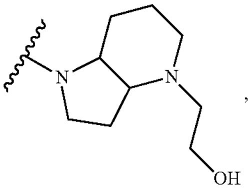,
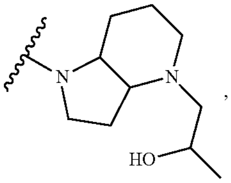, or
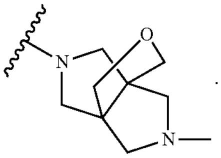.
In an embodiment of a compound of Formula I or a pharmaceutically acceptable salt thereof, $R_4$ is a N-linked cyclic amine selected from
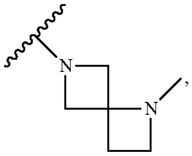
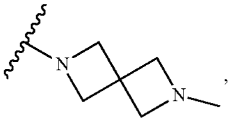,
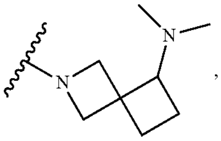,
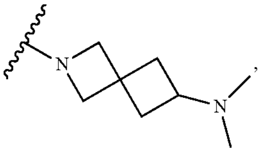
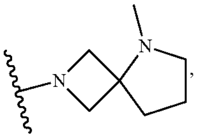
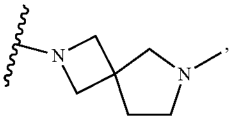
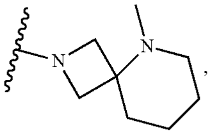,
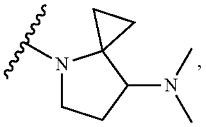
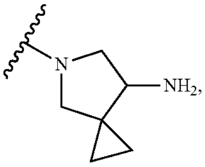,
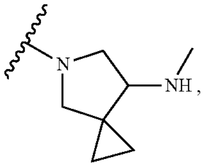, -continued

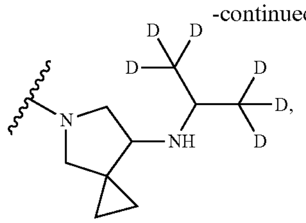

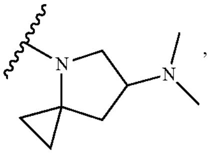,

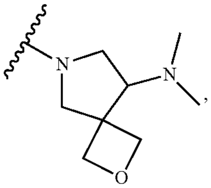,

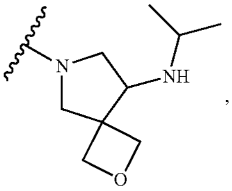,

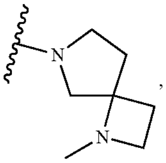,

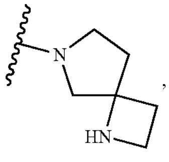,

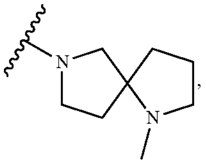,

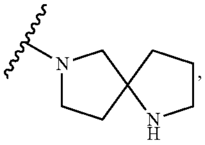,

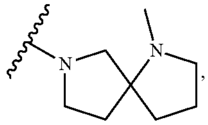,

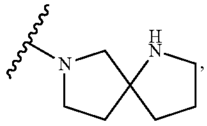,

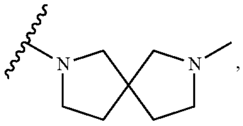,

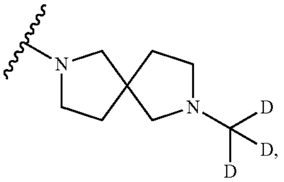 or

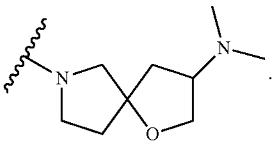.

In the above embodiments of the compounds of Formula I, the chemical drawings are shown flat without chiral information. These compounds often have multiple chiral centers and are contemplated to exist is various forms with various combinations of chiral centers. Additionally, these compounds have various enantiomers, diastereomers, and atropisomers that can exist and are included herein.

In an embodiment of a compound of Formula I or a pharmaceutically acceptable salt thereof, the compound is an isotopic derivative of any one of the compounds described herein or a pharmaceutically acceptable salt thereof.

It is understood that the isotopic derivative can be prepared using any of a variety of art-recognized techniques. For example, the isotopic derivatives can generally be prepared by carrying out the procedures disclosed in the schemes and/or in the examples described herein or a pharmaceutically acceptable salt thereof, by substituting an isotopically labeled reagent for a non-isotopically labeled reagent.

In an embodiment of a compound of Formula I or a pharmaceutically acceptable salt thereof, the compound is a deuterium labeled compound of any one of the compounds described herein and pharmaceutically acceptable salts thereof.

A further compound of Formula I or a pharmaceutically acceptable salt thereof, the compound is selected from:

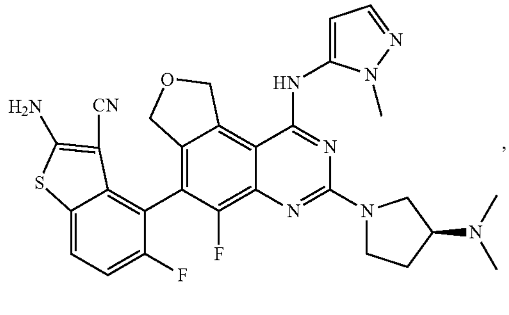,

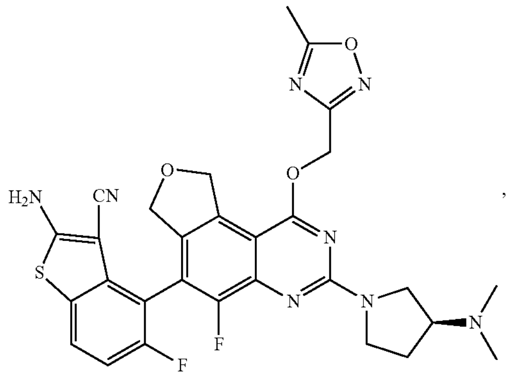,

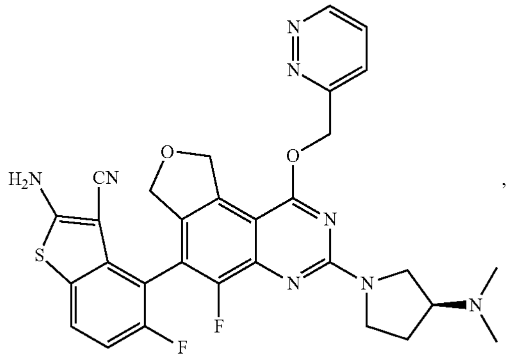,

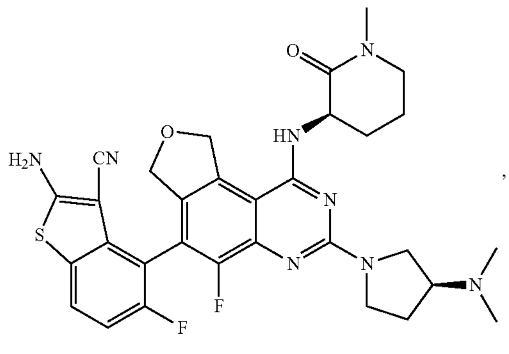,

-continued
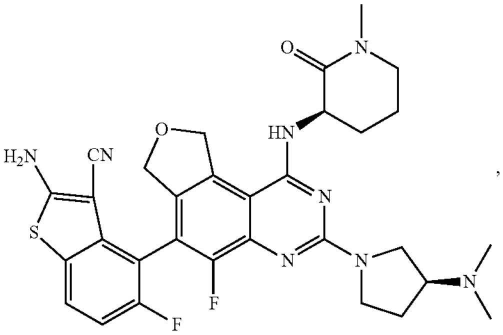
,
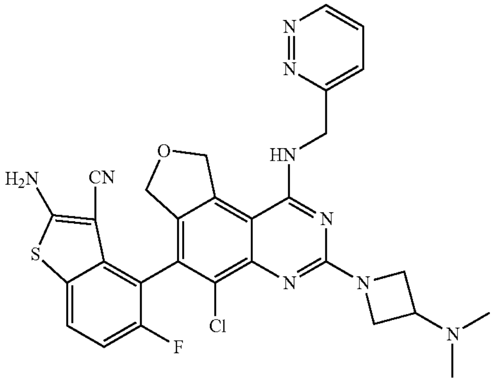
,
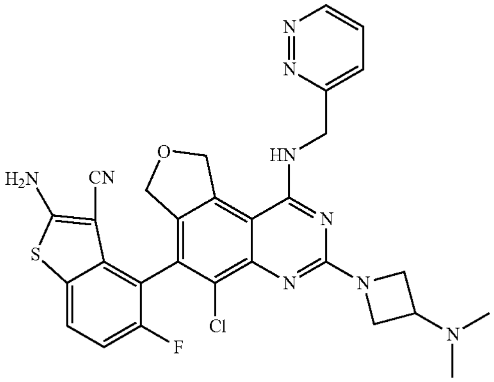
,
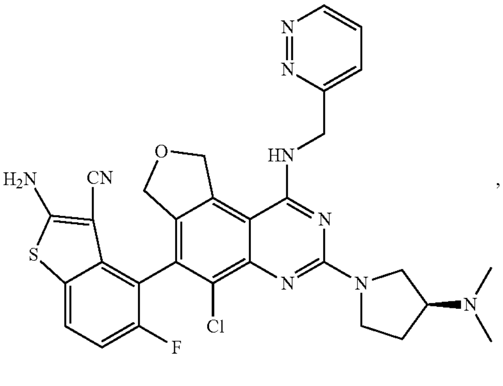
,
-continued
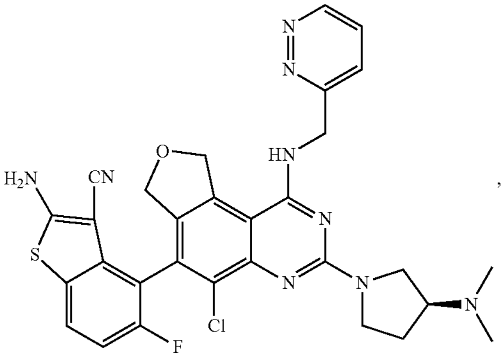
,
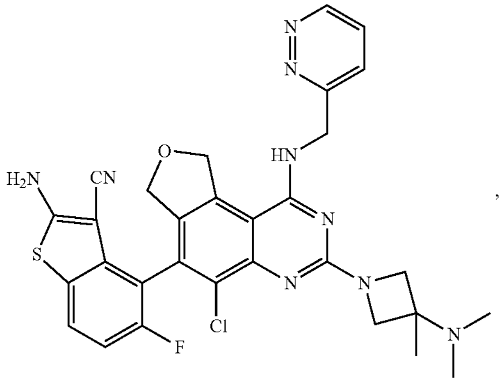
,
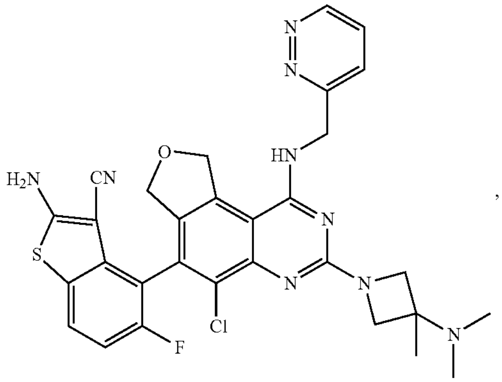
,
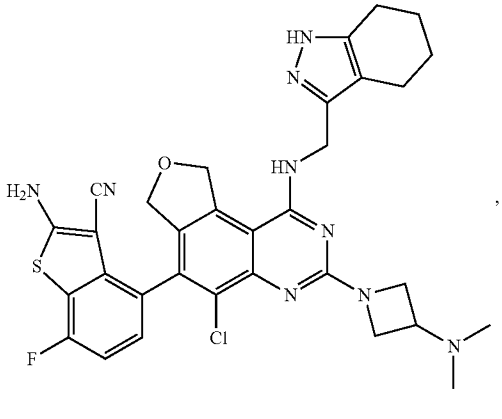
, -continued
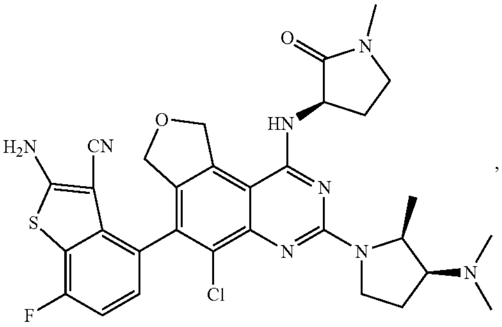
,
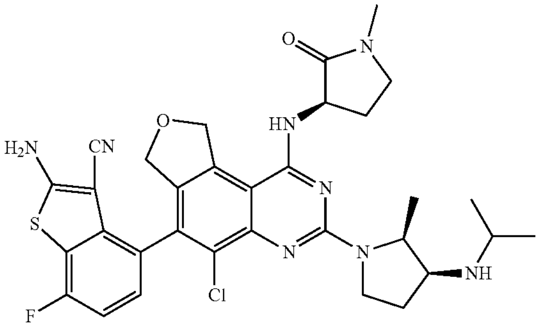
,
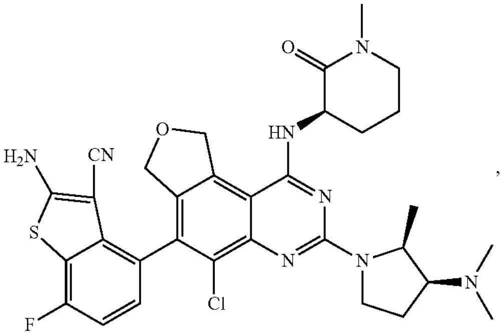
,
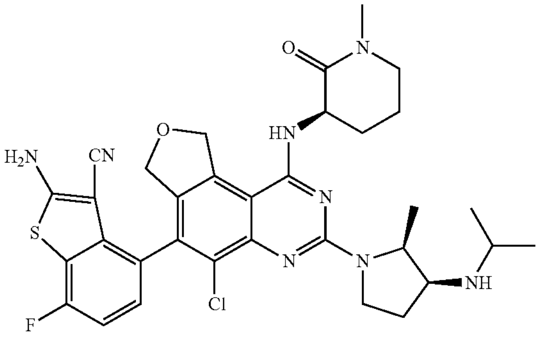
,
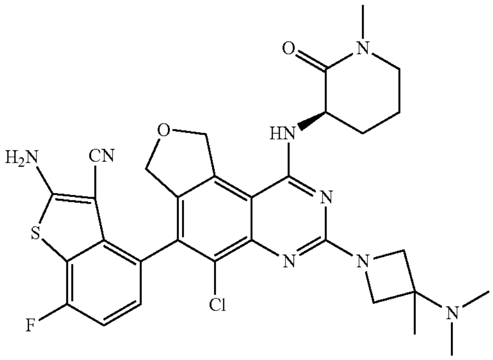
,
-continued
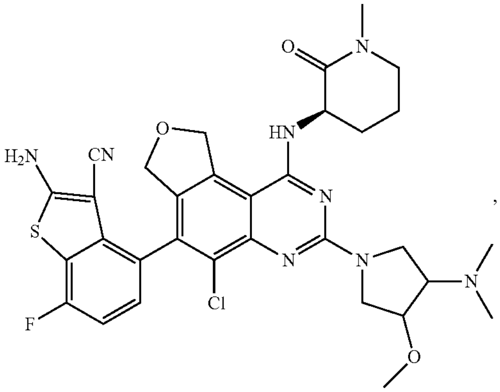
,
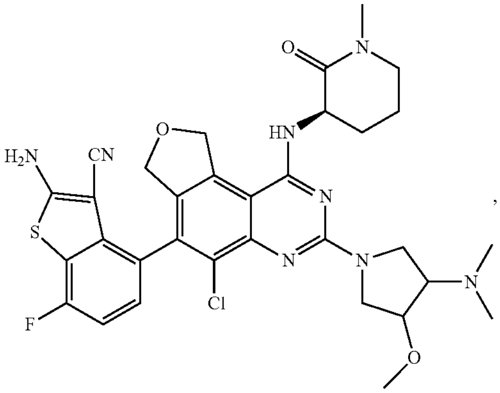
,
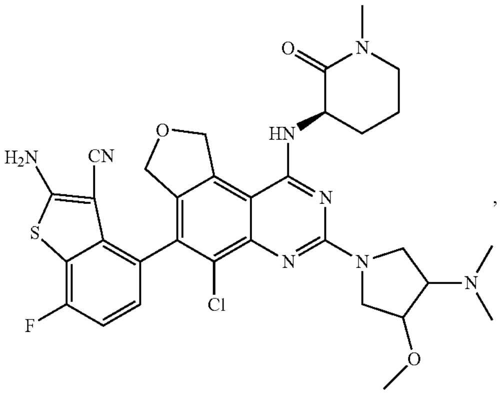
,
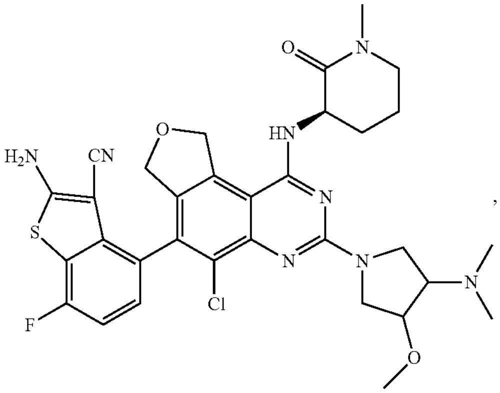
, -continued
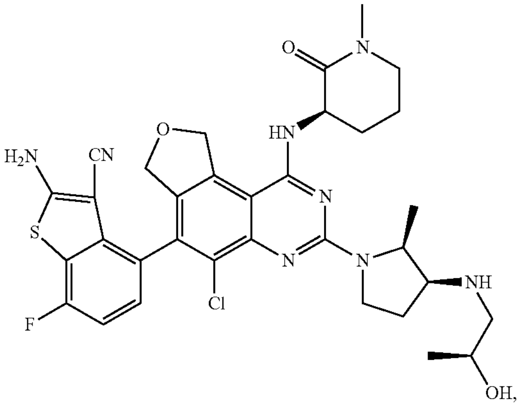
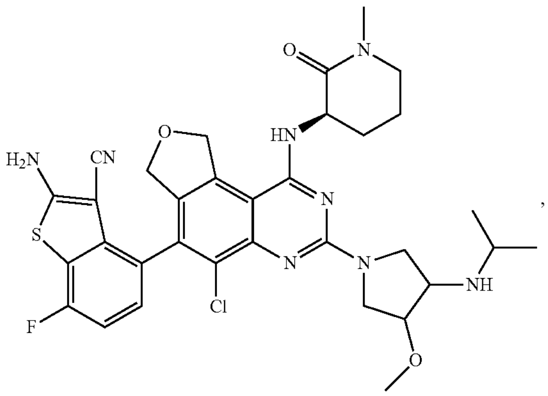
,
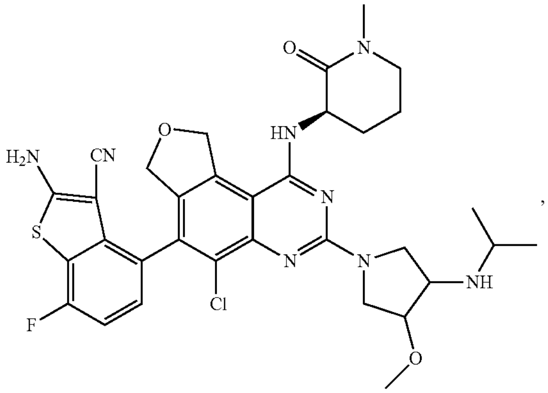
,
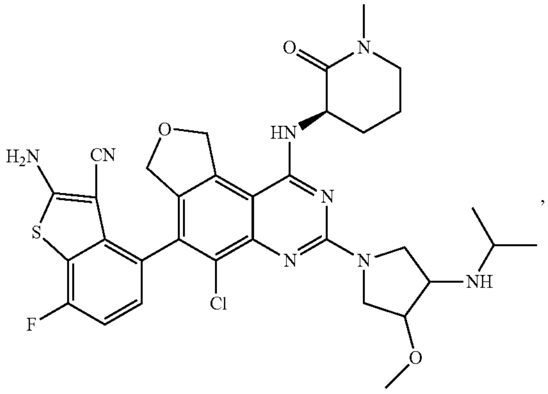
,
-continued
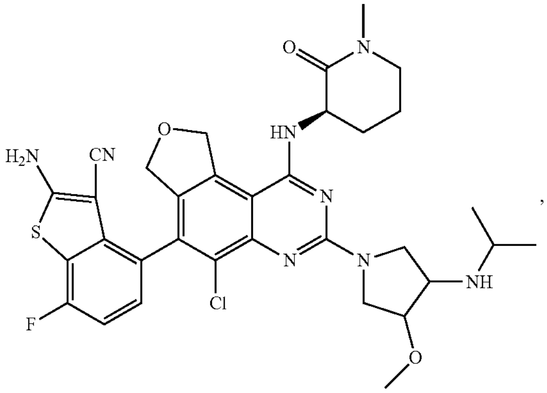
,
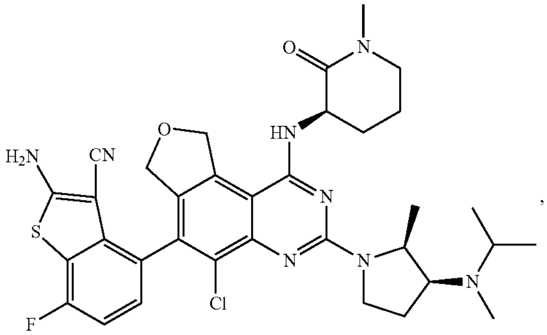
,
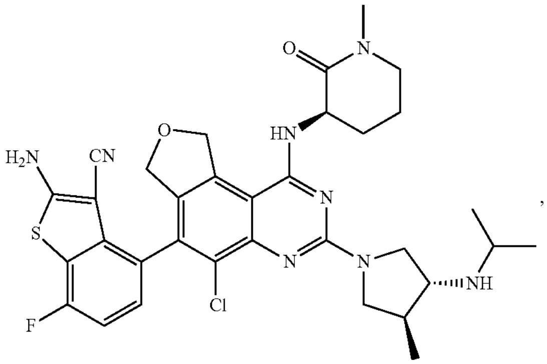
,
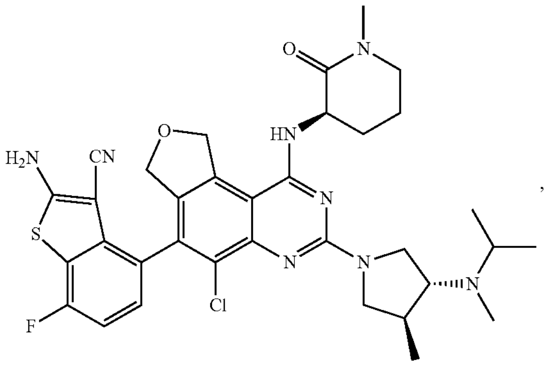
, -continued
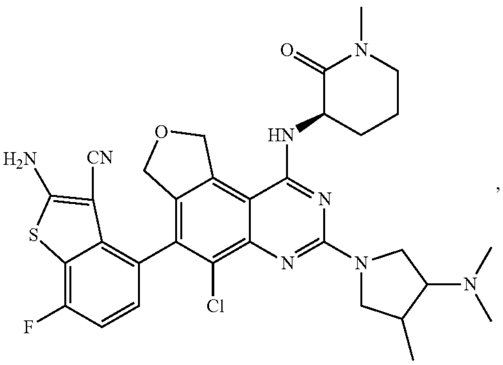
,
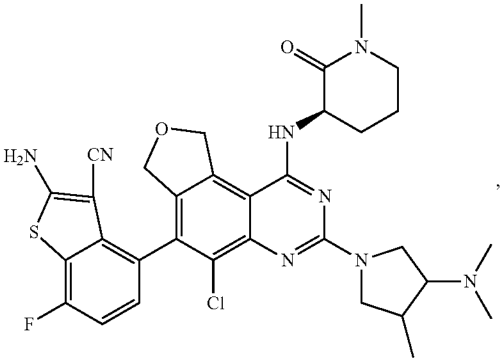
,
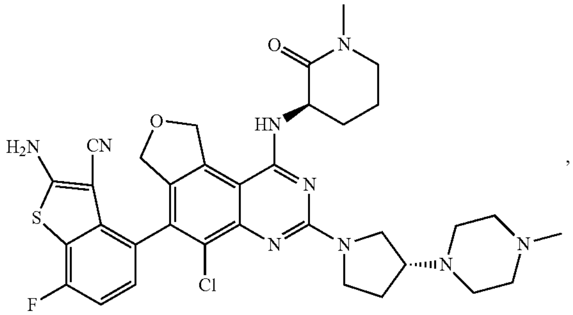
,
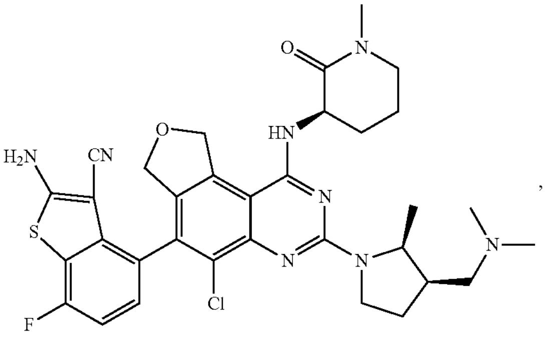
,
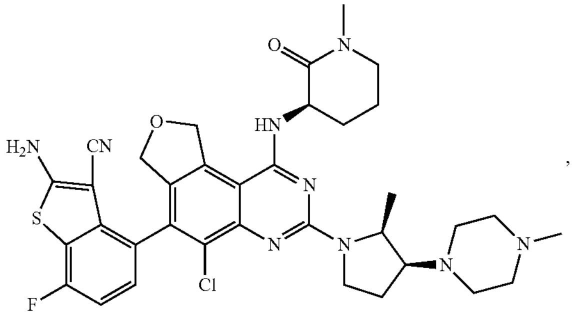
,
-continued
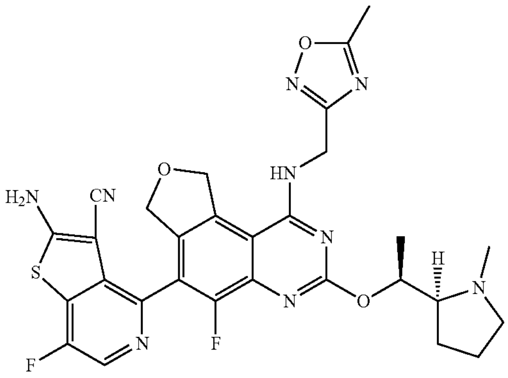
,
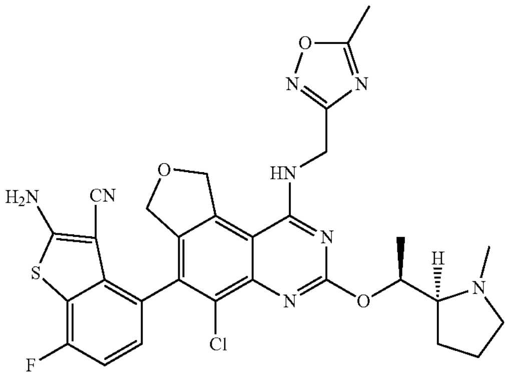
,
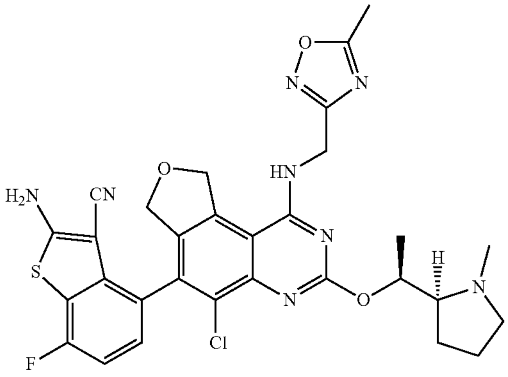
,
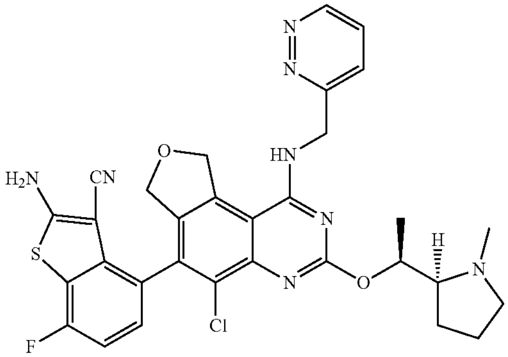
, -continued
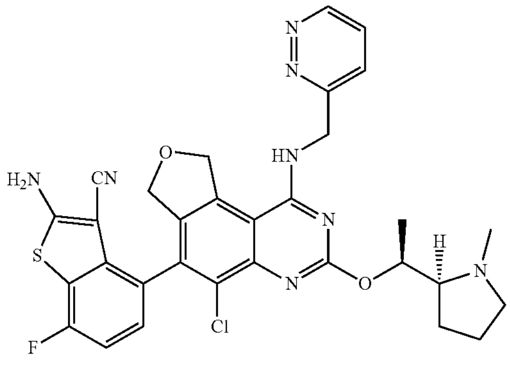
,
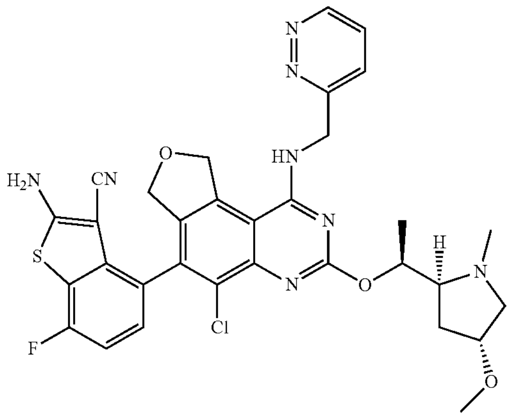
,
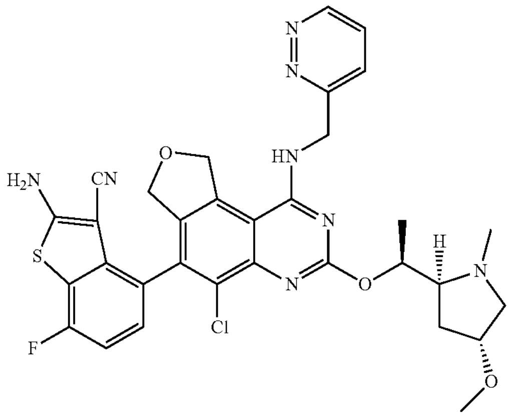
,
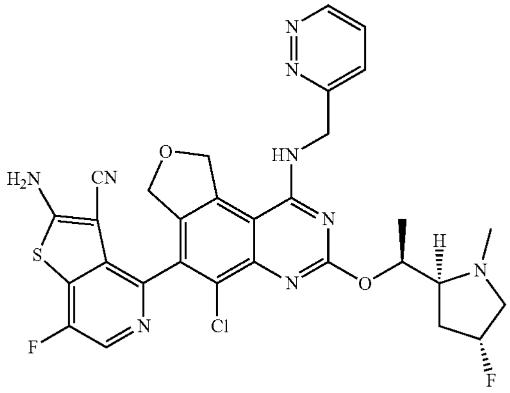
,
-continued
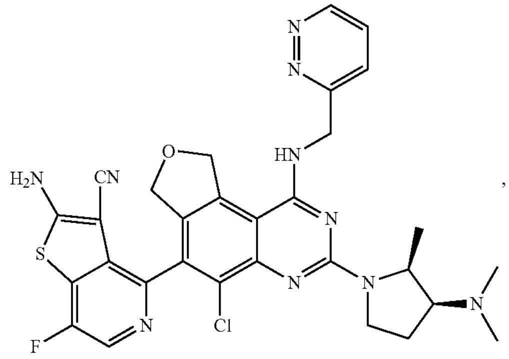
, or
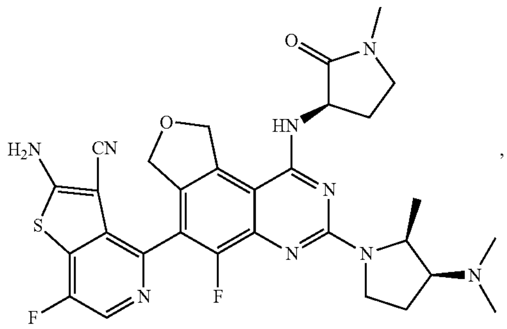
,
or a pharmaceutically acceptable salt thereof.
A further compound of Formula I or a pharmaceutically acceptable salt thereof, the compound is selected from:
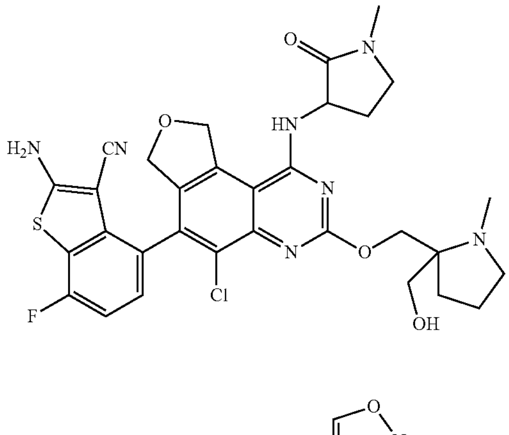
,
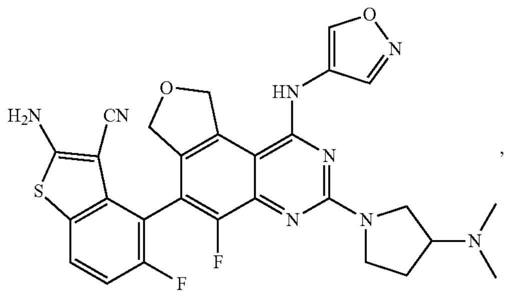
, -continued
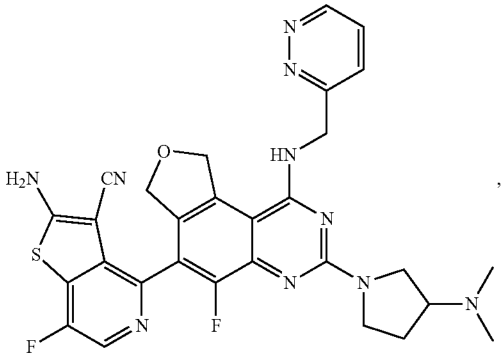
,
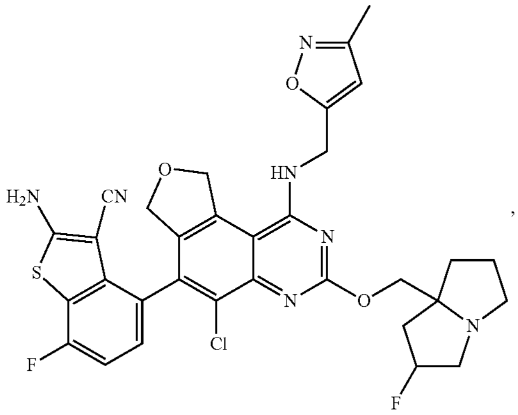
,
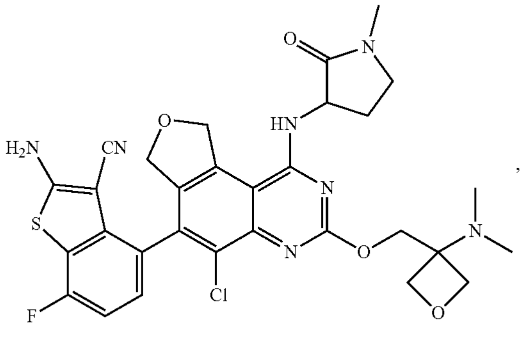
,
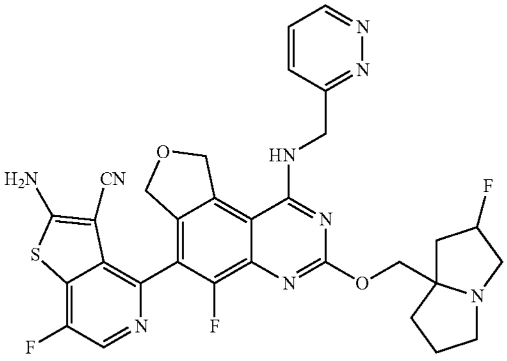
,
-continued
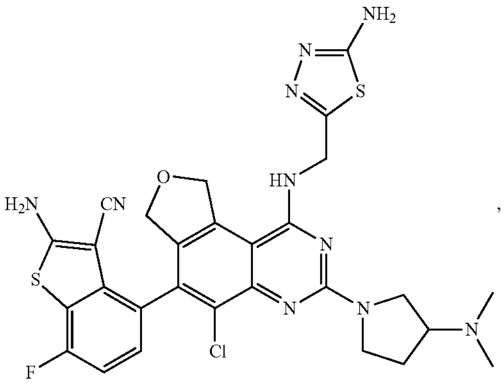
,
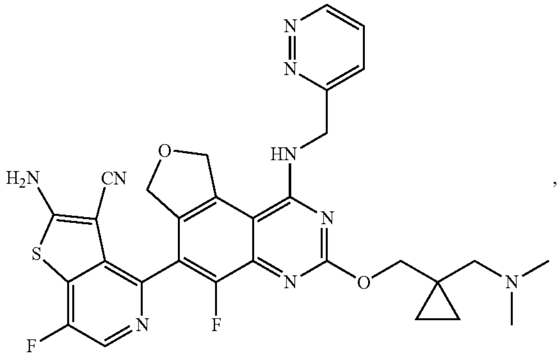
,
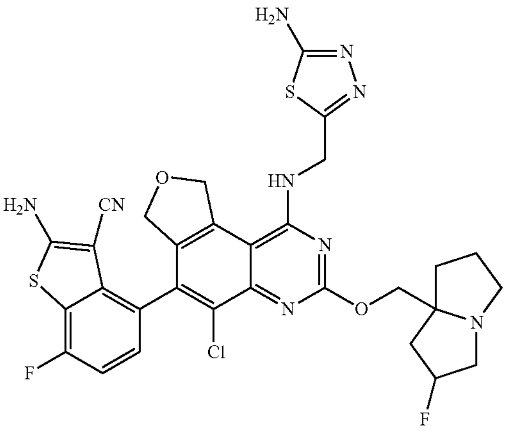
,
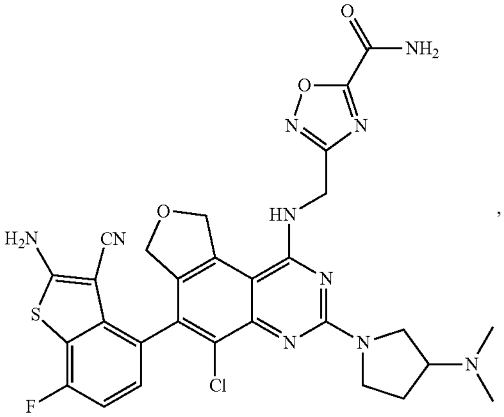
, -continued
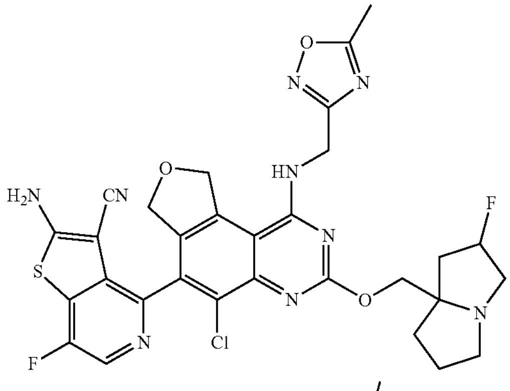
,
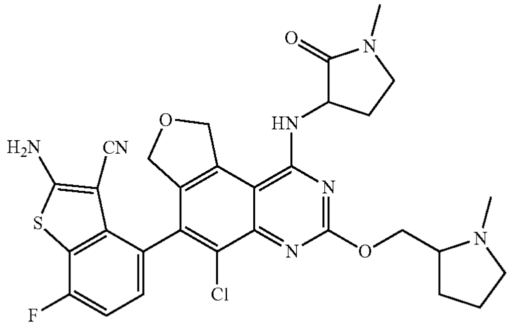
,
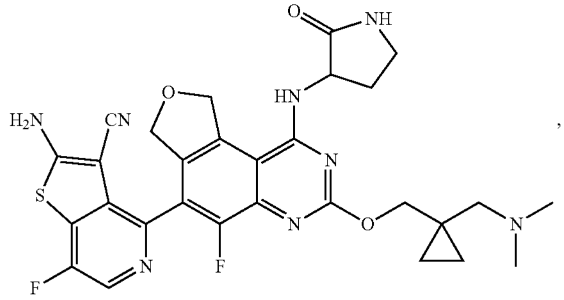
,
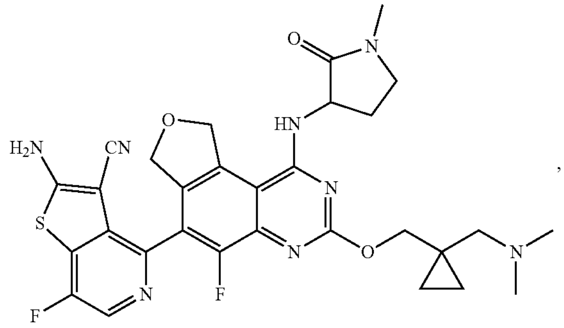
,
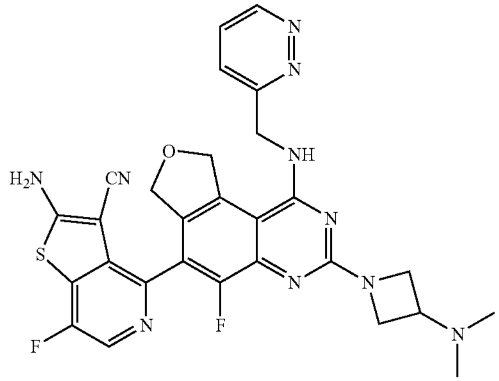
,
-continued
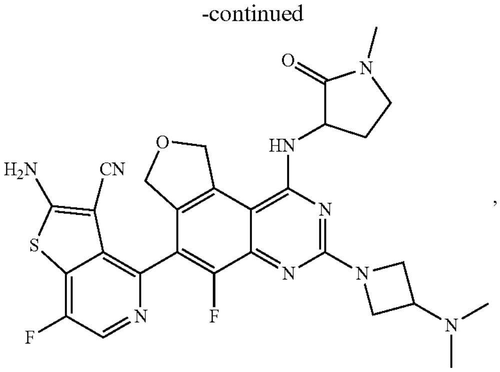
,
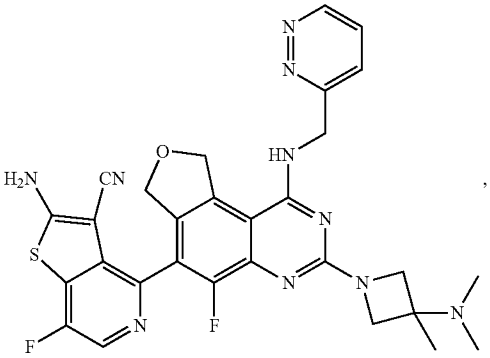
,
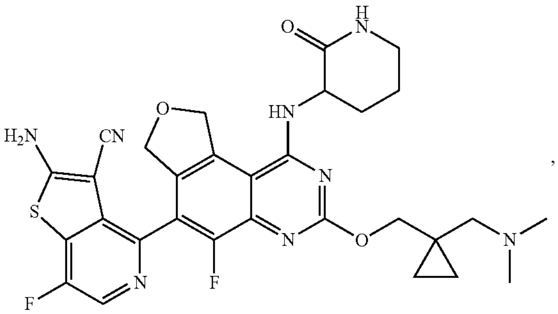
,
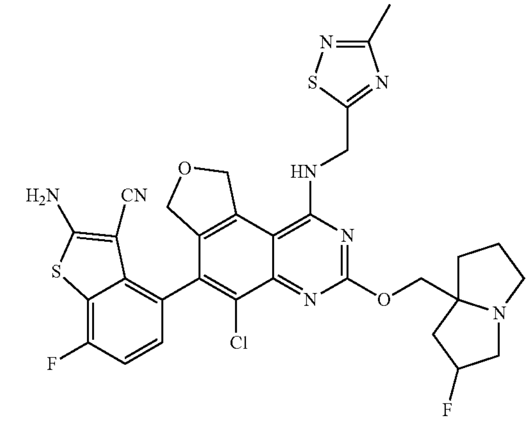
, -continued
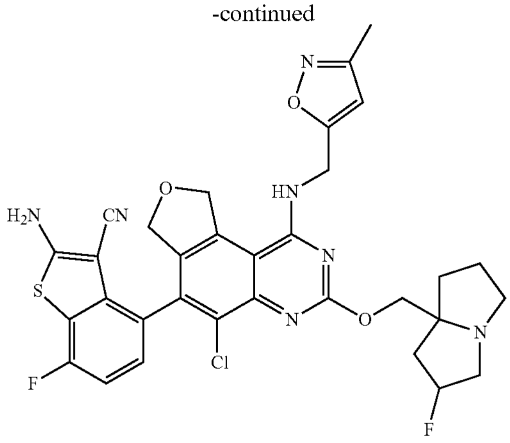
,
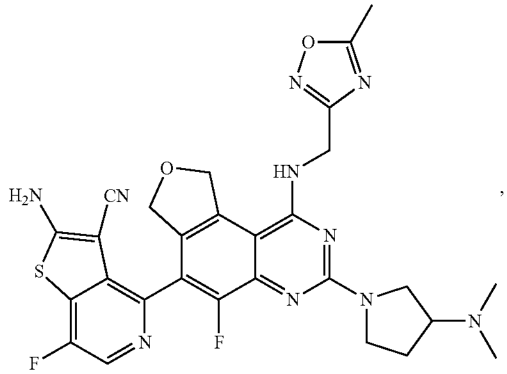
,
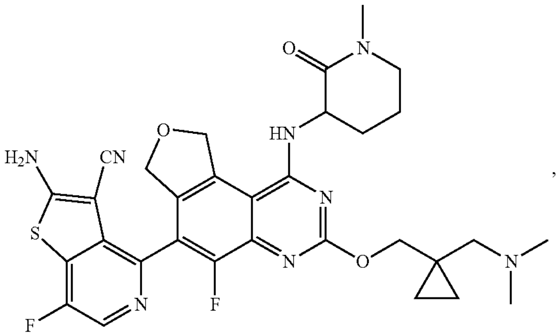
,
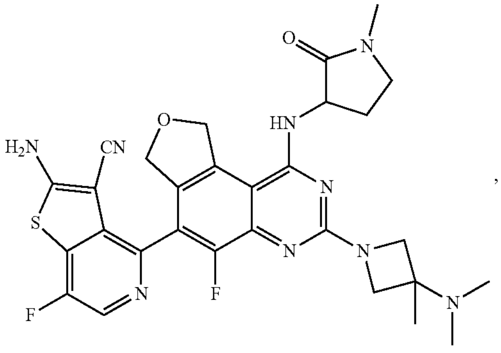
,
-continued
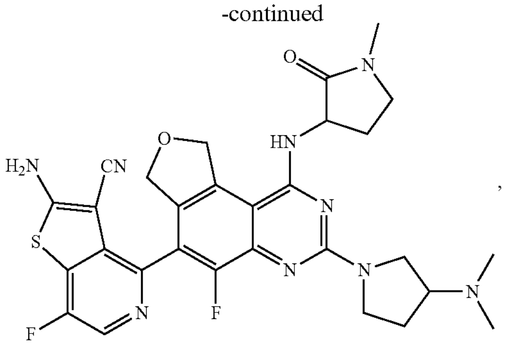
, or
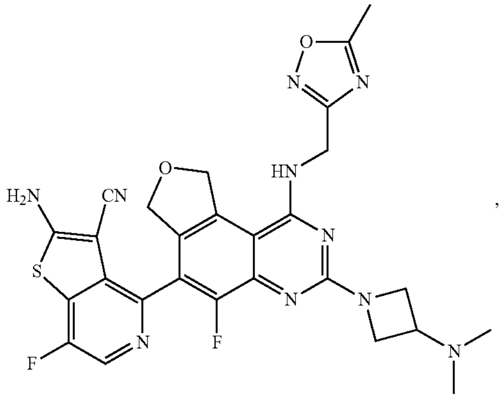 [SMILES: Cc1nc(CNc2nc(N3CC(N(C)C)C3)nc3c(F)c(-c4ncc(F)c5sc(N)c(C#N)c45)c4c(c23)COC4)no1]
,
or a pharmaceutically acceptable salt thereof.
A further compound of Formula I or a pharmaceutically acceptable salt thereof, the compound is selected from:
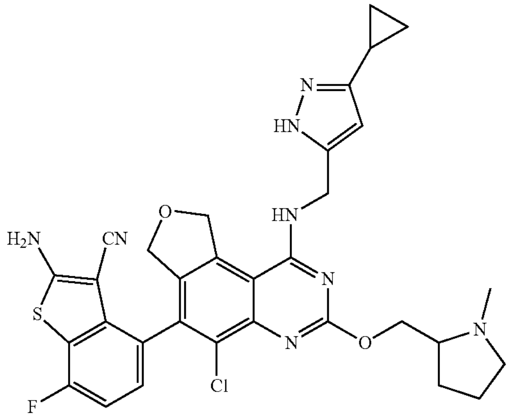
,
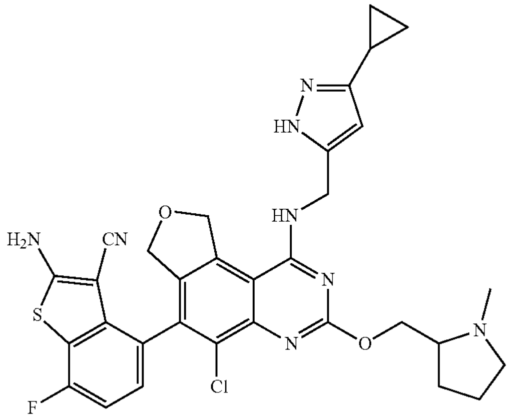
, -continued
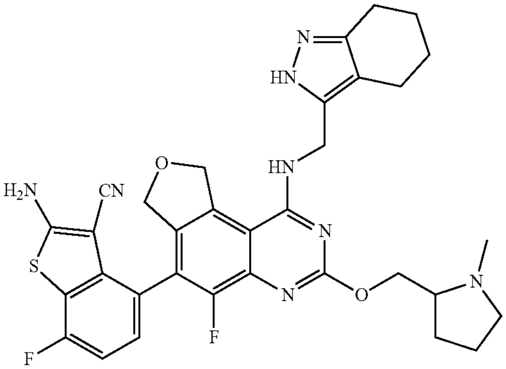
,
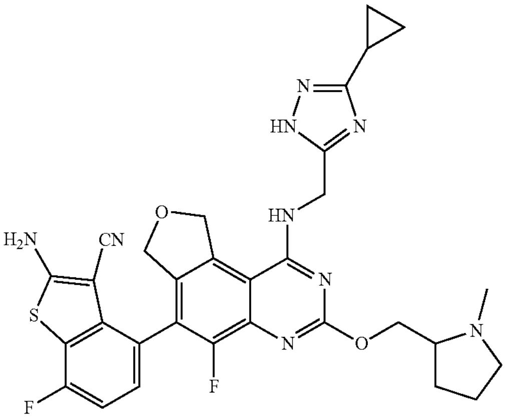
,
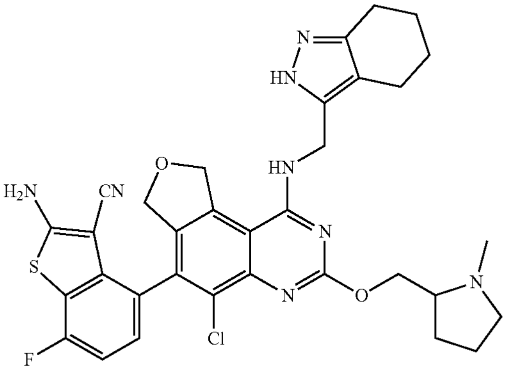
,
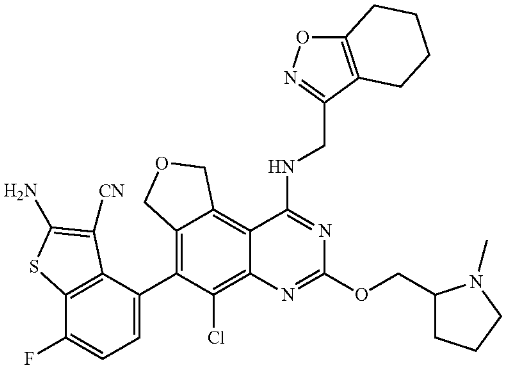
,
-continued
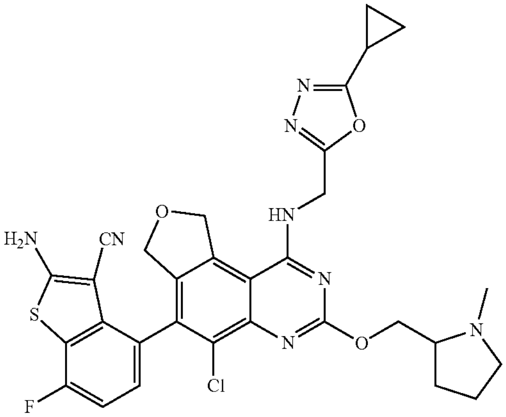
,
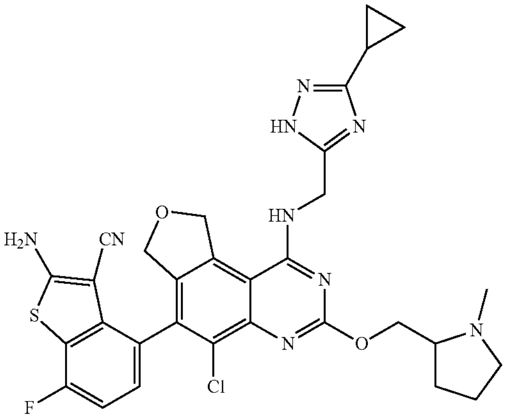
,
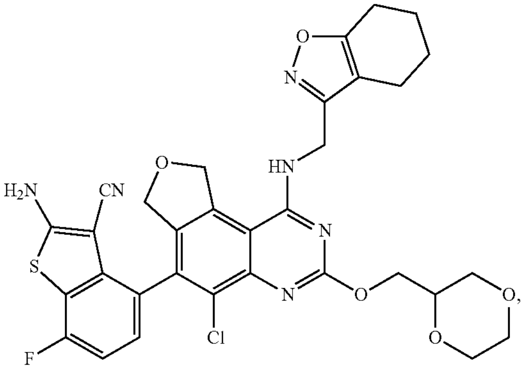
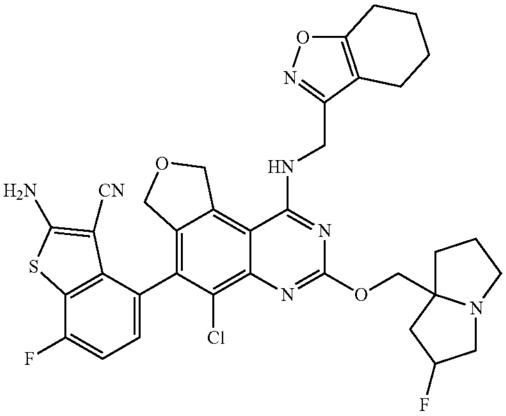
, -continued
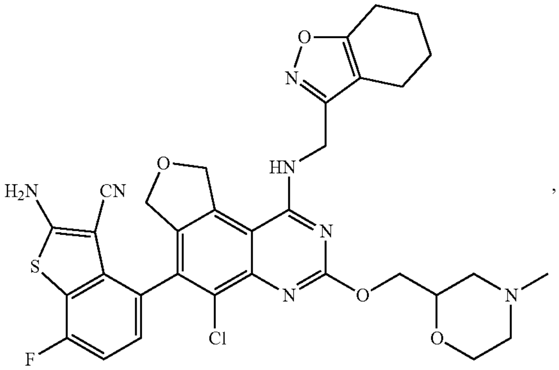
,
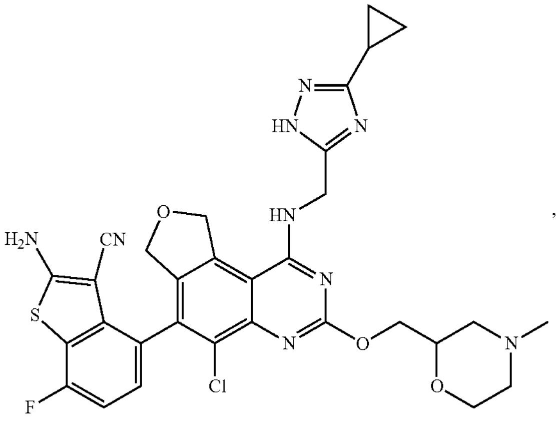
,
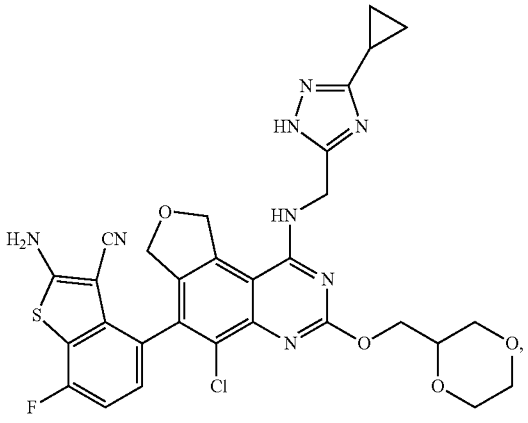
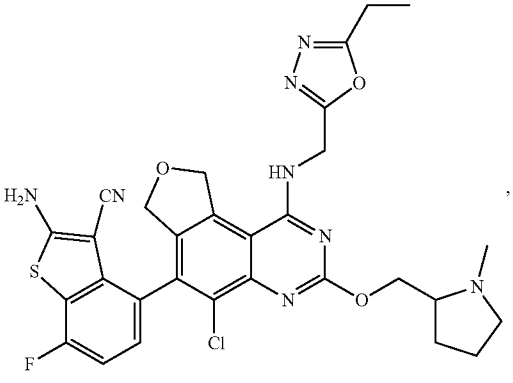
,
-continued
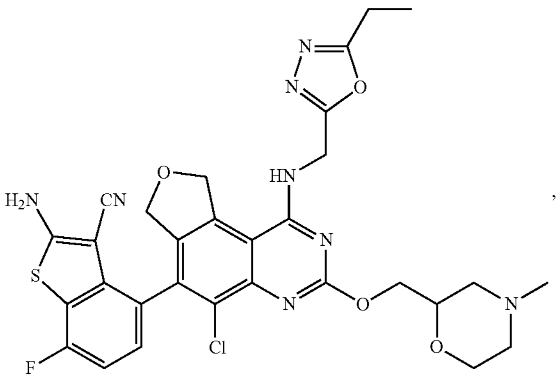
,
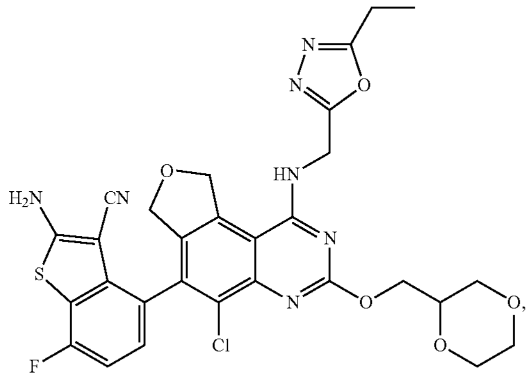
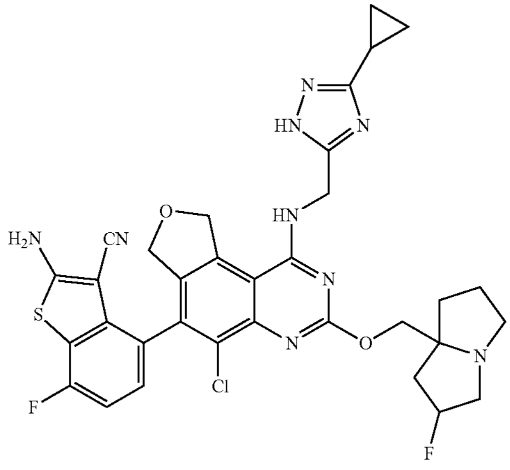
,
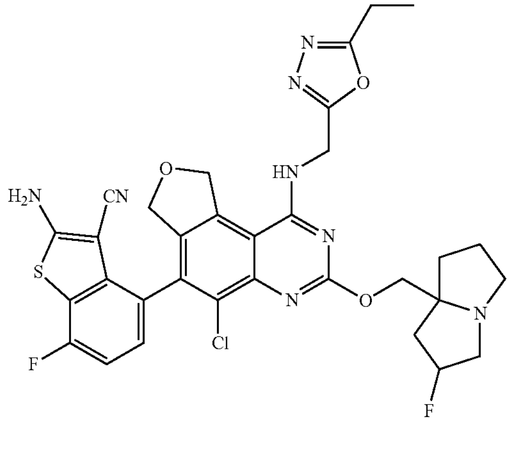
, -continued
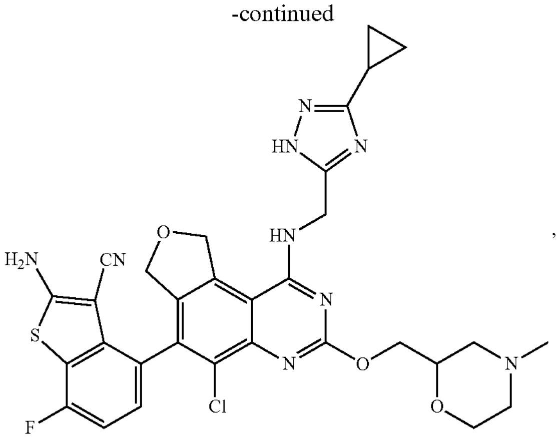
,
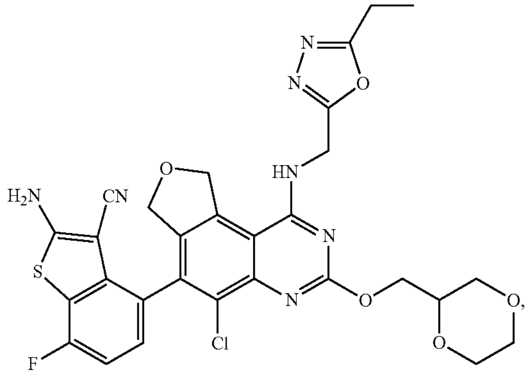
,
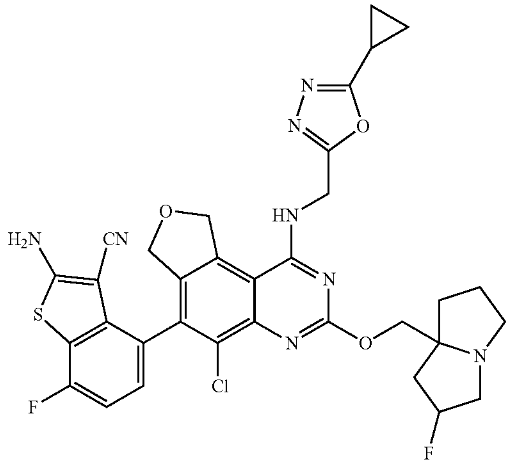
,
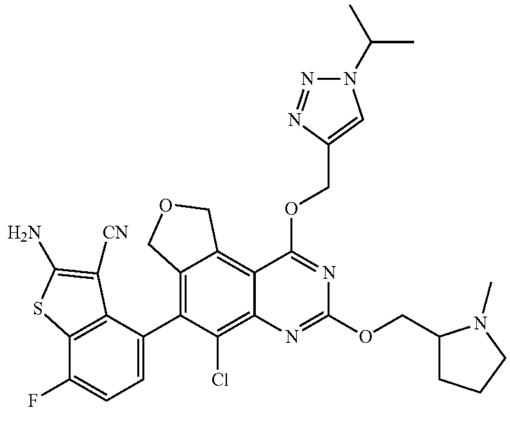
,
-continued
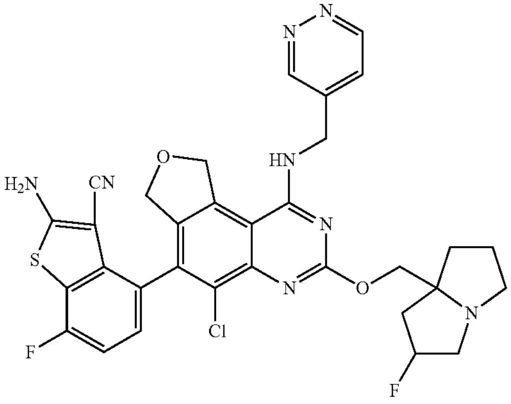
,
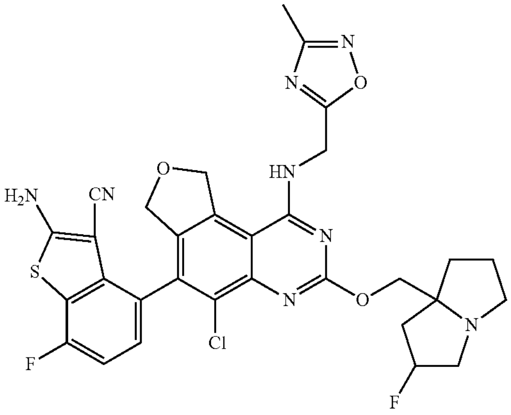
,
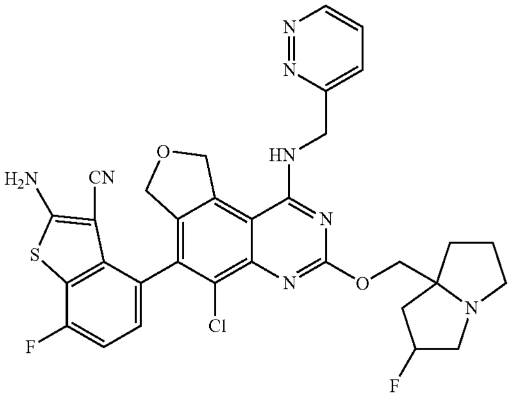
,
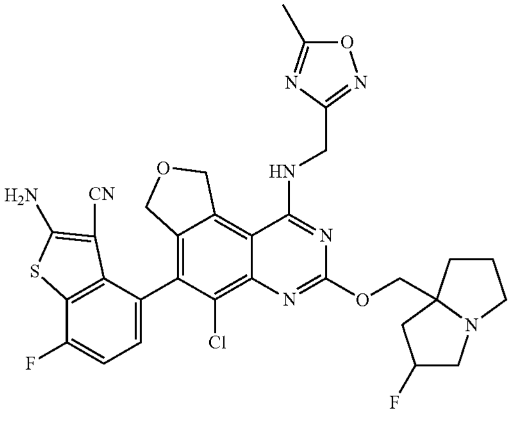
, -continued
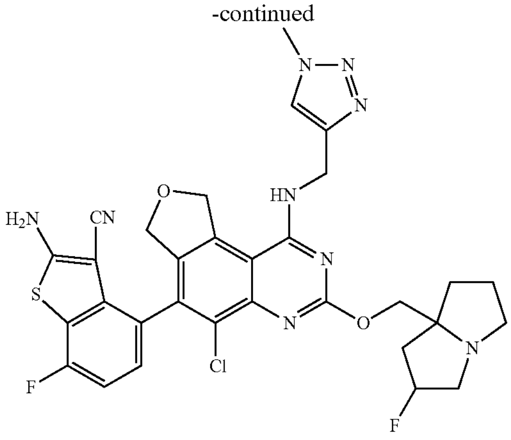
,
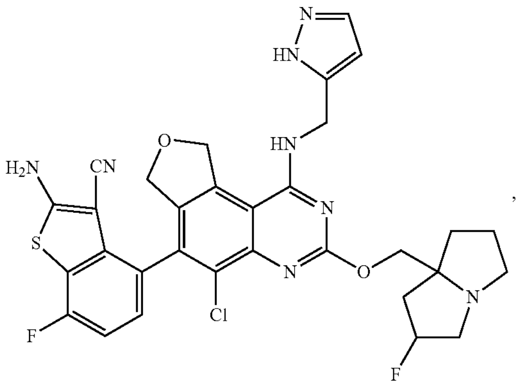
,
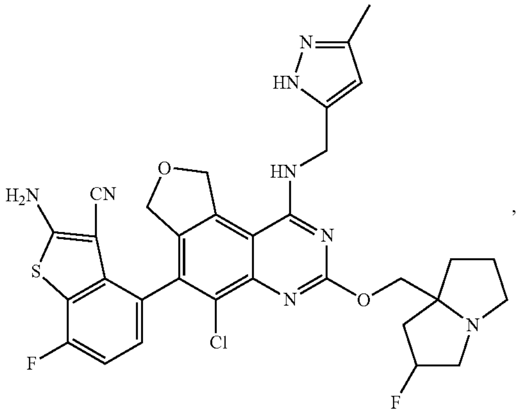
,
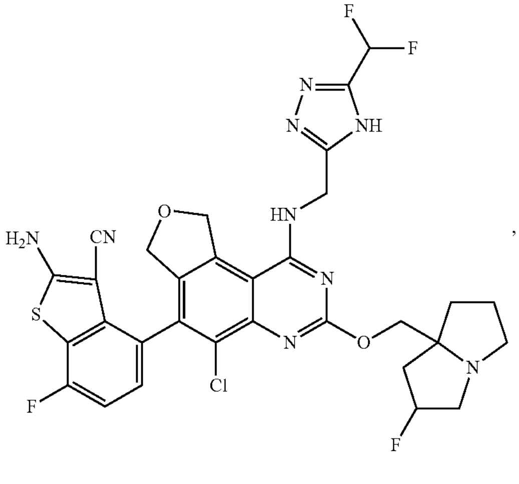
,
-continued
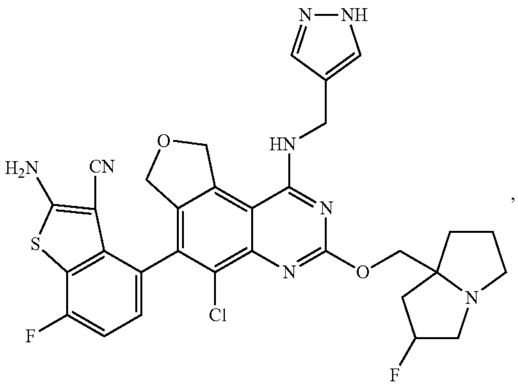
,
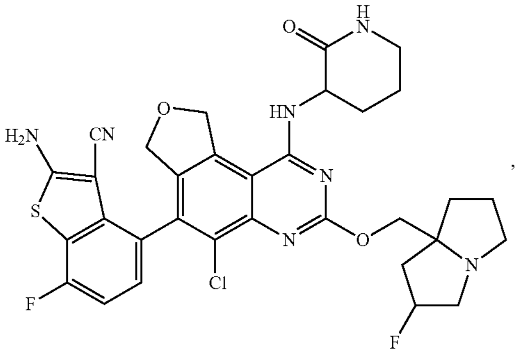
,
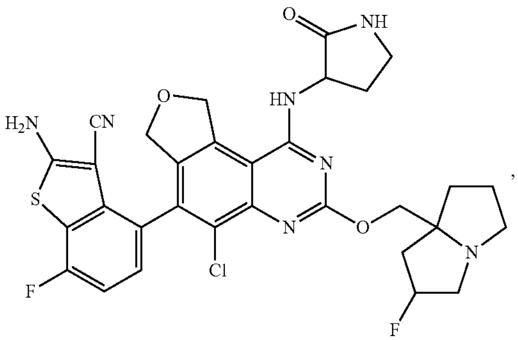
,
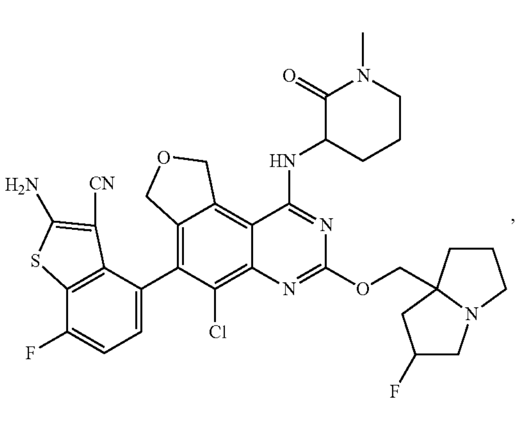
, -continued

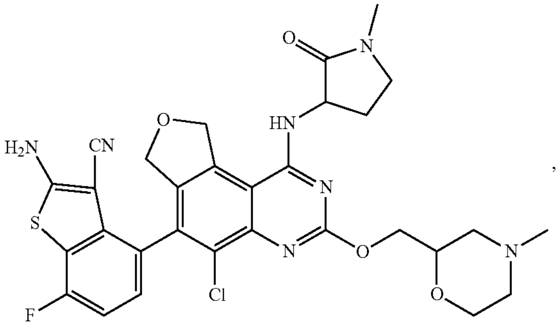

,

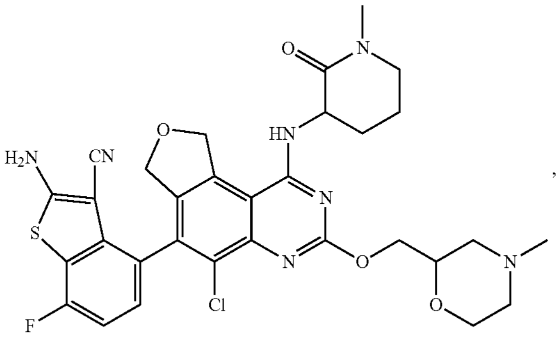

,

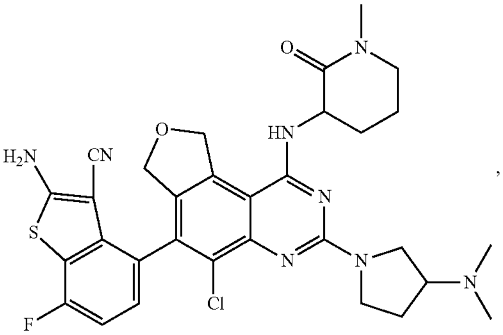

,

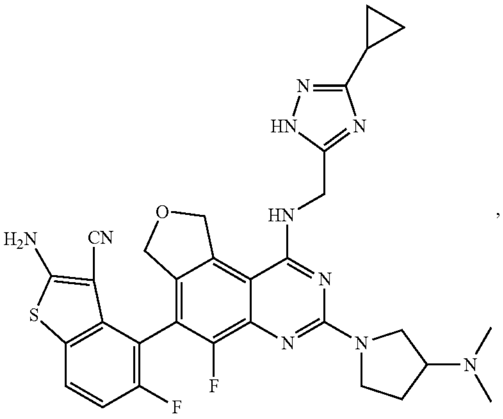

,

-continued

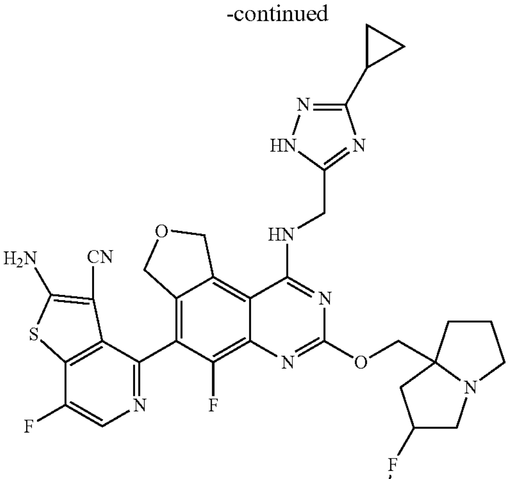

, or

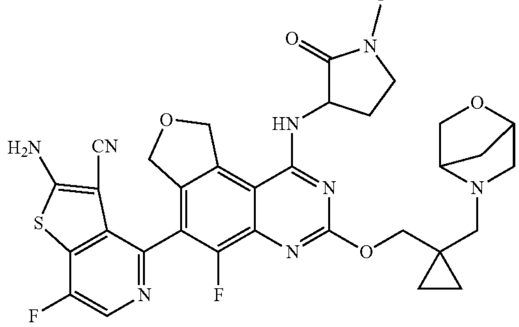

, or a pharmaceutically acceptable salt thereof.

The chemical drawings in the compounds above contain indications of chiral aspects of the specific compounds shown. However, the chemical drawings in the compounds above do not contain all the possible chiral features of these compounds and the chiral indications shown are not intended to exclude changes to the chiral aspects shown. Thus, alternate chiral versions of the compounds as well as different combinations of chiral attributes are contemplated and included herein.

Further provided herein are methods of treating cancer, comprising administering to a patient in need thereof, an effective amount of a compound according to Formula I, or a pharmaceutically acceptable salt thereof. In this method, the cancer can be lung cancer, colorectal cancer, pancreatic cancer, bladder cancer, cervical cancer, endometrial cancer, ovarian cancer, cholangiocarcinoma, gastric, or esophageal cancer. In this method, the cancer can more specifically be non-small cell lung cancer, pancreatic cancer, or colorectal cancer. In an embodiment the cancer can be non-small cell lung cancer. In an embodiment the cancer can be pancreatic cancer. In an embodiment the cancer can be colorectal cancer.

Also provided herein is a method of treating cancer, comprising administering to a patient in need thereof, an effective amount of a compound according to Formula I, or a pharmaceutically acceptable salt thereof, in which the cancer has one or more cells that express a mutant KRas G12C, G12D, and/or G12V protein. In this method, the cancer can be non-small cell lung cancer, pancreatic cancer, or colorectal cancer, in which the cancer has one or more cells that express a KRas G12C, G12D, and/or G12V mutant protein. In an embodiment, the cancer is non-small cell lung carcinoma in which the cancer has one or more cells that express a KRas G12C, G12D, and/or G12V mutant protein.

In an embodiment, the cancer is mutant pancreatic cancer in which the cancer has one or more cells that express a KRas G12C, G12D, and/or G12V mutant protein. In an embodiment, the cancer is colorectal carcinoma in which the cancer has one or more cells that express a KRas G12C, G12D, and/or G12V mutant protein. This method also includes treating KRas G12C, G12D, and/or G12V mutant bearing cancers of other origins.

Further provided herein is a method of treating a patient with a cancer that has a KRas G12C, G12D, and/or G12V mutation comprising administering to a patient in need thereof an effective amount of a compound according to Formula I or a pharmaceutically acceptable salt thereof. In this method, the cancer that has a KRas G12C, G12D, and/or G12V mutation can be KRas G12C, G12D, and/or G12V mutant lung cancer, KRas G12C, G12D, and/or G12V mutant pancreatic cancer, KRas G12C, G12D, and/or G12V mutant cervical cancer, KRas G12C, G12D, and/or G12V mutant esophageal cancer, KRas G12C, G12D, and/or G12V mutant endometrial cancer, KRas G12C, G12D, and/or G12V mutant ovarian cancer, KRas G12C, G12D, and/or G12V mutant cholangiocarcinoma, and KRas G12C, G12D, and/or G12V mutant colorectal cancer. In an embodiment the cancer that has a KRas G12C, G12D, and/or G12V mutation can be KRas G12C, G12D, and/or G12V mutant non-small cell lung cancer. In an embodiment the cancer that has a KRas G12C, G12D, and/or G12V mutation can be KRas G12C, G12D, and/or G12V mutant pancreatic cancer. In an embodiment the cancer that has a KRas G12C, G12D, and/or G12V mutation can be KRas G12C, G12D, and/or G12V mutant colorectal cancer.

Additionally provided herein is a method of modulating a mutant KRas G12C, G12D, and/or G12V enzyme in a patient in need thereof, by administering a compound according to Formula I, or a pharmaceutically acceptable salt thereof. In one embodiment this method comprises inhibiting a human mutant KRas G12C, G12D, and/or G12V enzyme.

Also provided herein is a method of treating cancer in a patient in need thereof, wherein the patient has a cancer that was determined to express the KRas G12C, G12D, and/or G12V mutant protein. The method comprises administering to a patient an effective amount of a compound according to Formula I, or a pharmaceutically acceptable salt thereof. The G12C, G12D, and/or G12V mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g., G12C, G12D, and/or G12V mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

Further provided herein is a compound or a pharmaceutically acceptable salt thereof according to Formula I for use in therapy. The compound or a pharmaceutically acceptable salt thereof, can be for use in treating cancer. For this use in treating cancer, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12C, G12D, and/or G12V protein such as KRas G12C, G12D, and/or G12V mutant lung cancer, KRas G12C, G12D, and/or G12V mutant pancreatic cancer, KRas G12C, G12D, and/or G12V mutant cervical cancer, KRas G12C, G12D, and/or G12V mutant esophageal cancer, KRas G12C, G12D, and/or G12V mutant endometrial cancer, KRas G12C, G12D, and/or G12V mutant ovarian cancer, KRas G12C, G12D, and/or G12V mutant cholangiocarcinoma, and KRas G12C, G12D, and/or G12V mutant colorectal cancer. In these uses, the cancer is selected from: KRas G12C, G12D, and/or G12V mutant non-small cell lung cancer, KRas G12C, G12D, and/or G12V mutant colorectal cancer, and KRas G12C, G12D, and/or G12V mutant pancreatic cancer. Additionally, the cancer can be non-small cell lung cancer, and one or more cells express KRas G12C, G12D, and/or G12V mutant protein. Further, the cancer can be colorectal cancer, and one or more cells express KRas G12C, G12D, and/or G12V mutant protein. Additionally, the cancer can be pancreatic cancer, and one or more cells express KRas G12C, G12D, and/or G12V mutant protein. The patient can have a cancer that was determined to have one or more cells expressing the KRas G12C, G12D, and/or G12V mutant protein prior to administration of the compound or a pharmaceutically acceptable salt thereof. The patient may have been treated with a different course of treatment prior to being treated as described herein.

The compounds provided herein according to Formula I, or a pharmaceutically acceptable salt thereof, may also be used in the manufacture of a medicament for treating cancer. When used in the manufacture of a medicament, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12C, G12D, and/or G12V protein. When the cancer cells express KRas G12C, G12D, and/or G12V protein, the cancer can be selected from KRas G12C, G12D, and/or G12V mutant non-small cell lung cancer, KRas G12C, G12D, and/or G12V mutant colorectal cancer, and KRas G12C, G12D, and/or G12V mutant pancreatic cancer.

Also provided herein is a method of treating cancer, comprising administering to a patient in need thereof, an effective amount of a compound according to Formula I, or a pharmaceutically acceptable salt thereof, and one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in which the cancer has one or more cells that express a mutant KRas G12C, G12D, and/or G12V protein. Further provided herein is a compound according to Formula I, or a pharmaceutically acceptable salt thereof, for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer. Additionally provided is a combination comprising a compound according to Formula I, or a pharmaceutically acceptable salt thereof, and one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, for simultaneous, separate, or sequential use in the treatment of cancer.

Also provided is a method of treating cancer, comprising administering to a patient in need thereof, an effective amount of a compound according to Formula I, or a pharmaceutically acceptable salt thereof, and a PD-1 or PD-L1 inhibitor, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a PD-1 or PD-L1 inhibitor, for use in the treatment of cancer. Additionally provided is a combination comprising a compound according to Formula I, or a pharmaceutically acceptable salt thereof, and a PD-1 or PD-L1 inhibitor, for simultaneous, separate, or sequential use in the treatment of cancer. As used herein, the PD-1 or PD-L1 inhibitor can be pembrolizumab; the PD-1 or PD-L1 inhibitor can be nivolumab; the PD-1 or PD-L1 inhibitor can be cemiplimab; the PD-1 or PD-L1 inhibitor can be sintilimab; the PD-1 or PD-L1 inhibitor can be atezolizumab; the PD-1 or PD-L1 inhibitor can be avelumab; the PD-1 or PD-L1 inhibitor can be durvalumab; or the PD-1 or PD-L1 inhibitor can be lodapilimab. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and a CDK4/CDK6 inhibitor, or a pharmaceutically acceptable salt thereof, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a CDK4/CDK6 inhibitor, or a pharmaceutically acceptable salt thereof, for use in the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRas G12C, G12D, and/or G12V protein. As used herein, the CDK4/CDK6 inhibitor can be abemaciclib; the CDK4/CDK6 inhibitor can be palbociclib; or the CDK4/CDK6 inhibitor can be ribociclib. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and an EGFR inhibitor, or a pharmaceutically acceptable salt thereof, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with an EGFR inhibitor, or a pharmaceutically acceptable salt thereof, for the treatment of cancer. Additional provided is a combination comprising a compound according to Formula I, or a pharmaceutically acceptable salt thereof, and an EGFR inhibitor, or a pharmaceutically acceptable salt thereof, for simultaneous, separate, or sequential use in the treatment of cancer. As used herein, the EGFR inhibitor can be erlotinib; the EGFR inhibitor can be afatinib; the EGFR inhibitor can be gefitinib; the EGFR inhibitor can be cetuximab. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and an ERK inhibitor, or a pharmaceutically acceptable salt thereof, in which the cancer has one or more cells that express a mutant KRas G12C, G12D, and/or G12V protein. Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with an ERK inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and an ERK inhibitor, or a pharmaceutically acceptable salt thereof, for simultaneous, separate, or sequential use in the treatment of cancer. As used herein, the ERK inhibitor can be LY3214996; the ERK inhibitor can be LTT462; or the ERK inhibitor can be KO-947. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and an Aurora A inhibitor, for simultaneous, separate, or sequential use in the treatment of cancer. As used herein, the Aurora A inhibitor can be alisertib, tozasertib, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid: 2-methyl-propan-2-amine (1:1) salt, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:amine (1:1) salt, or a pharmaceutically acceptable salt thereof. In one embodiment, the Aurora A inhibitor is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and a SHP2 inhibitor, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a SHP2 inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and a SHP2 inhibitor, for simultaneous, separate, or sequential use in the treatment of cancer. As used herein, the SHP2 inhibitor, or a pharmaceutically acceptable salt thereof, can be a Type I SHP2 Inhibitor or a Type II SHP2 Inhibitor. Examples of Type I SHP2 inhibitors include, but are not limited to, PHPS1, GS-493, NSC-87877, NSC-117199, and Cefsulodin, and pharmaceutically acceptable salts thereof. Examples of Type II SHP2 inhibitors include, but are not limited to, JAB-3068, JAB-3312, RMC-4550, RMC-4630, SHP099, SHP244, SHP389, SHP394, TNO155, RG-6433, and RLY-1971, and pharmaceutically acceptable salts thereof. Additional examples of SHP2 inhibitors include, but are not limited to, BBP-398, IACS-15509, IACS-13909, X37, ERAS-601, SH3809, HBI-2376, ETS-001, and PCC0208023, and pharmaceutically acceptable salts thereof. This method also includes treating KRas G12C, G12D, and/or G12V mutant protein mutant bearing cancers of other origins. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and a platinum agent, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a platinum agent, or a pharmaceutically acceptable salt thereof, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and a platinum agent, for simultaneous, separate, or sequential use in the treatment of cancer. As used herein, the platinum agent can be cisplatin; the platinum agent can be carboplatin; or the platinum agent can be oxaliplatin. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and pemetrexed, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with pemetrexed, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and pemetrexed, for simultaneous, separate, or sequential use in the treatment of cancer, in which the cancer has one or more cells that express a mutant KRas G12C, G12D, and/or G12V protein. As described herein, the cancer can be colorectal carcinoma in which the cancer has one or more cells that express a KRas G12C, G12D, and/or G12V mutant protein or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

The term "pharmaceutically acceptable salt" as used herein refers to a salt of a compound considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences,* 1977, 66(1), 1-19.

Pharmaceutical compositions containing the compounds of Formula I as described herein may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., $22^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in achieve a desired therapeutic result such as treating a disorder or disease, like a cancerous lesion or progression of abnormal cell growth and/or cell division. Factors considered in the determination of an effective amount or dose of a compound include: whether the compound or its salt will be administered; the co-administration of other agents, if used; the species of patient to be treated; the patient's size, age, gender, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Pharmaceutical compositions can be formulated as a tablet or capsule for oral administration, a solution for oral administration, or an injectable solution. The tablet, capsule, or solution can include a compound of the present invention in an amount effective for treating a patient in need of treatment for cancer.

As used herein, the terms "treating", "to treat", or "treatment", includes slowing, controlling, delaying, reducing, stopping, reversing, preventing, or ameliorating the progression or severity of an existing symptom, disorder, condition, which can include specifically slowing the growth of a cancerous lesion or progression of abnormal cell growth and/or cell division. Treating does not necessarily indicate a total elimination of all disorder or disease symptoms.

As used herein, the term "patient" refers to a mammal in need of treatment. Specifically, the patient can be a human that is in need of treatment for cancer, for example, KRas G12C, G12D, and/or G12V mutant protein mutant bearing cancers.

Certain abbreviations are defined as follows: "ACN" refers to acetonitrile; "AcOH" or "HOAc" refer to acetic acid; AIBN" refers to azobisisobutyronitrile; "Alloc" refers to the allyloxycarbonyl group; "aq." refers to aqueous; "atm" refers to atmosphere or atmospheres; "Boc-Gly-OH" refers to N-(tert-butoxycarbonyl)glycine; "BrettPhos" refers to 2-dicyclohexylphosphino-3,6-dimethoxy-2',4',6'-triisopropyl-1,1'-biphenyl; "BroP" refers to bromo tris(dimethylamino) phosphonium hexafluorophosphate; "Cbz" refers to the benzyloxycarbonyl group; "Cbz-Cl" refers to benzyl chloroformate; "conc." refers to concentrated; "CSI" refers to chlorosulfonyl isocyanate; "CV" refers to column volumes; "DCM" refers to dichloromethane; "DIAD" refers to diisopropyl azodicarboxylate; "DIBAL-H" refers to diisobutylaluminum hydride; "DIEA" and "DIPEA" refer to N,N-diisopropyl ethylamine; "(dippf)Rh(cod)BF4" refers to [1,4-bis(diphenylphosphino)butane](1,5-cyclooctadiene) rhodium(I) tetrafluoroborate; "DMAP" refers to 4-dimethylaminopyridine; "DMEA" refers to N,N-dimethylethylamine; "DMEM" refers to Dulbecco's modified Eagle's medium; "DMF" refers to N,N-dimethylformamide; "DMSO" refers to dimethylsulfoxide; "DNA" refers to deoxyribonucleic acid; "DPEPhosPd$Cl_2$" refers to dichlorobis(diphenylphosphinophenyl)ether palladium (II); "DTT" refers to dithiothreitol; "EDTA" refers to ethylenediaminetetraacetic acid; "EGTA" refers to ethylene glycol-bis(b-aminoethyl ether)-N,N,N',N'-tetraacetic acid; "ELISA" refers to enzyme-linked immunosorbent assay; "ERK" refers to extracellular signal-regulated kinases; "EtOAc" refers to ethyl acetate; "$Et_2O$" refers to diethyl ether; "EtOH" refers to ethanol; "FA" refers to formic acid; "FBS" refers to fetal bovine serum; "Fmoc" refers to the fluorenylmethyloxycarbonyl group; "GDP" refers to guanosine diphosphate; "GTP" refers to guanosine triphosphate; "h" refers to hour or hours; "HATU" refers to 1-[Bis(dimethylamino)methylene]-1H-1,2,3-triazolo[4,5-b]pyridinium 3-oxide hexafluorophosphate; "Hex" or "hex" refers to hexane or hexanes; "HPLC" refers to high-performance liquid chromatography; "HRP" refers to horseradish peroxidase; "IPA" refers to isopropyl alcohol; "IPAm" refers to isopropyl amine; "KOAc" refers to potassium acetate; "LC-ES/MS" refers to liquid chromatograph-electrospray mass spectrometry; "LC-MS" refers to liquid chromatography mass spectrometry; "LiHMDS" refers to lithium bis(trimethylsilyl)amide; "L-prolinol" refers to [(2S)-pyrrolidin-2yl] methanol; "MAPK" refers to mitogen-activated protein kinases; "mCPBA" refers to 3-chloro-peroxybenzoic acid; "Me" refers to a methyl group; "MeOH" refers to methanol; "min" refers to minute or minutes; "MTBE" refers to methyl tert-butyl ether; "NaBH$(OAc)_3$ refers to sodium triacetoxyborohydride; "NaOMe" refers to sodium methoxide; "NBS" refers to N-bromosuccinimide; "NCS" refers to N-chlorosuccinimide; "N-methyl-L-prolinol" refers to [(2S)-1-methylpyrrolidin-2-yl]methanol; "NMM" refers to N-methylmorpholine; "NMP" refers to 1-methylpyrrolidin-2-one; "NIS" refers to N-iodosuccinimide; "PCR" refers to polymerase chain reaction; "Pd-117" refers to dichloro[bis(2-(diphenylphosphino)phenyl)ether]palladium(II), CAS 205319-06-8; "Pd-118" refers to 1,1'-bis(di-tert-butylphosphino)ferrocene palladium dichloride, CAS 95408-45-0;

"$Pd_2(dba)_3$" refers to tris(dibenzylideneacetone)dipalladium (0); "$Pd(dppf)Cl_2$" refers to [1,1'-bis(diphenylphosphino) ferrocene]dichloropalladium(II); "$Pd(OAc)_2$ refers to palladium (II) acetate; $Pd(PPh_3)_4$ refers to tetrakis (triphenylphosphine)palladium(0); "PE" refers to petroleum ether or diethyl ether; "Ph" refers to phenyl; "RBF" refers to round bottom flask; "RPMI" refers to Roswell Park Memorial Institute; "RT" refers to room temperature; "RuPhos" refers to 2-dicyclohexylphosphino-2',6'-diisopropoxy-1,1'-biphenyl, CAS 787618-22-8; "sat." refers to saturated; "SCX" refers to strong cation exchange; "Selectfluor™" refers to 1-chloromethyl-4-fluoro-1,4-diazoniabicyclo [2.2.2]octane bis(tetrafluoroborate), "SPE" refers to solid phase extraction; "SPhos" refers to 2-dicyclohexylphosphino-2',6'-dimethoxy-1,1'-biphenyl; "TBAF" refers to tetrabutylammonium fluoride; "TBDMSCl" refers to tert-butyldimethylsilyl chloride; "TBDMS" refers to the tert-butyldimethylsilyl group; "ttBu" refers to the tert-butyl group; "t-BuOH" refers to tert-butanol or tert-butyl alcohol; A" refers to triethylamine; "TES" refers to triethylsilane; "$Tf_2O$" refers to trifluoromethanesulfonic anhydride; "TFA" refers to trifluoracetic acid; "THF" refers to tetrahydrofuran; "TMEDA" refers to tetramethylethylenediamine; "tR" refers to retention time; "XantPhos" refers to 4,5-bis(diphenylphosphino)-9,9-dimethylxanthene; "XPhos" refers to 2-(dicyclohexylphosphino)-2',4',6'-tri-isopropyl-1,1'-biphenyl; "XPhos Palladacycle G2" refers to chloro(2-dicyclohexylphosphino-2',4',6'-triisopropyl-1,1'-biphenyl)[2-(2'-amino-1,1'-biphenyl)]palladium(II), CAS 1310584-14-5; "XPhos Palladacycle Gen.4" or "XPhos Pd G4" refer to methanesulfonato(2-dicyclohexylphosphino-2',4',6'-triisopropyl-1,1'-biphenyl)(2'-methylamino-1,1'-biphenyl-2-yl) palladium(II), CAS 1599466-81-5.

Individual isomers, enantiomers, diastereomers, and atropisomers may be separated or resolved at any convenient point in the synthesis of compounds listed below, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994). The molecules described herein include compounds that are atropisomers and which can exist in different conformations or as different rotomers. Atropisomers are compounds that exist in different conformations arising from restricted rotation about a single bond. Atropisomers can be isolated as separate chemical species if the energy barrier to rotation about the single bond is sufficiently high that the rate of interconversion is slow enough to allow the individual rotomers to be separated from each other. This description is intended to include all of the isomers, enantiomers, diastereomers, and atropisomers possible for the compounds disclosed herein or that could be made using the compounds disclosed herein. In the molecules described herein, only molecules in which the absolute conformation of a chiral center (or atropisomer conformation) is known have used naming conventions or chemical formula that are drawn to indicate the chirality or atropisomerism. Those of skill in the art will readily understand when other chiral centers are present in the molecules described herein and be able to identify the same.

Compounds of any one of Formula I that are chemically capable of forming salts are readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977).

LIST OF EMBODIMENTS

The following is a list of embodiments which are illustrative and should not be interpreted to limit the scope of the claimed subject matter.

1. A compound of the formula:

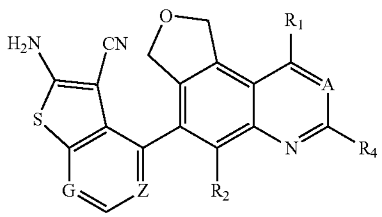

wherein:

A is —C(H)—, or —N—;

Z is —$C(R_{3c})$— or —N—;

G is —$C(R_{3b})$— or —N—;

$R_1$ is a group of the formula

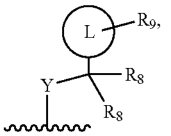

or

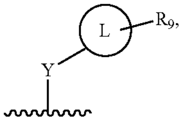

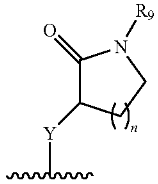

wherein n is 0, 1, or 2;

Y is either —$N(R_8)$—, or —O—;

L is a 5-6 membered heteroaryl containing 1 to 3 heteroatoms selected from O, N, or S, wherein the 5-6 membered heteroaryl may be optionally fused with a $C_{3-6}$ cycloalkyl ring to form a bicyclic ring structure;

$R_2$ is H, halogen, or methyl;

$R_{3b}$, and $R_{3c}$ are each independently H, halogen, or methyl;

$R_4$ is H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; or $R_4$ is a N-linked cyclic amine or a group of the formula

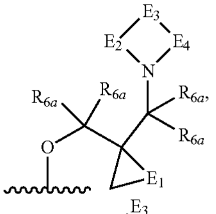

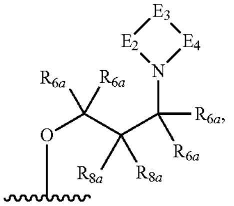

or

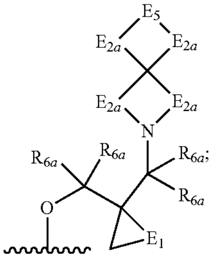

wherein the N-linked cyclic amine is a N-linked:

i. azetidine substituted with $R_{4a}$ and $R_{4b}$ ii. pyrrolidine, piperidine, piperazine, morpholine, diazepane, imidazole or pyrazole; each of which is optionally bridged by a $C_{1-3}$ alkylene, and each of which is optionally substituted with one or more halogen; hydroxyl; —$NR_{6a}R_{6a}$; (1-methylpiperidin-4-yl)oxy; $C_{1-3}$ alkoxy optionally substituted with —$NR_{6a}R_{6a}$; $C_{1-3}$ alkyl optionally substituted with one or more halogen, —$NR_{6a}R_{6a}$ or hydroxyl; an imidazole optionally substituted with a methyl; a monocyclic ring selected from azetidine, piperidine, piperazine, morpholine, oxazepane, or diazepane; a bicycle selected from hexahydro-1H-furo[3,4-c]pyrrole, octahydropyrrolo[3,4-c]pyrrole, or octahydropyrrolo[1,2-a]pyrazine; or a spirocycle selected from 4,7-diazaspiro[2.5]octane, 2-oxa-7-azaspiro[3.5]nonane, 2,6-diazaspiro[3.4]octane or 2-azaspiro[3.3]heptane; wherein the monocyclic ring is optionally bridged by a $C_{1-3}$ alkylene, and can optionally be substituted with one or more halogen, hydroxyl, —CN, $C_{1-3}$ alkoxy, —$NR_{10}R_{10}$, cyclopropyl, oxetane, —CO—$C_{1-3}$ alkyl, or a $C_{1-3}$ alkyl optionally substituted with hydroxyl, $C_{1-3}$ alkoxy, —$NR_{10}R_{10}$, halogen, or —$CF_3$; and wherein the bicyclo or spirocyclo is each optionally substituted with a methyl or a halogen; or iii. iii. 2,6-diazabicyclo[3.2.0]heptane, 3,6-diazabicyclo[3.2.0]heptane, 3,6-diazabicyclo[3.2.1]octane, 2,6-diazabicyclo[3.2.1]octane, 3-azabicyclo[3.1.0]hexane, 3-azabicyclo[3.2.0]heptane, 2-azabicyclo[3.2.0]heptane, octahydro-1H-pyrrolo[3,4-b]pyridine, octahydro-1H-pyrrolo[3,2-b]pyridine, octahydro-6H-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, hexahydro-1H-furo[3,4-b]pyrrole, octahydro-1H-pyrrolo[3,2-b]pyridine, (3as,6as)-tetrahydro-1H,4H-3a,6a-(methanooxymethano)pyrrolo[3,4-c]pyrrole, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, 5-azaspiro[2.4]heptane, 2-oxa-6-azaspiro[3.4]octane, 2,7-diazaspiro[4.4]nonane, 2-oxa-6-azaspiro[3.4]octane or 1-oxa-7-azaspiro[4.4]nonane; each of which is optionally substituted with one or more halogen, —$NR_{6a}R_{6a}$ or a $C_{1-3}$ alkyl optionally substituted with —$NR_{6a}R_{6a}$ or hydroxyl;

$R_{4a}$ is $NR_{4c}R_{4d}$, cyclopropyl, azetidine, pyrrolidine, piperidine, piperazine, morpholine or imidazole, wherein the cyclopropyl, azetidine, pyrrolidine, piperidine, piperazine, or morpholine is optionally substituted with halogen, hydroxyl, $C_{1-3}$ alkoxy or —$NR_{6a}R_{6a}$;

$R_{4b}$ is H, hydroxyl, or $C_{1-3}$ alkyl;

$R_{4c}$ is independently cyclopropyl, or oxetane;

$R_{4d}$ is independently $C_{1-3}$ alkyl;

each $R_{6a}$ is independently H or deuterium;

each $R_{6b}$ is independently H, trideuteromethyl, a $C_{3-5}$ cycloalkyl, a N-methyl pyrrolidine, tetrahydrofuran, tetrahydropyran, bicyclo[1.1.1]pentan-1-yl, bicyclo[1.1.1]pentan-1-ol, or a $C_{1-3}$ alkyl optionally substituted with one or more deuterium, hydroxyl, methyl, methoxy, halogen, cyclopropyl, oxetane, tetrahydrofuran, tetrahydropyran, —CO—NHMe, or —CO—$NH_2$, wherein the $C_{3-5}$ cycloalkyl is optionally substituted with one or more hydroxyl or methyl;

$E_1$ is —O—$C_{1-3}$ alkylene, or $C_{1-3}$ alkylene optionally substituted with one or more halogens;

$E_2$, and $E_4$ are each independently $C_{1-3}$ alkylene optionally substituted with one or more hydroxyl, $C_{1-3}$ alkoxy, or halogen, and wherein $E_2$ and $E_4$ can optionally be bridged by a bond or a $C_{1-3}$ alkylene; and $E_3$ is —O—, —$CR_{7a}R_{7a}$—, —$NR_{9a}$—, or —CO—$NR_{6b}$—; or the ring

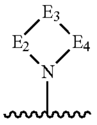

is hexahydro-1H-furo[3,4-c]pyrrole;

Each $E_{2a}$ is independently a $C_{1-3}$ alkylene optionally substituted with one or more hydroxyls;

$E_5$ is —O—, —$CR_{7a}R_{7a}$—, or —$NR_{9a}$—;

each $R_7$ is independently H, or $C_{1-3}$ alkyl;

each $R_{7a}$ is independently H, halogen, CN, hydroxyl, $C_{1-3}$ alkoxy, or $C_{1-3}$ alkyl optionally substituted with one or more halogens or hydroxyls;

each $R_8$ is each independently H or $C_{1-3}$ alkyl; and each $R_{8a}$ is independently a $C_{1-3}$ alkyl; and $R_9$ is a H, —CO—$C_{1-3}$ alkyl, —CO—$NR_8R_8$, —$NR_{9a}R_{9a}$, $C_{1-4}$ alkyl, or $C_{3-6}$ cycloalkyl, wherein the $C_{1-4}$ alkyl or $C_{3-6}$ cycloalkyl is optionally substituted with one or more halogen;

$R_{9a}$ is each independently H, optionally substituted $C_{1-3}$ alkyl or —CO—$C_{1-3}$ alkyl; wherein the optionally substituted $C_{1-3}$ alkyl is optionally substituted with one or more halogens; and $R_{10}$ is H or $C_{1-3}$ alkyl optionally substituted with one or more deuterium or a pharmaceutically acceptable salt thereof.

2. The compound according to embodiment 1, wherein $R_4$ is H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —CH($CH_3$)—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; or $R_4$ is a N-linked cyclic amine or a group of the formula

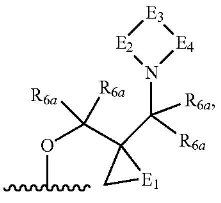

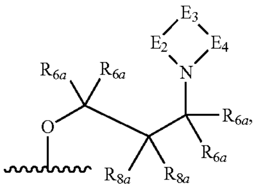

or

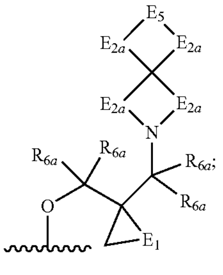

wherein the N-linked cyclic amine is a N-linked:

i. azetidine substituted with $R_{4a}$ and $R_{4b}$ ii. pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, a $C_{1-3}$ alkyl, or an imidazole optionally substituted with a methyl; wherein the azetidine is optionally substituted with hydroxyl or $C_{1-3}$ alkoxy; and the $C_{1-3}$ alkyl is optionally substituted with halogen-$NR_{6a}R_{6a}$ or hydroxyl; or iii. 2,6-diazabicyclo[3.2.0]heptane, 3,6-diazabicyclo[3.2.0]heptane, 3-azabicyclo[3.1.0]hexane, 3-azabicyclo[3.2.0]heptane, octahydro-1H-pyrrolo[3,4-b]pyridine, octahydro-6-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, or 5-azaspiro[2.4]heptane; each of which is optionally substituted with one or more halogen, —$NR_{6a}R_{6a}$ or a $C_{1-3}$ alkyl optionally substituted with —$NR_{6a}R_{6a}$;

$R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$ each $R_{6b}$ is independently H, trideuteromethyl, a $C_{3-5}$ cycloalkyl, or a $C_{1-3}$ alkyl optionally substituted with hydroxyl; and $R_9$ is a H, —CO—$C_{1-3}$ alkyl, —$NR_{9a}R_{9a}$, $C_{1-4}$ alkyl, or $C_{3-6}$ cycloalkyl; or a pharmaceutically acceptable salt thereof.

3. The compound according to embodiment 1 or 2, wherein $R_{3b}$, and $R_{3c}$ are each independently H or halogen, and $R_1$ is a group of the formula

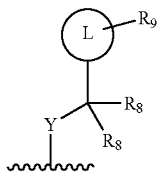

or

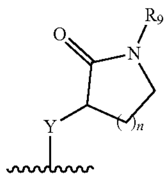

wherein n is 0, 1, or 2;

Y is either —N($R_8$)—, or —O—;

L is a 5-6 membered heteroaryl containing 1 to 3 heteroatoms selected from O, N, or S, wherein the 5-6 membered heteroaryl may be optionally fused with a $C_{3-6}$ cycloalkyl ring to form a bicyclic ring structure;

$R_2$ is H, halogen, or methyl;

$R_4$ is H, methyl, —$CH_2$—OH, —O—$R_5$—$R_6$, —O—$R_6$, N-linked cyclic amine, or azetidine optionally substituted with $NR_7R_7$, wherein $R_8$ is —$CH_2$—, —CH($CH_3$)—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; and $R_9$ is a H, $C_{1-4}$ alkyl, or $C_{3-6}$ cycloalkyl, or a pharmaceutically acceptable salt thereof wherein the $C_{1-4}$ alkyl or $C_{3-6}$ cycloalkyl is optionally substituted with one or more halogen; or a pharmaceutically acceptable salt thereof.

4. The compound according to any one of embodiments 1-3, wherein:

$R_1$ is a group of the formula

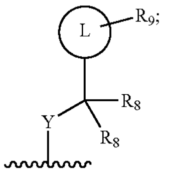

L is a 5-membered heteroaryl containing 1 to three heteroatoms selected from O, N, or S, wherein the 5-membered heteroaryl may be optionally fused with a $C_{3-6}$ cycloalkyl ring to form a bicyclic ring structure;

$R_4$ is H, methyl, —$CH_2$—OH, —O—$R_5$—$R_6$, —O—$R_6$, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; and $R_9$ is a H, $C_{1-4}$ alkyl, or $C_{3-6}$ cycloalkyl, or a pharmaceutically acceptable salt thereof.

5. The compound according to any one of embodiments 1-4, wherein G is —N—, or a pharmaceutically acceptable salt thereof.

6. The compound according to any one of embodiments 1-4, wherein G is —C($R_{3b}$)—, or a pharmaceutically acceptable salt thereof.

7. The compound according to embodiment 6, wherein $R_{3b}$ is F, or a pharmaceutically acceptable salt thereof.

8. The compound according to any one of embodiments 1-7, wherein Z is —N—, or a pharmaceutically acceptable salt thereof.

9. The compound according to any one of embodiments 1-7, wherein Z is —C($R_{3c}$)—, or a pharmaceutically acceptable salt thereof.

10. The compound according to embodiment 9, wherein $R_{3c}$ is H or F, or a pharmaceutically acceptable salt thereof.

11. The compound according to any one of embodiments 1-4, 6, or 9, wherein $R_{3b}$, and $R_{3c}$ are each independently H or halogen, or a pharmaceutically acceptable salt thereof.

12. The compound according to any one of embodiments 1-11, wherein A is —N—, or a pharmaceutically acceptable salt thereof.

13. The compound according to any one of embodiments 1-11, wherein A is —C(H)—, or a pharmaceutically acceptable salt thereof.

14. The compound according to any one of embodiments 1-13, wherein $R_2$ is F or Cl, or a pharmaceutically acceptable salt thereof.

15. The compound according to any one of embodiments 1-13, wherein $R_2$ is F, or a pharmaceutically acceptable salt thereof.

16. The compound according to any one of embodiments 1-13, wherein $R_2$ is Cl, or a pharmaceutically acceptable salt thereof.

17. The compound according to any one of embodiments 1, or 5-16, wherein $R_1$ is selected from

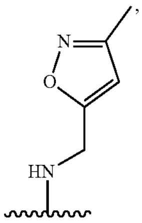 , 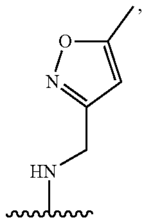 , 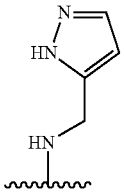 ,

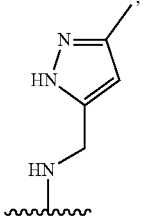 , 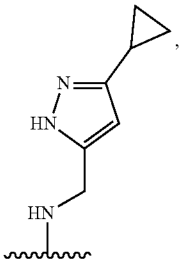 , 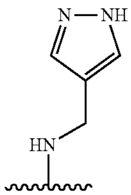 ,

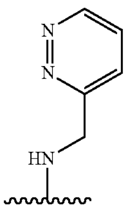 , 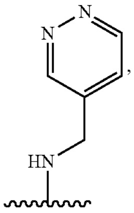 , 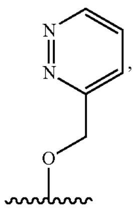 ,

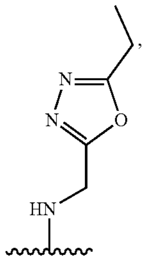 , 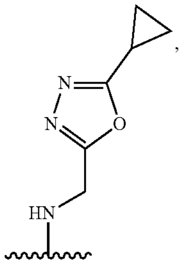 , 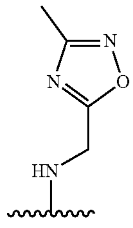 ,

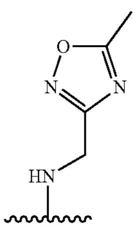 , 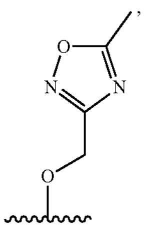 , 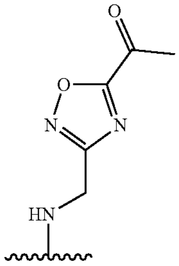 ,

-continued
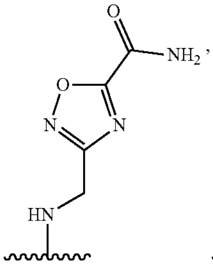,
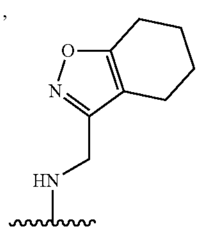,
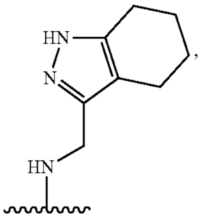,
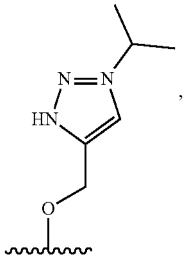,
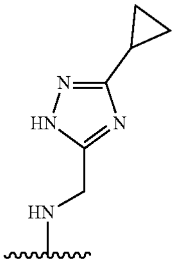,
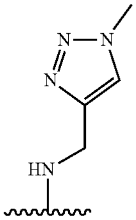,
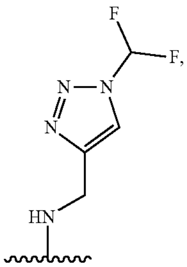,
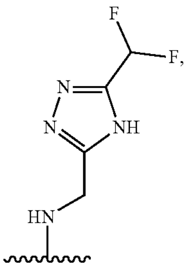,
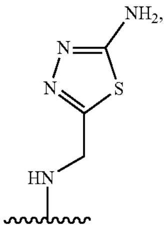,
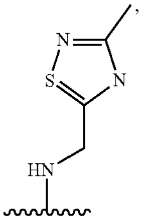,
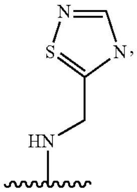,
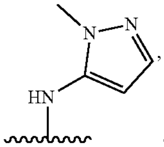,
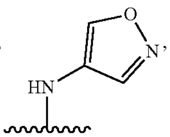,
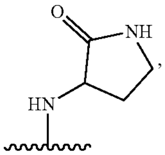,
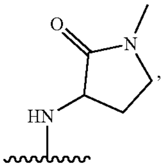,
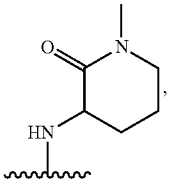, or
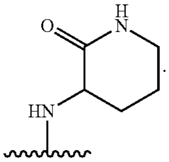.
or a pharmaceutically acceptable salt thereof.
18. The compound according to embodiment 17, wherein $R_1$ is selected from
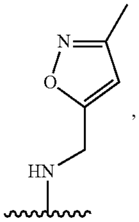,
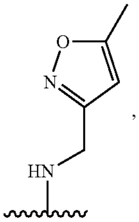,
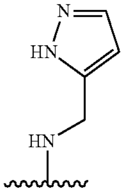,
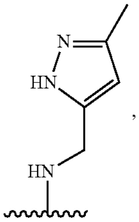,
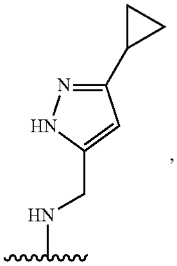,
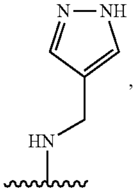,
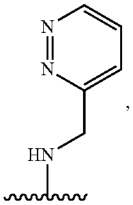,
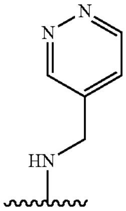,
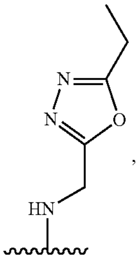,
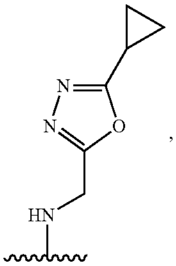,
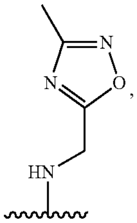,
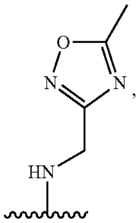,
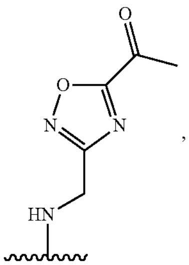,
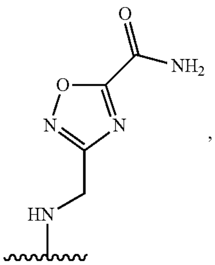, -continued

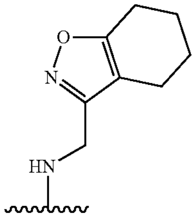, 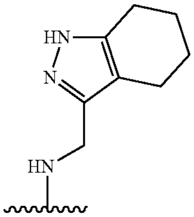,

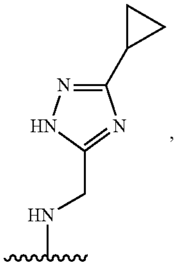, 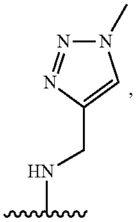, 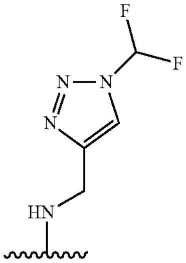,

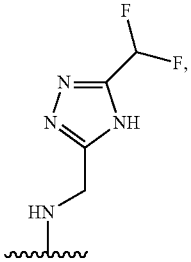 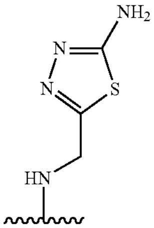, 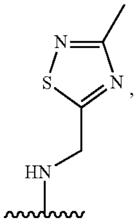

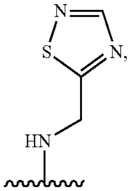

or a pharmaceutically acceptable salt thereof.

19. The compound according to embodiment 17, wherein $R_1$ is selected from

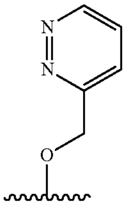, 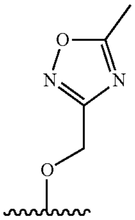, or 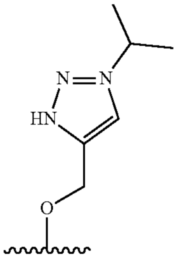, or a pharmaceutically acceptable salt thereof.

20. The compound according to embodiment 17, wherein $R_1$ is selected from

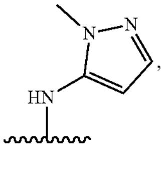, or 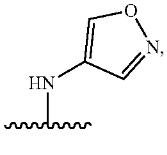

or a pharmaceutically acceptable salt thereof.

21. The compound according to embodiment 17, wherein $R_1$ is selected from

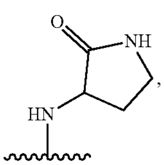 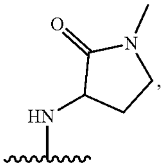 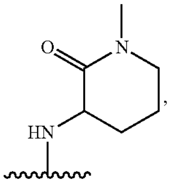, or

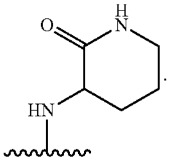

or a pharmaceutically acceptable salt thereof.

22. The compound according to embodiments 1-21, wherein $R_4$ is selected from

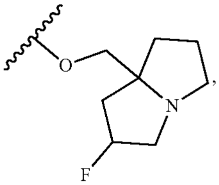 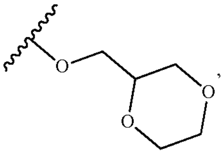

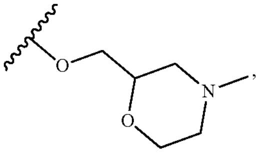 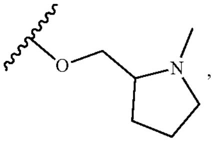

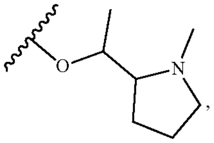 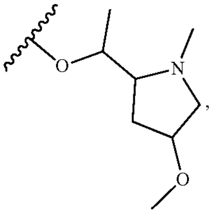

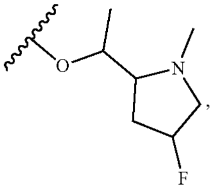 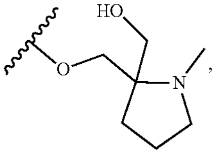

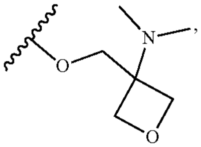 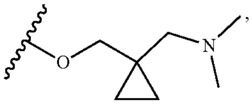

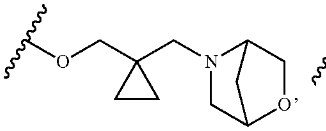 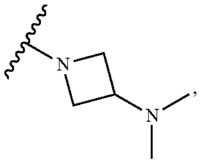

-continued

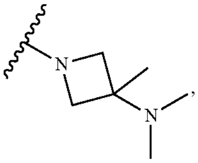,
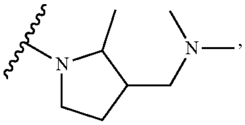,
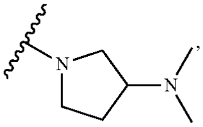,
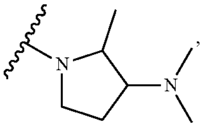,
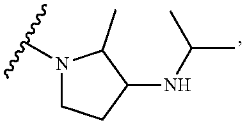,
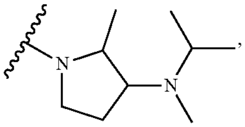,
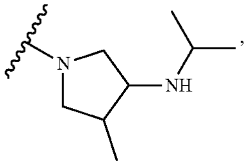,
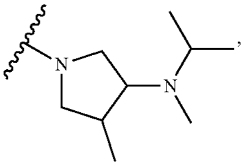,
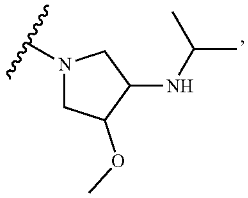,
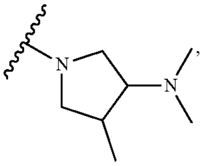,
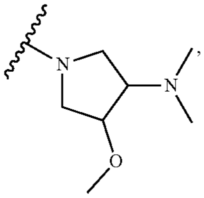,
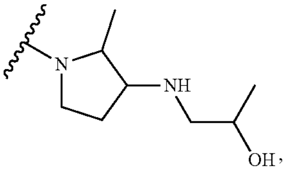,
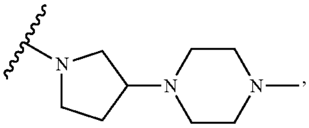, or
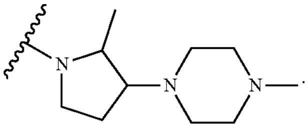.

or a pharmaceutically acceptable salt thereof.

23. A pharmaceutical composition comprising a compound according to any one of embodiments 1-22, or a pharmaceutically acceptable salt thereof, and a pharmaceutically acceptable carrier, diluent or excipient.

24. A method of treating a patient for cancer, comprising administering to a patient in need thereof, an effective amount of a pharmaceutical composition according to embodiment 23, wherein the cancer is selected from lung cancer, pancreatic cancer, cervical cancer, esophageal cancer, endometrial cancer, ovarian cancer, cholangiocarcinoma, and colorectal cancer.

25. A method of treating a patient for cancer, comprising administering to a patient in need thereof, an effective amount of a compound according to any one of embodiments 1-22, or a pharmaceutically acceptable salt thereof, wherein the cancer is selected from lung cancer, pancreatic cancer, cervical cancer, esophageal cancer, endometrial cancer, ovarian cancer, cholangiocarcinoma, and colorectal cancer.

26. The method according to embodiments 24 or 25 wherein the patient has a cancer that was determined to have one or more cells expressing the KRas G12D mutant protein prior to administration of the compound or a pharmaceutically acceptable salt thereof.

27. The method according to embodiments 24 or 25 wherein the patient has a cancer that was determined to have one or more cells expressing the KRas G12C, G12D, and/or G12V mutant proteins prior to administration of the compound or a pharmaceutically acceptable salt thereof.

28. The method according to any one of embodiments 24-27, wherein the cancer is non-small cell lung cancer.

29. The method according to any one of embodiments 24-27, wherein the cancer is colorectal cancer.

30. The method according to any one of embodiments 24-27, wherein the cancer is pancreatic cancer.

31. The method according to any one of embodiments 24, 25, or 28-30, wherein one or more cells express KRas G12D mutant protein.

32. The method according to any one of embodiments 24, 25, or 28-30, wherein one or more cells express KRas G12C, G12D, and/or G12V mutant proteins.

33. A method of treating a patient with a cancer that has a KRas G12D mutation comprising administering to a patient in need thereof an effective amount of a compound according to any one of embodiments 1-22, or a pharmaceutically acceptable salt thereof.

34. A method of treating a patient with a cancer that has a KRas G12C, G12D, and/or G12V mutation comprising administering to a patient in need thereof an effective amount of a compound according to any one of embodiments 1-22, or a pharmaceutically acceptable salt thereof.

35. The method according to embodiments 33 or 34, wherein the cancer is selected from lung cancer, pancreatic cancer, cervical cancer, esophageal cancer, endometrial cancer, mutant ovarian cancer, cholangiocarcinoma, and colorectal cancer.

36. The method according to embodiment 35, wherein the cancer is non-small cell lung cancer.

37. The method according to embodiment 35, wherein the cancer is colorectal cancer.

38. The method according to embodiment 35, wherein the cancer is pancreatic cancer.

39. The method according to any one of embodiments 24-38, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

40. The compound, or a pharmaceutically acceptable salt thereof, according to any one of embodiments 1-22, for use in therapy.

41. The compound, or a pharmaceutically acceptable salt thereof, according to any one of embodiments 1-22, for use in the treatment of cancer.

42. The compound, or a pharmaceutically acceptable salt thereof, for use according to embodiment 41 wherein the cancer has a KRas G12D mutation.
43. The compound, or a pharmaceutically acceptable salt thereof, for use according to embodiment 41 wherein the cancer has a KRas G12C, G12D, and/or G12V mutation.
44. The compound, or a pharmaceutically acceptable salt thereof, for use according to embodiment 41-43 wherein the cancer is selected from lung cancer, pancreatic cancer, cervical cancer, esophageal cancer, endometrial cancer, ovarian cancer, cholangiocarcinoma, and colorectal cancer.
45. The compound, or a pharmaceutically acceptable salt thereof, according to any one of embodiments 1-22 for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer.

EXAMPLES

The compounds of the present invention, or salts thereof, may be prepared by a variety of procedures, some of which are illustrated in the Schemes, Preparations, and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

Preparation 1

5-Fluoroisobenzofuran-1(3H)-one

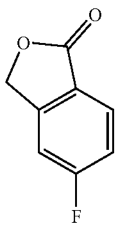 [SMILES: O=C1OCc2cc(F)ccc21]

To a stirred mixture of (2-bromo-5-fluorophenyl)methanol (500 g, 2.44 mol) and TEA (474.6 mL, 3.41 mol, 1.4 eq.) in ACN (2500 mL) was added $Pd(OAc)_2$ (10.95 g, 48.77 mmol, 0.02 eq.) and XantPhos (42.33 g, 73.16 mmol, 0.03 equiv.) at RT, then stirred for 3 days at 120° C. under 10 atm of carbon monoxide. The reaction was cooled to RT and concentrated. The residue was diluted with $H_2O$ (1,000 mL), then extracted with EtOAc (2×2000 mL). The combined organic layers were washed with brine (2×1,000 mL), dried over anhydrous $Na_2SO_4$, filtered and concentrated. The residue was triturated with 10:1 hexanes/EtOAc (1,100 mL) and then filtered. The filter cake was dried at 50° C. for ~18 h to obtain the title compound as a yellow solid (300 g, 81%). MS (ES) m/z=153 (M+1).

Preparation 2

4-Bromo-5-fluoro-6-nitroisobenzofuran-1(3H)-one

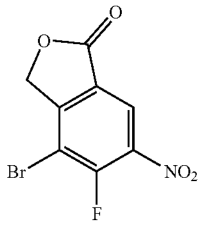 [SMILES: O=C1OCc2c1cc([N+](=O)[O-])c(F)c2Br]

To a stirred mixture of 5-fluoroisobenzofuran-1(3H)-one (300 g, 1.97 mol) in $H_2SO_4$ (1,500 mL) was added $HNO_3$ (273.38 g, 4.348 mol, 2.2 eq.) dropwise at 65° C. The reaction was stirred for 1 h then cooled to RT. 1,3-dibromo-5,5-dimethylimidazolidine-2,4-dione (2,255.43 g, 7.88 mol, 4 eq.) was added in portions over 20 min and was stirred at RT for ~18 h. The mixture was poured onto ice/water (pre-treated with 3 kg $Na_2SO_3$) and filtered. The filter cake was dissolved in EtOAc (3,000 mL), washed with sat. aq. $Na_2CO_3$ (2×1,000 mL), brine (2×1,000 mL), dried over anhydrous $Na_2SO_4$ and concentrated. The residue was triturated with 10:1 hexanes/EtOAc (660 mL) and was filtered and dried at 50° C. for ~18 h to obtain the title compound as a yellow solid (270 g, 49%) which was used in a subsequent step without further purification. $^1H$ NMR (400 MHz, DMSO-$d_6$) δ 8.58 (s, 1H), 5.51 (s, 2H).

Preparation 3

4-Bromo-5-fluoro-6-nitro-1,3-dihydroisobenzofuran

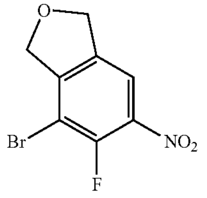 [SMILES: O=[N+]([O-])c1cc2c(c(Br)c1F)COC2]

To a stirred mixture of 4-bromo-5-fluoro-6-nitroisobenzofuran-1(3H)-one (270 g, 978 mmol) in DCM (2,500 mL) was added DIBAL-H (1M in THF, 1,467 mL, 1.467 mol, 1.5 eq.) dropwise at −78° C. under $N_2$. The reaction was stirred for 5 h at −78° C., then was quenched with 5N NaOH (300 mL) at −78° C. The resulting mixture was allowed to warm to RT, then was concentrated. The residue was diluted with EtOAc (2,500 mL), washed with brine (2×1,000 mL) and dried over anhydrous $Na_2SO_4$ and concentrated. The residue was triturated with 10:1 hexanes/EtOAc (550 mL) and filtered. The solids were dried (190 g, 683.4 mmol) then dissolved in DCM (1,500 mL) and treated dropwise with $Et_3SiH$ (662 mL, 4.10 mol, 6 eq.) at 0° C. The reaction was stirred for 20 min at 0° C. TFA (152 mL, 2.05 mol, 3 eq.) was added dropwise at 0° C. The ice bath was removed, and the reaction was stirred at RT for ~18 h. The reaction was concentrated to an oil, which was diluted with EtOAc (2,000 mL), washed with sat. aq. $Na_2CO_3$ (2×500 mL) and brine (2×500 mL), dried over anhydrous $Na_2SO_4$, filtered and concentrated to obtain the title compound (110 g, 42%) which was used in a subsequent step without further purification. $^1H$ NMR (400 MHz, DMSO-$d_6$) δ 8.16 (d, J=6.2 Hz, 1H), 5.18-5.15 (m, 2H), 5.11-5.06 (m, 2H).

Preparation 4

7-Bromo-6-fluoro-1,3-dihydroisobenzofuran-5-amine

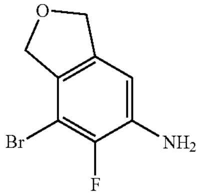 [SMILES: Nc1cc2c(c(Br)c1F)COC2]

To a stirred mixture of 4-bromo-5-fluoro-6-nitro-1,3-dihydroisobenzofuran (110 g, 420 mmol) and $NH_4Cl$ (112.3 g, 2.10 mol, 5 eq.) in EtOH (1,000 mL) and $H_2O$ (200 mL) was added Fe (117.22 g, 2.09 mol, 5 eq.) in portions at RT, then stirred for ~18 h at 80° C. The mixture was filtered and concentrated. The mixture was diluted with $H_2O$ (500 mL) and extracted with EtOAc (2×1,000 mL). The combined organic layers were washed with brine (2×500 mL), dried over anhydrous $Na_2SO_4$, filtered and concentrated. The residue was purified on silica (25% to 50% EtOAc/Hex) to afford the title compound (70 g, 72%) as a yellow solid. MS (ES) m/z=231 (M+1).

Preparation 5

(4-Chloro-1,2-phenylene)dimethanol

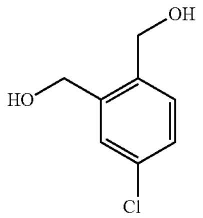

To a stirred mixture of $LiAlH_4$ (1.9 L, 2.74 mol, 2 eq., 2.5 M in THF) in THE (1 L) was added 4-chlorophthalic anhydride (250 g, 1.34 mol, 1.00 eq.) in THE (500 mL) dropwise at −20° C. under $N_2$. The resulting mixture was stirred for 30 min at 45° C. under $N_2$. The reaction was quenched by the addition of $H_2O$ (1.5 L) and 15% NaOH (500 mL) at RT. The mixture was filtered, and the filter cake was washed with MTBE (3×250 mL). The filtrate was extracted with MTBE (3×1.5 L). The combined organic layers were washed with brine (2×2 L) and dried over anhydrous $Na_2SO_4$. After filtration, the filtrate was concentrated under reduced pressure to obtain the title compound (219.5 g, 93%) as an off-white solid. $^1H$ NMR (300 MHz, DMSO-$d_6$) δ 7.45-7.36 (m, 2H), 7.28 (dd, J=8.2 Hz, 1H), 5.40-5.13 (m, 2H), 4.54 (s, 2H), 4.49 (s, 2H).

Preparation 6

5-Chloro-1,3-dihydroisobenzofuran

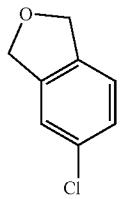

To a stirred mixture of (4-chloro-1,2-phenylene)dimethanol (219.5 g, 1.271 mol) and dimethyl carbonate (458.2 g, 5.082 mol, 4 eq.) in ACN (3 L) was added NaOMe (137.4 g, 2.544 mol, 2 eq.) in portions at RT. The resulting mixture was stirred for ~18 h at 80° C. under $N_2$. The mixture was concentrated under reduced pressure, diluted with $H_2O$ (2 L) and extracted with EtOAc (3×2 L). The combined organic layers were washed with brine (2×2 L) and dried over anhydrous $Na_2SO_4$. After filtration, the filtrate was concentrated under reduced pressure. The residue was purified on silica (10:1 to 8:1 hex/EtOAc) to obtain the title compound (165 g, 82%) as a light-brown solid. $^1H$ NMR (300 MHz, DMSO-$d_6$) δ 7.42-7.37 (m, 1H), 7.33 (d, J=1.4 Hz, 2H), 4.99 (s, 4H).

Preparation 7

5-Chloro-6-nitro-1,3-dihydroisobenzofuran

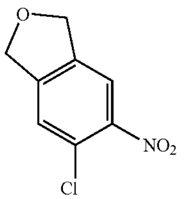 [SMILES: O=[N+]([O-])c1cc2c(cc1Cl)COC2]

A solution of 5-chloro-1,3-dihydroisobenzofuran (110 g, 712 mmol) in $H_2SO_4$ (700 mL) at −10° C. was charged with a solution of $KNO_3$ (64.74 g, 640 mmol, 0.9 eq.) in $H_2SO_4$ (200 mL) dropwise at −5° C.-0° C. The resulting mixture was stirred for additional 30 min at 0° C. and then was slowly added to stirred ice-cooled $H_2O$. The precipitated solids were collected by filtration and washed with $H_2O$ (3×1 L). The filter cake was dried in vacuo to afford the title compound (110 g, 77%) as a light-brown solid which was used in a subsequent step without further purification. $^1H$ NMR (400 MHz, DMSO-$d_6$) δ 8.05 (s, 1H), 7.75 (s, 1H), 5.07-5.02 (m, 4H).

Preparation 8

4-Bromo-5-chloro-6-nitro-1,3-dihydroisobenzofuran

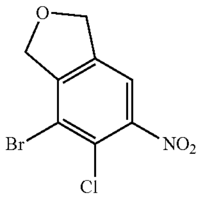 [SMILES: O=[N+]([O-])c1cc2c(c(Br)c1Cl)COC2]

To a stirred solution of 5-chloro-6-nitro-1,3-dihydroisobenzofuran (125 g, 626 mmol) in $H_2SO_4$ (700 mL) was added 1,3-dibromo-5,5-dimethylimidazolidine-2,4-dione (179.1 g, 626.3 mmol, 1 eq.) in portions at −10° C. The mixture was stirred for 1 h at −10° C. then slowly was added to stirred ice-cooled $H_2O$. The precipitated solids were collected by filtration and washed with $H_2O$ (3×0.5 L). The filter cake was dried in vacuo and purified on silica (10:1 to 5:1 Hex/EtOAc) to obtain the title compound (83.5 g, 47.9%) as a white solid. $^1H$ NMR (300 MHz, DMSO-$d_6$) δ 8.07 (d, J=1.1 Hz, 1H), 5.19 (dt, J=2.3, 1.1 Hz, 2H), 5.08 (t, 2H).

Preparation 9

7-Bromo-6-chloro-1,3-dihydroisobenzofuran-5-amine

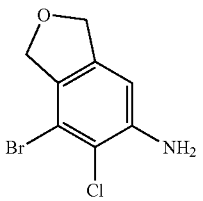 [SMILES: Nc1cc2c(c(Br)c1Cl)COC2]

To a stirred mixture of 4-bromo-5-chloro-6-nitro-1,3-dihydroisobenzofuran (37.0 g, 133 mmol) and $NH_4Cl$ (42.64 g, 797.2 mmol, 6 eq.) in EtOH (200 mL) and $H_2O$ (40 mL) was added Fe (44.52 g, 797.2 mmol, 6 equiv.) in portions at RT. The resulting mixture was stirred for ~18 h at 80° C. The resulting mixture was filtered hot and the filter cake was washed with EtOAc (3×500 mL). The filtrate was concentrated under reduced pressure and was purified on silica (15:1 to 10:1 Hex/EtOAc) to obtain the title compound (25 g, 76%) as a light-yellow solid. MS (ES) m/z=248 (M+1).

Preparation 10

Ethyl N-[(7-bromo-6-fluoro-1,3-dihydroisobenzofuran-5-yl)carbamothioyl]carbamate

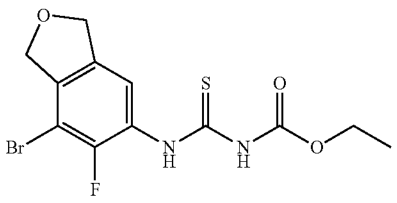 [SMILES: CCOC(=O)NC(=S)Nc1cc2c(c(Br)c1F)COC2]

A solution of 7-bromo-6-fluoro-1,3-dihydroisobenzofuran-5-amine (20.4 g, 87.9 mmol) in DCM (550 mL) was charged with ethoxycarbonyl isothiocyanate (9.7 mL, 82 mmol, 0.93 eq.) slowly via addition funnel and subsequently stirred at RT for ~4 h. The solids were filtered. The filtrate was concentrated, suspended in DCM (100 mL) and hexanes (350 mL) and stirred at RT. The resultant filtered solids and previous filtered solids were dried under vacuum at 50° C. for 2 h. The batches were combined to obtain the title compound (32.6 g, quantitative) as a white solid. MS (ES) m/z=363 (M+1).

Preparation 11

Ethyl N-[(7-bromo-6-chloro-1,3-dihydroisobenzofuran-5-yl)carbamothioyl]carbamate

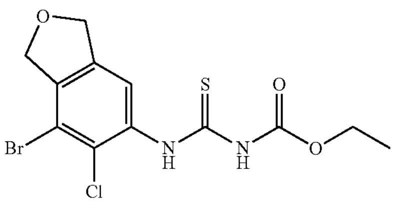 [SMILES: CCOC(=O)NC(=S)Nc1cc2c(c(Br)c1Cl)COC2]

7-Bromo-6-chloro-1,3-dihydroisobenzofuran-5-amine was used in a manner analogous to the method of Preparation 10 to afford the title compound (14 g, 92%) as a white solid. MS (ES) m/z=379 (M+1).

Preparation 12

Ethyl (((7-bromo-6-fluoro-1,3-dihydroisobenzofuran-5-yl)amino)(ethylthio)methylene)carbamate

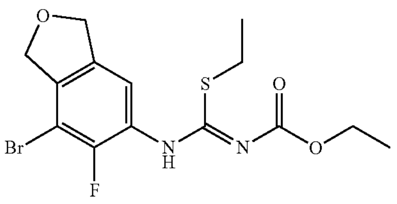 [SMILES: CCOC(=O)/N=C(/Nc1cc2c(c(Br)c1F)COC2)SCC]

A 2 L 3-necked RBF, equipped with an overhead stirrer, dropping funnel and thermocouple was charged with a suspension of ethyl N-[(7-bromo-6-fluoro-1,3-dihydroisobenzofuran-5-yl)carbamothioyl]carbamate (32.6 g, 89.8 mmol) and acetone (450 mL). To this was added solid $K_2CO_3$ (37.2 g, 269 mmol, 3.00 eq.) in several portions, followed by the dropwise addition of EtI (7.2 mL, 90 mmol, 1.0 eq.) over 20 min. The mixture was stirred at RT for ~18 h. The solids were filtered and the filtrate was concentrated and partitioned between DCM (500 mL) and $H_2O$ (500 mL). The organics were further washed with brine and dried over anhydrous $Na_2SO_4$, filtered and concentrated. The residue was purified on silica (0 to 30% EtOAc/Hex) to obtain the title compound (30.9 g, 85.6%) as a white solid. MS (ES) m/z=391 (M+1).

Preparation 13

Ethyl (((7-bromo-6-chloro-1,3-dihydroisobenzo-furan-5-yl)amino)(ethylthio)methylene)carbamate

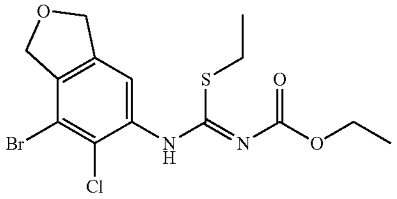 [SMILES: CCOC(=O)/N=C(/Nc1cc2c(c(Br)c1Cl)COC2)SCC]

Ethyl N-[(7-bromo-6-chloro-1,3-dihydroisobenzofuran-5-yl)carbamothioyl]carbamate was used in a manner analogous to the method of Preparation 12 to afford the title compound (15.4 g, crude) as a brown solid. MS (ES) m/z=407 (M+1).

Preparation 14

6-Bromo-3-(ethylthio)-5-fluoro-7,9-dihydrofuro[3,4-f]quinazolin-1-ol

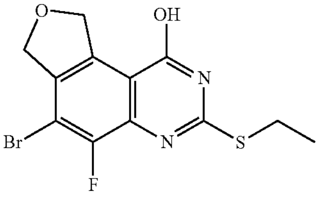 [SMILES: CCSc1nc(O)c2c3c(c(Br)c(F)c2n1)COC3]

A 2 L 4-necked RBF was equipped with an overhead stirrer, dropping funnel, $N_2$ inlet and thermocouple and was purged with $N_2$. NMP (anhydrous, 300 mL) was added. The mixture was heated to 175° C. In a second flask, ethyl (((7-bromo-6-fluoro-1,3-dihydroisobenzofuran-5-yl)amino)(ethylthio)methylene)carbamate (22.63 g, 57.83 mmol) and NMP (anhydrous, 100 mL) were combined and stirred under $N_2$ until a homogeneous solution was obtained. When the first flask had reached 175° C., the contents of the second flask were poured into the dropping funnel and were added dropwise but rapidly to the hot NMP. After 30 min, the heat was turned off and the reaction cooled to 45° C. $H_2O$ (500 mL) was slowly added and the mixture was stirred at RT for 1 h. The solids were filtered, rinsed with $H_2O$ (300 mL) and dried under vacuum at 50° C. for ~18 h to afford the title compound (15.2 g, 73%) as an off-white solid. MS (ES) m/z=363 (M+1).

Preparation 15

6-Bromo-5-chloro-3-(ethylthio)-7,9-dihydrofuro[3,4-f]quinazolin-1-ol

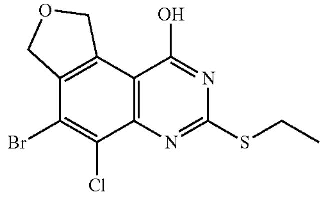 [SMILES: CCSc1nc(O)c2c3c(c(Br)c(Cl)c2n1)COC3]

Ethyl(((7-bromo-6-chloro-1,3-dihydroisobenzofuran-5-yl)amino)(ethylthio)methylene)carbamate was used in a manner analogous to the method of Preparation 14 to afford the title compound (11.4 g, 86%) as a white solid. MS (ES) m/z=361 (M+1).

Preparation 1B

6-Bromo-3-(ethylthio)-5-fluoro-1-((2-(trimethylsilyl)ethoxy)methoxy)-7,9-dihydrofuro[3,4-f]quinazoline

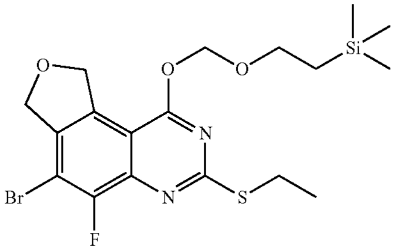 [SMILES: CCSc1nc(OCOCC[Si](C)(C)C)c2c3c(c(Br)c(F)c2n1)COC3]

A mixture of 6-bromo-3-(ethylthio)-5-fluoro-7,9-dihydrofuro[3,4-f]quinazolin-1-ol (30.1 g, 87.3 mmol) in DMF was heated to ~70° C. to dissolve the solids, then cooled to 40° C. To the mixture was added diisopropylethylamine (30.4 mL, 175 mmol) and 2-(chloromethoxyethyl)trimethyl silane (23.2 mL, 131 mmol). The reaction mixture was stirred for 1 h at 40° C., then cooled to room temperature and diluted with water (1 L) and EtOAc (500 mL). The layers were separated and the organic layer was washed with brine (2×500 mL), dried over magnesium sulfate, filtered, and concentrated under reduced pressure to give the crude title compound (49.2 g, 85% purity) as a yellow oil. MS (ES) m/z=475 (M+1).

Preparation 1C

6-Bromo-5-chloro-3-(ethylthio)-1-((2-(trimethylsilyl)ethoxy)methoxy)-7,9-dihydrofuro[3,4-f]quinazoline

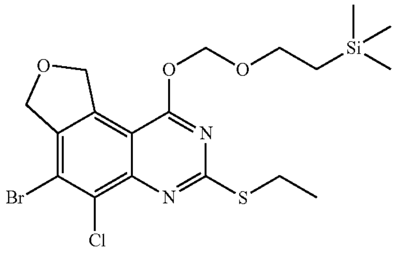 [SMILES: CCSc1nc(OCOCC[Si](C)(C)C)c2c3c(c(Br)c(Cl)c2n1)COC3]

6-Bromo-5-chloro-3-(ethylthio)-7,9-dihydrofuro[3,4-f]quinazolin-1-ol was used in a manner analogous to the method of Preparation 1B to afford the title compound (10.5 g, 96%) as a pink solid. MS (ES) m/z=491 (M+1).

Preparation 16

6-Bromo-1-chloro-3-(ethylthio)-5-fluoro-7,9-dihydrofuro[3,4-f]quinazoline

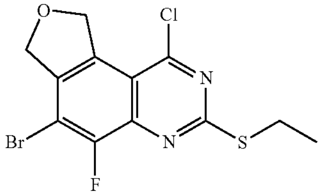

A 5 L 3-necked RBF, equipped with a dropping funnel, thermocouple and an overhead stirrer was charged with a solution of DMF (50 mL, 646 mmol, 4 eq.) in DCM (1,000 mL) and was placed in an ice/water bath and cooled to −4° C. Oxalyl chloride (50.0 mL, 576 mmol, 4 eq.) was added dropwise via addition funnel over −40 min. When the addition was complete, the reaction was stirred at −4° C. for 15 min. Solid 6-bromo-3-(ethylthio)-5-fluoro-7,9-dihydrofuro[3,4-f]quinazolin-1-ol (50.4 g, 140 mmol) was added in several portions to the reaction mixture and the resulting suspension was stirred at −4° C. for 30 min. The ice bath was removed and the reaction was allowed to warm to RT and stir for 1 h. Then $H_2O$ (1 L) was added and the mixture was stirred for 15 min. The mixture was partitioned and the organic layer was washed with brine (1 L) and dried over anhydrous $Na_2SO_4$, filtered and concentrated. The residue was purified on silica, eluting with DCM/Hex (60% to 90%)

to obtain the title compound (45.1 g, 89%) as a white solid. MS (ES) m/z=363 (M+1).

Preparation 17

6-Bromo-1,5-dichloro-3-(ethylthio)-7,9-dihydrofuro[3,4-f]quinazoline

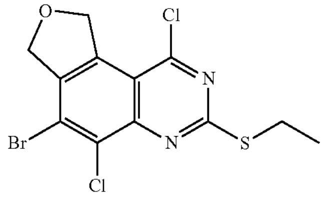 [SMILES: CCSc1nc(Cl)c2c3c(c(Br)c(Cl)c2n1)COC3]

6-Bromo-5-chloro-3-(ethylthio)-7,9-dihydrofuro[3,4-f]quinazolin-1-ol was used in a manner analogous to the method of Preparation 16 to afford the title compound (0.81 g, 77%) as a yellow solid. MS (ES) m/z=382 (M+1).

Preparation 2C

6-Bromo-3-(ethylthio)-5-fluoro-1-(2-(trimethylsilyl)ethoxy)-7,9-dihydrofuro[3,4-f]quinazoline

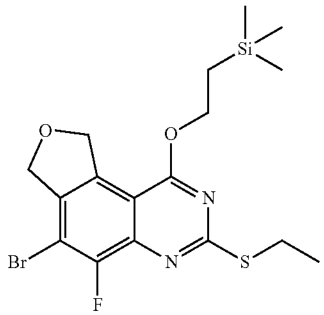 [SMILES: CCSc1nc(OCC[Si](C)(C)C)c2c3c(c(Br)c(F)c2n1)COC3]

To a 0° C. mixture of 6-bromo-1-chloro-3-(ethylthio)-5-fluoro-7,9-dihydrofuro[3,4-f]quinazoline (6.50 g, 17.9 mmol) and 2-(trimethylsilyl)ethan-1-ol (3.04 mL, 21.5 mmol) in THE (60 mL) was added potassium tert-butoxide (2.68 mL, 23.2 mmol) in three portions. The mixture was stirred at room temperature. After 1 h, the mixture was diluted with saturated aqueous ammonium chloride, then extracted with methyl-THF (200 mL). The organics were dried over magnesium sulfate and concentrated under reduced pressure to give the crude title compound (7.5 g, 94%) as a white solid. MS (ES) m/z=445 (M+1).

Preparation 18

6-Bromo-5-chloro-N-((5-ethyl-1,3,4-oxadiazol-2-yl)methyl)-3-(ethylthio)-7,9-dihydrofuro[3,4-f]quinazolin-1-amine

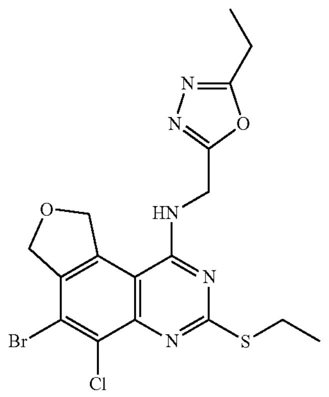 [SMILES: CCSc1nc(NCc2nnc(CC)o2)c2c3c(c(Br)c(Cl)c2n1)COC3]

To a mixture of 6-bromo-1,5-dichloro-3-(ethylthio)-7,9-dihydrofuro[3,4-f]quinazoline (0.500 g, 1.32 mmol) and (5-ethyl-1,3,4-oxadiazol-2-yl)methanamine hydrochloride (0.280 g, 1.71 mmol) in isopropanol (20 mL) was added triethylamine (0.367 mL, 2.63 mmol). The mixture was heated at 80° C. After 1 h, the mixture was filtered and the solids were washed with DCM. The filtrate was concentrated under reduced pressure and the residue was purified on silica, eluting with 60% EtOAc in DCM to yield product. Solids from the filtration and column purification were combined to obtain the title compound (0.437 g, 71%) as a white solid. MS (ES) m/z=472 (M+1).

Preparation 19

6-Bromo-5-chloro-3-(ethylthio)-N—((4,5,6,7-tetrahydrobenzo[d]isoxazol-3-yl)methyl)-7,9-dihydrofuro[3,4-f]quinazolin-1-amine

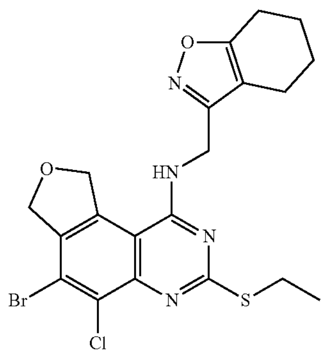 [SMILES: CCSc1nc(NCc2noc3c2CCCC3)c2c3c(c(Br)c(Cl)c2n1)COC3]

(4,5,6,7-Tetrahydrobenzo[d]isoxazol-3-yl)methanamine was used in a manner analogous to the method of Preparation 18 to afford the title compound (0.47 g, 67%) as a white solid. MS (ES) m/z=497 (M+1).

Preparation 3C tert-Butyl (2S,3S)-3-(dimethylcarbamoyl)-2-methylpyrrolidine-1-carboxylate

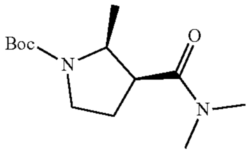 [SMILES: C[C@H]1[C@@H](C(=O)N(C)C)CCN1C(=O)OC(C)(C)C]

A mixture of (2S,3S)-1-(tert-butoxycarbonyl)-2-methylpyrrolidine-3-carboxylic acid (2.00 g, 8.72 mmol), hexafluorophosphate azabenzotriazole tetramethyl uranium (4.98 g, 13.1 mmol), and dimethylamine (2M in THF; 8.72 mL, 17.5 mmol) in DCM (30 mL) was treated with diisopropylethylamine (4.56 mL, 26.2 mmol). The mixture was stirred at 25° C. After 18 h, the mixture was concentrated under reduced pressure and the crude residue was purified by reversed phase purification, eluting with 0-100% ACN in 0.1% formic acid in water, to give the crude title compound (2.51 g) as a yellow oil. MS (ES) m/z=201 (M+1, -tBu).

Preparation 4C tert-Butyl (2S,3S)-2-methyl-3-(4-methylpiperazin-1-yl)pyrrolidine-1-carboxylate

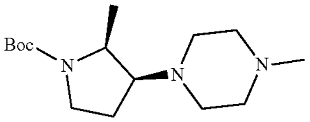 [SMILES: C[C@H]1[C@@H](N2CCN(C)CC2)CCN1C(=O)OC(C)(C)C]

Procedure Text Here for Building Block

To a solution of tert-butyl (S)-2-methyl-3-oxopyrrolidine-1-carboxylate (2.20 g, 11.0 mmol), 1-methylpiperazine (1.66 g, 16.6 mmol), and acetic acid (0.63 mL, 11.0 mmol) in DCM (15 mL) was added sodium triacetoxyborohydride (3.74 g, 17.7 mmol) in portions. The mixture was stirred at room temperature. After 28 h, the mixture was cooled to 0° C. and diluted with saturated aqueous sodium bicarbonate. The layers were separated and the aqueous layer was extracted with DCM. The combined organic layers were washed with brine (25 mL), dried over anhydrous $Na_2SO_4$, filtered, and concentrated under reduced pressure to give the crude title compound (3.18 g) as a yellow oil. MS (ES) m/z=284 (M+1).

Preparation 5C tert-Butyl (2S,3S)-3-(isopropylamino)-2-methylpyrrolidine-1-carboxylate

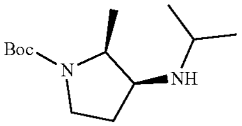 [SMILES: CC(C)N[C@H]1CCN(C(=O)OC(C)(C)C)[C@H]1C]

tert-Butyl (2S,3S)-3-amino-2-methylpyrrolidine-1-carboxylate (0.500 g, 2.50 mmol), acetone (0.275 mL, 3.74 mmol), and sodium triacetoxyborohydride (1.59 g, 7.49 mmol) were dissolved in methanol (6 mL). The mixture was heated at 50° C. After 18 h, the mixture was cooled, concentrated under reduced pressure, and diluted with saturated aqueous sodium bicarbonate (20 mL). The mixture was extracted with EtOAc (3×50 mL). The combined organic layers were washed with brine (25 mL), dried over anhydrous $Na_2SO_4$, filtered, and concentrated under reduced pressure to give the crude title compound (0.600 g) as a colorless oil. MS (ES) m/z=243 (M+1).

The following compounds in Table 1 were prepared in similar manner as described in Preparation 5C. Various methods were used to purify the compounds, which would be apparent to one skilled in the art.

TABLE 1

| Preparation | Chemical Name | Structure | MS (ES) m/z (M + 1) |
|---|---|---|---|
| 6C | tert-Butyl (2S,3S)-3-(dimethylamino)-2-methylpyrrolidine-1-carboxylate | 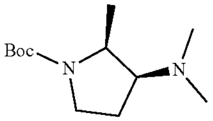 [SMILES: C[C@H]1[C@@H](N(C)C)CCN1C(=O)OC(C)(C)C] | 229 |
| 7C [1] | tert-Butyl 3-(dimethylamino)-4-methoxypyrrolidine-1-carboxylate | 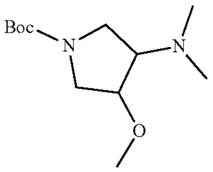 [SMILES: COC1CN(C(=O)OC(C)(C)C)CC1N(C)C] | 245 |
| 8C [2] | tert-Butyl 3-(dimethylamino)-4-methoxypyrrolidine-1-carboxylate | 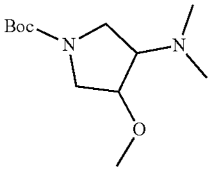 [SMILES: COC1CN(C(=O)OC(C)(C)C)CC1N(C)C] | 245 |
| 9C | tert-Butyl (2S,3S)-3-(((S)-2-((tert-butyldimethylsilyl)oxy)propyl)amino)-2-methylpyrrolidine-1-carboxylate | 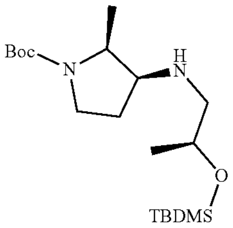 | 373 |
| 10C [1] | tert-Butyl 3-(isopropylamino)-4-methoxypyrrolidine-1-carboxylate | 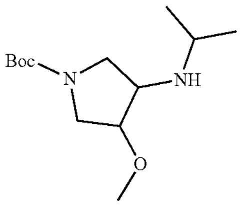 [SMILES: COC1CN(C(=O)OC(C)(C)C)CC1NC(C)C] | 259 |
| 11C [2] | tert-Butyl 3-(isopropylamino)-4-methoxypyrrolidine-1-carboxylate | 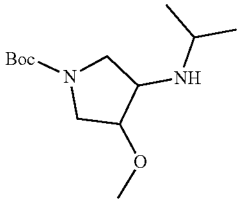 [SMILES: COC1CN(C(=O)OC(C)(C)C)CC1NC(C)C] | 259 |
| 12C | tert-Butyl (2S,3S)-3-(isopropyl(methyl)amino)-2-methylpyrrolidine-1-carboxylate | 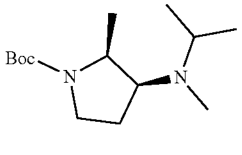 [SMILES: CC(C)N(C)[C@H]1CCN(C(=O)OC(C)(C)C)[C@H]1C] | 257 |

TABLE 1-continued

| Preparation | Chemical Name | Structure | MS (ES) m/z (M + 1) |
|---|---|---|---|
| 13C | tert-Butyl (3R,4S)-3-(isopropylamino)-4-methylpyrrolidine-1-carboxylate | 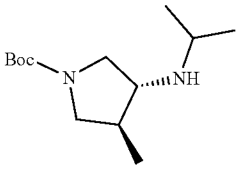 [SMILES: CC(C)N[C@H]1CN(C(=O)OC(C)(C)C)C[C@@H]1C] | 243 |
| 14C | tert-Butyl (3R,4S)-3-(isopropyl(methyl)amino)-4-methylpyrrolidine-1-carboxylate | 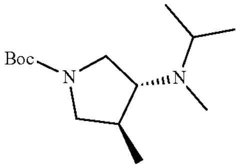 [SMILES: CC(C)N(C)[C@H]1CN(C(=O)OC(C)(C)C)C[C@@H]1C] | 257 |
| 15C [1] | tert-Butyl 3-(dimethylamino)-4-methylpyrrolidine-1-carboxylate | 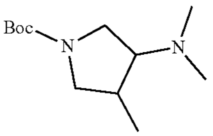 [SMILES: CC1CN(C(=O)OC(C)(C)C)CC1N(C)C] | 229 |

[1] Mix of Trans pyrrolidine isomers
[2] Mix of Cis pyrrolidine isomers

Preparation 16C

(2S,3S)-N-Isopropyl-2-methylpyrrolidin-3-amine dihydrochloride

HCl

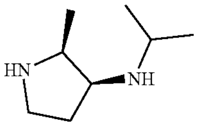

HCl

To a mixture of tert-butyl (2S,3S)-3-(isopropylamino)-2-methylpyrrolidine-1-carboxylate (0.600 g, 2.48 mmol) in DCM (3 mL) was added HCl (4M in 1,4-dioxane; 3 mL). The mixture was stirred at room temperature. After 6 h, the mixture was concentrated under reduced pressure to give the crude title compound (0.533 g) as a yellow solid. MS (ES) m/z=143 (M+1).

The following compounds in Table 2 were prepared in similar manner as described in Preparation 16C. Various methods were used to purify the compounds, which would be apparent to one skilled in the art.

TABLE 2

| Preparation | Chemical Name | Structure | MS (ES) m/z (M + 1) |
|---|---|---|---|
| 17C | (2S,3S)-N,N,2-Trimethylpyrrolidin-3-amine dihydrochloride | 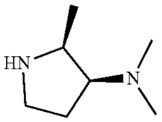 HCl HCl | 129 |
| 18C [1] | 4-Methoxy-N,N-dimethylpyrrolidin-3-amine dihydrochloride | 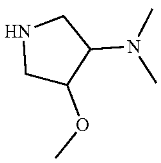 HCl HCl | 145 |

TABLE 2-continued

| Preparation | Chemical Name | Structure | MS (ES) m/z (M + 1) |
|---|---|---|---|
| 19C [2] | 4-Methoxy-N,N-dimethylpyrrolidin-3-amine dihydrochloride | 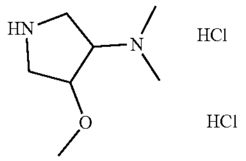 | 145 |
| 20C | (S)-1-(((2S,3S)-2-methylpyrrolidin-3-yl)amino)propan-2-ol dihydrochloride | 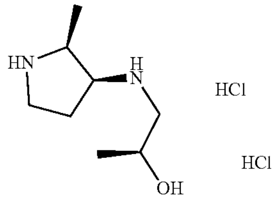 | 159 |
| 21C [1] | N-Isopropyl-4-methoxypyrrolidin-3-amine dihydrochloride | 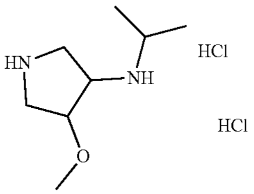 | 159 |
| 22C [2] | N-Isopropyl-4-methoxypyrrolidin-3-amine dihydrochloride | 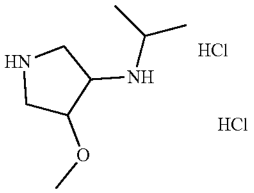 | 159 |
| 23C | (2S,3S)-N-Isopropyl-N,2-dimethylpyrrolidin-3-amine dihydrochloride | 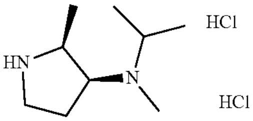 | 157 |
| 24C | (3R,4S)-N-Isopropyl-4-methylpyrrolidin-3-amine dihydrochloride | 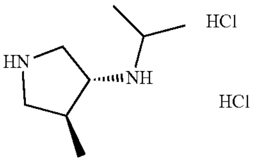 | 143 |
| 25C | (3R,4S)-N-Isopropyl-N,4-dimethylpyrrolidin-3-amine dihydrochloride | 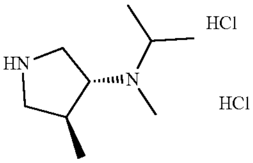 | 157 |
| 26C [1] | N,N,4-Trimethylpyrrolidin-3-amine dihydrochloride | 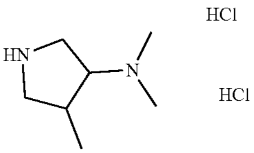 | 129 |

TABLE 2-continued

| Preparation | Chemical Name | Structure | MS (ES) m/z (M + 1) |
|---|---|---|---|
| 27C | (2S,3S)-N,N,2-Trimethylpyrrolidine-3-carboxamide hydrochloride | 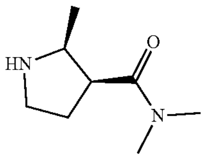 HCl | 157 |
| 28C | 1-Methyl-4-((2S,3S)-2-methylpyrrolidin-3-yl)piperazine dihydrochloride | 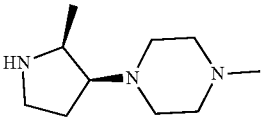 HCl HCl | 184 |

[1] Mix of Trans pyrrolidine isomers
[2] Mix of Cis pyrrolidine isomers

Preparation 29C

N,N-Dimethyl-1-((2 S,3R)-2-methylpyrrolidin-3-yl) methanamine

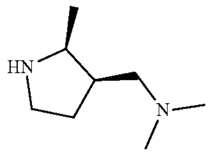

A 0° C. mixture of (2S,3S)-N,N,2-trimethylpyrrolidine-3-carboxamide hydrochloride (0.80 g, 4.15 mmol) in 1,4-dioxane (15 mL) was treated with lithium aluminum hydride (2M in THF; 8.30 mL, 16.6 mmol). The reaction mixture was stirred at 0° C. for 30 min, then heated at 70° C. for 3 h and 85° C. for 5 h. The mixture was cooled to 0° C. and quenched with water (6 mL), 15% aqueous NaOH (9 mL), and water (6 mL). The mixture was warmed to room temperature, anhydrous sodium sulfate was added, and stirred for 30 min. The resulting mixture was filtered and the filter cake was washed with EtOAC and DCM. The combined filtrates were concentrated under reduced pressure and diluted with DCM. The mixture was dried over anhydrous $Na_2SO_4$, filtered, washed with DCM, and the filtrates were concentrated under reduced pressure to obtain the title compound (0.56 g, 95%) as a yellow oil. MS (ES) m/z=143 (M+1).

Preparation 30C tert-Butyl (2S,4R)-4-fluoro-2-(hydroxymethyl)pyrrolidine-1-carboxylate

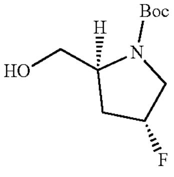 [SMILES: CC(C)(C)OC(=O)N1C[C@H](F)C[C@H]1CO]

A solution of 1-(tert-butyl) 2-methyl (2S,4R)-4-fluoropyrrolidine-1,2-dicarboxylate (53 g, 214 mmol) in THE (100 mL) was treated with lithium chloride (20 g, 472 mmol) under nitrogen. The mixture was cooled to 0° C. and sodium borohydride (20.3 g, 536 mmol) and ethanol (200 mL) were added. The reaction mixture was stirred under nitrogen at 0° C. for 1 h and room temperature for 48 h. The mixture was diluted with THE (50 mL), acidified to pH ~4 with 10% aqueous citric acid, and concentrated under reduced pressure to remove volatiles. The remaining material was diluted with water (200 mL) and extracted with DCM (3×200 mL). The combined organics were washed with brine (2×200 mL), dried over anhydrous $Na_2SO_4$, filtered, and concentrated under reduced pressure to obtain the crude title compound (41.4 g). MS (ES) m/z=164 (M+1, -tBu).

Preparation 31C tert-Butyl (2S,4R)-4-fluoro-2-formylpyrrolidine-1-carboxylate

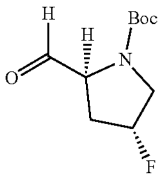 [SMILES: CC(C)(C)OC(=O)N1C[C@H](F)C[C@H]1C=O]

A 0° C. mixture of tert-butyl (2S,4R)-4-fluoro-2-(hydroxymethyl)pyrrolidine-1-carboxylate (40 g, 182 mmol) in THE (150 mL) was treated with Dess-Martin periodinane (116 g, 274 mmol) under nitrogen. The reaction mixture was stirred under nitrogen at 0° C. for 24 h, concentrated under reduced pressure, and diluted with EtOAc (200 mL). The mixture was treated with saturated aqueous sodium bicarbonate (300 mL) and extracted with EtOAc (2×400 mL). The combined organics were washed with saturated aqueous sodium sulfite (5×200 mL), dried over anhydrous $Na_2SO_4$, filtered, and concentrated under reduced pressure. The residue was purified on silica, eluting with 20% EtOAc in petroleum ether to obtain the title compound (9.6 g, 19%) as a yellow/green oil. MS (ES) m/z=162 (M+1, -tBu).

Preparation 32C tert-Butyl (2S,4R)-2-formyl-4-methoxypyrrolidine-1-carboxylate

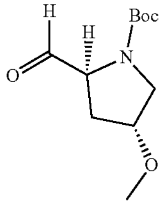

A −78° C. mixture of 1-(tert-butyl) 2-methyl (2S,4R)-4-methoxypyrrolidine-1,2-dicarboxylate (18 g, 69.4 mmol) in DCM (400 mL) was treated with dropwise addition of diisobutylaluminium hydride (1M in DCM; 146 mL, 146 mmol). The reaction mixture was stirred at −78° C. for 3 h, diluted with MeOH (30 mL), slowly added to saturated aqueous potassium sodium tartrate (500 mL) at 0° C., stirred for 3 h, and extracted with DCM (3×400 mL). The combined organics were filtered and concentrated under reduced pressure. The residue was purified on silica, eluting with 40-50% EtOAc in petroleum ether to obtain the title compound (10.3 g, 65%) as a colorless oil. $^1$H NMR (400 MHz, DMSO-$d_6$) δ 9.38 (dd, 1H), 4.08-3.96 (m, 1H), 3.94 (dq, 1H), 3.52-3.36 (m, 2H), 3.23 (s, 3H), 2.21-2.08 (m, 1H), 2.01-1.87 (m, 1H), 1.38 (d, 9H).

Preparation 33C tert-Butyl (2S,4R)-4-fluoro-2-((S)-1-hydroxyethyl)pyrrolidine-1-carboxylate

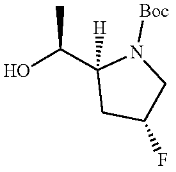 [SMILES: C[C@H](O)[C@@H]1C[C@@H](F)CN1C(=O)OC(C)(C)C]

A −65° C. solution of tert-butyl (2S,4R)-4-fluoro-2-formylpyrrolidine-1-carboxylate (9.4 g, 43.3 mmol) in THE (50 mL) was treated with methylmagnesium bromide (3M in THF; 43.3 mL, 130 mmol). The reaction mixture was stirred at room temperature overnight, then cooled to 0° C. and diluted with saturated aqueous ammonium chloride (5 mL). The mixture was diluted with water (100 mL) and extracted with EtOAc (2×100 mL). The combined organics were washed with brine (2×100 mL), dried over anhydrous $Na_2SO_4$, filtered, and concentrated under reduced pressure. The crude product was purified by reversed phase purification, eluting with 15-45% ACN in (water; 10 mM ammonium bicarbonate w/0.05% ammonium hydroxide), to give the racemic title compound (4.1 g, 37%) as a white oil. MS (ES) m/z=178 (M+1, -tBu).

Chiral separation was carried out utilizing chiral SFC; (S,S)-Whelk-01, 30×250 mm, 10% (1:2 EtOH:hexanes) in $CO_2$, 90 mL/min, to obtain the title compound as the second eluting fraction (1.4 g, white oil after lyophilization) MS (ES) m/z=178 (M+1, -tBu). Note that the desired target was the first eluting peak in silica gel column chromatography with 5:1 DCM:MTBE (literature reference).

The following compound in Table 3 was prepared in similar manner as described in Preparation 33C. Various methods were used to purify the compounds, which would be apparent to one skilled in the art.

TABLE 3

| Preparation | Chemical Name | Structure | MS (ES) m/z (M + 1) |
|---|---|---|---|
| 34C [1] | tert-Butyl (2S,4R)-2-((S)-1-hydroxyethyl)-4-methoxypyrrolidine-1-carboxylate | 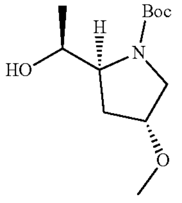 [SMILES: CO[C@@H]1C[C@@H]([C@H](C)O)N(C(=O)OC(C)(C)C)C1] | |

[1] Chiral SFC; Phenomenex Lux Cellulose-2, 50 x 250 mm, 25% EtOH in $CO_2$, 200 mL/min, Isomer 2; $^1$H NMR (400 MHz, DMSO-d6) δ 4.65 (d, 1H), 3.95-3.81 (m, 3H), 3.53 (d, 1H), 3.18 (s, 4H), 2.04-1.80 (m, 2H), 1.39 (s, 9H), 0.92 (d, 3H).

Preparation 35C (S)-1-((2S,4R)-4-Fluoro-1-methylpyrrolidin-2-yl)ethan-1-ol

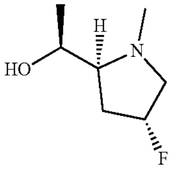

A 0° C. mixture of tert-butyl (2S,4R)-4-fluoro-2-((S)-1-hydroxyethyl)pyrrolidine-1-carboxylate (1.3 g, 5.57 mmol) in THE (20 mL) was treated with lithium aluminum hydride (1M in THF; 16.7 mL, 16.7 mmol). The reaction mixture was stirred at room temperature for 1 h, then heated at 60° C. for 16 h. The mixture was cooled to 0° C. and quenched with water (0.6 mL), 10M aqueous NaOH (0.6 mL), and water (1.8 mL). The resulting mixture was filtered and the filter cake was washed with THE (3×10 mL). The combined filtrates were concentrated under reduced pressure to obtain the crude title compound (0.53 g). MS (ES) m/z=148 (M+1).

The following compound in Table 4 was prepared in similar manner as described in Preparation 35C. Various methods were used to purify the compounds, which would be apparent to one skilled in the art.

TABLE 4

| Preparation | Chemical Name | Structure | MS (ES) m/z (M + 1) |
|---|---|---|---|
| 36C [1] | (S)-1-((2S,4R)-4-Methoxy-1-methylpyrrolidin-2-yl)ethan-1-ol | 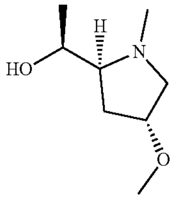 | |

[1] $^1$H NMR (300 MHz, DMSO-d6) δ 4.42 (s, 1H), 3.74 (dtd, 1H), 3.61 (p, 1H), 3.24-3.13 (m, 4H), 2.36 (td, 1H), 2.28 (s, 3H), 2.11 (dd, 1H), 1.77-1.55 (m, 2H), 0.95 (d, 3H).

Preparation 1A (1-(((1R,4R)-2-Oxa-5-azabicyclo[2.2.1]heptan-5-yl)methyl)cyclopropyl)methanol

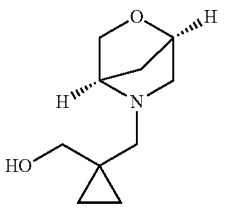 [SMILES: OCC1(CN2C[C@H]3C[C@@H]2CO3)CC1]

1-(Methoxycarbonyl)cyclopropane-1-carboxylic acid (1.69 g, 11.4 mmol), oxalyl chloride (1.1 mL, 12.0 mmol), DCM (30 mL) and DMF (0.05 mL) were combined under nitrogen and stirred at room temperature for 40 min.

To the crude acid chloride mixture was added (1R,4R)-2-oxa-5-azabicyclo[2.2.1]heptane hydrochloride (1.64 g, 12.1 mmol) and triethylamine (7.5 mL, 54 mmol). The mixture was stirred at room temperature overnight, then concentrated under reduced pressure. The residue was dissolved in EtOAc (40 mL) and water (10 mL). The layers were separated and the organic layer was washed with aqueous $KHSO_4$ (1M, 10 mL), saturated aqueous $NaHCO_3$ (10 mL), and brine (10 mL). The organics were dried over sodium sulfate, filtered, and concentrated under reduced pressure to give crude methyl 1-((1R,4R)-2-oxa-5-azabicyclo[2.2.1]heptane-5-carbonyl)cyclopropane-1-carboxylate (1.34 g, 50%).

The crude methyl ester was mixed with THE (19 mL) and cooled to 0° C. Lithium aluminum hydride (2.3M in 2-MeTHF, 8.5 mL, 20.0 mmol) was added dropwise and the mixture was stirred for 30 min, then allowed to warm to room temperature. After 3 h, the reaction mixture was quenched with sodium sulfate decahydrate (until bubbling ceased). diluted with THF, and filtered. The solids were washed with EtOAc. The combined filtrates were concentrated under reduced pressure to give the title compound (1.00 g, 91%) as a colorless oil, with no further purification. MS (ES) m/z=184 (M+1).

Preparation 2A tert-Butyl (4-chloro-3-cyano-7-fluorothieno[3,2-c]pyridin-2-yl)carbamate

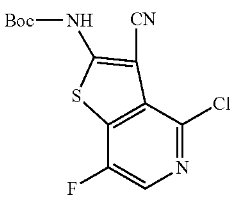 [SMILES: CC(C)(C)OC(=O)Nc1sc2c(F)cnc(Cl)c2c1C#N]

Ethyl (3-cyano-7-fluorothieno[3,2-c]pyridin-2-yl)carbamate. A solution of 2-(4-chloro-5-fluoropyridin-3-yl)acetonitrile (11.8 g, 56.1 mmol) in DMF (112 mL) was cooled to 0° C. Potassium tert-butoxide (7.00 g, 61.1 mmol) was added. After 15 min, ethoxycarbonyl isothiocyanate (7.45 mL, 61.8 mmol) was added dropwise. The reaction mixture was allowed to slowly warm to room temperature overnight. The reaction mixture was poured into a mixture of ice/water (1.5 L), stirred until all ice had melted, and filtered through diatomaceous earth. The solids were dried in a vacuum oven (60° C.) overnight and separated from the diatomaceous earth to give ethyl N-(3-cyano-7-fluoro-thieno[3,2-c]pyridin-2-yl)carbamate (11.9 g, 79%) as a solid. MS (ES) m/z=266 (M+1).

2-Amino-7-fluorothieno[3,2-c]pyridine-3-carbonitrile. A suspension of ethyl (3-cyano-7-fluorothieno[3,2-c]pyridin-2-yl)carbamate (11.9 g, 44.4 mmol) in DMSO (90 mL) was cooled to 0° C. NaOH (5 M in water, 90 mL) was added dropwise over 15 min. The reaction mixture was heated to 105° C. for 1 h, then cooled to room temperature. The reaction mixture was poured into a mixture of ice/water (1.8 L), stirred until all ice had melted, and filtered through diatomaceous earth. The solids were dried in a vacuum oven (50° C.) overnight and separated from the diatomaceous earth to give crude 2-amino-7-fluoro-thieno[3,2-c]pyridine-3-carbonitrile.

tert-Butyl (3-cyano-7-fluorothieno[3,2-c]pyridin-2-yl)carbamate. A mixture of crude 2-amino-7-fluorothieno[3,2-c]pyridine-3-carbonitrile (8.6 g, 44.4 mmol), DCM (90 mL), DMF (90 mL) and N,N-diisopropylethylamine (15.5 mL, 88.9 mmol) was cooled to 0° C. 4-dimethylaminopyridine (0.54 g, 4.42 mmol) and di-tert-butyl dicarbonate (14.6 g, 66.7 mmol) were added. The reaction mixture was stirred at room temperature for 2 h. The solvents were removed under reduced pressure and the remaining material was diluted with DCM (400 mL) and 5% aq. citric acid (250 mL). The aqueous phase was washed twice with DCM. The combined organic phases were washed with sat. aq. $NaHCO_3$, dried over $MgSO_4$, filtered, and concentrated to give tert-butyl N-(3-cyano-7-fluoro-thieno[3,2-c]pyridin-2-yl)carbamate (7.5 g, 58%) as a brown solid. MS (ES) m/z=294 (M+1).

2-((tert-Butoxycarbonyl)amino)-3-cyano-7-fluorothieno[3,2-c]pyridine 5-oxide. 3-Chloroperoxybenzoic acid (9.00 g, 40.2 mmol) was added to a solution of tert-butyl (3-cyano-7-fluorothieno[3,2-c]pyridin-2-yl)carbamate (7.85 g, 26.8 mmol) in DCM (180 mL). The reaction mixture was stirred at room temperature overnight, then cooled to 0° C. for −15 min. Solids were collected by filtration and dried in a vacuum oven (60° C.). The filtrate was diluted with MeOH and silica gel, concentrated, and the residue was purified on silica, eluting with 0-6% MeOH in DCM. Fractions containing desired material were combined with the solids from the filtration and concentrated to give tert-butyl N-(3-cyano-7-fluoro-5-oxido-thieno[3,2-c]pyridin-5-ium-2-yl)carbamate (7.26 g, 88%) as an off-white solid. MS (ES) m/z=310 (M+1).

tert-Butyl (4-chloro-3-cyano-7-fluorothieno[3,2-c]pyridin-2-yl)carbamate. A suspension of 2-((tert-butoxycarbonyl)amino)-3-cyano-7-fluorothieno[3,2-c]pyridine 5-oxide (5.27 g, 17.0 mmol) in 1,2-dichloroethane (34 mL) was cooled to 0° C. A solution of phosphoryl chloride (32 mL, 344 mmol) in 1,2-dichloroethane (34 mL) was added dropwise. The reaction mixture was stirred at room temperature for 30 min, at 45° C. for 90 min, and cooled to room temperature. The reaction mixture was diluted with 1,2-dichloroethane (100 mL) and added to a mixture of sat. aq. $NaHCO_3$ (500 mL), NaOH (5 M in water, 40 mL), and ice. Solid $NaHCO_3$ was added to the stirred mixture to maintain pH ~6-7. Once bubbling ceased, the phases were separated. The aqueous phase was extracted 3× with DCM. The combined organic phases were dried over $MgSO_4$ and filtered. The filtrate was diluted with MeOH and silica gel, concentrated, and the residue was purified on silica, eluting with 50-100% DCM in hexanes. Fractions containing desired material were concentrated to give the title compound (3.87 g, 69%) as a white solid. MS (ES) m/z=328 (M+1).

Preparation 3A

Methyl 4-bromo-5-fluorobenzo[b]thiophene-2-carboxylate

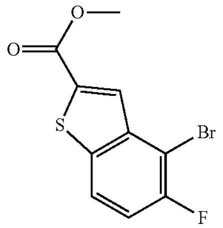

A solution of methyl thioglycolate (0.18 mL, 2.0 mmol, 1 eq.) in THE (5 mL) was flushed with $N_2$ and charged with NaH (60 mass %) in mineral oil (0.101 g, 2.53 mmol, 1.24 eq.) at RT. Gas evolution was observed, and a precipitate formed in the flask. The reaction was stirred at RT for 20 min. A solution of 2-bromo-3,6-difluorobenzaldehyde (0.475 g, 2.04 mmol) in THF (5 mL) was added slowly via syringe over −2 min. The reaction was stirred at RT for 9 h. Additional methyl thioglycolate (0.1 mL, 1 mmol, 0.5 eq.) and sodium hydride (60 mass %) in mineral oil (0.050 g, 1.3 mmol, 0.6 eq.) were added and stirring was continued at RT for ~18 h. The mixture was diluted with EtOAc and washed with sat. aq. $NH_4Cl$ and brine. The organics were dried over anhydrous $Na_2SO_4$, filtered and concentrated. The residue was purified on silica, eluting with 2% MTBE/Hex to obtain the title compound (0.346 g, 59%) as a white solid. $^1H$ NMR (400 MHz, DMSO-$d_6$) δ 8.23-8.19 (dd, J=4.49, 8.9 Hz, 1H), 8.05 (s, 1H), 7.62 (t, J=9.0 Hz, 1H), 3.93 (s, 3H).

Preparation 4A

4-Bromo-5-fluorobenzo[b]thiophene-2-carboxylic acid

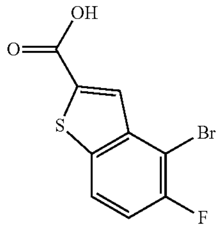 [SMILES: O=C(O)c1cc2c(Br)c(F)ccc2s1]

A solution of methyl 4-bromo-5-fluorobenzo[b]thiophene-2-carboxylate (19.2 g, 66.4 mmol, 1 eq.) in MeOH (130 mL) and THE (130 mL) was charged with 5N NaOH (66 mL, 330 mmol, 5 eq.) and stirred at RT for 40 min. The mixture was concentrated and $H_2O$ (500 mL) was added. The pH was adjusted to ~2 with 5N HCl. The mixture was extracted with EtOAc (2×500 mL) and the combined organic layers were dried over anhydrous $Na_2SO_4$, filtered and concentrated. The solids were dried under vacuum at 50° C. to afford the title compound (17.6 g, 96%) as a white solid. MS (ES) m/z=229 (M-1-$CO_2$).

Preparation 5A tert-Butyl (4-bromo-5-fluorobenzo[b]thiophen-2-yl)carbamate

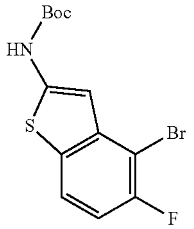 [SMILES: CC(C)(C)OC(=O)Nc1cc2c(Br)c(F)ccc2s1]

A solution of 4-bromo-5-fluorobenzo[b]thiophene-2-carboxylic acid (1.5 g, 5.5 mmol) in t-butanol (30 mL) was charged with TEA (1.5 mL, 11 mmol, 2.0 eq.) and diphenylphosphoryl azide (1.5 mL, 6.9 mmol, 1.3 eq.) and heated at 95° C. for 1 h. The mixture was cooled and concentrated. The residue was purified on silica, eluting with MTBE/Hex (4% to 20%) to obtain the title compound (0.987 g, 52%) as a white solid. MS (ES) m/z=290 (M+1).

Preparation 6A tert-Butyl (4-(5,5-dimethyl-1,3,2-dioxaborinan-2-yl)-5-fluorobenzo[b]thiophen-2-yl)carbamate

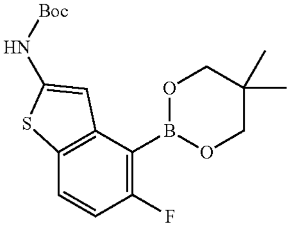 [SMILES: CC1(C)COB(c2c(F)ccc3sc(NC(=O)OC(C)(C)C)cc23)OC1]

A mixture of tert-butyl (4-bromo-5-fluorobenzo[b]thiophen-2-yl)carbamate (3.08 g, 8.90 mmol) and bis(neopentyl glycolato)diboron (4.02 g, 17.8 mmol, 2 eq.) and KOAc (2.62 g, 26.7 mmol, 3 eq.) in 1,4-dioxane (70 mL, 819.9 mmol) was sparged with $N_2$ for 20 min. To the mixture was added Pd(ddpf)$Cl_2$ (0.69 g, 0.90 mmol, 0.1 eq.). The reaction was sonicated for 3 min, then put through a vacuum/$N_2$ refill cycle (3λ) and was heated at 100° C. for 3 h. The mixture was cooled to RT, filtered through diatomaceous earth and was rinsed with 1:4 EtOAc/Hex. The filtrate was concentrated and the residue was purified on silica (0-40% MTBE/Hex) to obtain the title compound (2.95 g, 87%) as a white solid. $^1H$ NMR (400 MHz, DMSO-$d_6$) δ 10.81-10.79 (bs, 1H), 7.84-7.74 (dd, J=5.07, 8.59, 1H), 7.14 (s, 1H), 6.94-6.88 (m, 1H), 3.89 (bs, 4H), 1.49 (s, 10H), 1.03 (s, 6H).

Preparation 20 tert-Butyl (3-cyano-4-(3-(ethylthio)-5-fluoro-1-hydroxy-7,9-dihydrofuro[3,4-f]quinazolin-6-yl)-7-fluorobenzo[b]thiophen-2-yl)carbamate

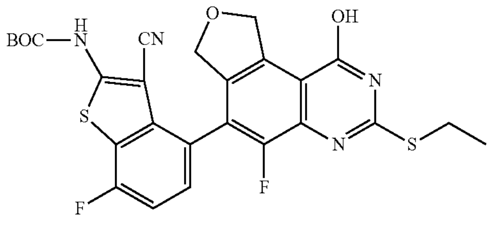 [SMILES: CCSc1nc(O)c2c3c(c(-c4ccc(F)c5sc(NC(=O)OC(C)(C)C)c(C#N)c45)c(Cl)c2n1)COC3]

6-Bromo-3-(ethylthio)-5-fluoro-7,9-dihydrofuro[3,4-f]quinazolin-1-ol (0.80 g, 2.32 mmol), tert-butyl (3-cyano-4-(5,5-dimethyl-1,3,2-dioxaborinan-2-yl)-7-fluorobenzo[b]thiophen-2-yl)carbamate (1.12 g, 2.78 mmol) and cesium carbonate (2.27 g, 6.95 mmol) were combined in DMF (12 mL) and the mixture was degassed by sparging with argon for 10 min. Dichloro[bis(2-(diphenylphosphino)phenyl) ether]palladium(II) (Pd-117, 0.166 g, 0.232 mmol) was added and the mixture was heated to 100° C. After 24 h, the mixture was concentrated under reduced pressure. The residue was purified on silica, eluting with 0-10% MeOH in DCM to obtain the title compound (0.96 g, 74%) as a yellow solid. MS (ES) m/z=557 (M+1).

The following compounds in Table 5 were prepared in similar manner as described in Preparation 20. Various methods were used to purify the compounds, which would be apparent to one skilled in the art.

TABLE 5

| Preparation | Chemical Name | Structure | MS (ES) m/z (M + 1) |
|---|---|---|---|
| 21 | tert-Butyl (4-(5-chloro-3-(ethylthio)-1-hydroxy-7,9-dihydrofuro[3,4-f]quinazolin-6-yl)-3-cyano-7-fluorobenzo[b]thiophen-2-yl)carbamate | 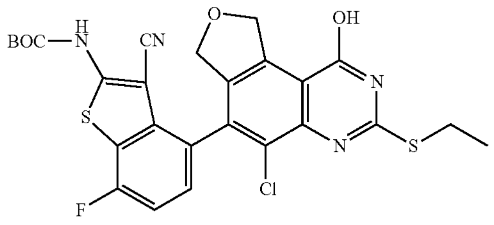 | 573 |
| 22 | tert-Butyl (4-(5-chloro-1-(((5-ethyl-1,3,4-oxadiazol-2-yl)methyl)amino)-3-(ethylthio)-7,9-dihydrofuro[3,4-f]quinazolin-6-yl)-3-cyano-7-fluorobenzo[b]thiophen-2-yl)carbamate | 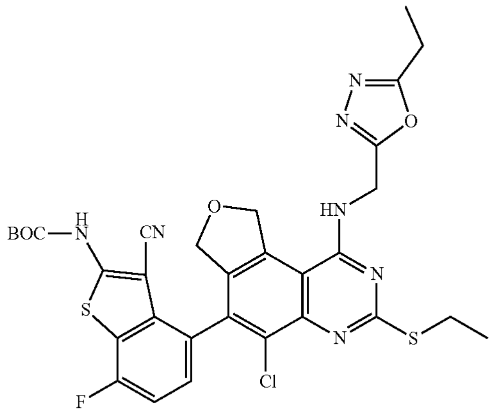 [SMILES: CCSc1nc(NCc2nnc(CC)o2)c2c3c(c(-c4ccc(F)c5sc(NC(=O)OC(C)(C)C)c(C#N)c45)c(Cl)c2n1)COC3] | 682 |
| 23 | tert-Butyl (4-(5-chloro-3-(ethylthio)-1-(((4,5,6,7-tetrahydrobenzo[d]isoxazol-3-yl)methyl)amino)-7,9-dihydrofuro[3,4-f]quinazolin-6-yl)-3-cyano-7-fluorobenzo[b]thiophen-2-yl)carbamate | 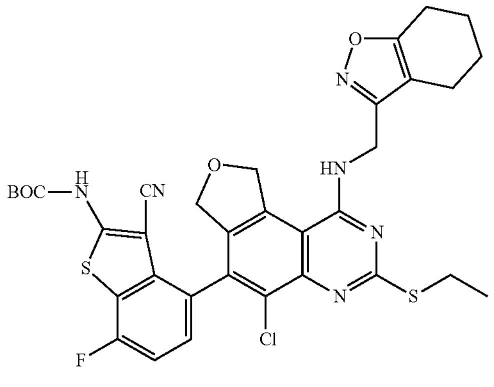 [SMILES: CCSc1nc(NCc2noc3c2CCCC3)c2c3c(c(-c4ccc(F)c5sc(NC(=O)OC(C)(C)C)c(C#N)c45)c(Cl)c2n1)COC3] | 707 |

TABLE 5-continued

| Preparation | Chemical Name | Structure | MS (ES) m/z (M + 1) |
|---|---|---|---|
| 7A [1] | tert-Butyl (4-(5-chloro-3-(ethylthio)-1-hydroxy-7,9-dihydrofuro[3,4-f]quinazolin-6-yl)-3-cyano-7-fluorobenzo[b]thiophen-2-yl)carbamate, Atropisomer 2 | 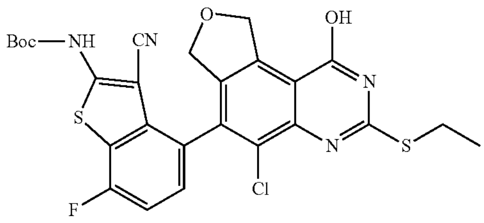 [SMILES: CCSc1nc(O)c2c3c(c(-c4ccc(F)c5sc(NC(=O)OC(C)(C)C)c(C#N)c45)c(Cl)c2n1)COC3] | 573 |
| 8A | tert-Butyl (4-(3-(ethylthio)-5-fluoro-1-hydroxy-7,9-dihydrofuro[3,4-f]quinazolin-6-yl)-5-fluorobenzo[b]thiophen-2-yl)carbamate | 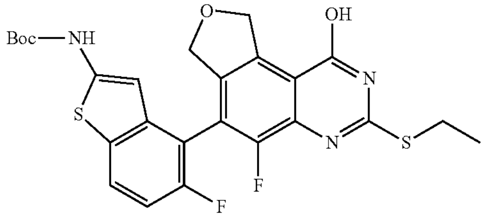 [SMILES: CCSc1nc(O)c2c3c(c(-c4c(F)ccc5sc(NC(=O)OC(C)(C)C)cc45)c(F)c2n1)COC3] | 532 |
| 2B [2] | tert-Butyl (4-(3-(ethylthio)-5-fluoro-1-((2-(trimethylsilyl)ethoxy)methoxy)-7,9-dihydrofuro[3,4-f]quinazolin-6-y1)-5-fluorobenzo[b]thiophen-2-yl)carbamate, Atropisomer 1 | 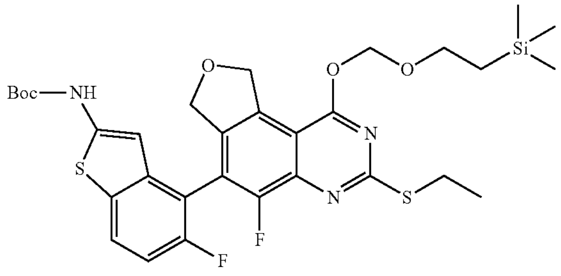 [SMILES: CCSc1nc(OCOCC[Si](C)(C)C)c2c3c(c(-c4c(F)ccc5sc(NC(=O)OC(C)(C)C)cc45)c(F)c2n1)COC3] | 662 |
| 37C | tert-Butyl (4-(5-chloro-3-(ethylthio)-1-((2-(trimethylsilyl)ethoxy)methoxy)-7,9-dihydrofuro[3,4-f]quinazolin-6-yl)-5-fluorobenzo[b]thiophen-2-y1)carbamate | 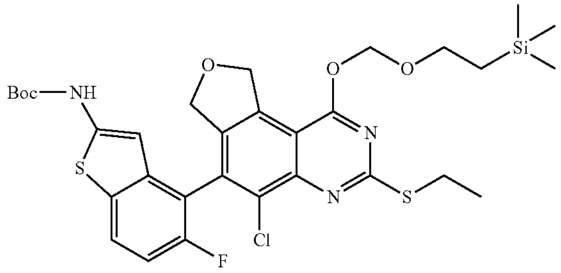 [SMILES: CCSc1nc(OCOCC[Si](C)(C)C)c2c3c(c(-c4c(F)ccc5sc(NC(=O)OC(C)(C)C)cc45)c(Cl)c2n1)COC3] | 678 |
| 38C | tert-Butyl (4-(5-chloro-3-(ethylthio)-1-((2-(trimethylsilyl)ethoxy)methoxy)-7,9-dihydrofuro[3,4-f]quinazolin-6-yl)-3-cyano-7-fluorobenzo[b]thiophen-2-yl)carbamate | 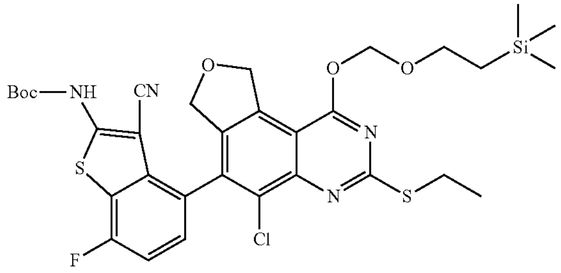 [SMILES: CCSc1nc(OCOCC[Si](C)(C)C)c2c3c(c(-c4ccc(F)c5sc(NC(=O)OC(C)(C)C)c(C#N)c45)c(Cl)c2n1)COC3] | 703 |

[1] Prep-Chiral-HPLC; Phenomenex Lux Cellulose-5, 30 × 150 mm, 18-30% (1:1 MeOH:EtOH) in Heptane, 42.5 mL/min

[2] Chiral SFC; Chiralpak IC, 50 × 250 mm, 25% (MeOH w/ 0.2% dimethylethylamine) in $CO_2$, 300 g/min Preparation 9A tert-Butyl (3-cyano-4-(3-(ethylthio)-5-fluoro-1-hydroxy-7,9-dihydrofuro[3,4-f]quinazolin-6-yl)-5-fluorobenzo[b]thiophen-2-yl)carbamate

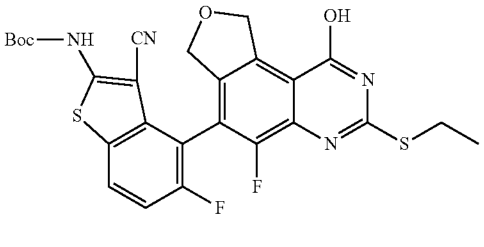

A mixture of tert-butyl (4-(3-(ethylthio)-5-fluoro-1-hydroxy-7,9-dihydrofuro[3,4-f]quinazolin-6-yl)-5-fluorobenzo[b]thiophen-2-yl)carbamate (0.750 g, 1.41 mmol) and acetonitrile (10 mL) was stirred at −40° C. Sulfurisocyanatidic chloride (0.184 mL, 2.12 mmol) was slowly added and the mixture was allowed to warm to 0° C. After consumption of the starting material (monitored by LCMS), the mixture was cooled to 0° C. DMF (4 mL) was slowly added. Upon reaction completion (monitored by LCMS), the mixture was diluted with DCM (20 mL) and saturated aq. ammonium chloride (20 mL). The layers were separated and the aqueous layer was extracted with DCM (3×30 mL). The combined organics were passed through a hydrophobic frit and concentrated under reduced pressure to obtain the crude title compound. MS (ES) m/z=557 (M+1).

Preparation 3B tert-Butyl (3-cyano-4-(3-(ethylthio)-5-fluoro-1-((2-(trimethylsilyl)ethoxy)methoxy)-7,9-dihydrofuro[3,4-f]quinazolin-6-yl)-5-fluorobenzo[b]thiophen-2-yl)carbamate

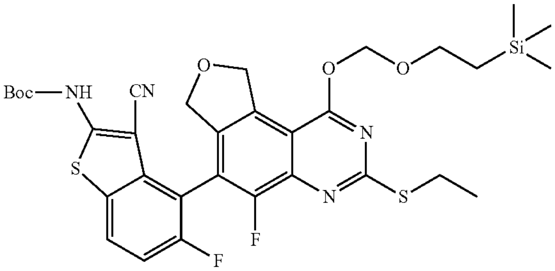 [SMILES: CCSc1nc(OCOCC[Si](C)(C)C)c2c3c(c(-c4c(F)ccc5sc(NC(=O)OC(C)(C)C)c(C#N)c45)c(F)c2n1)COC3]

tert-Butyl (4-(3-(ethylthio)-5-fluoro-1-((2-(trimethylsilyl)ethoxy)methoxy)-7,9-dihydrofuro[3,4-f]quinazolin-6-yl)-5-fluorobenzo[b]thiophen-2-yl)carbamate, Atropisomer 1 was used in a manner analogous to the method of Preparation 9A to afford the title compound (19.2 g, 87% purity, 94%) as a white solid. MS (ES) m/z=687 (M+1). Clean atropisomer, chiral purification from Preparation 2B.

Preparation 39C tert-Butyl (4-(5-chloro-3-(ethylthio)-1-((2-(trimethylsilyl)ethoxy)methoxy)-7,9-dihydrofuro[3,4-f]quinazolin-6-yl)-3-cyano-5-fluorobenzo[b]thiophen-2-yl)carbamate

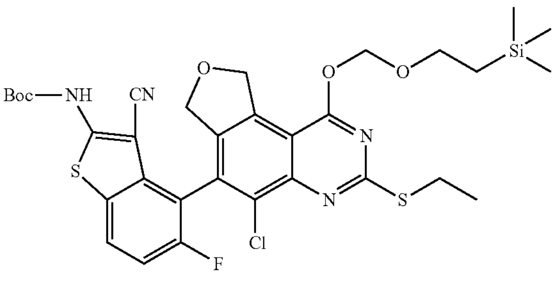 [SMILES: CCSc1nc(OCOCC[Si](C)(C)C)c2c3c(c(-c4c(F)ccc5sc(NC(=O)OC(C)(C)C)c(C#N)c45)c(Cl)c2n1)COC3]

tert-Butyl (4-(5-chloro-3-(ethylthio)-1-((2-(trimethylsilyl)ethoxy)methoxy)-7,9-dihydrofuro[3,4-f]quinazolin-6-yl)-5-fluorobenzo[b]thiophen-2-yl)carbamate was used in a manner analogous to the method of Preparation 9A to afford the crude title compound (13.6 g) as a yellow solid. MS (ES) m/z=703 (M+1).

Preparation 4B tert-Butyl (3-cyano-4-(3-(ethylthio)-5-fluoro-1-hydroxy-7,9-dihydrofuro[3,4-f]quinazolin-6-yl)-5-fluorobenzo[b]thiophen-2-yl)carbamate

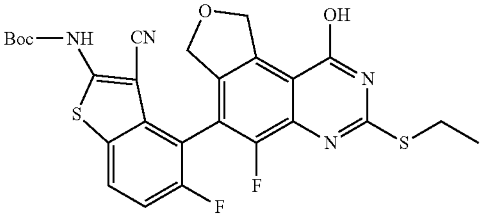 [SMILES: CCSc1nc(O)c2c3c(c(-c4c(F)ccc5sc(NC(=O)OC(C)(C)C)c(C#N)c45)c(F)c2n1)COC3]

To a mixture of tert-butyl (3-cyano-4-(3-(ethylthio)-5-fluoro-1-((2-(trimethylsilyl)ethoxy)methoxy)-7,9-dihydrofuro[3,4-f]quinazolin-6-yl)-5-fluorobenzo[b]thiophen-2-yl)carbamate (19.2 g, 26.3 mmol) in THE (192 mL) was added activated molecular sieves (4 angstrom, 38 g), followed by tetrabutylammonium fluoride (1M in THF, 105 mL, 105 mmol). The reaction mixture was heated for 9 h at a bath temperature of 80° C., then cooled to room temperature. Additional activated molecular sieves (4 angstrom, 17 g) were added, and the reaction mixture was heated overnight at a bath temperature of 80° C., then cooled to room temperature. The mixture was filtered and the filter cake was washed with EtOAc. The combined filtrates were concentrated under reduced pressure, diluted with 2-methyltetrahydrofuran (300 mL), and washed with water (3×300 mL). The combined aqueous layers were extracted with 2-methyltetrahydrofuran (300 mL). The combined organic layers were washed with 5% aqueous citric acid (300 mL), dried over magnesium sulfate, filtered, and concentrated under reduced pressure. The crude material was purified on silica, eluting with 0-60% EtOAc in cyclohexane to obtain the title compound (9.42 g) as a yellow foam. MS (ES) m/z=557 (M+1). Clean atropisomer, chiral purification from Preparation 2B.

Preparation 40C tert-Butyl (4-(5-chloro-3-(ethylthio)-1-hydroxy-7,9-dihydrofuro[3,4-f]quinazolin-6-yl)-3-cyano-5-fluorobenzo[b]thiophen-2-yl)carbamate

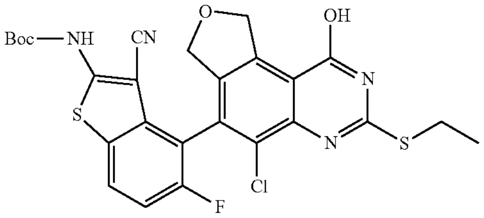 [SMILES: CCSc1nc(O)c2c3c(c(-c4c(F)ccc5sc(NC(=O)OC(C)(C)C)c(C#N)c45)c(Cl)c2n1)COC3]

tert-Butyl (4-(5-chloro-3-(ethylthio)-1-((2-(trimethylsilyl)ethoxy)methoxy)-7,9-dihydrofuro[3,4-f]quinazolin-6-yl)-3-cyano-5-fluorobenzo[b]thiophen-2-yl)carbamate was used in a manner analogous to the method of Preparation 4B to afford the crude title compound (4.0 g) as a yellow solid. MS (ES) m/z=573 (M+1).

The following compounds in Table 6 were prepared in similar manner as described in Preparation 16. Various methods were used to purify the compounds, which would be apparent to one skilled in the art.

Preparation 5B

6-Bromo-1-chloro-3-(ethylsulfinyl)-5-fluoro-7,9-dihydrofuro[3,4-f]quinazoline

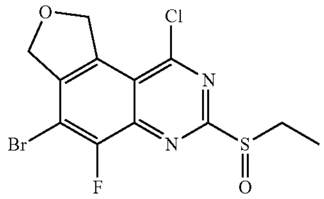

To a 0° C. mixture of 6-bromo-1-chloro-3-(ethylthio)-5-fluoro-7,9-dihydrofuro[3,4-f]quinazoline (2 g, 6 mmol) in DCM (30 mL) was added potassium hydrogenperoxomonosulphate (0.7M in water; 8 mL, 6 mmol). The reaction mixture was stirred for 1 h at 0° C., then allowed to warm to room temperature and stirred overnight. Water and DCM were added and the layers were separated. The organic layer was dried over sodium sulfate, filtered, and concentrated under reduced pressure to obtain the crude title compound (1.48 g, ~55:45 sulfoxide:sulfone). MS (ES) m/z=379 (M+1).

The following compounds in Table 7 were prepared in similar manner as described in Preparation 18. Various methods were used to purify the compounds, which would be apparent to one skilled in the art.

TABLE 6

| Preparation | Chemical Name | Structure | MS (ES) m/z (M + 1) |
|---|---|---|---|
| 10A | tert-Butyl (3-cyano-4-(1,5-dichloro-3-(ethylthio)-7,9-dihydrofuro[3,4-f]quinazolin-6-yl)-7-fluorobenzo[b]thiophen-2-yl)carbamate | 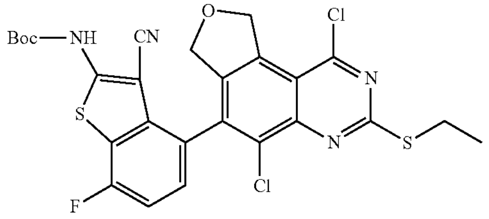 [SMILES: CCSc1nc(Cl)c2c3c(c(-c4ccc(F)c5sc(NC(=O)OC(C)(C)C)c(C#N)c45)c(Cl)c2n1)COC3] | 591 |
| 11A [1] | tert-Butyl (3-cyano-4-(1,5-dichloro-3-(ethylthio)-7,9-dihydrofuro[3,4-f]quinazolin-6-yl)-7-fluorobenzo[b]thiophen-2-yl)carbamate | 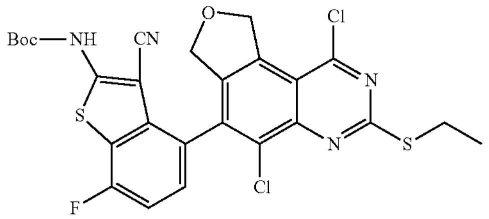 [SMILES: CCSc1nc(Cl)c2c3c(c(-c4ccc(F)c5sc(NC(=O)OC(C)(C)C)c(C#N)c45)c(Cl)c2n1)COC3] | 591 |
| 12A | tert-Butyl (4-(1-chloro-3-(ethylthio)-5-fluoro-7,9-dihydrofuro[3,4-f]quinazolin-6-yl)-3-cyano-5-fluorobenzo[b]thiophen-2-yl)carbamate | 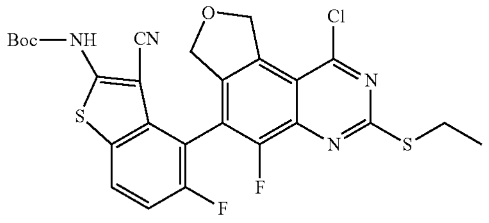 [SMILES: CCSc1nc(Cl)c2c3c(c(-c4c(F)ccc5sc(NC(=O)OC(C)(C)C)c(C#N)c45)c(F)c2n1)COC3] | 575 |

[1] Clean atropisomer, chiral purification from Preparation 7A

TABLE 7

| Preparation | Chemical Name | Structure | MS (ES) m/z (M + 1) |
| --- | --- | --- | --- |
| 13A | tert-Butyl (4-(1-(((1H-pyrazol-5-yl)methyl)amino)-5-chloro-3-(ethylthio)-7,9-dihydrofuro[3,4-f]quinazolin-6-yl)-3-cyano-7-fluorobenzo[b]thiophen-2-yl)carbamate | 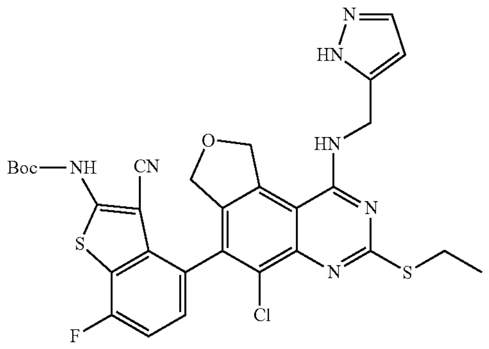 [SMILES: CCSc1nc(NCc2ccn[nH]2)c2c3c(c(-c4ccc(F)c5sc(NC(=O)OC(C)(C)C)c(C#N)c45)c(Cl)c2n1)COC3] | 652 |
| 14A | tert-Butyl (4-(5-chloro-3-(ethylthio)-1-(((3-methyl-1H-pyrazol-5-yl)methyl)amino)-7,9-dihydrofuro[3,4-f]quinazolin-6-yl)-3-cyano-7-fluorobenzo[b]thiophen-2-yl)carbamate | 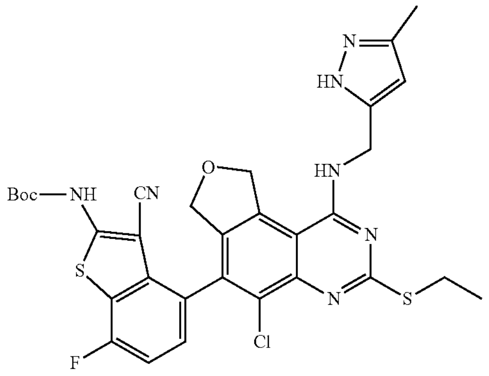 [SMILES: CCSc1nc(NCc2cc(C)n[nH]2)c2c3c(c(-c4ccc(F)c5sc(NC(=O)OC(C)(C)C)c(C#N)c45)c(Cl)c2n1)COC3] | 666 |
| 15A | tert-Butyl (4-(5-chloro-1-(((5-(difluoromethyl)-4H-1,2,4-triazol-3-yl)methyl)amino)-3-(ethylthio)-7,9-dihydrofuro[3,4-f]quinazolin-6-yl)-3-cyano-7-fluorobenzo[b]thiophen-2-yl)carbamate | 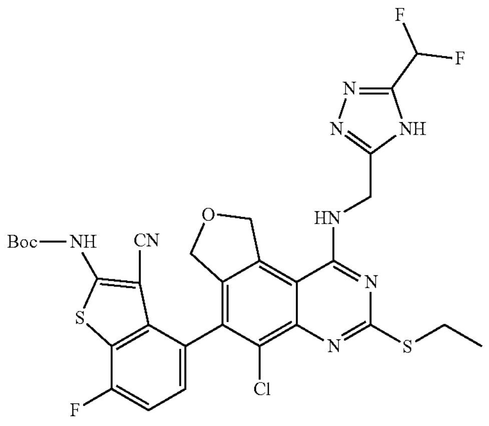 [SMILES: CCSc1nc(NCc2nnc(C(F)F)[nH]2)c2c3c(c(-c4ccc(F)c5sc(NC(=O)OC(C)(C)C)c(C#N)c45)c(Cl)c2n1)COC3] | 703 |
| 16A [1] | tert-Butyl (4-(1-(((1H-pyrazol-4-yl)methyl)amino)-5-chloro-3-(ethylthio)-7,9-dihydrofuro[3,4-f]quinazolin-6-y1)-3-cyano-7-fluorobenzo[b]thiophen-2-yl)carbamate | 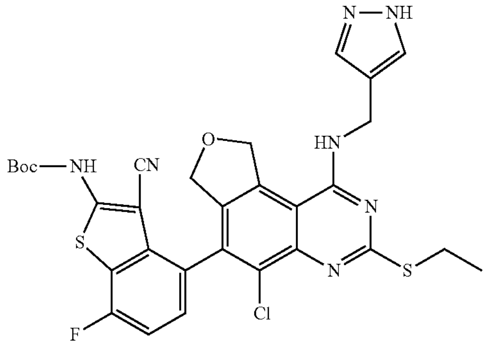 [SMILES: CCSc1nc(NCc2cn[nH]c2)c2c3c(c(-c4ccc(F)c5sc(NC(=O)OC(C)(C)C)c(C#N)c45)c(Cl)c2n1)COC3] | 652 |

TABLE 7-continued

| Preparation | Chemical Name | Structure | MS (ES) m/z (M + 1) |
|---|---|---|---|
| 17A | tert-Butyl (4-(5-chloro-3-(ethylthio)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 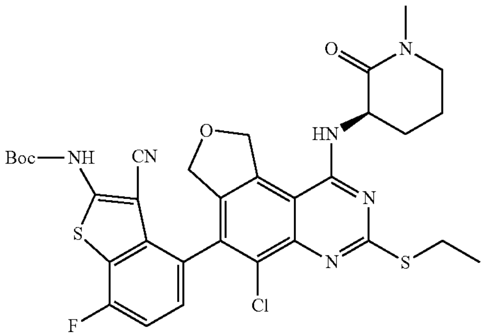 [SMILES: CCSc1nc(N[C@@H]2CCCN(C)C2=O)c2c3c(c(-c4ccc(F)c5sc(NC(=O)OC(C)(C)C)c(C#N)c45)c(Cl)c2n1)COC3] | 683 |
| 18A | tert-Butyl (4-(5-chloro-3-(ethylthio)-1-(((5-methyl-1,2,4-oxadiazol-3-yl)methyl)amino)-7,9-dihydrofuro[3,4-f]quinazolin-6-yl)-3-cyano-7-fluorobenzo[b]thiophen-2-yl)carbamate | 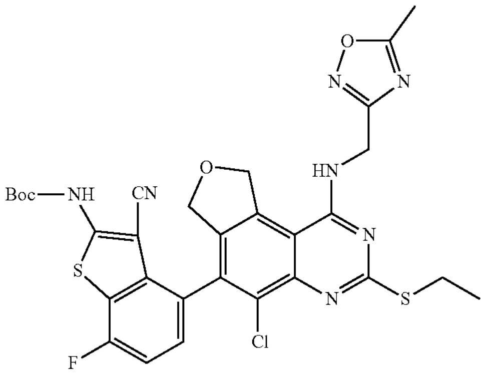 [SMILES: CCSc1nc(NCc2noc(C)n2)c2c3c(c(-c4ccc(F)c5sc(NC(=O)OC(C)(C)C)c(C#N)c45)c(Cl)c2n1)COC3] | 668 |
| 19A | tert-Butyl (4-(5-chloro-1-(((5-ethyl-1,3,4-oxadiazol-2-yl)methyl)amino)-3-(ethylthio)-7,9-dihydrofuro[3,4-f]quinazolin-6-yl)-3-cyano-7-fluorobenzo[b]thiophen-2-yl)carbamate | 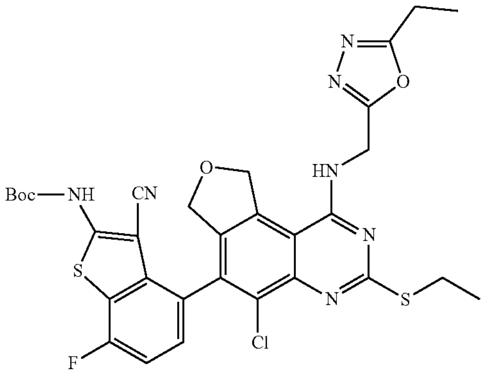 [SMILES: CCSc1nc(NCc2nnc(CC)o2)c2c3c(c(-c4ccc(F)c5sc(NC(=O)OC(C)(C)C)c(C#N)c45)c(Cl)c2n1)COC3] | 682 |
| 20A | tert-Butyl (3-cyano-4-(3-(ethylthio)-5-fluoro-1-(((R)-1-methyl-2-oxopyrrolidin-3-yl)amino)-7,9-dihydrofuro[3,4-f]quinazolin-6-yl)-5-fluorobenzo[b]thiophen-2-yl)carbamate | 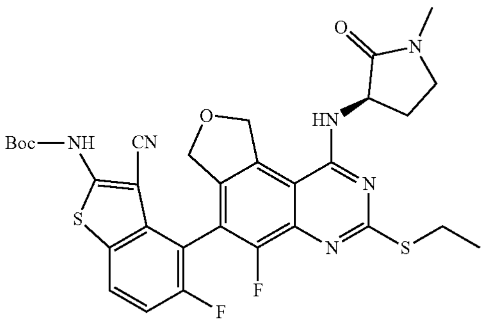 [SMILES: CCSc1nc(N[C@@H]2CCN(C)C2=O)c2c3c(c(-c4c(F)ccc5sc(NC(=O)OC(C)(C)C)c(C#N)c45)c(F)c2n1)COC3] | 653 |

TABLE 7-continued

| Preparation | Chemical Name | Structure | MS (ES) m/z (M + 1) |
|---|---|---|---|
| 21A | tert-Butyl (3-cyano-4-(1-(((3-cyclopropyl-1H-1,2,4-triazol-5-yl)methyl)amino)-3-(ethylthio)-5-fluoro-7,9-dihydrofuro[3,4-f]quinazolin-6-yl)-5-fluorobenzo[b]thiophen-2-yl)carbamate | 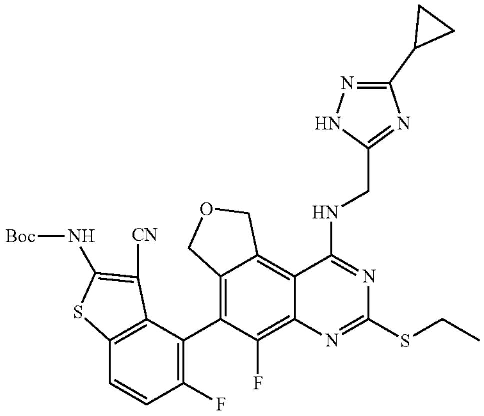 [SMILES: CCSc1nc(NCc2nc(C3CC3)n[nH]2)c2c3c(c(-c4c(F)ccc5sc(NC(=O)OC(C)(C)C)c(C#N)c45)c(F)c2n1)COC3] | 677 |
| 6B | (R)-3-((6-Bromo-5-chloro-3-(ethylthio)-7,9-dihydrofuro[3,4-f]quinazolin-1-yl)amino)-1-methylpyrrolidin-2-one | 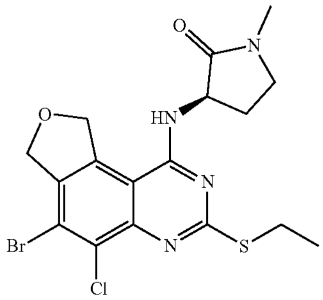 [SMILES: CCSc1nc(N[C@@H]2CCN(C)C2=O)c2c3c(c(Br)c(Cl)c2n1)COC3] | 457 |
| 7B | (3R)-3-((6-Bromo-3-(ethylsulfinyl)-5-fluoro-7,9-dihydrofuro[3,4-f]quinazolin-1-yl)amino)-1-methylpyrrolidin-2-one | 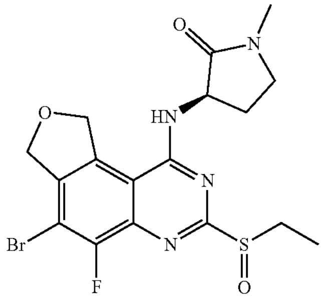 [SMILES: CCS(=O)c1nc(N[C@@H]2CCN(C)C2=O)c2c3c(c(Br)c(F)c2n1)COC3] | 457 |
| 8B | 6-Bromo-3-(ethylsulfinyl)-5-fluoro-N-((5-methyl-1,2,4-oxadiazol-3-yl)methyl)-7,9-dihydrofuro[3,4-f]quinazolin-1-amine | 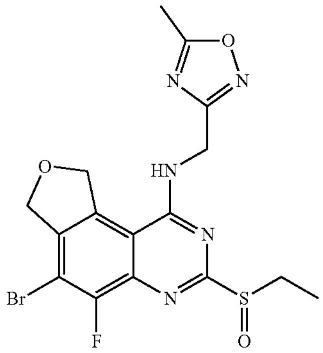 [SMILES: CCS(=O)c1nc(NCc2noc(C)n2)c2c3c(c(Br)c(F)c2n1)COC3] | 456 |

TABLE 7-continued

| Preparation | Chemical Name | Structure | MS (ES) m/z (M + 1) |
|---|---|---|---|
| 9B | tert-Butyl (4-(5-chloro-3-(ethylthio)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 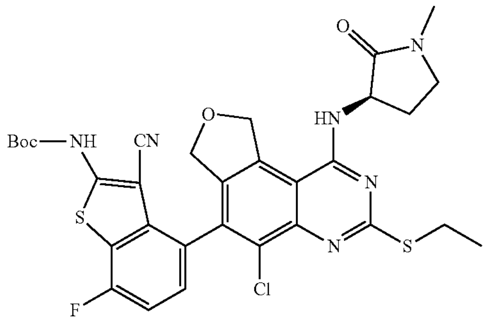 [SMILES: CCSc1nc(N[C@@H]2CCN(C)C2=O)c2c3c(c(-c4ccc(F)c5sc(NC(=O)OC(C)(C)C)c(C#N)c45)c(Cl)c2n1)COC3] | 669 |
| 10B | tert-Butyl (4-(1-(((5-carbamoyl-1,2,4-oxadiazol-3-yl)methyl)amino)-5-chloro-3-(ethylthio)-7,9-dihydrofuro[3,4-f]quinazolin-6-yl)-3-cyano-7-fluorobenzo[b]thiophen-2-yl)carbamate | 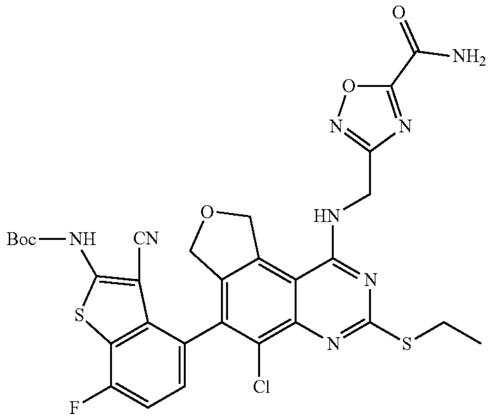 [SMILES: CCSc1nc(NCc2noc(C(N)=O)n2)c2c3c(c(-c4ccc(F)c5sc(NC(=O)OC(C)(C)C)c(C#N)c45)c(Cl)c2n1)COC3] | 697 |
| 11B | tert-Butyl (4-(1-(((5-amino-1,3,4-thiadiazol-2-yl)methyl)amino)-5-chloro-3-(ethylthio)-7,9-dihydrofuro[3,4-f]quinazolin-6-yl)-3-cyano-7-fluorobenzo[b]thiophen-2-yl)carbamate | 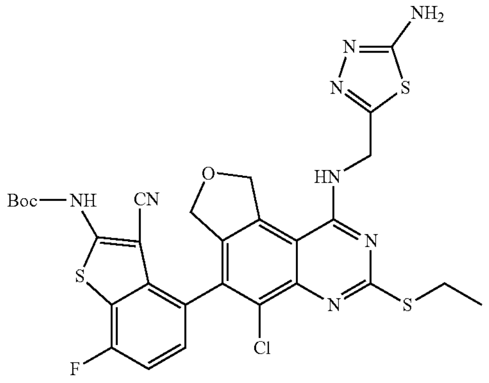 [SMILES: CCSc1nc(NCc2nnc(N)s2)c2c3c(c(-c4ccc(F)c5sc(NC(=O)OC(C)(C)C)c(C#N)c45)c(Cl)c2n1)COC3] | 685 |
| 41C | tert-Butyl (3-cyano-4-(3-(ethylthio)-5-fluoro-1-(((R)-1-methyl-2-oxopiperidin-3-yl)amino)-7,9-dihydrofuro[3,4-f]quinazolin-6-yl)-5-fluorobenzo[b]thiophen-2-yl)carbamate | 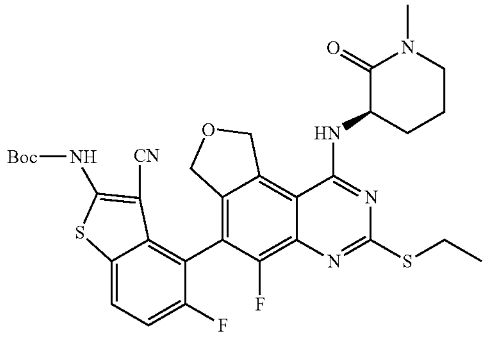 [SMILES: CCSc1nc(N[C@@H]2CCCN(C)C2=O)c2c3c(c(-c4c(F)ccc5sc(NC(=O)OC(C)(C)C)c(C#N)c45)c(F)c2n1)COC3] | 667 |

TABLE 7-continued

| Preparation | Chemical Name | Structure | MS (ES) m/z (M + 1) |
| --- | --- | --- | --- |
| 42C [1] | tert-Butyl (4-(5-chloro-3-(ethylthio)-1-(((4,5,6,7-tetrahydro-1H-indazol-3-yl)methyl)amino)-7,9-dihydrofuro[3,4-f]quinazolin-6-yl)-3-cyano-7-fluorobenzo[b]thiophen-2-yl)carbamate | 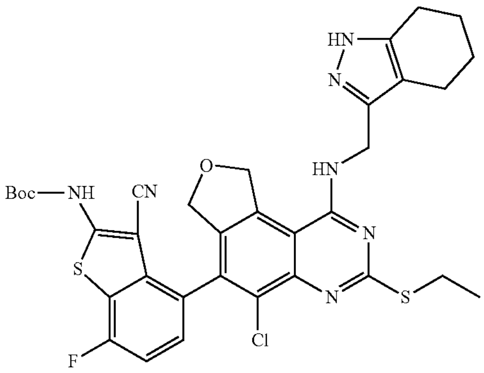 [SMILES: CCSc1nc(NCc2n[nH]c3c2CCCC3)c2c3c(c(-c4ccc(F)c5sc(NC(=O)OC(C)(C)C)c(C#N)c45)c(Cl)c2n1)COC3] | 706 |
| 43C [1] | tert-Butyl (4-(5-chloro-3-(ethylthio)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 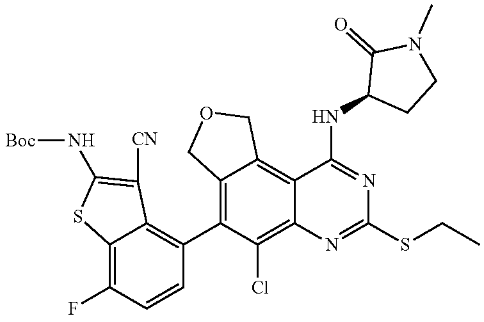 [SMILES: CCSc1nc(N[C@@H]2CCN(C)C2=O)c2c3c(c(-c4ccc(F)c5sc(NC(=O)OC(C)(C)C)c(C#N)c45)c(Cl)c2n1)COC3] | 669 |
| 44C [1] | tert-Butyl (4-(5-chloro-3-(ethylthio)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 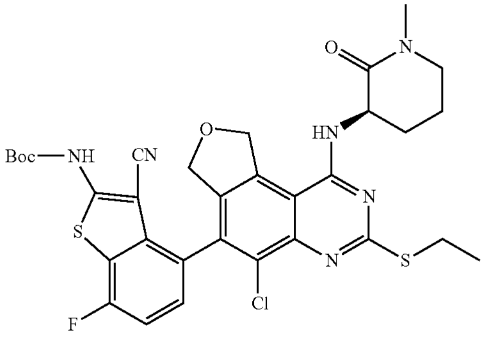 [SMILES: CCSc1nc(N[C@@H]2CCCN(C)C2=O)c2c3c(c(-c4ccc(F)c5sc(NC(=O)OC(C)(C)C)c(C#N)c45)c(Cl)c2n1)COC3] | 683 |

[1] Clean atropisomer, chiral purification from Preparation 7A

Preparation 24 tert-Butyl (4-(5-chloro-3-(ethylthio)-1-((1-isopropyl-1H-1,2,3-triazol-4-yl)methoxy)-7,9-dihydrofuro[3,4-f]quinazolin-6-yl)-3-cyano-7-fluorobenzo[b]thiophen-2-yl)carbamate

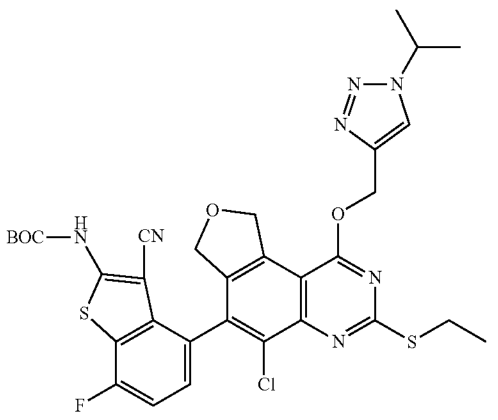 [SMILES: CCSc1nc(OCc2cn(C(C)C)nn2)c2c3c(c(-c4ccc(F)c5sc(NC(=O)OC(C)(C)C)c(C#N)c45)c(Cl)c2n1)COC3]

A mixture of tert-butyl (4-(5-chloro-3-(ethylthio)-1-hydroxy-7,9-dihydrofuro[3,4-f]quinazolin-6-yl)-3-cyano-7-fluorobenzo[b]thiophen-2-yl)carbamate (0.120 g, 0.209 mmol), (1-isopropyl-1,2,3-triazol-4-yl)methanol (0.059 g, 0.418 mmol), bromotriisopropyl phosphonium hexafluorophosphate (0.161 g, 0.418 mmol), and 1,8-diazabicyclo (5.4.0)undec-7-ene (0.159 g, 1.05 mmol) in 1,4-dioxane (10 mL) was stirred at 80° C. under nitrogen. After 4 h, the mixture was diluted with DCM (50 mL) and concentrated under reduced pressure. The residue was purified on silica, eluting with 0-10% MeOH in DCM to obtain the title compound (0.110 g, 75%) as an off-white solid. MS (ES) m/z=696 (M+1).

Preparation 45C tert-Butyl (4-(5-chloro-3-(ethylthio)-1-((pyridazin-3-ylmethyl)amino)-7,9-dihydrofuro[3,4-f]quinazolin-6-yl)-3-cyano-5-fluorobenzo[b]thiophen-2-yl)carbamate

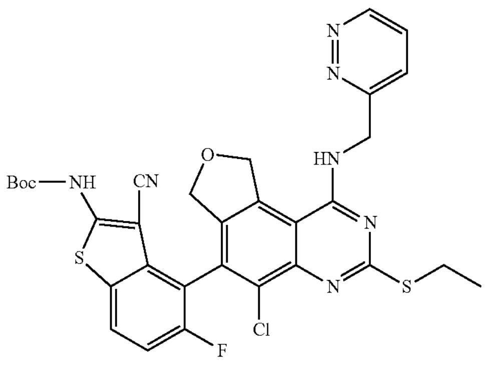 [SMILES: CCSc1nc(NCc2cccnn2)c2c3c(c(-c4c(F)ccc5sc(NC(=O)OC(C)(C)C)c(C#N)c45)c(Cl)c2n1)COC3]

To a stirred solution of tert-butyl (4-(5-chloro-3-(ethylthio)-1-hydroxy-7,9-dihydrofuro[3,4-f]quinazolin-6-yl)-3-cyano-5-fluorobenzo[b]thiophen-2-yl)carbamate (4.0 g, 6.98 mmol) and bromotris(dimethylamino)phosphanium (8.13 g, 20.9 mmol) in acetonitrile (150 mL) was added diisopropylethylamine (4.51 g, 34.9 mmol) dropwise at room temperature under nitrogen. The mixture was stirred at 50° C. under nitrogen for 2 h, then concentrated under reduced pressure and diluted with water (100 mL). The mixture was extracted with EtOAc (2×50 mL). The combined organic layers were washed with brine (30 mL), dried over anhydrous $Na_2SO_4$, filtered, and concentrated under reduced pressure. The residue was purified by reversed phase purification, eluting with 50-100% ACN in (water w/0.1% ammonium hydroxide), to give the title compound (3.7 g) as a yellow solid. MS (ES) m/z=664 (M+1).

Preparation 46C tert-Butyl (4-(5-chloro-3-(ethylsulfinyl)-1-((pyridazin-3-ylmethyl)amino)-7,9-dihydrofuro[3,4-f]quinazolin-6-yl)-3-cyano-5-fluorobenzo[b]thiophen-2-yl)carbamate

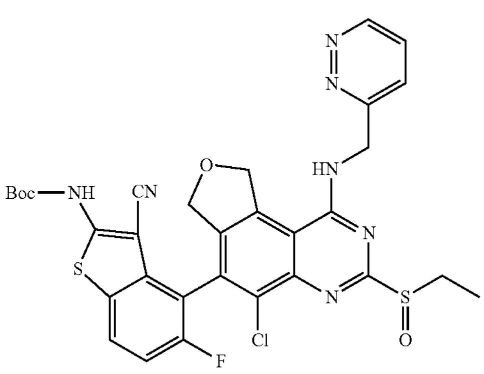 [SMILES: CCS(=O)c1nc(NCc2cccnn2)c2c3c(c(-c4c(F)ccc5sc(NC(=O)OC(C)(C)C)c(C#N)c45)c(Cl)c2n1)COC3]

A solution of tert-butyl (4-(5-chloro-3-(ethylthio)-1-((pyridazin-3-ylmethyl)amino)-7,9-dihydrofuro[3,4-f]quinazolin-6-yl)-3-cyano-5-fluorobenzo[b]thiophen-2-yl)carbamate (1.20 g, 1.81 mmol) and oxone (0.608 g, 3.62 mmol) in 4:1 dioxane:water (60 mL) was stirred at room temperature under nitrogen for 1 h, then concentrated under reduced pressure and diluted with water (200 mL). The mixture was extracted with EtOAc (2×100 mL). The combined organic layers were washed with brine (30 mL), dried over anhydrous $Na_2SO_4$, filtered, and concentrated under reduced pressure to give the crude title compound (1.13 g) as a yellow solid. MS (ES) m/z=680 (M+1).

Preparation 22A

6-Bromo-3-(ethylsulfinyl)-5-fluoro-7,9-dihydrofuro[3,4-f]quinazolin-1-ol

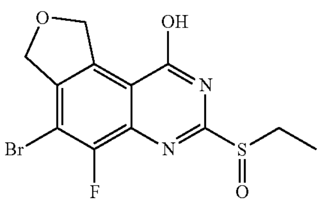 [SMILES: CCS(=O)c1nc(O)c2c3c(c(Br)c(F)c2n1)COC3]

To a mixture of 6-bromo-3-(ethylthio)-5-fluoro-7,9-dihydrofuro[3,4-f]quinazolin-1-ol (18.03 g, 87% purity, 45.44 mmol) in DCM (450 mL) and EtOH (450 mL) was added a solution of hexaammonium heptamolybdate tetrahydrate (2.05 g, 1.76 mmol) in water (~5 mL). Hydrogen peroxide (20 mL, 35 wt %, 230 mmol) was added dropwise over 10-15 min (a water bath was used to maintain the internal temperature at −16° C.). After 24 h, additional hydrogen peroxide (10 mL, 35 wt %, 110 mmol) was added dropwise. After 3 days, water (60 mL) was added and the mixture was concentrated under reduced pressure to remove the majority of the DCM. The resulting suspension was filtered, washed with water (2×200 mL), washed with EtOH (2×200 mL), and dried in a vacuum oven (40° C.) to obtain the title compound (16.2 g, 82%, ~87:13 sulfoxide:sulfone) as an off-white solid. MS (ES) m/z=361,363 (M+1, Br).

Preparation 12B tert-Butyl (3-cyano-4-(3-(ethylsulfonyl)-5-fluoro-1-hydroxy-7,9-dihydrofuro[3,4-f]quinazolin-6-yl)-5-fluorobenzo[b]thiophen-2-yl)carbamate

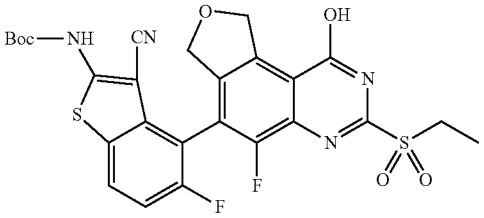 [SMILES: CCS(=O)(=O)c1nc(O)c2c3c(c(-c4c(F)ccc5sc(NC(=O)OC(C)(C)C)c(C#N)c45)c(F)c2n1)COC3]

tert-Butyl (3-cyano-4-(3-(ethylthio)-5-fluoro-1-hydroxy-7,9-dihydrofuro[3,4-f]quinazolin-6-yl)-5-fluorobenzo[b]thiophen-2-yl)carbamate was used in a manner analogous to the method of Preparation 22A to afford the title compound (6.6 g, 91%, ~14:86 sulfoxide:sulfone) as a white solid. MS (ES) m/z=589 (M+1). Clean atropisomer, chiral purification from Preparation 2B.

Preparation 25 tert-Butyl (4-(5-chloro-3-(ethylsulfonyl)-1-((1-isopropyl-1H-1,2,3-triazol-4-yl)methoxy)-7,9-dihydrofuro[3,4-f]quinazolin-6-yl)-3-cyano-7-fluorobenzo[b]thiophen-2-yl)carbamate

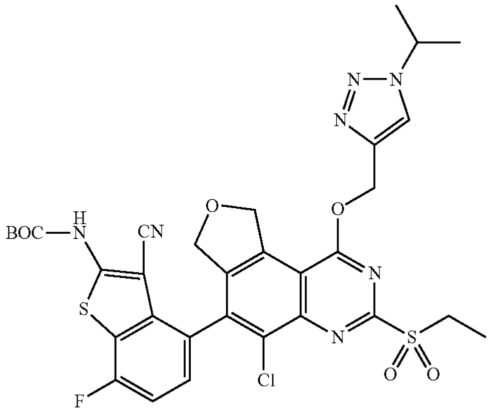 [SMILES: CCS(=O)(=O)c1nc(OCc2cn(C(C)C)nn2)c2c3c(c(-c4ccc(F)c5sc(NC(=O)OC(C)(C)C)c(C#N)c45)c(Cl)c2n1)COC3]

A mixture of tert-butyl (4-(5-chloro-3-(ethylthio)-1-((1-isopropyl-1H-1,2,3-triazol-4-yl)methoxy)-7,9-dihydrofuro[3,4-f]quinazolin-6-yl)-3-cyano-7-fluorobenzo[b]thiophen-2-yl)carbamate (0.100 g, 0.144 mmol) and mCPBA (0.062 g, 0.360 mmol) in DCM (10 mL) was stirred at room temperature under nitrogen. After 2 h, the mixture was diluted with water (30 mL) and extracted with DCM (3×50 mL). The combined organics were concentrated under reduced pressure. The residue was purified on silica, eluting with 0-10% MeOH in DCM to obtain the title compound (0.090 g, 86%) as a white solid. MS (ES) m/z=728 (M+1).

The following compounds in Table 8 were prepared in similar manner as described in Preparation 25. Various methods were used to purify the compounds, which would be apparent to one skilled in the art.

TABLE 8

| Preparation | Chemical Name | Structure | MS (ES) m/z (M + 1) |
|---|---|---|---|
| 26 | tert-Butyl (3-cyano-4-(3-(ethylsulfonyl)-5-fluoro-1-hydroxy-7,9-dihydrofuro[3,4-f]quinazolin-6-yl)-7-fluorobenzo[b]thiophen-2-yl)carbamate | 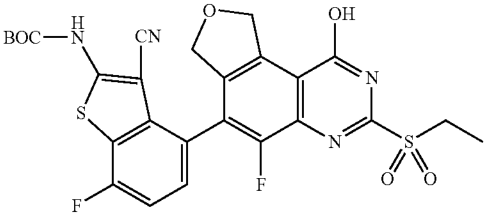 [SMILES: CCS(=O)(=O)c1nc(O)c2c3c(c(-c4ccc(F)c5sc(NC(=O)OC(C)(C)C)c(C#N)c45)c(F)c2n1)COC3] | 589 |
| 27 | tert-Butyl (4-(5-chloro-3-(ethylsulfonyl)-1-hydroxy-7,9-dihydrofuro[3,4-f]quinazolin-6-yl)-3-cyano-7-fluorobenzo[b]thiophen-2-yl)carbamate | 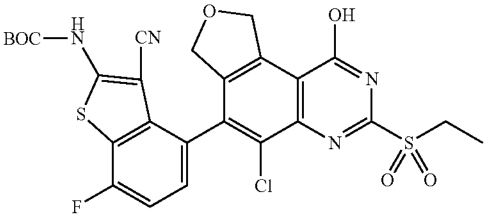 [SMILES: CCS(=O)(=O)c1nc(O)c2c3c(c(-c4ccc(F)c5sc(NC(=O)OC(C)(C)C)c(C#N)c45)c(Cl)c2n1)COC3] | 605 |

TABLE 8-continued

| Preparation | Chemical Name | Structure | MS (ES) m/z (M + 1) |
|---|---|---|---|
| 28 | tert-Butyl (4-(5-chloro-1-(((5-ethyl-1,3,4-oxadiazol-2-yl)methyl)amino)-3-(ethylsulfonyl)-7,9-dihydrofuro[3,4-f]quinazolin-6-y1)-3-cyano-7-fluorobenzo[b]thiophen-2-yl)carbamate | 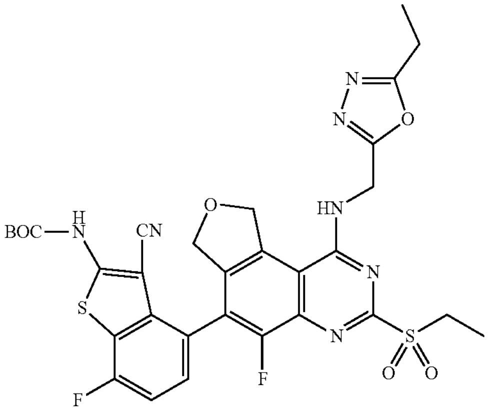 [SMILES: CCc1nnc(CNc2nc(S(=O)(=O)CC)nc3c(F)c(-c4ccc(F)c5sc(NC(=O)OC(C)(C)C)c(C#N)c45)c4c(c23)COC4)o1] | 714 |
| 29 | tert-Butyl (4-(5-chloro-3-(ethylsulfonyl)-1-(((4,5,6,7-tetrahydrobenzo[d] isoxazol-3-yl)methyl) amino)-7,9-dihydrofuro[3,4-f]quinazolin-6-yl)-3-cyano-7-fluorobenzo[b]thiophen-2-yl)carbamate | 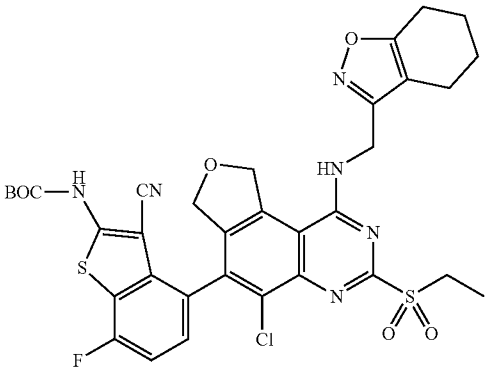 [SMILES: CCS(=O)(=O)c1nc(NCc2noc3c2CCCC3)c2c3c(c(-c4ccc(F)c5sc(NC(=O)OC(C)(C)C)c(C#N)c45)c(Cl)c2n1)COC3] | 739 |
| 23A | tert-Butyl (4-(1-(((1H-pyrazol-5-yl)methyl)amino)-5-chloro-3-(ethylsulfonyl)-7,9-dihydrofuro[3,4-f]quinazolin-6-yl)-3-cyano-7-fluorobenzo[b]thiophen-2-yl)carbamate | 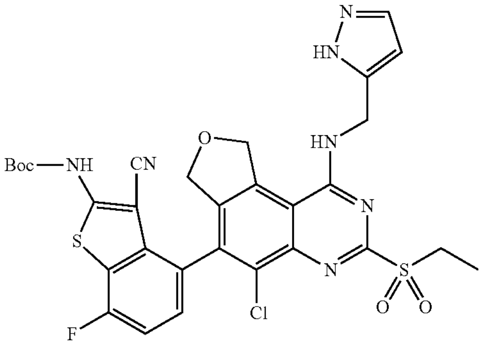 [SMILES: CCS(=O)(=O)c1nc(NCc2ccn[nH]2)c2c3c(c(-c4ccc(F)c5sc(NC(=O)OC(C)(C)C)c(C#N)c45)c(Cl)c2n1)COC3] | 684 |
| 24A | tert-Butyl (4-(5-chloro-3-(ethylsulfony1)-1-(((3-methyl-1H-pyrazol-5-yl)methyl)amino)-7,9-dihydrofuro[3,4-f]quinazolin-6-yl)-3-cyano-7-fluorobenzo[b]thiophen-2-yl)carbamate | 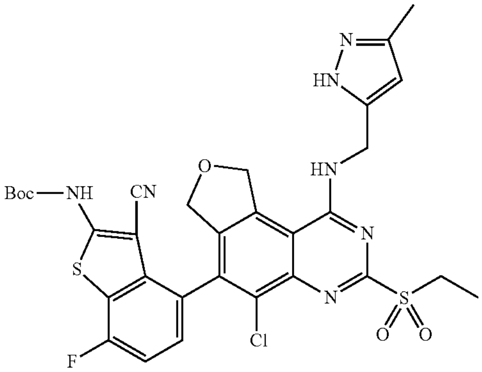 [SMILES: CCS(=O)(=O)c1nc(NCc2cc(C)n[nH]2)c2c3c(c(-c4ccc(F)c5sc(NC(=O)OC(C)(C)C)c(C#N)c45)c(Cl)c2n1)COC3] | 698 |

TABLE 8-continued

| Preparation | Chemical Name | Structure | MS (ES) m/z (M + 1) |
|---|---|---|---|
| 25A | tert-Butyl (4-(5-chloro-1-(((5-(difluoromethyl)-4H-1,2,4-triazol-3-yl)methyl)amino)-3-(ethylsulfony1)-7,9-dihydrofuro[3,4-f]quinazolin-6-yl)-3-cyano-7-fluorobenzo[b]thiophen-2-yl)carbamate | 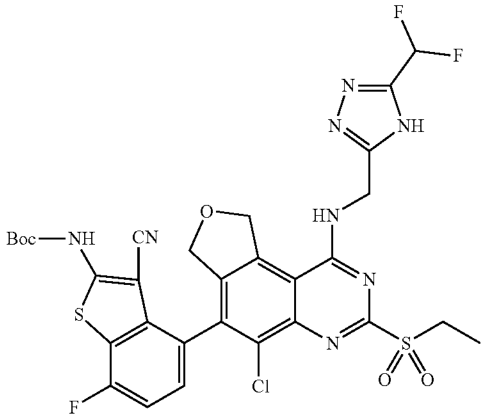 [SMILES: CCS(=O)(=O)c1nc(NCc2nnc(C(F)F)[nH]2)c2c3c(c(-c4ccc(F)c5sc(NC(=O)OC(C)(C)C)c(C#N)c45)c(Cl)c2n1)COC3] | 735 |
| 26A [1] | tert-Butyl (4-(1-(((1H-pyrazol-4-yl)methyl)amino)-5-chloro-3-(ethylsulfonyl)-7,9-dihydrofuro[3,4-f]quinazolin-6-yl)-3-cyano-7-fluorobenzo[b]thiophen-2-yl)carbamate | 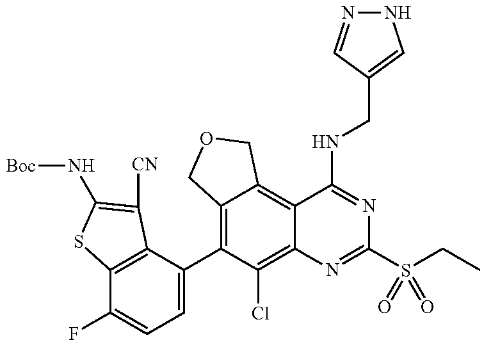 [SMILES: CCS(=O)(=O)c1nc(NCc2cn[nH]c2)c2c3c(c(-c4ccc(F)c5sc(NC(=O)OC(C)(C)C)c(C#N)c45)c(Cl)c2n1)COC3] | 684 |
| 27A | tert-Butyl (4-(5-chloro-3-(ethylsulfonyl)-1-(((R)-1-methyl-2-oxopiperidin-3-yl)amino)-7,9-dihydrofuro[3,4-f]quinazolin-6-y1)-3-cyano-7-fluorobenzo[b]thiophen-2-y1)carbamate | 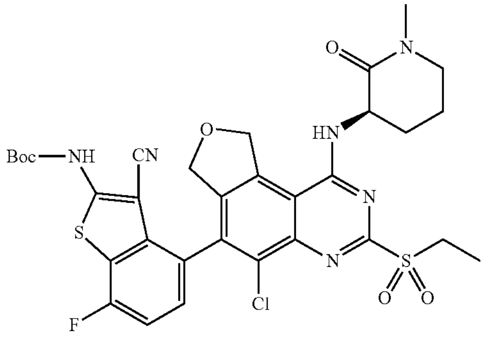 [SMILES: CCS(=O)(=O)c1nc(N[C@@H]2CCCN(C)C2=O)c2c3c(c(-c4ccc(F)c5sc(NC(=O)OC(C)(C)C)c(C#N)c45)c(Cl)c2n1)COC3] | 715 |
| 28A | tert-Butyl (4-(5-chloro-3-(ethylsulfony1)-1-(((5-methyl-1,2,4-oxadiazol-3-yl)methyl)amino)-7,9-dihydrofuro[3,4-f]quinazolin-6-y1)-3-cyano-7-fluorobenzo[b]thiophen-2-yl)carbamate | 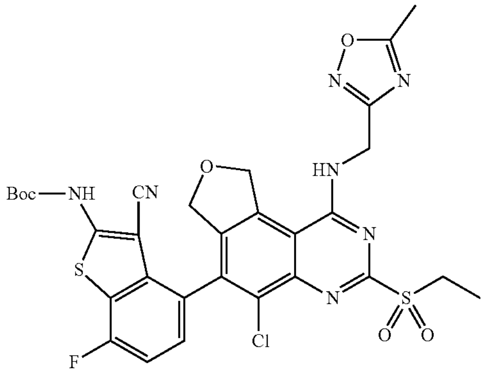 [SMILES: CCS(=O)(=O)c1nc(NCc2noc(C)n2)c2c3c(c(-c4ccc(F)c5sc(NC(=O)OC(C)(C)C)c(C#N)c45)c(Cl)c2n1)COC3] | 700 |

TABLE 8-continued

| Preparation | Chemical Name | Structure | MS (ES) m/z (M + 1) |
|---|---|---|---|
| 29A | tert-Butyl (4-(5-chloro-1-(((5-ethyl-1,3,4-oxadiazol-2-yl)methyl)amino)-3-(ethylsulfonyl)-7,9-dihydrofuro[3,4-f]quinazolin-6-yl)-3-cyano-7-fluorobenzo[b]thiophen-2-yl)carbamate | 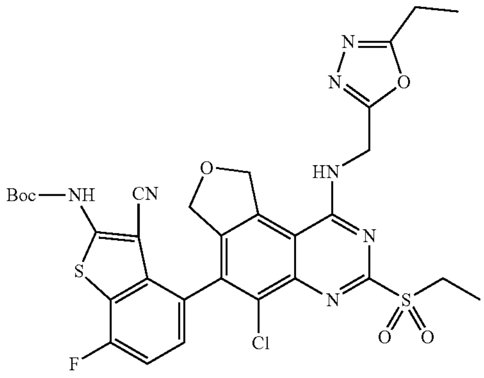 [SMILES: CCc1nnc(CNc2nc(S(=O)(=O)CC)nc3c(Cl)c(-c4ccc(F)c5sc(NC(=O)OC(C)(C)C)c(C#N)c45)c4c(c23)COC4)o1] | 714 |
| 30A | tert-Butyl (3-cyano-4-(3-(ethylsulfonyl)-5-fluoro-1-(((R)-1-methyl-2-oxopyrrolidin-3-yl)amino)-7,9-dihydrofuro[3,4-f]quinazolin-6-yl)-5-fluorobenzo[b]thiophen-2-yl)carbamate | 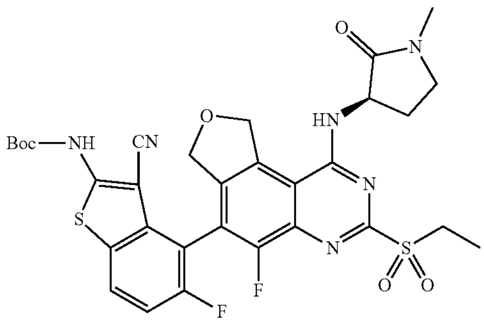 [SMILES: CCS(=O)(=O)c1nc(N[C@@H]2CCN(C)C2=O)c2c3c(c(-c4c(F)ccc5sc(NC(=O)OC(C)(C)C)c(C#N)c45)c(F)c2n1)COC3] | 685 |
| 31A | tert-Butyl (3-cyano-4-(1-(((3-cyclopropyl-1H-1,2,4-triazol-5-yl)methyl)amino)-3-(ethylsulfonyl)-5-fluoro-7,9-dihydrofuro[3,4-f]quinazolin-6-yl)-5-fluorobenzo[b]thiophen-2-yl)carbamate | 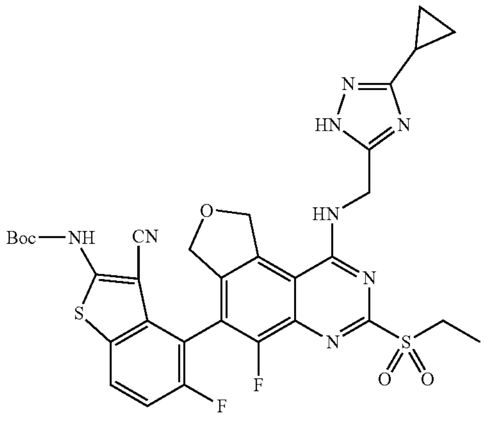 [SMILES: CCS(=O)(=O)c1nc(NCc2nc(C3CC3)n[nH]2)c2c3c(c(-c4c(F)ccc5sc(NC(=O)OC(C)(C)C)c(C#N)c45)c(F)c2n1)COC3] | 709 |
| 13B | (R)-3-((6-Bromo-5-chloro-3-(ethylsulfonyl)-7,9-dihydrofuro[3,4-f]quinazolin-1-yl)amino)-1-methylpyrrolidin-2-one | 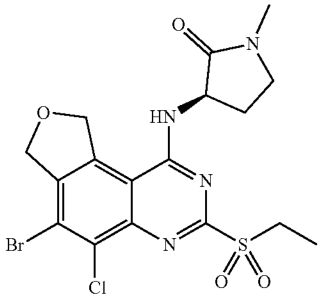 [SMILES: CCS(=O)(=O)c1nc(N[C@@H]2CCN(C)C2=O)c2c3c(c(Br)c(Cl)c2n1)COC3] | 489 |

TABLE 8-continued

| Preparation | Chemical Name | Structure | MS (ES) m/z (M + 1) |
|---|---|---|---|
| 14B | tert-Butyl (4-(5-chloro-3-(ethylsulfonyl)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 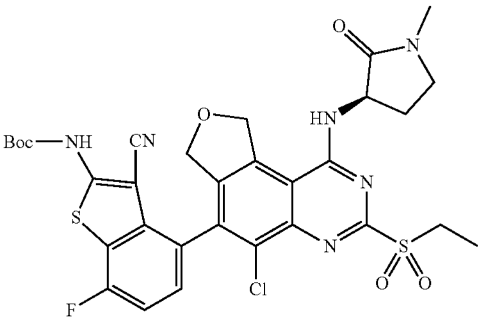 [SMILES: CCS(=O)(=O)c1nc(N[C@@H]2CCN(C)C2=O)c2c3c(c(-c4ccc(F)c5sc(NC(=O)OC(C)(C)C)c(C#N)c45)c(Cl)c2n1)COC3] | 701 |
| 15B | tert-Butyl (4-(1-(((5-carbamoyl-1,2,4-oxadiazol-3-yl)methyl)amino)-5-chloro-3-(ethylsulfonyl)-7,9-dihydrofuro[3,4-f]quinazolin-6-yl)-3-cyano-7-fluorobenzo[b]thiophen-2-yl)carbamate | 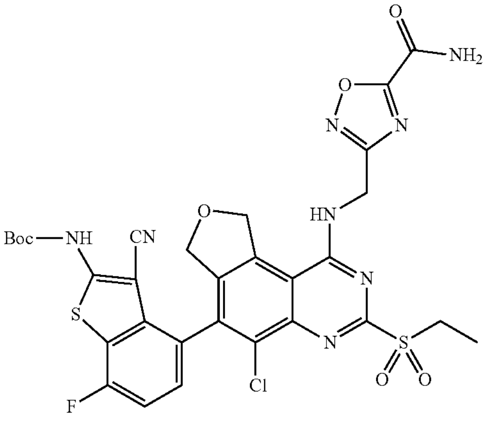 [SMILES: CCS(=O)(=O)c1nc(NCc2noc(C(N)=O)n2)c2c3c(c(-c4ccc(F)c5sc(NC(=O)OC(C)(C)C)c(C#N)c45)c(Cl)c2n1)COC3] | 729 |
| 16B | tert-Butyl (4-(1-(((5-amino-1,3,4-thiadiazol-2-yl)methyl)amino)-5-chloro-3-(ethylsulfonyl)-7,9-dihydrofuro[3,4-f]quinazolin-6-yl)-3-cyano-7-fluorobenzo[b]thiophen-2-yl)carbamate | 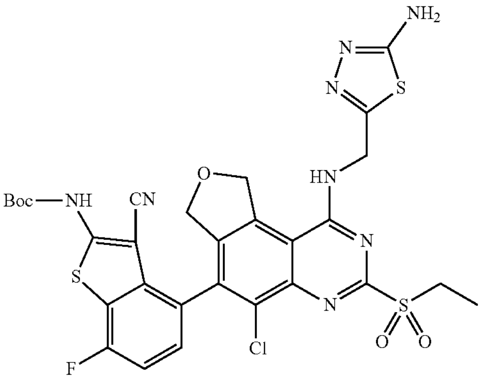 [SMILES: CCS(=O)(=O)c1nc(NCc2nnc(N)s2)c2c3c(c(-c4ccc(F)c5sc(NC(=O)OC(C)(C)C)c(C#N)c45)c(Cl)c2n1)COC3] | 717 |
| 47C | tert-Butyl (3-cyano-4-(3-(ethylsulfonyl)-5-fluoro-1-(((R)-1-methyl-2-oxopiperidin-3-yl)amino)-7,9-dihydrofuro[3,4-f]quinazolin-6-yl)-5-fluorobenzo[b]thiophen-2-yl)carbamate | 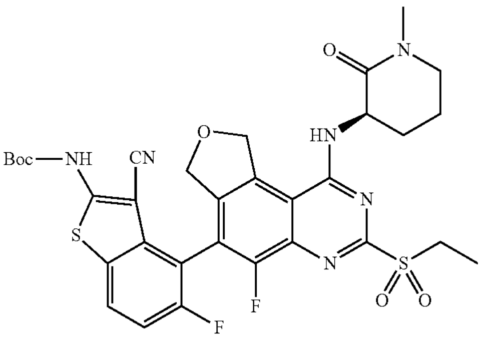 [SMILES: CCS(=O)(=O)c1nc(N[C@@H]2CCCN(C)C2=O)c2c3c(c(-c4c(F)ccc5sc(NC(=O)OC(C)(C)C)c(C#N)c45)c(F)c2n1)COC3] | 699 |

TABLE 8-continued

| Preparation | Chemical Name | Structure | MS (ES) m/z (M + 1) |
|---|---|---|---|
| 48C [1] | tert-Butyl (4-(5-chloro-3-(ethylsulfonyl)-1-(((4,5,6,7-tetrahydro-1H-indazol-3-yl)methyl)amino)-7,9-dihydrofuro[3,4-f]quinazolin-6-yl)-3-cyano-7-fluorobenzo[b]thiophen-2-yl)carbamate | 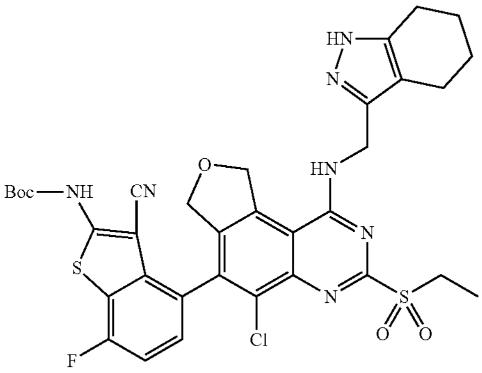 [SMILES: CCS(=O)(=O)c1nc(NCc2n[nH]c3c2CCCC3)c2c3c(c(-c4ccc(F)c5sc(NC(=O)OC(C)(C)C)c(C#N)c45)c(Cl)c2n1)COC3] | 738 |
| 49C [1] | tert-Butyl (4-(5-chloro-3-(ethylsulfonyl)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 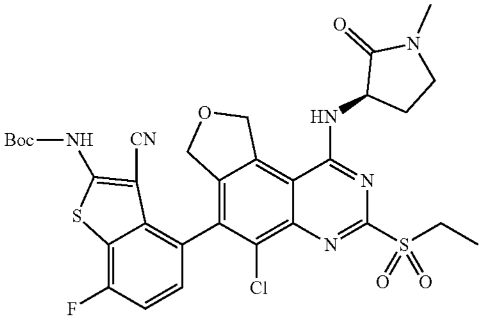 [SMILES: CCS(=O)(=O)c1nc(N[C@@H]2CCN(C)C2=O)c2c3c(c(-c4ccc(F)c5sc(NC(=O)OC(C)(C)C)c(C#N)c45)c(Cl)c2n1)COC3] | 701 |
| 50C [1] | tert-Butyl (4-(5-chloro-3-(ethylsulfonyl)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 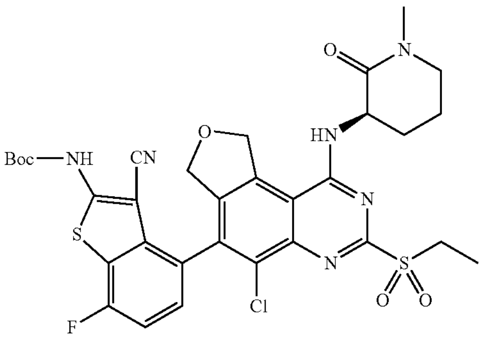 [SMILES: CCS(=O)(=O)c1nc(N[C@@H]2CCCN(C)C2=O)c2c3c(c(-c4ccc(F)c5sc(NC(=O)OC(C)(C)C)c(C#N)c45)c(Cl)c2n1)COC3] | 715 |
| 51C | tert-Butyl (4-(5-chloro-3-(ethylsulfonyl)-1-((2-(trimethylsilyl)ethoxy)methoxy)-7,9-dihydrofuro[3,4-f]quinazolin-6-yl)-3-cyano-7-fluorobenzo[b]thiophen-2-yl)carbamate | 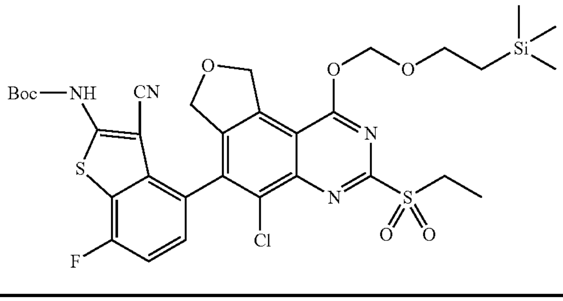 | 733 (M − H) |

[1] Clean atropisomer, chiral purification from Preparation 7A

Preparation 30 tert-Butyl (4-(S-chloro-1-((1-isopropyl-1H-1,2,3-triazol-4-yl)methoxy)-3-(((S)-1-methylpyrrolidin-2-yl)methoxy)-7,9-dihydrofuro[3,4-f]quinazolin-6-yl)-3-cyano-7-fluorobenzo[b]thiophen-2-yl)carbamate

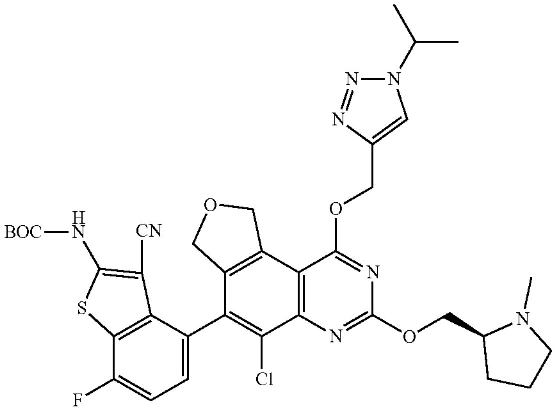 [SMILES: CC(C)n1cc(COc2nc(OC[C@@H]3CCCN3C)nc3c(Cl)c(-c4ccc(F)c5sc(NC(=O)OC(C)(C)C)c(C#N)c45)c4c(c23)COC4)nn1]

To a solution of (S)-(1-methylpyrrolidin-2-yl)methanol (0.038 g, 0.33 mmol) in THE (6 mL) at 0° C. was added lithium bis(trimethylsilyl)amide (1 M in THF, 0.27 mL, 0.27 mmol) at 0° C. under nitrogen. After 10 min, a solution of tert-butyl (4-(5-chloro-3-(ethylsulfonyl)-1-((1-isopropyl-1H-1,2,3-triazol-4-yl)methoxy)-7,9-dihydrofuro[3,4-f]quinazolin-6-yl)-3-cyano-7-fluorobenzo[b]thiophen-2-yl)carbamate (0.080 g, 0.11 mmol) in THE (3 mL) was added dropwise. The mixture was warmed to room temperature. After 4 h, the reaction mixture was diluted with water (20 mL) and extracted with DCM (4×50 mL). The combined organics were concentrated under reduced pressure. The residue was purified on silica, eluting with 0-10% MeOH in DCM to obtain the title compound (0.080 g, 97%) as a white solid. MS (ES) m/z=749 (M+1).

The following compounds in Table 9 were prepared in similar manner as described in Preparation 30. Various methods were used to purify the compounds, which would be apparent to one skilled in the art.

Table 9

| Preparation | Chemical Name | Structure | MS (ES) m/z (M + 1) |
|---|---|---|---|
| 31 | tert-Butyl (4-(5-chloro-1-hydroxy-3-(((S)-1-methylpyrrolidin-2-yl)methoxy)-7,9-dihydrofuro[3,4-f]quinazolin-6-yl)-3-cyano-7-fluorobenzo[b]thiophen-2-yl)carbamate | 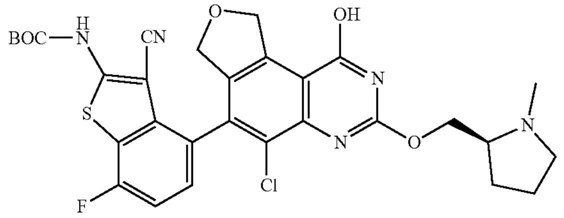 [SMILES: CN1CCC[C@H]1COc1nc(O)c2c3c(c(-c4ccc(F)c5sc(NC(=O)OC(C)(C)C)c(C#N)c45)c(Cl)c2n1)COC3] | 626 |
| 32 | tert-Butyl (3-cyano-7-fluoro-4-(5-fluoro-1-hydroxy-3-(((S)-1-methylpyrrolidin-2-yl)methoxy)-7,9-dihydrofuro[3,4-f]quinazolin-6-yl)benzo[b]thiophen-2-yl)carbamate | 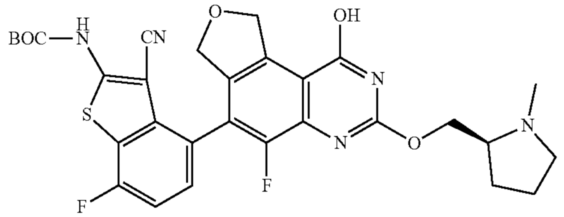 [SMILES: CN1CCC[C@H]1COc1nc(O)c2c3c(c(-c4ccc(F)c5sc(NC(=O)OC(C)(C)C)c(C#N)c45)c(F)c2n1)COC3] | 610 |
| 33 | tert-Butyl (4-(3-(((R)-1,4-dioxan-2-yl)methoxy)-5-chloro-1-hydroxy-7,9-dihydrofuro[3,4-f]quinazolin-6-yl)-3-cyano-7-fluorobenzo[b]thiophen-2-yl)carbamate | 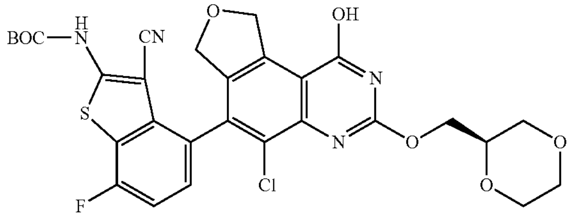 [SMILES: CC(C)(C)OC(=O)Nc1sc2c(F)ccc(-c3c4c(c5c(O)nc(OC[C@H]6COCCO6)nc5c3Cl)COC4)c2c1C#N] | 629 |

Table 9-continued

| Preparation | Chemical Name | Structure | MS (ES) m/z (M + 1) |
|---|---|---|---|
| 34 | tert-Butyl (4-(5-chloro-1-hydroxy-3-(((R)-4-methylmorpholin-2-yl)methoxy)-7,9-dihydrofuro[3,4-f]quinazolin-6-yl)-3-cyano-7-fluorobenzo[b]thiophen-2-yl)carbamate | 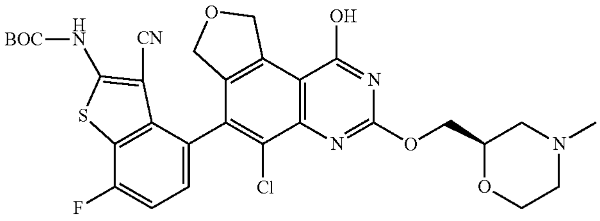 [SMILES: CN1CCO[C@@H](COc2nc(O)c3c4c(c(-c5ccc(F)c6sc(NC(=O)OC(C)(C)C)c(C#N)c56)c(Cl)c3n2)COC4)C1] | 642 |
| 35 | tert-Butyl (4-(5-chloro-3-(((2R,7aS)-2-fluorotetrahydro-1H-pyrrolizin-7a(5H)-yl)methoxy)-1-hydroxy-7,9-dihydrofuro[3,4-f]quinazolin-6-yl)-3-cyano-7-fluorobenzo[b]thiophen-2-yl)carbamate | 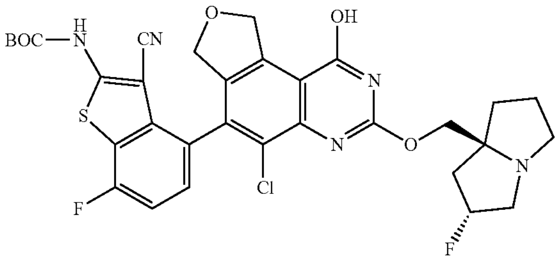 [SMILES: CC(C)(C)OC(=O)Nc1sc2c(F)ccc(-c3c4c(c5c(O)nc(OC[C@@]67CCCN6C[C@H](F)C7)nc5c3Cl)COC4)c2c1C#N] | 670 |
| 36 | tert-Butyl (4-(5-chloro-1-(((5-ethyl-1,3,4-oxadiazol-2-yl)methyl)amino)-3-(((S)-1-methylpyrrolidin-2-yl)methoxy)-7,9-dihydrofuro[3,4-f]quinazolin-6-yl)-3-cyano-7-fluorobenzo[b]thiophen-2-yl)carbamate | 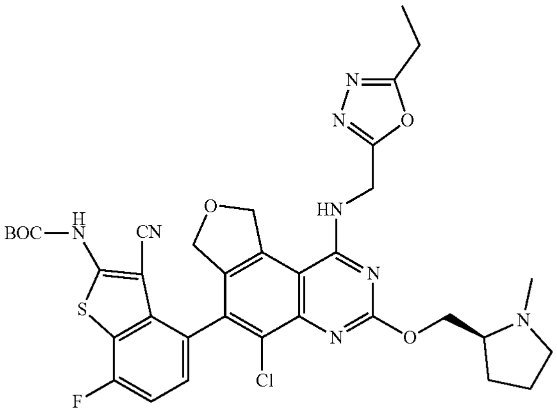 [SMILES: CCc1nnc(CNc2nc(OC[C@@H]3CCCN3C)nc3c(Cl)c(-c4ccc(F)c5sc(NC(=O)OC(C)(C)C)c(C#N)c45)c4c(c23)COC4)o1] | 735 |
| 37 | tert-Butyl (4-(3-(((R)-1,4-dioxan-2-yl)methoxy)-5-chloro-1-(((4,5,6,7-tetrahydrobenzo[d]isoxazol-3-yl)methyl)amino)-7,9-dihydrofuro[3,4-f]quinazolin-6-yl)-3-cyano-7-fluorobenzo[b]thiophen-2-yl)carbamate | 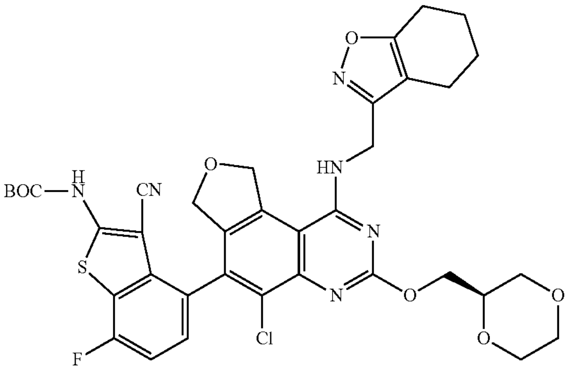 [SMILES: CC(C)(C)OC(=O)Nc1sc2c(F)ccc(-c3c4c(c5c(NCc6noc7c6CCCC7)nc(OC[C@H]6COCCO6)nc5c3Cl)COC4)c2c1C#N] | 763 |

Table 9-continued

| Preparation | Chemical Name | Structure | MS (ES) m/z (M + 1) |
|---|---|---|---|
| 38 | tert-Butyl (4-(5-chloro-3-(((R)-4-methylmorpholin-2-yl)methoxy)-1-(((4,5,6,7-tetrahydrobenzo[d]isoxazol-3-yl)methyl)amino)-7,9-dihydrofuro[3,4-f]quinazolin-6-yl)-3-cyano-7-fluorobenzo[b]thiophen-2-yl)carbamate | 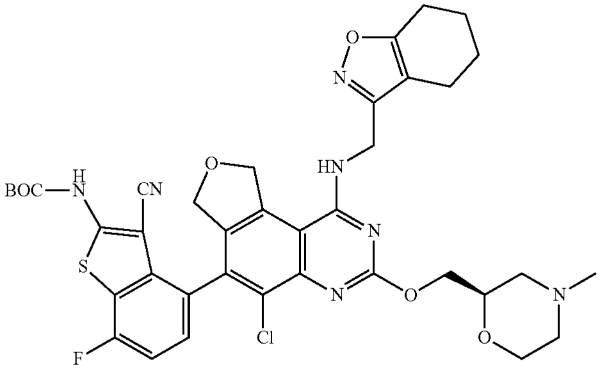 [SMILES: CN1CCO[C@@H](COc2nc(NCc3noc4c3CCCC4)c3c4c(c(-c5ccc(F)c6sc(NC(=O)OC(C)(C)C)c(C#N)c56)c(Cl)c3n2)COC4)C1] | 776 |
| 39 | tert-Butyl (4-(5-chloro-3-(((2R,7aS)-2-fluorotetrahydro-1H-pyrrolizin-7a(5H)-yl)methoxy)-1-(((4,5,6,7-tetrahydrobenzo[d]isoxazol-3-yl)methyl)amino)-7,9-dihydrofuro[3,4-f]quinazolin-6-yl)-3-cyano-7-fluorobenzo[b]thiophen-2-yl)carbamate | 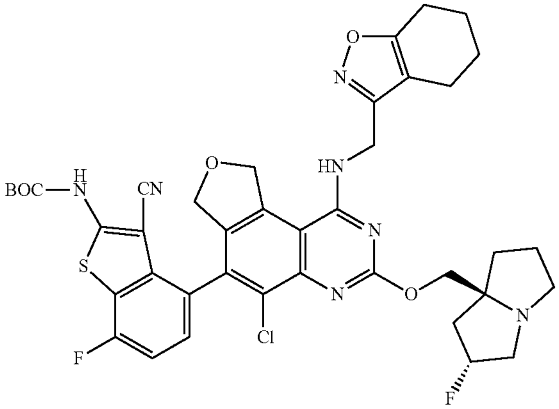 [SMILES: CC(C)(C)OC(=O)Nc1sc2c(F)ccc(-c3c4c(c5c(NCc6noc7c6CCCC7)nc(OC[C@@]67CCCN6C[C@H](F)C7)nc5c3Cl)COC4)c2c1C#N] | 804 |
| 32A | tert-Butyl (4-(1-(((1H-pyrazol-5-yl)methyl)amino)-5-chloro-3-(((2R,7aS)-2-fluorotetrahydro-1H-pyrrolizin-7a(5H)-yl)methoxy)-7,9-dihydrofuro[3,4-f]quinazolin-6-yl)-3-cyano-7-fluorobenzo[b]thiophen-2-yl)carbamate | 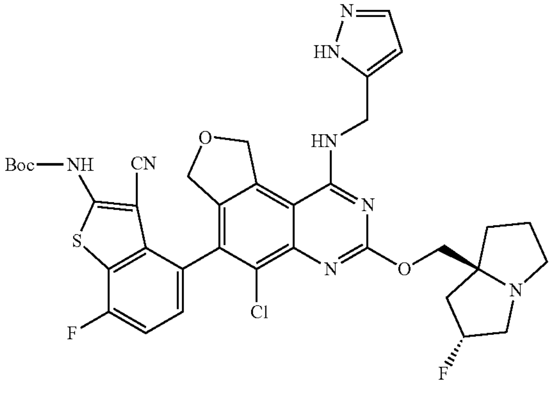 [SMILES: CC(C)(C)OC(=O)Nc1sc2c(F)ccc(-c3c4c(c5c(NCc6ccn[nH]6)nc(OC[C@@]67CCCN6C[C@H](F)C7)nc5c3Cl)COC4)c2c1C#N] | 749 |

Table 9-continued

| Preparation | Chemical Name | Structure | MS (ES) m/z (M + 1) |
|---|---|---|---|
| 33A | tert-Butyl (4-(5-chloro-3-(((2R,7aS)-2-fluorotetrahydro-1H-pyrrolizin-7a(5H)-yl)methoxy)-1-(((3-methyl-1H-pyrazol-5-yl)methyl)amino)-7,9-dihydrofuro[3,4-f]quinazolin-6-yl)-3-cyano-7-fluorobenzo[b]thiophen-2-yl)carbamate | 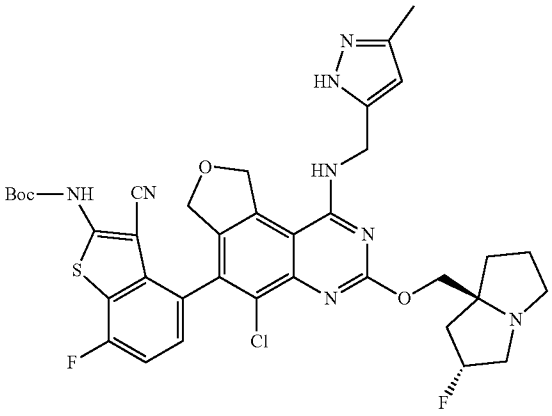 [SMILES: Cc1cc(CNc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)[nH]n1] | 763 |
| 34A | tert-Butyl (4-(5-chloro-1-(((5-(difluoromethyl)-4H-1,2,4-triazol-3-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-3-cyano-7-fluorobenzo[b]thiophen-2-yl)carbamate | 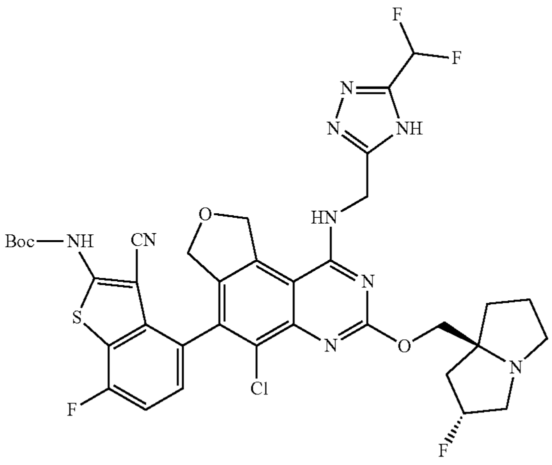 [SMILES: CC(C)(C)OC(=O)Nc1sc2c(F)ccc(-c3c4c(c5c(NCc6nnc(C(F)F)[nH]6)nc(OC[C@@]67CCCN6C[C@H](F)C7)nc5c3Cl)COC4)c2c1C#N] | 800 |
| 35A [1] | tert-Butyl (4-(1-(((1H-pyrazol-4-yl)methyl)amino)-5-chloro-3-(((2R,7aS)-2-fluorotetrahydro-1H-pyrrolizin-7a(5H)-yl)methoxy)-7,9-dihydrofuro[3,4-f]quinazolin-6-yl)-3-cyano-7-fluorobenzo[b]thiophen-2-yl)carbamate | 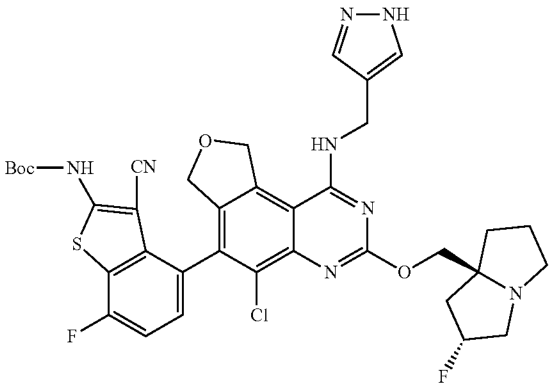 [SMILES: CC(C)(C)OC(=O)Nc1sc2c(F)ccc(-c3c4c(c5c(NCc6cn[nH]c6)nc(OC[C@@]67CCCN6C[C@H](F)C7)nc5c3Cl)COC4)c2c1C#N] | 749 |

Table 9-continued

| Preparation | Chemical Name | Structure | MS (ES) m/z (M + 1) |
|---|---|---|---|
| 36A | tert-Butyl (4-(5-chloro-3-((1-((dimethylamino) methyl) cyclopropyl)methoxy)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 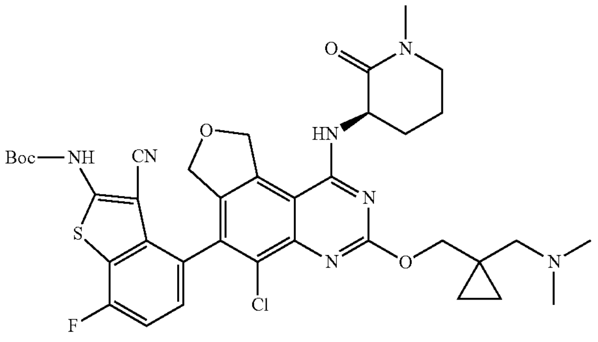 [SMILES: CN(C)CC1(COc2nc(N[C@@H]3CCCN(C)C3=O)c3c4c(c(-c5ccc(F)c6sc(NC(=O)OC(C)(C)C)c(C#N)c56)c(Cl)c3n2)COC4)CC1] | 750 |
| 37A | 6-Bromo-5-fluoro-3-(((2R,7aS)-2-fluorotetrahydro-1H-pyrrolizin-7a(5H)-yl)methoxy)-7,9-dihydrofuro[3,4-f]quinazolin-1-ol | 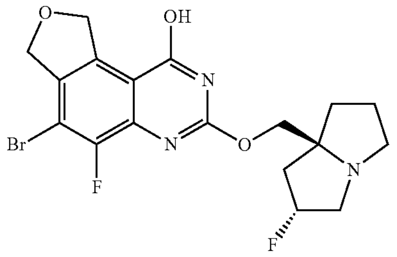 [SMILES: Oc1nc(OC[C@@]23CCCN2C[C@H](F)C3)nc2c(F)c(Br)c3c(c12)COC3] | 442, 444 |
| 38A | 3-((1-(((1R,4R)-2-Oxa-5-azabicyclo[2.2.1] heptan-5-yl)methyl)cyclopropyl) methoxy)-6-bromo-5-fluoro-7,9-dihydrofuro[3,4-f]quinazolin-1-ol | 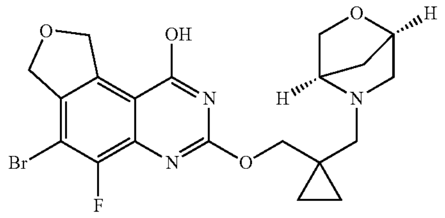 [SMILES: Oc1nc(OCC2(CN3C[C@H]4C[C@@H]3CO4)CC2)nc2c(F)c(Br)c3c(c12)COC3] | 466, 468 |
| 17B | (R)-3-((6-Bromo-5-chloro-3-(((2R,7aS)-2-fluorotetrahydro-1H-pyrrolizin-7a(5H)-yl)methoxy)-7,9-dihydrofuro[3,4-f]quinazolin-1-yl)amino)-1-methylpyrrolidin-2-one | 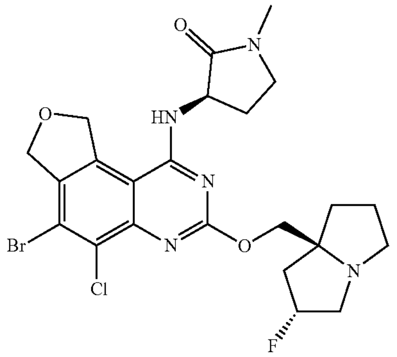 [SMILES: CN1CC[C@@H](Nc2nc(OC[C@@]34CCCN3C[C@H](F)C4)nc3c(Cl)c(Br)c4c(c23)COC4)C1=O] | 554 |
| 18B | tert-Butyl (4-(5-chloro-1-(((R)-1-methyl-2-oxopyrrolidin-3-yl)amino)-3-(((S)-1-methylpyrrolidin-2-yl)methoxy)-7,9-dihydrofuro[3,4-f]quinazolin-6-yl)-3-cyano-7-fluorobenzo[b]thiophen-2-yl)carbamate | 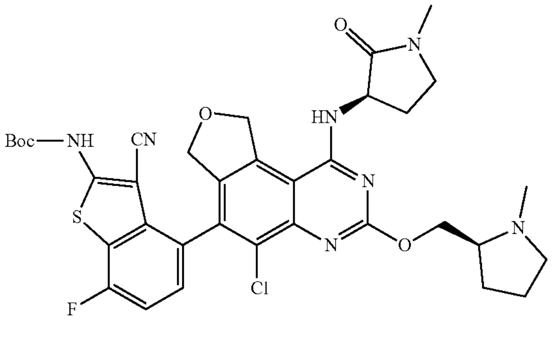 [SMILES: CN1CC[C@@H](Nc2nc(OC[C@@H]3CCCN3C)nc3c(Cl)c(-c4ccc(F)c5sc(NC(=O)OC(C)(C)C)c(C#N)c45)c4c(c23)COC4)C1=O] | 722 |

Table 9-continued

| Preparation | Chemical Name | Structure | MS (ES) m/z (M + 1) |
|---|---|---|---|
| 19B | tert-Butyl (4-(5-chloro-3-((2-(hydroxymethyl)-1-methylpyrrolidin-2-yl)methoxy)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 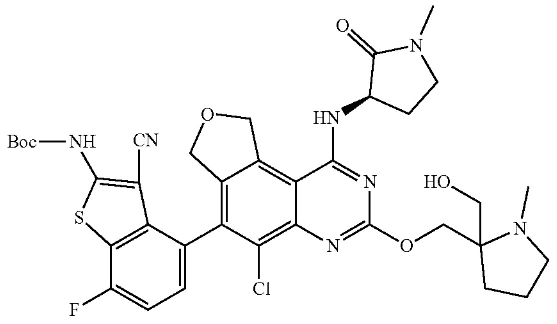 [SMILES: CN1CC[C@@H](Nc2nc(OCC3(CO)CCCN3C)nc3c(Cl)c(-c4ccc(F)c5sc(NC(=O)OC(C)(C)C)c(C#N)c45)c4c(c23)COC4)C1=O] | 752 |
| 20B | tert-Butyl (4-(5-chloro-3-((3-(dimethylamino) oxetan-3-yl) methoxy)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 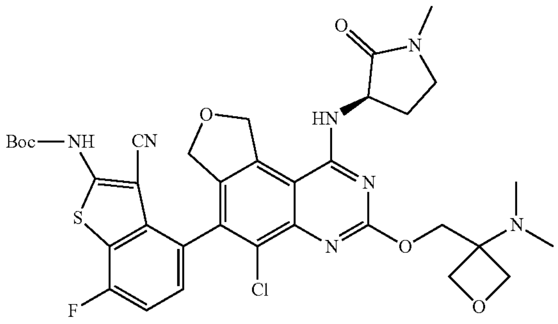 [SMILES: CN1CC[C@@H](Nc2nc(OCC3(N(C)C)COC3)nc3c(Cl)c(-c4ccc(F)c5sc(NC(=O)OC(C)(C)C)c(C#N)c45)c4c(c23)COC4)C1=O] | 738 |
| 21B | 6-Bromo-3-((1-((dimethylamino)methyl) cyclopropyl)methoxy)-5-fluoro-7,9-dihydrofuro[3,4-f]quinazolin-1-ol | 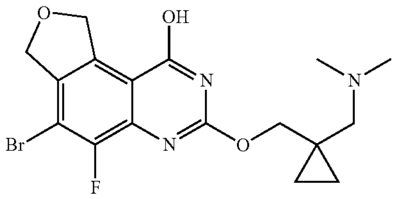 [SMILES: CN(C)CC1(COc2nc(O)c3c4c(c(Br)c(F)c3n2)COC4)CC1] | 412 |
| 52C | tert-Butyl (4-(5-chloro-3-((S)-1-((S)-1-methylpyrrolidin-2-yl)ethoxy)-1-((2-(trimethylsilyl)ethoxy) methoxy)-7,9-dihydrofuro[3,4-f]quinazolin-6-yl)-3-cyano-7-fluorobenzo[b]thiophen-2-yl)carbamate | 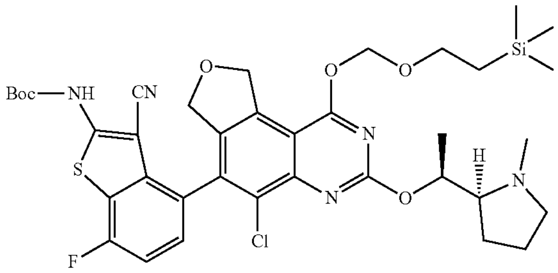 [SMILES: C[C@H](Oc1nc(OCOCC[Si](C)(C)C)c2c3c(c(-c4ccc(F)c5sc(NC(=O)OC(C)(C)C)c(C#N)c45)c(Cl)c2n1)COC3)[C@@H]1CCCN1C] | 770 |
| 53C | tert-Butyl (4-(5-chloro-3-((S)-1-((2S,4R)-4-methoxy-1-methylpyrrolidin-2-yl)ethoxy)-1-((2-(trimethylsilyl)ethoxy) methoxy)-7,9-dihydrofuro[3,4-f]quinazolin-6-yl)-3-cyano-7-fluorobenzo[b]thiophen-2-yl)carbamate | 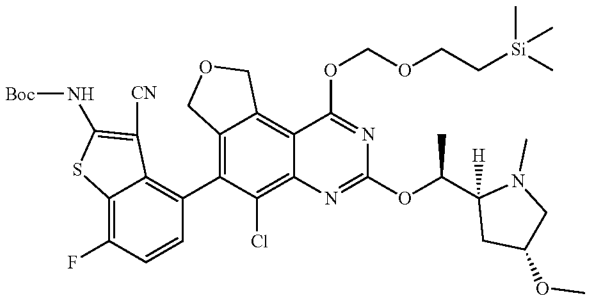 [SMILES: CO[C@@H]1C[C@@H]([C@H](C)Oc2nc(OCOCC[Si](C)(C)C)c3c4c(c(-c5ccc(F)c6sc(NC(=O)OC(C)(C)C)c(C#N)c56)c(Cl)c3n2)COC4)N(C)C1] | 800 |

[1] Clean atropisomer, chiral purification from Preparation 7A

Preparation 39A tert-Butyl (4-(5-chloro-3-((S)-3-(dimethylamino) pyrrolidin-1-yl)-1-(((5-ethyl-1,3,4-oxadiazol-2-yl) methyl)amino)-7,9-dihydrofuro[3,4-f]quinazolin-6-yl)-3-cyano-7-fluorobenzo[b]thiophen-2-yl) carbamate

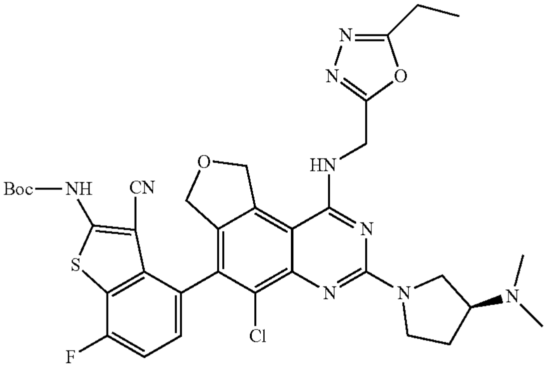 [SMILES: CCc1nnc(CNc2nc(N3CC[C@H](N(C)C)C3)nc3c(Cl)c(-c4ccc(F)c5sc(NC(=O)OC(C)(C)C)c(C#N)c45)c4c(c23)COC4)o1]

To tert-butyl (4-(5-chloro-1-(((5-ethyl-1,3,4-oxadiazol-2-yl)methyl)amino)-3-(ethylsulfonyl)-7,9-dihydrofuro[3,4-f] quinazolin-6-yl)-3-cyano-7-fluorobenzo[b]thiophen-2-yl) carbamate (0.065 g, 0.091 mmol) was added diisopropylethylamine (0.32 mL, 1.8 mmol), (S)-N,N-dimethylpyrrolidin-3-amine (0.052 g, 0.46 mmol), and acetonitrile (2 mL). The reaction mixture was heated at 70° C. After 3 h, the mixture was concentrated under reduced pressure. The residue was purified on silica, eluting with 0-40% MeOH in DCM to obtain the title compound (0.050 g, 75%) as a light yellow solid. MS (ES) m/z=734 (M+1).

The following compounds in Table 10 were prepared in similar manner as described in Preparation 39A. Various methods were used to purify the compounds, which would be apparent to one skilled in the art.

TABLE 10

| Preparation | Chemical Name | Structure | MS (ES) m/z (M + 1) |
|---|---|---|---|
| 40A | tert-Butyl (4-(5-chloro-3-((S)-3-(dimethyl-amino)pyrrolidin-1-yl)-1-(((R)-1-methyl-2-oxopiperidin-3-yl)-amino)-7,9-dihydro-furo[3,4-f]quinazolin-6-yl)-3-cyano-7-fluoro-benzo[b]thiophen-2-yl)-carbamate | 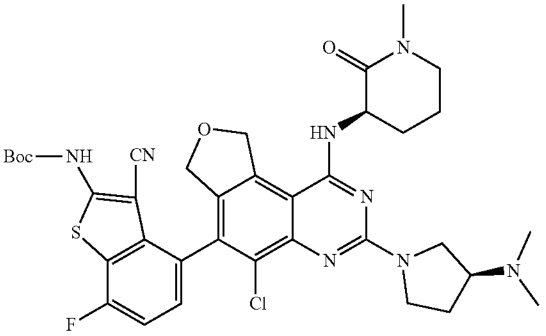 [SMILES: CN1CCC[C@@H](Nc2nc(N3CC[C@H](N(C)C)C3)nc3c(Cl)c(-c4ccc(F)c5sc(NC(=O)OC(C)(C)C)c(C#N)c45)c4c(c23)COC4)C1=O] | |
| 41A | tert-Butyl (4-(5-chloro-3-(3-(dimethylamino)-azetidin-1-yl)-1-(((R)-1-methyl-2-oxopiperi-din-3-yl)amino)-7,9-dihydrofuro[3,4-f]quin-azolin-6-yl)-3-cyano-7-fluorobenzo[b]thiophen-2-yl)carbamate | 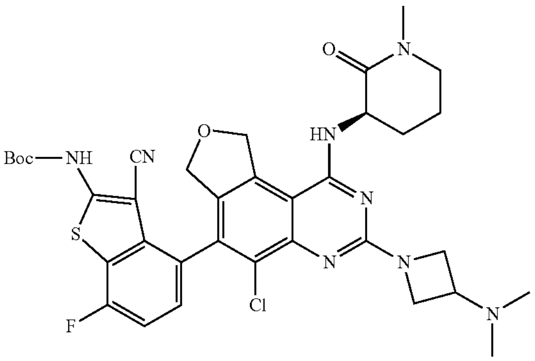 [SMILES: CN1CCC[C@@H](Nc2nc(N3CC(N(C)C)C3)nc3c(Cl)c(-c4ccc(F)c5sc(NC(=O)OC(C)(C)C)c(C#N)c45)c4c(c23)COC4)C1=O] | 721 |

TABLE 10-continued

| Preparation | Chemical Name | Structure | MS (ES) m/z (M + 1) |
| --- | --- | --- | --- |
| 42A | tert-Butyl (4-(5-chloro-3-((S)-3-(dimethyl-amino)-pyrrolidin-1-yl)-1-(((5-methyl-1,2,4-oxadiazol-3-yl)methyl)-amino)-7,9-dihydrofuro-[3,4-f]quinazolin-6-yl)-3-cyano-7-fluorobenzo-[b]thiophen-2-yl)-carbamate | 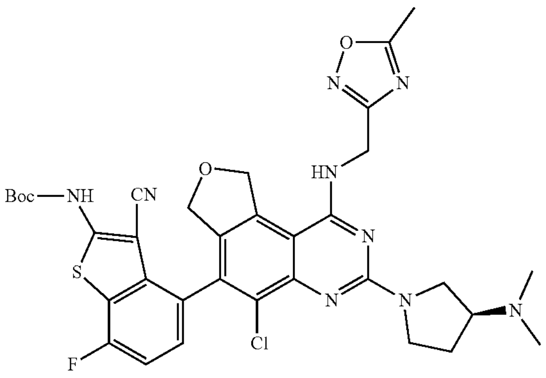 [SMILES: Cc1nc(CNc2nc(N3CC[C@H](N(C)C)C3)nc3c(Cl)c(-c4ccc(F)c5sc(NC(=O)OC(C)(C)C)c(C#N)c45)c4c(c23)COC4)no1] | 720 |
| 43A | tert-Butyl (4-(5-chloro-3-(3-(dimethylamino)-azetidin-1-yl)-1-(((5-ethyl-1,3,4-oxadiazol-2-yl)methyl)amino)-7,9-dihydrofuro[3,4-f]quin-azolin-6-yl)-3-cyano-7-fluorobenzo[b]thiophen-2-yl)carbamate | 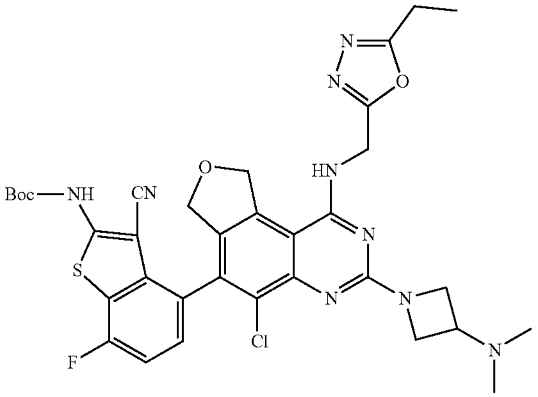 [SMILES: CCc1nnc(CNc2nc(N3CC(N(C)C)C3)nc3c(Cl)c(-c4ccc(F)c5sc(NC(=O)OC(C)(C)C)c(C#N)c45)c4c(c23)COC4)o1] | 720 |
| 44A | tert-Butyl (3-cyano-4-(3-(3-(dimethylamino)-azetidin-1-yl)-5-fluoro-1-(((R)-1-methyl-2-oxo-pyrrolidin-3-yl)amino)-7,9-dihydrofuro[3,4-f]-quinazolin-6-yl)-5-fluorobenzo[b]thiophen-2-yl)carbamate | 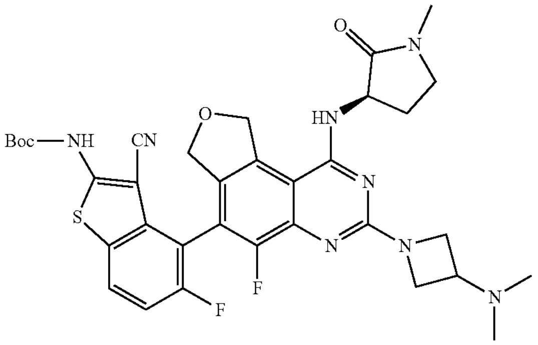 [SMILES: CN1CC[C@@H](Nc2nc(N3CC(N(C)C)C3)nc3c(F)c(-c4c(F)ccc5sc(NC(=O)OC(C)(C)C)c(C#N)c45)c4c(c23)COC4)C1=O] | 691 |
| 45A | tert-Butyl (3-cyano-4-(3-((S)-3-(dimethyl-amino)pyrrolidin-1-yl)-5-fluoro-1-(((R)-1-meth-yl-2-oxopyrrolidin-3-yl)-amino)-7,9-dihydrofuro-[3,4-f]quinazolin-6-yl)-5-fluorobenzo[b]thio-phen-2-yl)carbamate | 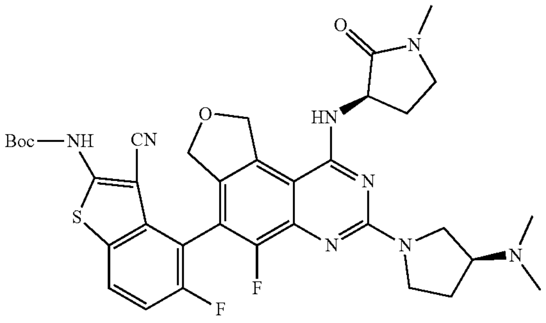 [SMILES: CN1CC[C@@H](Nc2nc(N3CC[C@H](N(C)C)C3)nc3c(F)c(-c4c(F)ccc5sc(NC(=O)OC(C)(C)C)c(C#N)c45)c4c(c23)COC4)C1=O] | 705 |

TABLE 10-continued

| Preparation | Chemical Name | Structure | MS (ES) m/z (M + 1) |
|---|---|---|---|
| 46A | tert-Butyl (3-cyano-4-(1-(((3-cyclopropyl-1H-1,2,4-triazol-5-yl)-methyl)amino)-3-((S)-3-(dimethylamino)-pyrrolidin-1-yl)-5-fluoro-7,9-dihydrofuro-[3,4-f]quinazolin-6-yl)-5-fluorobenzo[b]thio-phen-2-yl)carbamate | 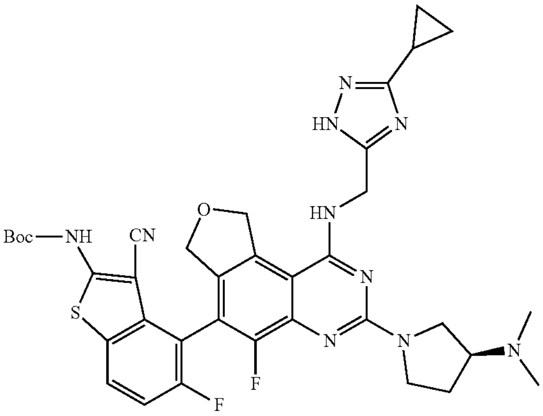 [SMILES: CN(C)[C@H]1CCN(c2nc(NCc3nc(C4CC4)n[nH]3)c3c4c(c(-c5c(F)ccc6sc(NC(=O)OC(C)(C)C)c(C#N)c56)c(F)c3n2)COC4)C1] | 729 |
| 22B | (R)-3-((6-Bromo-3-((S)-3-(dimethylamino)-pyrrolidin-1-yl)-5-fluoro-7,9-dihydrofuro-[3,4-f]quinazolin-1-yl)-amino)-1-methylpyrroli-din-2-one | 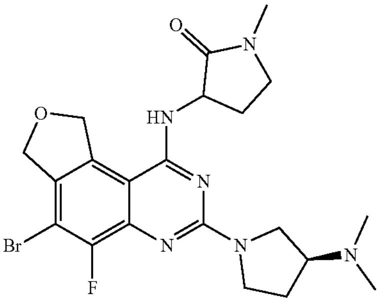 [SMILES: CN1CCC(Nc2nc(N3CC[C@H](N(C)C)C3)nc3c(F)c(Br)c4c(c23)COC4)C1=O] | 493 |
| 23B | (S)-6-Bromo-3-(3-(dimethylamino)pyrroli-din-1-yl)-5-fluoro-N-((5-methyl-1,2,4-oxa-diazol-3-yl)methyl)-7,9-dihydrofuro[3,4-f]quin-azolin-1-amine | 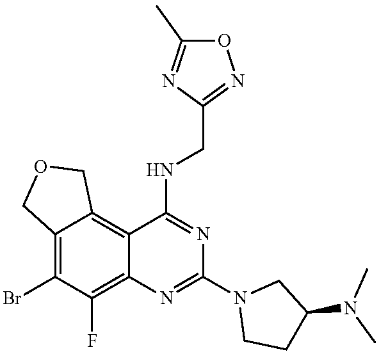 [SMILES: Cc1nc(CNc2nc(N3CC[C@H](N(C)C)C3)nc3c(F)c(Br)c4c(c23)COC4)no1] | 492 |
| 24B | 6-Bromo-3-(3-(dimeth-ylamino)azetidin-1-yl)-5-fluoro-N-((5-methyl-1,2,4-oxadiazol-3-yl)-methyl)-7,9-dihydro-furo[3,4-f]quinazolin-1-amine | 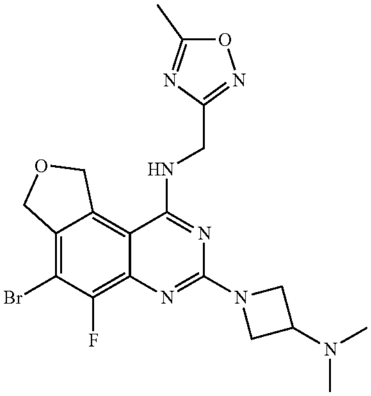 [SMILES: Cc1nc(CNc2nc(N3CC(N(C)C)C3)nc3c(F)c(Br)c4c(c23)COC4)no1] | 478 |

TABLE 10-continued

| Preparation | Chemical Name | Structure | MS (ES) m/z (M + 1) |
| --- | --- | --- | --- |
| 25B | 6-Bromo-3-(3-(dimethylamino)azetidin-1-yl)-5-fluoro-7,9-dihydrofuro[3,4-f]quinazolin-1-ol | 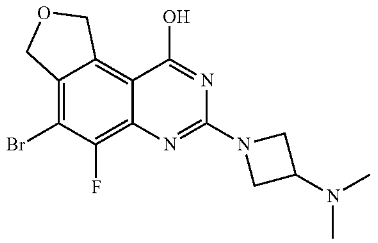 [SMILES: CN(C)C1CN(c2nc(O)c3c4c(c(Br)c(F)c3n2)COC4)C1] | 383 |
| 26B | (S)-6-Bromo-3-(3-(dimethylamino)pyrrolidin-1-yl)-5-fluoro-7,9-dihydrofuro[3,4-f]quinazolin-1-ol | 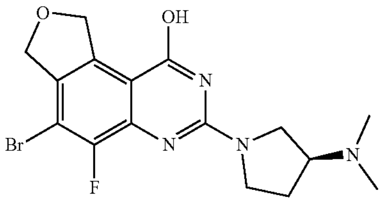 [SMILES: CN(C)[C@H]1CCN(c2nc(O)c3c4c(c(Br)c(F)c3n2)COC4)C1] | 397 |
| 27B | 6-Bromo-3-(3-(dimethylamino)-3-methylazetidin-1-yl)-5-fluoro-7,9-dihydrofuro[3,4-f]quinazolin-1-ol | 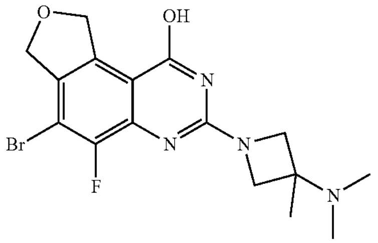 [SMILES: CN(C)C1(C)CN(c2nc(O)c3c4c(c(Br)c(F)c3n2)COC4)C1] | 397 |
| 28B | tert-Butyl (4-(1-(((5-carbamoyl-1,2,4-oxadiazol-3-yl)methyl)amino)-5-chloro-3-((S)-3-(dimethylamino)pyrrolidin-1-yl)-7,9-dihydrofuro[3,4-f]quinazolin-6-yl)-3-cyano-7-fluorobenzo[b]thiophen-2-yl)carbamate | 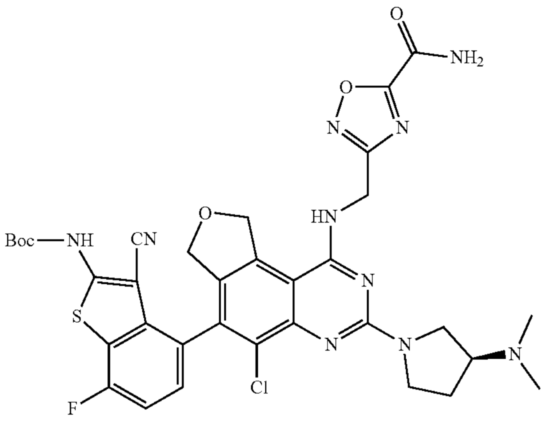 [SMILES: CN(C)[C@H]1CCN(c2nc(NCc3noc(C(N)=O)n3)c3c4c(c(-c5ccc(F)c6sc(NC(=O)OC(C)(C)C)c(C#N)c56)c(Cl)c3n2)COC4)C1] | 749 |
| 29B | tert-Butyl (4-(1-(((5-amino-1,3,4-thiadiazol-2-yl)methyl)amino)-5-chloro-3-((S)-3-(dimethylamino)pyrrolidin-1-yl)-7,9-dihydrofuro[3,4-f]quinazolin-6-yl)-3-cyano-7-fluorobenzo[b]thiophen-2-yl)carbamate | 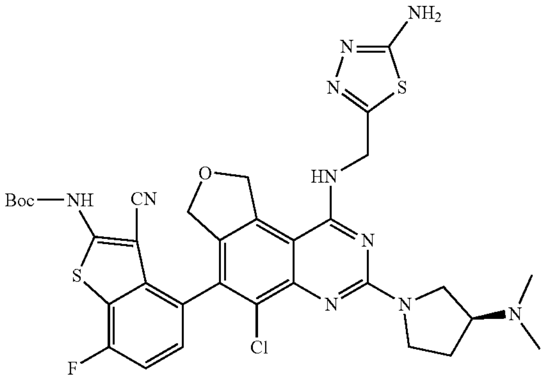 [SMILES: CN(C)[C@H]1CCN(c2nc(NCc3nnc(N)s3)c3c4c(c(-c5ccc(F)c6sc(NC(=O)OC(C)(C)C)c(C#N)c56)c(Cl)c3n2)COC4)C1] | 737 |

TABLE 10-continued

| Preparation | Chemical Name | Structure | MS (ES) m/z (M + 1) |
|---|---|---|---|
| 30B[1] | tert-Butyl (3-cyano-4-(3-((S)-3-(dimethyl-amino)pyrrolidin-1-yl)-5-fluoro-1-hydroxy-7,9-dihydrofuro[3,4-f]quin-azolin-6-yl)-5-fluoro-benzo[b]thiophen-2-yl)-carbamate | 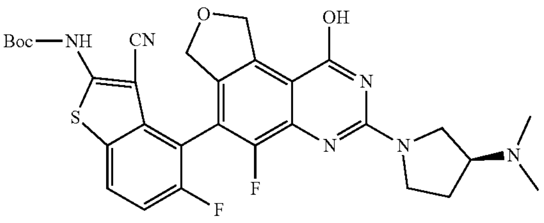 [SMILES: CN(C)[C@H]1CCN(c2nc(O)c3c4c(c(-c5c(F)ccc6sc(NC(=O)OC(C)(C)C)c(C#N)c56)c(F)c3n2)COC4)C1] | 609 |
| 54C | tert-Butyl (3-cyano-4-(3-((S)-3-(dimethyl-amino)pyrrolidin-1-yl)-5-fluoro-1-(((R)-1-meth-yl-2-oxopiperidin-3-yl)-amino)-7,9-dihydrofuro-[3,4-f]quinazolin-6-yl)-5-fluorobenzo[b]thio-phen-2-yl)carbamate | 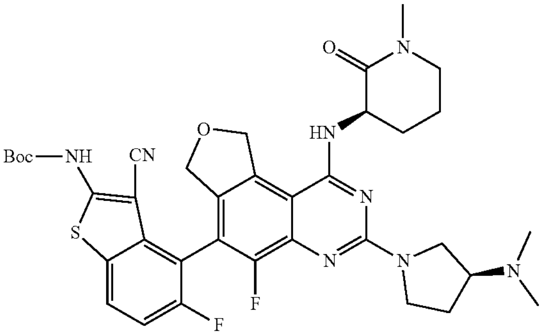 [SMILES: CN1CCC[C@@H](Nc2nc(N3CC[C@H](N(C)C)C3)nc3c(F)c(-c4c(F)ccc5sc(NC(=O)OC(C)(C)C)c(C#N)c45)c4c(c23)COC4)C1=O] | 719 |
| 55C | tert-Butyl (4-(5-chloro-3-(3-(dimethylamino)-azetidin-1-yl)-1-((pyrid-azin-3-ylmethyl)amino)-7,9-dihydrofuro[3,4-f]-quinazolin-6-yl)-3-cyano-5-fluorobenzo[b]-thiophen-2-yl)carbamate | 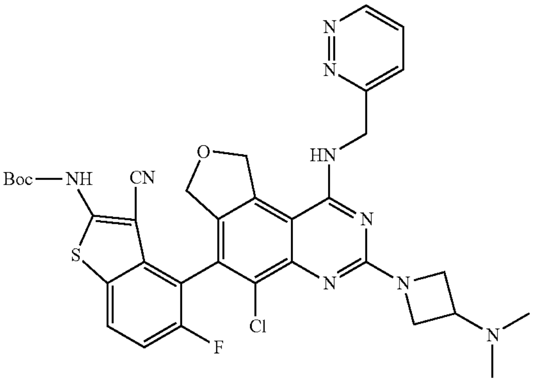 [SMILES: CN(C)C1CN(c2nc(NCc3cccnn3)c3c4c(c(-c5c(F)ccc6sc(NC(=O)OC(C)(C)C)c(C#N)c56)c(Cl)c3n2)COC4)C1] | 702 |
| 56C | tert-Butyl (4-(5-chloro-3-((S)-3-(dimethyl-amino)pyrrolidin-1-yl)-1-((pyridazin-3-ylmeth-yl)amino)-7,9-dihydro-furo[3,4-f]quinazolin-6-yl)-3-cyano-5-fluoro-benzo[b]thiophen-2-yl)-carbamate | 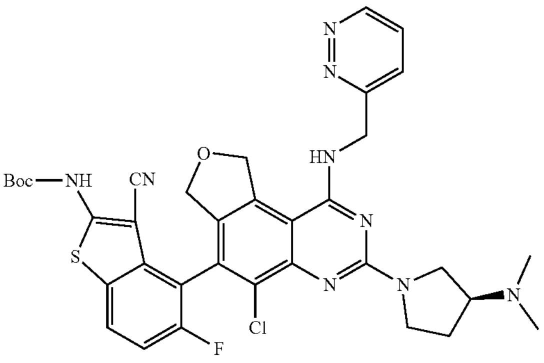 [SMILES: CN(C)[C@H]1CCN(c2nc(NCc3cccnn3)c3c4c(c(-c5c(F)ccc6sc(NC(=O)OC(C)(C)C)c(C#N)c56)c(Cl)c3n2)COC4)C1] | 716 |

TABLE 10-continued

| Preparation | Chemical Name | Structure | MS (ES) m/z (M + 1) |
|---|---|---|---|
| 57C | tert-Butyl (4-(5-chloro-3-(3-(dimethylamino)-3-methylazetidin-1-yl)-1-((pyridazin-3-ylmethyl)amino)-7,9-dihydrofuro[3,4-f]quinazolin-6-yl)-3-cyano-5-fluorobenzo[b]thiophen-2-yl)carbamate | 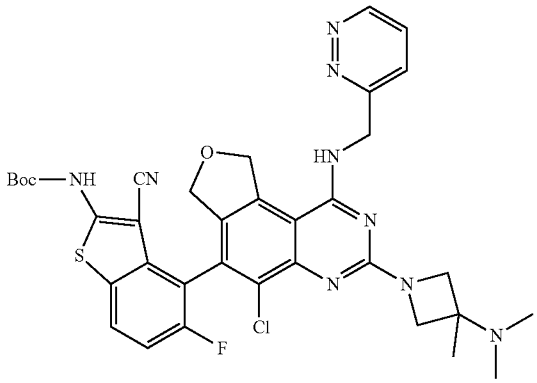 [SMILES: CN(C)C1(C)CN(c2nc(NCc3cccnn3)c3c4c(c(-c5c(F)ccc6sc(NC(=O)OC(C)(C)C)c(C#N)c56)c(Cl)c3n2)COC4)C1] | 716 |
| 58C[2] | tert-Butyl (4-(5-chloro-3-(3-(dimethylamino)azetidin-1-yl)-1-(((4,5,6,7-tetrahydro-1H-indazol-3-yl)methyl)amino)-7,9-dihydrofuro[3,4-f]quinazolin-6-yl)-3-cyano-7-fluorobenzo[b]thiophen-2-yl)carbamate | 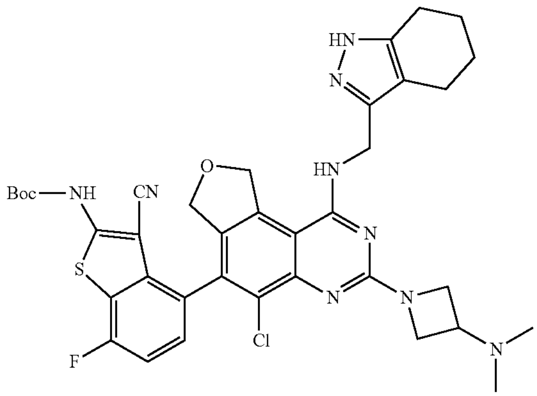 [SMILES: CN(C)C1CN(c2nc(NCc3n[nH]c4c3CCCC4)c3c4c(c(-c5ccc(F)c6sc(NC(=O)OC(C)(C)C)c(C#N)c56)c(Cl)c3n2)COC4)C1] | 744 |
| 59C[2] | tert-Butyl (4-(5-chloro-3-((2S,3S)-3-(dimethylamino)-2-methylpyrrolidin-1-yl)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 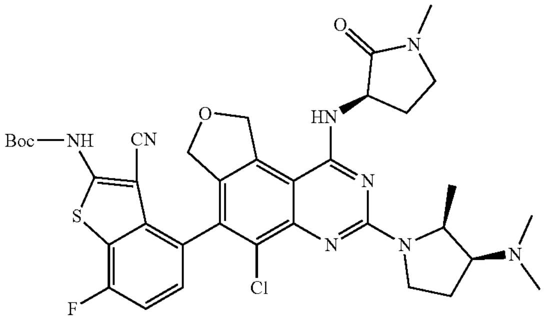 [SMILES: C[C@H]1[C@@H](N(C)C)CCN1c1nc(N[C@@H]2CCN(C)C2=O)c2c3c(c(-c4ccc(F)c5sc(NC(=O)OC(C)(C)C)c(C#N)c45)c(Cl)c2n1)COC3] | 735 |
| 60C[2] | tert-Butyl (4-(5-chloro-3-((2S,3S)-3-(isopropylamino)-2-methylpyrrolidin-1-yl)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 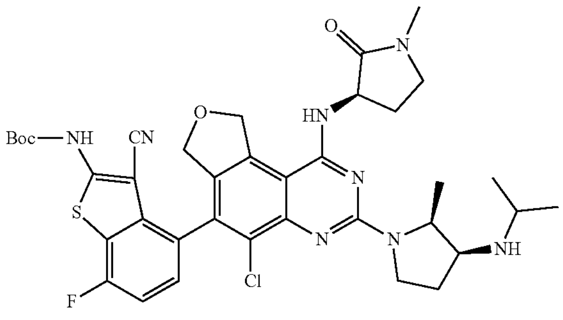 [SMILES: CC(C)N[C@H]1CCN(c2nc(N[C@@H]3CCN(C)C3=O)c3c4c(c(-c5ccc(F)c6sc(NC(=O)OC(C)(C)C)c(C#N)c56)c(Cl)c3n2)COC4)[C@H]1C] | 749 |

TABLE 10-continued

| Preparation | Chemical Name | Structure | MS (ES) m/z (M + 1) |
|---|---|---|---|
| 61C[2] | tert-Butyl (4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 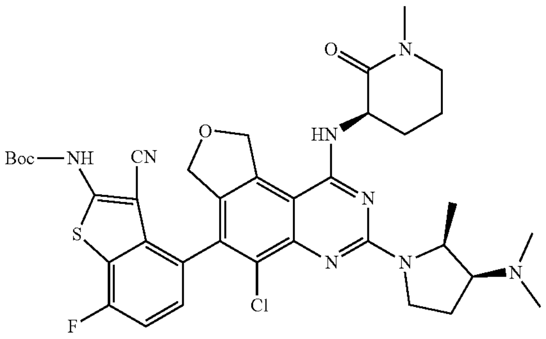 [SMILES: C[C@H]1[C@@H](N(C)C)CCN1c1nc(N[C@@H]2CCCN(C)C2=O)c2c3c(c(-c4ccc(F)c5sc(NC(=O)OC(C)(C)C)c(C#N)c45)c(Cl)c2n1)COC3] | 749 |
| 62C[2] | tert-Butyl (4-(5-chloro-3-((2S,3S)-3-(isopropylamino)-2-methylpyrrolidin-1-yl)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 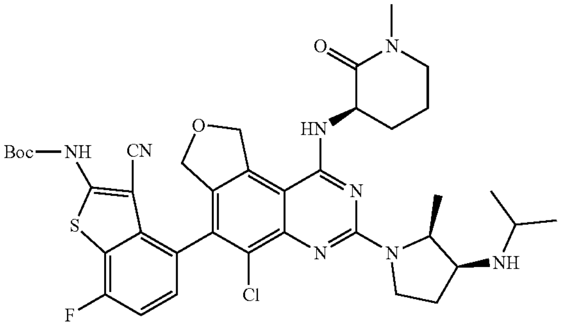 [SMILES: CC(C)N[C@H]1CCN(c2nc(N[C@@H]3CCCN(C)C3=O)c3c4c(c(-c5ccc(F)c6sc(NC(=O)OC(C)(C)C)c(C#N)c56)c(Cl)c3n2)COC4)[C@H]1C] | 763 |
| 63C[2] | tert-Butyl (4-(5-chloro-3-(3-(dimethylamino)-3-methylazetidin-1-yl)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 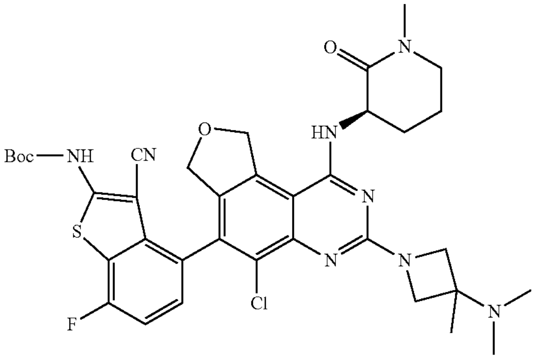 [SMILES: CN1CCC[C@@H](Nc2nc(N3CC(C)(N(C)C)C3)nc3c(Cl)c(-c4ccc(F)c5sc(NC(=O)OC(C)(C)C)c(C#N)c45)c4c(c23)COC4)C1=O] | 735 |
| 64C[2, 3] | tert-Butyl (4-(5-chloro-3-(3-(dimethylamino)-4-methoxypyrrolidin-1-yl)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 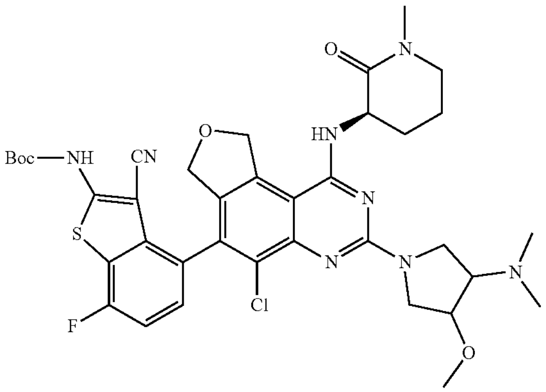 [SMILES: COC1CN(c2nc(N[C@@H]3CCCN(C)C3=O)c3c4c(c(-c5ccc(F)c6sc(NC(=O)OC(C)(C)C)c(C#N)c56)c(Cl)c3n2)COC4)CC1N(C)C] | 765 |

TABLE 10-continued

| Preparation | Chemical Name | Structure | MS (ES) m/z (M + 1) |
|---|---|---|---|
| 65C[2, 4] | tert-Butyl (4-(5-chloro-3-(3-(dimethylamino)-4-methoxypyrrolidin-1-yl)-1-(((R)-1-methyl-2-oxopiperidin-3-yl)-amino)-7,9-dihydro-furo[3,4-f]quinazolin-6-yl)-3-cyano-7-fluoro-benzo[b]thiophen-2-yl)-carbamate | 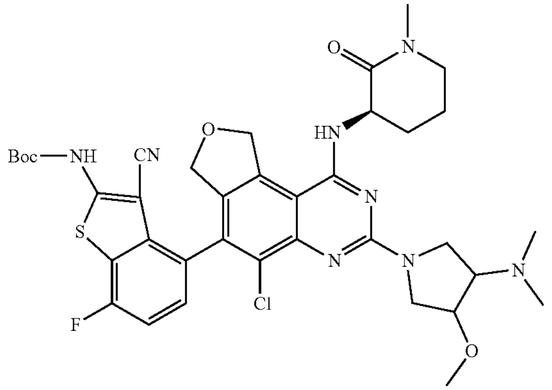 [SMILES: COC1CN(c2nc(N[C@@H]3CCCN(C)C3=O)c3c4c(c(-c5ccc(F)c6sc(NC(=O)OC(C)(C)C)c(C#N)c56)c(Cl)c3n2)COC4)CC1N(C)C] | 765 |
| 66C[2] | tert-Butyl (4-(5-chloro-3-((2S,3S)-3-(((S)-2-hydroxypropyl)amino)-2-methylpyrrolidin-1-yl)-1-(((R)-1-methyl-2-oxopiperidin-3-yl)-amino)-7,9-dihydrofuro-[3,4-f]quinazolin-6-yl)-3-cyano-7-fluorobenzo-[b]thiophen-2-yl)-carbamate | 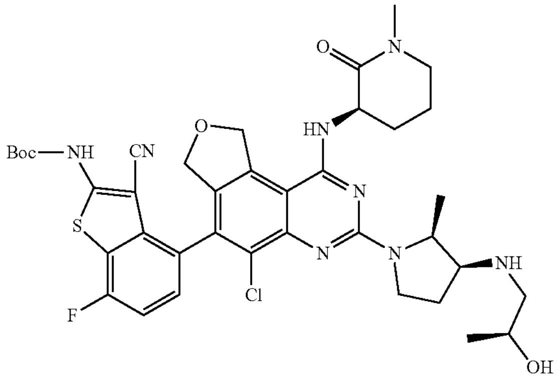 [SMILES: C[C@H](O)CN[C@H]1CCN(c2nc(N[C@@H]3CCCN(C)C3=O)c3c4c(c(-c5ccc(F)c6sc(NC(=O)OC(C)(C)C)c(C#N)c56)c(Cl)c3n2)COC4)[C@H]1C] | 779 |
| 67C[2, 3] | tert-Butyl (4-(5-chloro-3-(3-(isopropylamino)-4-methoxypyrrolidin-1-yl)-1-(((R)-1-methyl-2-oxopiperidin-3-yl)-amino)-7,9-dihydrofuro-[3,4-f]quinazolin-6-yl)-3-cyano-7-fluorobenzo-[b]thiophen-2-yl)-carbamate | 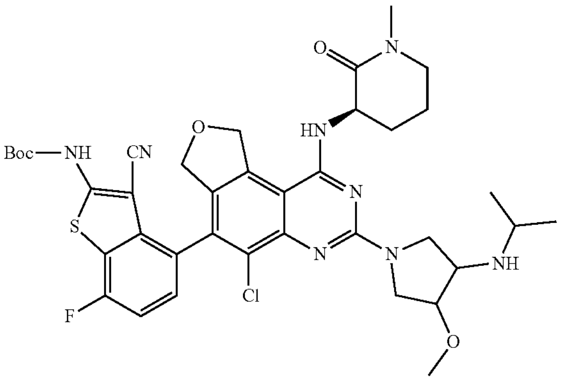 [SMILES: COC1CN(c2nc(N[C@@H]3CCCN(C)C3=O)c3c4c(c(-c5ccc(F)c6sc(NC(=O)OC(C)(C)C)c(C#N)c56)c(Cl)c3n2)COC4)CC1NC(C)C] | 779 |
| 68C[2, 4] | tert-Butyl (4-(5-chloro-3-(3-(isopropylamino)-4-methoxypyrrolidin-1-yl)-1-(((R)-1-methyl-2-oxopiperidin-3-yl)-amino)-7,9-dihydrofuro-[3,4-f]quinazolin-6-yl)-3-cyano-7-fluorobenzo-[b]thiophen-2-yl)-carbamate | 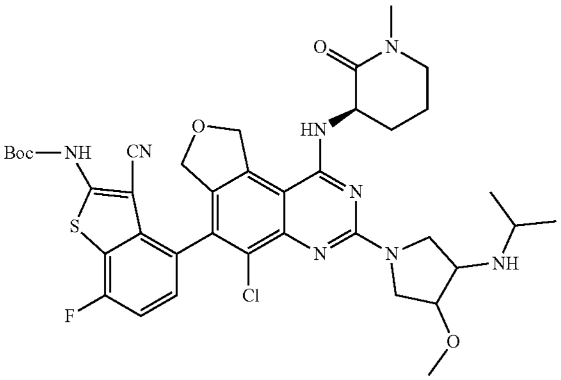 [SMILES: COC1CN(c2nc(N[C@@H]3CCCN(C)C3=O)c3c4c(c(-c5ccc(F)c6sc(NC(=O)OC(C)(C)C)c(C#N)c56)c(Cl)c3n2)COC4)CC1NC(C)C] | 779 |

TABLE 10-continued

| Preparation | Chemical Name | Structure | MS (ES) m/z (M + 1) |
|---|---|---|---|
| 69C[2] | tert-Butyl (4-(5-chloro-3-((2S,3S)-3-(isopropyl(methyl)amino)-2-methylpyrrolidin-1-yl)-1-(((R)-1-methyl-2-oxo-piperidin-3-yl)amino)-7,9-dihydrofuro[3,4-f]-quinazolin-6-yl)-3-cyano-7-fluorobenzo-[b]thiophen-2-yl)-carbamate | 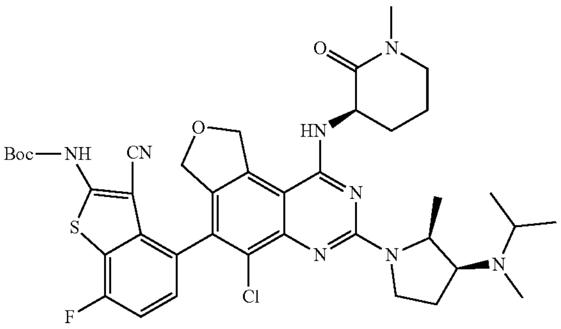 [SMILES: CC(C)N(C)[C@H]1CCN(c2nc(N[C@@H]3CCCN(C)C3=O)c3c4c(c(-c5ccc(F)c6sc(NC(=O)OC(C)(C)C)c(C#N)c56)c(Cl)c3n2)COC4)[C@H]1C] | 777 |
| 70C[2] | tert-Butyl (4-(5-chloro-3-((3R,4S)-3-(isopropylamino)-4-methylpyrrolidin-1-yl)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 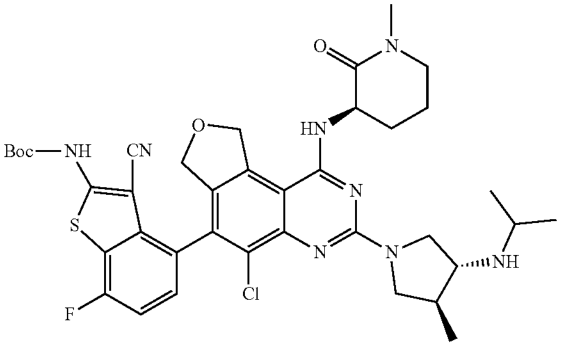 [SMILES: CC(C)N[C@H]1CN(c2nc(N[C@@H]3CCCN(C)C3=O)c3c4c(c(-c5ccc(F)c6sc(NC(=O)OC(C)(C)C)c(C#N)c56)c(Cl)c3n2)COC4)C[C@@H]1C] | 763 |
| 71C[2] | tert-Butyl (4-(5-chloro-3-((3R,4S)-3-(isopropyl(methyl)amino)-4-methylpyrrolidin-1-yl)-1-(((R)-1-methyl-2-oxopiperidin-3-yl)-amino)-7,9-dihydrofuro-[3,4-f]quinazolin-6-yl)-3-cyano-7-fluorobenzo-[b]thiophen-2-yl)-carbamate | 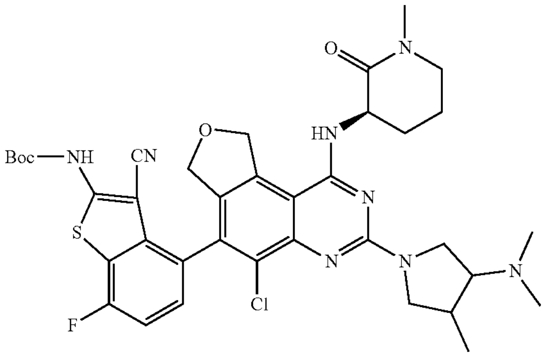 [SMILES: CC1CN(c2nc(N[C@@H]3CCCN(C)C3=O)c3c4c(c(-c5ccc(F)c6sc(NC(=O)OC(C)(C)C)c(C#N)c56)c(Cl)c3n2)COC4)CC1N(C)C] | 777 |
| 72C[2, 3] | tert-Butyl (4-(5-chloro-3-(3-(dimethylamino)-4-methylpyrrolidin-1-yl)-1-(((R)-1-methyl-2-oxo-piperidin-3-yl)amino)-7,9-dihydrofuro[3,4-f]-quinazolin-6-yl)-3-cyano-7-fluorobenzo-[b]thiophen-2-yl)-carbamate | 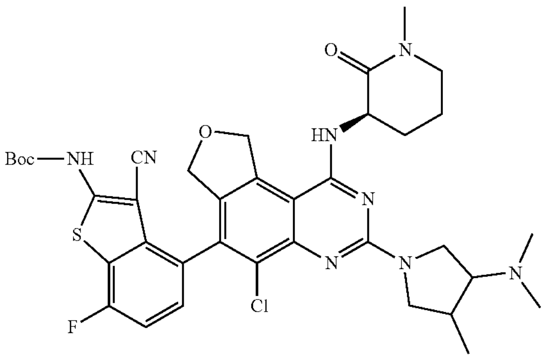 [SMILES: CC1CN(c2nc(N[C@@H]3CCCN(C)C3=O)c3c4c(c(-c5ccc(F)c6sc(NC(=O)OC(C)(C)C)c(C#N)c56)c(Cl)c3n2)COC4)CC1N(C)C] | 749 |

TABLE 10-continued

| Preparation | Chemical Name | Structure | MS (ES) m/z (M + 1) |
|---|---|---|---|
| 73C[2] | tert-Butyl (4-(5-chloro-1-(((R)-1-methyl-2-oxopiperidin-3-yl)-amino)-3-((R)-3-(4-methylpiperazin-1-yl)-pyrrolidin-1-yl)-7,9-dihydrofuro[3,4-f]-quinazolin-6-yl)-3-cyano-7-fluorobenzo-[b]thiophen-2-yl)-carbamate | 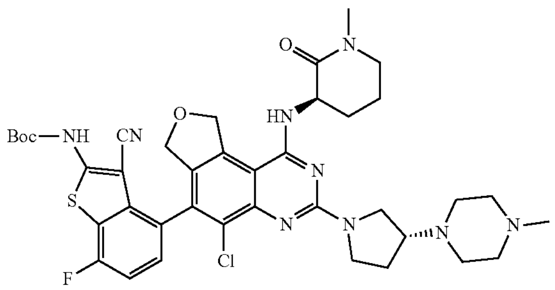 [SMILES: CN1CCN([C@@H]2CCN(c3nc(N[C@@H]4CCCN(C)C4=O)c4c5c(c(-c6ccc(F)c7sc(NC(=O)OC(C)(C)C)c(C#N)c67)c(Cl)c4n3)COC5)C2)CC1] | 790 |
| 74C[2] | tert-Butyl (4-(5-chloro-3-((2S,3R)-3-((dimethyl-mino)methyl)-2-methyl-pyrrolidin-1-yl)-1-(((R)-1-methyl-2-oxopiper-idin-3-yl)amino)-7,9-dihydrofuro[3,4-f]quin-azolin-6-yl)-3-cyano-7-fluorobenzo[b]thiophen-2-yl)carbamate | 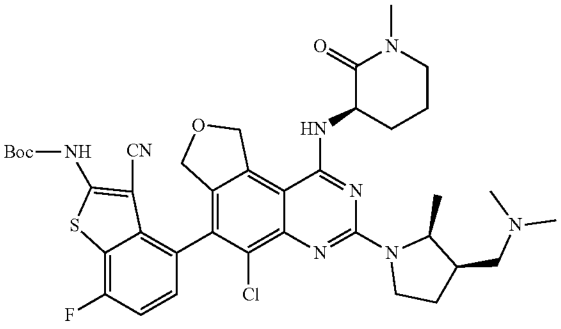 [SMILES: C[C@H]1[C@@H](CN(C)C)CCN1c1nc(N[C@@H]2CCCN(C)C2=O)c2c3c(c(-c4ccc(F)c5sc(NC(=O)OC(C)(C)C)c(C#N)c45)c(Cl)c2n1)COC3] | 763 |
| 75C[2] | tert-Butyl (4-(5-chloro-1-(((R)-1-methyl-2-oxopiperidin-3-yl)-amino)-3-((2S,3S)-2-methyl-3-(4-methyl-piperazin-1-yl)pyrrol-idin-1-yl)-7,9-dihydro-furo[3,4-f]quinazolin-6-yl)-3-cyano-7-fluoro-benzo[b]thiophen-2-yl)carbamate | 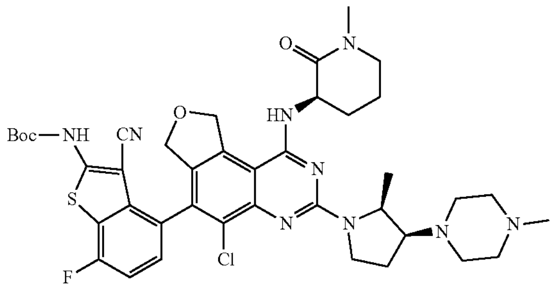 [SMILES: C[C@H]1[C@@H](N2CCN(C)CC2)CCN1c1nc(N[C@@H]2CCCN(C)C2=O)c2c3c(c(-c4ccc(F)c5sc(NC(=O)OC(C)(C)C)c(C#N)c45)c(Cl)c2n1)COC3] | 804 |

[1]Clean atropisomer, chiral purification from Preparation 2B
[2]Clean atropisomer, chiral purification from Preparation 7A
[3]Mix of Trans pyrrolidine isomers

Preparation 47A

6-Bromo-1-chloro-5-fluoro-3-(((2R,7aS)-2-fluorotetrahydro-1H-pyrrolizin-7a(5H)-yl)methoxy)-7,9-dihydrofuro[3,4-f]quinazoline

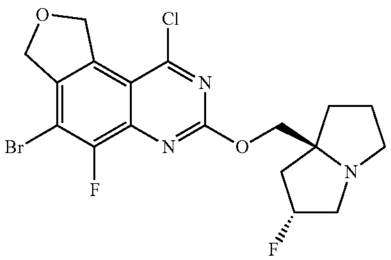 [SMILES: Fc1c(Br)c2c(c3c(Cl)nc(OC[C@@]45CCCN4C[C@H](F)C5)nc13)COC2]

A mixture of N-(chloromethylene)-N-methylmethanaminium chloride (6.0 g, 50 mmol) in DCM (80 mL) was cooled to 0° C. under nitrogen. 6-Bromo-5-fluoro-3-(((2R,7aS)-2-fluorotetrahydro-1H-pyrrolizin-7a(5H)-yl)methoxy)-7,9-dihydrofuro[3,4-f]quinazolin-1-ol (5.0 g, 10 mmol) was added portionwise over 2 min. After stirring at 0° C. for 5 min, the reaction mixture was warmed to room temperature. After 18 h, the mixture was filtered. The solids were washed with water, washed with DCM, and dried under reduced pressure. The solids were dissolved in DCM and cooled to 0° C. N-(chloromethylene)-N-methylmethanaminium chloride (3.0 g, 20 mmol) was added portionwise over 2 min. After stirring at 0° C. for 5 min, the reaction mixture was warmed to room temperature. After 18 h, the mixture was quenched with ice/water (100 mL), then filtered. The solids were washed with water and dried under reduced pressure to obtain the title compound (0.050 g, 75%) as a white solid. MS (ES) m/z=460 (M+1).

The following compounds in Table 11 were prepared in similar manner as described in Preparation 47A. Various methods were used to purify the compounds, which would be apparent to one skilled in the art.

TABLE 11

| Preparation | Chemical Name | Structure | MS (ES) m/z (M + 1) |
|---|---|---|---|
| 48A | 3-((1-(((1R,4R)-2-Oxa-5-azabicyclo[2.2.1]heptan-5-yl)methyl)cyclopropyl)-methoxy)-6-bromo-1-chloro-5-fluoro-7,9-dihydrofuro[3,4-f]quin-azoline | 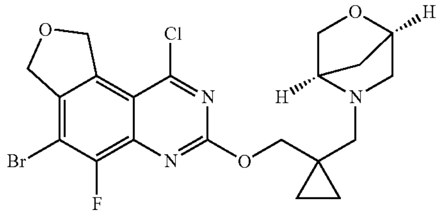 | 484 |
| 31B | 1-(6-Bromo-1-chloro-5-fluoro-7,9-dihydrofuro-[3,4-f]quinazolin-3-yl)-N,N-dimethylazetidin-3-amine | 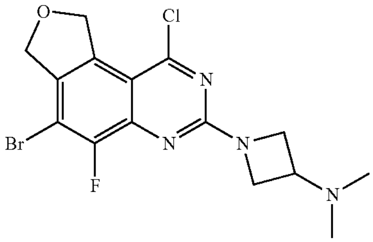 [SMILES: CN(C)C1CN(c2nc(Cl)c3c4c(c(Br)c(F)c3n2)COC4)C1] | 401 |
| 32B | (S)-1-(6-Bromo-1-chloro-5-fluoro-7,9-dihydro-furo[3,4-f]quinazolin-3-yl)-N,N-dimethylpyrrol-idin-3-amine | 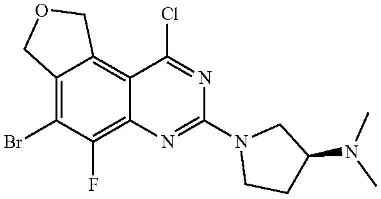 [SMILES: CN(C)[C@H]1CCN(c2nc(Cl)c3c4c(c(Br)c(F)c3n2)COC4)C1] | 415 |
| 33B | 1-(6-Bromo-1-chloro-5-fluoro-7,9-dihydrofuro-[3,4-f]quinazolin-3-yl)-N,N,3-trimethylazetidin-3-amine | 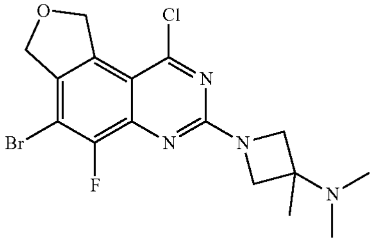 [SMILES: CN(C)C1(C)CN(c2nc(Cl)c3c4c(c(Br)c(F)c3n2)COC4)C1] | 415 |
| 34B | tert-Butyl (3-cyano-4-(1,5-dichloro-3-(((2R,7aS)-2-fluorotetrahydro-1H-pyrrolizin-7a(5H)-yl)methoxy)-7,9-dihydro-furo[3,4-f]quinazolin-6-yl)-7-fluorobenzo[b]-thiophen-2-yl)carbamate | 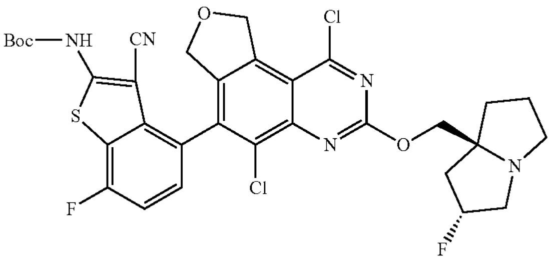 [SMILES: CC(C)(C)OC(=O)Nc1sc2c(F)ccc(-c3c4c(c5c(Cl)nc(OC[C@@]67CCCN6C[C@H](F)C7)nc5c3Cl)COC4)c2c1C#N] | 688 |
| 35B[1] | tert-Butyl (4-(1-chloro-3-((S)-3-(dimethylamino)-pyrrolidin-1-yl)-5-fluoro-7,9-dihydrofuro[3,4-f]-quinazolin-6-yl)-3-cyano-5-fluorobenzo[b]-thiophen-2-yl)carbamate | 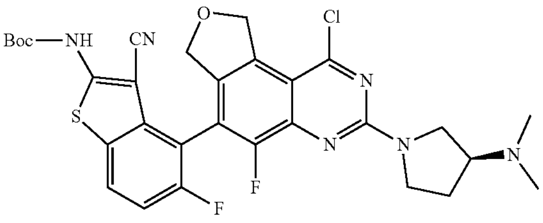 [SMILES: CN(C)[C@H]1CCN(c2nc(Cl)c3c4c(c(-c5c(F)ccc6sc(NC(=O)OC(C)(C)C)c(C#N)c56)c(F)c3n2)COC4)C1] | 627 |

[1]Clean atropisomer, chiral purification from Preparation 2B

Preparation 36B 1-(1-(((6-Bromo-1-chloro-5-fluoro-7,9-dihydrofuro[3,4-f]quinazolin-3-yl)oxy)methyl)cyclopropyl)-N,N-dimethylmethanamine

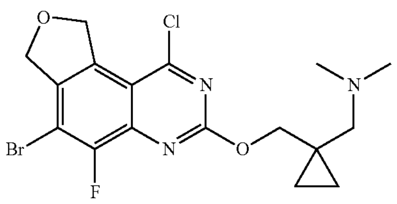

To a mixture of 6-bromo-3-((1-((dimethylamino)methyl)cyclopropyl)methoxy)-5-fluoro-7,9-dihydrofuro[3,4-f]quinazolin-1-ol (1.5 g, 3.64 mmol) and diisopropylethylamine (1.90 mL, 10.9 mmol) in toluene (25 mL) was added $POCl_3$ (1.02 mL, 10.9 mmol) dropwise at room temperature. The reaction mixture was stirred for 1 h at 110° C., then concentrated under reduced pressure and diluted with EtOAc (300 mL). The resulting mixture was washed with saturated aqueous $NaHCO_3$ (100 mL), water (2×100 mL), and brine (100 mL), then dried over sodium sulfate, filtered, and concentrated under reduced pressure to obtain the title compound (1.2 g). MS (ES) m/z=430 (M+1).

The following compounds in Table 12 were prepared in similar manner as described in Preparation 18. Various methods were used to purify the compounds, which would be apparent to one skilled in the art.

TABLE 12

| Preparation | Chemical Name | Structure | MS (ES) m/z (M + 1) |
|---|---|---|---|
| 49A | 6-Bromo-N-((3-cyclopropyl-1H-1,2,4-triazol-5-yl)methyl)-5-fluoro-3-(((2R,7aS)-2-fluorotetrahydro-1H-pyrrolizin-7a(5H)-yl)methoxy)-7,9-dihydrofuro[3,4-f]quinazolin-1-amine | 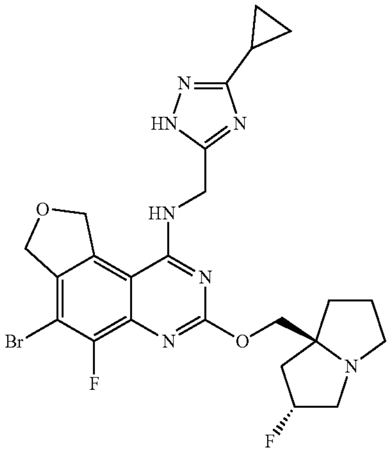 [SMILES: Fc1c(Br)c2c(c3c(NCc4nc(C5CC5)n[nH]4)nc(OC[C@@]45CCCN4C[C@H](F)C5)nc13)COC2] | 562 |
| 50A | (R)-3-((3-((1-(((1R,4R)-2-Oxa-5-azabicyclo[2.2.1]heptan-5-yl)methyl)cyclopropyl)methoxy)-6-bromo-5-fluoro-7,9-dihydrofuro[3,4-f]quinazolin-1-yl)amino)-1-methylpyrrolidin-2-one | 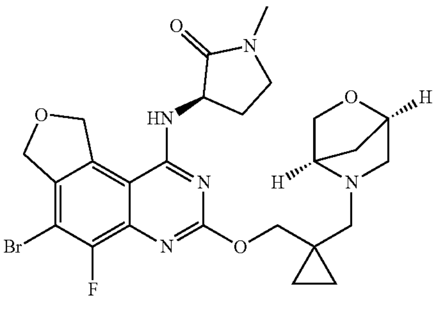 [SMILES: CN1CC[C@@H](Nc2nc(OCC3(CN4C[C@H]5C[C@@H]4CO5)CC3)nc3c(F)c(Br)c4c(c23)COC4)C1=O] | 562 |

TABLE 12-continued

| Preparation | Chemical Name | Structure | MS (ES) m/z (M + 1) |
|---|---|---|---|
| 37B | 6-Bromo-5-fluoro-3-(((2R,7aS)-2-fluoro-tetrahydro-1H-pyrrolizin-7a(5H)-yl)methoxy)-N-(pyridazin-3-ylmethyl)-7,9-dihydrofuro[3,4-f]-quinazolin-1-amine | 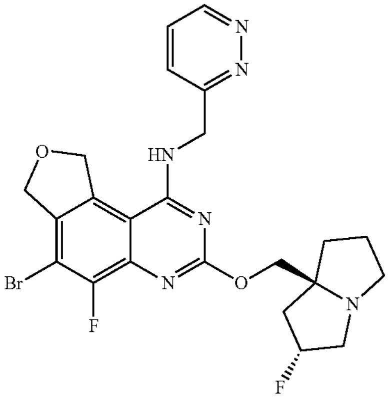 [SMILES: Fc1c(Br)c2c(c3c(NCc4cccnn4)nc(OC[C@@]45CCCN4C[C@H](F)C5)nc13)COC2] | 533 |
| 38B | (R)-3-((6-Bromo-3-(3-(dimethylamino)azetidin-1-yl)-5-fluoro-7,9-dihydrofuro[3,4-f]quin-azolin-1-yl)amino)-1-methylpyrrolidin-2-one | 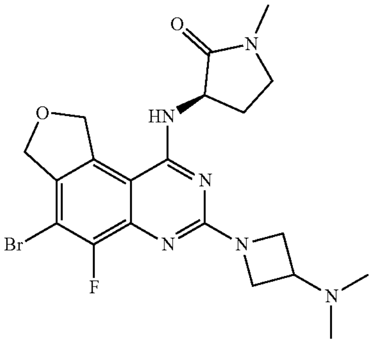 [SMILES: CN1CC[C@@H](Nc2nc(N3CC(N(C)C)C3)nc3c(F)c(Br)c4c(c23)COC4)C1=O] | 479 |
| 39B | 6-Bromo-3-(3-(dimethyl-amino)azetidin-1-yl)-5-fluoro-N-(pyridazin-3-ylmethyl)-7,9-dihydro-furo[3,4-f]quinazolin-1-amine | 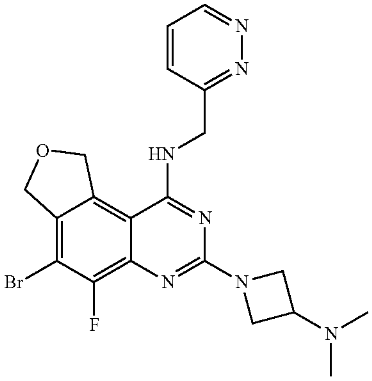 [SMILES: CN(C)C1CN(c2nc(NCc3cccnn3)c3c4c(c(Br)c(F)c3n2)COC4)C1] | 474 |
| 40B | 6-Bromo-5-fluoro-3-(((2R,7aS)-2-fluorotetra-hydro-1H-pyrrolizin-7a(5H)-yl)methoxy)-N-((5-methyl-1,2,4-oxa-diazol-3-yl)methyl)-7,9-dihydrofuro[3,4-f]quin-azolin-1-amine | 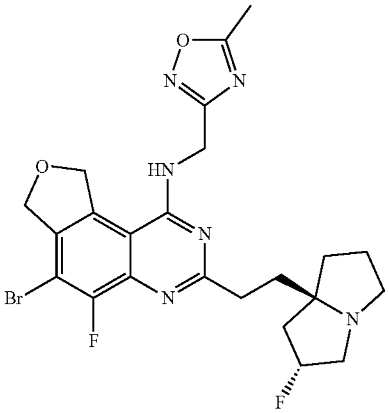 [SMILES: Cc1nc(CNc2nc(CC[C@@]34CCCN3C[C@H](F)C4)nc3c(F)c(Br)c4c(c23)COC4)no1] | 537 |

TABLE 12-continued

| Preparation | Chemical Name | Structure | MS (ES) m/z (M + 1) |
|---|---|---|---|
| 41B | (S)-6-Bromo-3-(3-(dimethylamino)pyrrolidin-1-yl)-5-fluoro-N-(pyridazin-3-ylmethyl)-7,9-dihydrofuro[3,4-f]quinazolin-1-amine | 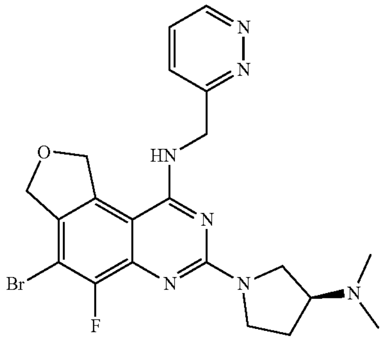 [SMILES: CN(C)[C@H]1CCN(c2nc(NCc3cccnn3)c3c4c(c(Br)c(F)c3n2)COC4)C1] | 488 |
| 42B | (R)-3-((6-Bromo-3-(3-(dimethylamino)-3-methylazetidin-1-yl)-5-fluoro-7,9-dihydrofuro-[3,4-f]quinazolin-1-yl)-amino)-1-methylpyrrolidin-2-one | 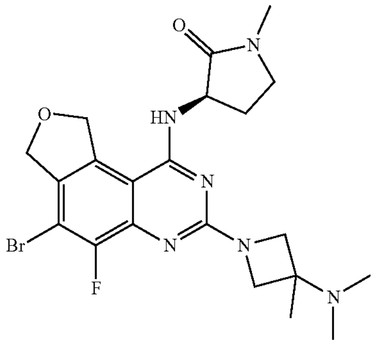 [SMILES: CN1CC[C@@H](Nc2nc(N3CC(C)(N(C)C)C3)nc3c(F)c(Br)c4c(c23)COC4)C1=O] | 493 |
| 43B | 6-Bromo-3-(3-(dimethylamino)-3-methylazetidin-1-yl)-5-fluoro-N-(pyridazin-3-ylmethyl)-7,9-dihydrofuro[3,4-f]-quinazolin-1-amine | 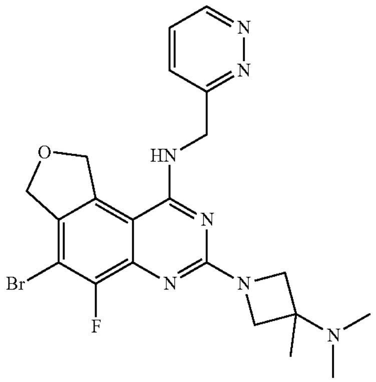 [SMILES: CN(C)C1(C)CN(c2nc(NCc3cccnn3)c3c4c(c(Br)c(F)c3n2)COC4)C1] | 488 |
| 44B | tert-Butyl (4-(5-chloro-3-(((2R,7aS)-2-fluoro-tetrahydro-1H-pyrrolizin-7a(5H)-yl)methoxy)-1-(((5-methylisoxazol-3-yl)methyl)amino)-7,9-dihydrofuro[3,4-f]quinazolin-6-yl)-3-cyano-7-fluorobenzo[b]thiophen-2-yl)carbamate | 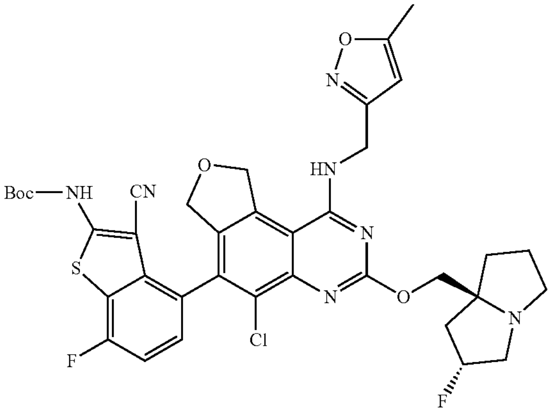 [SMILES: Cc1cc(CNc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)no1] | 764 |

TABLE 12-continued

| Preparation | Chemical Name | Structure | MS (ES) m/z (M + 1) |
|---|---|---|---|
| 45B | tert-Butyl (4-(5-chloro-3-(((2R,7aS)-2-fluorotetrahydro-1H-pyrrolizin-7a(5H)-yl)methoxy)-1-(((3-methylisoxazol-5-yl)-methyl)amino)-7,9-dihydrofuro[3,4-f]quinazolin-6-yl)-3-cyano-7-fluorobenzo[b]thiophen-2-yl)carbamate | 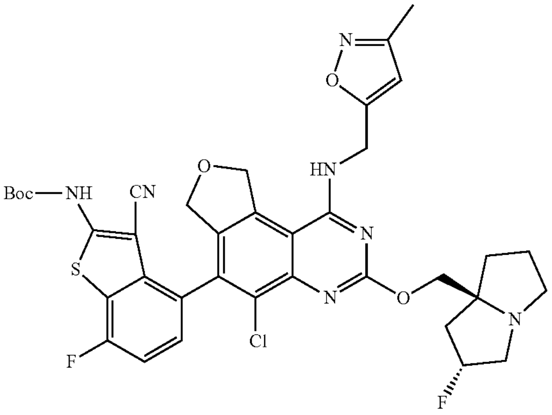 [SMILES: Cc1cc(CNc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)on1] | 764 |
| 46B | tert-Butyl (4-(1-(((5-amino-1,3,4-thiadiazol-2-yl)methyl)amino)-5-chloro-3-(((2R,7aS)-2-fluorotetrahydro-1H-pyrrolizin-7a(5H)-yl)-methoxy)-7,9-dihydro-furo[3,4-f]quinazolin-6-yl)-3-cyano-7-fluoro-benzo[b]thiophen-2-yl)-carbamate | 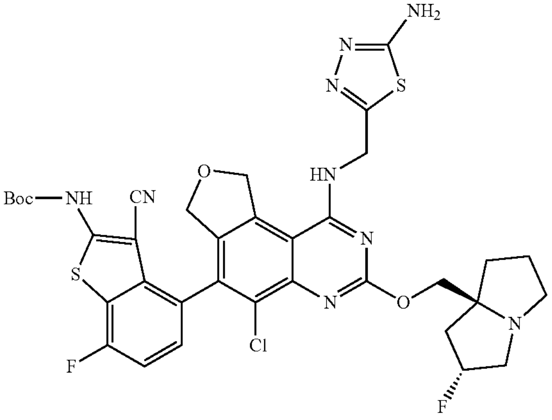 [SMILES: CC(C)(C)OC(=O)Nc1sc2c(F)ccc(-c3c4c(c5c(NCc6nnc(N)s6)nc(OC[C@@]67CCCN6C[C@H](F)C7)nc5c3Cl)COC4)c2c1C#N] | 782 |
| 47B | 6-Bromo-3-((1-((dimethylamino)methyl)cyclopropyl)methoxy)-5-fluoro-N-(pyridazin-3-ylmethyl)-7,9-dihydrofuro-[3,4-f]quinazolin-1-amine | 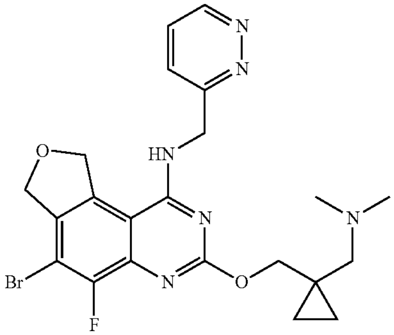 [SMILES: CN(C)CC1(COc2nc(NCc3cccnn3)c3c4c(c(Br)c(F)c3n2)COC4)CC1] | 503 |
| 48B | (R)-3-((6-Bromo-3-((1-((dimethylamino)methyl)cyclopropyl)methoxy)-5-fluoro-7,9-dihydrofuro-[3,4-f]quinazolin-1-yl)-amino)-1-methylpiperidin-2-one | 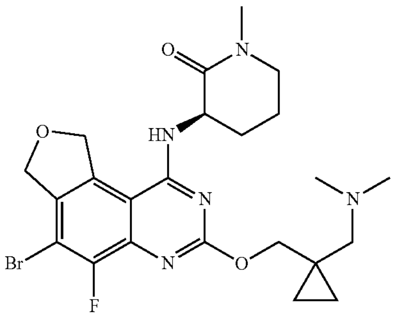 [SMILES: CN(C)CC1(COc2nc(N[C@@H]3CCCN(C)C3=O)c3c4c(c(Br)c(F)c3n2)COC4)CC1] | 522 |

TABLE 12-continued

| Preparation | Chemical Name | Structure | MS (ES) m/z (M + 1) |
|---|---|---|---|
| 49B | (R)-3-((6-Bromo-3-((1-((dimethylamino)meth-yl)cyclopropyl)methoxy)-5-fluoro-7,9-dihydrofuro-[3,4-f]quinazolin-1-yl)-amino)piperidin-2-one | 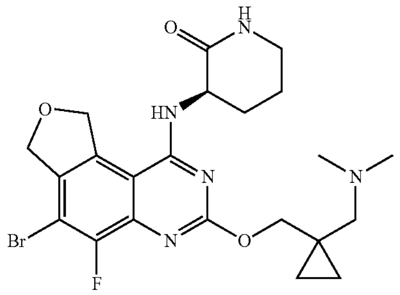 [SMILES: CN(C)CC1(COc2nc(N[C@@H]3CCCNC3=O)c3c4c(c(Br)c(F)c3n2)COC4)CC1] | 508 |
| 50B | (R)-3-((6-Bromo-3-((1-((dimethylamino)meth-yl)cyclopropyl)methoxy)-5-fluoro-7,9-dihydrofuro-[3,4-f]quinazolin-1-yl)-amino)-1-methylpyrrol-idin-2-one | 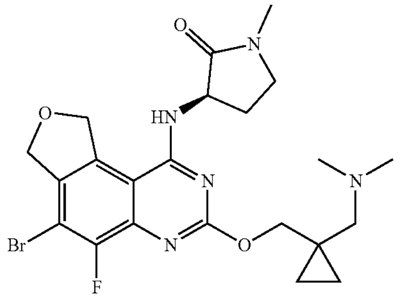 [SMILES: CN(C)CC1(COc2nc(N[C@@H]3CCN(C)C3=O)c3c4c(c(Br)c(F)c3n2)COC4)CC1] | 508 |
| 51B | (R)-3-((6-Bromo-3-((1-((dimethylamino)meth-yl)cyclopropyl)methoxy)-5-fluoro-7,9-dihydrofuro-[3,4-f]quinazolin-1-yl)-amino)pyrrolidin-2-one | 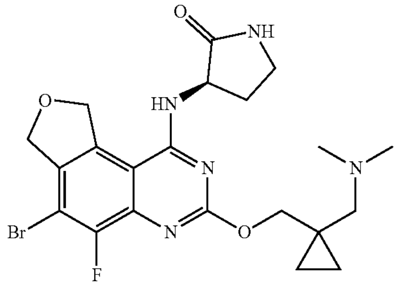 [SMILES: CN(C)CC1(COc2nc(N[C@@H]3CCNC3=O)c3c4c(c(Br)c(F)c3n2)COC4)CC1] | 494 |
| 52B[1] | tert-Butyl (3-cyano-4-(3-((S)-3-(dimethylamino)-pyrrolidin-1-yl)-5-fluoro-1-(isoxazol-4-ylamino)-7,9-dihydrofuro[3,4-f]-quinazolin-6-yl)-5-fluoro-benzo[b]thiophen-2-yl)-carbamate | 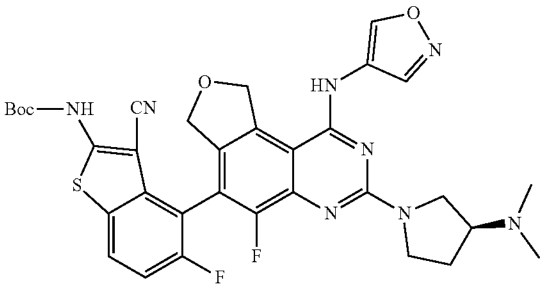 [SMILES: CN(C)[C@H]1CCN(c2nc(Nc3cnoc3)c3c4c(c(-c5c(F)ccc6sc(NC(=O)OC(C)(C)C)c(C#N)c56)c(F)c3n2)COC4)C1] | 675 |
| 76C[1] | tert-Butyl (3-cyano-4-(3-((S)-3-(dimethylamino)-pyrrolidin-1-yl)-5-fluoro-1-((1-methyl-1H-pyrazol-5-yl)amino)-7,9-dihydro-furo[3,4-f]quinazolin-6-yl)-5-fluorobenzo[b]-thiophen-2-yl)carbamate | 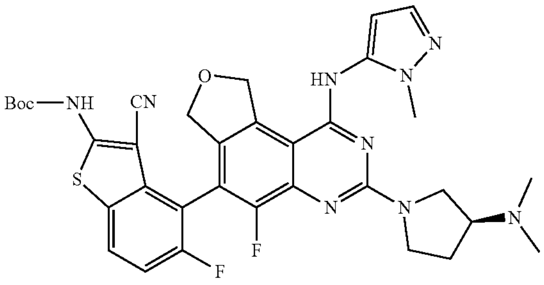 [SMILES: CN(C)[C@H]1CCN(c2nc(Nc3ccnn3C)c3c4c(c(-c5c(F)ccc6sc(NC(=O)OC(C)(C)C)c(C#N)c56)c(F)c3n2)COC4)C1] | 688 |

TABLE 12-continued

| Preparation | Chemical Name | Structure | MS (ES) m/z (M + 1) |
|---|---|---|---|
| 77C[1] | tert-Butyl (3-cyano-4-(3-((S)-3-(dimethylamino)-pyrrolidin-1-yl)-5-fluoro-1-((5-methyl-1,2,4-oxa-diazol-3-yl)methoxy)-7,9-dihydrofuro[3,4-f]quin-azolin-6-yl)-5-fluoro-benzo[b]thiophen-2-yl)-carbamate | 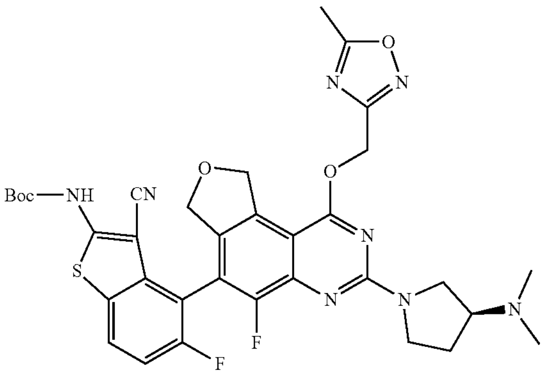 [SMILES: Cc1nc(COc2nc(N3CC[C@H](N(C)C)C3)nc3c(F)c(-c4c(F)ccc5sc(NC(=O)OC(C)(C)C)c(C#N)c45)c4c(c23)COC4)no1] | 705 |
| 78C[1] | tert-Butyl (3-cyano-4-(3-((S)-3-(dimethylamino)-pyrrolidin-1-yl)-5-fluoro-1-(pyridazin-3-ylmeth-oxy)-7,9-dihydrofuro[3,4-f]quinazolin-6-yl)-5-fluorobenzo[b]thiophen-2-yl)carbamate | 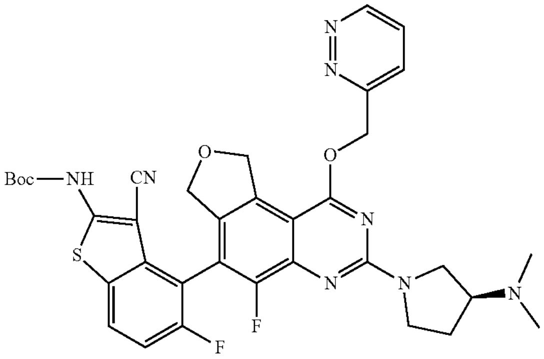 [SMILES: CN(C)[C@H]1CCN(c2nc(OCc3cccnn3)c3c4c(c(-c5c(F)ccc6sc(NC(=O)OC(C)(C)C)c(C#N)c56)c(F)c3n2)COC4)C1] | 701 |

[1]Clean atropisomer, chiral purification from Preparation 2B

Preparation 51A tert-Butyl 5-(((6-bromo-5-fluoro-3-(((2R,7aS)-2-fluorotetrahydro-1H-pyrrolizin-7a(5H)-yl)methoxy)-7,9-dihydrofuro[3,4-f]quinazolin-1-yl)amino)methyl)-3-cyclopropyl-1H-1,2,4-triazole-1-carboxylate

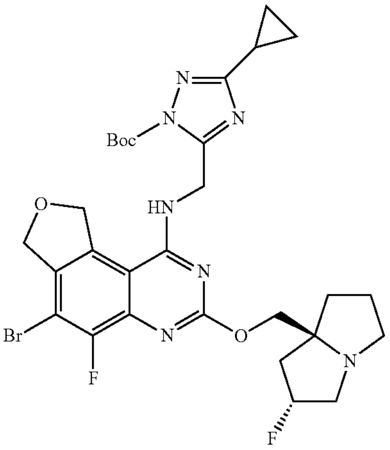 [SMILES: CC(C)(C)OC(=O)n1nc(C2CC2)nc1CNc1nc(OC[C@@]23CCCN2C[C@H](F)C3)nc2c(F)c(Br)c3c(c12)COC3]

To a mixture of 6-bromo-N-((3-cyclopropyl-1H-1,2,4-triazol-5-yl)methyl)-5-fluoro-3-(((2R,7aS)-2-fluorotetrahydro-1H-pyrrolizin-7a(5H)-yl)methoxy)-7,9-dihydrofuro[3,4-f]quinazolin-1-amine (0.35 g, 0.63 mmol) and di-tert-butyl dicarbonate (0.27 g, 1.26 mmol) in DCM (6.3 mL), under nitrogen, was added triethylamine (0.175 mL, 1.26 mmol) and 4-dimethylaminopyridine (0.0077 g, 0.063 mmol). The mixture was stirred at room temperature. After 2 h, the mixture was diluted with MeOH and concentrated under reduced pressure. The residue was purified on silica, eluting with 0-10% ammoniated MeOH in DCM to obtain the title compound (0.19 g, 46%, mix of Boc-triazole isomers) as a white solid. MS (ES) m/z=662 (M+1).

The following compounds in Table 13 were prepared in similar manner as described in Preparation 51A. Various methods were used to purify the compounds, which would be apparent to one skilled in the art.

TABLE 13

| Preparation | Chemical Name | Structure | MS (ES) m/z (M + 1) |
|---|---|---|---|
| 53B | tert-Butyl (6-bromo-5-fluoro-3-(((2R,7aS)-2-fluorotetrahydro-1H-pyrrolizin-7a(5H)-yl)methoxy)-7,9-dihydrofuro[3,4-f]quinazolin-1-yl)(pyridazin-3-ylmethyl)carbamate | 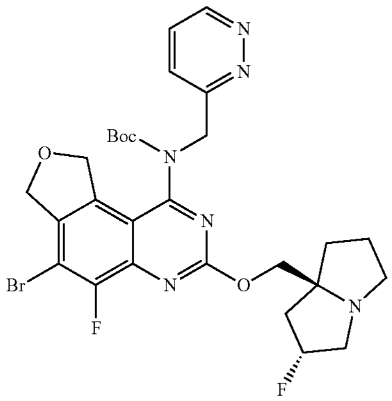 [SMILES: CC(C)(C)OC(=O)N(Cc1cccnn1)c1nc(OC[C@@]23CCCN2C[C@H](F)C3)nc2c(F)c(Br)c3c(c12)COC3] | 633 |
| 54B | tert-Butyl (6-bromo-3-(3-(dimethylamino)azetidin-1-yl)-5-fluoro-7,9-dihydrofuro[3,4-f]quinazolin-1-yl)(pyridazin-3-ylmethyl)carbamate | 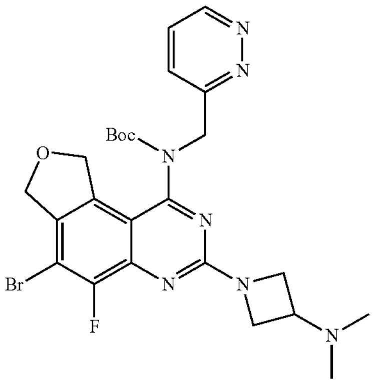 [SMILES: CN(C)C1CN(c2nc(N(Cc3cccnn3)C(=O)OC(C)(C)C)c3c4c(c(Br)c(F)c3n2)COC4)C1] | 574 |
| 55B | tert-Butyl (S)-(6-bromo-3-(3-(dimethylamino)pyrrolidin-1-yl)-5-fluoro-7,9-dihydrofuro[3,4-f]quinazolin-1-yl)(pyridazin-3-ylmethyl)carbamate | 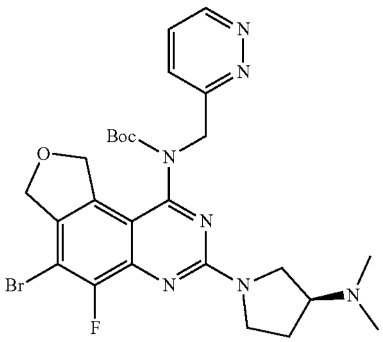 [SMILES: CN(C)[C@H]1CCN(c2nc(N(Cc3cccnn3)C(=O)OC(C)(C)C)c3c4c(c(Br)c(F)c3n2)COC4)C1] | 588 |

Preparation 52A tert-Butyl 5-(((6-(2-((tert-butoxycarbonyl)amino)-3-cyano-7-fluorothieno[3,2-c]pyridin-4-yl)-5-fluoro-3-(((2R,7aS)-2-fluorotetrahydro-1H-pyrrolizin-7a(5H)-yl)methoxy)-7,9-dihydrofuro[3,4-f]quinazolin-1-yl)amino)methyl)-3-cyclopropyl-1H-1,2,4-triazole-1-carboxylate

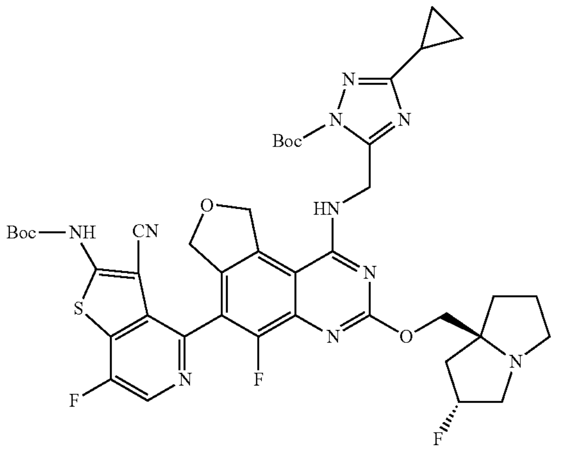 [SMILES: CC(C)(C)OC(=O)Nc1sc2c(F)cnc(-c3c4c(c5c(NCc6nc(C7CC7)nn6C(=O)OC(C)(C)C)nc(OC[C@@]67CCCN6C[C@H](F)C7)nc5c3F)COC4)c2c1C#N]

Split evenly between five reaction vials, under nitrogen, was added tert-butyl 5-(((6-bromo-5-fluoro-3-(((2R,7aS)-2-fluorotetrahydro-1H-pyrrolizin-7a(5H)-yl)methoxy)-7,9-dihydrofuro[3,4-f]quinazolin-1-yl)amino)methyl)-3-cyclopropyl-1H-1,2,4-triazole-1-carboxylate (0.25 g, 0.38 mmol), 5,5,5',5'-tetramethyl-2,2'-bi(1,3,2-dioxaborinane) (0.17 g, 0.76 mmol), potassium acetate (0.11 g, 1.13 mmol), Pd-117 (CAS #205319-06-8; 0.054 g, 0.076 mmol), and toluene (4.7 mL). Each reaction mixture was purged with nitrogen and stirred at 90° C. After 30 min, each was diluted with DCM, filtered through diatomaceous earth, and concentrated under reduced pressure to obtain (1-(((1-(tert-butoxycarbonyl)-3-cyclopropyl-1H-1,2,4-triazol-5-yl)methyl)amino)-5-fluoro-3-(((2R,7aS)-2-fluorotetrahydro-1H-pyrrolizin-7a(5H)-yl)methoxy)-7,9-dihydrofuro[3,4-f]quinazolin-6-yl)boronic acid in a new reaction vial. MS (ES) m/z=628 (M+1).

Split evenly between the five reaction vials containing crude (1-(((1-(tert-butoxycarbonyl)-3-cyclopropyl-1H-1,2,4-triazol-5-yl)methyl)amino)-5-fluoro-3-(((2R,7aS)-2-fluorotetrahydro-1H-pyrrolizin-7a(5H)-yl)methoxy)-7,9-dihydrofuro[3,4-f]quinazolin-6-yl)boronic acid was added tert-butyl (4-chloro-3-cyano-7-fluorothieno[3,2-c]pyridin-2-yl)carbamate (0.124 g, 0.38 mmol), [2-dicyclohexylphosphino-2',4',6'-triisopropylbiphenyl] (0.036 g, 0.076 mmol), chloro(crotyl)(2-dicyclohexylphosphino-2',4',6'-triisopropyl-1,1'-biphenyl)palladium(II) (0.051 g, 0.076 mmol), toluene (12.6 mL), and 1,4-dioxane (3.15 mL). Split evenly, under nitrogen, was added a solution of potassium phosphate, dibasic (1M in water, 1.13 mL, 1.13 mmol) and water (1.70 mL), dropwise. Each reaction mixture was stirred at 90° C. After 40 min, each was diluted with DCM/MeOH. The mixtures were combined, filtered through diatomaceous earth, and concentrated under reduced pressure. The residue was purified on silica, eluting with 0-0 ammoniated MeOH in DCM to obtain the title compound (0.21 g). MS (ES) m/z=875 (M+1).

The following compounds in Table 14 were prepared in similar manner as described in Preparation 52A. Various methods were used to purify the compounds, which would be apparent to one skilled in the art.

TABLE 14

| Preparation | Chemical Name | Structure | MS (ES) m/z (M + 1) |
|---|---|---|---|
| 53A | tert-Butyl (4-(3-((1-(((1R,4R)-2-oxa-5-azabicyclo[2.2. 1 ]heptan-5-yl)methyl)cyclopropyl)methoxy)-5-fluoro-1-(((R)-1-methyl-2-oxopyrrolidin-3-yl)amino)-7,9-dihydrofuro[3,4-f]quinazolin-6-yl)-3-cyano-7-fluorothieno[3,2-c]pyridin-2-yl)carbamate | 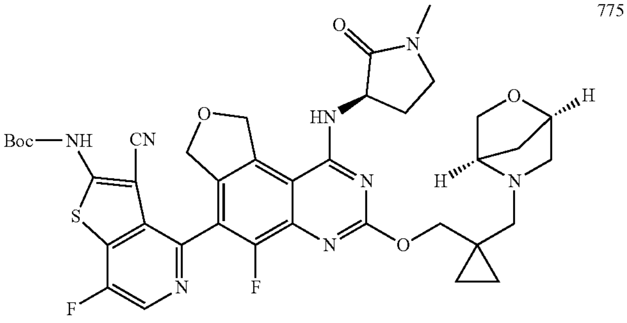 | 775 |
| 56B | tert-Butyl (3-cyano-4-(3-((S)-3-(dimethylamino)pyrrolidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridin-2-yl)carbamate | 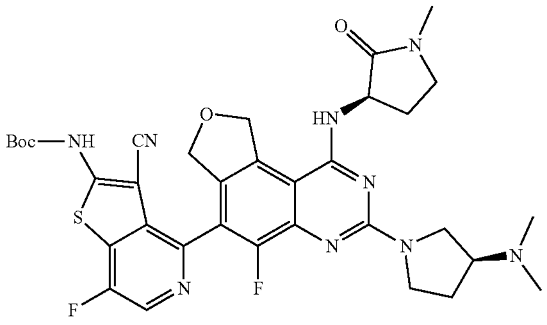 [SMILES: CN1CC[C@@H](Nc2nc(N3CC[C@H](N(C)C)C3)nc3c(F)c(-c4ncc(F)c5sc(NC(=O)OC(C)(C)C)c(C#N)c45)c4c(c23)COC4)C1=O] | 706 |

TABLE 14-continued

| Preparation | Chemical Name | Structure | MS (ES) m/z (M + 1) |
|---|---|---|---|
| 57B | tert-Butyl (3-cyano-4-(3-((S)-3-(dimethylamino)pyrrolidin-1-yl)-5-fluoro-1-(((5-methyl-1,2,4-oxadiazol-3-yl)methyl)amino)-7,9-dihydrofuro[3,4-f]quinazolin-6-yl)-7-fluorothieno[3,2-c]pyridin-2-yl)carbamate | 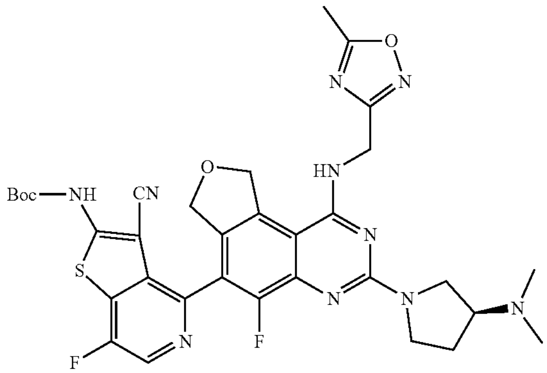 [SMILES: Cc1nc(CNc2nc(N3CC[C@H](N(C)C)C3)nc3c(F)c(-c4ncc(F)c5sc(NC(=O)OC(C)(C)C)c(C#N)c45)c4c(c23)COC4)no1] | 705 |
| 58B | tert-Butyl (6-(2-((tert-butoxycarbonyl)amino)-3-cyano-7-fluorothieno[3,2-c]pyridin-4-yl)-5-fluoro-3-(((2R,7aS)-2-fluorotetrahydro-1H-pyrrolizin-7a(5H)-yl)methoxy)-7,9-dihydrofuro[3,4-f]quinazolin-1-yl)(pyridazin-3-ylmethyl)carbamate | 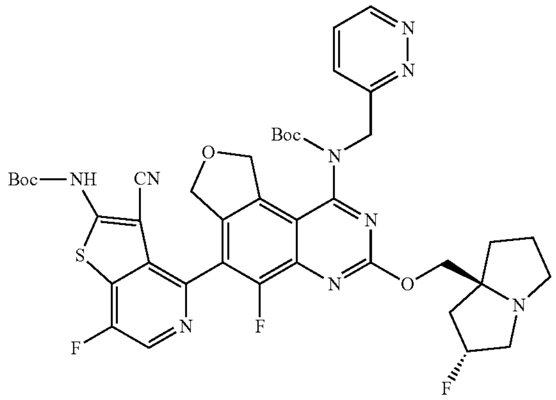 [SMILES: CC(C)(C)OC(=O)Nc1sc2c(F)cnc(-c3c4c(c5c(N(Cc6cccnn6)C(=O)OC(C)(C)C)nc(OC[C@@]67CCCN6C[C@H](F)C7)nc5c3F)COC4)c2c1C#N] | 746-BOC |
| 59B | tert-Butyl (3-cyano-4-(3-(3-(dimethylamino)azetidin-1-yl)-5-fluoro-1-(((5-methyl-1,2,4-oxadiazol-3-yl)methyl)amino)-7,9-dihydrofuro[3,4-f]quinazolin-6-yl)-7-fluorothieno[3,2-c]pyridin-2-yl)carbamate | 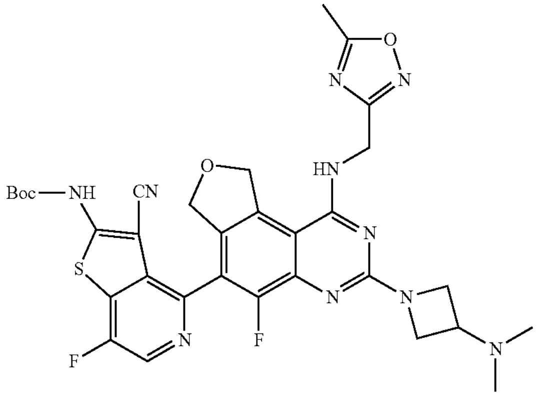 [SMILES: Cc1nc(CNc2nc(N3CC(N(C)C)C3)nc3c(F)c(-c4ncc(F)c5sc(NC(=O)OC(C)(C)C)c(C#N)c45)c4c(c23)COC4)no1] | 691 |
| 60B | tert-Butyl (3-cyano-4-(3-(3-(dimethylamino)azetidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridin-2-yl)carbamate | 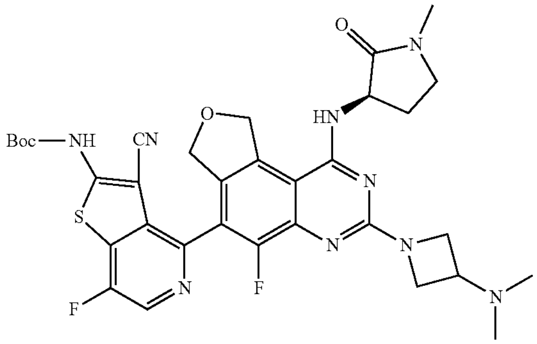 [SMILES: CN1CC[C@@H](Nc2nc(N3CC(N(C)C)C3)nc3c(F)c(-c4ncc(F)c5sc(NC(=O)OC(C)(C)C)c(C#N)c45)c4c(c23)COC4)C1=O] | 692 |

TABLE 14-continued

| Preparation | Chemical Name | Structure | MS (ES) m/z (M + 1) |
|---|---|---|---|
| 61B | tert-Butyl (6-(2-((tert-butoxycarbonyl)amino)-3-cyano-7-fluorothieno[3,2-c]pyridin-4-yl)-3-(3-(dimethylamino)azetidin-1-yl)-5-fluoro-7,9-dihydrofuro[3,4-f]quinazolin-1-yl)(pyridazin-3-ylmethyl)carbamate | 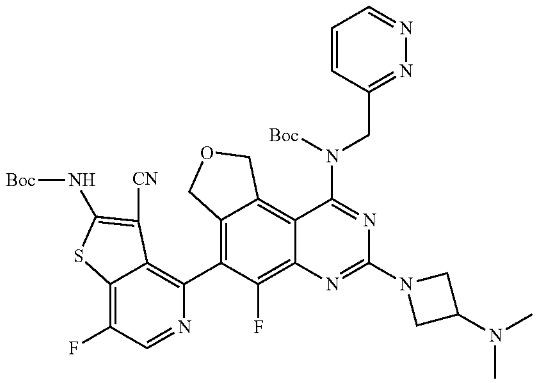 [SMILES: CN(C)C1CN(c2nc(N(Cc3cccnn3)C(=O)OC(C)(C)C)c3c4c(c(-c5ncc(F)c6sc(NC(=O)OC(C)(C)C)c(C#N)c56)c(F)c3n2)COC4)C1] | 787 |
| 62B | tert-Butyl (3-cyano-7-fluoro-4-(5-fluoro-3-(((2R,7aS)-2-fluorotetrahydro-1H-pyrrolizin-7a(5H)-yl)methoxy)-1-(((5-methyl-1,2,4-oxadiazol-3-yl)methyl)amino)-7,9-dihydrofuro[3,4-f]quinazolin-6-yl)thieno[3,2-c]pyridin-2-yl)carbamate | 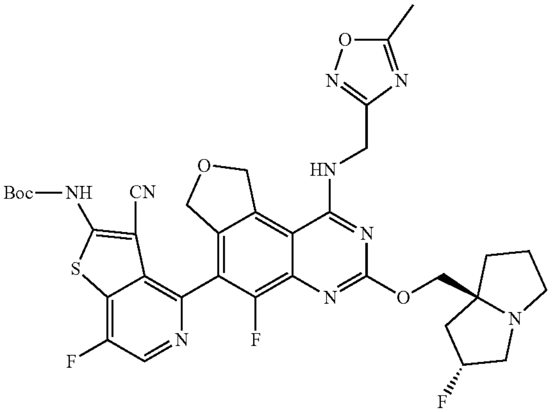 [SMILES: Cc1nc(CNc2nc(OC[C@@]34CCCN3C[C@H](F)C4)nc3c(F)c(-c4ncc(F)c5sc(NC(=O)OC(C)(C)C)c(C#N)c45)c4c(c23)COC4)no1] | 750 |
| 63B | tert-Butyl (6-(2-((tert-butoxycarbonyl)amino)-3-cyano-7-fluorothieno[3,2-c]pyridin-4-yl)-3-((S)-3-(dimethylamino)pyrrolidin-1-yl)-5-fluoro-7,9-dihydrofuro[3,4-f]quinazolin-1-yl)(pyridazin-3-ylmethyl)carbamate | 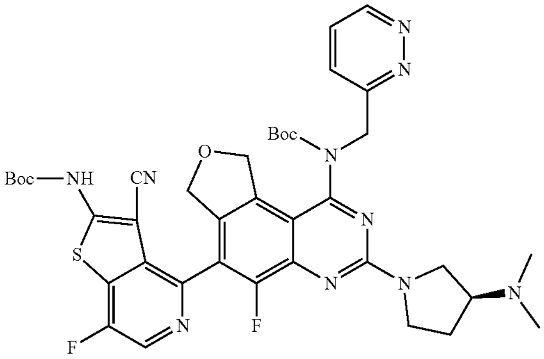 [SMILES: CN(C)[C@H]1CCN(c2nc(N(Cc3cccnn3)C(=O)OC(C)(C)C)c3c4c(c(-c5ncc(F)c6sc(NC(=O)OC(C)(C)C)c(C#N)c56)c(F)c3n2)COC4)C1] | 801 |
| 64B | tert-Butyl (3-cyano-4-(3-(3-(dimethylamino)-3-methylazetidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridin-2-yl)carbamate | 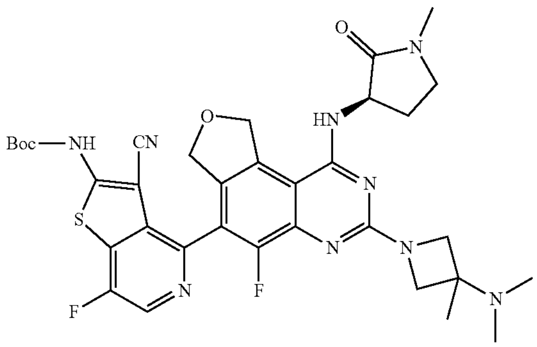 [SMILES: CN1CC[C@@H](Nc2nc(N3CC(C)(N(C)C)C3)nc3c(F)c(-c4ncc(F)c5sc(NC(=O)OC(C)(C)C)c(C#N)c45)c4c(c23)COC4)C1=O] | 706 |

TABLE 14-continued

| Preparation | Chemical Name | Structure | MS (ES) m/z (M + 1) |
|---|---|---|---|
| 65B | tert-Butyl (3-cyano-4-(3-(3-(dimethylamino)-3-methylazetidin-1-yl)-5-fluoro-1-((pyridazin-3-ylmethyl)amino)-7,9-dihydrofuro[3,4-f]quinazolin-6-yl)-7-fluorothieno[3,2-c]pyridin-2-yl)carbamate | 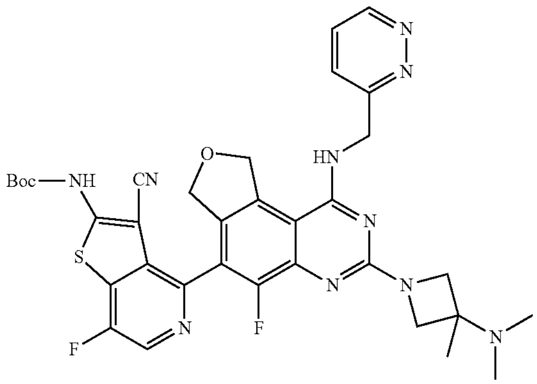 [SMILES: CN(C)C1(C)CN(c2nc(NCc3cccnn3)c3c4c(c(-c5ncc(F)c6sc(NC(=O)OC(C)(C)C)c(C#N)c56)c(F)c3n2)COC4)C1] | 701 |
| 66B | tert-Butyl (3-cyano-4-(3-((1-((dimethylamino)methyl) cyclopropyl)methoxy)-5-fluoro-1-((pyridazin-3-ylmethyl)amino)-7,9-dihydrofuro[3,4-f]quinazolin-6-yl)-7-fluorothieno[3,2-c]pyridin-2-yl)carbamate | 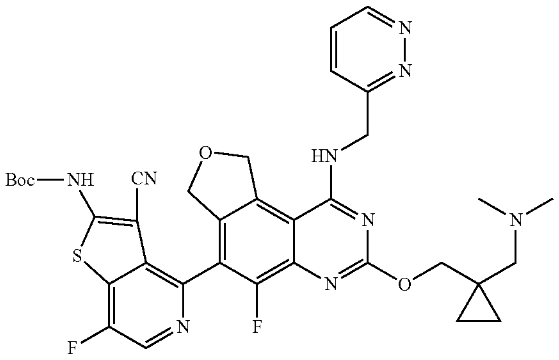 [SMILES: CN(C)CC1(COc2nc(NCc3cccnn3)c3c4c(c(-c5ncc(F)c6sc(NC(=O)OC(C)(C)C)c(C#N)c56)c(F)c3n2)COC4)CC1] | 716 |
| 67B | tert-Butyl (3-cyano-4-(3-((1-((dimethylamino)methyl) cyclopropyl)methoxy)-5-fluoro-1-(((R)-1-methyl-2-oxopiperidin-3-yl)amino)-7,9-dihydrofuro[3,4-f]quinazolin-6-yl)-7-fluorothieno[3,2-c]pyridin-2-yl)carbamate | 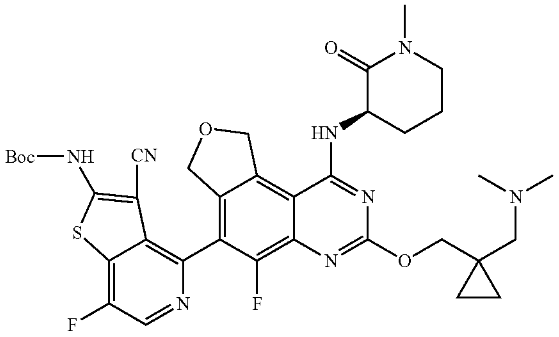 [SMILES: CN(C)CC1(COc2nc(N[C@@H]3CCCN(C)C3=O)c3c4c(c(-c5ncc(F)c6sc(NC(=O)OC(C)(C)C)c(C#N)c56)c(F)c3n2)COC4)CC1] | 735 |
| 68B | tert-Butyl (3-cyano-4-(3-((1-((dimethylamino)methyl) cyclopropyl)methoxy)-5-fluoro-1-(((R)-2-oxopiperidin-3-yl)amino)-7,9-dihydrofuro[3,4-f]quinazolin-6-yl)-7-fluorothieno[3,2-c]pyridin-2-yl)carbamate | 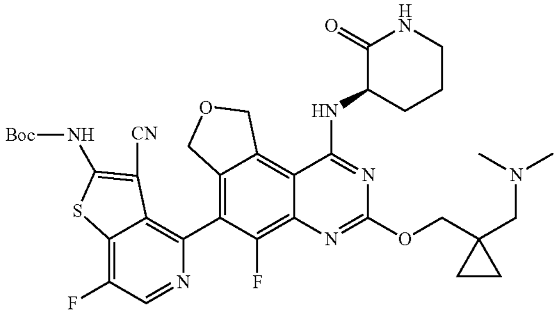 [SMILES: CN(C)CC1(COc2nc(N[C@@H]3CCCNC3=O)c3c4c(c(-c5ncc(F)c6sc(NC(=O)OC(C)(C)C)c(C#N)c56)c(F)c3n2)COC4)CC1] | 721 |

TABLE 14-continued

| Preparation | Chemical Name | Structure | MS (ES) m/z (M + 1) |
|---|---|---|---|
| 69B | tert-Butyl (3-cyano-4-(3-((1-((dimethylamino)methyl) cyclopropyl)methoxy)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridin-2-yl)carbamate | 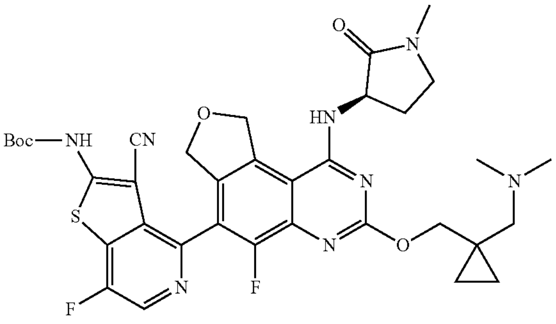 [SMILES: CN(C)CC1(COc2nc(N[C@@H]3CCN(C)C3=O)c3c4c(c(-c5ncc(F)c6sc(NC(=O)OC(C)(C)C)c(C#N)c56)c(F)c3n2)COC4)CC1] | 721 |
| 70B | tert-Butyl (3-cyano-4-(3-((1-((dimethylamino)methyl) cyclopropyl)methoxy)-5-fluoro-1-(((R)-2-oxopyrrolidin-3-yl)amino)-7,9-dihydrofuro[3,4-f]quinazolin-6-yl)-7-fluorothieno[3,2-c]pyridin-2-yl)carbamate | 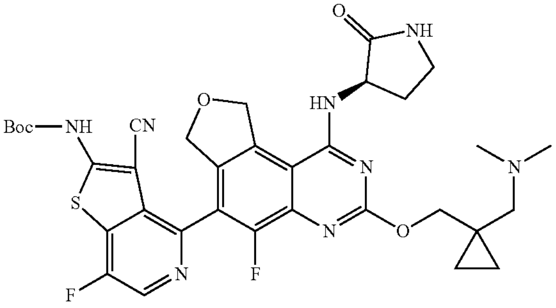 [SMILES: CN(C)CC1(COc2nc(N[C@@H]3CCNC3=O)c3c4c(c(-c5ncc(F)c6sc(NC(=O)OC(C)(C)C)c(C#N)c56)c(F)c3n2)COC4)CC1] | 707 |
| 79C | tert-Butyl (3-cyano-4-(3-(ethylthio)-5-fluoro-1-((2- (trimethylsilyl)ethoxy) methoxy)-7,9- dihydrofuro[3,4-f]quinazolin-6-yl)-7-fluorothieno[3,2-c]pyridin-2-yl)carbamate | 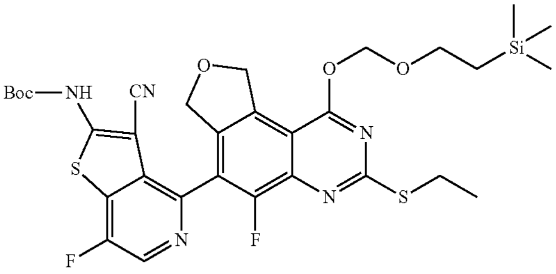 | 688 |
| 80C | tert-Butyl (3-cyano-4-(3-(ethylthio)-5-fluoro-1-(2-(trimethylsilyl)ethoxy)-7,9-dihydrofuro[3,4-f]quinazolin-6-yl)-7-fluorothieno[3,2-c]pyridin-2-yl)carbamate | 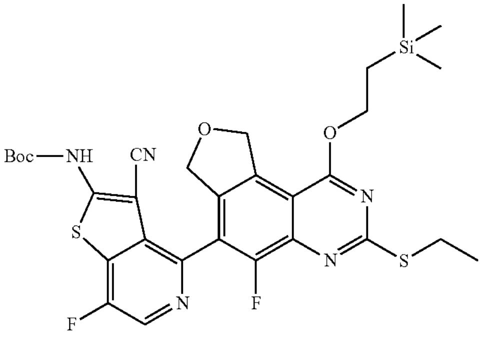 [SMILES: CCSc1nc(OCC[Si](C)(C)C)c2c3c(c(-c4ncc(F)c5sc(NC(=O)OC(C)(C)C)c(C#N)c45)c(F)c2n1)COC3] | 658 |

Preparation 81C tert-Butyl (3-cyano-4-(3-(ethylsulfonyl)-5-fluoro-1-((2-(trimethylsilyl)ethoxy)methoxy)-7,9-dihydrofuro[3,4-f]quinazolin-6-yl)-7-fluorothieno[3,2-c]pyridin-2-yl)carbamate

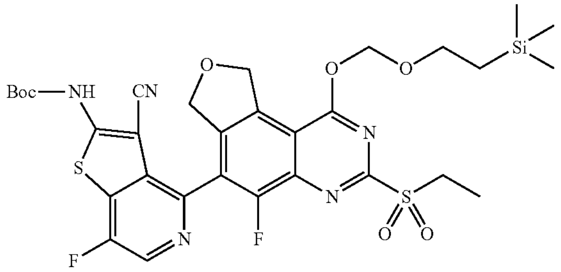 [SMILES: CCS(=O)(=O)c1nc(OCOCC[Si](C)(C)C)c2c3c(c(-c4ncc(F)c5sc(NC(=O)OC(C)(C)C)c(C#N)c45)c(F)c2n1)COC3]

tert-Butyl (3-cyano-4-(3-(ethylthio)-5-fluoro-1-((2-(trimethylsilyl)ethoxy)methoxy)-7,9-dihydrofuro[3,4-f]quinazolin-6-yl)-7-fluorothieno[3,2-c]pyridin-2-yl)carbamate was used in a manner analogous to the method of Preparation 25 to afford the crude title compound (1.05 g) as a yellow solid. MS (ES) m/z=720 (M+1).

Preparation 82C tert-Butyl (3-cyano-4-(3-(ethylsulfonyl)-5-fluoro-1-(2-(trimethylsilyl)ethoxy)-7,9-dihydrofuro[3,4-f]quinazolin-6-yl)-7-fluorothieno[3,2-c]pyridin-2-yl)carbamate

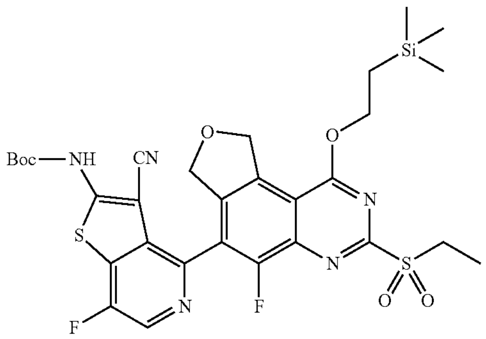 [SMILES: CCS(=O)(=O)c1nc(OCC[Si](C)(C)C)c2c3c(c(-c4ncc(F)c5sc(NC(=O)OC(C)(C)C)c(C#N)c45)c(F)c2n1)COC3]

tert-Butyl (3-cyano-4-(3-(ethylthio)-5-fluoro-1-(2-(trimethylsilyl)ethoxy)-7,9-dihydrofuro[3,4-f]quinazolin-6-yl)-7-fluorothieno[3,2-c]pyridin-2-yl)carbamate was used in a manner analogous to the method of Preparation 22A to afford the crude title compound (4.2 g, 70%) as a yellow solid. MS (ES) m/z=690 (M+1).

Preparation 83C tert-Butyl (3-cyano-7-fluoro-4-(5-fluoro-3-((S)-1-((S)-1-methylpyrrolidin-2-yl)ethoxy)-1-((2-(trimethylsilyl)ethoxy)methoxy)-7,9-dihydrofuro[3,4-f]quinazolin-6-yl)thieno[3,2-c]pyridin-2-yl)carbamate

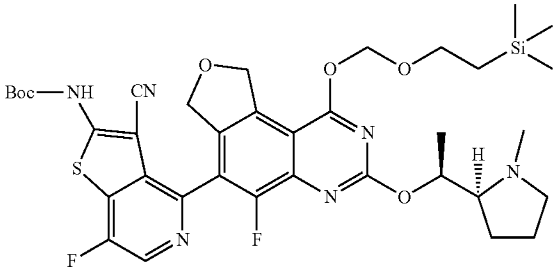 [SMILES: C[C@H](Oc1nc(OCOCC[Si](C)(C)C)c2c3c(c(-c4ncc(F)c5sc(NC(=O)OC(C)(C)C)c(C#N)c45)c(F)c2n1)COC3)[C@@H]1CCCN1C]

tert-Butyl (3-cyano-4-(3-(ethylsulfonyl)-5-fluoro-1-((2-(trimethylsilyl)ethoxy)methoxy)-7,9-dihydrofuro[3,4-f]quinazolin-6-yl)-7-fluorothieno[3,2-c]pyridin-2-yl)carbamate and (S)-1-((S)-1-methylpyrrolidin-2-yl)ethan-1-ol were used in a manner analogous to the method of Preparation 30 to afford the title compound (0.60 g, 52%) as a yellow solid. MS (ES) m/z=755 (M+1).

Preparation 84C tert-Butyl (3-cyano-7-fluoro-4-(5-fluoro-3-((S)-1-((2S,4R)-4-fluoro-1-methylpyrrolidin-2-yl)ethoxy)-1-((2-(trimethylsilyl)ethoxy)methoxy)-7,9-dihydrofuro[3,4-f]quinazolin-6-yl)thieno[3,2-c]pyridin-2-yl)carbamate

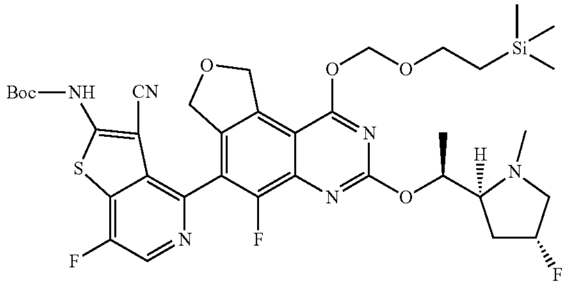 [SMILES: C[C@H](Oc1nc(OCOCC[Si](C)(C)C)c2c3c(c(-c4ncc(F)c5sc(NC(=O)OC(C)(C)C)c(C#N)c45)c(F)c2n1)COC3)[C@@H]1C[C@@H](F)CN1C]

tert-Butyl (3-cyano-4-(3-(ethylsulfonyl)-5-fluoro-1-((2-(trimethylsilyl)ethoxy)methoxy)-7,9-dihydrofuro[3,4-f]quinazolin-6-yl)-7-fluorothieno[3,2-c]pyridin-2-yl)carbamate and (S)-1-((2S,4R)— 4-fluoro-1-methylpyrrolidin-2-yl)ethan-1-ol were used in a manner analogous to the method of Preparation 30 to afford the title compound (0.37 g, 60%) as a white solid. MS (ES) m/z=773 (M+1).

Preparation 85C tert-Butyl (3-cyano-4-(3-((2S,3S)-3-(dimethylamino)-2-methylpyrrolidin-1-yl)-5-fluoro-1-(2-(trimethylsilyl)ethoxy)-7,9-dihydrofuro[3,4-f]quinazolin-6-yl)-7-fluorothieno[3,2-c]pyridin-2-yl)carbamate

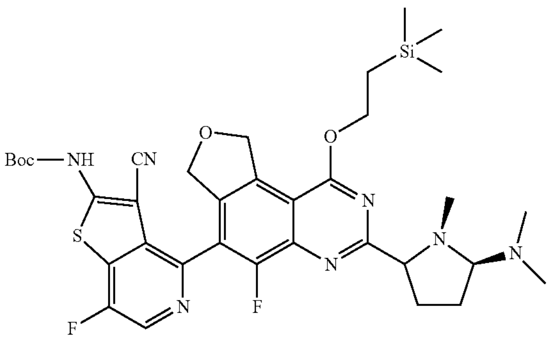

tert-Butyl (3-cyano-4-(3-(ethylsulfonyl)-5-fluoro-1-(2-(trimethylsilyl)ethoxy)-7,9-dihydrofuro[3,4-f]quinazolin-6-yl)-7-fluorothieno[3,2-c]pyridin-2-yl)carbamate and (2S,3S)-N,N,2-trimethylpyrrolidin-3-amine dihydrochloride were used in a manner analogous to the method of Preparation 39A to afford the title compound (1.9 g, 60%) as a yellow solid. MS (ES) m/z=724 (M+1).

Preparation 86C tert-Butyl (3-cyano-7-fluoro-4-(5-fluoro-1-hydroxy-3-((S)-1-((S)-1-methylpyrrolidin-2-yl)ethoxy)-7,9-dihydrofuro[3,4-f]quinazolin-6-yl)thieno[3,2-c]pyridin-2-yl)carbamate

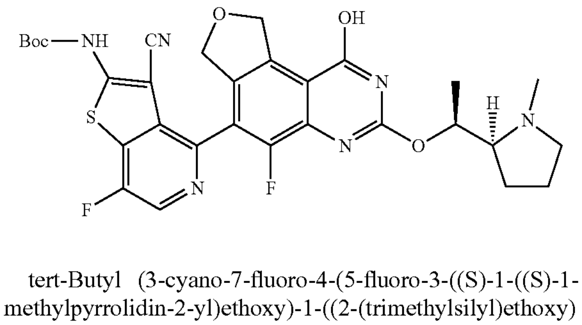

tert-Butyl (3-cyano-7-fluoro-4-(5-fluoro-3-((S)-1-((S)-1-methylpyrrolidin-2-yl)ethoxy)-1-((2-(trimethylsilyl)ethoxy)methoxy)-7,9-dihydrofuro[3,4-f]quinazolin-6-yl)thieno[3,2-c]pyridin-2-yl)carbamate was used in a manner analogous to the method of Preparation 4B to afford the title compound (0.38 g, 75%) as a yellow solid. MS (ES) m/z=625 (M+1).

Preparation 87C tert-Butyl (4-(5-chloro-1-hydroxy-3-((S)-1-((S)-1-methylpyrrolidin-2-yl)ethoxy)-7,9-dihydrofuro[3,4-f]quinazolin-6-yl)-3-cyano-7-fluorobenzo[b]thiophen-2-yl)carbamate

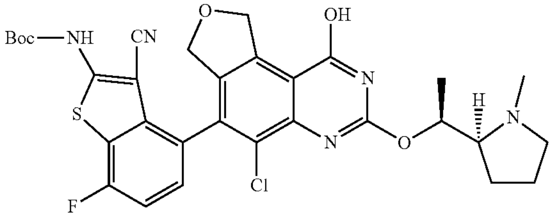 [SMILES: C[C@H](Oc1nc(O)c2c3c(c(-c4ccc(F)c5sc(NC(=O)OC(C)(C)C)c(C#N)c45)c(Cl)c2n1)COC3)[C@@H]1CCCN1C]

tert-Butyl (4-(5-chloro-3-((S)-1-((S)-1-methylpyrrolidin-2-yl)ethoxy)-1-((2-(trimethylsilyl)ethoxy)methoxy)-7,9-dihydrofuro[3,4-f]quinazolin-6-yl)-3-cyano-7-fluorobenzo[b]thiophen-2-yl)carbamate was used in a manner analogous to the method of Preparation 4B to afford the title compound (2.0 g, 73%) as a yellow solid. MS (ES) m/z=640 (M+1).

Preparation 88C tert-Butyl (4-(5-chloro-1-hydroxy-3-((S)-1-((2S,4R)-4-methoxy-1-methylpyrrolidin-2-yl)ethoxy)-7,9-dihydrofuro[3,4-f]quinazolin-6-yl)-3-cyano-7-fluorobenzo[b]thiophen-2-yl)carbamate

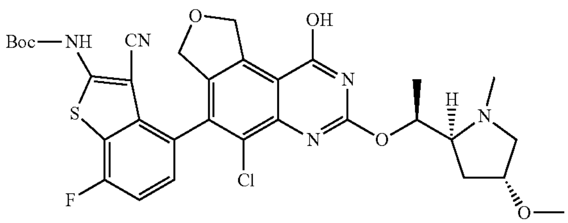 [SMILES: CO[C@@H]1C[C@@H]([C@H](C)Oc2nc(O)c3c4c(c(-c5ccc(F)c6sc(NC(=O)OC(C)(C)C)c(C#N)c56)c(Cl)c3n2)COC4)N(C)C1]

tert-Butyl (4-(5-chloro-3-((S)-1-((2S,4R)-4-methoxy-1-methylpyrrolidin-2-yl)ethoxy)-1-((2-(trimethylsilyl)ethoxy)methoxy)-7,9-dihydrofuro[3,4-f]quinazolin-6-yl)-3-cyano-7-fluorobenzo[b]thiophen-2-yl)carbamate was used in a manner analogous to the method of Preparation 4B to afford the title compound (0.40 g, 68%) as a yellow solid. MS (ES) m/z=669 (M+1).

Preparation 89C tert-Butyl (3-cyano-7-fluoro-4-(5-fluoro-3-((S)-1-((2S,4R)-4-fluoro-1-methylpyrrolidin-2-yl)ethoxy)-1-hydroxy-7,9-dihydrofuro[3,4-f]quinazolin-6-yl)thieno[3,2-c]pyridin-2-yl)carbamate

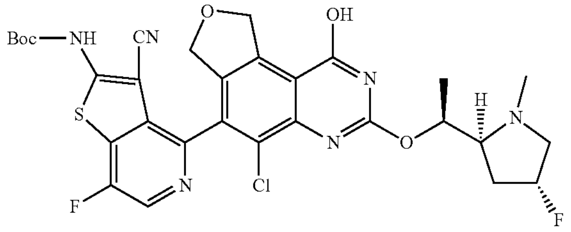 [SMILES: C[C@H](Oc1nc(O)c2c3c(c(-c4ncc(F)c5sc(NC(=O)OC(C)(C)C)c(C#N)c45)c(Cl)c2n1)COC3)[C@@H]1C[C@@H](F)CN1C]

tert-Butyl (3-cyano-7-fluoro-4-(5-fluoro-3-((S)-1-((2S, 4R)-4-fluoro-1-methylpyrrolidin-2-yl)ethoxy)-1-((2-(trimethylsilyl)ethoxy)methoxy)-7,9-dihydrofuro[3,4-f]quinazolin-6-yl)thieno[3,2-c]pyridin-2-yl)carbamate was used in a manner analogous to the method of Preparation 4B to afford the title compound (0.11 g, 33%) as a yellow solid. MS (ES) m/z=643 (M+1).

Preparation 90C tert-Butyl (3-cyano-4-(3-((2S,3S)-3-(dimethylamino)-2-methylpyrrolidin-1-yl)-5-fluoro-1-hydroxy-7,9-dihydrofuro[3,4-f]quinazolin-6-yl)-7-fluorothieno[3,2-c]pyridin-2-yl)carbamate

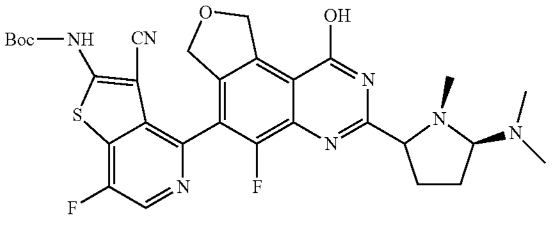

tert-Butyl (3-cyano-4-(3-((2S,3S)-3-(dimethylamino)-2-methylpyrrolidin-1-yl)-5-fluoro-1-(2-(trimethylsilyl)ethoxy)-7,9-dihydrofuro[3,4-f]quinazolin-6-yl)-7-fluorothieno[3,2-c]pyridin-2-yl)carbamate was used in a manner analogous to the method of Preparation 4B to afford the title compound (1.4 g, 86%) as a yellow solid. MS (ES) m/z=624 (M+1).

Preparation 91C tert-Butyl (4-(1-chloro-3-((2S,3S)-3-(dimethylamino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate

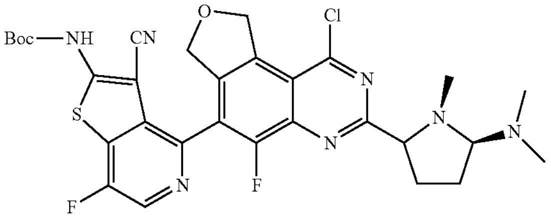

tert-Butyl (3-cyano-4-(3-((2S,3S)-3-(dimethylamino)-2-methylpyrrolidin-1-yl)-5-fluoro-1-hydroxy-7,9-dihydrofuro[3,4-f]quinazolin-6-yl)-7-fluorothieno[3,2-c]pyridin-2-yl)carbamate was used in a manner analogous to the method of Preparation 47A to afford the title compound (0.55 g, 100%) as a yellow solid. MS (ES) m/z=642 (M+1).

Preparation 92C tert-Butyl (3-cyano-4-(3-((2S,3S)-3-(dimethylamino)-2-methylpyrrolidin-1-yl)-5-fluoro-1-((pyridazin-3-ylmethyl)amino)-7,9-dihydrofuro[3,4-f]quinazolin-6-yl)-7-fluorothieno[3,2-c]pyridin-2-yl)carbamate

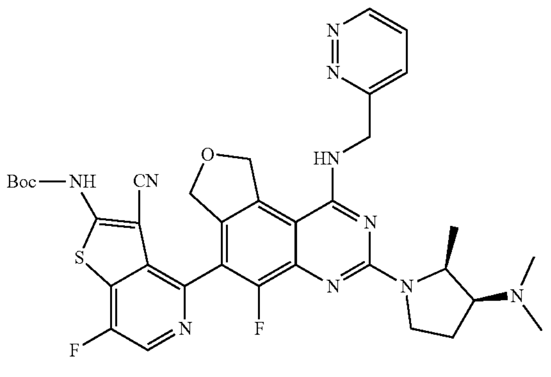 [SMILES: C[C@H]1[C@@H](N(C)C)CCN1c1nc(NCc2cccnn2)c2c3c(c(-c4ncc(F)c5sc(NC(=O)OC(C)(C)C)c(C#N)c45)c(F)c2n1)COC3]

tert-Butyl (4-(1-chloro-3-((2S,3S)-3-(dimethylamino)-2-methylpyrrolidin-1-yl)-5-fluoro-7,9-dihydrofuro[3,4-f]quinazolin-6-yl)-3-cyano-7-fluorothieno[3,2-c]pyridin-2-yl) carbamate and pyridazin-3-ylmethanamine dihydrochloride were used in a manner analogous to the method of Preparation 18 to afford the crude title compound (0.30 g, 100%) as a red solid. MS (ES) m/z=715 (M+1).

Preparation 93C tert-Butyl (3-cyano-4-(3-((2S,3S)-3-(dimethylamino)-2-methylpyrrolidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridin-2-yl)carbamate

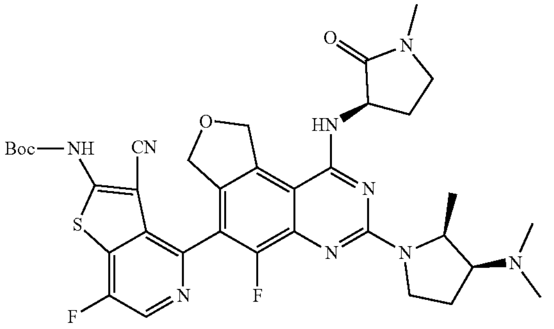 [SMILES: C[C@H]1[C@@H](N(C)C)CCN1c1nc(N[C@@H]2CCN(C)C2=O)c2c3c(c(-c4ncc(F)c5sc(NC(=O)OC(C)(C)C)c(C#N)c45)c(F)c2n1)COC3]

tert-Butyl (4-(1-chloro-3-((2S,3S)-3-(dimethylamino)-2-methylpyrrolidin-1-yl)-5-fluoro-7,9-dihydrofuro[3,4-f]quinazolin-6-yl)-3-cyano-7-fluorothieno[3,2-c]pyridin-2-yl) carbamate and (R)-3-amino-1-methylpyrrolidin-2-one 4-methylbenzenesulfonate were used in a manner analogous to the method of Preparation 18 to afford the crude title compound (0.30 g, 100%) as a red solid. MS (ES) m/z=720 (M+1).

Preparation 54A tert-Butyl (4-(5-chloro-3-(((2R,7aS)-2-fluorotetrahydro-1H-pyrrolizin-7a(5H)-yl)methoxy)-1-((pyridazin-4-ylmethyl)amino)-7,9-dihydrofuro[3,4-f]quinazolin-6-yl)-3-cyano-7-fluorobenzo[b]thiophen-2-yl)carbamate

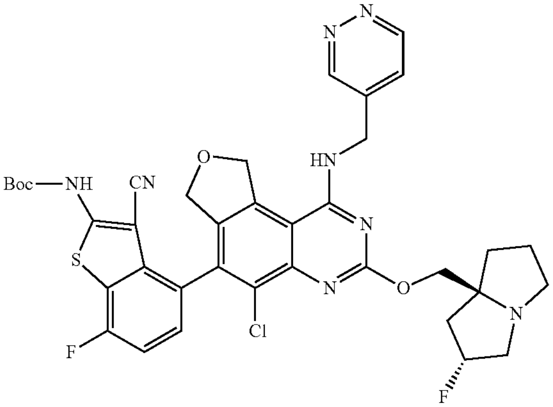 [SMILES: CC(C)(C)OC(=O)Nc1sc2c(F)ccc(-c3c4c(c5c(NCc6ccnnc6)nc(OC[C@@]67CCCN6C[C@H](F)C7)nc5c3Cl)COC4)c2c1C#N]

To a solution of tert-butyl (4-(5-chloro-3-(((2R,7aS)-2-fluorotetrahydro-1H-pyrrolizin-7a(5H)-yl)methoxy)-1-hydroxy-7,9-dihydrofuro[3,4-f]quinazolin-6-yl)-3-cyano-7-fluorobenzo[b]thiophen-2-yl)carbamate (0.082 g, 0.12 mmol) in acetonitrile (1.5 mL) was added (benzotriazol-1-yloxy)tripyrrolidinophosphonium hexafluorophosphate (0.13 g, 0.24 mmol) and diisopropylethylamine (0.064 mL, 0.37 mmol). The mixture was stirred at room temperature. After 1 h, pyridazin-4-ylmethanamine hydrochloride (0.036 g, 0.24 mmol) was added. After 2.5 h, the mixture was concentrated under reduced pressure. The residue was purified by reversed phase purification, eluting with 0-50% ACN in water, to give the title compound (0.070 g, 75%). MS (ES) m/z=761 (M+1).

The following compounds in Table 15 were prepared in similar manner as described in Preparation 54A. Similar coupling agents, such as bromo tris(dimethylamino) phosphonium hexafluorophosphate, may have been substituted. Various methods were used to purify the compounds, which would be apparent to one skilled in the art.

TABLE 15

| Preparation | Chemical Name | Structure | MS (ES) m/z (M + 1) |
|---|---|---|---|
| 55A | tert-Butyl (4-(5-chloro-3-(((2R,7aS)-2-fluorotetrahydro-1H-pyrrolizin-7a(5H)-yl)methoxy)-1-(((3-methyl-1,2,4-oxadiazol-5-yl)methyl)amino)-7,9-dihydrofuro[3,4-f]quinazolin-6-yl)-3-cyano-7-fluorobenzo[b]thiophen-2-yl)carbamate | 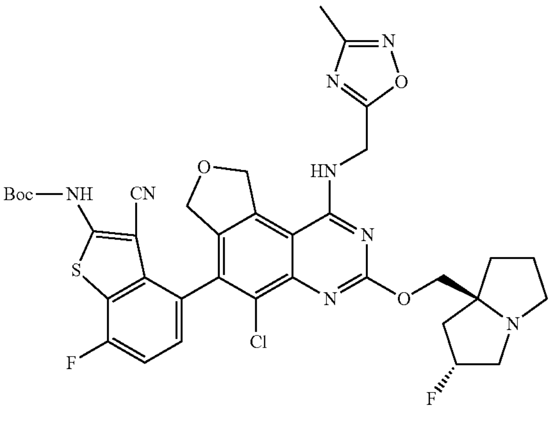 [SMILES: Cc1noc(CNc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)n1] | 765 |

TABLE 15-continued

| Preparation | Chemical Name | Structure | MS (ES) m/z (M + 1) |
| --- | --- | --- | --- |
| 56A | tert-Butyl (4-(5-chloro-3-(((2R,7aS)-2-fluorotetrahydro-1H-pyrrolizin-7a(5H)-yl)methoxy)-1-((pyridazin-3-ylmethyl)amino)-7,9-dihydrofuro[3,4-f]quinazolin-6-yl)-3-cyano-7-fluorobenzo[b]thiophen-2-yl)carbamate | 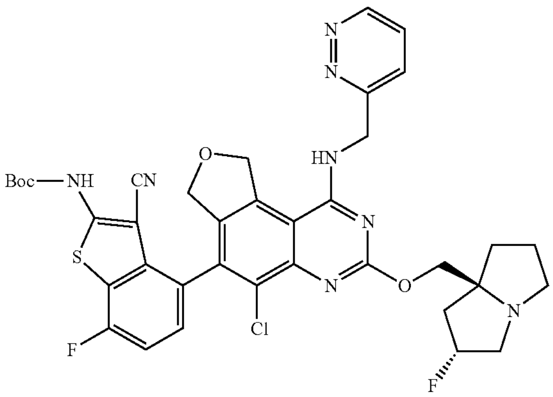 [SMILES: CC(C)(C)OC(=O)Nc1sc2c(F)ccc(-c3c4c(c5c(NCc6cccnn6)nc(OC[C@@]67CCCN6C[C@H](F)C7)nc5c3Cl)COC4)c2c1C#N] | 761 |
| 57A | tert-Butyl (4-(5-chloro-3-(((2R, 7aS)-2-fluorotetrahydro-1H-pyrrolizin-7a(5H)-yl)methoxy)-1-(((5-methyl-1,2,4-oxadiazol-3-yl)methyl)amino)-7,9-dihydrofuro[3,4-f]quinazolin-6-yl)-3-cyano-7-fluorobenzo[b]thiophen-2-yl)carbamate | 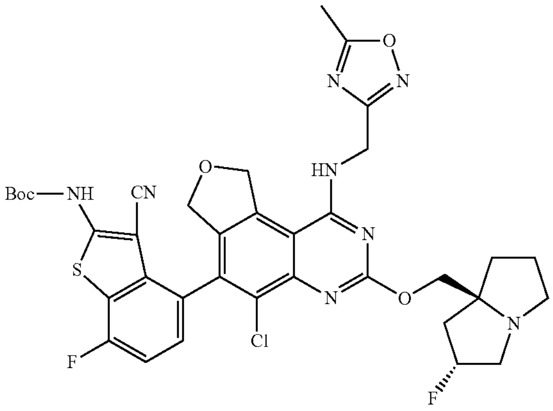 [SMILES: Cc1nc(CNc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)no1] | 765 |
| 58A | tert-Butyl (4-(5-chloro-3-(((2R,7aS)-2-fluorotetrahydro-1H-pyrrolizin-7a(5H)-yl)methoxy)- 1-(((1-methyl-1H-1,2,3-triazol-4-yl)methyl)amino)-7,9-dihydrofuro[3,4-f]quinazolin-6-yl)-3-cyano-7-fluorobenzo[b]thiophen-2-yl)carbamate | 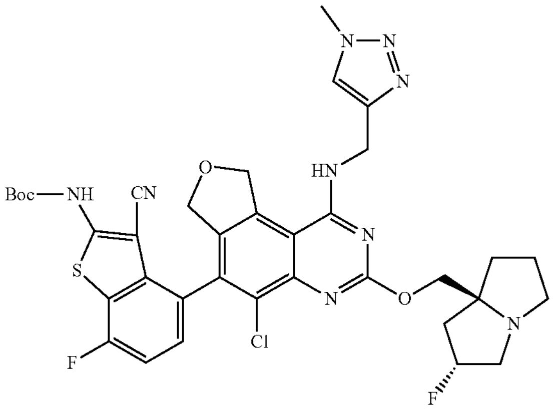 [SMILES: Cn1cc(CNc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)nn1] | 764 |

TABLE 15-continued

| Preparation | Chemical Name | Structure | MS (ES) m/z (M + 1) |
| --- | --- | --- | --- |
| 59A | tert-Butyl (4-(5-chloro-3-(((2R,7aS)-2-fluorotetrahydro-1H-pyrrolizin-7a(5H)-yl)methoxy)-1-(((R)-2-oxopiperidin-3-yl)amino)-7,9-dihydrofuro[3,4-f]quinazolin-6-yl)-3-cyano-7-fluorobenzo[b]thiophen-2-yl)carbamate | 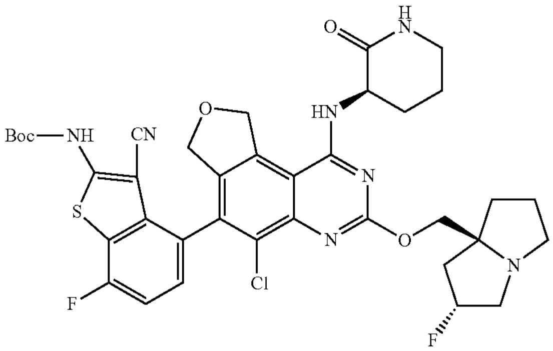 [SMILES: CC(C)(C)OC(=O)Nc1sc2c(F)ccc(-c3c4c(c5c(N[C@@H]6CCCNC6=O)nc(OC[C@@]67CCCN6C[C@H](F)C7)nc5c3Cl)COC4)c2c1C#N] | 766 |
| 60A | tert-Butyl (4-(5-chloro-3-(((2R,7aS)-2-fluorotetrahydro-1H-pyrrolizin-7a(5H)-yl)methoxy)-1-(((S)-2-oxopyrrolidin-3-yl)amino)-7,9-dihydrofuro[3,4-f]quinazolin-6-yl)-3-cyano-7-fluorobenzo[b]thiophen-2-yl)carbamate | 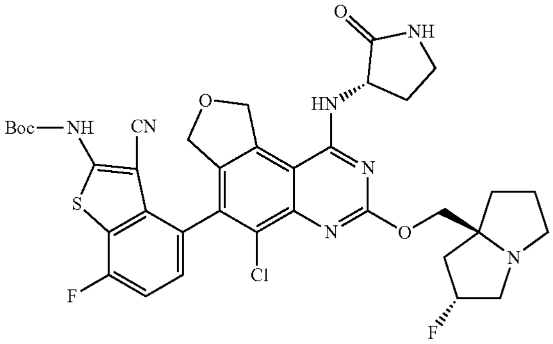 [SMILES: CC(C)(C)OC(=O)Nc1sc2c(F)ccc(-c3c4c(c5c(N[C@H]6CCNC6=O)nc(OC[C@@]67CCCN6C[C@H](F)C7)nc5c3Cl)COC4)c2c1C#N] | 752 |
| 61A | tert-Butyl (4-(5-chloro-3-(((2R, 7aS)-2-fluorotetrahydro-1H-pyrrolizin-7a(5H)-yl)methoxy)-1-(((S)-2-oxopiperidin-3-yl)amino)-7,9-dihydrofuro[3,4-f]quinazolin-6-yl)-3-cyano-7-fluorobenzo[b]thiophen-2-yl)carbamate | 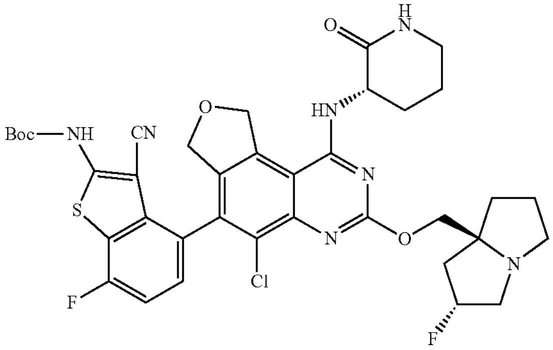 [SMILES: CC(C)(C)OC(=O)Nc1sc2c(F)ccc(-c3c4c(c5c(N[C@H]6CCCNC6=O)nc(OC[C@@]67CCCN6C[C@H](F)C7)nc5c3Cl)COC4)c2c1C#N] | 766 |
| 62A | tert-Butyl (4-(5-chloro-3-(((2R,7aS)-2-fluorotetrahydro-1H-pyrrolizin-7a(5H)-yl)methoxy)-1-(((R)-1-methyl-2-oxopyrrolidin-3-yl)amino)-7,9-dihydrofuro[3,4-f]quinazolin-6-yl)-3-cyano-7-fluorobenzo[b]thiophen-2-yl)carbamate | 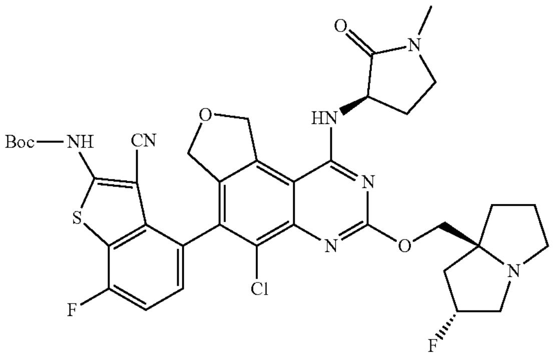 [SMILES: CN1CC[C@@H](Nc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)C1=O] | 766 |

TABLE 15-continued

| Preparation | Chemical Name | Structure | MS (ES) m/z (M + 1) |
|---|---|---|---|
| 63A | tert-Butyl (4-(5-chloro-3-(((2R,7aS)-2-fluorotetrahydro-1H-pyrrolizin-7a(5H)-yl)methoxy)-1-(((R)-2-oxopyrrolidin-3-yl)amino)-7,9-dihydrofuro[3,4-f]quinazolin-6-yl)-3-cyano-7-fluorobenzo[b]thiophen-2-yl)carbamate | 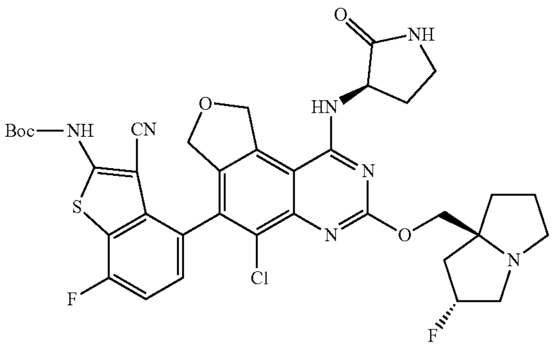 [SMILES: CC(C)(C)OC(=O)Nc1sc2c(F)ccc(-c3c4c(c5c(N[C@@H]6CCNC6=O)nc(OC[C@@]67CCCN6C[C@H](F)C7)nc5c3Cl)COC4)c2c1C#N] | 752 |
| 64A | tert-Butyl (4-(5-chloro-3-(((2R,7aS)-2-fluorotetrahydro-1H-pyrrolizin-7a(5H)-yl)methoxy)-1-(((R)-1-methyl-2-oxopiperidin-3-yl)amino)-7,9-dihydrofuro[3,4-f]quinazolin-6-yl)-3-cyano-7-fluorobenzo[b]thiophen-2-yl)carbamate | 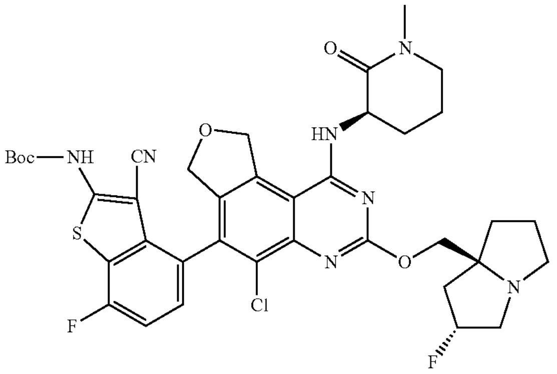 [SMILES: CN1CCC[C@@H](Nc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)C1=O] | 780 |
| 65A | tert-Butyl (4-(5-chloro-1-(((R)-1-methyl-2-oxopyrrolidin-3-yl)amino)-3-(((R)-4-methylmorpholin-2-yl)methoxy)-7,9-dihydrofuro[3,4-f]quinazolin-6-yl)-3-cyano-7-fluorobenzo[b]thiophen-2-yl)carbamate | 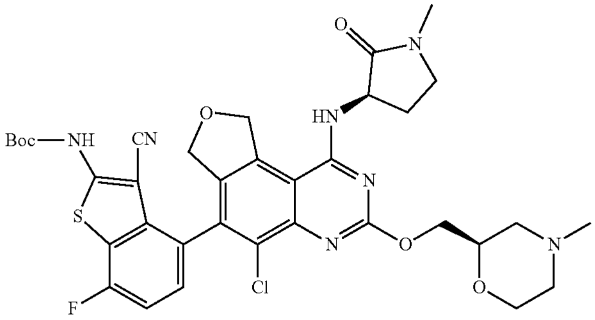 [SMILES: CN1CCO[C@@H](COc2nc(N[C@@H]3CCN(C)C3=O)c3c4c(c(-c5ccc(F)c6sc(NC(=O)OC(C)(C)C)c(C#N)c56)c(Cl)c3n2)COC4)C1] | 738 |
| 66A | tert-Butyl (4-(5-chloro-1-(((R)-1-methyl-2-oxopiperidin-3-yl)amino)-3-(((R)-4-methylmorpholin-2-yl)methoxy)-7,9-dihydrofuro[3,4-f]quinazolin-6-yl)-3-cyano-7-fluorobenzo[b]thiophen-2-yl)carbamate | 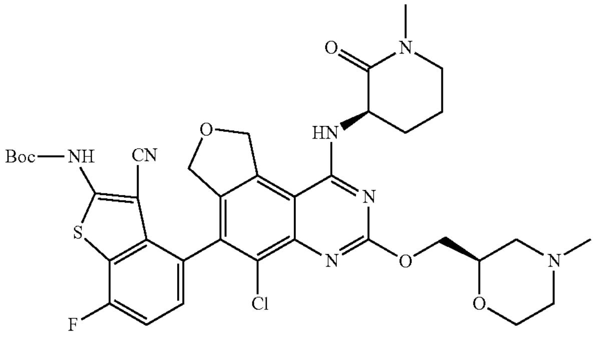 [SMILES: CN1CCO[C@@H](COc2nc(N[C@@H]3CCCN(C)C3=O)c3c4c(c(-c5ccc(F)c6sc(NC(=O)OC(C)(C)C)c(C#N)c56)c(Cl)c3n2)COC4)C1] | 752 |

TABLE 15-continued

| Preparation | Chemical Name | Structure | MS (ES) m/z (M + 1) |
|---|---|---|---|
| 71B | tert-Butyl (4-(5-chloro-3-(((2R, 7aS)-2-fluorotetrahydro-1H-pyrrolizin-7a(5H)-yl)methoxy)-1-(((3-methyl-1,2,4-thiadiazol-5-yl)methyl)amino)-7,9-dihydrofuro[3,4-f]quinazolin-6-yl)-3-cyano-7-fluorobenzo[b]thiophen-2-yl)carbamate | 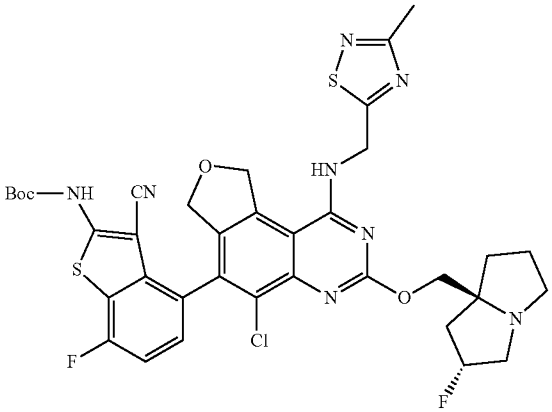 [SMILES: Cc1nsc(CNc2nc(OC[C@@]34CCCN3C[C@H](F)C4)nc3c(Cl)c(-c4ccc(F)c5sc(NC(=O)OC(C)(C)C)c(C#N)c45)c4c(c23)COC4)n1] | 781 |
| 94C | tert-Butyl (3-cyano-7-fluoro-4-(5-fluoro-1-(((5-methyl-1,2,4-oxadiazol-3-yl)methyl)amino)-3-((S)-1-((S)-1-methylpyrrolidin-2-yl)ethoxy)-7,9-dihydrofuro[3,4-f]quinazolin-6-yl)thieno[3,2-c]pyridin-2-yl)carbamate | 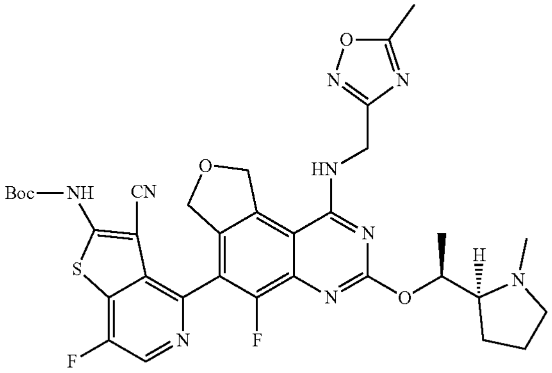 [SMILES: Cc1nc(CNc2nc(O[C@@H](C)[C@@H]3CCCN3C)nc3c(F)c(-c4ncc(F)c5sc(NC(=O)OC(C)(C)C)c(C#N)c45)c4c(c23)COC4)no1] | 720 |
| 95C | tert-Butyl (4-(5-chloro-1-(((5-methyl-1,2,4-oxadiazol-3-yl)methyl)amino)-3-((S)-1-((S)-1-methylpyrrolidin-2-yl)ethoxy)-7,9-dihydrofuro[3,4-f]quinazolin-6-yl)-3-cyano-7-fluorobenzo[b]thiophen-2-yl)carbamate | 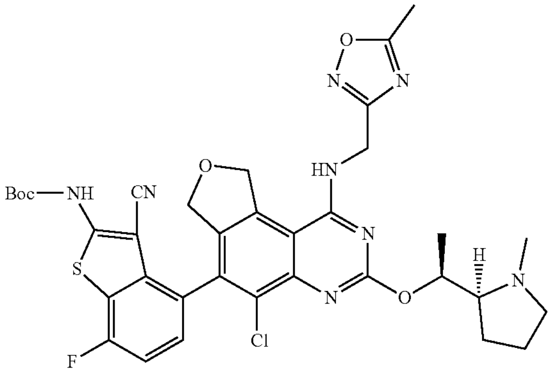 [SMILES: Cc1nc(CNc2nc(O[C@@H](C)[C@@H]3CCCN3C)nc3c(Cl)c(-c4ccc(F)c5sc(NC(=O)OC(C)(C)C)c(C#N)c45)c4c(c23)COC4)no1] | 735 |

TABLE 15-continued

| Preparation | Chemical Name | Structure | MS (ES) m/z (M + 1) |
|---|---|---|---|
| 96C | tert-Butyl (4-(5-chloro-3-((S)-1-((S)-1-methylpyrrolidin-2-yl)ethoxy)-1-((pyridazin-3-ylmethyl)amino)-7,9-dihydrofuro[3,4-f]quinazolin-6-yl)-3-cyano-7-fluorobenzo[b]thiophen-2-yl)carbamate | 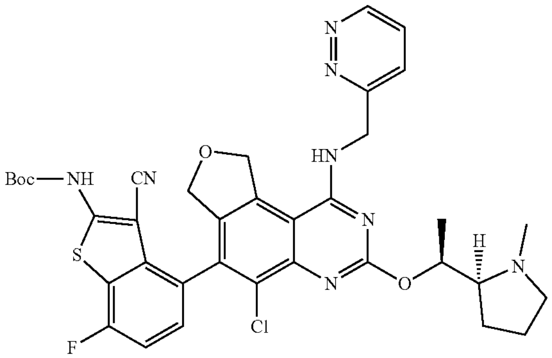 [SMILES: C[C@H](Oc1nc(NCc2cccnn2)c2c3c(c(-c4ccc(F)c5sc(NC(=O)OC(C)(C)C)c(C#N)c45)c(Cl)c2n1)COC3)[C@@H]1CCCN1C] | 731 |
| 97C | tert-Butyl (4-(5-chloro-3-((S)-1-((2S,4R)-4-methoxy-1-methylpyrrolidin-2-yl)ethoxy)-1-((pyridazin-3-ylmethyl)amino)-7,9-dihydrofuro[3,4-f]quinazolin-6-yl)-3-cyano-7-fluorobenzo[b]thiophen-2-yl)carbamate | 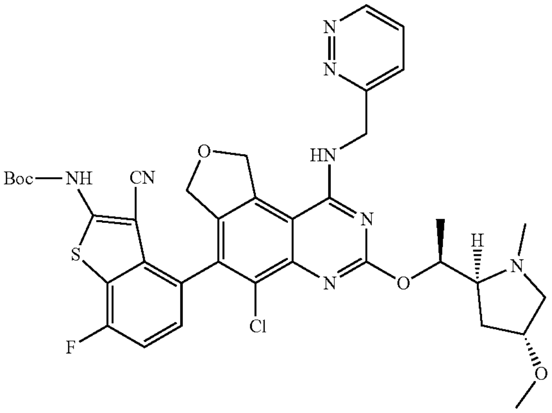 [SMILES: CO[C@@H]1C[C@@H]([C@H](C)Oc2nc(NCc3cccnn3)c3c4c(c(-c5ccc(F)c6sc(NC(=O)OC(C)(C)C)c(C#N)c56)c(Cl)c3n2)COC4)N(C)C1] | 761 |
| 98C | tert-Butyl (3-cyano-7-fluoro-4-(5-fluoro-3-((S)-1-((2S,4R)-4-fluoro-1-methylpyrrolidin-2-yl)ethoxy)-1-((pyridazin-3-ylmethyl)amino)-7,9-dihydrofuro[3,4-f]quinazolin-6-yl)thieno[3,2-c]pyridin-2-yl)carbamate | 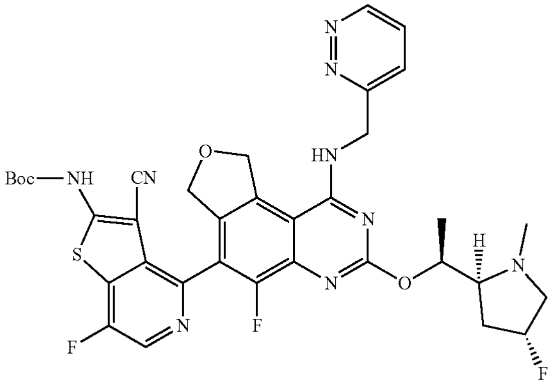 [SMILES: C[C@H](Oc1nc(NCc2cccnn2)c2c3c(c(-c4ncc(F)c5sc(NC(=O)OC(C)(C)C)c(C#N)c45)c(F)c2n1)COC3)[C@@H]1C[C@@H](F)CN1C] | 734 |

Example 1

2-Amino-4-(5-chloro-1-(((5-cyclopropyl-1,3,4-oxadiazol-2-yl)methyl)amino)-3-(((S)-1-methylpyrrolidin-2-yl)methoxy)-7,9-dihydrofuro[3,4-f]quinazolin-6-yl)-7-fluorobenzo[b]thiophene-3-carbonitrile

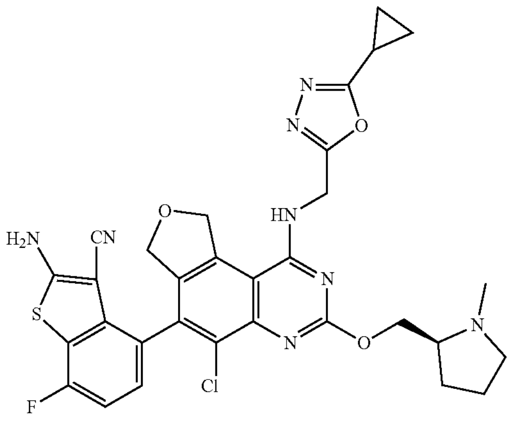 [SMILES: CN1CCC[C@H]1COc1nc(NCc2nnc(C3CC3)o2)c2c3c(c(-c4ccc(F)c5sc(N)c(C#N)c45)c(Cl)c2n1)COC3]

To a solution of tert-butyl (4-(5-chloro-1-hydroxy-3-(((S)-1-methylpyrrolidin-2-yl)methoxy)-7,9-dihydrofuro[3,4-f]quinazolin-6-yl)-3-cyano-7-fluorobenzo[b]thiophen-2-yl)carbamate (0.030 g, 0.048 mmol) in acetonitrile (1 mL) was added (benzotriazol-1-yloxy)tripyrrolidinophosphonium hexafluorophosphate (0.016 g, 0.031 mmol) and 1,8-diazabicyclo(5.4.0)undec-7-ene (0.0095 g, 0.062 mmol). The mixture was stirred at room temperature. After 3 h, (benzotriazol-1-yloxy)tripyrrolidinophosphonium hexafluorophosphate (0.016 g, 0.031 mmol) was added. After 2 h, 5-cyclopropyl-1,3,4-oxadiazol-2-yl)methanamine (0.033 g, 0.24 mmol) was added. After 2 h, the mixture was concentrated under reduced pressure. The residue was dissolved in DCM (2 mL) and TFA (1 mL) was added. After 1 h, the mixture was concentrated under reduced pressure. The residue was purified by reversed phase purification, eluting with 80% ACN in 0.1% formic acid in water, to give the title compound (0.008 g, 20%) after lyophilization as a white solid. MS (ES) m/z=647 (M+1).

The following compounds in Table 16 were prepared in similar manner as described in Example 1. Various methods were used to purify the compounds, which would be apparent to one skilled in the art.

| Preparation | Chemical Name | Structure | MS (ES) m/z (M + 1) |
|---|---|---|---|
| 2 | 2-Amino-4-(5-chloro-1-(((3-cyclopropyl-1H-pyrazol-5-yl)methyl)amino)-3-(((S)-1-methylpyrrolidin-2-yl)methoxy)-7,9-dihydrofuro[3,4-f]quinazolin-6-yl)-7-fluorobenzo[b]thiophene-3-carbonitrile | 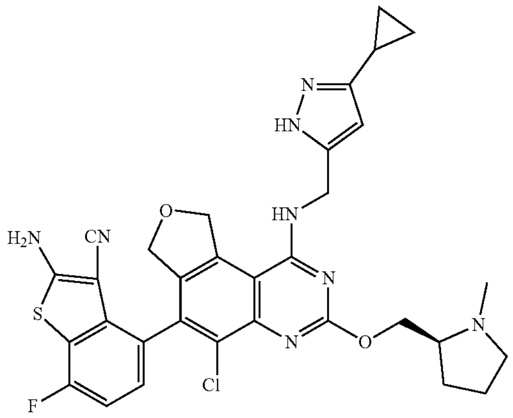 | 645 |
| 3 | 2-Amino-4-(1-(((3-cyclopropyl-1H-pyrazol-5-yl)methyl)amino)-5-fluoro-3-(((S)-1-methylpyrrolidin-2-yl)methoxy)-7,9-dihydrofuro[3,4-f]quinazolin-6-yl)-7-fluorobenzo[b]thiophene-3-carbonitrile | 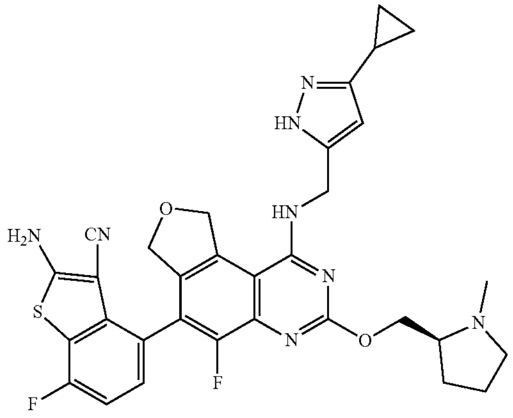 | 629 |

-continued

| Preparation | Chemical Name | Structure | MS (ES) m/z (M + 1) |
|---|---|---|---|
| 4 | 2-Amino-7-fluoro-4-(5-fluoro-3-(((S)-1-methylpyrrolidin-2-yl)methoxy)-1-(((4,5,6,7-tetrahydro-2H-indazol-3-yl)methyl)amino)-7,9-dihydrofuro[3,4-f]quinazolin-6-yl)benzo[b]thiophene-3-carbonitrile | 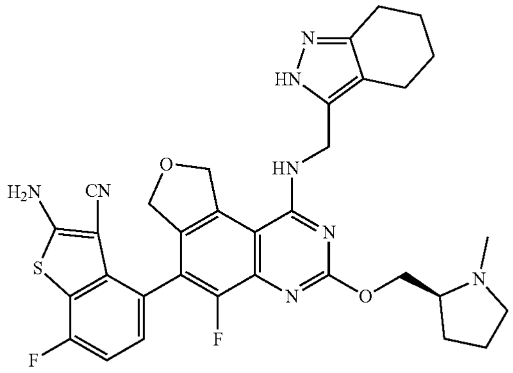 | 643 |
| 5 | 2-Amino-4-(1-(((3-cyclopropyl-1H-1,2,4-triazol-5-yl)methyl)amino)-5-fluoro-3-(((S)-1-methylpyrrolidin-2-yl)methoxy)-7,9-dihydrofuro[3,4-f]quinazolin-6-yl)-7-fluorobenzo[b]thiophene-3-carbonitrile | 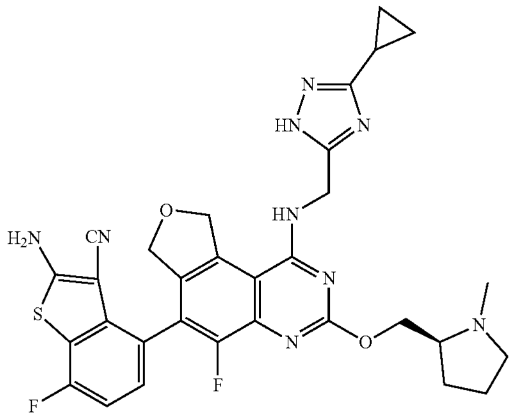 | 630 |
| 6 | 2-Amino-4-(5-chloro-3-(((S)-1-methylpyrrolidin-2-yl)methoxy)-1-(((4,5,6,7-tetrahydro-2H-indazol-3-yl)methyl)amino)-7,9-dihydrofuro[3,4-f]quinazolin-6-yl)-7-fluorobenzo[b]thiophene-3-carbonitrile | 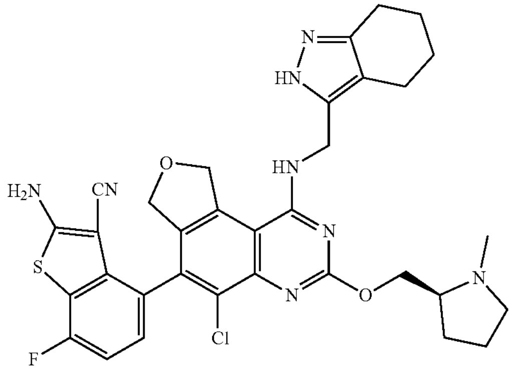 [SMILES: CN1CCC[C@H]1COc1nc(NCc2[nH]nc3c2CCCC3)c2c3c(c(-c4ccc(F)c5sc(N)c(C#N)c45)c(Cl)c2n1)COC3] | 659 |
| 7 | 2-Amino-4-(5-chloro-3-(((S)-1-methylpyrrolidin-2-yl)methoxy)-1-(((4,5,6,7-tetrahydrobenzo[d]isoxazol-3-yl)methyl)amino)-7,9-dihydrofuro[3,4-f]quinazolin-6-yl)-7-fluorobenzo[b]thiophene-3-carbonitrile | 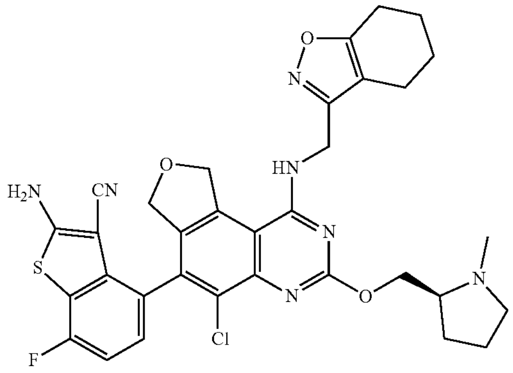 [SMILES: CN1CCC[C@H]1COc1nc(NCc2noc3c2CCCC3)c2c3c(c(-c4ccc(F)c5sc(N)c(C#N)c45)c(Cl)c2n1)COC3] | 660 |

-continued

| Preparation | Chemical Name | Structure | MS (ES) m/z (M + 1) |
|---|---|---|---|
| 8 | 2-Amino-4-(5-chloro-1-(((3-cyclopropyl-1H-1,2,4-triazol-5-yl)methyl)amino)-3-(((S)-1-methylpyrrolidin-2-yl)methoxy)-7,9-dihydrofuro[3,4-f]quinazolin-6-yl)-7-fluorobenzo[b]thiophene-3-carbonitrile | 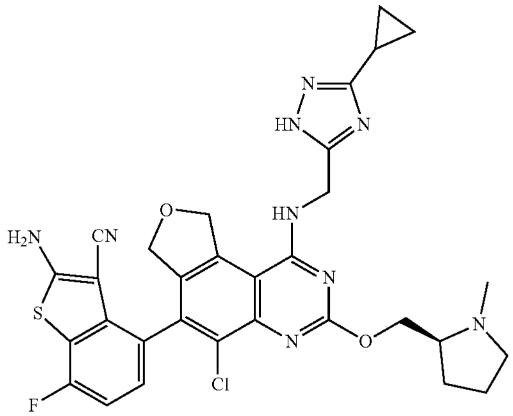 [SMILES: CN1CCC[C@H]1COc1nc(NCc2nc(C3CC3)n[nH]2)c2c3c(c(-c4ccc(F)c5sc(N)c(C#N)c45)c(Cl)c2n1)COC3] | 646 |
| 9 | 4-(3-(((R)-1,4-Dioxan-2-yl)methoxy)-5-chloro-1-(((3-cyclopropyl-1H-1,2,4-triazol-5-yl)methyl)amino)-7,9-dihydrofuro[3,4-f]quinazolin-6-yl)-2-amino-7-fluorobenzo[b]thiophene-3-carbonitrile | 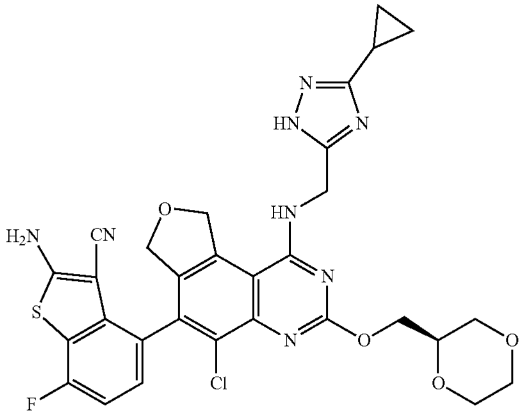 [SMILES: N#Cc1c(N)sc2c(F)ccc(-c3c4c(c5c(NCc6nc(C7CC7)n[nH]6)nc(OC[C@H]6COCCO6)nc5c3Cl)COC4)c12] | 649 |
| 10 [1] | 4-(3-(((R)-1,4-Dioxan-2-yl)methoxy)-5-chloro-1-(((3-cyclopropyl-1H-1,2,4-triazol-5-yl)methyl)amino)-7,9-dihydrofuro[3,4-f]quinazolin-6-yl)-2-amino-7-fluorobenzo[b]thiophene-3-carbonitrile, Atropisomer 1 | 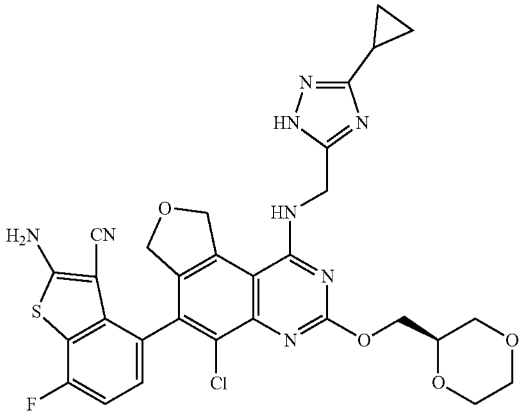 [SMILES: N#Cc1c(N)sc2c(F)ccc(-c3c4c(c5c(NCc6nc(C7CC7)n[nH]6)nc(OC[C@H]6COCCO6)nc5c3Cl)COC4)c12] | 649 |

-continued

| Preparation | Chemical Name | Structure | MS (ES) m/z (M + 1) |
|---|---|---|---|
| 11 [1] | 4-(3-(((R)-1,4-Dioxan-2-yl)methoxy)-5-chloro-1-(((3-cyclopropyl-1H-1,2,4-triazol-5-yl)methyl)amino)-7,9-dihydrofuro[3,4-f]quinazolin-6-yl)-2-amino-7-fluorobenzo[b]thiophene-3-carbonitrile, Atropisomer 2 | 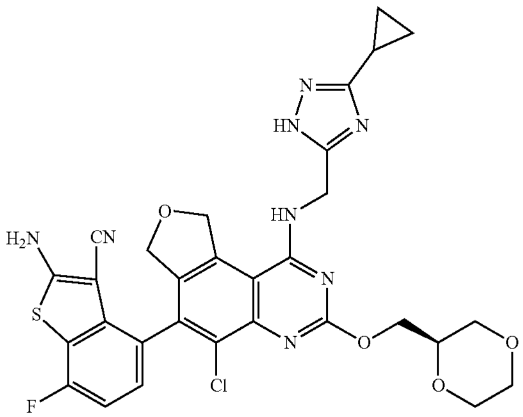 [SMILES: N#Cc1c(N)sc2c(F)ccc(-c3c4c(c5c(NCc6nc(C7CC7)n[nH]6)nc(OC[C@H]6COCCO6)nc5c3Cl)COC4)c12] | 649 |
| 12 | 4-(3-(((R)-1,4-Dioxan-2-yl)methoxy)-5-chloro-1-(((5-ethyl-1,3,4-oxadiazol-2-yl)methyl)amino)-7,9-dihydrofuro[3,4-f]quinazolin-6-yl)-2-amino-7-fluorobenzo[b]thiophene-3-carbonitrile | 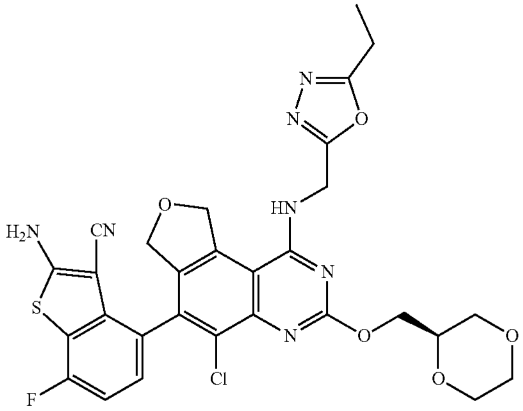 [SMILES: CCc1nnc(CNc2nc(OC[C@H]3COCCO3)nc3c(Cl)c(-c4ccc(F)c5sc(N)c(C#N)c45)c4c(c23)COC4)o1] | 638 |
| 13 [2] | 4-(3-(((R)-1,4-Dioxan-2-yl)methoxy)-5-chloro-1-(((5-ethyl-1,3,4-oxadiazol-2-yl)methyl)amino)-7,9-dihydrofuro[3,4-f]quinazolin-6-yl)-2-amino-7-fluorobenzo[b]thiophene-3-carbonitrile, Atropisomer 1 | 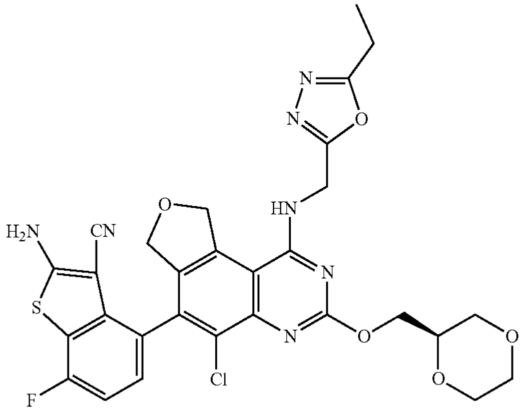 [SMILES: CCc1nnc(CNc2nc(OC[C@H]3COCCO3)nc3c(Cl)c(-c4ccc(F)c5sc(N)c(C#N)c45)c4c(c23)COC4)o1] | 638 |

-continued

| Preparation | Chemical Name | Structure | MS (ES) m/z (M + 1) |
|---|---|---|---|
| 14 [2] | 4-(3-(((R)-1,4-Dioxan-2-yl)methoxy)-5-chloro-1-(((5-ethyl-1,3,4-oxadiazol-2-yl)methyl)amino)-7,9-dihydrofuro[3,4-f]quinazolin-6-yl)-2-amino-7-fluorobenzo[b]thiophene-3-carbonitrile, Atropisomer 2 | 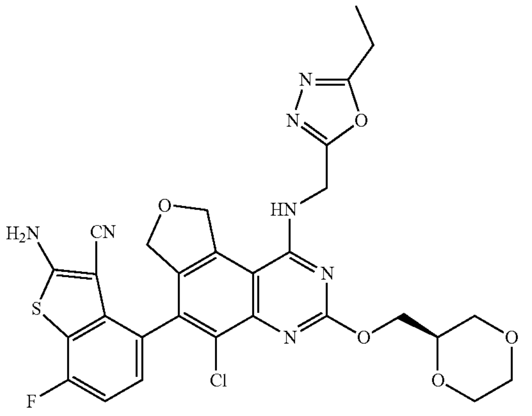 [SMILES: CCc1nnc(CNc2nc(OC[C@H]3COCCO3)nc3c(Cl)c(-c4ccc(F)c5sc(N)c(C#N)c45)c4c(c23)COC4)o1] | 638 |
| 15 | 2-Amino-4-(5-chloro-1-(((3-cyclopropyl-1H-1,2,4-triazol-5-yl)methyl)amino)-3-(((R)-4-methylmorpholin-2-yl)methoxy)-7,9-dihydrofuro[3,4-f]quinazolin-6-yl)-7-fluorobenzo[b]thiophene-3-carbonitrile | 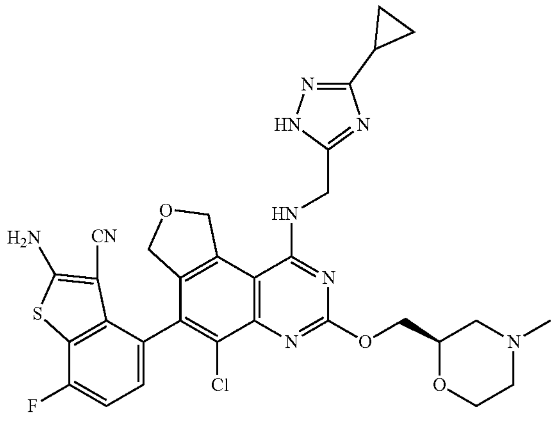 [SMILES: CN1CCO[C@@H](COc2nc(NCc3nc(C4CC4)n[nH]3)c3c4c(c(-c5ccc(F)c6sc(N)c(C#N)c56)c(Cl)c3n2)COC4)C1] | 662 |
| 16 [3] | 2-Amino-4-(5-chloro-1-(((3-cyclopropyl-1H-1,2,4-triazol-5-yl)methyl)amino)-3-(((R)-4-methylmorpholin-2-yl)methoxy)-7,9-dihydrofuro[3,4-f]quinazolin-6-yl)-7-fluorobenzo[b]thiophene-3-carbonitrile, Atropisomer 1 | 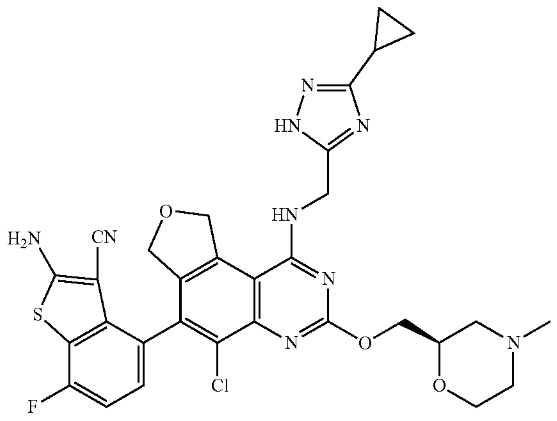 [SMILES: CN1CCO[C@@H](COc2nc(NCc3nc(C4CC4)n[nH]3)c3c4c(c(-c5ccc(F)c6sc(N)c(C#N)c56)c(Cl)c3n2)COC4)C1] | 662 |

-continued

| Preparation | Chemical Name | Structure | MS (ES) m/z (M + 1) |
|---|---|---|---|
| 17 [3] | 2-Amino-4-(5-chloro-1-(((3-cyclopropyl-1H-1,2,4-triazol-5-yl)methyl)amino)-3-(((R)-4-methylmorpholin-2-yl)methoxy)-7,9-dihydrofuro[3,4-f]quinazolin-6-yl)-7-fluorobenzo[b]thiophene-3-carbonitrile, Atropisomer 2 | 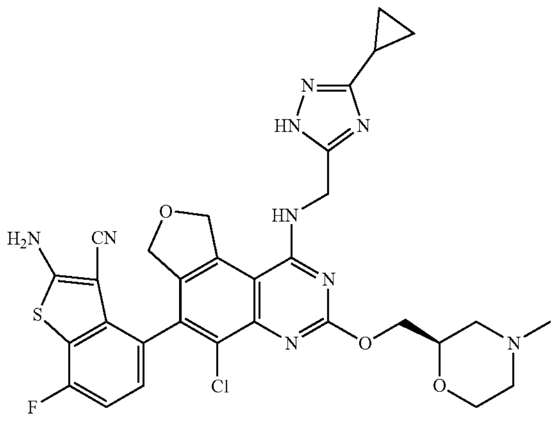 [SMILES: CN1CCO[C@@H](COc2nc(NCc3nc(C4CC4)n[nH]3)c3c4c(c(-c5ccc(F)c6sc(N)c(C#N)c56)c(Cl)c3n2)COC4)C1] | 662 |
| 18 | 2-Amino-4-(5-chloro-1-(((5-ethyl-1,3,4-oxadiazol-2-yl)methyl)amino)-3-(((R)-4-methylmorpholin-2-yl)methoxy)-7,9-dihydrofuro[3,4-f]quinazolin-6-yl)-7-fluorobenzo[b]thiophene-3-carbonitrile | 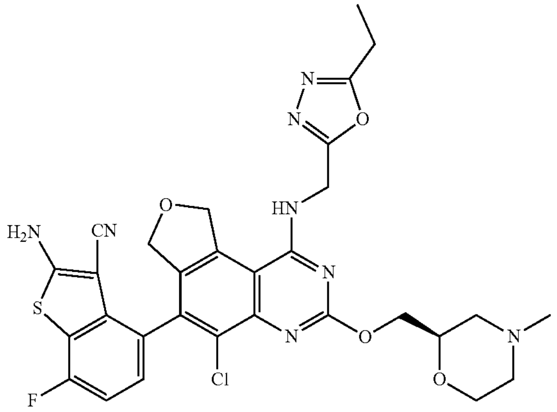 [SMILES: CCc1nnc(CNc2nc(OC[C@H]3CN(C)CCO3)nc3c(Cl)c(-c4ccc(F)c5sc(N)c(C#N)c45)c4c(c23)COC4)o1] | 651 |
| 19 | 2-Amino-4-(5-chloro-1-(((3-cyclopropyl-1H-1,2,4-triazol-5-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile | 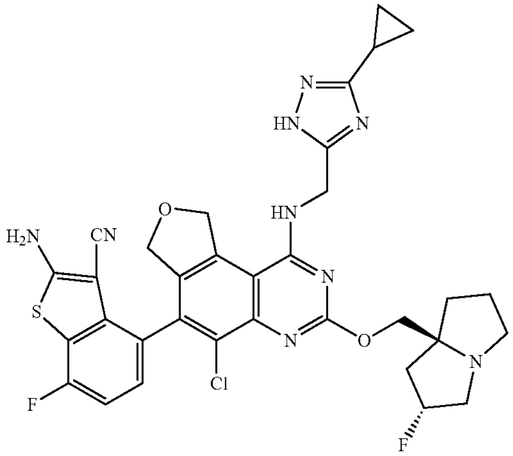 [SMILES: N#Cc1c(N)sc2c(F)ccc(-c3c4c(c5c(NCc6nc(C7CC7)n[nH]6)nc(OC[C@@]67CCCN6C[C@H](F)C7)nc5c3Cl)COC4)c12] | 690 |

-continued

| Preparation | Chemical Name | Structure | MS (ES) m/z (M + 1) |
| --- | --- | --- | --- |
| 20 [4] | 2-Amino-4-(5-chloro-1-(((3-cyclopropyl-1H-1,2,4-triazol-5-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile, Atropisomer 1 | 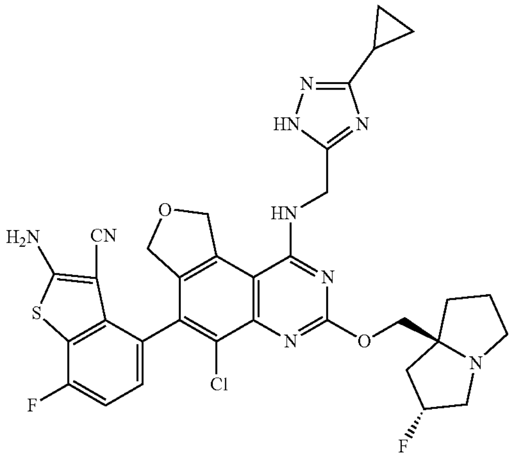 [SMILES: N#Cc1c(N)sc2c(F)ccc(-c3c4c(c5c(NCc6nc(C7CC7)n[nH]6)nc(OC[C@@]67CCCN6C[C@H](F)C7)nc5c3Cl)COC4)c12] | 690 |
| 21 [4] | 2-Amino-4-(5-chloro-1-(((3-cyclopropyl-1H-1,2,4-triazol-5-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile, Atropisomer 2 | 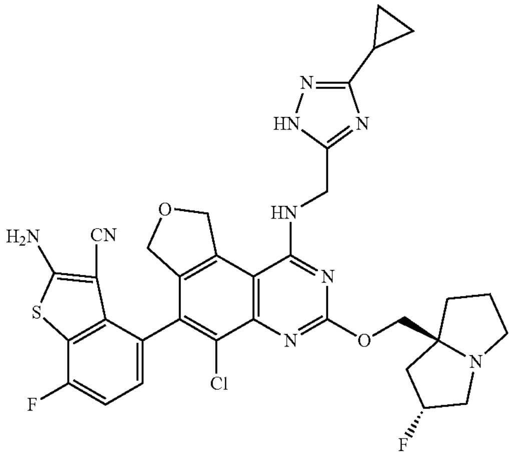 [SMILES: N#Cc1c(N)sc2c(F)ccc(-c3c4c(c5c(NCc6nc(C7CC7)n[nH]6)nc(OC[C@@]67CCCN6C[C@H](F)C7)nc5c3Cl)COC4)c12] | 690 |
| 22 | 2-Amino-4-(5-chloro-1-(((5-ethyl-1,3,4-oxadiazol-2-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile | 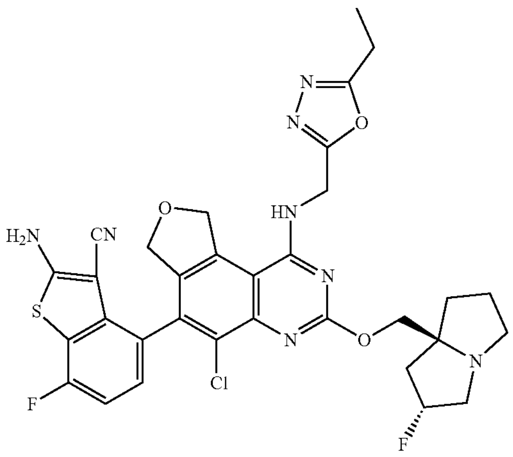 [SMILES: CCc1nnc(CNc2nc(OC[C@@]34CCCN3C[C@H](F)C4)nc3c(Cl)c(-c4ccc(F)c5sc(N)c(C#N)c45)c4c(c23)COC4)o1] | 679 |

-continued

| Preparation | Chemical Name | Structure | MS (ES) m/z (M + 1) |
|---|---|---|---|
| 23 [5] | 2-Amino-4-(5-chloro-1-(((5-ethyl-1,3,4-oxadiazol-2-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile, Atropisomer 1 | 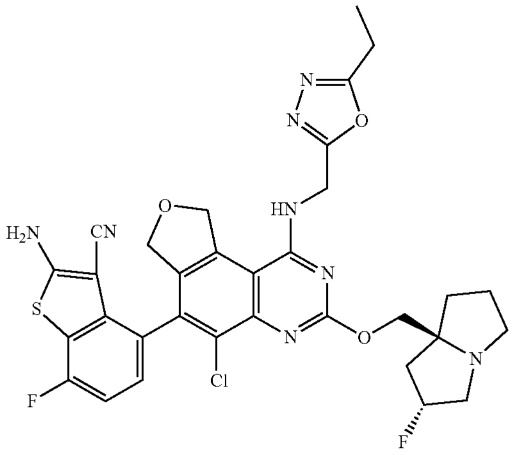 [SMILES: CCc1nnc(CNc2nc(OC[C@@]34CCCN3C[C@H](F)C4)nc3c(Cl)c(-c4ccc(F)c5sc(N)c(C#N)c45)c4c(c23)COC4)o1] | 679 |
| 24 [5] | 2-Amino-4-(5-chloro-1-(((5-ethyl-1,3,4-oxadiazol-2-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile, Atropisomer 2 | 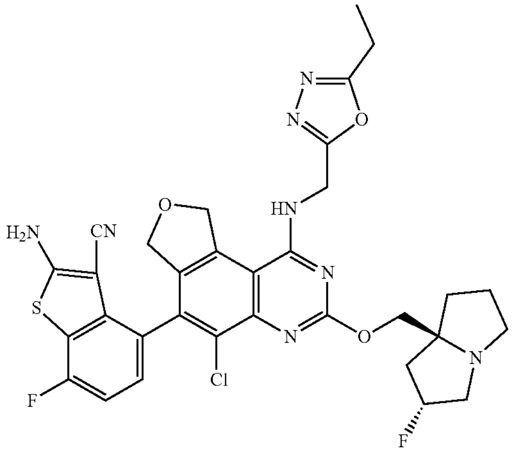 [SMILES: CCc1nnc(CNc2nc(OC[C@@]34CCCN3C[C@H](F)C4)nc3c(Cl)c(-c4ccc(F)c5sc(N)c(C#N)c45)c4c(c23)COC4)o1] | 679 |

[1] Prep-Chiral-HPLC; Phenomenex Lux Cellulose-2, 30 × 150 mm, 40-100% (1:1 MeOH:EtOH) in Heptane, 42.5 mL/min

[2] Prep-Chiral-HPLC; Phenomenex Lux Cellulose-4, 30 × 150 mm, 20-100% EtOH in Heptane, 50 mL/min

[3] Prep-Chiral-HPLC; Phenomenex Lux Cellulose-2, 30 × 150 mm, 20-100% (1:1 MeOH:EtOH) in Heptane, 42.5 mL/min

[4] Prep-Chiral-HPLC; Phenomenex Lux Cellulose-4, 30 × 150 mm, 10-100% EtOH in Heptane, 50 mL/min

[5] Prep-Chiral-HPLC; Phenomenex Lux Cellulose-4, 30 × 150 mm, 10-65% EtOH in Heptane, 50 mL/min Example 25

2-Amino-4-(5-chloro-1-(((5-ethyl-1,3,4-oxadiazol-2-yl)methyl)amino)-3-(((S)-1-methylpyrrolidin-2-yl)methoxy)-7,9-dihydrofuro[3,4-f]quinazolin-6-yl)-7-fluorobenzo[b]thiophene-3-carbonitrile

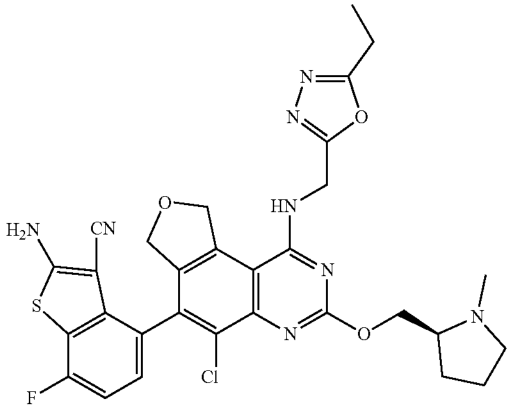 [SMILES: CCc1nnc(CNc2nc(OC[C@@H]3CCCN3C)nc3c(Cl)c(-c4ccc(F)c5sc(N)c(C#N)c45)c4c(c23)COC4)o1]

To a solution of tert-butyl (4-(5-chloro-1-(((5-ethyl-1,3,4-oxadiazol-2-yl)methyl)amino)-3-(((S)-1-methylpyrrolidin-2-yl)methoxy)-7,9-dihydrofuro[3,4-f]quinazolin-6-yl)-3-cyano-7-fluorobenzo[b]thiophen-2-yl)carbamate (0.090 g, 0.12 mmol) in DCM (2 mL) was added TFA (1 mL). The mixture was stirred at room temperature. After 1 h, the mixture was concentrated under reduced pressure and the residue was purified by reversed phase purification, eluting with 80% ACN in (5 mM ammonium acetate in 95:5 water:MeOH), to give the title compound (0.008 g, 20%) after lyophilization as a white solid. MS (ES) m/z=635 (M+1).

The following compounds in Table 17 were prepared in similar manner as described in Example 25. Various methods were used to purify the compounds, which would be apparent to one skilled in the art.

TABLE 17

| Preparation | Chemical Name | Structure | MS (ES) m/z (M + 1) |
|---|---|---|---|
| 26 | 4-(3-(((R)-1,4-Dioxan-2-yl)methoxy)-5-chloro-1-(((4,5,6,7-tetrahydrobenzo[d]isoxazol-3-yl)methyl)amino)-7,9-dihydrofuro[3,4-f]quinazolin-6-yl)-2-amino-7-fluorobenzo[b]thiophene-3-carbonitrile | 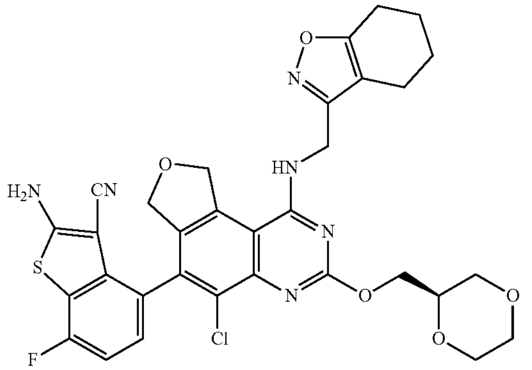 [SMILES: N#Cc1c(N)sc2c(F)ccc(-c3c4c(c5c(NCc6noc7c6CCCC7)nc(OC[C@H]6COCCO6)nc5c3Cl)COC4)c12] | 663 |
| 27 | 2-Amino-4-(5-chloro-3-(((R)-4-methylmorpholin-2-yl)methoxy)-1-(((4,5,6,7-tetrahydrobenzo[d]isoxazol-3-yl)methyl)amino)-7,9-dihydrofuro[3,4-f]quinazolin-6-yl)-7-fluorobenzo[b]thiophene-3-carbonitrile | 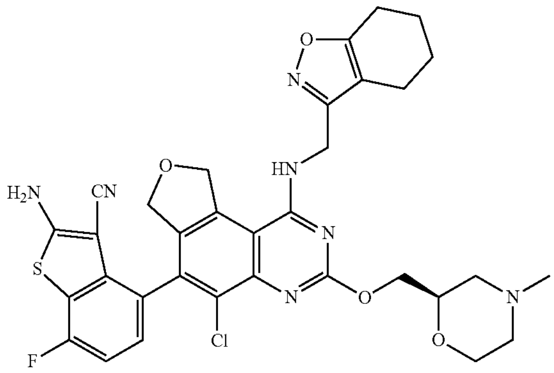 [SMILES: CN1CCO[C@@H](COc2nc(NCc3noc4c3CCCC4)c3c4c(c(-c5ccc(F)c6sc(N)c(C#N)c56)c(Cl)c3n2)COC4)C1] | 676 |

TABLE 17-continued

| Preparation | Chemical Name | Structure | MS (ES) m/z (M + 1) |
|---|---|---|---|
| 28 | 2-Amino-4-(5-chloro-3-(((2R,7aS)-2-fluorotetrahydro-1H-pyrrolizin-7a(5H)-yl)methoxy)-1-(((4,5,6,7-tetrahydrobenzo[d]isoxazol-3-yl)methyl)amino)-7,9-dihydrofuro[3,4-f]quinazolin-6-yl)-7-fluorobenzo[b]thiophene-3-carbonitrile | 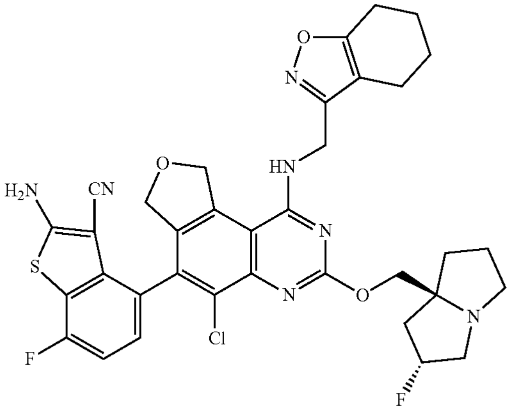 [SMILES: N#Cc1c(N)sc2c(F)ccc(-c3c4c(c5c(NCc6noc7c6CCCC7)nc(OC[C@@]67CCCN6C[C@H](F)C7)nc5c3Cl)COC4)c12] | 704 |
| 29 | 2-Amino-4-(5-chloro-1-((1-isopropyl-1H-1,2,3-triazol-4-yl)methoxy)-3-(((S)-1-methylpyrrolidin-2-yl)methoxy)-7,9-dihydrofuro[3,4-f]quinazolin-6-yl)-7-fluorobenzo[b]thiophene-3-carbonitrile | 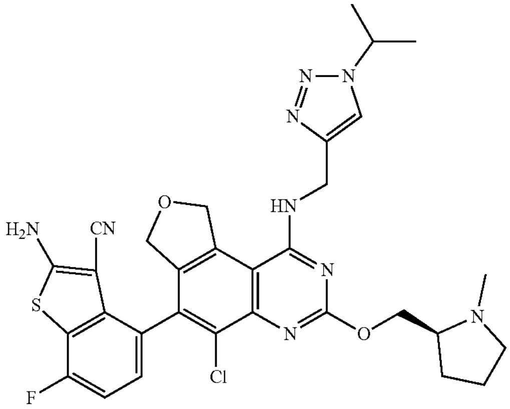 [SMILES: CC(C)n1cc(CNc2nc(OC[C@@H]3CCCN3C)nc3c(Cl)c(-c4ccc(F)c5sc(N)c(C#N)c45)c4c(c23)COC4)nn1] | 649 |
| 1A [1] | 2-Amino-4-(5-chloro-3-(((2R,7aS)-2-fluorotetrahydro-1H-pyrrolizin-7a(5H)-yl)methoxy)-1-((pyridazin-4-ylmethyl)amino)-7,9-dihydrofuro[3,4-f]quinazolin-6-yl)-7-fluorobenzo[b]thiophene-3-carbonitrile, Atropisomer 1 | 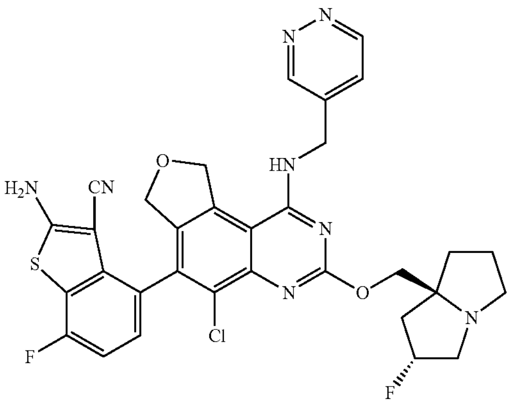 [SMILES: N#Cc1c(N)sc2c(F)ccc(-c3c4c(c5c(NCc6ccnnc6)nc(OC[C@@]67CCCN6C[C@H](F)C7)nc5c3Cl)COC4)c12] | 661 |

TABLE 17-continued

| Preparation | Chemical Name | Structure | MS (ES) m/z (M + 1) |
|---|---|---|---|
| 2A [1] | 2-Amino-4-(5-chloro-3-(((2R,7aS)-2-fluorotetrahydro-1H-pyrrolizin-7a(5H)-yl)methoxy)-1-((pyridazin-4-ylmethyl)amino)-7,9-dihydrofuro[3,4-f]quinazolin-6-yl)-7-fluorobenzo[b]thiophene-3-carbonitrile, Atropisomer 2 | 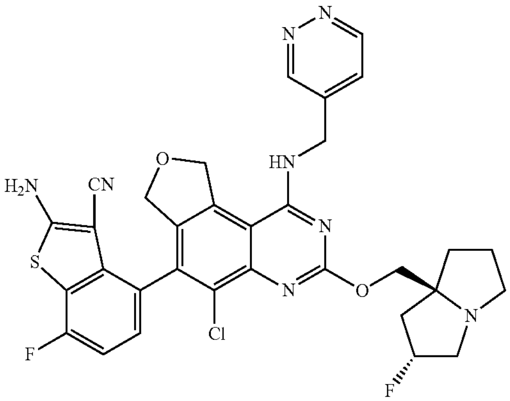 [SMILES: N#Cc1c(N)sc2c(F)ccc(-c3c4c(c5c(NCc6ccnnc6)nc(OC[C@@]67CCCN6C[C@H](F)C7)nc5c3Cl)COC4)c12] | 661 |
| 3A [2] | 2-Amino-4-(5-chloro-3-(((2R,7aS)-2-fluorotetrahydro-1H-pyrrolizin-7a(5H)-yl)methoxy)-1-(((3-methyl-1,2,4-oxadiazol-5-yl)methyl)amino)-7,9-dihydrofuro[3,4-f]quinazolin-6-yl)-7-fluorobenzo[b]thiophene-3-carbonitrile, Atropisomer 1 | 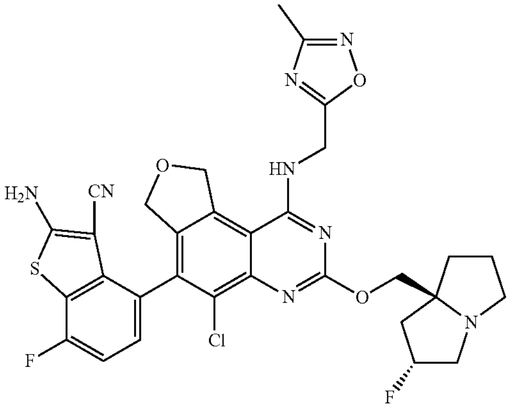 [SMILES: Cc1noc(CNc2nc(OC[C@@]34CCCN3C[C@H](F)C4)nc3c(Cl)c(-c4ccc(F)c5sc(N)c(C#N)c45)c4c(c23)COC4)n1] | 665 |
| 4A [2] | 2-Amino-4-(5-chloro-3-(((2R, 7aS)-2-fluorotetrahydro-1H-pyrrolizin-7a(5H)-yl)methoxy)-1-(((3-methyl-1,2,4-oxadiazol-5-yl)methyl)amino)-7,9-dihydrofuro[3,4-f]quinazolin-6-yl)-7-fluorobenzo[b]thiophene-3-carbonitrile, Atropisomer 2 | 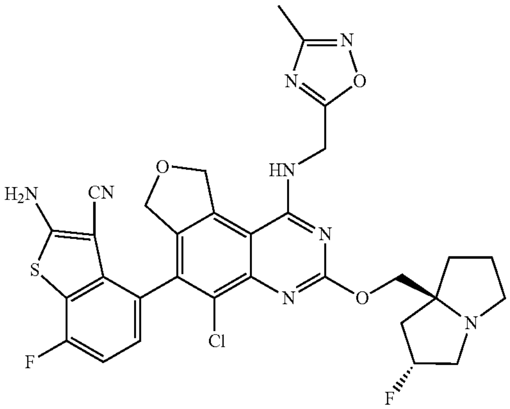 [SMILES: Cc1noc(CNc2nc(OC[C@@]34CCCN3C[C@H](F)C4)nc3c(Cl)c(-c4ccc(F)c5sc(N)c(C#N)c45)c4c(c23)COC4)n1] | 665 |

TABLE 17-continued

| Preparation | Chemical Name | Structure | MS (ES) m/z (M + 1) |
|---|---|---|---|
| 5A [3] | 2-Amino-4-(5-chloro-3-(((2R,7aS)-2-fluorotetrahydro-1H-pyrrolizin-7a(5H)-yl)methoxy)-1-((pyridazin-3-ylmethyl)amino)-7,9-dihydrofuro[3,4-f]quinazolin-6-yl)-7-fluorobenzo[b]thiophene-3-carbonitrile, Atropisomer 1 | 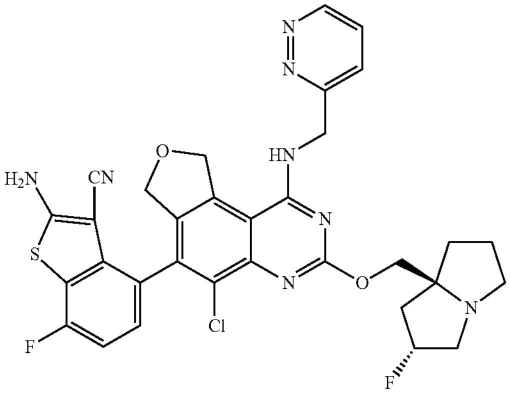 [SMILES: N#Cc1c(N)sc2c(F)ccc(-c3c4c(c5c(NCc6cccnn6)nc(OC[C@@]67CCCN6C[C@H](F)C7)nc5c3Cl)COC4)c12] | 661 |
| 6A [3] | 2-Amino-4-(5-chloro-3-(((2R, 7aS)-2-fluorotetrahydro-1H-pyrrolizin-7a(5H)-yl)methoxy)-1-((pyridazin-3-ylmethyl)amino)-7,9-dihydrofuro[3,4-f]quinazolin-6-yl)-7-fluorobenzo[b]thiophene-3-carbonitrile, Atropisomer 2 | 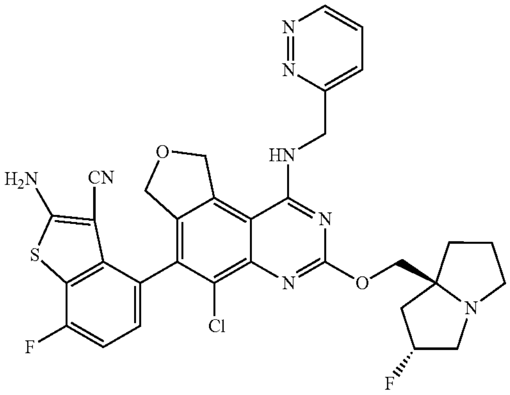 [SMILES: N#Cc1c(N)sc2c(F)ccc(-c3c4c(c5c(NCc6cccnn6)nc(OC[C@@]67CCCN6C[C@H](F)C7)nc5c3Cl)COC4)c12] | 661 |
| 7A [4] | 2-Amino-4-(5-chloro-3-(((2R,7aS)-2-fluorotetrahydro-1H-pyrrolizin-7a(5H)-yl)methoxy)-1-(((5-methyl-1,2,4-oxadiazol-3-yl)methyl)amino)-7,9-dihydrofuro[3,4-f]quinazolin-6-yl)-7-fluorobenzo[b]thiophene-3-carbonitrile, Atropisomer 1 | 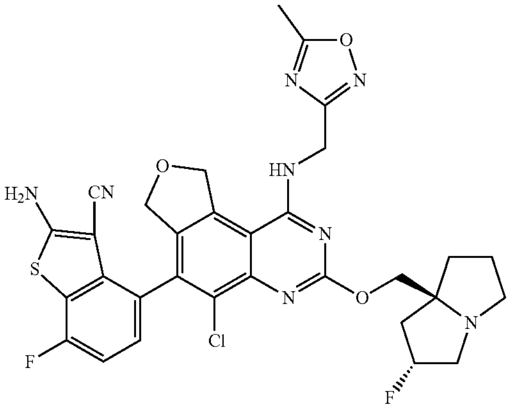 [SMILES: Cc1nc(CNc2nc(OC[C@@]34CCCN3C[C@H](F)C4)nc3c(Cl)c(-c4ccc(F)c5sc(N)c(C#N)c45)c4c(c23)COC4)no1] | 665 |

TABLE 17-continued

| Preparation | Chemical Name | Structure | MS (ES) m/z (M + 1) |
| --- | --- | --- | --- |
| 8A [4] | 2-Amino-4-(5-chloro-3-(((2R,7aS)-2-fluorotetrahydro-1H-pyrrolizin-7a(5H)-yl)methoxy)-1-(((5-methyl-1,2,4-oxadiazol-3-yl)methyl)amino)-7,9-dihydrofuro[3,4-f]quinazolin-6-yl)-7-fluorobenzo[b]thiophene-3-carbonitrile, Atropisomer 2 | 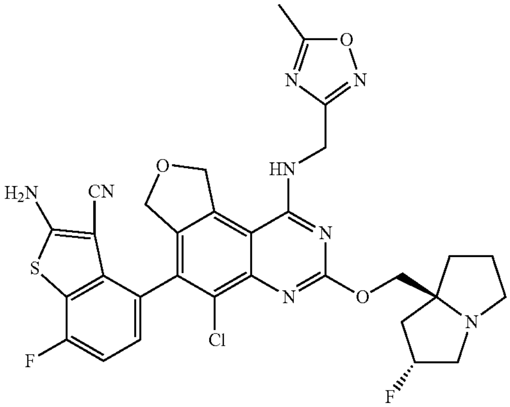 [SMILES: Cc1nc(CNc2nc(OC[C@@]34CCCN3C[C@H](F)C4)nc3c(Cl)c(-c4ccc(F)c5sc(N)c(C#N)c45)c4c(c23)COC4)no1] | 665 |
| 9A [5] | 2-Amino-4-(5-chloro-3-(((2R,7aS)-2-fluorotetrahydro-1H-pyrrolizin-7a(5H)-yl)methoxy)-1-(((1-methyl-1H-1,2,3-triazol-4-yl)methyl)amino)-7,9-dihydrofuro[3,4-f]quinazolin-6-yl)-7-fluorobenzo[b]thiophene-3-carbonitrile, Atropisomer 1 | 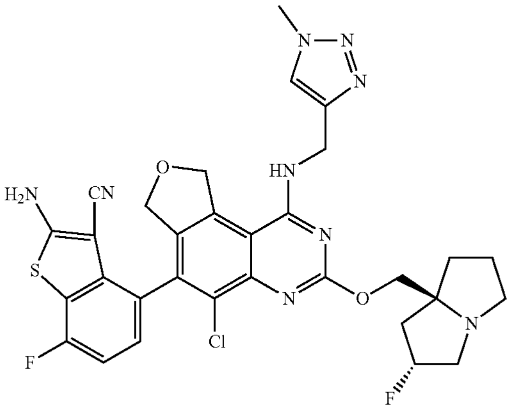 [SMILES: Cn1cc(CNc2nc(OC[C@@]34CCCN3C[C@H](F)C4)nc3c(Cl)c(-c4ccc(F)c5sc(N)c(C#N)c45)c4c(c23)COC4)nn1] | 664 |
| 10A [5] | 2-Amino-4-(5-chloro-3-(((2R, 7aS)-2-fluorotetrahydro-1H-pyrrolizin-7a(5H)-yl)methoxy)-1-(((1-methyl-1H-1,2,3-triazol-4-yl)methyl)amino)-7,9-dihydrofuro[3,4-f]quinazolin-6-yl)-7-fluorobenzo[b]thiophene-3-carbonitrile, Atropisomer 2 | 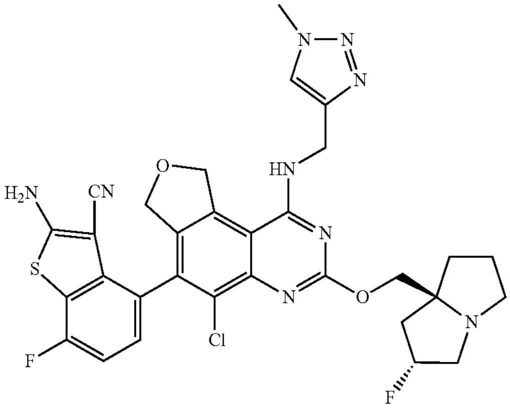 [SMILES: Cn1cc(CNc2nc(OC[C@@]34CCCN3C[C@H](F)C4)nc3c(Cl)c(-c4ccc(F)c5sc(N)c(C#N)c45)c4c(c23)COC4)nn1] | 664 |

TABLE 17-continued

| Preparation | Chemical Name | Structure | MS (ES) m/z (M + 1) |
|---|---|---|---|
| 11A | 4-(1-(((1H-Pyrazol-5-yl)methyl)amino)-5-chloro-3-(((2R,7aS)-2-fluorotetrahydro-1H-pyrrolizin-7a(5H)-yl)methoxy)-7,9-dihydrofuro[3,4-f]quinazolin-6-yl)-2-amino-7-fluorobenzo[b]thiophene-3-carbonitrile | 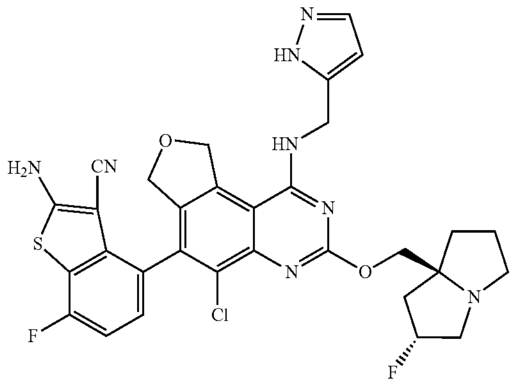 [SMILES: N#Cc1c(N)sc2c(F)ccc(-c3c4c(c5c(NCc6ccn[nH]6)nc(OC[C@@]67CCCN6C[C@H](F)C7)nc5c3Cl)COC4)c12] | 649 |
| 12A [6] | 4-(1-(((1H-Pyrazol-5-yl)methyl)amino)-5-chloro-3-(((2R,7aS)-2-fluorotetrahydro-1H-pyrrolizin-7a(5H)-yl)methoxy)-7,9-dihydrofuro[3,4-f]quinazolin-6-yl)-2-amino-7-fluorobenzo[b]thiophene-3-carbonitrile, Atropisomer 1 | 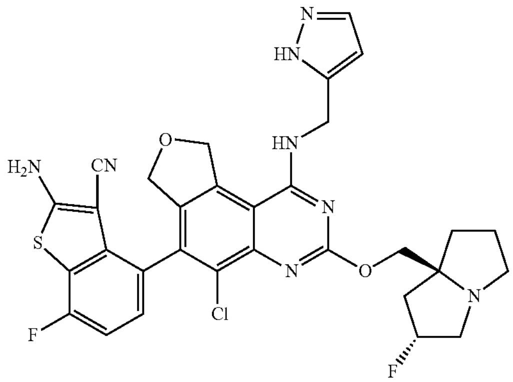 [SMILES: N#Cc1c(N)sc2c(F)ccc(-c3c4c(c5c(NCc6ccn[nH]6)nc(OC[C@@]67CCCN6C[C@H](F)C7)nc5c3Cl)COC4)c12] | 649 |
| 13A [6] | 4-(1-(((1H-Pyrazol-5-yl)methyl)amino)-5-chloro-3-(((2R,7aS)-2-fluorotetrahydro-1H-pyrrolizin-7a(5H)-yl)methoxy)-7,9-dihydrofuro[3,4-f]quinazolin-6-yl)-2-amino-7-fluorobenzo[b]thiophene-3-carbonitrile, Atropisomer 2 | 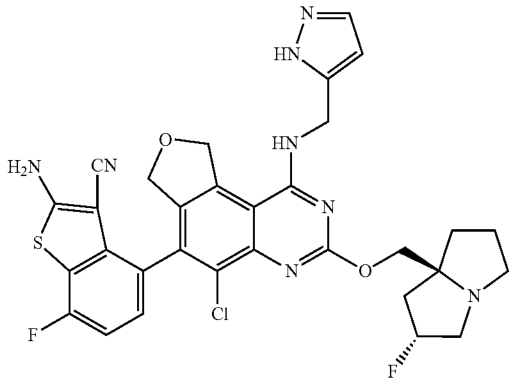 [SMILES: N#Cc1c(N)sc2c(F)ccc(-c3c4c(c5c(NCc6ccn[nH]6)nc(OC[C@@]67CCCN6C[C@H](F)C7)nc5c3Cl)COC4)c12] | 649 |

TABLE 17-continued

| Preparation | Chemical Name | Structure | MS (ES) m/z (M + 1) |
|---|---|---|---|
| 14A | 2-Amino-4-(5-chloro-3-(((2R, 7aS)-2-fluorotetrahydro-1H-pyrrolizin-7a(5H)-yl)methoxy)-1-(((3-methyl-1H-pyrazol-5-yl)methyl)amino)-7,9-dihydrofuro[3,4-f]quinazolin-6-yl)-7-fluorobenzo[b]thiophene-3-carbonitrile | 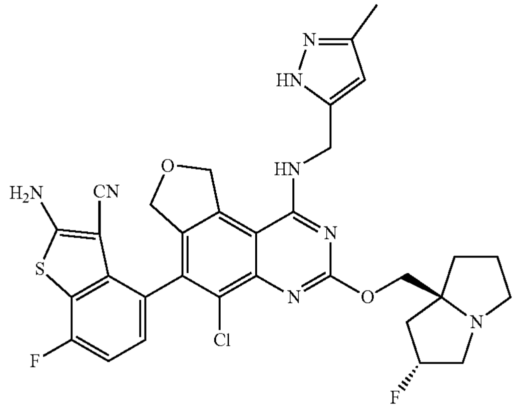 [SMILES: Cc1cc(CNc2nc(OC[C@@]34CCCN3C[C@H](F)C4)nc3c(Cl)c(-c4ccc(F)c5sc(N)c(C#N)c45)c4c(c23)COC4)[nH]n1] | 663 |
| 15A [7] | 2-Amino-4-(5-chloro-1-(((5-(difluoromethyl)-4H-1,2,4-triazol-3-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile, Atropisomer 1 | 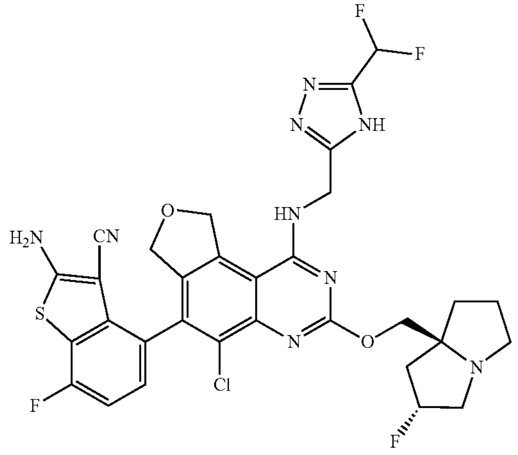 [SMILES: N#Cc1c(N)sc2c(F)ccc(-c3c4c(c5c(NCc6nnc(C(F)F)[nH]6)nc(OC[C@@]67CCCN6C[C@H](F)C7)nc5c3Cl)COC4)c12] | 700 |
| 16A [7] | 2-Amino-4-(5-chloro-1-(((5-(difluoromethyl)-4H-1,2,4-triazol-3-yl)methyl)amino)-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile, Atropisomer 2 | 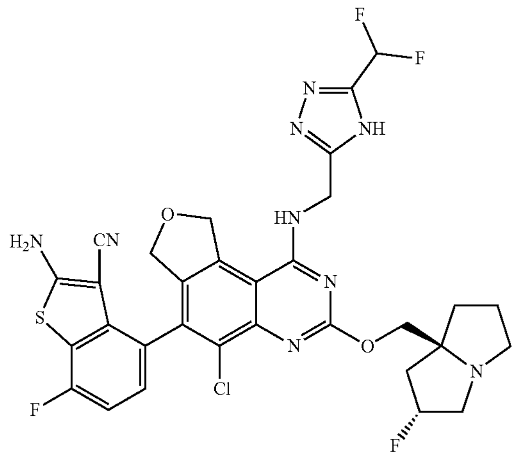 [SMILES: N#Cc1c(N)sc2c(F)ccc(-c3c4c(c5c(NCc6nnc(C(F)F)[nH]6)nc(OC[C@@]67CCCN6C[C@H](F)C7)nc5c3Cl)COC4)c12] | 700 |

TABLE 17-continued

| Preparation | Chemical Name | Structure | MS (ES) m/z (M + 1) |
|---|---|---|---|
| 17A [8] | 4-(1-(((1H-Pyrazol-4-yl)methyl)amino)-5-chloro-3-(((2R,7aS)-2-fluorotetrahydro-1H-pyrrolizin-7a(5H)-yl)methoxy)-7,9-dihydrofuro[3,4-f]quinazolin-6-yl)-2-amino-7-fluorobenzo[b]thiophene-3-carbonitrile | 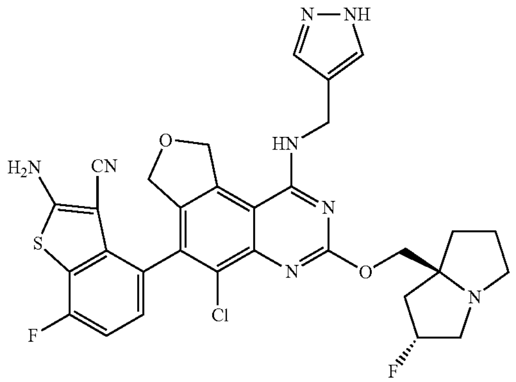 [SMILES: N#Cc1c(N)sc2c(F)ccc(-c3c4c(c5c(NCc6cn[nH]c6)nc(OC[C@@]67CCCN6C[C@H](F)C7)nc5c3Cl)COC4)c12] | 649 |
| 18A [9] | 2-Amino-4-(5-chloro-3-(((2R,7aS)-2-fluorotetrahydro-1H-pyrrolizin-7a(5H)-yl)methoxy)-1-(((R)-2-oxopiperidin-3-yl)amino)-7,9-dihydrofuro[3,4-f]quinazolin-6-yl)-7-fluorobenzo[b]thiophene-3-carbonitrile, Atropisomer 1 | 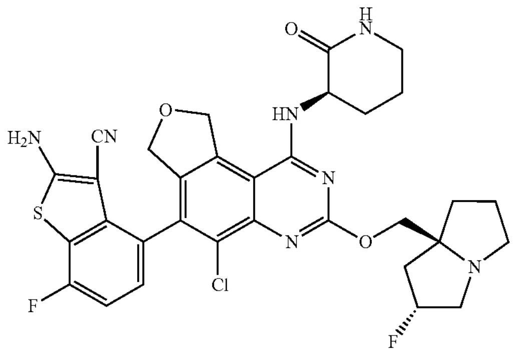 [SMILES: N#Cc1c(N)sc2c(F)ccc(-c3c4c(c5c(N[C@@H]6CCCNC6=O)nc(OC[C@@]67CCCN6C[C@H](F)C7)nc5c3Cl)COC4)c12] | 666 |
| 19A [9] | 2-Amino-4-(5-chloro-3-(((2R,7aS)-2-fluorotetrahydro-1H-pyrrolizin-7a(5H)-yl)methoxy)-1-(((R)-2-oxopiperidin-3-yl)amino)-7,9-dihydrofuro[3,4-f]quinazolin-6-yl)-7-fluorobenzo[b]thiophene-3-carbonitrile, Atropisomer 2 | 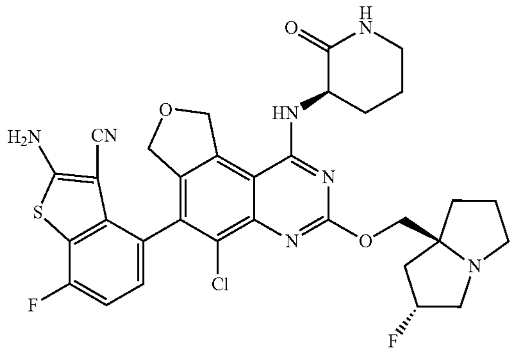 [SMILES: N#Cc1c(N)sc2c(F)ccc(-c3c4c(c5c(N[C@@H]6CCCNC6=O)nc(OC[C@@]67CCCN6C[C@H](F)C7)nc5c3Cl)COC4)c12] | 666 |
| 20A [10] | 2-Amino-4-(5-chloro-3-(((2R,7aS)-2-fluorotetrahydro-1H-pyrrolizin-7a(5H)-yl)methoxy)-1-(((S)-2-oxopyrrolidin-3-yl)amino)-7,9-dihydrofuro[3,4-f]quinazolin-6-yl)-7-fluorobenzo[b]thiophene-3-carbonitrile, Atropisomer 1 | 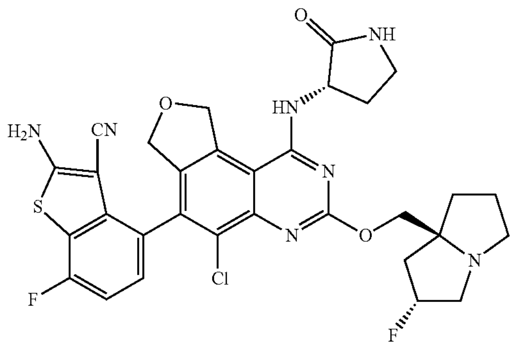 [SMILES: N#Cc1c(N)sc2c(F)ccc(-c3c4c(c5c(N[C@H]6CCNC6=O)nc(OC[C@@]67CCCN6C[C@H](F)C7)nc5c3Cl)COC4)c12] | 652 |

TABLE 17-continued

| Preparation | Chemical Name | Structure | MS (ES) m/z (M + 1) |
|---|---|---|---|
| 21A [10] | 2-Amino-4-(5-chloro-3-(((2R,7aS)-2-fluorotetrahydro-1H-pyrrolizin-7a(5H)-yl)methoxy)-1-(((S)-2-oxopyrrolidin-3-yl)amino)-7,9-dihydrofuro[3,4-f]quinazolin-6-yl)-7-fluorobenzo[b]thiophene-3-carbonitrile, Atropisomer 2 | 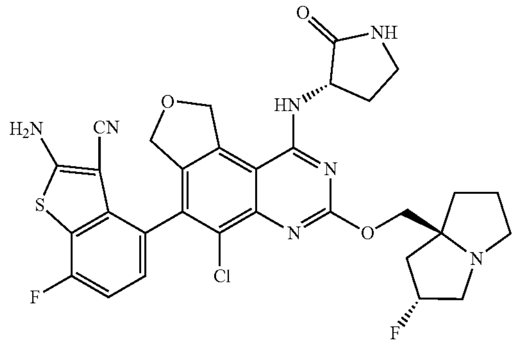 [SMILES: N#Cc1c(N)sc2c(F)ccc(-c3c4c(c5c(N[C@H]6CCNC6=O)nc(OC[C@@]67CCCN6C[C@H](F)C7)nc5c3Cl)COC4)c12] | 652 |
| 22A [11] | 2-Amino-4-(5-chloro-3-(((2R,7aS)-2-fluorotetrahydro-1H-pyrrolizin-7a(5H)-yl)methoxy)-1-(((S)-2-oxopiperidin-3-yl)amino)-7,9-dihydrofuro[3,4-f]quinazolin-6-yl)-7-fluorobenzo[b]thiophene-3-carbonitrile, Atropisomer 1 | 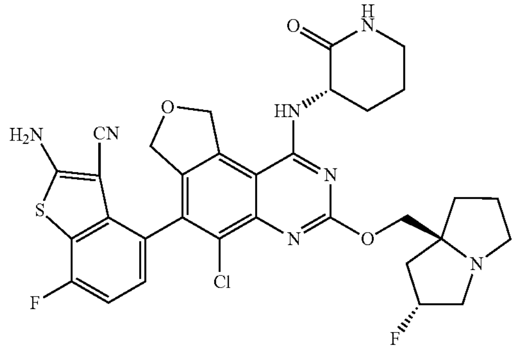 [SMILES: N#Cc1c(N)sc2c(F)ccc(-c3c4c(c5c(N[C@H]6CCCNC6=O)nc(OC[C@@]67CCCN6C[C@H](F)C7)nc5c3Cl)COC4)c12] | 666 |
| 23A [11] | 2-Amino-4-(5-chloro-3-(((2R,7aS)-2-fluorotetrahydro-1H-pyrrolizin-7a(5H)-yl)methoxy)-1-(((S)-2-oxopiperidin-3-yl)amino)-7,9-dihydrofuro[3,4-f]quinazolin-6-yl)-7-fluorobenzo[b]thiophene-3-carbonitrile, Atropisomer 2 | 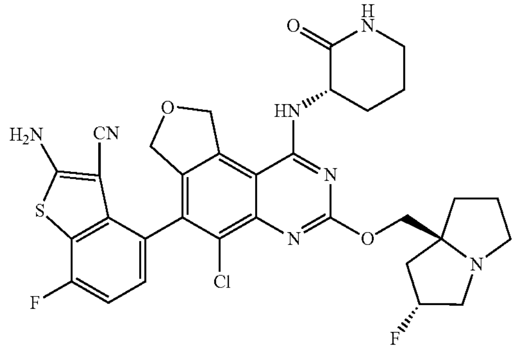 [SMILES: N#Cc1c(N)sc2c(F)ccc(-c3c4c(c5c(N[C@H]6CCCNC6=O)nc(OC[C@@]67CCCN6C[C@H](F)C7)nc5c3Cl)COC4)c12] | 666 |
| 24A [12] | 2-Amino-4-(5-chloro-3-(((2R,7aS)-2-fluorotetrahydro-1H-pyrrolizin-7a(5H)-yl)methoxy)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile, Atropisomer 1 | 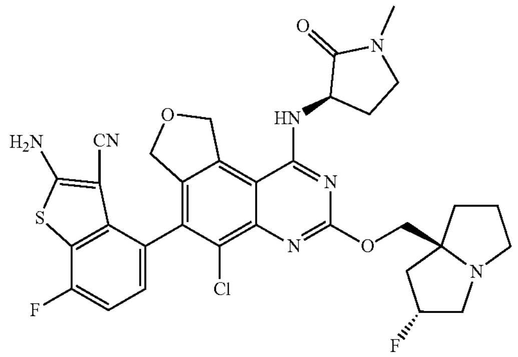 [SMILES: CN1CC[C@@H](Nc2nc(OC[C@@]34CCCN3C[C@H](F)C4)nc3c(Cl)c(-c4ccc(F)c5sc(N)c(C#N)c45)c4c(c23)COC4)C1=O] | 666 |

TABLE 17-continued

| Preparation | Chemical Name | Structure | MS (ES) m/z (M + 1) |
| --- | --- | --- | --- |
| 25A [12] | 2-Amino-4-(5-chloro-3-(((2R,7aS)-2-fluorotetrahydro-1H-pyrrolizin-7a(5H)-yl)methoxy)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile, Atropisomer 2 | 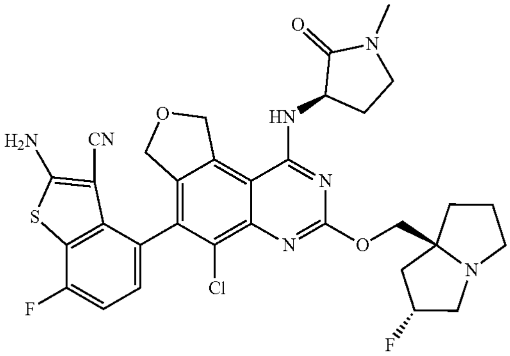 [SMILES: CN1CC[C@@H](Nc2nc(OC[C@@]34CCCN3C[C@H](F)C4)nc3c(Cl)c(-c4ccc(F)c5sc(N)c(C#N)c45)c4c(c23)COC4)C1=O] | 666 |
| 26A [13] | 2-Amino-4-(5-chloro-3-(((2R,7aS)-2-fluorotetrahydro-1H-pyrrolizin-7a(5H)-yl)methoxy)-1-(((R)-2-oxopyrrolidin-3-yl)amino)-7,9-dihydrofuro[3,4-f]quinazolin-6-yl)-7-fluorobenzo[b]thiophene-3-carbonitrile, Atropisomer 1 | 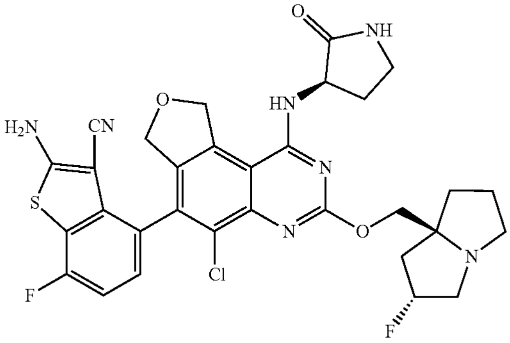 [SMILES: N#Cc1c(N)sc2c(F)ccc(-c3c4c(c5c(N[C@@H]6CCNC6=O)nc(OC[C@@]67CCCN6C[C@H](F)C7)nc5c3Cl)COC4)c12] | 652 |
| 27A [13] | 2-Amino-4-(5-chloro-3-(((2R,7aS)-2-fluorotetrahydro-1H-pyrrolizin-7a(5H)-yl)methoxy)-1-(((R)-2-oxopyrrolidin-3-yl)amino)-7,9-dihydrofuro[3,4-f]quinazolin-6-yl)-7-fluorobenzo[b]thiophene-3-carbonitrile, Atropisomer 2 | 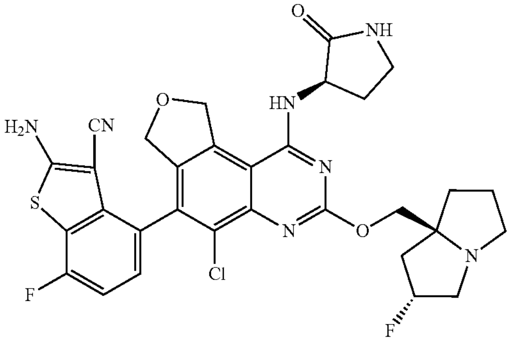 [SMILES: N#Cc1c(N)sc2c(F)ccc(-c3c4c(c5c(N[C@@H]6CCNC6=O)nc(OC[C@@]67CCCN6C[C@H](F)C7)nc5c3Cl)COC4)c12] | 652 |
| 28A [14] | 2-Amino-4-(5-chloro-3-(((2R,7aS)-2-fluorotetrahydro-1H-pyrrolizin-7a(5H)-yl)methoxy)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Atropisomer 1 | 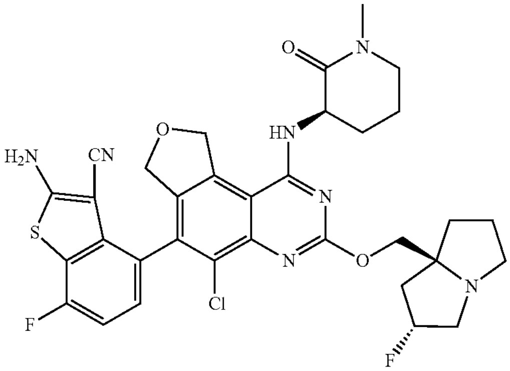 [SMILES: CN1CCC[C@@H](Nc2nc(OC[C@@]34CCCN3C[C@H](F)C4)nc3c(Cl)c(-c4ccc(F)c5sc(N)c(C#N)c45)c4c(c23)COC4)C1=O] | 680 |

TABLE 17-continued

| Preparation | Chemical Name | Structure | MS (ES) m/z (M + 1) |
|---|---|---|---|
| 29A [14] | 2-Amino-4-(5-chloro-3-(((2R,7aS)-2-fluorotetrahydro-1H-pyrrolizin-7a(5H)-yl)methoxy)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Atropisomer 2 | 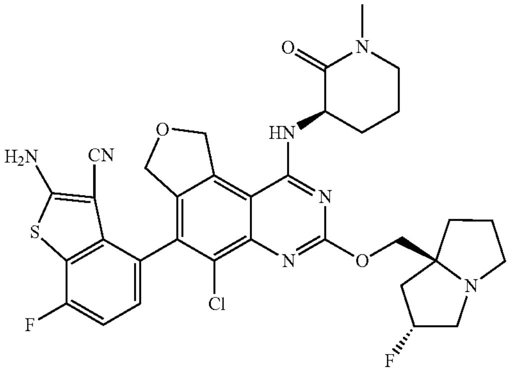 [SMILES: CN1CCC[C@@H](Nc2nc(OC[C@@]34CCCN3C[C@H](F)C4)nc3c(Cl)c(-c4ccc(F)c5sc(N)c(C#N)c45)c4c(c23)COC4)C1=O] | 680 |
| 30A [15] | 2-Amino-4-(5-chloro-1-(((R)-1-methyl-2-oxopyrrolidin-3-yl)amino)-3-(((R)-4-methylmorpholin-2-yl)methoxy)-7,9-dihydrofuro[3,4-f]quinazolin-6-yl)-7-fluorobenzo[b]thiophene-3-carbonitrile, Atropisomer 1 | 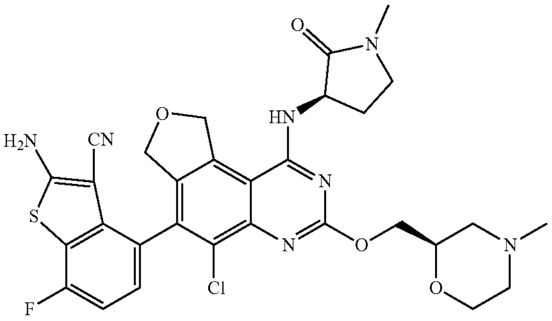 [SMILES: CN1CCO[C@@H](COc2nc(N[C@@H]3CCN(C)C3=O)c3c4c(c(-c5ccc(F)c6sc(N)c(C#N)c56)c(Cl)c3n2)COC4)C1] | 638 |
| 31A [15] | 2-Amino-4-(5-chloro-1-(((R)-1-methyl-2-oxopyrrolidin-3-yl)amino)-3-(((R)-4-methylmorpholin-2-yl)methoxy)-7,9-dihydrofuro[3,4-f]quinazolin-6-yl)-7-fluorobenzo[b]thiophene-3-carbonitrile, Atropisomer 2 | 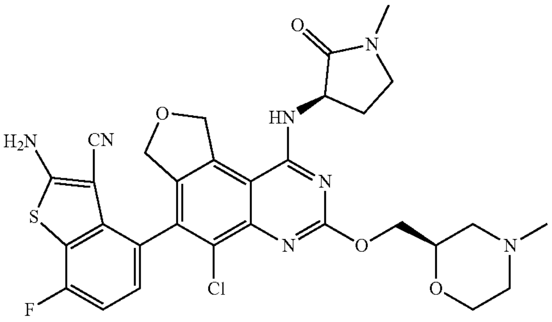 [SMILES: CN1CCO[C@@H](COc2nc(N[C@@H]3CCN(C)C3=O)c3c4c(c(-c5ccc(F)c6sc(N)c(C#N)c56)c(Cl)c3n2)COC4)C1] | 638 |
| 32A [16] | 2-Amino-4-(5-chloro-1-(((R)-1-methyl-2-oxopiperidin-3-yl)amino)-3-(((R)-4-methylmorpholin-2-yl)methoxy)-7,9-dihydrofuro[3,4-f]quinazolin-6-yl)-7-fluorobenzo[b]thiophene-3-carbonitrile, Atropisomer 1 | 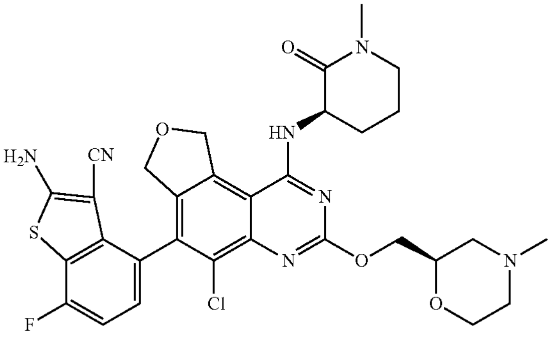 [SMILES: CN1CCO[C@@H](COc2nc(N[C@@H]3CCCN(C)C3=O)c3c4c(c(-c5ccc(F)c6sc(N)c(C#N)c56)c(Cl)c3n2)COC4)C1] | 652 |

TABLE 17-continued

| Preparation | Chemical Name | Structure | MS (ES) m/z (M + 1) |
|---|---|---|---|
| 33A [16] | 2-Amino-4-(5-chloro-1-(((R)-1-methyl-2-oxopiperidin-3-yl)amino)-3-(((R)-4-methylmorpholin-2-yl)methoxy)-7,9-dihydrofuro[3,4-f]quinazolin-6-yl)-7-fluorobenzo[b]thiophene-3-carbonitrile, Atropisomer 2 | 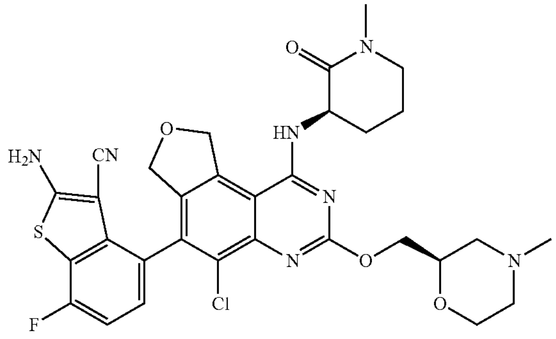 [SMILES: CN1CCO[C@@H](COc2nc(N[C@@H]3CCCN(C)C3=O)c3c4c(c(-c5ccc(F)c6sc(N)c(C#N)c56)c(Cl)c3n2)COC4)C1] | 652 |
| 34A | 2-Amino-4-(5-chloro-3-((S)-3-(dimethylamino)pyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 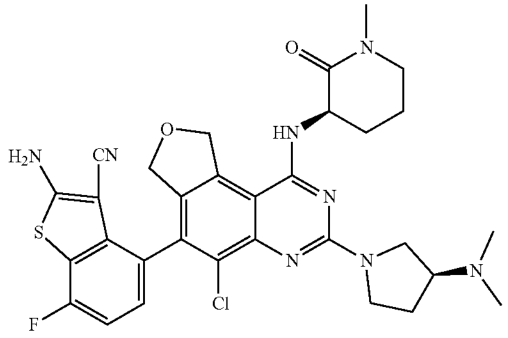 [SMILES: CN1CCC[C@@H](Nc2nc(N3CC[C@H](N(C)C)C3)nc3c(Cl)c(-c4ccc(F)c5sc(N)c(C#N)c45)c4c(c23)COC4)C1=O] | 635 |
| 35A [17] | 2-Amino-4-(5-chloro-3-(3-(dimethylamino)azetidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Atropisomer 1 | 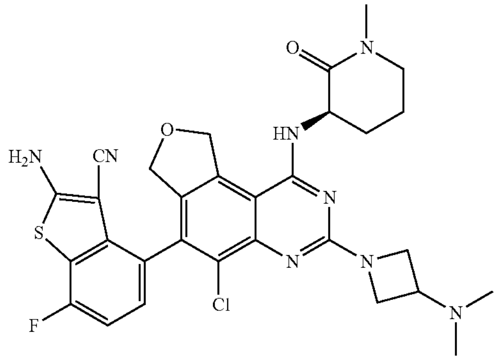 [SMILES: CN1CCC[C@@H](Nc2nc(N3CC(N(C)C)C3)nc3c(Cl)c(-c4ccc(F)c5sc(N)c(C#N)c45)c4c(c23)COC4)C1=O] | 621 |
| 36A [17] | 2-Amino-4-(5-chloro-3-(3-(dimethylamino)azetidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Atropisomer 2 | 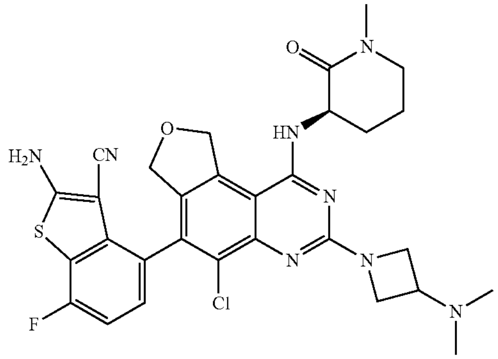 [SMILES: CN1CCC[C@@H](Nc2nc(N3CC(N(C)C)C3)nc3c(Cl)c(-c4ccc(F)c5sc(N)c(C#N)c45)c4c(c23)COC4)C1=O] | 621 |

TABLE 17-continued

| Preparation | Chemical Name | Structure | MS (ES) m/z (M + 1) |
|---|---|---|---|
| 37A [18] | 2-Amino-4-(5-chloro-3-((1-((dimethylamino)methyl)cyclopropyl)methoxy)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Atropisomer 1 | 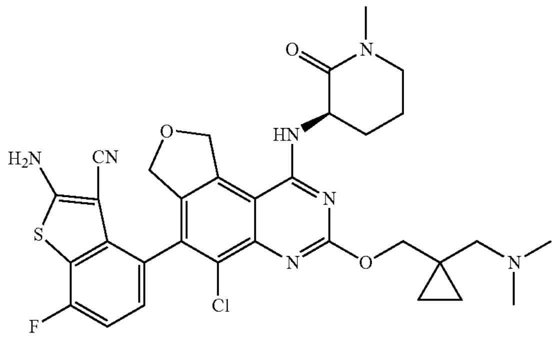 [SMILES: CN(C)CC1(COc2nc(N[C@@H]3CCCN(C)C3=O)c3c4c(c(-c5ccc(F)c6sc(N)c(C#N)c56)c(Cl)c3n2)COC4)CC1] | 650 |
| 38A [18] | 2-Amino-4-(5-chloro-3-(1-((dimethylamino)methyl)cyclopropyl)methoxy)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Atropisomer 2 | 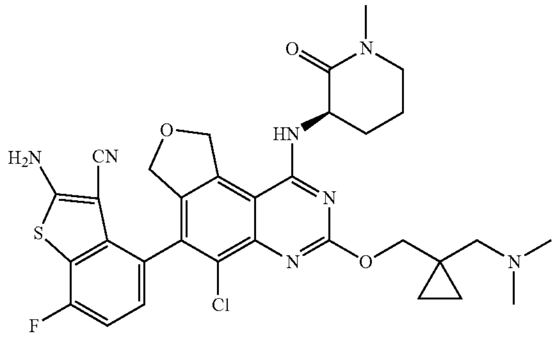 [SMILES: CN(C)CC1(COc2nc(N[C@@H]3CCCN(C)C3=O)c3c4c(c(-c5ccc(F)c6sc(N)c(C#N)c56)c(Cl)c3n2)COC4)CC1] | 650 |
| 39A [19] | 2-Amino-4-(5-chloro-3-((S)-3-(dimethylamino)pyrrolidin-1-yl)-1-(((5-methyl-1,2,4-oxadiazol-3-yl)methyl)amino)-7,9-dihydrofuro[3,4-f]quinazolin-6-yl)-7-fluorobenzo[b]thiophene-3-carbonitrile, Atropisomer 1 | 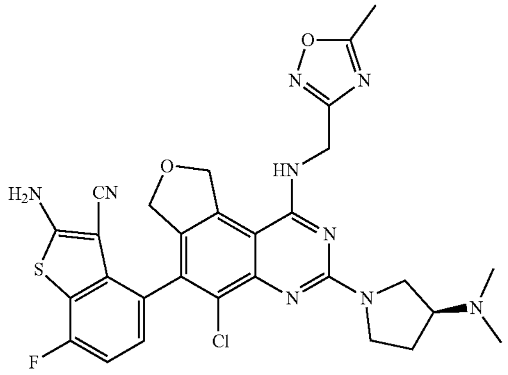 [SMILES: Cc1nc(CNc2nc(N3CC[C@H](N(C)C)C3)nc3c(Cl)c(-c4ccc(F)c5sc(N)c(C#N)c45)c4c(c23)COC4)no1] | 620 |
| 40A [19] | 2-Amino-4-(5-chloro-3-((S)-3-(dimethylamino)pyrrolidin-1-yl)-1-(((5-methyl-1,2,4-oxadiazol-3-yl)methyl)amino)-7,9-dihydrofuro[3,4-f]quinazolin-6-yl)-7-fluorobenzo[b]thiophene-3-carbonitrile, Atropisomer 2 | 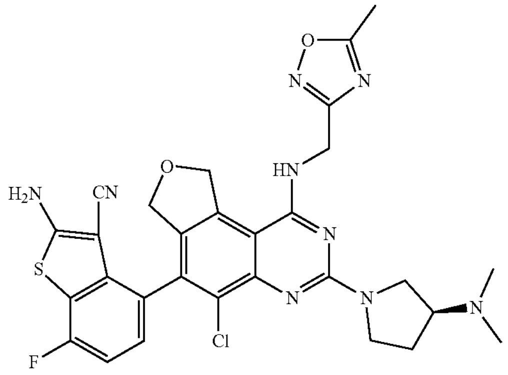 [SMILES: Cc1nc(CNc2nc(N3CC[C@H](N(C)C)C3)nc3c(Cl)c(-c4ccc(F)c5sc(N)c(C#N)c45)c4c(c23)COC4)no1] | 620 |

TABLE 17-continued

| Preparation | Chemical Name | Structure | MS (ES) m/z (M + 1) |
|---|---|---|---|
| 41A [20] | 2-Amino-4-(5-chloro-3-((S)-3-(dimethylamino)pyrrolidin-1-yl)-1-(((5-ethyl-1,3,4-oxadiazol-2-yl)methyl)amino)-7,9-dihydrofuro[3,4-f]quinazolin-6-yl)-7-fluorobenzo[b]thiophene-3-carbonitrile, Atropisomer 1 | 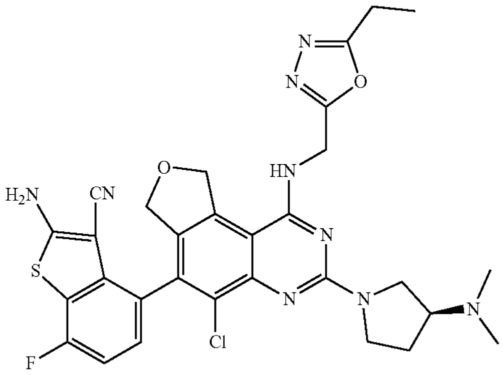 [SMILES: CCc1nnc(CNc2nc(N3CC[C@H](N(C)C)C3)nc3c(Cl)c(-c4ccc(F)c5sc(N)c(C#N)c45)c4c(c23)COC4)o1] | 634 |
| 42A [20] | 2-Amino-4-(5-chloro-3-((S)-3-(dimethylamino)pyrrolidin-1-yl)-1-(((5-ethyl-1,3,4-oxadiazol-2-yl)methyl)amino)-7,9-dihydrofuro[3,4-f]quinazolin-6-yl)-7-fluorobenzo[b]thiophene-3-carbonitrile, Atropisomer 2 | 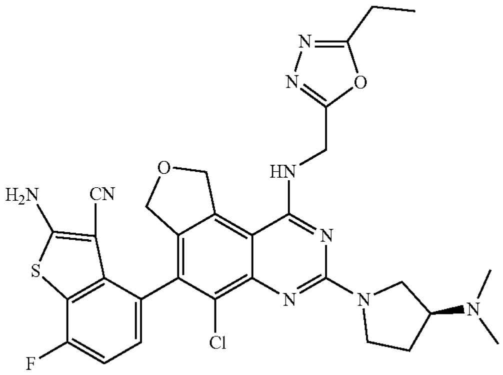 [SMILES: CCc1nnc(CNc2nc(N3CC[C@H](N(C)C)C3)nc3c(Cl)c(-c4ccc(F)c5sc(N)c(C#N)c45)c4c(c23)COC4)o1] | 634 |
| 43A [21] | 2-Amino-4-(5-chloro-3-(3-(dimethylamino)azetidin-1-yl)-1-(((5-ethyl-1,3,4-oxadiazol-2-yl)methyl)amino)-7,9-dihydrofuro[3,4-f]quinazolin-6-yl)-7-fluorobenzo[b]thiophene-3-carbonitrile, Atropisomer 1 | 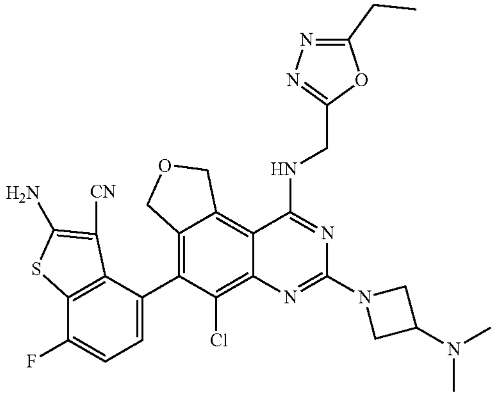 [SMILES: CCc1nnc(CNc2nc(N3CC(N(C)C)C3)nc3c(Cl)c(-c4ccc(F)c5sc(N)c(C#N)c45)c4c(c23)COC4)o1] | 620 |
| 44A [21] | 2-Amino-4-(5-chloro-3-(3-(dimethylamino)azetidin-1-yl)-1-(((5-ethyl-1,3,4-oxadiazol-2-yl)methyl)amino)-7,9-dihydrofuro[3,4-f]quinazolin-6-yl)-7-fluorobenzo[b]thiophene-3-carbonitrile, Atropisomer 2 | 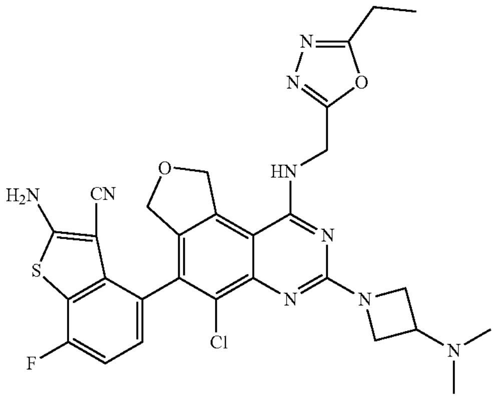 [SMILES: CCc1nnc(CNc2nc(N3CC(N(C)C)C3)nc3c(Cl)c(-c4ccc(F)c5sc(N)c(C#N)c45)c4c(c23)COC4)o1] | 620 |

TABLE 17-continued

| Preparation | Chemical Name | Structure | MS (ES) m/z (M + 1) |
|---|---|---|---|
| 45A [22] | 2-Amino-4-(3-(3-(dimethylamino)azetidin-1-yl)-5-fluoro-1-(((R)-1-methyl-2-oxopyrrolidin-3-yl)amino)-7,9-dihydrofuro[3,4-f]quinazolin-6-yl)-5-fluorobenzo[b]thiophene-3-carbonitrile, Atropisomer 1 2,2,2-trifluoroacetic acid | 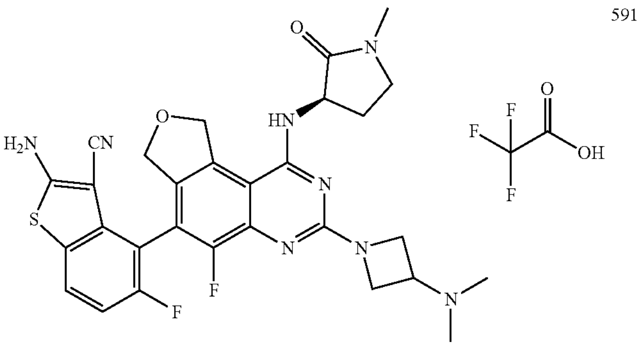 | 591 |
| 46A [22] | 2-Amino-4-(3-(3-(dimethylamino)azetidin-1-yl)-5-fluoro-1-(((R)-1-methyl-2-oxopyrrolidin-3-yl)amino)-7,9-dihydrofuro[3,4-f]quinazolin-6-yl)-5-fluorobenzo[b]thiophene-3-carbonitrile, Atropisomer 2 2,2,2-trifluoroacetic acid | 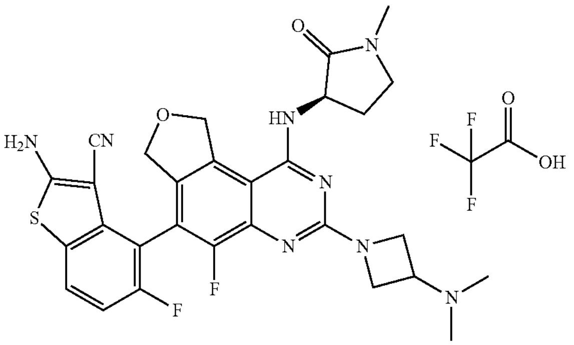 [SMILES: CN1CC[C@@H](Nc2nc(N3CC(N(C)C)C3)nc3c(F)c(-c4c(F)ccc5sc(N)c(C#N)c45)c4c(c23)COC4)C1=O ; O=C(O)C(F)(F)F] | 591 |
| 47A [23] | 2-Amino-4-(3-((S)-3-(dimethylamino)pyrrolidin-1-yl)-5-fluoro-1-(((R)-1-methyl-2-oxopyrrolidin-3-yl)amino)-7,9-dihydrofuro[3,4-f]quinazolin-6-yl)-5-fluorobenzo[b]thiophene-3-carbonitrile, Atropisomer 1 2,2,2-trifluoroacetic acid | 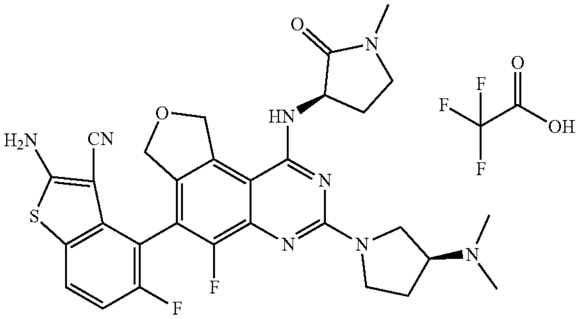 | 605 |
| 48A [23] | 2-Amino-4-(3-((S)-3-(dimethylamino)pyrrolidin-1-yl)-5-fluoro-1-(((R)-1-methyl-2-oxopyrrolidin-3-yl)amino)-7,9-dihydrofuro[3,4-f]quinazolin-6-yl)-5-fluorobenzo[b]thiophene-3-carbonitrile, Atropisomer 2 2,2,2-trifluoroacetic acid | 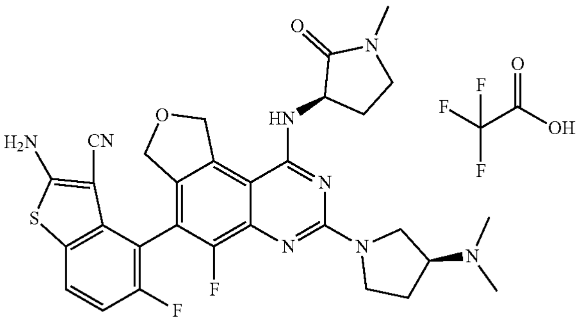 | 605 |

TABLE 17-continued

| Preparation | Chemical Name | Structure | MS (ES) m/z (M + 1) |
|---|---|---|---|
| 49A [24] | 2-Amino-4-(1-(((3-cyclopropyl-1H-1,2,4-triazol-5-yl)methyl)amino)-3-((S)-3-(dimethylamino)pyrrolidin-1-yl)-5-fluoro-7,9-dihydrofuro[3,4-f]quinazolin-6-yl)-5-fluorobenzo[b]thiophene-3-carbonitrile, Atropisomer 1 2,2,2-trifluoroacetic acid | 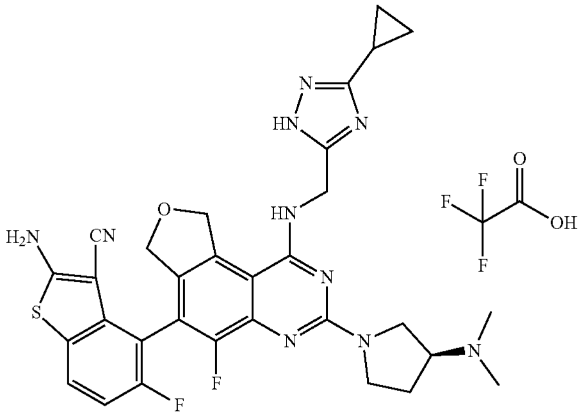 | 629 |
| 50A [24] | 2-Amino-4-(1-(((3-cyclopropyl-1H-1,2,4-triazol-5-yl)methyl)amino)-3-((S)-3-(dimethylamino)pyrrolidin-1-yl)-5-fluoro-7,9-dihydrofuro[3,4-f]quinazolin-6-yl)-5-fluorobenzo[b]thiophene-3-carbonitrile, Atropisomer 2 2,2,2-trifluoroacetic acid | 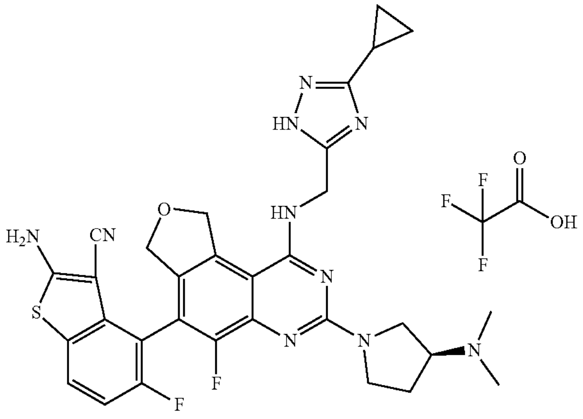 | 629 |
| 51A | 2-Amino-4-(1-(((3-cyclopropyl-1H-1,2,4-triazol-5-yl)methyl)amino)-5-fluoro-3-(((2R, 7aS)-2-fluorotetrahydro-1H-pyrrolizin-7a(5H)-yl)methoxy)-7,9-dihydrofuro[3,4-f]quinazolin-6-yl)-7-fluorothieno[3,2-c]pyridine-3-carbonitrile | 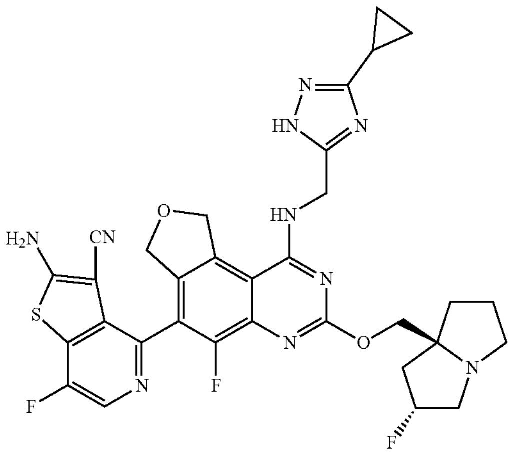 [SMILES: N#Cc1c(N)sc2c(F)cnc(-c3c4c(c5c(NCc6nc(C7CC7)n[nH]6)nc(OC[C@@]67CCCN6C[C@H](F)C7)nc5c3F)COC4)c12] | 675 |

TABLE 17-continued

| Preparation | Chemical Name | Structure | MS (ES) m/z (M + 1) |
|---|---|---|---|
| 52A | 4-(3-((1-(((1R,4R)-2-Oxa-5-azabicyclo[2.2.1]heptan-5-yl)methyl)cyclopropyl)methoxy)-5-fluoro-1-(((R)-1-methyl-2-oxopyrrolidin-3-yl)amino)-7,9-dihydrofuro[3,4-f]quinazolin-6-yl)-2-amino-7-fluorothieno[3,2-c]pyridine-3-carbonitrile | 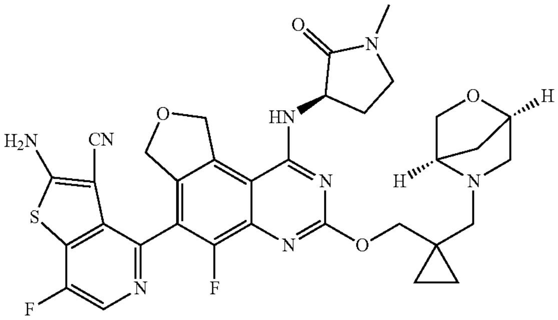 [SMILES: CN1CC[C@@H](Nc2nc(OCC3(CN4C[C@H]5C[C@@H]4CO5)CC3)nc3c(F)c(-c4ncc(F)c5sc(N)c(C#N)c45)c4c(c23)COC4)C1=O] | 675 |
| 1B | 2-Amino-4-(3-((S)-3-(dimethylamino)pyrrolidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridine-3-carbonitrile | 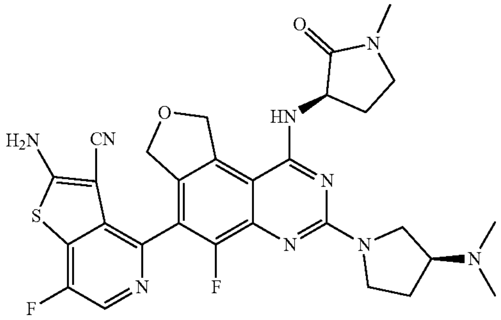 [SMILES: CN1CC[C@@H](Nc2nc(N3CC[C@H](N(C)C)C3)nc3c(F)c(-c4ncc(F)c5sc(N)c(C#N)c45)c4c(c23)COC4)C1=O] | 606 |
| 2B | 2-Amino-4-(3-((S)-3-(dimethylamino)pyrrolidin-1-yl)-5-fluoro-1-(((5-methyl-1,2,4-oxadiazol-3-yl)methyl)amino)-7,9-dihydrofuro[3,4-f]quinazolin-6-yl)-7-fluorothieno[3,2-c]pyridine-3-carbonitrile | 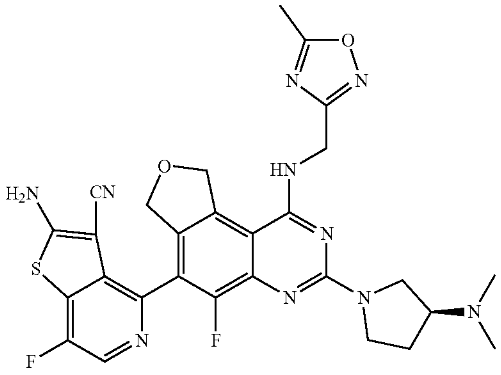 [SMILES: Cc1nc(CNc2nc(N3CC[C@H](N(C)C)C3)nc3c(F)c(-c4ncc(F)c5sc(N)c(C#N)c45)c4c(c23)COC4)no1] | 605 |
| 3B | 2-Amino-7-fluoro-4-(5-fluoro-3-(((2R,7aS)-2-fluorotetrahydro-1H-pyrrolizin-7a(5H)-yl)methoxy)-1-((pyridazin-3-ylmethyl)amino)-7,9-dihydrofuro[3,4-f]quinazolin-6-yl)thieno[3,2-c]pyridine-3-carbonitrile | 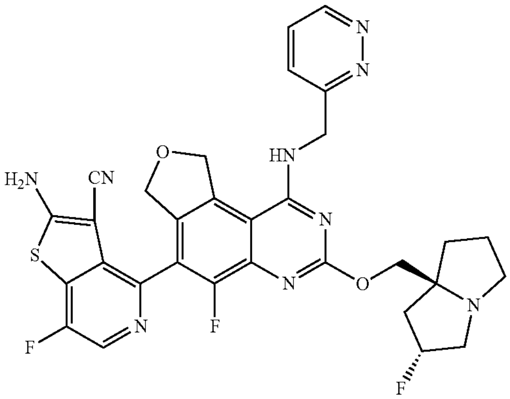 [SMILES: N#Cc1c(N)sc2c(F)cnc(-c3c4c(c5c(NCc6cccnn6)nc(OC[C@@]67CCCN6C[C@H](F)C7)nc5c3F)COC4)c12] | 646 |

TABLE 17-continued

| Preparation | Chemical Name | Structure | MS (ES) m/z (M + 1) |
|---|---|---|---|
| 4B | 2-Amino-4-(3-(3-(dimethylamino)azetidin-1-yl)-5-fluoro-1-(((5-methyl-1,2,4-oxadiazol-3-yl)methyl)amino)-7,9-dihydrofuro[3,4-f]quinazolin-6-yl)-7-fluorothieno[3,2-c]pyridine-3-carbonitrile | 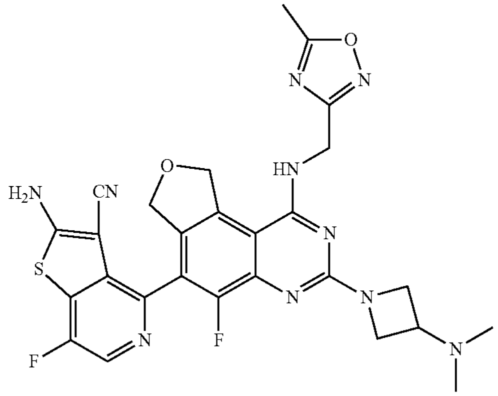 [SMILES: Cc1nc(CNc2nc(N3CC(N(C)C)C3)nc3c(F)c(-c4ncc(F)c5sc(N)c(C#N)c45)c4c(c23)COC4)no1] | 591 |
| 5B | 2-Amino-4-(3-(3-(dimethylamino)azetidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridine-3-carbonitrile | 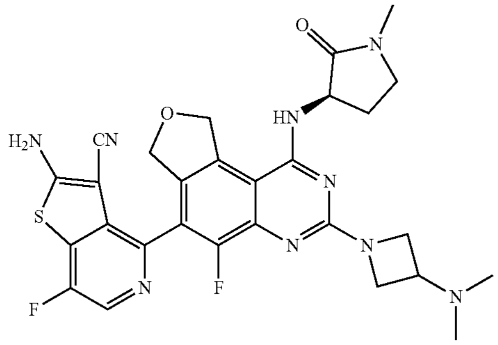 | 592 |
| 6B | 2-Amino-4-(3-(3-(dimethylamino)azetidin-1-yl)-5-fluoro-1-((pyridazin-3-ylmethyl)amino)-7,9-dihydrofuro[3,4-f]quinazolin-6-yl)-7-fluorothieno[3,2-c]pyridine-3-carbonitrile | 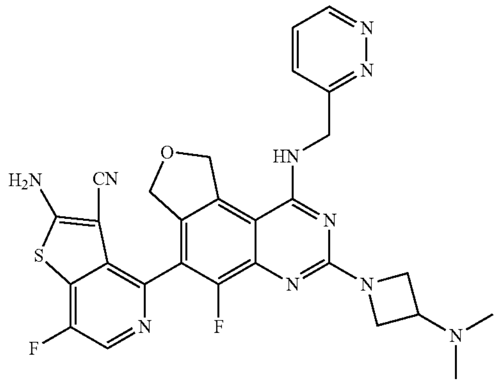 [SMILES: CN(C)C1CN(c2nc(NCc3cccnn3)c3c4c(c(-c5ncc(F)c6sc(N)c(C#N)c56)c(F)c3n2)COC4)C1] | 587 |
| 7B | 2-Amino-7-fluoro-4-(5-fluoro-3-(((2R,7aS)-2-fluorotetrahydro-1H-pyrrolizin-7a(5H)-yl)methoxy)-1-(((5-methyl-1,2,4-oxadiazol-3-yl)methyl)amino)-7,9-dihydrofuro[3,4-f]quinazolin-6-yl)thieno[3,2-c]pyridine-3-carbonitrile | 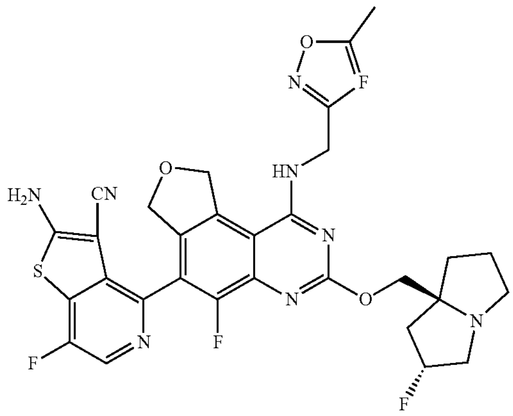 | 650 |

TABLE 17-continued

| Preparation | Chemical Name | Structure | MS (ES) m/z (M + 1) |
|---|---|---|---|
| 8B | 2-Amino-4-(3-((S)-3-(dimethylamino)pyrrolidin-1-yl)-5-fluoro-1-((pyridazin-3-ylmethyl)amino)-7,9-dihydrofuro[3,4-f]quinazolin-6-yl)-7-fluorothieno[3,2-c]pyridine-3-carbonitrile | 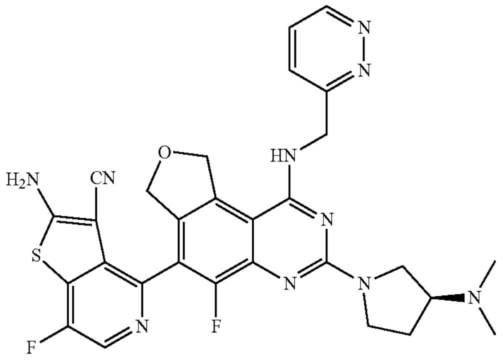 [SMILES: CN(C)[C@H]1CCN(c2nc(NCc3cccnn3)c3c4c(c(-c5ncc(F)c6sc(N)c(C#N)c56)c(F)c3n2)COC4)C1] | 601 |
| 9B | 2-Amino-4-(3-(3-(dimethylamino)-3-methylazetidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridine-3-carbonitrile | 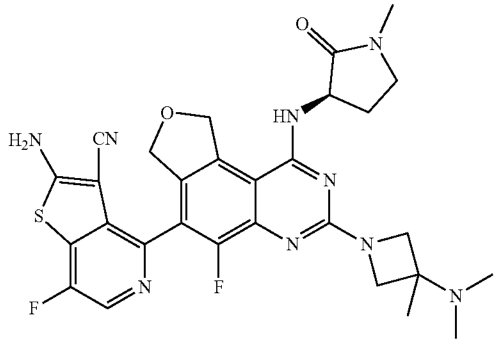 [SMILES: CN1CC[C@@H](Nc2nc(N3CC(C)(N(C)C)C3)nc3c(F)c(-c4ncc(F)c5sc(N)c(C#N)c45)c4c(c23)COC4)C1=O] | 606 |
| 10B | 2-Amino-4-(3-(3-(dimethylamino)-3-methylazetidin-1-yl)-5-fluoro-1-((pyridazin-3-ylmethyl)amino)-7,9-dihydrofuro[3,4-f]quinazolin-6-yl)-7-fluorothieno[3,2-c]pyridine-3-carbonitrile | 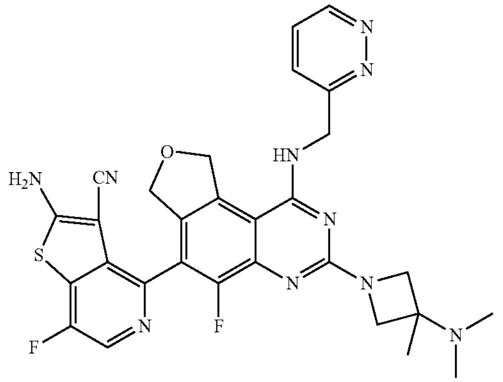 [SMILES: CN(C)C1(C)CN(c2nc(NCc3cccnn3)c3c4c(c(-c5ncc(F)c6sc(N)c(C#N)c56)c(F)c3n2)COC4)C1] | 601 |
| 11B | 2-Amino-4-(5-chloro-3-(((2R,7aS)-2-fluorotetrahydro-1H-pyrrolizin-7a(5H)-yl)methoxy)-1-(((5-methylisoxazol-3-yl)methyl)amino)-7,9-dihydrofuro[3,4-f]quinazolin-6-yl)-7-fluorobenzo[b]thiophene-3-carbonitrile | 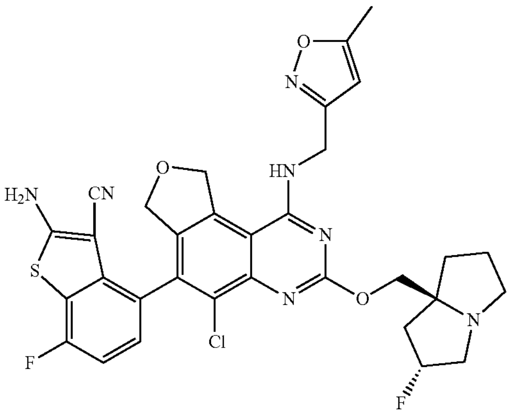 [SMILES: Cc1cc(CNc2nc(OC[C@@]34CCCN3C[C@H](F)C4)nc3c(Cl)c(-c4ccc(F)c5sc(N)c(C#N)c45)c4c(c23)COC4)no1] | 664 |

TABLE 17-continued

| Preparation | Chemical Name | Structure | MS (ES) m/z (M + 1) |
|---|---|---|---|
| 12B [25] | 2-Amino-4-(5-chloro-3-(((2R,7aS)-2-fluorotetrahydro-1H-pyrrolizin-7a(5H)-yl)methoxy)-1-(((3-methyl-1,2,4-thiadiazol-5-yl)methyl)amino)-7,9-dihydrofuro[3,4-f]quinazolin-6-yl)-7-fluorobenzo[b]thiophene-3-carbonitrile, Atropisomer 1 | 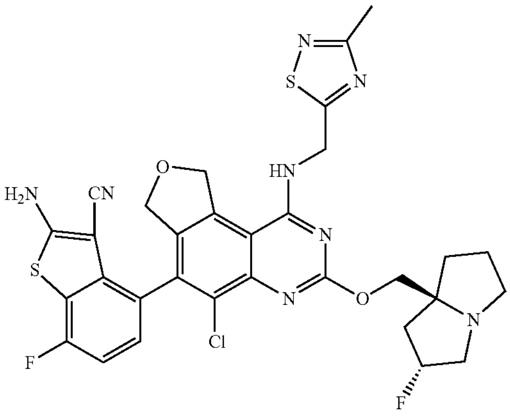 [SMILES: Cc1nsc(CNc2nc(OC[C@@]34CCCN3C[C@H](F)C4)nc3c(Cl)c(-c4ccc(F)c5sc(N)c(C#N)c45)c4c(c23)COC4)n1] | 681 |
| 13B [25] | 2-Amino-4-(5-chloro-3-(((2R,7aS)-2-fluorotetrahydro-1H-pyrrolizin-7a(5H)-yl)methoxy)-1-(((3-methyl-1,2,4-thiadiazol-5-yl)methyl)amino)-7,9-dihydrofuro[3,4-f]quinazolin-6-yl)-7-fluorobenzo[b]thiophene-3-carbonitrile, Atropisomer 2 | 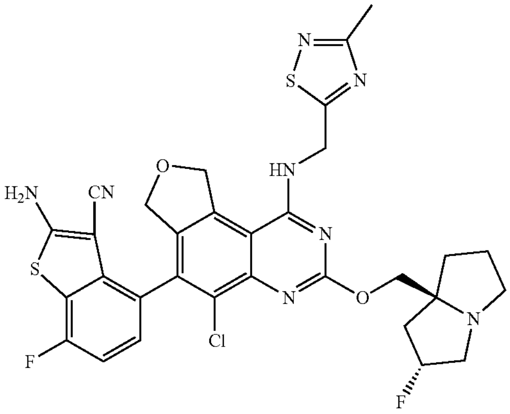 [SMILES: Cc1nsc(CNc2nc(OC[C@@]34CCCN3C[C@H](F)C4)nc3c(Cl)c(-c4ccc(F)c5sc(N)c(C#N)c45)c4c(c23)COC4)n1] | 681 |
| 14B [26] | 2-Amino-4-(5-chloro-1-(((R)-1-methyl-2-oxopyrrolidin-3-yl)amino)-3-(((S)-1-methylpyrrolidin-2-yl)methoxy)-7,9-dihydrofuro[3,4-f]quinazolin-6-yl)-7-fluorobenzo[b]thiophene-3-carbonitrile, Atropisomer 1 | 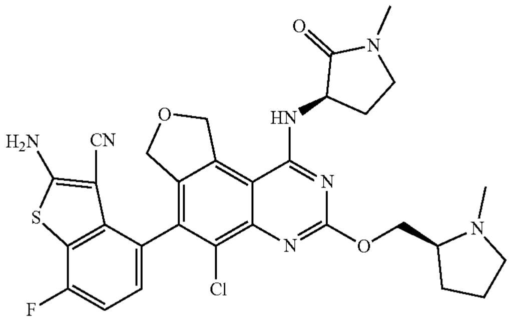 [SMILES: CN1CC[C@@H](Nc2nc(OC[C@@H]3CCCN3C)nc3c(Cl)c(-c4ccc(F)c5sc(N)c(C#N)c45)c4c(c23)COC4)C1=O] | 622 |
| 15B [26] | 2-Amino-4-(5-chloro-1-(((R)-1-methyl-2-oxopyrrolidin-3-yl)amino)-3-(((S)-1-methylpyrrolidin-2-yl)methoxy)-7,9-dihydrofuro[3,4-f]quinazolin-6-yl)-7-fluorobenzo[b]thiophene-3-carbonitrile, Atropisomer 2 | 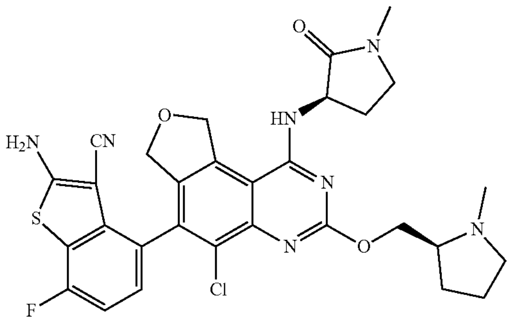 [SMILES: CN1CC[C@@H](Nc2nc(OC[C@@H]3CCCN3C)nc3c(Cl)c(-c4ccc(F)c5sc(N)c(C#N)c45)c4c(c23)COC4)C1=O] | 622 |

TABLE 17-continued

| Preparation | Chemical Name | Structure | MS (ES) m/z (M + 1) |
|---|---|---|---|
| 16B | 3-(((6-(2-Amino-3-cyano-7-fluorobenzo[b]thiophen-4-yl)-5-chloro-3-((S)-3-(dimethylamino)pyrrolidin-1-yl)-7,9-dihydrofuro[3,4-f]quinazolin-1-yl)amino)methyl)-1,2,4-oxadiazole-5-carboxamide | 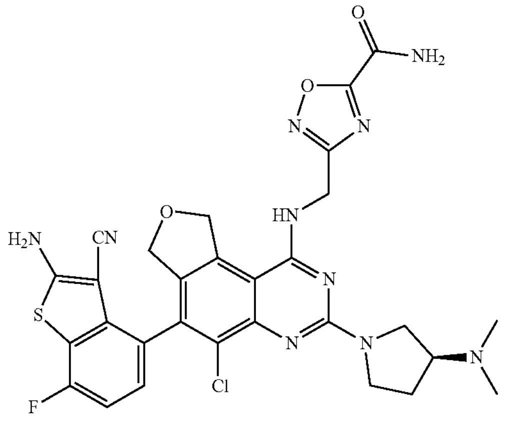 [SMILES: CN(C)[C@H]1CCN(c2nc(NCc3noc(C(N)=O)n3)c3c4c(c(-c5ccc(F)c6sc(N)c(C#N)c56)c(Cl)c3n2)COC4)C1] | 649 |
| 17B | 2-Amino-4-(1-(((5-amino-1,3,4-thiadiazol-2-yl)methyl)amino)-5-chloro-3-(((2R,7aS)-2-fluorotetrahydro-1H-pyrrolizin-7a(5H)-yl)methoxy)-7,9-dihydrofuro[3,4-f]quinazolin-6-yl)-7-fluorobenzo[b]thiophene-3-carbonitrile | 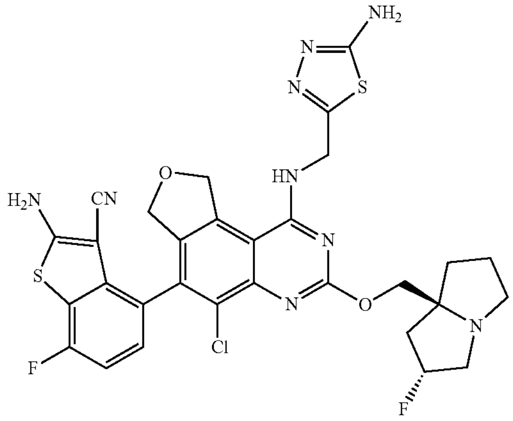 [SMILES: N#Cc1c(N)sc2c(F)ccc(-c3c4c(c5c(NCc6nnc(N)s6)nc(OC[C@@]67CCCN6C[C@H](F)C7)nc5c3Cl)COC4)c12] | 682 |
| 18B | 2-Amino-4-(1-(((5-amino-1,3,4-thiadiazol-2-yl)methyl)amino)-5-chloro-3-((S)-3-(dimethylamino)pyrrolidin-1-yl)-7,9-dihydrofuro[3,4-f]quinazolin-6-yl)-7-fluorobenzo[b]thiophene-3-carbonitrile | 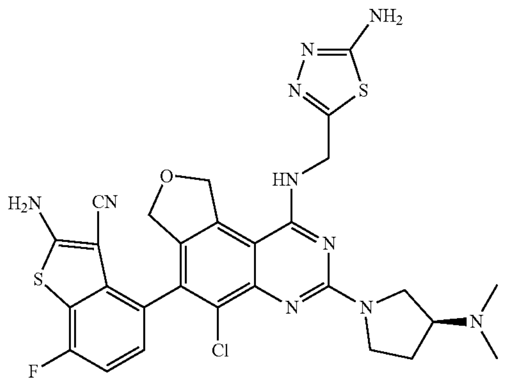 [SMILES: CN(C)[C@H]1CCN(c2nc(NCc3nnc(N)s3)c3c4c(c(-c5ccc(F)c6sc(N)c(C#N)c56)c(Cl)c3n2)COC4)C1] | 637 |

TABLE 17-continued

| Preparation | Chemical Name | Structure | MS (ES) m/z (M + 1) |
|---|---|---|---|
| 19B | 2-Amino-4-(5-chloro-3-(((2R,7aS)-2-fluorotetrahydro-1H-pyrrolizin-7a(5H)-yl)methoxy)-1-(((3-methylisoxazol-5-yl)methyl)amino)-7,9-dihydrofuro[3,4-f]quinazolin-6-yl)-7-fluorobenzo[b]thiophene-3-carbonitrile | 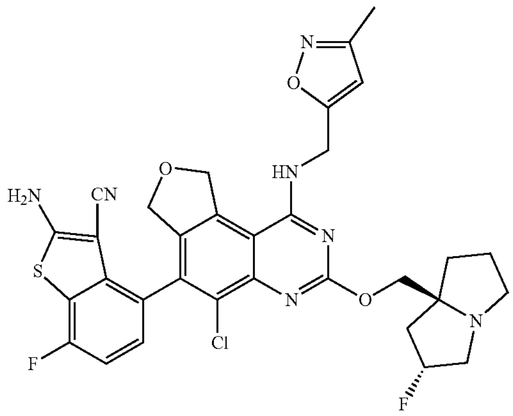 [SMILES: Cc1cc(CNc2nc(OC[C@@]34CCCN3C[C@H](F)C4)nc3c(Cl)c(-c4ccc(F)c5sc(N)c(C#N)c45)c4c(c23)COC4)on1] | 664 |
| 20B [27] | 2-Amino-4-(5-chloro-3-(((2R,7aS)-2-fluorotetrahydro-1H-pyrrolizin-7a(5H)-yl)methoxy)-1-(((3-methylisoxazol-5-yl)methyl)amino)-7,9-dihydrofuro[3,4-f]quinazolin-6-yl)-7-fluorobenzo[b]thiophene-3-carbonitrile, Atropisomer 1 | 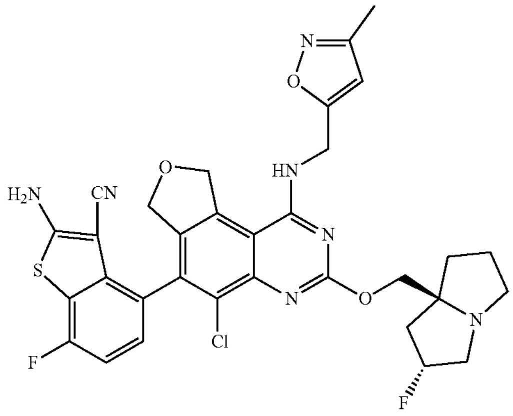 [SMILES: Cc1cc(CNc2nc(OC[C@@]34CCCN3C[C@H](F)C4)nc3c(Cl)c(-c4ccc(F)c5sc(N)c(C#N)c45)c4c(c23)COC4)on1] | 664 |
| 21B [27] | 2-Amino-4-(5-chloro-3-(((2R,7aS)-2-fluorotetrahydro-1H-pyrrolizin-7a(5H)-yl)methoxy)-1-(((3-methylisoxazol-5-yl)methyl)amino)-7,9-dihydrofuro[3,4-f]quinazolin-6-yl)-7-fluorobenzo[b]thiophene-3-carbonitrile, Atropisomer 2 | 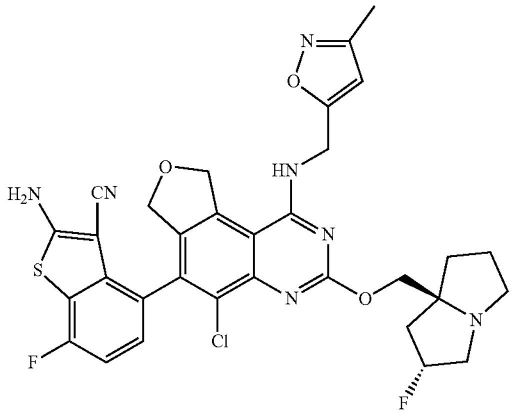 [SMILES: Cc1cc(CNc2nc(OC[C@@]34CCCN3C[C@H](F)C4)nc3c(Cl)c(-c4ccc(F)c5sc(N)c(C#N)c45)c4c(c23)COC4)on1] | 664 |

TABLE 17-continued

| Preparation | Chemical Name | Structure | MS (ES) m/z (M + 1) |
| --- | --- | --- | --- |
| 22B [28] | 2-Amino-4-(5-chloro-3-((2-(hydroxymethyl)-1-methylpyrrolidin-2-yl)methoxy)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile, Atropisomer 1 | 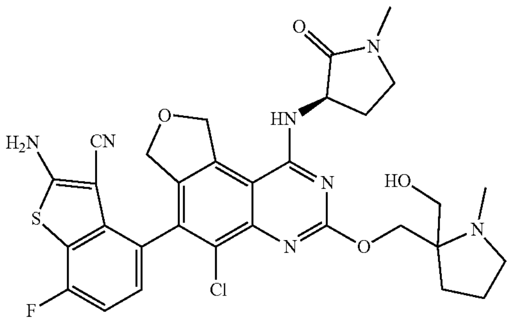 [SMILES: CN1CC[C@@H](Nc2nc(OCC3(CO)CCCN3C)nc3c(Cl)c(-c4ccc(F)c5sc(N)c(C#N)c45)c4c(c23)COC4)C1=O] | 652 |
| 23B [28] | 2-Amino-4-(5-chloro-3-((2-(hydroxymethyl)-1-methylpyrrolidin-2-yl)methoxy)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile, Atropisomer 2 | 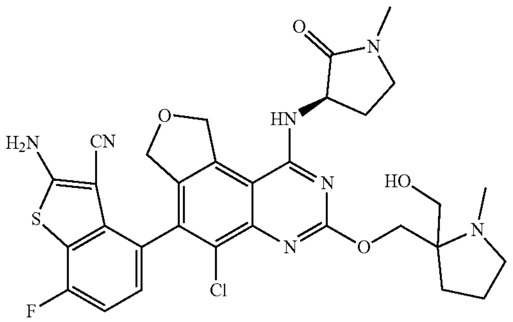 [SMILES: CN1CC[C@@H](Nc2nc(OCC3(CO)CCCN3C)nc3c(Cl)c(-c4ccc(F)c5sc(N)c(C#N)c45)c4c(c23)COC4)C1=O] | 652 |
| 24B [29] | 2-Amino-4-(5-chloro-3-((3-(dimethylamino)oxetan-3-yl)methoxy)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile, Atropisomer 1 | 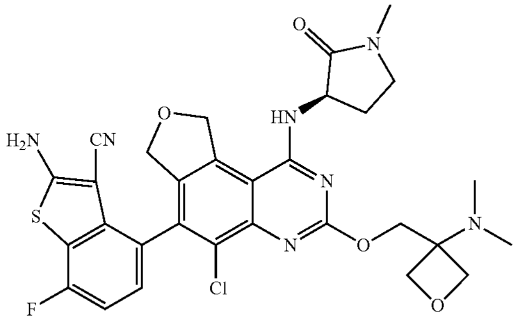 [SMILES: CN1CC[C@@H](Nc2nc(OCC3(N(C)C)COC3)nc3c(Cl)c(-c4ccc(F)c5sc(N)c(C#N)c45)c4c(c23)COC4)C1=O] | 638 |
| 25B [29] | 2-Amino-4-(5-chloro-3-((3-(dimethylamino)oxetan-3-yl)methoxy)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile, Atropisomer 2 | 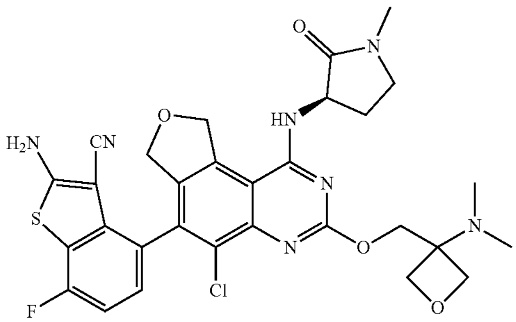 [SMILES: CN1CC[C@@H](Nc2nc(OCC3(N(C)C)COC3)nc3c(Cl)c(-c4ccc(F)c5sc(N)c(C#N)c45)c4c(c23)COC4)C1=O] | 638 |

TABLE 17-continued

| Preparation | Chemical Name | Structure | MS (ES) m/z (M + 1) |
| --- | --- | --- | --- |
| 26B | 2-Amino-4-(3-((1-((dimethylamino)methyl) cyclopropyl)methoxy)-5-fluoro-1-((pyridazin-3-ylmethyl)amino)-7,9-dihydrofuro[3,4-f]quinazolin-6-yl)-7-fluorothieno[3,2-c]pyridine-3-carbonitrile | 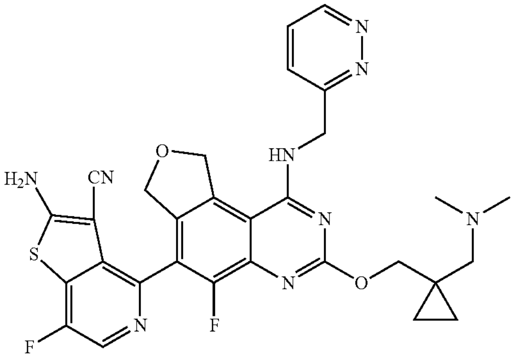 [SMILES: CN(C)CC1(COc2nc(NCc3cccnn3)c3c4c(c(-c5ncc(F)c6sc(N)c(C#N)c56)c(F)c3n2)COC4)CC1] | 616 |
| 27B | 2-Amino-4-(3-((1-((dimethylamino)methyl) cyclopropyl)methoxy)-5-fluoro-1-(((R)-1-methyl-2-oxopiperidin-3-yl)amino)-7,9-dihydrofuro[3,4-f]quinazolin-6-yl)-7-fluorothieno[3,2-c]pyridine-3-carbonitrile | 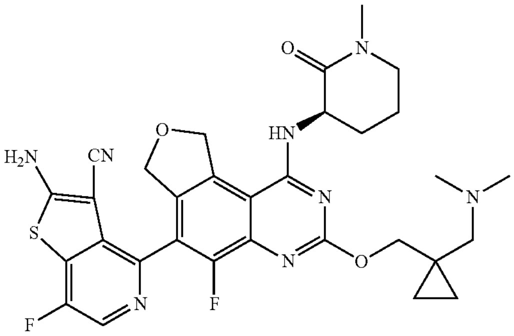 [SMILES: CN(C)CC1(COc2nc(N[C@@H]3CCCN(C)C3=O)c3c4c(c(-c5ncc(F)c6sc(N)c(C#N)c56)c(F)c3n2)COC4)CC1] | 635 |
| 28B | 2-Amino-4-(3-((1-((dimethylamino)methyl) cyclopropyl)methoxy)-5-fluoro-1-(((R)-2-oxopiperidin-3-yl)amino)-7,9-dihydrofuro[3,4-f]quinazolin-6-yl)-7-fluorothieno[3,2-c]pyridine-3-carbonitrile | 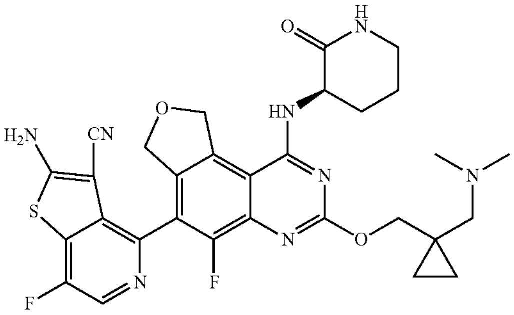 [SMILES: CN(C)CC1(COc2nc(N[C@@H]3CCCNC3=O)c3c4c(c(-c5ncc(F)c6sc(N)c(C#N)c56)c(F)c3n2)COC4)CC1] | 621 |
| 29B | 2-Amino-4-(3-((1-((dimethylamino)methyl) cyclopropyl)methoxy)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridine-3-carbonitrile | 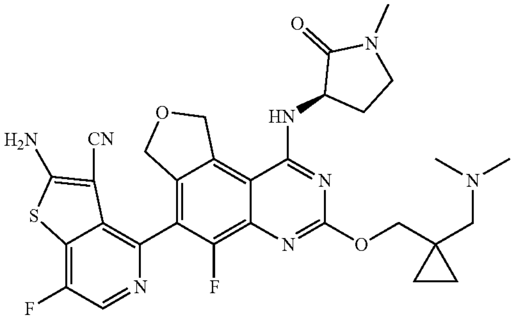 [SMILES: CN(C)CC1(COc2nc(N[C@@H]3CCN(C)C3=O)c3c4c(c(-c5ncc(F)c6sc(N)c(C#N)c56)c(F)c3n2)COC4)CC1] | 621 |

TABLE 17-continued

| Preparation | Chemical Name | Structure | MS (ES) m/z (M + 1) |
|---|---|---|---|
| 30B | 2-Amino-4-(3-((1-((dimethylamino)methyl) cyclopropyl)methoxy)-5-fluoro-1-(((R)-2-oxopyrrolidin-3-yl)amino)-7,9-dihydrofuro[3,4-f]quinazolin-6-yl)-7-fluorothieno[3,2-c]pyridine-3-carbonitrile | 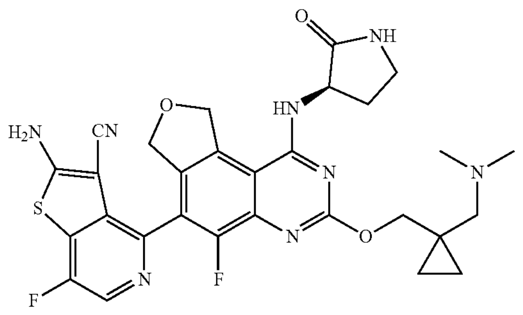 [SMILES: CN(C)CC1(COc2nc(N[C@@H]3CCNC3=O)c3c4c(c(-c5ncc(F)c6sc(N)c(C#N)c56)c(F)c3n2)COC4)CC1] | 607 |
| 31B [30] | 2-Amino-4-(3-((S)-3-(dimethylamino)pyrrolidin-1-yl)-5-fluoro-1-(isoxazol-4-ylamino)-7,9-dihydrofuro[3,4-f]quinazolin-6-yl)-5-fluorobenzo[b]thiophene-3-carbonitrile | 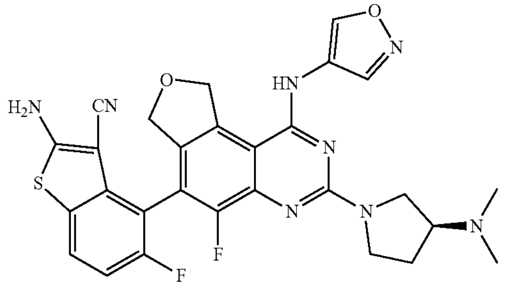 [SMILES: CN(C)[C@H]1CCN(c2nc(Nc3cnoc3)c3c4c(c(-c5c(F)ccc6sc(N)c(C#N)c56)c(F)c3n2)COC4)C1] | 575 |
| 1C [30] | 2-Amino-4-(3-((S)-3-(dimethylamino)pyrrolidin-1-yl)-5-fluoro-1-((1-methyl-1H-pyrazol-5-yl)amino)-7,9-dihydrofuro[3,4-f]quinazolin-6-yl)-5-fluorobenzo[b]thiophene-3-carbonitrile | 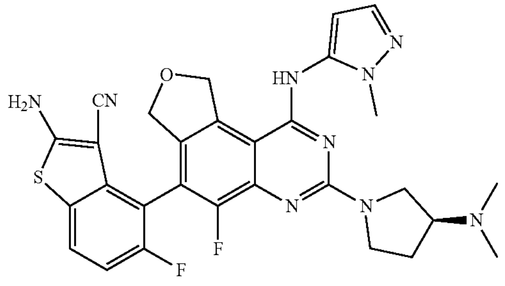 [SMILES: CN(C)[C@H]1CCN(c2nc(Nc3ccnn3C)c3c4c(c(-c5c(F)ccc6sc(N)c(C#N)c56)c(F)c3n2)COC4)C1] | 588 |
| 2C [30] | 2-Amino-4-(3-((S)-3-(dimethylamino)pyrrolidin-1-yl)-5-fluoro-1-((5-methyl-1,2,4-oxadiazol-3-yl)methoxy)-7,9-dihydrofuro[3,4-f]quinazolin-6-yl)-5-fluorobenzo[b]thiophene-3-carbonitrile | 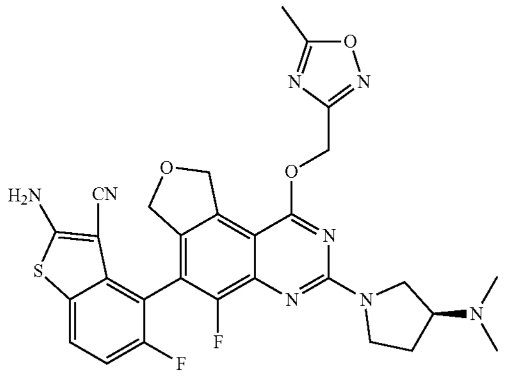 [SMILES: Cc1nc(COc2nc(N3CC[C@H](N(C)C)C3)nc3c(F)c(-c4c(F)ccc5sc(N)c(C#N)c45)c4c(c23)COC4)no1] | 605 |

TABLE 17-continued

| Preparation | Chemical Name | Structure | MS (ES) m/z (M + 1) |
| --- | --- | --- | --- |
| 3C [30] | 2-Amino-4-(3-((S)-3-(dimethylamino)pyrrolidin-1-yl)-5-fluoro-1-(pyridazin-3-ylmethoxy)-7,9-dihydrofuro[3,4-f]quinazolin-6-yl)-5-fluorobenzo[b]thiophene-3-carbonitrile | 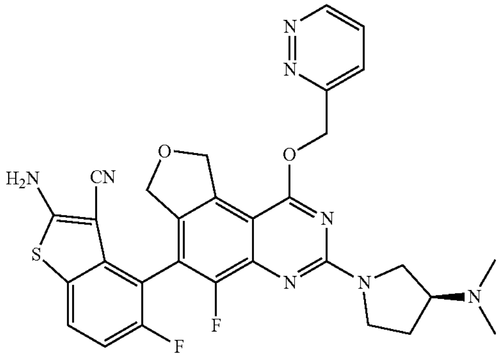 [SMILES: CN(C)[C@H]1CCN(c2nc(OCc3cccnn3)c3c4c(c(-c5c(F)ccc6sc(N)c(C#N)c56)c(F)c3n2)COC4)C1] | 601 |
| 4C [31] | 2-Amino-4-(3-((S)-3-(dimethylamino)pyrrolidin-1-yl)-5-fluoro-1-(((R)-1-methyl-2-oxopiperidin-3-yl)amino)-7,9-dihydrofuro[3,4-f]quinazolin-6-yl)-5-fluorobenzo[b]thiophene-3-carbonitrile, Atropisomer 1 | 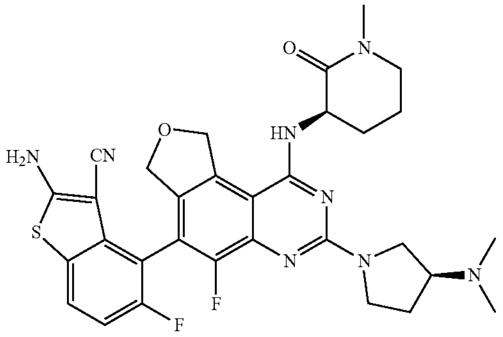 [SMILES: CN1CCC[C@@H](Nc2nc(N3CC[C@H](N(C)C)C3)nc3c(F)c(-c4c(F)ccc5sc(N)c(C#N)c45)c4c(c23)COC4)C1=O] | 619 |
| 5C [31] | 2-Amino-4-(3-((S)-3-(dimethylamino)pyrrolidin-1-yl)-5-fluoro-1-(((R)-1-methyl-2-oxopiperidin-3-yl)amino)-7,9-dihydrofuro[3,4-f]quinazolin-6-yl)-5-fluorobenzo[b]thiophene-3-carbonitrile, Atropisomer 2 | 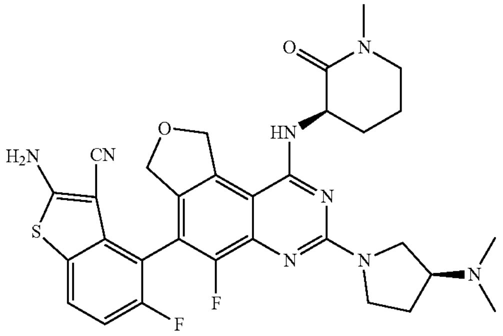 [SMILES: CN1CCC[C@@H](Nc2nc(N3CC[C@H](N(C)C)C3)nc3c(F)c(-c4c(F)ccc5sc(N)c(C#N)c45)c4c(c23)COC4)C1=O] | 619 |
| 6C [32] | 2-Amino-4-(5-chloro-3-(3-(dimethylamino)azetidin-1-yl)-1-((pyridazin-3-ylmethyl)amino)-7,9-dihydrofuro[3,4-f]quinazolin-6-yl)-5-fluorobenzo[b]thiophene-3-carbonitrile, Atropisomer 1 | 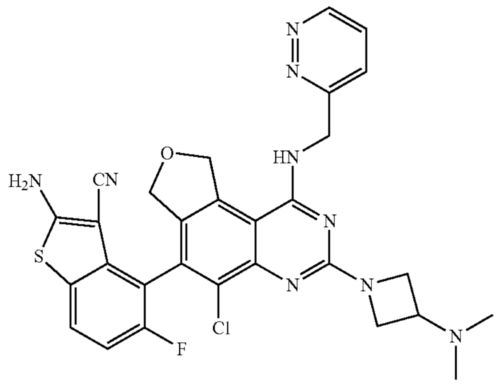 [SMILES: CN(C)C1CN(c2nc(NCc3cccnn3)c3c4c(c(-c5c(F)ccc6sc(N)c(C#N)c56)c(Cl)c3n2)COC4)C1] | 602 |

TABLE 17-continued

| Preparation | Chemical Name | Structure | MS (ES) m/z (M + 1) |
|---|---|---|---|
| 7C [32] | 2-Amino-4-(5-chloro-3-(3-(dimethylamino)azetidin-1-yl)-1-((pyridazin-3-ylmethyl)amino)-7,9-dihydrofuro[3,4-f]quinazolin-6-yl)-5-fluorobenzo[b]thiophene-3-carbonitrile, Atropisomer 2 | 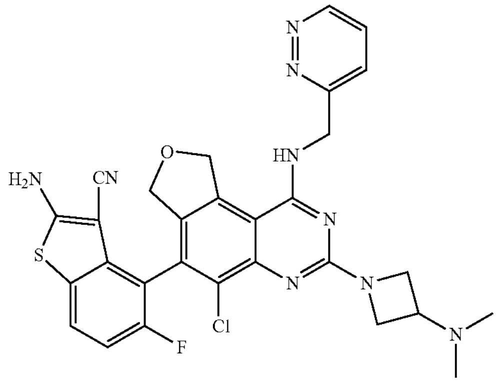 [SMILES: CN(C)C1CN(c2nc(NCc3cccnn3)c3c4c(c(-c5c(F)ccc6sc(N)c(C#N)c56)c(Cl)c3n2)COC4)C1] | 602 |
| 8C [33] | 2-Amino-4-(5-chloro-3-((S)-3-(dimethylamino)pyrrolidin-1-yl)-1-((pyridazin-3-ylmethyl)amino)-7,9-dihydrofuro[3,4-f]quinazolin-6-yl)-5-fluorobenzo[b]thiophene-3-carbonitrile, Atropisomer 1 | 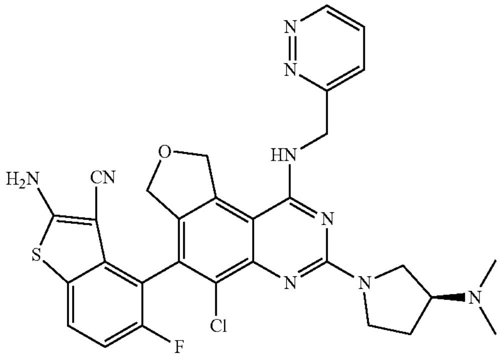 [SMILES: CN(C)[C@H]1CCN(c2nc(NCc3cccnn3)c3c4c(c(-c5c(F)ccc6sc(N)c(C#N)c56)c(Cl)c3n2)COC4)C1] | 616 |
| 9C [33] | 2-Amino-4-(5-chloro-3-((S)-3-(dimethylamino)pyrrolidin-1-yl)-1-((pyridazin-3-ylmethyl)amino)-7,9-dihydrofuro[3,4-f]quinazolin-6-yl)-5-fluorobenzo[b]thiophene-3-carbonitrile, Atropisomer 2 | 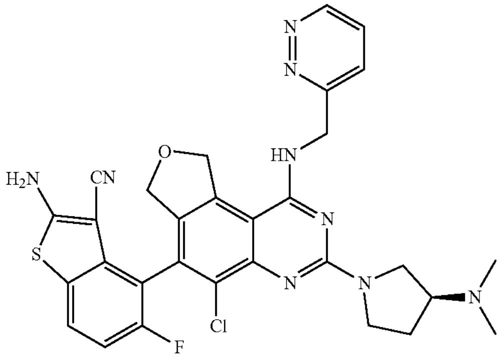 [SMILES: CN(C)[C@H]1CCN(c2nc(NCc3cccnn3)c3c4c(c(-c5c(F)ccc6sc(N)c(C#N)c56)c(Cl)c3n2)COC4)C1] | 616 |
| 10C [34] | 2-Amino-4-(5-chloro-3-(3-(dimethylamino)-3-methylazetidin-1-yl)-1-((pyridazin-3-ylmethyl)amino)-7,9-dihydrofuro[3,4-f]quinazolin-6-yl)-5-fluorobenzo[b]thiophene-3-carbonitrile, Atropisomer 1 | 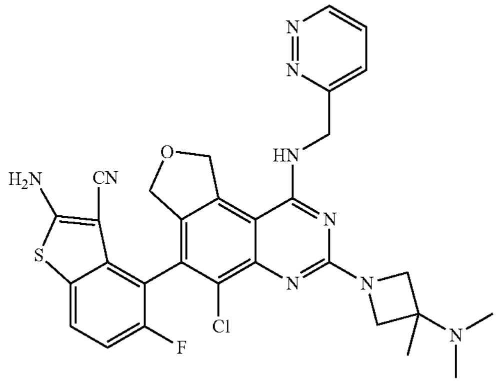 [SMILES: CN(C)C1(C)CN(c2nc(NCc3cccnn3)c3c4c(c(-c5c(F)ccc6sc(N)c(C#N)c56)c(Cl)c3n2)COC4)C1] | 616 |

TABLE 17-continued

| Preparation | Chemical Name | Structure | MS (ES) m/z (M + 1) |
| --- | --- | --- | --- |
| 11C [34] | 2-Amino-4-(5-chloro-3-(3-(dimethylamino)-3-methylazetidin-1-yl)-1-((pyridazin-3-ylmethyl)amino)-7,9-dihydrofuro[3,4-f]quinazolin-6-yl)-5-fluorobenzo[b]thiophene-3-carbonitrile, Atropisomer 2 | 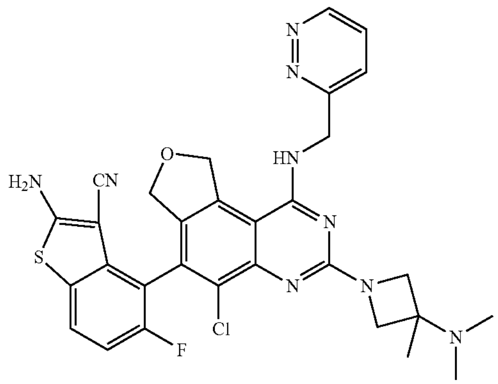 [SMILES: CN(C)C1(C)CN(c2nc(NCc3cccnn3)c3c4c(c(-c5c(F)ccc6sc(N)c(C#N)c56)c(Cl)c3n2)COC4)C1] | 616 |
| 12C [8] | 2-Amino-4-(5-chloro-3-(3-(dimethylamino)azetidin-1-yl)-1-(((4,5,6,7-tetrahydro-1H-indazol-3-yl)methyl)amino)-7,9-dihydrofuro[3,4-f]quinazolin-6-yl)-7-fluorobenzo[b]thiophene-3-carbonitrile | 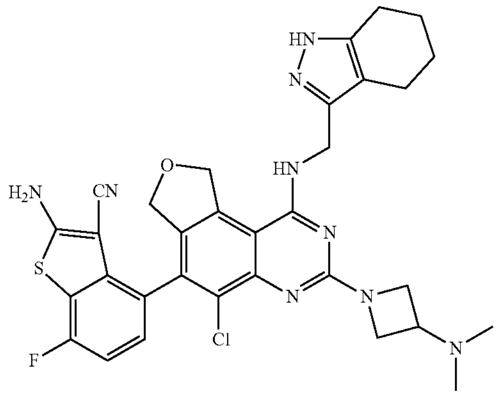 [SMILES: CN(C)C1CN(c2nc(NCc3n[nH]c4c3CCCC4)c3c4c(c(-c5ccc(F)c6sc(N)c(C#N)c56)c(Cl)c3n2)COC4)C1] | 644 |
| 13C [8] | 2-Amino-4-(5-chloro-3-((2S,3S)-3-(dimethylamino)-2-methylpyrrolidin-1-yl)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile | 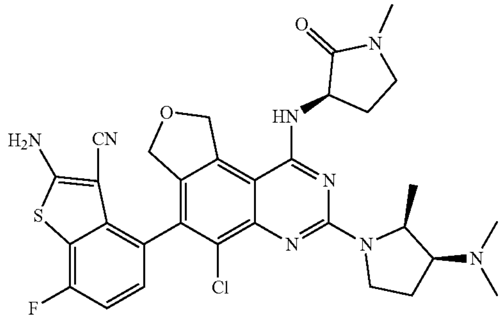 [SMILES: C[C@H]1[C@@H](N(C)C)CCN1c1nc(N[C@@H]2CCN(C)C2=O)c2c3c(c(-c4ccc(F)c5sc(N)c(C#N)c45)c(Cl)c2n1)COC3] | 635 |
| 14C [8] | 2-Amino-4-(5-chloro-3-((2S,3S)-3-(isopropylamino)-2-methylpyrrolidin-1-yl)-1-(((R)-1-methyl-2-oxopyrrolidin-3-yl)amino)-7,9-dihydrofuro[3,4-f]quinazolin-6-yl)-7-fluorobenzo[b]thiophene-3-carbonitrile | 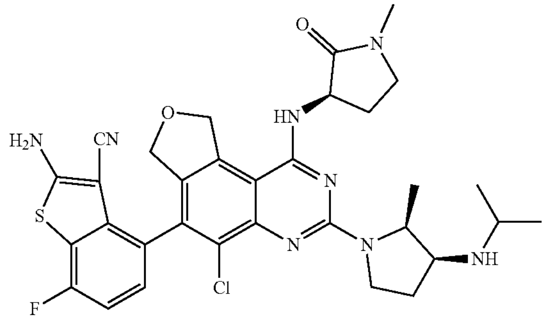 [SMILES: CC(C)N[C@H]1CCN(c2nc(N[C@@H]3CCN(C)C3=O)c3c4c(c(-c5ccc(F)c6sc(N)c(C#N)c56)c(Cl)c3n2)COC4)[C@H]1C] | 649 |

TABLE 17-continued

| Preparation | Chemical Name | Structure | MS (ES) m/z (M + 1) |
|---|---|---|---|
| 15C [8] | 2-Amino-4-(5-chloro-3-((2S,3S)-3-(dimethylamino)-2-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 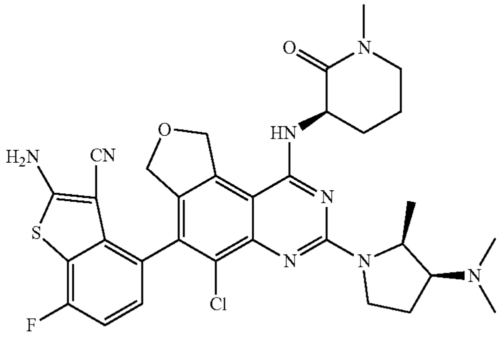 [SMILES: C[C@H]1[C@@H](N(C)C)CCN1c1nc(N[C@@H]2CCCN(C)C2=O)c2c3c(c(-c4ccc(F)c5sc(N)c(C#N)c45)c(Cl)c2n1)COC3] | 649 |
| 16C [8] | 2-Amino-4-(5-chloro-3-((2S,3S)-3-(isopropylamino)-2-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 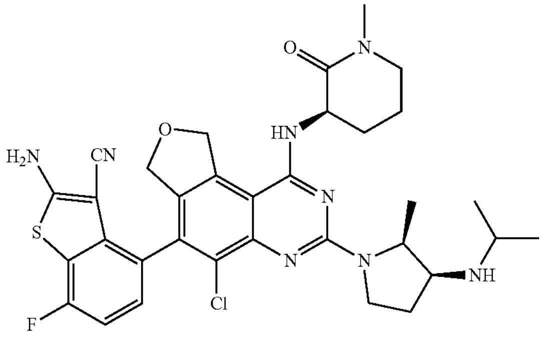 [SMILES: CC(C)N[C@H]1CCN(c2nc(N[C@@H]3CCCN(C)C3=O)c3c4c(c(-c5ccc(F)c6sc(N)c(C#N)c56)c(Cl)c3n2)COC4)[C@H]1C] | 663 |
| 17C [8] | 2-Amino-4-(5-chloro-3-(3-(dimethylamino)-3-methylazetidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 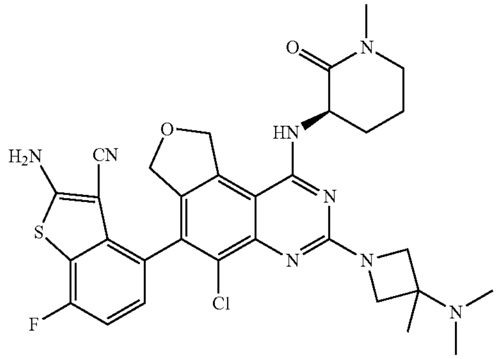 [SMILES: CN1CCC[C@@H](Nc2nc(N3CC(C)(N(C)C)C3)nc3c(Cl)c(-c4ccc(F)c5sc(N)c(C#N)c45)c4c(c23)COC4)C1=O] | 635 |
| 18C [8, 35] | 2-Amino-4-(5-chloro-3-(3-(dimethylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 1 | 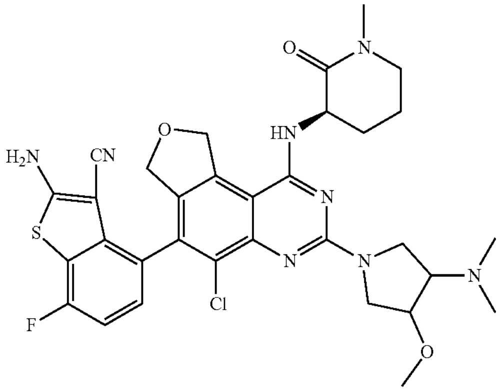 [SMILES: COC1CN(c2nc(N[C@@H]3CCCN(C)C3=O)c3c4c(c(-c5ccc(F)c6sc(N)c(C#N)c56)c(Cl)c3n2)COC4)CC1N(C)C] | 665 |

TABLE 17-continued

| Preparation | Chemical Name | Structure | MS (ES) m/z (M + 1) |
|---|---|---|---|
| 19C [8, 35] | 2-Amino-4-(5-chloro-3-(3-(dimethylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 2 | 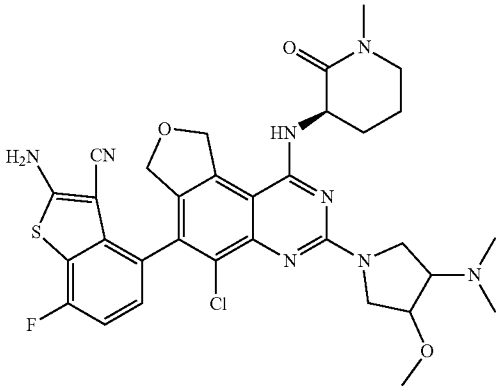 [SMILES: COC1CN(c2nc(N[C@@H]3CCCN(C)C3=O)c3c4c(c(-c5ccc(F)c6sc(N)c(C#N)c56)c(Cl)c3n2)COC4)CC1N(C)C] | 665 |
| 20C [8, 36] | 2-Amino-4-(5-chloro-3-(3-(dimethylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 1 | 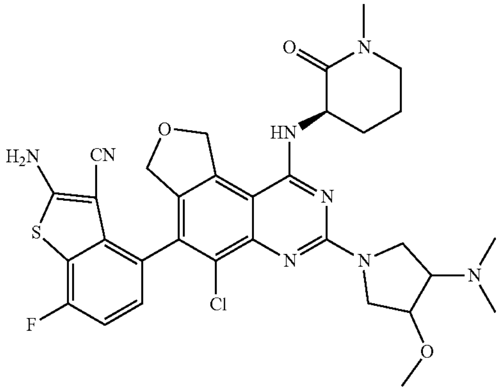 [SMILES: COC1CN(c2nc(N[C@@H]3CCCN(C)C3=O)c3c4c(c(-c5ccc(F)c6sc(N)c(C#N)c56)c(Cl)c3n2)COC4)CC1N(C)C] | 665 |
| 21C [8, 36] | 2-Amino-4-(5-chloro-3-(3-(dimethylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 2 | 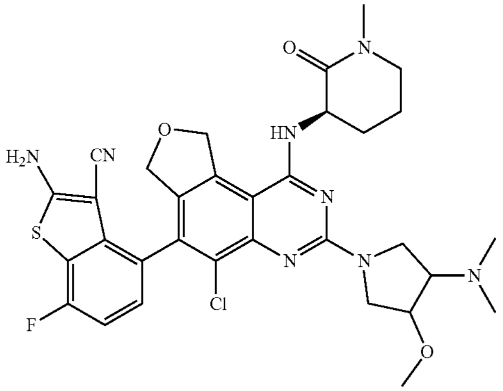 [SMILES: COC1CN(c2nc(N[C@@H]3CCCN(C)C3=O)c3c4c(c(-c5ccc(F)c6sc(N)c(C#N)c56)c(Cl)c3n2)COC4)CC1N(C)C] | 665 |

TABLE 17-continued

| Preparation | Chemical Name | Structure | MS (ES) m/z (M + 1) |
|---|---|---|---|
| 22C [8] | 2-Amino-4-(5-chloro-3-((2S,3S)-3-(((S)-2-hydroxypropyl)amino)-2-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 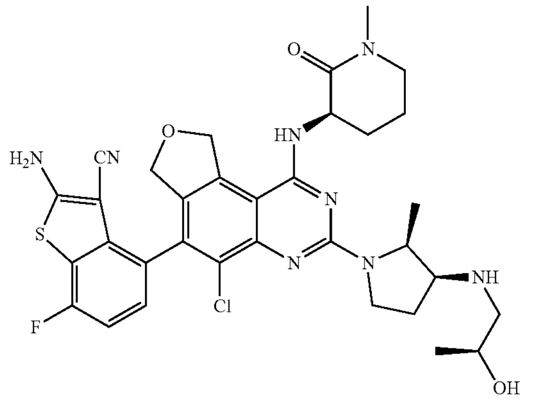 [SMILES: C[C@H](O)CN[C@H]1CCN(c2nc(N[C@@H]3CCCN(C)C3=O)c3c4c(c(-c5ccc(F)c6sc(N)c(C#N)c56)c(Cl)c3n2)COC4)[C@H]1C] | 679 |
| 23C [8, 37] | 2-Amino-4-(5-chloro-3-(3-(isopropylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 1 | 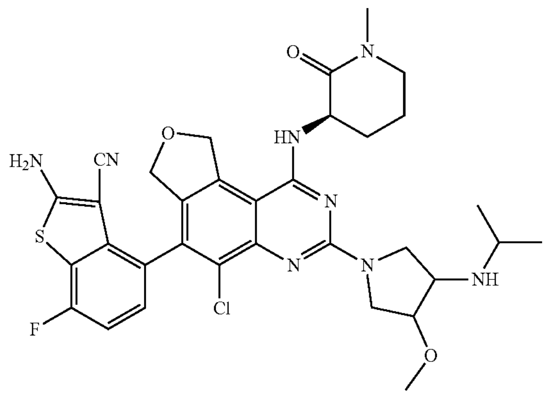 [SMILES: COC1CN(c2nc(N[C@@H]3CCCN(C)C3=O)c3c4c(c(-c5ccc(F)c6sc(N)c(C#N)c56)c(Cl)c3n2)COC4)CC1NC(C)C] | 679 |
| 24C [8, 37] | 2-Amino-4-(5-chloro-3-(3-(isopropylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 2 | 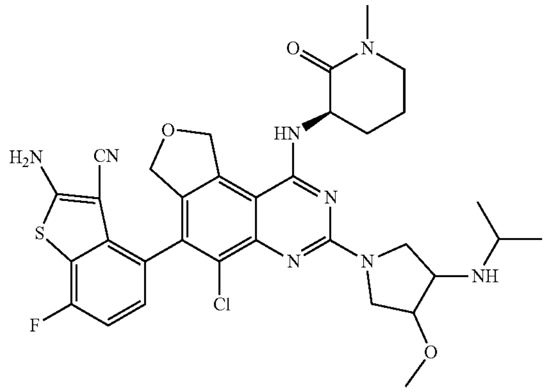 [SMILES: COC1CN(c2nc(N[C@@H]3CCCN(C)C3=O)c3c4c(c(-c5ccc(F)c6sc(N)c(C#N)c56)c(Cl)c3n2)COC4)CC1NC(C)C] | 679 |

TABLE 17-continued

| Preparation | Chemical Name | Structure | MS (ES) m/z (M + 1) |
| --- | --- | --- | --- |
| 25C [8, 38] | 2-Amino-4-(5-chloro-3-(3-(isopropylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 1 | 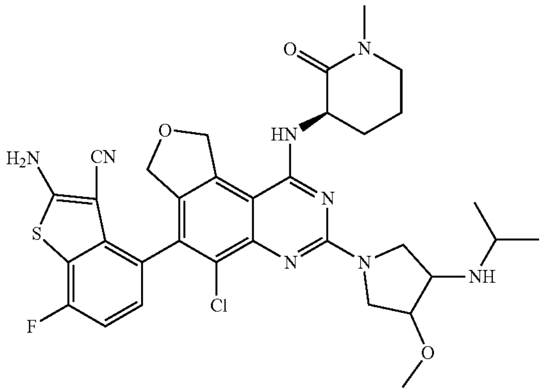 [SMILES: COC1CN(c2nc(N[C@@H]3CCCN(C)C3=O)c3c4c(c(-c5ccc(F)c6sc(N)c(C#N)c56)c(Cl)c3n2)COC4)CC1NC(C)C] | 679 |
| 26C [8, 38] | 2-Amino-4-(5-chloro-3-(3-(isopropylamino)-4-methoxypyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile, Isomer 2 | 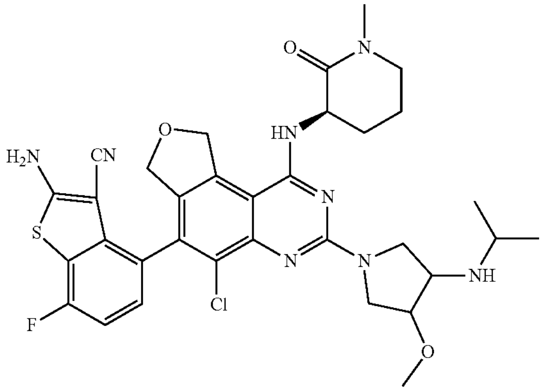 [SMILES: COC1CN(c2nc(N[C@@H]3CCCN(C)C3=O)c3c4c(c(-c5ccc(F)c6sc(N)c(C#N)c56)c(Cl)c3n2)COC4)CC1NC(C)C] | 679 |
| 27C [8] | 2-Amino-4-(5-chloro-3-((2S,3S)-3-(isopropyl(methyl)amino)-2-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 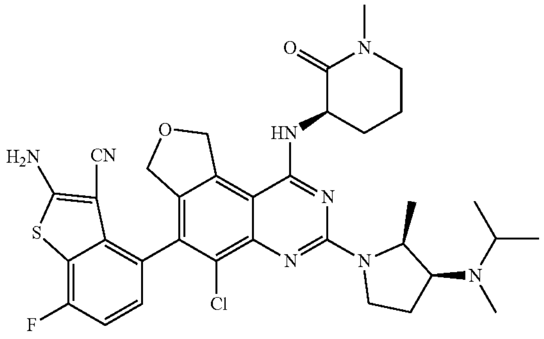 [SMILES: CC(C)N(C)[C@H]1CCN(c2nc(N[C@@H]3CCCN(C)C3=O)c3c4c(c(-c5ccc(F)c6sc(N)c(C#N)c56)c(Cl)c3n2)COC4)[C@H]1C] | 677 |
| 28C [8] | 2-Amino-4-(5-chloro-3-((3R,4S)-3-(isopropylamino)-4-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 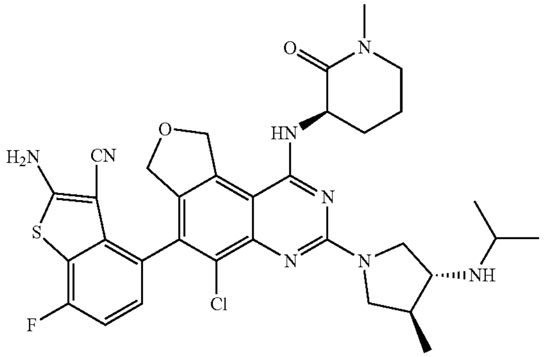 [SMILES: CC(C)N[C@H]1CN(c2nc(N[C@@H]3CCCN(C)C3=O)c3c4c(c(-c5ccc(F)c6sc(N)c(C#N)c56)c(Cl)c3n2)COC4)C[C@@H]1C] | 663 |

TABLE 17-continued

| Preparation | Chemical Name | Structure | MS (ES) m/z (M + 1) |
|---|---|---|---|
| 29C [8] | 2-Amino-4-(5-chloro-3-((3R,4S)-3-(isopropyl(methyl)amino)-4-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 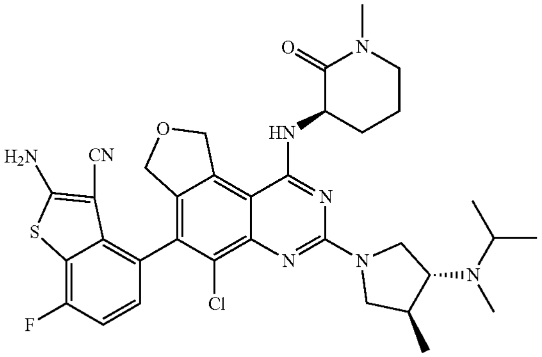 [SMILES: CC(C)N(C)[C@H]1CN(c2nc(N[C@@H]3CCCN(C)C3=O)c3c4c(c(-c5ccc(F)c6sc(N)c(C#N)c56)c(Cl)c3n2)COC4)C[C@@H]1C] | 677 |
| 30C [8, 39] | 2-Amino-4-(5-chloro-3-(3-(dimethylamino)-4-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile. Isomer 1 | 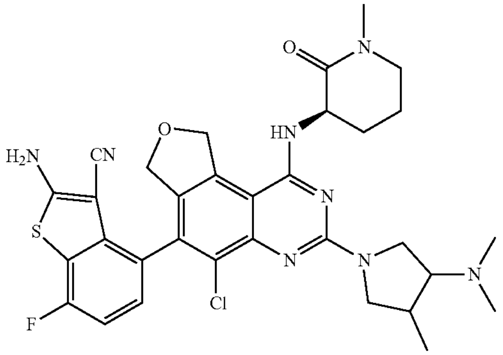 [SMILES: CC1CN(c2nc(N[C@@H]3CCCN(C)C3=O)c3c4c(c(-c5ccc(F)c6sc(N)c(C#N)c56)c(Cl)c3n2)COC4)CC1N(C)C] | 649 |
| 31C [8, 39] | 2-Amino-4-(5-chloro-3-(3-(dimethylamino)-4-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile. Isomer 2 | 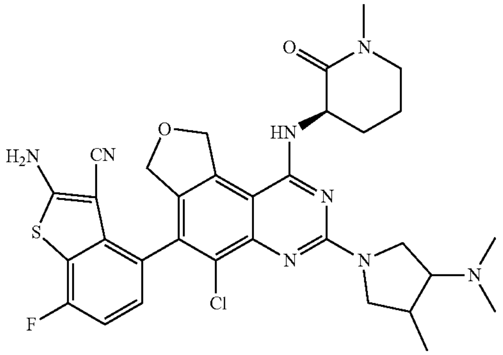 [SMILES: CC1CN(c2nc(N[C@@H]3CCCN(C)C3=O)c3c4c(c(-c5ccc(F)c6sc(N)c(C#N)c56)c(Cl)c3n2)COC4)CC1N(C)C] | 649 |
| 32C [8] | 2-Amino-4-(5-chloro-1-(((R)-1-methyl-2-oxopiperidin-3-yl)amino)-3-((R)-3-(4-methylpiperazin-1-yl)pyrrolidin-1-yl)-7,9-dihydrofuro[3,4-f]quinazolin-6-yl)-7-fluorobenzo[b]thiophene-3-carbonitrile | 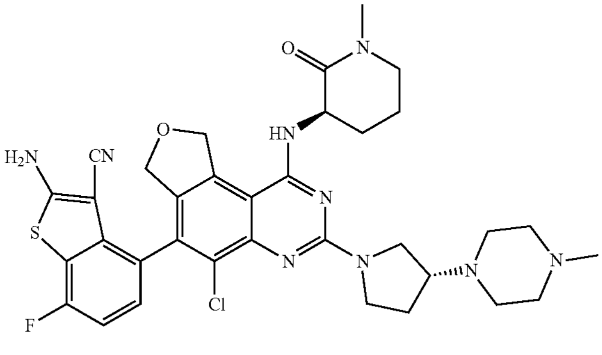 [SMILES: CN1CCN([C@@H]2CCN(c3nc(N[C@@H]4CCCN(C)C4=O)c4c5c(c(-c6ccc(F)c7sc(N)c(C#N)c67)c(Cl)c4n3)COC5)C2)CC1] | 690 |

TABLE 17-continued

| Preparation | Chemical Name | Structure | MS (ES) m/z (M + 1) |
|---|---|---|---|
| 33C [8] | 2-Amino-4-(5-chloro-3-((2S,3R)-3-((dimethylamino)methyl)-2-methylpyrrolidin-1-yl)-1-(((R)-1-methyl-2-oxopiperidin-3-yl)amino)-7,9-dihydrofuro[3,4-f]quinazolin-6-yl)-7-fluorobenzo[b]thiophene-3-carbonitrile | 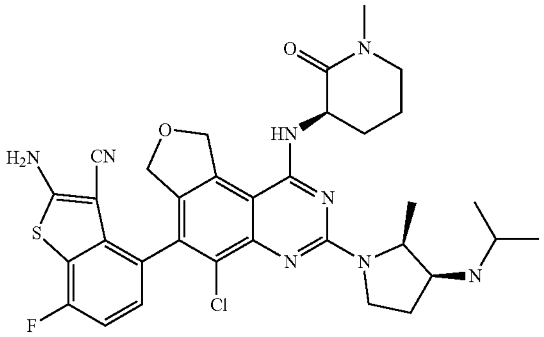 [SMILES: CC(C)N[C@H]1CCN(c2nc(N[C@@H]3CCCN(C)C3=O)c3c4c(c(-c5ccc(F)c6sc(N)c(C#N)c56)c(Cl)c3n2)COC4)[C@H]1C] | 663 |
| 34C [8] | 2-Amino-4-(5-chloro-1-(((R)-1-methyl-2-oxopiperidin-3-yl)amino)-3-((2S,3S)-2-methyl-3-(4-methylpiperazin-1-yl)pyrrolidin-1-yl)-7,9-dihydrofuro[3,4-f]quinazolin-6-yl)-7-fluorobenzo[b]thiophene-3-carbonitrile | 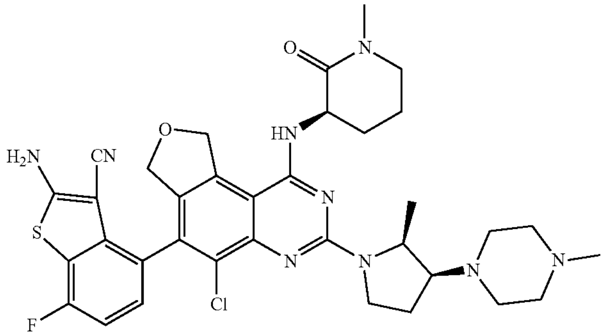 [SMILES: C[C@H]1[C@@H](N2CCN(C)CC2)CCN1c1nc(N[C@@H]2CCCN(C)C2=O)c2c3c(c(-c4ccc(F)c5sc(N)c(C#N)c45)c(Cl)c2n1)COC3] | 704 |
| 35C | 2-Amino-7-fluoro-4-(5-fluoro-1-(((5-methyl-1,2,4-oxadiazol-3-yl)methyl)amino)-3-((S)-1-((S)-1-methylpyrrolidin-2-yl)ethoxy)-7,9-dihydrofuro[3,4-f]quinazolin-6-yl)thieno[3,2-c]pyridine-3-carbonitrile | 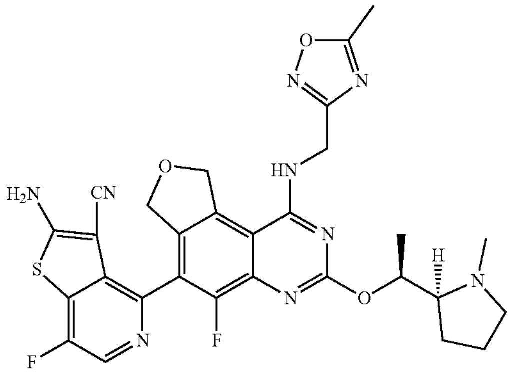 [SMILES: Cc1nc(CNc2nc(O[C@@H](C)[C@@H]3CCCN3C)nc3c(F)c(-c4ncc(F)c5sc(N)c(C#N)c45)c4c(c23)COC4)no1] | 620 |
| 36C [40] | 2-Amino-4-(5-chloro-1-(((5-methyl-1,2,4-oxadiazol-3-yl)methyl)amino)-3-((S)-1-((S)-1-methylpyrrolidin-2-yl)ethoxy)-7,9-dihydrofuro[3,4-f]quinazolin-6-yl)-7-fluorobenzo[b]thiophene-3-carbonitrile, Atropisomer 1 | 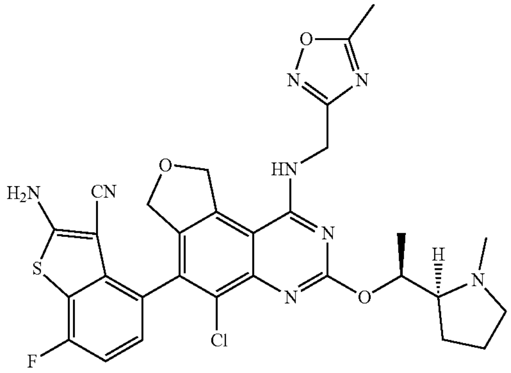 [SMILES: Cc1nc(CNc2nc(O[C@@H](C)[C@@H]3CCCN3C)nc3c(Cl)c(-c4ccc(F)c5sc(N)c(C#N)c45)c4c(c23)COC4)no1] | 635 |

TABLE 17-continued

| Preparation | Chemical Name | Structure | MS (ES) m/z (M + 1) |
|---|---|---|---|
| 37C [40] | 2-Amino-4-(5-chloro-1-(((5-methyl-1,2,4-oxadiazol-3-yl)methyl)amino)-3-((S)-1-((S)-1-methylpyrrolidin-2-yl)ethoxy)-7,9-dihydrofuro[3,4-f]quinazolin-6-yl)-7-fluorobenzo[b]thiophene-3-carbonitrile, Atropisomer 2 | 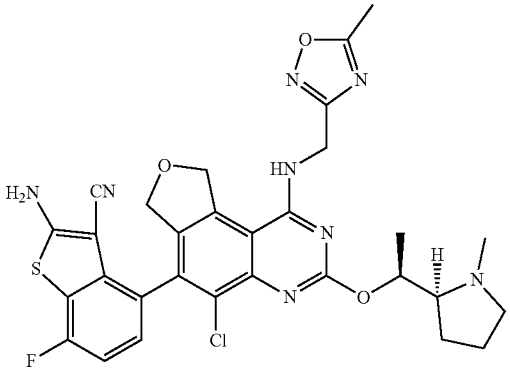 [SMILES: Cc1nc(CNc2nc(O[C@@H](C)[C@@H]3CCCN3C)nc3c(Cl)c(-c4ccc(F)c5sc(N)c(C#N)c45)c4c(c23)COC4)no1] | 635 |
| 38C [41] | 2-Amino-4-(5-chloro-3-((S)-1-((S)-1-methylpyrrolidin-2-yl)ethoxy)-1-((pyridazin-3-ylmethyl)amino)-7,9-dihydrofuro[3,4-f]quinazolin-6-yl)-7-fluorobenzo[b]thiophene-3-carbonitrile, Atropisomer 1 | 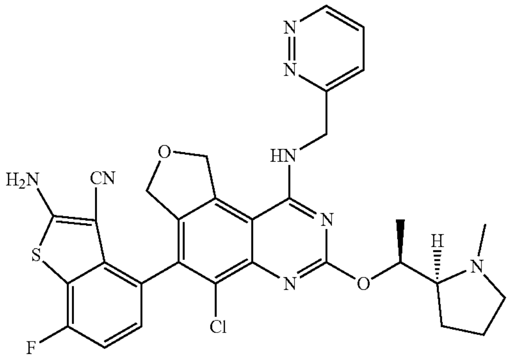 [SMILES: C[C@H](Oc1nc(NCc2cccnn2)c2c3c(c(-c4ccc(F)c5sc(N)c(C#N)c45)c(Cl)c2n1)COC3)[C@@H]1CCCN1C] | 631 |
| 39C [41] | 2-Amino-4-(5-chloro-3-((S)-1-((S)-1-methylpyrrolidin-2-yl)ethoxy)-1-((pyridazin-3-ylmethyl)amino)-7,9-dihydrofuro[3,4-f]quinazolin-6-yl)-7-fluorobenzo[b]thiophene-3-carbonitrile, Atropisomer 2 | 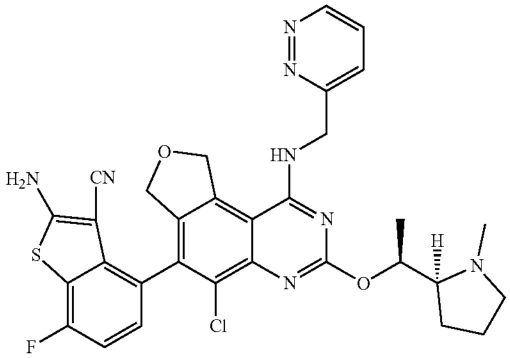 [SMILES: C[C@H](Oc1nc(NCc2cccnn2)c2c3c(c(-c4ccc(F)c5sc(N)c(C#N)c45)c(Cl)c2n1)COC3)[C@@H]1CCCN1C] | 631 |
| 40C [42] | 2-Amino-4-(5-chloro-3-((S)-1-((2S,4R)-4-methoxy-1-methylpyrrolidin-2-yl)ethoxy)-1-((pyridazin-3-ylmethyl)amino)-7,9-dihydrofuro[3,4-f]quinazolin-6-yl)-7-fluorobenzo[b]thiophene-3-carbonitrile, Atropisomer 1 | 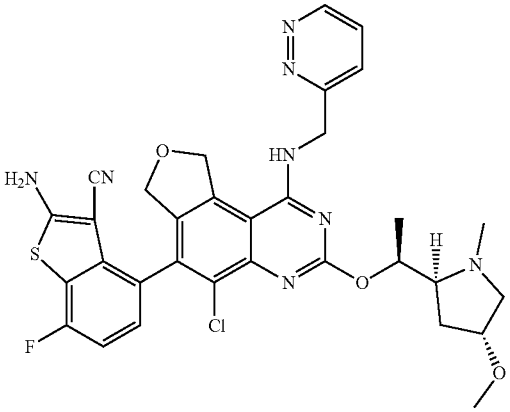 [SMILES: CO[C@@H]1C[C@@H]([C@H](C)Oc2nc(NCc3cccnn3)c3c4c(c(-c5ccc(F)c6sc(N)c(C#N)c56)c(Cl)c3n2)COC4)N(C)C1] | 661 |

TABLE 17-continued

| Preparation | Chemical Name | Structure | MS (ES) m/z (M + 1) |
|---|---|---|---|
| 41C [42] | 2-Amino-4-(5-chloro-3-((S)-1-((2S,4R)-4-methoxy-1-methylpyrrolidin-2-yl)ethoxy)-1-((pyridazin-3-ylmethyl)amino)-7,9-dihydrofuro[3,4-f]quinazolin-6-yl)-7-fluorobenzo[b]thiophene-3-carbonitrile, Atropisomer 2 | 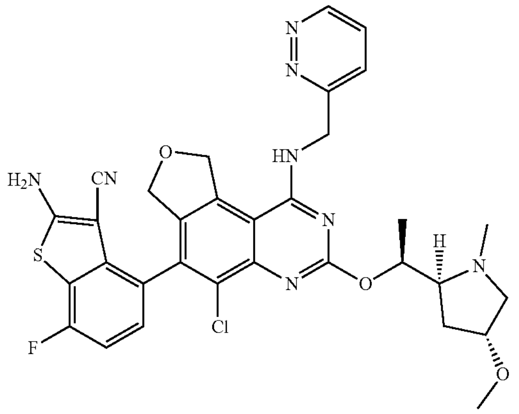 [SMILES: CO[C@@H]1C[C@@H]([C@H](C)Oc2nc(NCc3cccnn3)c3c4c(c(-c5ccc(F)c6sc(N)c(C#N)c56)c(Cl)c3n2)COC4)N(C)C1] | 661 |
| 42C | 2-Amino-7-fluoro-4-(5-fluoro-3-((S)-1-((2S,4R)-4-fluoro-1-methylpyrrolidin-2-yl)ethoxy)-1-((pyridazin-3-ylmethyl)amino)-7,9-dihydrofuro[3,4-f]quinazolin-6-yl)thieno[3,2-c]pyridine-3-carbonitrile | 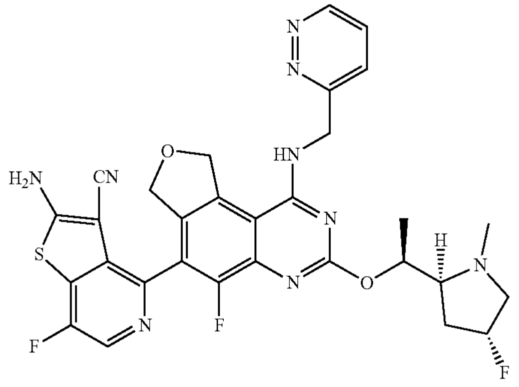 [SMILES: C[C@H](Oc1nc(NCc2cccnn2)c2c3c(c(-c4ncc(F)c5sc(N)c(C#N)c45)c(F)c2n1)COC3)[C@@H]1C[C@@H](F)CN1C] | 634 |
| 43C | 2-Amino-4-(3-((2S,3S)-3-(dimethylamino)-2-methylpyrrolidin-1-yl)-5-fluoro-1-((pyridazin-3-ylmethyl)amino)-7,9-dihydrofuro[3,4-f]quinazolin-6-yl)-7-fluorothieno[3,2-c]pyridine-3-carbonitrile | 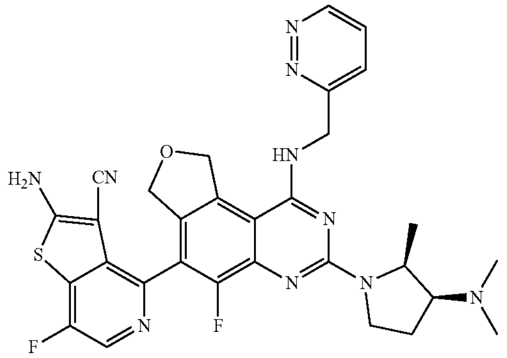 [SMILES: C[C@H]1[C@@H](N(C)C)CCN1c1nc(NCc2cccnn2)c2c3c(c(-c4ncc(F)c5sc(N)c(C#N)c45)c(F)c2n1)COC3] | 615 |
| 44C | 2-Amino-4-(3-((2S,3S)-3-(dimethylamino)-2-methylpyrrolidin-1-yl)-5-fluoro-1-(((R)-1-methyl-2-oxopyrrolidin-3-yl)amino)-7,9-dihydrofuro[3,4-f]quinazolin-6-yl)-7-fluorothieno[3,2-c]pyridine-3-carbonitrile | 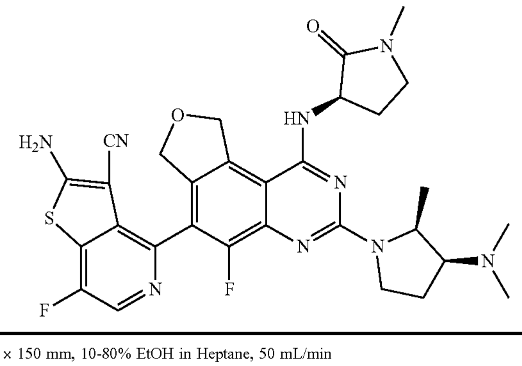 | 620 |

[1] Prep-Chiral-HPLC; Phenomenex Lux Cellulose-4, 30 × 150 mm, 10-80% EtOH in Heptane, 50 mL/min

[2] Prep-Chiral-HPLC; Phenomenex Lux Cellulose-4, 30 × 150 mm, 10-50% (1:1 MeOH:EtOH) in Heptane, 50 mL/min TABLE 17-continued

| Preparation Chemical Name | Structure | MS (ES) m/z (M + 1) |
|---|---|---|

[3] Prep-Chiral-HPLC; Phenomenex Lux Cellulose-4, 30 × 150 mm, 10-60% (1:1 MeOH:EtOH) in Heptane, 50 mL/min
[4] Prep-Chiral-HPLC; Phenomenex Lux Cellulose-4, 30 × 150 mm, 10-60% (1:1 MeOH:EtOH) in Heptane, 50 mL/min
[5] Reverse Phase; C18, 25-100% Acetonitrile in (5 mM ammonium acetate in 95:5 water:MeOH)
[6] Prep-Chiral-HPLC; Phenomenex Lux i-Amylose-1, 30 × 150 mm, 10-50% EtOH in Heptane, 42.5 mL/min
[7] Chiral SFC; Phenomenex Lux Cellulose-4, 30 × 150 mm, 34% (MeOH w/0.1% isopropylamine) in $CO_2$, 50 mL/min
[8] Clean atropisomer, chiral purification from Preparation 7A
[9] Prep-Chiral-HPLC; Phenomenex Lux Cellulose-4, 30 × 150 mm, 20-90% EtOH in Heptane, 50 mL/min
[10] Prep-Chiral-HPLC; Phenomenex Lux Cellulose-4, 30 × 150 mm, 20-100% EtOH in Heptane, 50 mL/min
[11] Prep-Chiral-HPLC; Phenomenex Lux Cellulose-2, 30 × 150 mm, 25-95% EtOH in Heptane, 42.5 mL/min
[12] Reverse Phase; C18, 25-100% Acetonitrile in (0.1% formic acid in water)
[13] Prep-Chiral-HPLC; Phenomenex Lux Cellulose-4, 30 × 150 mm, 20-90% EtOH in Heptane, 50 mL/min
[14] Reverse Phase; C18, 28-100% Acetonitrile in (5 mM ammonium acetate in 95:5 water:MeOH)
[15] Reverse Phase; C18, 5-100% (95:5 Acetonitrile:water) in (10 mM ammonium bicarbonate pH 10, 5% MeOH)
[16] Reverse Phase; C18, 5-100% Acetonitrile in (5 mM ammonium acetate in 95:5 water:MeOH)
[17] Prep-Chiral-HPLC; Phenomenex Lux Cellulose-4, 30 × 150 mm, 10-85% EtOH in Heptane, 50 mL/min
[18] Reverse Phase; C18, 26-100% Acetonitrile in (5 mM ammonium acetate in 95:5 water:MeOH)
[19] Prep-Chiral-HPLC; Phenomenex Lux Cellulose-4, 30 × 150 mm, 20-80% EtOH in Heptane, 50 mL/min
[20] Prep-Chiral-HPLC; Phenomenex Lux Cellulose-4, 30 × 150 mm, 10-65% (1:1 MeOH:EtOH) in Heptane, 50 mL/min
[21] Prep-Chiral-HPLC; Phenomenex Lux Cellulose-4, 30 × 150 mm, 10-82% EtOH in Heptane, 40 mL/min
[22] Prep-Chiral-HPLC; Phenomenex Lux Cellulose-4, 30 × 150 mm, 10-75% EtOH in Heptane, 50 mL/min
[23] Prep-Chiral-HPLC; Phenomenex Lux Cellulose-4, 30 × 150 mm, 10-80% EtOH in Heptane, 50 mL/min
[24] Prep-Chiral-HPLC; Phenomenex Lux Cellulose-4, 30 × 150 mm, 15-85% EtOH in Heptane, 50 mL/min
[25] Prep-Chiral-HPLC; Phenomenex Lux Cellulose-4, 30 × 150 mm, 10-50% (1:1 MeOH:EtOH) in Heptane, 50 mL/min
[26] Prep-Chiral-HPLC; Phenomenex Lux i-Amylose-3, 30 × 150 mm, 10-70% (EtOH w/0.1% isopropylamine) in Heptane, 42.5 mL/min
[27] Prep-Chiral-HPLC; Phenomenex Lux Cellulose-4, 30 × 150 mm, 10-45% (1:1 MeOH:EtOH) in Heptane, 42.5 mL/min
[28] Prep-Chiral-HPLC; Phenomenex Lux Cellulose-4, 30 × 150 mm, 10-75% (1:1 MeOH:EtOH w/0.1% isopropylamine) in Heptane, 42.5 mL/min
[29] Prep-Chiral-HPLC; Phenomenex Lux Cellulose-4, 30 × 150 mm, 10-75% (1:1 MeOH:EtOH w/0.1% isopropylamine) in Heptane, 50 mL/min
[30] Clean atropisomer, chiral purification from Preparation 2B
[31] Reverse Phase; C18, 38-40% Acetonitrile in (10 mM ammonium bicarbonate in water) to give Atropisomer 1. Atropisomer 2 was further purified with Reverse Phase; C18, 36-50% Acetonitrile in (10 mM ammonium bicarbonate in water w/0.05% ammonium hydroxide)
[32] Prep-Chiral-HPLC; Chiralpak IA, 30 × 250 mm, 50% EtOH in (10 mM ammoniated methanol in Hexanes), 40 mL/min
[33] Prep-Chiral-HPLC; Chiralpak AD-3, 30 × 100 mm, 50% EtOH in (10 mM ammoniated methanol in Hexanes), 40 mL/min
[34] Prep-Chiral-HPLC; Chiralpak IA, 30 × 250 mm, 50% EtOH in (10 mM ammoniated methanol in Hexanes), 40 mL/min
[35] Clean Trans Isomer, Prep-Chiral-HPLC; Phenomenex Lux Cellulose-4, 30 × 150 mm, 10-100% (EtOH w/0.1% isopropylamine) in Heptane, 37.5 mL/min
[36] Clean Cis Isomer, Prep-Chiral-HPLC; Phenomenex Lux i-Cellulose-5, 30 × 150 mm, 10-75% (1:1 MeOH:EtOH w/0.1% isopropylamine) in Heptane, 37.5 mL/min
[37] Clean Trans Isomer, Prep-Chiral-HPLC; Phenomenex Lux i-Amylose-1, 30 × 150 mm, 15-50% (EtOH w/0.1% isopropylamine) in Heptane, 35.0 mL/min
[38] Clean Cis Isomer, Prep-Chiral-HPLC; Phenomenex Lux i-Amylose-1, 30 × 150 mm, 15-100% (EtOH w/0.1% isopropylamine) in Heptane, 35.0 mL/min
[39] Clean Trans Isomer, Prep-Chiral-HPLC; Phenomenex Lux Cellulose-2, 30 × 150 mm, 10-90% (EtOH w/0.1% isopropylamine) in Heptane, 42.5 mL/min
[40] Prep-Chiral-HPLC; Chiral NX(2), 30 × 250 mm, 30% EtOH in (10 mM ammoniated methanol in Hexanes), 40 mL/min
[41] Prep-Chiral-HPLC; Chiral NX(2), 30 × 250 mm, 30% EtOH in (10 mM ammoniated methanol in Hexanes), 40 mL/min
[42] Prep-Chiral-HPLC; Chiral NX(2), 30 × 250 mm, 30% EtOH in (10 mM ammoniated methanol in Hexanes), 40 mL/min

Biological Assays

The following assays demonstrate that the exemplified compounds are potent inhibitors of KRas G12C, G12D, and/or G12V and inhibit growth of certain tumors in vitro and/or in vivo.

Cellular Phospho-ERK AlphaLISA® Assay for KRAS Inhibition

The purpose of these assays is to quantify the ability of test compounds to selectively inhibit KRAS signaling in cells with amplified KRAS and expressing activating KRAS G12 mutations (Table 14). Cancer cell lines used in this study were selected based on the presence of homozygous activating KRAS G12 mutations, or amplification of the KRAS gene. In addition, these assays were performed in a set of RAS-less mouse embryonic fibroblast (MEF) cells which were engineered to only express KRAS wild type, HRAS, and NRAS, respectively (Table 14). MEF cells were used to confirm KRAS selectivity of the test compounds.

TABLE 14

Cell Line Information

| Cell Line Name | RAS Mutation/Features | Assay Seeding Density (Cells/Well) |
|---|---|---|
| MKN45 | WT KRAS Amplification/Human Gastric Cancer | 20,000 |
| SW620 | KRAS G12V/Human Colorectal Cancer | 20,000 |
| HPAC | KRAS G12D/Human Pancreatic Cancer | 2,500 |
| NCI-1373 | KRAS G12C/Human Lung Cancer | 5,000 |
| MEF-NRAS | RAS-less MEFs Expressing NRAS only | 20,000 |
| MEF-HRAS | RAS-less MEFs Expressing HRAS only | 10,000 |
| MEF-KRAS | RAS-less MEFs Expressing KRAS only | 2,500 |

The compounds' activity is determined by measuring changes in the phosphorylation levels of the downstream effector Extracellular Signal-regulated Kinase-1 and 2 (ERK1/2) in the compound treated cells. Phosphorylation levels of ERK-1/2 are measured using the AlphaLISA® SureFire® Ultra™ p-ERK 1/2 (Thr202/Tyr204) Assay Kit (#ALSU-PERK-A50K, PerkinElmer® Waltham, MA). The AlphaLISA® assay is a quantitative sandwich immunoassay that can be used to detect phosphorylation of target proteins from cellular lysates using bead-based Alpha technology. The assay kit contains two antibodies, one that binds the phospho-Thr202/Tyr204 epitope on ERK-1/2, and another one that recognizes a separate site on the protein. One of these antibodies is biotinylated and associated with streptavidin-coated Alpha Donor beads, the other antibody is conjugated to AlphaLISA® Acceptor beads. When ERK-1/2 is phosphorylated in cellular lysate, the Donor and Acceptor beads are brought into proximity with each other. When the Donor bead is excited by 600 nm wavelength light, a photosensitizer inside the bead converts ambient oxygen to an excited singlet state. When the Acceptor bead is within 200 nm of this reaction, the singlet oxygen reacts with the Acceptor leading to a chemiluminescent emission. The amount of light measured is proportional to the amount of phosphorylated ERK-1/2 in the lysate. The AlphaLISA® SureFire® Ultra™ p-ERK 1/2 (Thr202/Tyr204) Assay Kit contains AlphaLISA® antibody-conjugated Donor and Acceptor Beads, Lysis buffer concentrate, and a set of proprietary buffers (Activation Buffer, Reaction Buffer 1, Reaction Buffer 2, and Dilution Buffer).

To perform the assays, test compounds and controls are acoustically dispensed (Labcyte ECHO®, San Jose, CA) into a white 384-well assay plate (Proxiplate-384, PerkinElmer #6008280) in a 10-point 3-fold dilution series in 30 nL DMSO. Cells are then added to the assay plate in 8 μL per well assay medium (HBSS, Sigma #55021C, 10% FBS, GIBCO #10082-147) at a cell line specific density (Table 14). The final compound concentrations range from 0.5 to 10,000 nM and the final DMSO concentration is 0.375% in each well. Maximum signal control wells contain 0.375% DMSO only (negative control), and minimum signal control wells contain 10,000 nM control compound (positive control). Cells in suspension are incubated with the test and reference compounds for 2 h at 37° C./5% $CO_2$. Following the 2 h incubation, cells are lysed by adding 2 μL of the AlphaLISA® Lysis buffer concentrate (5×) supplemented with protease/phosphatase inhibitor cocktail (Thermo Scientific #78442). The assay plate is covered with an opaque lid and shaken at 750 rpm on a multi-plate shaker (Heidolph, Schwabach, Germany) for 30 min at room temperature to induce cell lysis. During the lysis, the AlphaLISA® Acceptor beads are diluted 1:50 in a prepared buffer mixture (1:1 AlphaLISA® Reaction Buffers 1 and 2 with a 1:25 dilution of AlphaLISA® Activation Buffer). Following cell lysis, plates are centrifuged briefly, and 5 μL per well prepared Acceptor beads are added. The plate is then covered and incubated in the dark for 2 h at room temperature. During the Acceptor bead incubation, Donor beads are prepared by diluting the Alpha streptavidin Donor beads 1:50 in AlphaLISA® Dilution buffer. Following the Acceptor bead incubation, 5 μL per well of Donor bead mixture is added to the plates. Plates are then covered and allowed to incubate in the dark at room temperature for 2 h. After this incubation period, the AlphaLISA signal is read using a PHERAstar® FSX multimode plate reader (BMG Labtech, Ortenberg, Germany) equipped with an AlphaLISA® compatible optics cube.

Raw signal obtained from the AlphaLISA® assay is analyzed using Genedata Screener® 17.0.3. Within the program, data is normalized to 32 wells treated with inhibition control (max inhibition/positive control) and 32 wells treated with 0.375% DMSO only (minimum inhibition/negative control) to calculate the % Activity of the compound:

$$\%\ \text{Activity} = 100 \times \left(1 - \frac{(\text{treated value} - \text{positive control})}{(\text{negative control} - \text{positive control})}\right) \quad \text{eq. 1}$$

% Activity values are fit to a four-parameter non-linear logistic equation using Genedata Screener® 17.0.3. to determine $IC_{50}$ values:

$$y = \text{Bottom} + \frac{\text{Top} - \text{Bottom}}{1 + \left(\frac{10^{Log(IC_{50})}}{10^{x}}\right)^{h}} \quad \text{eq. 2}$$

Where y=% Activity, Bottom=minimum asymptote, Top=maximum asymptote, x=compound concentration, $IC_{50}$=the compound concentration where half maximal activity is achieved, and h=the Hill Coefficient.

In the above assays, compounds of Examples indicated herein were tested and exhibited an ability to reduce levels of phosphorylated ERK-1/2 in cells expressing KRAS and KRAS variants indicating inhibition of constitutive RAS activity in cells expressing KRAS G12C (Examples 1-10, 12, 13, 15, 16, 18-20, 22, 23, 25, 28, 1A, 3A-5A, 7A-12A, 14A, 15A, 17A-20A, 22A-26A, 28A, 29A, 31A-35A, 37A-39A, 41A-43A, 45A, 47A, 49A, 51A, 52A, 2B-4B, 7B, 10B-12B, 14B, 15B, 18B-22B, 24B-28B, 31B, 1C-4C, 6C, 8C, 10C, 12C-36C, 38C, and 40C-44C), KRAS G12D (Examples 1, 2, 5, 6, 9, 10, 13, 15, 16, 18-20, 22, 23, 25, 28, 1A, 3A-5A, 7A-12A, 14A, 15A, 17A, 18A, 20A, 22A, 24A-26A, 28A, 31A, 32A, 34A, 35A, 37A, 39A, 41A, 43A, 52A, 7B, 11B, 12B, 14B, 19B-22B, 24B, 31B, 3C, 6C, 10C, 13C-19C, 21C-34C, 36C, 38C, 40C, and 44C), KRAS G12V (Examples 1-10, 12, 13, 15, 16, 18-20, 22, 23, 25-29, 1A, 3A-5A, 7A-12A, 14A, 15A, 17A-20A, 22A, 24A-26A, 28A-35A, 37A-39A, 41A, 43A, 45A, 47A, 49A, 51A, 52A, 2B, 4B, 5B, 7B, 10B-16B, 18B-25B, 27B, 31B, 1C-4C, 6C, 8C, 10C, 12C-34C, 36C, 38C, 40C, and 42C-44C), or KRAS WT (Examples 1-10, 12, 13, 15, 16, 18-20, 22, 23, 25, 27-29, 1A, 3A-5A, 7A-12A, 14A, 15A, 17A-20A, 22A, 24A-26A, 28A, 29A, 31A, 32A, 34A, 35A, 37A, 39A, 41A, 43A, 45A, 47A, 49A, 51A, 52A, 3B, 4B, 7B, 11B, 12B, 14B, 16B, 19B, 20B, 22B, 24B, 31B, 3C, 4C, 6C, 8C, 1° C., 12C-36C, 38C, 40C, and 42C-44C), with a relative IC50 of <500 nM. Compounds of Examples 1-6, 8-11, 14-21, 24, 26, 1A, 2A, 4A-6A, 8A-16A, 19A-23A, 25A, 27A, 29A-33A, 36A, 38A, 40A, 42A, 44A-52A, 113-1013, 1313-1813, 21-23B, 2513-3013, 1C-9C, 11C, 20C, 21C, 24C, 26C, 32C, 35C, 37C, 39C, and 41C-44C were tested in the Mouse Embryonic Fibroblasts cell line assays above (MEF-NRAS, MEF-HRAS) and all exhibited a relative IC50 of >2 μM. Compounds of Examples 1, 3-6, 8-10, 12, 13, 15, 16, 18-20, 22, 23, 25, 26, 28, 1A, 3A-12A, 14A, 15A, 17A-20A, 22A-26A, 28A-35A, 37A-39A, 41A, 43A, 45A, 47A, 49A, 51A, 52A, 2B-5B, 7B, 8B, 10B, 11B, 13B-16B, 18B-25B, 27B, 31B, 2C, 4C, 6C, 8C, 10C, 13C-34C, 38C, 40C, and 42C-44C were tested in the three assays above (SW620, MEF-NRAS and MEF-HRAS Cellular Phospho-ERK AlphaLISA® Assays) and all showed a significant (i.e., greater than 10-fold) selective inhibition preference for KRas G12V mutant over HRAS and NRAS.

This data shows that compounds of Formula I as described herein are potent inhibitors of KRAS human cancer cells expressing KRAS demonstrating the ability to inhibit KRAS G12C, G12D or G12V mutants with a significant selective inhibition preference for KRAS mutants over HRAS or NRAS.

TABLE 15

| Abbreviations | |
|---|---|
| KRAS | Kirsten Rat Sarcoma Virus |
| NRAS | Neuroblastoma RAS Viral Oncogene Homolog |
| HRAS | Harvey Rat Sarcoma Virus |
| MEF | Mouse Embryonic Fibroblasts |
| ERK | Extracellular Signal-Regulated Kinase |
| AlphaLISA | Alpha-Linked Immunosorbent Assay |
| DMSO | Dimethyl Sulfoxide |
| HBSS | Hank's Balanced Salt Solution |
| FBS | Fetal Bovine Serum |
| $CO_2$ | Carbon Dioxide |

What is claimed is:

1. A compound of the formula:

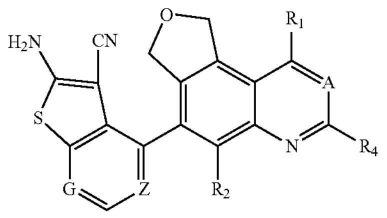

wherein:

A is —C(H)—, or —N—;

Z is —C($R_{3c}$)— or —N—;

G is —C($R_{3b}$)— or —N—;

$R_1$ is a group of the formula

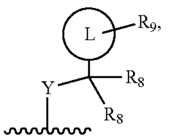

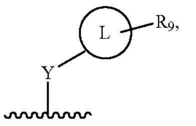

or

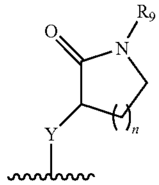

wherein n is 0, 1, or 2;

Y is either —N($R_8$)—, or —O—;

L is a 5-6 membered heteroaryl containing 1 to 3 heteroatoms selected from O, N, or S, wherein the 5-6 membered heteroaryl may be optionally fused with a $C_{3-6}$ cycloalkyl ring to form a bicyclic ring structure;

$R_2$ is H, halogen, or methyl;

$R_{3b}$, and $R_{3c}$ are each independently H, halogen, or methyl;

$R_4$ is H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —CH($CH_3$)—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; or $R_4$ is a N-linked cyclic amine or a group of the formula

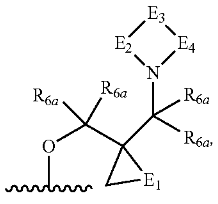

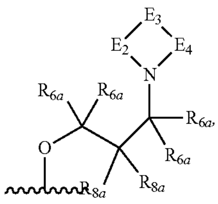

or

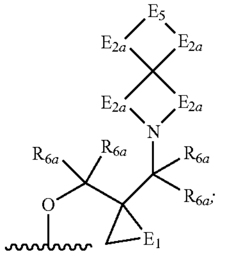

wherein the N-linked cyclic amine is a N-linked:

azetidine substituted with $R_{4a}$ and $R_{4b}$;

pyrrolidine, piperidine, piperazine, morpholine, diazepane, imidazole or pyrazole; each of which is optionally bridged by a $C_{1-3}$ alkylene, and each of which is optionally substituted with one or more halogen; hydroxyl; —$NR_{6a}R_{6a}$; (1-methylpiperidin-4-yl)oxy; $C_{1-3}$ alkoxy optionally substituted with —$NR_{6a}R_{6a}$; $C_{1-3}$ alkyl optionally substituted with one or more halogen, —$NR_{6a}R_{6a}$ or hydroxyl; an imidazole optionally substituted with a methyl; a monocyclic ring selected from azetidine, piperidine, piperazine, morpholine, oxazepane, or diazepane; a bicycle selected from hexahydro-1H-furo[3,4-c]pyrrole, octahydropyrrolo[3,4-c]pyrrole, or octahydropyrrolo[1,2-a]pyrazine; or a spirocycle selected from 4,7-diazaspiro[2.5]octane, 2-oxa-7-azaspiro[3.5]nonane, 2,6-diazaspiro[3.4]octane or 2-azaspiro[3.3]heptane; wherein the monocyclic ring is optionally bridged by a $C_{1-3}$ alkylene, and can optionally be substituted with one or more halogen, hydroxyl, —CN, $C_{1-3}$ alkoxy, —$NR_{10}R_{10}$, cyclopropyl, oxetane, —CO—$C_{1-3}$ alkyl, or a $C_{1-3}$ alkyl optionally substituted with hydroxyl, $C_{1-3}$ alkoxy, —$NR_{10}R_{10}$, halogen, or —$CF_3$; and wherein the bicyclo or spirocyclo is each optionally substituted with a methyl or a halogen; or 2,6-diazabicyclo[3.2.0]heptane, 3,6-diazabicyclo[3.2.0]heptane, 3,6-diazabicyclo[3.2.1]octane, 2,6-diazabicyclo[3.2.1]octane, 3-azabicyclo[3.1.0]hexane, 3-azabicyclo[3.2.0]heptane, 2-azabicyclo[3.2.0]heptane, octahydro-1H-pyrrolo[3,4-b]pyridine, octahydro-1H-pyrrolo[3,2-b]pyridine, octahydro-6H-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2 (3H)-one, hexahydro-1H-furo[3,4-b]pyrrole, octahydro-1H-pyrrolo[3,2-b]pyridine, (3as, 6as)-tetrahydro-1H,4H-3a,6a-(methanooxymethano)pyrrolo[3, 4-c]pyrrole, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, 5-azaspiro[2.4]heptane, 2-oxa-6-azaspiro[3.4]octane, 2,7-diazaspiro[4.4]nonane, 2-oxa-6-azaspiro[3.4]octane or 1-oxa-7-azaspiro[4.4]nonane; each of which is optionally substituted with one or more halogen, —$NR_{6a}R_{6a}$ or a $C_{1-3}$ alkyl optionally substituted with —$NR_{6a}R_{6a}$ or hydroxyl;

$R_{4a}$ is $NR_{4c}R_{4d}$, cyclopropyl, azetidine, pyrrolidine, piperidine, piperazine, morpholine or imidazole, wherein the cyclopropyl, azetidine, pyrrolidine, piperidine, piperazine, or morpholine is optionally substituted with halogen, hydroxyl, $C_{1-3}$ alkoxy or —$NR_{6a}R_{6a}$;

$R_{4b}$ is H, hydroxyl, or $C_{1-3}$ alkyl;

$R_{4c}$ is independently cyclopropyl, or oxetane;

$R_{4d}$ is independently $C_{1-3}$ alkyl;

each $R_{6a}$ is independently H or deuterium;

each $R_{6b}$ is independently H, trideuteromethyl, a $C_{3-5}$ cycloalkyl, a N-methyl pyrrolidine, tetrahydrofuran, tetrahydropyran, bicyclo[1.1.1]pentan-1-yl, bicyclo[1.1.1]pentan-1-ol, or a $C_{1-3}$ alkyl optionally substituted with one or more deuterium, hydroxyl, methyl, methoxy, halogen, cyclopropyl, oxetane, tetrahydrofuran, tetrahydropyran, —CO—NHMe, or —CO—$NH_2$, wherein the $C_{3-5}$ cycloalkyl is optionally substituted with one or more hydroxyl or methyl;

$E_1$ is —O—$C_{1-3}$ alkylene, or $C_{1-3}$ alkylene optionally substituted with one or more halogens;

$E_2$, and $E_4$ are each independently $C_{1-3}$ alkylene optionally substituted with one or more hydroxyl, $C_{1-3}$ alkoxy, or halogen, and wherein $E_2$ and $E_4$ can optionally be bridged by a bond or a $C_{1-3}$ alkylene; and $E_3$ is —O—, —$CR_{7a}R_{7a}$—, —$NR_{9a}$—, or —CO—$NR_{6b}$—; or the ring

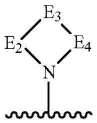

is hexahydro-1H-furo[3,4-c]pyrrole;

Each $E_{2a}$ is independently a $C_{1-3}$ alkylene optionally substituted with one or more hydroxyls;

$E_5$ is —O—, —$CR_{7a}R_{7a}$—, or —$NR_{9a}$—;

each $R_7$ is independently H, or $C_{1-3}$ alkyl;

each $R_{7a}$ is independently H, halogen, CN, hydroxyl, $C_{1-3}$ alkoxy, or $C_{1-3}$ alkyl optionally substituted with one or more halogens or hydroxyls;

each $R_8$ is each independently H or $C_{1-3}$ alkyl; and each $R_{8a}$ is independently a $C_{1-3}$ alkyl; and $R_9$ is a H, —CO—$C_{1-3}$ alkyl, —CO—$NR_8R_8$, —$NR_{9a}R_{9a}$, $C_{1-4}$ alkyl, or $C_{3-6}$ cycloalkyl, wherein the $C_{1-4}$ alkyl or $C_{3-6}$ cycloalkyl is optionally substituted with one or more halogen;

$R_{9a}$ is each independently H, optionally substituted $C_{1-3}$ alkyl or —CO—$C_{1-3}$ alkyl; wherein the optionally substituted $C_{1-3}$ alkyl is optionally substituted with one or more halogens; and $R_{10}$ is H or $C_{1-3}$ alkyl optionally substituted with one or more deuterium or a pharmaceutically acceptable salt thereof.

2. The compound according to claim 1, wherein $R_4$ is H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; or $R_4$ is a N-linked cyclic amine or a group of the formula

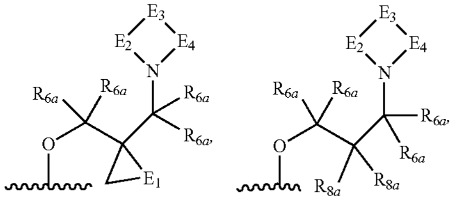

or

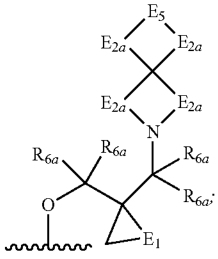

wherein the N-linked cyclic amine is a N-linked:

azetidine substituted with $R_{4a}$ and $R_{4b}$;

pyrrolidine, piperidine, piperazine, morpholine, imidazole or pyrazole;

each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, a $C_{1-3}$ alkyl, or an imidazole optionally substituted with a methyl; wherein the azetidine is optionally substituted with hydroxyl or $C_{1-3}$ alkoxy; and the $C_{1-3}$ alkyl is optionally substituted with halogen —$NR_{6a}R_{6a}$ or hydroxyl; or vi. 2,6-diazabicyclo[3.2.0]heptane, 3,6-diazabicyclo[3.2.0]heptane, 3-azabicyclo[3.1.0]hexane, 3-azabicyclo[3.2.0]heptane, octahydro-1H-pyrrolo[3,4-b]pyridine, octahydro-6-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, or 5-azaspiro[2.4]heptane; each of which is optionally substituted with one or more halogen, —$NR_{6a}R_{6a}$ or a $C_{1-3}$ alkyl optionally substituted with —$NR_{6a}R_{6a}$;

$R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$ each $R_{6b}$ is independently H, trideuteromethyl, a $C_{3-5}$ cycloalkyl, or a $C_{1-3}$ alkyl optionally substituted with hydroxyl; and $R_9$ is a H, —CO—$C_{1-3}$ alkyl, —$NR_{9a}R_{9a}$, $C_{1-4}$ alkyl, or $C_{3-6}$ cycloalkyl; or a pharmaceutically acceptable salt thereof.

3. The compound according to claim 1, wherein $R_{3b}$, and $R_{3c}$ are each independently H or halogen, and $R_1$ is a group of the formula

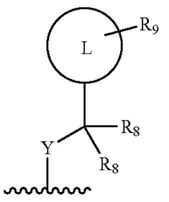

or

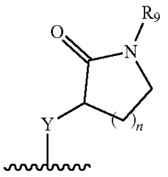

wherein n is 0, 1, or 2;

Y is either —$N(R_8)$—, or —O—;

L is a 5-6 membered heteroaryl containing 1 to 3 heteroatoms selected from O, N, or S, wherein the 5-6 membered heteroaryl may be optionally fused with a $C_{3-6}$ cycloalkyl ring to form a bicyclic ring structure;

$R_2$ is H, halogen, or methyl;

$R_4$ is H, methyl, —$CH_2$—OH, —O—$R_5$—$R_6$, —O—$R_6$, N-linked cyclic amine, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; and $R_9$ is a H, $C_{1-4}$ alkyl, or $C_{3-6}$ cycloalkyl, or a pharmaceutically acceptable salt thereof wherein the $C_{1-4}$ alkyl or $C_{3-6}$ cycloalkyl is optionally substituted with one or more halogen; or a pharmaceutically acceptable salt thereof.

4. The compound according to claim 1, wherein:

$R_1$ is a group of the formula

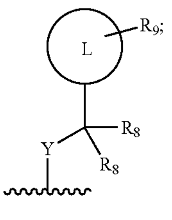

L is a 5-membered heteroaryl containing 1 to three heteroatoms selected from O, N, or S, wherein the 5-membered heteroaryl may be optionally fused with a $C_{3-6}$ cycloalkyl ring to form a bicyclic ring structure;

$R_4$ is H, methyl, —$CH_2$—OH, —O—$R_5$—$R_6$, —O—$R_6$, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; and $R_9$ is a H, $C_{1-4}$ alkyl, or $C_{3-6}$ cycloalkyl, or a pharmaceutically acceptable salt thereof.

5. The compound according to claim 1, wherein G is —N—, or a pharmaceutically acceptable salt thereof.

6. The compound according to claim 1, wherein G is —$C(R_{3b})$—, or a pharmaceutically acceptable salt thereof.

7. The compound according to claim 6, wherein $R_{3b}$ is F, or a pharmaceutically acceptable salt thereof.

8. The compound according to claim 1, wherein Z is —N—, or a pharmaceutically acceptable salt thereof.

9. The compound according to claim 1, wherein Z is —$C(R_{3c})$—, or a pharmaceutically acceptable salt thereof.

10. The compound according to claim 9, wherein $R_{3c}$ is H or F, or a pharmaceutically acceptable salt thereof.

11. The compound according to claim 1, wherein $R_{3b}$, and $R_{3c}$ are each independently H or halogen, or a pharmaceutically acceptable salt thereof.

12. The compound according to claim 1, wherein A is —N—, or a pharmaceutically acceptable salt thereof.

13. The compound according to claim 1, wherein A is —C(H)—, or a pharmaceutically acceptable salt thereof.

14. The compound according to claim 1, wherein $R_2$ is F or Cl, or a pharmaceutically acceptable salt thereof.

15. The compound according to claim 1, wherein $R_2$ is F, or a pharmaceutically acceptable salt thereof.

16. The compound according to claim 1, wherein $R_2$ is Cl, or a pharmaceutically acceptable salt thereof.

17. The compound according to claim 1, wherein $R_1$ is selected from

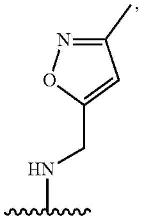,

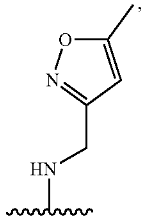,

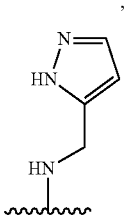,

-continued
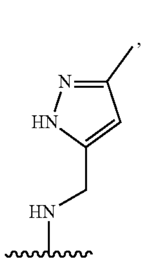,
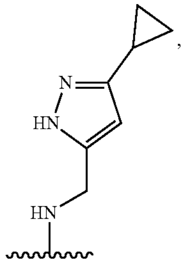,
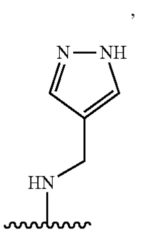,
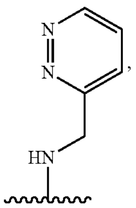,
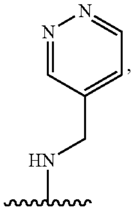,
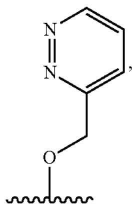,
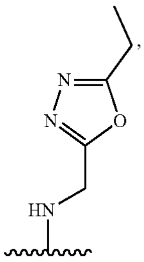,
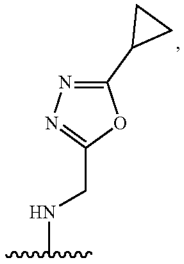,
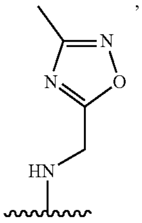,
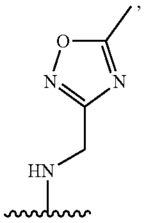,
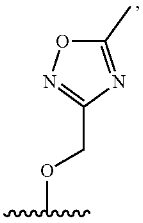,
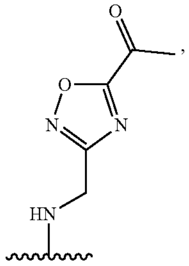,
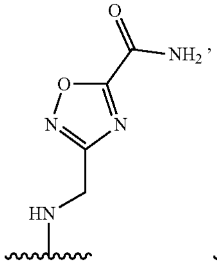,
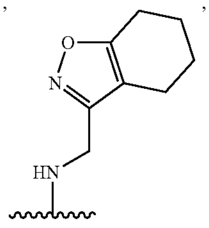,
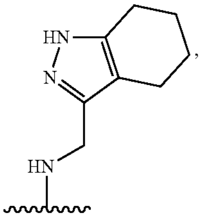,
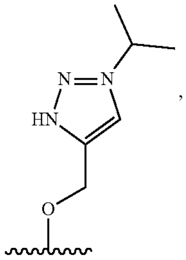,
-continued
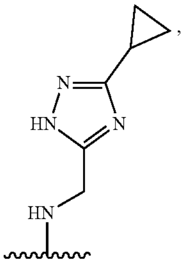,
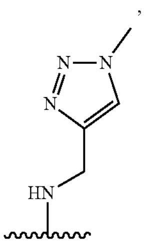,
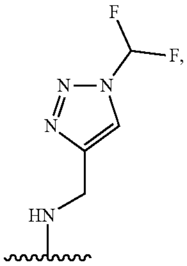,
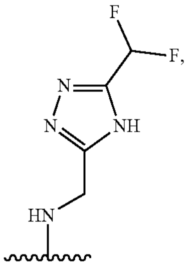,
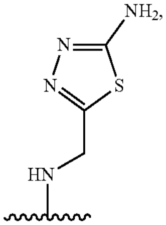,
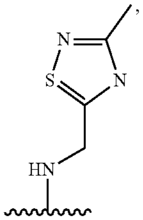,
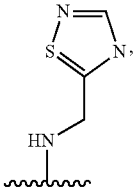,
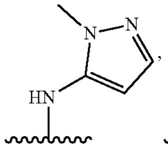,
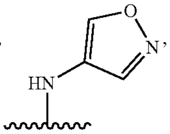,
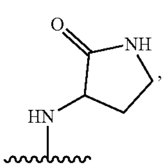,
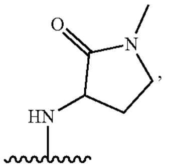,
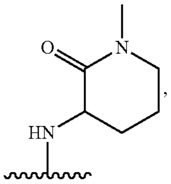, or
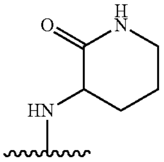
or a pharmaceutically acceptable salt thereof.
18. The compound according to claim 17, wherein $R_1$ is selected from
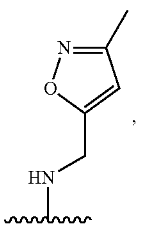,
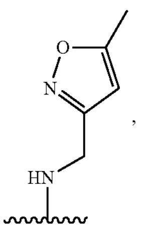,
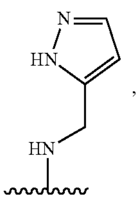, -continued
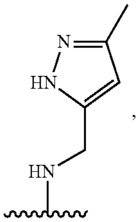 , 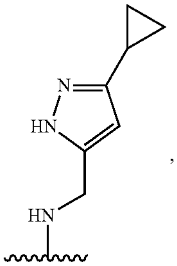 , 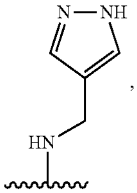 ,
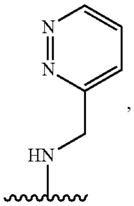 , 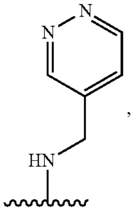 , 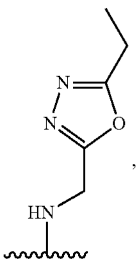 ,
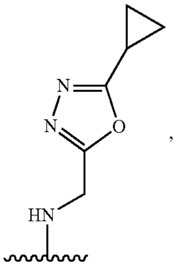 , 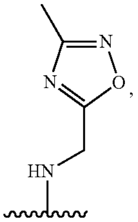 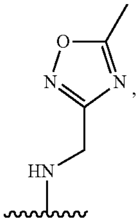
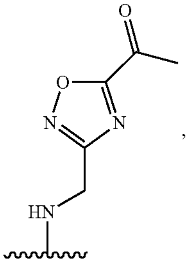 , 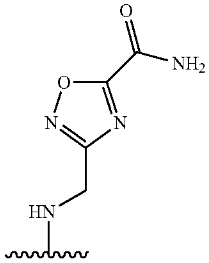 ,
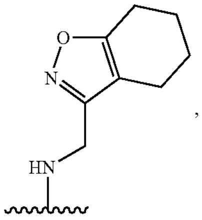 , 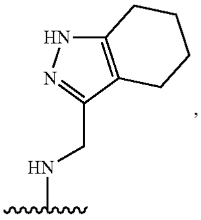 ,
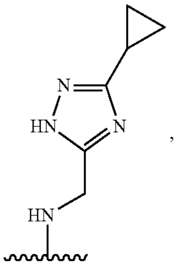 , 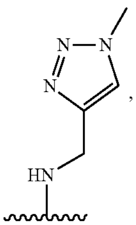 , 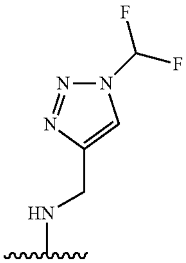 ,
-continued
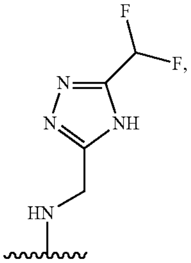 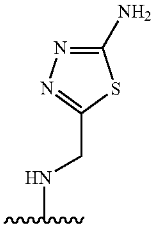 , 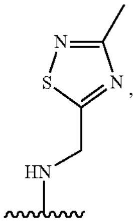
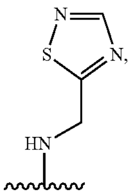
or a pharmaceutically acceptable salt thereof.
19. The compound according to claim 17, wherein $R_1$ is selected from
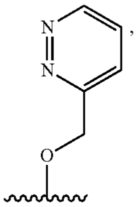 , 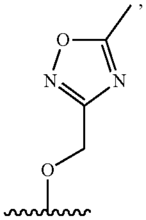 , or
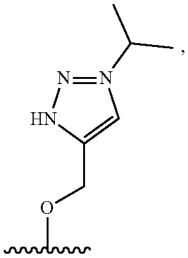 ,
or a pharmaceutically acceptable salt thereof.
20. The compound according to claim 17, wherein $R_1$ is selected from
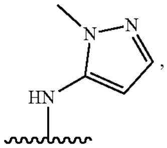 , or 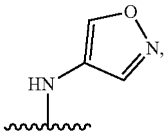
or a pharmaceutically acceptable salt thereof.
21. The compound according to claim 17, wherein $R_1$ is selected from

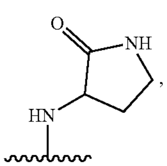,
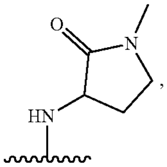,
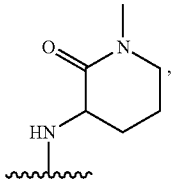, or
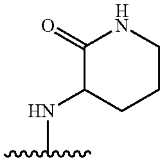

or a pharmaceutically acceptable salt thereof.

22. The compound according to claim 1, wherein $R_4$ is selected from

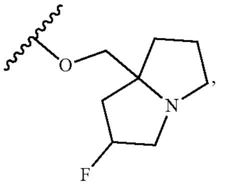,
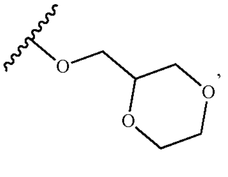,
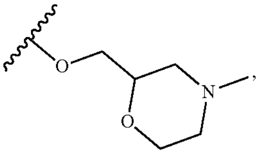,
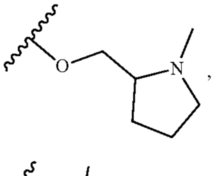,
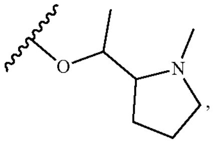,
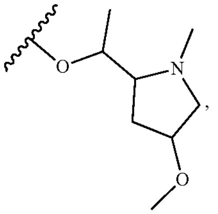,
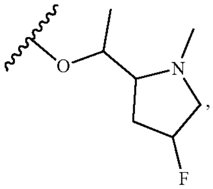,
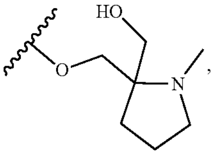,
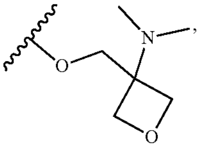,
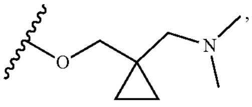,
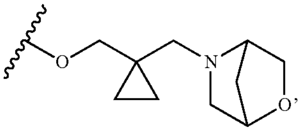,
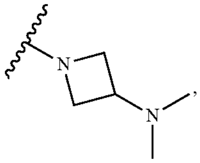, -continued

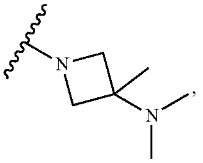,
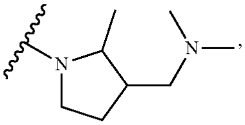,
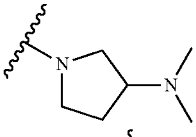,
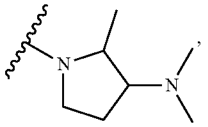,
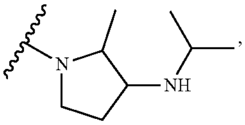,
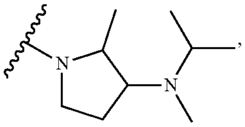,
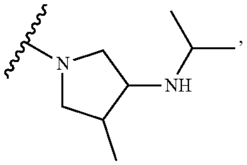,
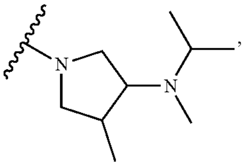,
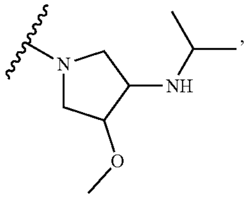,
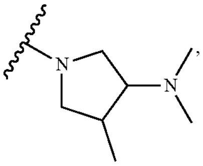,
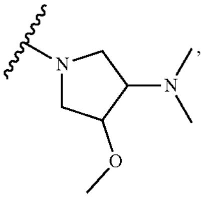,
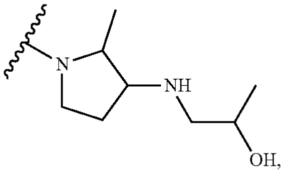
OH,
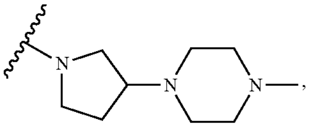, or
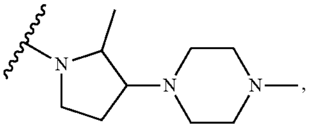, or a pharmaceutically acceptable salt thereof.

23. A pharmaceutical composition comprising a compound according to claim 1, or a pharmaceutically acceptable salt thereof, and a pharmaceutically acceptable carrier, diluent or excipient.

24. A method of treating a patient for cancer, comprising administering to a patient in need thereof, an effective amount of a pharmaceutical composition according to claim 23, wherein the cancer is selected from lung cancer, pancreatic cancer, cervical cancer, esophageal cancer, endometrial cancer, ovarian cancer, cholangiocarcinoma, and colorectal cancer.

25. A method of treating a patient for cancer, comprising administering to a patient in need thereof, an effective amount of a compound according to claim 1, or a pharmaceutically acceptable salt thereof, wherein the cancer is selected from lung cancer, pancreatic cancer, cervical cancer, esophageal cancer, endometrial cancer, ovarian cancer, cholangiocarcinoma, and colorectal cancer.

26. The method according to claim 25 wherein the patient has a cancer that was determined to have one or more cells expressing the KRas G12C, G12D, and/or G12V mutant proteins prior to administration of the compound or a pharmaceutically acceptable salt thereof.

27. The method according to claim 25 wherein the patient has a cancer that was determined to have one or more cells expressing the KRas G12D mutant protein prior to administration of the compound or a pharmaceutically acceptable salt thereof.

28. The method according to claim 25, wherein the cancer is non-small cell lung cancer.

29. The method according to claim 25, wherein the cancer is colorectal cancer.

30. The method according to claim 25, wherein the cancer is pancreatic cancer.

31. A method of treating a patient with a cancer that has a KRas G12C, G12D, and/or G12V mutation comprising administering to a patient in need thereof an effective amount of a compound according to claim 1, or a pharmaceutically acceptable salt thereof.

32. A method of treating a patient with a cancer that has a KRas G12D mutation comprising administering to a patient in need thereof an effective amount of a compound according to claim 1, or a pharmaceutically acceptable salt thereof.

33. The method according to claim 31, wherein the cancer is selected from lung cancer, pancreatic cancer, cervical cancer, esophageal cancer, endometrial cancer, mutant ovarian cancer, cholangiocarcinoma, and colorectal cancer.

34. The method according to claim 33, wherein the cancer is non-small cell lung cancer.

35. The method according to claim 33, wherein the cancer is colorectal cancer.

36. The method according to claim 33, wherein the cancer is pancreatic cancer.

37. The method according to claim 25, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

* * * * *